US011512096B2

(12) United States Patent
Fajdetic et al.

(10) Patent No.: US 11,512,096 B2
(45) Date of Patent: Nov. 29, 2022

(54) SECO MACROLIDE COMPOUNDS

(71) Applicant: SELVITA D.O.O., Zagreb (HR)

(72) Inventors: Andrea Fajdetic, Zagreb (HR); Maja Matanovic Skugor, Zagreb (HR); Ivaylo Jivkov Elenkov, Zagreb (HR); Goran Kragol, Zagreb (HR); Mirjana Bukvic, Zagreb (HR); Zorica Marusic Istuk, Zagreb (HR); Sanja Kostrun, Zagreb (HR); Dinko Ziher, Zagreb (HR); Renata Rupcic, Zagreb (HR); Kristina Butkovic, Zagreb (HR); Marko Duksi, Zagreb (HR); Ivana Ozimec Landek, Zagreb (HR); Dijana Pesic, Zagreb (HR); Antun Hutinec, Zagreb (HR); Milan Mesic, Zagreb (HR); Gordon Saxty, Zagreb (HR); Visnja Poljak, Copenhagen (DK)

(73) Assignee: SELVITA D.O.O., Zagreb (HR)

( * ) Notice: Subject to any disclaimer, the term of this patent is extended or adjusted under 35 U.S.C. 154(b) by 0 days.

(21) Appl. No.: 17/133,979

(22) Filed: Dec. 24, 2020

(65) Prior Publication Data

US 2021/0198278 A1 Jul. 1, 2021

Related U.S. Application Data

(63) Continuation of application No. 16/300,495, filed as application No. PCT/EP2017/060889 on May 8, 2017, now Pat. No. 10,919,910.

(30) Foreign Application Priority Data

May 11, 2016 (GB) .................................... 1608236

(51) Int. Cl.
| | | |
|---|---|---|
| *C07D 498/04* | (2006.01) | |
| *C07D 405/14* | (2006.01) | |
| *C07D 409/14* | (2006.01) | |
| *C07D 413/14* | (2006.01) | |
| *C07D 471/04* | (2006.01) | |
| *C07D 487/08* | (2006.01) | |
| *C07D 491/08* | (2006.01) | |

(52) U.S. Cl.
CPC ......... *C07D 498/04* (2013.01); *C07D 405/14* (2013.01); *C07D 409/14* (2013.01); *C07D 413/14* (2013.01); *C07D 471/04* (2013.01); *C07D 487/08* (2013.01); *C07D 491/08* (2013.01)

(58) Field of Classification Search
CPC .. C07D 498/04; C07D 405/14; C07D 409/14; C07D 413/14; C07D 471/04; C07D 487/08; C07D 491/08
USPC .................................................. 514/210.16
See application file for complete search history.

(56) References Cited

U.S. PATENT DOCUMENTS

| 3,725,385 A | 4/1973 | Freiberg |
| 5,250,518 A | 10/1993 | Kobrehel et al. |

FOREIGN PATENT DOCUMENTS

| EP | 0 283 055 A2 | 9/1988 |
| EP | 0 508 725 A1 | 10/1992 |
| EP | 0 735 041 A1 | 10/1996 |
| EP | 1 633 764 B1 | 9/2009 |
| GB | 2 270 072 A | 3/1994 |
| WO | WO 2000/042055 A2 | 7/2000 |
| WO | WO 2000/063223 A1 | 10/2000 |
| WO | WO 2003/014136 A1 | 2/2003 |
| WO | WO 2004/005310 A2 | 1/2004 |
| WO | WO 2004/013153 A2 | 2/2004 |
| WO | WO 2004/029067 A1 | 4/2004 |
| WO | WO 2004/101591 A1 | 11/2004 |
| WO | WO 2005/108412 A1 | 11/2005 |
| WO | WO 2014/165792 A2 | 10/2014 |

OTHER PUBLICATIONS

Robert B. Layzer, Section Five-Degenerative Diseases of the Nervous System, Cecil Textbook of Medicine, 20th edition (1996), vol. 2, pp. 2050-2057 (Year: 1996).*
Antonio R. Damasio, Alzheimer's Disease and Related Dementias, Cecil Textbook of Medicine, 20th edition (1996), vol. 2, pp. 1992-1996 (Year: 1996).*
"FDA mulls drug to slow late-stage Alzheimer's," [retrieved on Sep. 23, 2003]. Retrieved online via Internet, URL: http://www.cnn.com/2003/HEALTH/conditions/O9/24/alzheimers.drug.ap/index.html (Year: 2003).*
Djokic, S., et al., "Erythromycin Series", The Journal of Antibiotics, vol. 40, No. 7, 1987, pp. 1006-1015.
Bock V.D., et al., "Click Chemistry as a Route to Cyclic Tetrapeptide Analogues: Synthesis of Cyclo-[Pro-Val-ψ(Triazole)-Pro-Tyr]", Organic Letters, vol. 8, No. 5, 2006, pp. 919-922.
Borisova, S.A., et al., A De Novo Approach to the Synthesis of Glycosylated Methymycin Analogues with Structural and Stereochemical Diversity, Organic Letters, vol. 12, No. 22, 2006, pp. 5150-5153.
Djokic, S., et al., "Erythromycin Series. Part 11. Ring Expansion of Erythromycin A Oxime by the Beckmann Rearrangement", Journal of the Chemical Society, Perkin Transactions, 1986, Issue 1, pp. 1881-1890.

(Continued)

*Primary Examiner* — Kristin A Vajda
(74) *Attorney, Agent, or Firm* — ArentFox Schiff LLP

(57) ABSTRACT

The present invention relates to seco (opened ring) macrolide compounds, to the process for preparation thereof, to the use of said seco macrolide compounds as intermediates for preparation of macrolide based macrocycles, to macrolide based macrocycles obtained from said seco macrolide compounds, to the process for preparation of macrolide based macrocycles, to the pharmaceutical compositions comprising macrolide based macrocycles, and to the use of macrolide based macrocycles as therapeutic agents.

20 Claims, No Drawings

(56) References Cited

OTHER PUBLICATIONS

Dube, P., et al., "Carbonyldiimidazole-Mediated Lossen Rearrangement", Organic Letters, vol. 11, No. 24, (2009), pp. 5622-5625.
Dubois, N., et al., "On DABAL-Me3 promoted formation of amides", Tetrahedron, vol. 69, No. 46, (2013), pp. 9890-9897.
Erlanson, D.A., et al., "Fragment-Based Drug Discovery", 2004, Journal of Medicinal Chemistry, vol. 47, No. 14, pp. 3463-3482.
Fleisher, D., et al., "Improved Oral Drug Delivery: Solubility Limitations Overcome by the Use of Prodrugs", Advanced Drug Delivery Reviews, Low Molecular Weight Pro Drugs, 1996, vol. 19, No. 2, pp. 115-130.
Furstner, A., et al., "Total Syntheses of (+)-Ricinelaidic Acid Lactone and of (−)-Gloeosporone Based on Transition-Metal-Catalyzed C-C Bond Formations," Journal of the American Chemical Society, 1997, vol. 119 , No. 39, pp. 9130-9136.
Grubbs, R.H., "Olefin Metathesis", Tetrahedron, Tetrahedron Prize 2003—Olefin Metathesis: A Powerful and Versatile Instrument for Organic Synthesis, 2004, vol. 60, No. 34, pp. 7117-7140.
Hajduk, P.J., et al., "A Decade of Fragment-Based Drug Design: Strategic Advances and Lessons Learned", 2007, Nature Reviews Drug Discovery, vol. 6, No. 3, pp. 211-219.
International Search Report as cited in International Application No. PCT/EP2017/060889 dated Jul. 21, 2017.
Johannsen, M., et al., "Allylic Amination", Chemical Reviews, vol. 98, No. 4, 1998, pp. 1689-1708.
Katoh, T., et al., "Selective C—N bond oxidation: demethylation of N-methyl group in N-arylmethyl-N-methyl-a-amino esters utilizing N-iodosuccinimide (NIS)", Tetrahedron Letters, vol. 49, No. 4, 2008, pp. 598-600.
Kotha, S., et al., "Strategies and tactics in olefin metathesis", Tetrahedron, 2008, vol. 68, No. 2, (2012), pp. 397-421.
Lalli, C., et al., "LiNTf2-catalyzed Aminolysis of Lactones with Stoichiometric Quantities of Amines," Synlett, 2008, No. 2, pp. 189-192.
Londregan, A.T., et al., "General and Mild Preparation of 2-Aminopyridines", Organic Letters, vol. 12, No. 22, 2010, pp. 5254-5257.
Londregan, A.T.., et al., "A New and Useful Method for the Macrocyclization of Linear Peptides", 2012, Organic Letters, vol. 14, No. 11, pp. 2890-2893.
Maryanoff, B.E., et al., "The Wittig Olefination Reaction and Modifications Involving Phosphoryl-Stabilized Carbanions. Stereochemistry, Mechanism, and Selected Synthetic Aspects", Chemical Reviews, vol. 89, No. 4, 1989, pp. 863-927.
Nicolaou, K.C., et al., "Palladium-Catalyzed Cross-Coupling Reactions in Total Synthesis", Angewandte Chemie International Edition, vol. 44, No. 29, 2005, pp. 4442-4489.
Njardarson, J.R., et al., "Application of Hitherto Unexplored Macrocyclization Strategies in the Epothilone Series: Novel Epothilone Analogs by Total Synthesis" Chemical Communications, 2002, pp. 2759-2761.
Pirrung, M.C., et al., "A Convenient Procedure for the Preparation of Amino Acid Hydroxamates from Esters", The Journal of Organic Chemistry, vol. 60, No. 24, 1995, pp. 8084-8085.
Rathke, M.W., et al., "The Horner-Wadsworth-Emmons Modification of the Wittig Reaction Using Triethylamine and Lithium or Magnesium Salts", The Journal of Organic Chemistry, 1985, vol. 50, No. 15, pp. 2624-2626.
Shioiri, T., et al., "Diphenylphosphoryl Azide. New Convenient Reagent for a Modified Curtius Reaction and for Peptide Synthesis", Journal of the American Chemical Society, 1972, vol. 94, No. 17, pp. 6203-6205.
Stenmark, H.G., et al., "Biomimetic Synthesis of Macrolide/Ketolide Metabolites through a Selective N-Demethylation Reaction", The Journal of Organic Chemistry, 2000, vol. 65, No. 12, pp. 3875-3876.
Sugimoto, T., et al., "Synthesis and Structure-Activity Relationship of a Novel Class of 15-Membered Macrolide Antibiotics Known as '11a-Azalides'", Bioorganic & Medicinal Chemistry, 2012, vol. 20, No. 19. pp. 5787-5801.
Sugiomoto, T., et al., "Synthesis and Antibacterial Activity of a Novel Class of 15-Membered Macrolide Antibiotics, '11a-Azalides'", ACS Medicinal Chemistry Letters, 2011, vol. 2, No. 3, pp. 234-237.
Turner, R., et al., "Click Chemistry as a Macrocyclization Tool in the Solid-Phase Synthesis of Small Cyclic Peptides", Organic Letters, 2007, vol. 9, No. 24, pp. 5011-5014.
Valeur, E., et al., "Amide Bond Formation: Beyond the Myth of Coupling Reagents", 2009, Chemical Society Reviews, vol. 38, No. 2, pp. 606-631.
Vercillo, O.E., et al., "Design and Synthesis of Cyclic RGD Pentapeptoids by Consecutive Ugi Reactions", 2008, Organic Letters, vol. 10, No. 2, pp. 205-208.
Waddell, S.T., et al., "Synthesis and Antibacterial Activity of O-Methyl Derivatives of Azalide Antibiotics: II. 6-OMe Derivatives VIA Clarithromycin", Bioorganic & Medicinal Chemistry Letters, 1998, vol. 8, No. 11, pp. 1321-1326.
Barton, D.H.R., et al., "A New Method for the Deoxygenation of Secondary Alcohols", Journal of the Chemical Society, Perkin Transactions, 1975, vol. 10, No. 16, pp. 1574-1585.

* cited by examiner

SECO MACROLIDE COMPOUNDS

CROSS-REFERENCE TO RELATED APPLICATIONS

This application is a Continuation of U.S. patent application Ser. No. 16/300,495, filed Nov. 9, 2018, which claims priority to International Application No. PCT/EP2017/060889, filed May 8, 2017, which claims priority to GB Patent Application No. GB 1608236.4, filed May 11, 2016, the disclosures of which are hereby incorporated by reference in their entireties.

FIELD OF THE INVENTION

The present invention relates to seco (opened ring) macrolide compounds, to the process for preparation thereof, to the use of said seco macrolide compounds as intermediates for preparation of macrolide based macrocycles, to macrolide based macrocycles obtained from said seco macrolide compounds, to the process for preparation of macrolide based macrocycles, to the pharmaceutical compositions comprising macrolide based macrocycles, and to the use of macrolide based macrocycles as therapeutic agents.

BACKGROUND OF THE INVENTION

Success in development of new drug products requires that the pharmaceutical compound satisfies numerous requirements imposed by the physiology of the host and of the disease or condition. The requirements include: (i) adequate ability to interact with the target receptor(s); (ii) appropriate physical properties for presence at the location of the receptors in concentrations that permit the interactions noted above; (iii) appropriate physical properties to allow the agent to enter the body and distribute to the location of the receptors by any means; (iv) sufficient stability in fluids of the body; (v) the absence of toxic effects in compartments where the therapeutic agent is most concentrated, or in any other compartment where the therapeutic agent is located; and (vi) the absence of sequestration into non-physiological compartments and so on. These demanding requirements severely reduce the number of compounds that ultimately develop into a drug product. All new medicines introduced into the market are the result of lengthy, costly and risky research and development (R&D) conducted by pharmaceutical companies. By the time a medicinal product reaches the market, an average of 12-13 years will have elapsed since the first synthesis of the new active compound. The cost of researching and developing a new chemical or biological entity was estimated at € 1,059 million ($1,318 million) (Di Masi J., Tufts University, Centre for the Study of Drug Development, 28 (2007) p. 469-479). In average, only one or two of every 10,000 substances synthesised in laboratories will successfully pass all the stages to become marketable medicine. Macrolide compound research and development follows this pattern. Starting in the 1980's numerous synthetic efforts had been conducted in desire to modify naturally occurring macrolides, especially 14-membered erythromycin A. During the last decades second generation 15-membered macrolide azithromycin has been widely investigated in an effort to develop new antibacterial, anti-inflammatory as well as anti-malarial medicines. However, the demanding requirements that a drug product has to satisfy represent a tough obstacle in the successful development of macrolide medicines. Often, compounds that already satisfied numerous requirements have been finally discharged due to a single undesirable property. Therefore, there is a constant need for development of new macrolide intermediates as well as robust synthetic methods that allow not only synthesis of novel scaffolds but more importantly further robust modification of already developed semisynthetic macrolide molecules by using simple high-throughput synthetic process. It is particularly desirable that such simple high-throughput synthetic processes allow to keep the essential components of the molecule which has already developed, but then introducing beneficial substituents and modifications in the eastern part of the macrolide molecule and to enable subsequent robust screening for diverse western fragments which can substitute those that are derived from the parent naturally occurring macrolide. Such simple high-throughput synthetic process would be particularly desirable for development of compound libraries where the eastern part of the macrolide molecule with beneficial substituents needs to be preserved and where the western portion of the molecule needs to be robustly investigated. For such high-throughput synthetic processes it would be desirable that it is simple, i.e. that there are not many synthetic steps which, in addition, require introduction of protecting groups and/or prior modification of functional groups which need to be reintroduced or removed in the final step. In that way simple high-throughput synthetic processes would enable easy and quick development of compound libraries with considerable structural diversity at the western site of the molecule.

PCT Application WO9415617 discloses a process for the preparation of certain 8a-aza and 9a-aza macrolide antibacterial compounds using a multistep base catalyzed synthetic pathway for the synthesis of a required 8a-aza-fragment and a 9-ethyl-9a-aza-fragment, where protection of the 9a-amino or 8a-amino has to be introduced giving as a result homologues of 9-ethyl-9-deoxo-9a-aza-9a-methyl-9a-homoerythromycin A and of 9-deoxo-8a-aza-8a-methyl-8a-homoerythromycin A (azithromycin 8a-aza analogue) having a substantially simplified western portion of the ring.

Sugimoto and Tanikawa in *ACS Med. Chem. Lett.* 2 (2011) p. 234-237 disclose certain 15-membered 11a-aza macrolide antibiotics in which the C/12 and/or C/13 position is unsubstituted or substituted by $CH_2OCH_2$-phenyl moiety. These analogues had been obtained from 14-membered (9S)-hydroxy-9-dihydroerythromycin A using lead tetraacetate $(Pb(OAc)_4)$ for ring opening. As reported the original antibacterialy active erythromycin A (9-keto analogue) cannot be used because of instability of the β-keto aldehyde intermediate. To avoid side reactions the 9-keto analogue has been first converted to the 9-hydroxy analogue where the 9-hydroxy group has to be protected before C/11-C/12 oxidative ring opening is performed giving the C/11-aldehyde, which after a multistep synthetic process and final ring closure gave macrolide derivatives with antibacterial activity.

Sugimoto et al. J. Bioorg. Med. Chem. 20 (2012) p. 5787-5801 shows similar C/12-C/13 substituted antibacterial analogues of 6-O-methyl erythromycin A (clarithromycin) and of 9-amino-erythromycin A where conversion of the 9-keto to the 9-OH and protection of the 9-OH in case of clarithromycin or protection of the 9-amino in the case of 9-amino-erythromycin A is required before ring opening with $Pb(OAc)_4$ is performed.

However, prior art documents do not disclose synthetic processes which allow single step ring opening of a wide variety of semisynthetic 9a-aza-9a-homoerythromycin macrolides, and immediate use of thus obtained seco macrolide compounds as intermediates whereby the previously introduced eastern portion substitution pattern has been preserved. Moreover, prior art documents do not disclose processes that allow for keeping beneficial substituents, linkers and other modifications previously introduced into the semisynthetic 9a-aza-9a-homoerythromycin macrolide by which the western portion can be subsequently substantially diversified using simple and robust process resulting in new macrolide based macrocycles having from 11 to multi-number ring members depending on the nature of the fragment inserted to the west side of the seco macrolide and therefore providing a powerful tool in development of novel macrolide based macrocycles. The present invention therefore provides novel seco (opened ring) macrolide compounds which are useful as intermediates for preparation of macrolide based macrocycles and the process for preparation thereof. The seco (opened ring) macrolide compounds of the invention may already have diverse substituents introduced in eastern portion of molecule allowing western portion to be further diversified resulting in macrolide based macrocycles having from 11 to multi-number ring members which can be used as therapeutic agents.

SUMMARY OF THE INVENTION

The present invention is based on the identification that seco (opened ring) macrolide compounds of the invention may be useful as intermediates for preparation of macrolide based macrocycles. Therefore, the present invention relates to seco (opened ring) macrolide compounds, to the process for preparation thereof, to their use as intermediates for preparation of macrolide based macrocycles, to macrolide based macrocycles obtained from said seco macrolide compounds, to the process for preparation of macrolide based macrocycles, to the pharmaceutical compositions comprising macrolide based macrocycles, and to the use of macrolide based macrocycles as therapeutic agents.

In the first aspect, the present invention relates to seco (opened ring) macrolide compound of Formula (I)

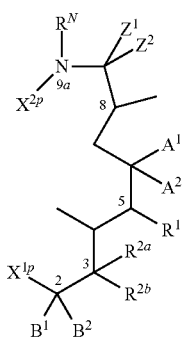

wherein,
$X^{1p}$ is

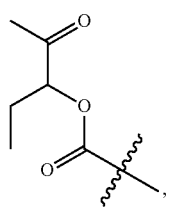

$-C(=O)OH$, $-C(=O)NH_2$, $-C(=S)NH_2$, $-C(=O)NHNH_2$, $-CH_2NH_2$, $-CH_2OH$, $-C(=O)H$, $-CN$ or $NH_2$;

$X^{2p}$ is hydrogen, $-CH(CH_3)C(=O)H$, $-C(=S)NH_2$ or $-C(=O)NH_2$;

$Z^1$ and $Z^2$ are
  (i) both hydrogen, or
  (ii) together with carbon atom to which they are attached form a keto group provided $R^N$ is hydrogen and $A^1$ is $OC_{1-6}$alkyl, $A^1$ is OH, $OC_{1-6}$ alkyl, $OC_{2-6}$ alkenyl, $OC_{2-6}$ alkynyl, $OR^p$, or $A^1$ together with $R^{2b}$ forms cyclic hemiketal or ether;

$A^2$ is $CH_3$ or H;

$B^1$ and $B^2$ are independently H, $C_{1-6}$alkyl or halogen, or $B^2$ together with $R^{2a}$ forms a double bond;

$R^1$ is $S^1$, OH, $OC_{1-6}$ alkyl or $OR^p$;

wherein,
  $S^1$ is sugar group of formula (b1):

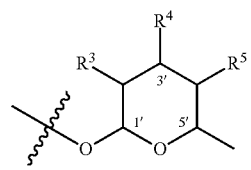

wherein,
$R^3$ is OH, H, $OR^p$, $-O-L^1-G$ or $-OC(=O)G$, provided when $R^3$ is $O-L^1-G$ or $-OC(=O)G$ group then $R^4$ is $N(CH_3)_2$ and $R^5$ is H, wherein
$L^1$ $-(CH_2)_{a1}-U^1-(CH_2)_{b1}-$;
$U^1$ is $-N(R^6)-$, $-NHC(=O)-$ or $-C(=O)NH-$;
$R^6$ is H or $C_{1-3}$alkyl;
$a^1$ is an integer from 2 to 6;
$b^1$ is an integer from 0 to 6;
G is selected from:
  (i) $G^1$, wherein $G^1$ is $C_{1-8}$alkyl, wherein alkyl may be optionally interrupted by 1 to 3 bivalent radical groups selected from $-O-$, $-S-$ and $-N(R^{g1})-$, where $R^{g1}$ is H or $C_{1-6}$alkyl, and where alkyl may be optionally substituted by one or more groups independently selected from halogen, OH, keto, $C_{2-6}$alkenyl, $C_{2-6}$alkynyl, $haloC_{1-6}$ alkyl, $haloC_{1-6}$alkyloxy, $-C(=O)OC_{1-6}$ alkyl, $NH_2$, $N-(C_{1-6}$-alkyl)amino, $N,N$-di($C_{1-6}$alkyl)amino; aryl or heteroaryl wherein said aryl and heteroaryl may be mono or biyclic and independently each may be optionally substituted by one or more groups independently selected from halogen, CN, OH, $NO_2$, $OC_{1-6}$ alkyl, $NH_2$, $N-(C_{1-6}$-alkyl)amino, $N,N$-di($C_{1-6}$alkyl)amino, $-C(=O)C_{1-6}$ alkyl, $-OC(=O)C_{1-6}$ alkyl, $-C(=O)OH$, $-C(=O)OC_{1-6}$ alkyl, $-C(=O)NHC_{1-6}$ alkyl and $-NHC(=O)C_{1-6}$ alkyl;
  (ii) $G^2$, wherein $G^2$ is 3-7 membered cycloalkyl which may be optionally substituted by one or more groups independently selected from OH, halogen, CN, $NH_2$, $C_{1-6}$ alkyl, $C_{2-6}$alkenyl, $C_{2-6}$alkynyl, $haloC_{1-6}$alkyloxy, $-C_{1-6}$alkyl-OH, $-C(=O)C_{1-6}$ alkyl, $-C(=O)OC_{1-6}$ alkyl, $-C(=O)OH$, $-C(=O)NH_2$, $-C_{0-6}$alkyl-aryl or $C_{0-6}$ alkyl-heteroaryl wherein aryl and heteroaryl independently from each other may be optionally substituted by one or more groups independently selected from halogen, CN, OH, $NO_2$, $C_{2-6}$alkenyl, $C_{2-6}$alkynyl, $haloC_{1-6}$alkyloxy, $-C_{1-6}$alkyl-OH, $NH_2$, $N-(O_{1-6}$-alkyl)amino, N,N-di($C_{1-6}$alkyl)amino, —C(=O)$C_{1-6}$ alkyl, —OC(=O)$C_{1-6}$ alkyl, —C(=O)OH, —C(=O)O$C_{1-6}$ alkyl, —C(=O)NH$C_{1-6}$ alkyl and —NHC(=O)$C_{1-6}$ alkyl;
(iii) $G^3$, wherein $G^3$ is 3-7 membered heterocycloalkyl containing one or two heteroatoms independently selected from N, O and S, where heterocycloalkyl may be optionally substituted by one or more groups independently selected from OH, halogen, CN, NH$_2$, $C_{1-6}$alkyl, $C_{2-6}$alkenyl, $C_{2-6}$ alkynyl, halo$C_{1-6}$alkyl, —O$C_{1-6}$alkyl, halo$C_{1-6}$alkyloxy, —$C_{1-6}$alkyl-OH, —C(=O)$C_{1-6}$ alkyl, —C(=O)O$C_{1-6}$ alkyl, —C(=O)OH and —C(=O)NH$_2$;
(iv) $G^4$, wherein $G^4$ is aryl wherein aryl may be optionally substituted by one or more groups independently selected from halogen, CN, OH, NO$_2$, $C_{1-6}$alkyl, $C_{2-6}$alkenyl, $C_{2-6}$alkynyl, halo$C_{1-6}$alkyloxy, —$C_{1-6}$alkyl-OH, NH$_2$, N—($C_{1-6}$-alkyl)amino, N,N-di($C_{1-6}$alkyl)amino, —C(=O)$C_{1-6}$ alkyl, —O(C=O)$C_{1-6}$ alkyl, —C(=O)OH, —C(=O)O$C_{1-6}$ alkyl, —C(=O)NH$C_{1-6}$ alkyl and —NHC(=O)$C_{1-6}$ alkyl;
(v) $G^5$, wherein $G^5$ is heteroaryl wherein heteroaryl may be optionally substituted by one or more groups independently selected from halogen, CN, OH, NO$_2$, $C_{2-6}$alkenyl, $C_{2-6}$alkynyl, halo$C_{1-6}$alkyloxy, —$C_{1-6}$alkyl-OH, NH$_2$, N—(O$_{1-6}$-alkyl)amino, N,N-di($C_{1-6}$alkyl)amino, —C(=O)$C_{1-6}$ alkyl, —O(C=O)$C_{1-6}$ alkyl, —C(=O)OH, —C(=O)O$C_{1-6}$ alkyl, —C(=O)NH$C_{1-6}$ alkyl and —NHC(=O)$C_{1-6}$ alkyl;
$R^4$ is —N($R^7$)$R^8$, wherein
  $R^7$ is CH$_3$,
  $R^8$ is $C_{1-6}$alkyl, H, —C(=O)$R^9$ or $R^p$ wherein $R^9$ is $C_{1-6}$alkyl or H;
$R^5$ is hydrogen;
or both $R^4$ and $R^5$ are hydrogen or together form a bond;
or $S^1$ is sugar group of formula (b2):

(b2)

wherein:
$R^5$ is H;
d is an integer from zero to 3;
$R^{10}$ is $C_{1-4}$alkyl;
$R^{2a}$ is:
(i) $S^2$;
(ii) —OH;
(iii) —O$C_{1-6}$ alkyl,
(iv) H;
(v) together with $R^{2b}$ forms a keto group (=O);
(vi) together with B$^2$ forms a double bond;
(vii) —OC(=O)$Y^1$, wherein $Y^1$ is $G^1$, $G^2$, $G^3$, $G^4$, $G^5$ or H; or
(viii) —O$R^p$;

$R^{2b}$ is H, together with $R^{2a}$ forms a keto group, together with A$^1$ forms cyclic hemiketal and $R^{2a}$ is OH or together with A$^1$ forms cyclic ether group and $R^{2a}$ is H;
$S^2$ is sugar group of formula (d)

(d)

wherein,
$R^{11}$ is:
(i) H;
(ii) together with $R^{12}$ and carbon atom to which they are attached forms a keto or epoxy group;
(iii) one of $R^{11}$ and $R^{12}$ is OH and the other is CH$_2$N($R^{13}$)$R^{14}$, wherein one of $R^{13}$ and $R^{14}$ is $C_{1-6}$alkyl and the other is H, $G^1$, $G^2$, $G^3$, $G^4$, $G^5$ or $R^p$, or wherein $R^{13}$ and $R^{14}$ taken together with the nitrogen atom to which they are attached form a non-aromatic heterocyclic ring containing between 2 and 6 carbon atoms which is:
  a. saturated or unsaturated and contains zero or 1 additional heteroatom selected from O, S and N; and/or
  b. unsubstituted or substituted by from 1 to 2 groups selected from $C_{1-5}$alkanoyl; $C_{1-6}$alkyl wherein alkyl is uninterrupted or is interrupted by 1-3 bivalent radical groups selected from —O—, —S— and —N($R^{18}$)—, and/or wherein $C_{1-6}$alkyl is unsubstituted or substituted by from 1 to 2 groups selected from OH, NH$_2$, a non-aromatic heterocyclic ring containing between 2 and 6 carbon atoms which is unsubstituted or is substituted by a group selected from $C_{1-4}$alkyl, halogen, NH$_2$, OH, SH, $C_{1-6}$ alkoxy and $C_{1-4}$hydroxyalkyl, and $C_{3-7}$cycloalkyl which is unsubstituted or is substituted by a group selected from $C_{1-4}$alkyl, halogen, NH$_2$, OH, SH, $C_{1-6}$ alkoxy, $C_{1-4}$hydroxyalkyl; and $C_{1-4}$dialkylamino;
$R^{12}$ is:
(i) OH;
(ii) together with $R^{11}$ and carbon atom to which they are attached forms a keto or epoxy group;
(iii) —OC(=O)$Y^3$, wherein $Y^3$ is H, $G^1$, $G^2$, $G^3$, $G^4$, or $G^5$; or
(iv) O$R^p$;
$R^N$ is hydrogen, $G^1$ (preferably CH$^3$), $G^2$, $G^3$, $G^4$, $G^5$, $R^p$, or $R^{15}$ wherein $R^{15}$ is —$C_{1-4}$alkyl-G, —C(=O)G, —C(=O)NH—$C_{0-4}$alkyl-G, wherein G is $G^1$, $G^2$, $G^3$, $G^4$ or $G^5$;
$R^p$ is a protective group;
or a salt or solvate thereof.

In another aspect, the invention relates to the use of seco (opened ring) macrolide compound of Formula (I) as intermediate for preparation of macrolide based macrocycles of formula (III). In particular, the invention relates to seco (opened ring) macrolide compound of Formula (I) for use as intermediate for preparation of macrolide based macrocycles of formula (III).

In a further aspect, the invention relates to the process for preparation of seco (opened ring) macrolide compound of Formula (I). In particular, the invention relates to the process of preparation of seco (opened ring) macrolide compound of Formula (I) wherein in the first step (a) the macrolide ring of compound of Formula (II) is cleaved using suitable oxidative cleavage reactant (suitably lead tetracaetate or periodic acid salts such as sodium periodate) in a suitable solvent or mixture of solvents, said initial step (a) being optionally followed by steps selected form (b) to (m).

In another aspect, the invention relates to the macrolide compound of Formula (II-X), which is subset of Formula (II). In particular, the invention relates to compound of formula (II-X) for use as intermediate for preparation of compound of formula (I).

In another aspect, the invention relates to macrolide based macrocyle compound of Formula (III).

In a further aspect, the invention relates to the process for preparation of macrolide based macrocyle compound of Formula (III). In particular, the invention relates to the process for preparation of macrolide based macrocyle compound of Formula (III) from seco (opened ring) macrolide compound of Formula (I).

In another aspect, the invention relates to the pharmaceutical compositions comprising a macrolide based macrocyle compound of Formula (III).

In a further aspect, the present invention also relates to pharmaceutical compositions comprising a macrolide based macrocyle compound of Formula (III) and a pharmaceutical carrier, excipient or diluent.

In another aspect, the invention relates to a macrolide based macrocyle compound of Formula (III) for use in therapy.

In a further aspect, the invention relates to a macrolide based macrocyle compound of Formula (III) for use in the prophylaxis and/or treatment of conditions involving inflammation or immune responses and/or autoimmune diseases.

In another aspect, the invention relates to the use of a macrolide based macrocyle compound of Formula (III) in the manufacture of a medicament for the prophylaxis and/or treatment of conditions involving inflammation or immune responses and/or autoimmune diseases.

In further aspect, the invention relates to methods of prophylaxis and/or treatment of conditions involving inflammation or immune responses and/or autoimmune diseases by administering of an effective amount of a macrolide based macrocyle compound of compound of the invention or one or more pharmaceutical compositions of the invention. In another aspect of the invention, this invention provides a methods of prophylaxis and/or treatment of a subject, in particular humans, susceptible to or afflicted with a condition selected from among those listed herein, and particularly conditions involving inflammation or immune responses and/or autoimmune diseases, which methods comprise the administration of an effective amount of a macrolide based macrocyle compound of Formula (III) or one or more pharmaceutical compositions of the invention. Other objects and advantages will become apparent to those skilled in the art from a consideration of the ensuing detailed description.

DETAILED DESCRIPTION OF THE INVENTION

Definitions

It will be understood that the present invention covers all combinations of aspects, suitable, convenient and preferred groups described herein.

When describing the invention, which may include processes, compounds, pharmaceutical compositions containing such compounds and methods of using such compounds and compositions, the following terms, if present, have the following meanings unless otherwise indicated. Unless otherwise stated, the term "substituted" is to be defined as set out below. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

When ranges are referred to herein, for example but without limitation, $C_{0-6}$alkyl, the citation of a range should be considered a representation of each member of said range. By way of example $C_0$alkyl means that alkyl group is absent. Thus, for example, selected member $C_0$alkyl-arly of a range $C_{0-6}$alkyl-aryl means that aryl group is directly attached without an alkyl spacer.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxylacetyl, and the like.

The term "alkyl" as used herein as a group or a part of a group refers to a straight or branched aliphatic hydrocarbon having the specified number of carbon atoms. Particular alkyl groups have 1 to 18 carbon atoms; more particular alkyl groups have 1 to 6 carbon atoms, and even more particular alkyl groups have 1 to 4 carbon atoms. Suitably alkyl groups have 1 or 2 carbon atoms. Branched means that one or more alkyl groups such as methyl, ethyl or propyl is attached to a linear alkyl chain. Exemplary branched chain groups include isopropyl, iso-butyl, t-butyl and isoamyl. Examples of alkyl groups as used herein include methyl, ethyl, n-propyl, isopropyl, n-butyl, tert-butyl, sec-butyl, n-pentyl, n-hexyl, 1,2-dimethylbutyl, octyl, decyl, undecyl, dodecyl tridecyl, tetradecyl, pentadecyl, hexadecyl, heptadecyl and octadecyl.

The term "alkyloxy" or "alkoxy", as used herein, refers to a straight or branched chain alkyl group, as previously defined, attached to the parent molecular moiety through an oxygen atom containing the specified number of carbon atoms. Particular alkoxy groups have between 1 and 6 carbon atoms. More particular alkoxy groups have between 1 and 4 carbon atoms. For example, $C_{1-4}$alkoxy means a straight or branched alkoxy containing at least 1, and at most 4, carbon atoms. Examples of "alkoxy" as used herein include, but are not limited to, methoxy, ethoxy, n-propoxy, isopropoxy, n-butoxy, tert-butoxy, sec-butoxy, n-pentoxy, n-hexoxy, and 1,2-dimethylbutoxy.

The term "alkenyl" as used herein as a group or a part of a group refers to a straight or branched hydrocarbon chain containing the specified number of carbon atoms and containing at least one double bond. For example, the term "$C_{2-6}$alkenyl" means a straight or branched alkenyl containing at least 2, and at most 6, carbon atoms and containing at least one double bond. Particular "alkenyl" groups have 2 to 4 carbon atoms and containing at least one double bond. Examples of "alkenyl" as used herein include ethenyl, 2-propenyl, 3-butenyl, 2-butenyl, 2-pentenyl, 3-pentenyl, 3-methyl-2-butenyl, 3-methyl but-2-enyl, 3-hexenyl and 1,1-dimethylbut-2-enyl.

The term "alkynyl" as used herein as a group or a part of a group refers to a straight or branched hydrocarbon chain containing the specified number of carbon atoms and containing at least one triple bond. For example, the term "$C_{2-6}$alkynyl" means a straight or branched alkynyl containing at least 2, and at most 6, carbon atoms and containing at least one triple bond. Examples of "alkynyl" as used herein include, but are not limited to, propynyl, 1-butynyl, 2-butynyl, 1-pentynyl and 3-methyl-1-butynyl.

The term "alkylene" as used herein as a group or a part of a group refers to a branched or straight chained alkyl group containing from 1 to 6 carbon atoms, having single bonds for attachment to other groups at two different carbon atoms. Examples of such alkylene groups include methylene, ethylene, n-propylene, isopropylene, n-butylene, isobutylene, pentylene, and hexylene. Particular alkylene groups have between 1 and 4 carbon atoms. More particular it is methylene (—$CH_2$—) or ethylene (—$CH_2$—$CH_2$—).

The term "amino" refers to the radical —$NH_2$.

The term "amino protecting group" refers to a substituent on a functional amino group which prevent undesired reactions and degradations during synthetic procedures, and which may be selectively removed after certain synthetic step. Examples of 'amino protecting group' include: acyl type protecting groups (e.g. formyl, trifluoroacetyl and acetyl), aromatic urethane type protecting groups (e.g. benzyloxycarbonyl (Cbz) and substituted Cbz and 9-fluorenylmethoxycarbonyl (Fmoc)), aliphatic urethane protecting groups (e.g. methoxycarbonyl, ethoxycarbonyl, t-butyloxycarbonyl (Boc), isopropyloxycarbonyl and cyclohexyloxycarbonyl) and alkyl type protecting groups (e.g. benzyl, trityl, chlorotrityl).

The term "aryl" refers to a monovalent aromatic hydrocarbon group derived by the removal of one hydrogen atom from a single carbon atom of a parent aromatic ring system. In particular aryl refers to an aromatic ring structure, monocyclic or poly-cyclic that includes the number of ring members specified. Specifically, the term includes groups that have from 6 to 10 ring members. Where the aryl group is a monocyclic ring system it preferentially contains 6 carbon atoms. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, tetrahydronaphthalene and trinaphthalene. Particularly aryl groups include phenyl, naphthyl, indenyl, and tetrahydronaphthyl. More particular arly group is phenyl.

The term "carboxy" refers to the radical —C(O)OH.

The term "carbamoyl" or "amido" refers to the radical —C(O)$NH_2$.

The term "comprise", and variations such as "comprises" and "comprising", throughout the specification and the claims which follow, unless the context requires otherwise, will be understood to imply the inclusion of a stated integer or step or group of integers but not to the exclusion of any other integer or step or group of integers or steps.

The term "compound(s) of the invention" or "compound (s) according to the invention", and equivalent expressions refers to compounds of Formulae (I), and (III) (whether in solvated or unsolvated form), as herein described, including any subset or embodiment of compounds of Formulae (I) and (III) or their salts (whether in solvated or unsolvated form). In particular preferred subset, said expression refers to compounds of Formula (I) or their salts (whether in solvated or unsolvated form). Suitably, said expression includes the pharmaceutically acceptable salts, and solvates (e.g. hydrates) thereof. The compound(s) of the invention may possess one or more asymmetric centers; such compounds can therefore be produced as individual (R)- or (S)-stereoisomers or as mixtures thereof. Where stereochemistry is not defined in the relevant Formula(e), then the term compound(s) of the invention includes enantiomers and diastereoisomers of these compounds.

The term "cyano" as used herein, refers to the radical —CN.

The term "cycloalkyl" as used herein, refers to a monocyclic or polycyclic saturated hydrocarbon ring containing the stated number of carbon atoms, for example, 3 to 7 carbon atoms. Particular "cycloalkyl" groups are monocyclic. Examples of "cycloalkyl" groups include cyclopropyl, cyclobutyl, cyclopentyl, cyclohexyl, cycloheptyl and bicyclo[2.2.1]heptyl. Particular cycloalkyl groups include cyclopentyl and cyclohexyl. More particular cycloalkyl group is cyclohexyl.

The term "cycloalkenyl" as used herein, refers to a monocyclic hydrocarbon ring containing the stated number of carbon atoms, for example, 3 to 7 carbon atoms, and at least one double bond. Examples of "cycloalkenyl" groups include cyclopropenyl, cyclobutenyl, cyclopentenyl, cyclohexenyl and cycloheptenyl. Particular cycloalkenyl groups include cyclopentenyl and cyclohexenyl. More particular cycloalkenyl group is cyclohexenyl.

The term "halogen" or 'halo' refers to fluoro (F), chloro (Cl), bromo (Br) and iodo (I). Particular halo groups are either fluoro or chloro. More particular halo group is fluoro.

The term "hetero" when used to describe a compound or a group present on a compound means that one or more carbon atoms in the compound or group have been replaced by a nitrogen, oxygen, or sulfur heteroatom. For example, having from 1 to 4 heteroatoms, particularly from 1 to 3 heteroatoms, and more typically 1 or 2 heteroatoms, for example a single heteroatom.

The term "heteroaryl" means an aromatic ring structure, mono-cyclic or polycyclic, that includes one or more heteroatoms independently selected from O, N and S and the number of ring members specified. Particular heteroaryl groups have a five membered or six membered monocyclic ring. The heteroaryl ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, pyrazole, triazole, thiadiazole and tetrazole groups. Examples of six membered monocyclic heteroaryl groups include but are not limited to pyridine, pyrazine, pyridazine, pyrimidine, triazine and tetrazine. Examples of fused heteroaryl rings include, quinolinyl, isoquinolinyl, quinazolinyl, quinoxalinyl, pteridinyl, cinnolinyl, phthalazinyl, naphthyridinyl, indolyl, isoindolyl, azaindolyl, indolizinyl, indazolyl, purinyl, pyrrolopyridinyl, furopyridinyl, benzofuranyl, isobenzofuranyl, benzothienyl, benzoimidazolyl, benzoxazolyl, benzoisoxazolyl, benzothiazolyl, benzoisothiazolyl, benzoxadiazolyl, benzothiadiazolyl, and the like. Particular heteroaryl groups are those derived from thiophene, pyrrole, furan, pyrazole, imidazole, triazole, thiazole, pyridine, and pyrazine.

The term "heterocyclic" as used herein, refers to a non-aromatic 3-, 4-, 5-, 6- or 7-membered ring or a bi-cyclic group fused system, where (i) each ring contains between one and three heteroatoms independently selected from oxygen, sulfur and nitrogen, (ii) each 3-, 4- or 5-membered ring has 0 to 1 double bonds and each 6- or 7-membered ring has 0 to 2 double bonds, (iii) the nitrogen and sulfur heteroatoms may optionally be oxidized, (iv) the nitrogen heteroatom may optionally be quaternized, and (iv) the remaining ring atoms are carbon atoms which may be optionally oxo-substituted. Representative heterocycloalkyl groups include, but are not limited to, oxiranyl, oxirenyl, azepanyl, aziridinyl, azirenyl, thiiranyl, thiirenyl, oxaziridenyl, dioxolanyl, dioxanyl, diazirinyl, dihydrofuranyl, oxaziridinyl, azetidinyl, azetyl, oxetanyl, oxetyl, oxathiolanyl, oxathianyl, thietanyl, thietyl, diazetidinyl, diazepanyl, dioxetanyl, dihydropyranyl, dioxetyl, dithietanyl, dithietyl, pyrrolidinyl, pyrazolinyl, pyrazolidinyl, imidazolinyl, imidazolidinyl, piperidinyl, piperazinyl, pyranyl, oxazolidinyl, isoxazolidinyl, morpholinyl, thiazolidinyl, isothiazolidinyl, quinoxalinyl, pyridazinonyl, tetrahydrofury, tetrahydropyranyl, tetrahydrothiophenyl, tetrahydropyrimidinyl, thiolanyl, thiomorpholinyl, azepanyl, oxepanyl, and thiepanyl. Examples of such bicyclic rings include indolinyl, isoindolinyl, benzodioxolyl, benzopyranyl, quinuclindinyl, 2,3,4,5-tetrahydro-1H-3-benzazepine, tetrahydroisoquinolinyl and a like. Particular "heterocyclic" groups are monocyclic. Particular heterocyclic groups include pyrrolidinyl, piperidinyl, piperazinyl, tetrahydropyranyl, morpholinyl and azetidinyl.

As used herein, the term "heterocycloalkyl" refers to a stable non-aromatic ring structure, mono-cyclic or polycyclic, containing one or more heteroatoms, particularly one or two heteroatoms independently selected from N, O and S and the number of ring atoms specified. The heterocycloalkyl ring structure may have from 3 to 7 ring members. A fused heterocyclic ring system may include carbocyclic rings and need only include one heterocyclic ring. Examples of heterocyclic rings include morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone (2-pyrrolidone or 3-pyrrolidone), tetrahydrofuran, tetrahydrothiophene, dioxane, tetrahydropyran (e.g. 4-tetrahydro pyranyl), imidazolidinone, pyrazolidine, piperazine, and N-alkyl piperazines such as N-methyl piperazine and the like. Further examples include thiomorpholine and its S-oxide and S,S-dioxide (particularly thiomorpholine). Still further examples include azetidine, piperidone, piperazone, and N-alkyl piperidines such as N-methyl piperidine. Particular "heterocycloalkyl" groups are monocyclic. Particular heterocycloalkyl groups include pyrrolidinyl, piperidinyl, piperazinyl, tetrahydropyranyl, morpholinyl and azetidinyl.

As used herein, the term "heterocycloalkenyl" refers to a stable non-aromatic ring structure, mono-cyclic or polycyclic, containing one or more heteroatoms, particularly one or two heteroatoms independently selected from N, O and S, and the number of ring atoms specified, and further containing at least one carbon-carbon double bonds or carbon-heteroatom double bonds in the ring as long as the ring is not rendered aromatic by their presence. The heterocycloalkenyl structure may have from 3 to 7 ring members. A fused heterocycloalkenyl ring system may include carbocyclic rings and need only include one heterocycloalkenyl ring. Examples of heterocyclic rings include pyran (2H-pyran or 4H-pyran), dihydrothiophene, dihydropyran, dihydrofuran (2,3-dihydrofuran or 2,5-dihydrofuran), dihydrothiopyran, dihydrothiazole, imidazoline (2-imidazoline, 3-imidazoline, and 4-imidazoline), oxazoline, thiazoline, 2-pyrazoline, tetrahydropyridine, and the like. Still further examples include N-alkyl tetrahydropyridine such as N-methyl tetrahydropyridine.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

The term "hydroxy" or "hydroxyl" refers to the radical —OH.

The term "hydroxy protecting group" refers to a substituent on an functional hydroxyl group which prevent undesired reactions and degradations during synthetic procedures, and which may be selectively removed after certain synthetic step. Examples of 'hydroxy protecting group' include: ester and ether hydroxyl protecting group. Examples of ester hydroxyl protecting group include: formyl, —OC(O)$C_{1-4}$alkyl such as acetyl (Ac or —C(O)CH$_3$), methoxyacetyl, chloroacetyl, dichloroacetyl, trichloroacety, trifluoroacetyl, triphenylmethoxyacetyl, phenoxyacetyl, benzoylformyl, benzoyl (Bz or —C(O)C$_6$H$_5$), benzyloxycarbonyl (Cbz or —C(O)—O—CH$_2$C$_6$H$_5$), methoxycarbonyl, tert-butoxycarbonyl, isopropoxycarbonyl, diphenylmethoxycarbonyl or 2-(trimethylsilyl)ethoxycarbonyl and the like. Examples of ether hydroxyl protecting group include: alkyl silyl groups such as trimethylsilyl (TMS), tert-butyldimethylsilyl, triethylsilyl, triisopropylsilyl and the like. Examples of suitable "hydroxy protecting group" include; —OC(O)C$_{1-4}$ alkyl such as acetyl (Ac or —C(O)CH$_3$), benzoyl (Bz), benzyloxycarbonyl (Cbz) and trimethylsilyl (TMS). Suitably, "hydroxy protecting group" is: triethylsilyl or acetyl (Ac or —C(O)CH$_3$). Conveniently, "hydroxy protecting group" is: Ac or Cbz.

The term "intermediates(s) of the invention" or "intermediate(s) according to the invention", and equivalent expressions refers to compounds of Formula (II) (whether in solvated or unsolvated form), as herein described, including any subset or embodiment of compounds of Formula (II). In particular preferred subset, said expression refers to compounds of Formula (II-X), or their salts (whether in solvated or unsolvated form). Suitably, said expression includes the salts, and solvates (e.g. hydrates) thereof. The term intermediates(s) of the invention" or "intermediate(s) according to the invention", and equivalent expressions also refers to compounds resulting from reaction of compound of formula (I) and $X^{1m}$—$W^m$—$X^{2m}$ (whether in solvated or unsolvated form), as herein described, including any subset or embodiment thereof, and which are used in the process for preparation of compound of formula (III) (also referred herein and below as "precursor(s) of the invention" or "precursor(s) for compound of formula (III)". The intermediate(s) of the invention may possess one or more asymmetric centers; such intermediate(s) can therefore be produced as individual (R)- or (S)-stereoisomers or as mixtures thereof. Where stereochemistry is not defined in the relevant Formula(e), then the term intermediate(s) of the invention includes enantiomers and diastereoisomers of these compounds.

The term "inert solvent" or "solvent inert to the reaction", as used herein, refers to a solvent that cannot react with the dissolved compounds including non-polar solvent such as hexane, toluene, diethyl ether, diisopropylether, chloroform, ethyl acetate, THF, dichloromethane; polar aprotic solvents such as acetonitrile, acetone, N, N-dimethylformamide, N,N-dimethylacetamide, dimethyl sulfoxide, pyridine, and polar protic solvents such as lower alcohol, acetic acid, formic acid and water.

The term "lower alcohol", as used herein, refers to a $C_{1-4}$alcohol, such as for example, methanol, ethanol, propanol, isopropanol, butanol, t-butanol, and the like.

The term "substituted" refers to a group in which one or more hydrogen atoms are each independently replaced with the same or different substituent(s).

As used herein, the term "substituted with one or more" refers to one to four substituents. In one embodiment it refers to one to three substituents. In further embodiment it refers to one or two substituents. In a yet further embodiment it refers to one substituent.

The term "western portion" or "western fragment", as used herein, refers to fragment W or to its precursor $W^m$, wherein W is as defined for formula (III) and $W^m$ is fragment W or can be easily convertable to W. In one embodiment the term refers to bivalent radical $X^1$—W—$X^2$— of formula (III) or to its precursor of formula $X^{1m}$—$W^m$—$X^{2m}$, wherein $X^{1m}$ and $X^{2m}$ are the appropriate reactive or leaving groups or groups convertable to $X^1$ and $X^2$ as defined for formula (III), and $W^m$ is W or the appropriate precursor convertable to W wherein W is as defined for formula (III).

The term "pharmaceutically acceptable", as used herein, refers to salts, molecular entities and other ingredients of compositions that are generally physiologically tolerable and do not typically produce untoward reactions when administered to a mammal (e.g., human). Suitably, as used herein, the term "pharmaceutically acceptable" means approved by a regulatory agency of the Federal or a state government or the corresponding agency in countries other than the United States or listed in the U.S. Pharmacopoeia or other generally recognized pharmacopoeia for use in mammals, and more particularly in humans.

"Pharmaceutically acceptable salt" refers to a salt of a compound that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term 'pharmaceutically acceptable cation' refers to an acceptable cationic counterion of an acidic functional group. Such cations are exemplified by sodium, potassium, calcium, magnesium, ammonium, tetraalkylammonium cations, and the like.

The term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates. "Pharmaceutically acceptable vehicle" refers to a diluent, adjuvant, excipient or carrier with which a compound of the invention is administered.

The term "carrier" refers to a diluent, excipient, and/or vehicle with which an active compound is administered. The pharmaceutical compositions of the invention may contain combinations of more than one carrier. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition. The choice of pharmaceutical carrier can be selected with regard to the intended route of administration and standard pharmaceutical practice. The pharmaceutical compositions may comprise as, in addition to, the carrier any suitable binder(s), lubricant(s), suspending agent(s), coating agent(s), and/or solubilizing agent(s). The term "prodrug" or "pharmaceutically acceptable prodrug" as used herein refers to compounds, including derivatives of the compounds of the invention, which have metabolically cleavable groups and are converted within the body e.g. by solvolysis or under physiological conditions into the compounds of the invention which are pharmaceutically active in vivo. Pharmaceutically acceptable prodrugs are described in: Bundgard, H. Design of Prodrugs, pp. 7-9, 21-24, Elsevier, Amsterdam 1985, T. Higuchi and V. Stella, "Prodrugs as Novel Delivery Systems", Vol. 14 of the A.C.S. Symposium Series; Edward B. Roche, ed., "Bioreversible Carriers in Drug Design", American Pharmaceutical Association and Pergamon Press, 1987; and in D. Fleisher, S. Ramon and H. Barbra "Improved oral drug delivery: solubility limitations overcome by the use of prodrugs", Advanced Drug Delivery Reviews (1996) 19(2) 115-130. Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy) alkyl esters or ((alkoxycarbonyl)oxy)alkylesters. Particularly useful are the $C_1$-$C_8$ alkyl, $C_2$-$C_8$ alkenyl, aryl and arylalkyl esters of the compounds of the invention.

The term "solvate" refers to forms of the compound that are associated with a solvent, usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

The term "isotopic variant" refers to a compound that contains unnatural proportions of isotopes at one or more of the atoms that constitute such compound For example, an 'isotopic variant' of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy. All isotopic variants of the compounds provided herein, radioactive or not, are intended to be encompassed within the scope of the invention.

The term "isomer(s)" refers to compounds that have the same molecular formula but differ in the nature or sequence of bonding of their atoms or the arrangement of their atoms in space. Isomers that differ in the arrangement of their atoms in space are termed "stereoisomers".

"Diastereomers" are stereoisomers that are not mirror images of one another and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

The term "subject" refers to an animal, in particular a mammal and more particular to a human or a domestic animal serving as a model for a disease (for example guinea pigs, mice, rats, gerbils, fish, birds, cats, rabbits, dogs, horses, cows, monkeys, chimpanzees or like). Specifically the subject is a human. The terms "patient" and "subject" are used interchangeably herein.

"Effective amount" means the amount of a compound that, when administered to a subject for the prophylaxis or treatment of a disease and/or condition, is sufficient to effect such prophylaxis or such treatment for the disease and/or condition. The "effective amount" can vary depending on the compound, the disease and/or condition and its severity, and the age, weight, etc., of the subject.

"Preventing" or "prevention" refers to a reduction in risk of acquiring or developing a disease and/or condition (i.e., causing at least one of the clinical symptoms of the disease and/or condition not to develop in a subject that may be exposed to a disease and/or condition-causing agent, or predisposed to the disease and/or condition in advance of disease and/or condition onset).

The term "prophylaxis" is related to "prevention", and refers to a measure or procedure the purpose of which is to prevent, rather than to treat or cure a disease.

"Treating" or "treatment" of any disease and/or condition refers, in one embodiment, to ameliorating the disease and/or condition (i.e., arresting the disease or reducing the manifestation, extent or severity of at least one of the clinical symptoms thereof). In another embodiment "treating" or "treatment" refers to ameliorating at least one physical parameter, which may not be discernible by the subject. In yet another embodiment, "treating" or "treatment" refers to modulating the disease and/or condition, either physically, (e.g., stabilization of a discernible symptom), physiologically, (e.g., stabilization of a physical parameter), or both. In a further embodiment, "treating" or "treatment" relates to slowing the progression of the disease and/or condition.

"Maintenance therapy" refers to a preventive therapy that follows successful initial treatment of the acute phase of the illness where regular (usually smaller) doses of the drug are delivered to the patient to prevent recurrence and worsening of the disease.

"Inflammation" as used herein refers to a localized, protective response elicited by injury or destruction of tissues, which serves to destroy, dilute, or wall off (sequester) both the injurious agent and the injured tissue. Inflammation is characterized by activation of the immune system with recruitment and activation of inflammatory cells and production of pro-inflammatory mediators. Most inflammatory diseases are characterized by enhanced accumulation of differing proportions of inflammatory cells, including monocytes/macrophages, granulocytes, plasma cells, lymphocytes and platelets. Along with tissue endothelial cells and fibroblasts, these inflammatory cells release a complex array of lipids, growth factors, cytokines and destructive enzymes that cause local tissue damage. Inflammation can result from infection with pathogenic organisms and viruses and from noninfectious means such as trauma or reperfusion following myocardial infarction or stroke, immune response to foreign antigen, and autoimmune responses. As used herein the term "condition(s) involving inflammation or immune responses" refers to the group of conditions including rheumatoid arthritis, osteoarthritis, juvenile idiopathic arthritis, acute gout, psoriasis, psoriatic arthritis, allergic airway disease (e.g. asthma, or rhinitis), inflammatory bowel diseases (Crohn's disease or ulcerative colitis), chronic obstructive pulmonary disease (COPD), cystic fibrosis (CF), diffuse panbronchiolitis (DPB), bronchiolitis obliterans (BOS), bronchitis, bronchiectasis, adult respiratory distress syndrome (ARDS), severe or steroid-resistant asthma, emphysema, chronic rhinosinusitis (with or without nasal polyposis), rheumatoid arthritis, gouty arthritis, inflammatory bowel disease (ulcerative colitis and Crohn's disease), glomerulonephritis, damage from ischemic reperfusion, atherosclerosis, dermatoses such as psoriasis and vasculitis, systemic lupus erythematosus (SLE), systemic inflammatory response syndrome (SIRS), sepsis, ischemia-reperfusion injury, rosacea, periodontitis, gingival hyperplasia and prostatitis syndrome. endotoxin-driven disease states (e.g. complications after bypass surgery or chronic endotoxin states contributing to e.g. chronic cardiac failure), septic shock, pneumonitis, myocarditis, pericarditis, myositis, dermatitis, nephritis, vasculitis, retinitis, uveitis, scleritis, pancreatitis, primary biliary cirrhosis, hypophysitis, thyroiditis, sclerosing cholangitis, giant cell arteritis, nephritis including lupus nephritis, vasculitis with organ involvement such as glomerulonephritis, vasculitis including giant cell arteritis, Polyarteritis nodosa, Behcet's disease, Kawasaki disease, Takayasu's Arteritis, graft-versus-host disease (acute rejection of transplanted organs) and related diseases involving cartilage, such as that of the joints. Particularly the term refers to COPD, CF, diffuse panbronchiolitis, bronchiolitis obliterans, bronchitis, bronchiectasis, adult respiratory distress syndrome, severe or steroid-resistant asthma, emphysema and chronic rhinosinusitis (with or without nasal polyposis), psoriasis, rheumatoid arthritis, osteoarthritis, and inflammatory bowel diseases. More particularly, the term relates to chronic obstructive pulmonary disease, cystic fibrosis, diffuse panbronchiolitis, bronchiolitis obliterans, bronchitis, bronchiectasis, adult respiratory distress syndrome, severe asthma and emphysema.

As used herein the term "autoimmune disease(s)" refers to any group of disorders in which tissue injury is associated with humoral or cell-mediated responses to the body's own constituents including systemic lupus erythematosus (SLE), cutaneous lupus erythematosus (CLE), lupus nephritis, multiple sclerosis, diabetes (for example type I diabetes mellitus) and complications associated therewith, atopic eczema (atopic dermatitis), inflammatory bowel diseases (e.g. Crohn's disease or ulcerative colitis), alopecia areata, vitiligo, bullous skin diseases, Alzheimer's disease, depression, Wegener's granulomatosis, Addison's disease, Sjogren syndrome, and amyotrophic lateral sclerosis. Particularly the term refers to SLE, multiple sclerosis, diabetes (for example type I diabetes mellitus), Sjogren syndrome, and inflammatory bowel diseases. More specifically, the term relates to diabetes (for example type I diabetes mellitus) and SLE.

The term "amidation" used herein refers to a chemical process of formal union of carboxylic acids and amines and formation of amide functionality. It is necessary to first activate the carboxylic acid, in a process that usually takes place by converting the OH of the acid into a good leaving group prior to treatment with the amine in the presence of a base. Suitable methods for activation of carboxylic groups are, but not limited to, formation of acyl halides, acyl azides, mixed anhydrides, activated esters and the like. Acyl halides may be prepared in nonprotic solvents treating the carboxylic acid with halide sources like, but not limited to, thionyl chloride, oxalyl chloride, phosphorus pentachloride, triphosgene, cyanuric fluoride, cyanuric chloride, BoP-Cl, PyBroP and the like. Mixed anhydrides may be prepared in nonprotic solvents with reagents like, but not limited to, pivalyl chloride, EEDQ and the like. Suitable coupling reagents used in the process of amidation via active esters are, but not limited to, carbodiimides like DCC, DIC, EDAC, uronim salts like HATU, TATU, HBTU, TBTU, TDBTU, phosphonium salts like PyBoP, BoP, DEPBT. These coupling reagents can be used as stand-alone activators or in the presence of additives like, but not limited to, HOAt, HOBt and the like. Other suitable amidation coupling reagents that operate on different mechanism of carboxylic group activation are, but not limited to, DPPA, T3P®, CDI, Mukaiyama reagent and the like. Activation can also be performed by using solid supported versions of the abovementioned coupling reagents like, but not limited to, PS-CDI, PS-EDC, PS-BoP and the like. Suitable bases used in amidation process are, but not limited to, sodium hydrocarbonate, potassium hydrocarbonate, sodium carbonate, potassium carbonate, TEA, DIPEA, DBU, DBN, DABCO and the like. A more thorough discussion of amidation can be found in Valeur, E., et al. Chem. Soc. Rev. (2009), 38, 606.

The term "macrolactamization" used herein refers to specific amidation process in which ω-amino acids are turned to cyclic products called lactams. Process most often uses the same conditions and chemical reagents as amidation described above.

The term "esterification" used herein refers to a chemical process of formal union of carboxylic acids and alcohols and formation of ester functionality. Suitable methods for synthesis of esters are Fisher, Mitsunobu, Steglich conditions, transesterification, acylation with appropriate acyl halides, decarboxylative esterification, oxidative esterification and redox esterification. Acyl halides may be prepared in nonprotic solvents treating the carboxylic acid with halide sources like, but not limited to, thionyl chloride, oxalyl chloride, phosphorus pentachloride, triphosgene, fluoride, cyanuric chloride and the like. Suitable coupling reagents used in the process of esterification are, but not limited to, p-nitrophenylchloroformate, thiopyridyl chloroformate, 2,2'-(4-t-Bu-N-alkylimidazolyl)disulfide, Mukaiyama salts, 2,4,6-trichlorobenzoyl chloride, DEAD/PPh3, TFFH, DCC, TBTU, TATU, COMU and the like. Suitable bases used in esterification process are, but not limited to, sodium hydrocarbonate, potassium hydrocarbonate, sodium carbonate, potassium carbonate, TEA, DIPEA, DBU, DBN, DABCO and the like.

The term "macrolactonization" used herein refers to specific esterification process in which ω-hydroxy acids are turned to cyclic products called lactones. Process most often uses the same conditions and chemical reagents as esterification previously described.

The term "reductive alkylation" used herein refers to chemical process of conversion of a carbonyl group and an amine to higher substituted amine via an intermediate imine. The carbonyl group is most commonly a ketone or an aldehyde. The imine intermediate is reduced to the amine by various reducing agents including, but not limited to, sodium borohydride, sodium triacetoxyborohydride, sodium cyanoborohydride, zinc and hydrochloric acid, hydrogen and transition metal catalyst, formic acid and its organic or inorganic salts, iron pentacarbonyl. Generally alcoholic solvents are used. Preferred conditions are sodium cyanoborohydride in methanolic media in the presence of acetic acid.

The term "alkylation with alkyl halides" used herein refers to a chemical reaction between an alkyl halide, preferably iodide or bromide, and an amine. The reaction product is a higher substituted amine. Generally organic solvents are used as reaction media but aqueous conditions are also applied. Preferred conditions are alkyl bromides in acetonitrile in the presence of DIPEA at room temperature to reflux.

The term "Fragment Based Drug Design (FBDD)", "FBDD approach" or "FBDD method" used herein refers to the identification of initial fragments such as smaller pieces, or even discrete functional groups (i.e. "molecular anchors", "minimal recognition motifs", or "warheads") in interaction with the target macromolecule (e.g. protein (such as kinases, proteases, epigenetic targets, transmembrane proteins, GPCRs, and a like), DNA, RNA, enzymes and the like). The biophysical screening methods suitable for FBDD are for example nuclear magnetic resonance (NMR), surface plasmon resonance (SPR) and X-ray crystallography which provide rapid insight in binding affinities of examined fragments, contribute to understanding of structural features responsible of the ligand-target interactions which is crucial for identification and prioritization of fragment hits useful in the process of the present invention. Once obtained by FBDD approach, selected fragments can be further modified in order to be suitable for insertion into "western part" of the molecule and formation of macrolide based macrocycles of Formula (III) as well as their precursors. A more thorough discussion of FBDD can be found in P. J. Hajduk et al. Nature Rev. Drug Discovery (2007) 6, 211-219 and D. A. Erlanson et al. *J. of Med. Chem.* (2004) 47(14), 3463-3482.

The Compounds and Processes

The present invention relates to seco (opened ring) macrolide compound of Formula (I)

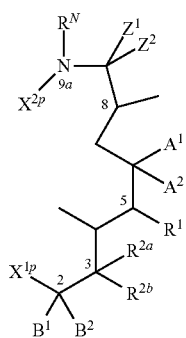

wherein,
$X^{1p}$ is

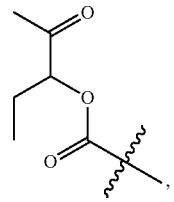 [SMILES: *C(=O)OC(CC)C(C)=O]

—C(=O)OH, C(=O)NH$_2$, —C(=S)NH$_2$, —C(=O)NHNH$_2$, —CH$_2$NH$_2$, —CH$_2$OH, —C(=O)H, —CN or NH$_2$;
$X^{2p}$ is hydrogen, CH(CH$_3$)C(=O)H, —C(=S)NH$_2$ or —C(=O)NH$_2$;
$Z^1$ and $Z^2$
(i) are both hydrogen, or
(ii) together with carbon atom to which they are attached form a keto group provided $R^N$ is hydrogen and $A^1$ is OC$_{1-6}$alkyl,
$A^1$ is OH, OC$_{1-6}$ alkyl, OC$_{2-6}$ alkenyl, OC$_{2-6}$ alkynyl, OR$^p$, or $A^1$ together with $R^{2b}$ forms cyclic hemiketal or ether;
$A^2$ is CH$_3$ or H;
$B^1$ and $B^2$ are independently H, C$_{1-6}$alkyl or halogen, or $B^2$ together with $R^{2a}$ forms a double bond;
$R^1$ is $S^1$, OH, OC$_{1-6}$alkyl or OR$^p$;
$S^1$ is sugar group of formula (b1):

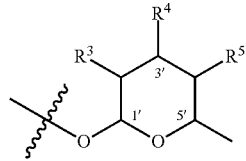

wherein,
$R^3$ is OH, H, OR$^p$, —O-L$^1$-G or —OC(=O)G, provided when $R^3$ is —O-L$^1$-G or —OC(=O)G group then $R^4$ is —N(CH$_3$)$_2$ and $R^5$ is H, wherein
$L^1$ —(CH$_2$)$_{a1}$—U$^1$—(CH$_2$)$_{b1}$—;
$U^1$ is —N(R$^6$)—, —NHC(=O)— or —C(=O)NH—;
$R^6$ is H or C$_{1-3}$alkyl;
$a^1$ is an integer from 2 to 6;
$b^1$ is an integer from 0 to 6;
G is selected from:
(i) G$^1$, wherein G$^1$ is C$_{1-8}$alkyl, wherein alkyl may be optionally interrupted by 1 to 3 bivalent radical groups selected from —O—, —S— and —N(R$^{g1}$)—, where R$^{g1}$ is H or C$_{1-6}$alkyl, and where alkyl may be optionally substituted by one or more groups independently selected from halogen, OH, keto, C$_{2-6}$alkenyl, C$_{2-6}$alkynyl, haloC$_{1-6}$ alkyl, haloC$_{1-6}$alkyloxy, —C(=O)OC$_{1-6}$ alkyl, NH$_2$, N—(O$_{1-6}$-alkyl)amino, N,N-di(C$_{1-6}$alkyl)amino; aryl or heteroaryl wherein said aryl and heteroaryl may be mono or biyclic and independently each may be optionally substituted by one or more groups independently selected from halogen, CN, OH, NO$_2$, OC$_{1-6}$ alkyl, NH$_2$, N—(C$_{1-6}$-alkyl)amino, N,N-di(C$_{1-6}$alkyl)amino, —C(=O)C$_{1-6}$ alkyl, —OC(=O)C$_{1-6}$ alkyl, —C(=O)OH, —C(=O)OC$_{1-6}$ alkyl, —C(=O)NHC$_{1-6}$ alkyl and —NHC(=O)C$_{1-6}$ alkyl;

(ii) G², wherein G² is 3-7 membered cycloalkyl which may be optionally substituted by one or more groups independently selected from OH, halogen, CN, NH₂, $C_{1-6}$ alkyl, $C_{2-6}$alkenyl, $C_{2-6}$alkynyl, halo$C_{1-6}$alkyloxy, —$C_{1-6}$alkyl-OH, —C(=O)$C_{1-6}$ alkyl, —C(=O)O$C_{1-6}$ alkyl, —C(=O)OH, —C(=O)NH₂, —$C_{0-6}$alkyl-aryl or $C_{0-6}$ alkyl-heteroaryl wherein aryl and heteroaryl independently from each other may be optionally substituted by one or more groups independently selected from halogen, CN, OH, NO₂, $C_{2-6}$alkenyl, $C_{2-6}$alkynyl, halo$C_{1-6}$alkyloxy, —$C_{1-6}$alkyl-OH, NH₂, N—(O$_{1-6}$-alkyl)amino, N,N-di($C_{1-6}$alkyl)amino, —C(=O)$C_{1-6}$ alkyl, —OC(=O)$C_{1-6}$ alkyl, —C(=O)OH, —C(=O)O$C_{1-6}$ alkyl, —C(=O)NH$C_{1-6}$ alkyl and —NHC(=O)$C_{1-6}$ alkyl;

(iii) G³, wherein G³ is 3-7 membered heterocycloalkyl containing one or two heteroatoms independently selected from N, O and S, where heterocycloalkyl may be optionally substituted by one or more groups independently selected from OH, halogen, CN, NH₂, $C_{1-6}$alkyl, $C_{2-6}$alkenyl, $C_{2-6}$ alkynyl, halo$C_{1-6}$alkyloxy, —C(=O)$C_{1-6}$ alkyl, —C(=O)O$C_{1-6}$ alkyl, —C(=O)OH and —C(=O)NH₂;

(iv) G⁴, wherein G⁴ is aryl wherein aryl may be optionally substituted by one or more groups independently selected from halogen, CN, OH, NO₂, $C_{1-6}$alkyl, $C_{2-6}$alkenyl, $C_{2-6}$alkynyl, halo$C_{1-6}$alkyloxy, —$C_{1-6}$ alkyl-OH, NH₂, N—($C_{1-6}$-alkyl)amino, N,N-di($C_{1-6}$alkyl)amino, —C(=O)$C_{1-6}$ alkyl, —O(C=O)$C_{1-6}$ alkyl, —C(=O)OH, —C(=O)O$C_{1-6}$ alkyl, —C(=O)NH$C_{1-6}$ alkyl and —NHC(=O)$C_{1-6}$ alkyl;

(v) G⁵, wherein G⁵ is heteroaryl wherein heteroaryl may be optionally substituted by one or more groups independently selected from halogen, CN, OH, NO₂, $C_{2-6}$alkenyl, $C_{2-6}$alkynyl, halo$C_{1-6}$alkyloxy, —$C_{1-6}$alkyl-OH, NH₂, N—(O$_{1-6}$-alkyl)amino, N,N-di($C_{1-6}$ alkyl)amino, —C(=O)$C_{1-6}$ alkyl, —O(C=O)$C_{1-6}$ alkyl, —C(=O)OH, —C(=O)O$C_{1-6}$ alkyl, —C(=O)NH$C_{1-6}$ alkyl and —NHC(=O)$C_{1-6}$ alkyl;

R⁴ is —N(R⁷)R⁸, wherein
R⁷ is CH₃,
R⁸ is $C_{1-6}$alkyl, H, —C(=O)R⁹ or R^p wherein R⁹ is $C_{1-6}$alkyl or H;
R⁵ is hydrogen;
or both R⁴ and R⁵ are hydrogen or together form a bond;
or S¹ is sugar group of formula (b2):

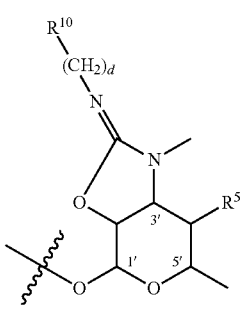

(b2)

wherein:
R⁵ is H;
d is an integer from zero to 3;
R¹⁰ is $C_{1-4}$alkyl;

R²ᵃ is:
(i) S²;
(ii) —OH;
(iii)
(iv) H;
(v) together with R²ᵇ forms a keto group (=O);
(vi) together with B² forms a double bond;
(vii) —OC(=O)Y¹, wherein Y¹ is G¹, G², G³, G⁴, G⁵ or H; or
(viii) —OR^p;

R²ᵇ is H, together with R²ᵃ forms a keto group, together with A¹ forms cyclic hemiketal and R²ᵃ is OH, or together with A¹ forms cyclic ether group and R²ᵃ is H;

S² is sugar group of formula (d)

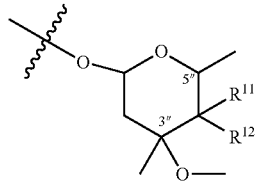

(d)

wherein,
R¹¹ is:
(i) H;
(ii) together with R¹² and carbon atom to which they are attached forms a keto or epoxy group;
(iii) one of R¹¹ and R¹² is OH and the other is CH₂N(R¹³)R¹⁴, wherein one of R¹³ and R¹⁴ is $C_{1-6}$alkyl and the other is H, G¹, G², G³, G⁴, G⁵ or R^p, or wherein R¹³ and R¹⁴ taken together with the nitrogen atom to which they are attached form a non-aromatic heterocyclic ring containing between 2 and 6 carbon atoms which is:
  a. saturated or unsaturated and contains zero or 1 additional heteroatom selected from O, S and N; and/or
  b. unsubstituted or substituted by from 1 to 2 groups selected from $C_{1-5}$alkanoyl; $C_{1-6}$alkyl wherein alkyl is uninterrupted or is interrupted by 1-3 bivalent radical groups selected from —O—, —S— and N(R¹⁸)—, and/or wherein $C_{1-6}$alkyl is unsubstituted or substituted by from 1 to 2 groups selected from OH, NH₂, a non-aromatic heterocyclic ring containing between 2 and 6 carbon atoms which is unsubstituted or is substituted by a group selected from $C_{1-4}$alkyl, halogen, NH₂, OH, SH, $C_{1-6}$ alkoxy and $C_{1-4}$hydroxyalkyl, and $C_{3-7}$cycloalkyl which is unsubstituted or is substituted by a group selected from $C_{1-4}$alkyl, halogen, NH₂, OH, SH, $C_{1-6}$ alkoxy, $C_{1-4}$hydroxyalkyl; and $C_{1-4}$dialkylamino;

R¹² is:
(i) OH,
(ii) together with R¹¹ and carbon atom to which they are attached forms a keto or epoxy group;
(iii) —OC(=O)Y³, wherein Y³ is H, G¹, G², G³, G⁴, or G⁵; or
(iv) OR^p;

R^N is hydrogen, G¹ (preferably CH³), G², G³, G⁴, G⁵, R^p, or R¹⁵ wherein R¹⁵ is —C(=O)G, —C(=O)NH—$C_{0-4}$alkyl-G, wherein G is G¹, G², G³, G⁴ or G⁵;

R^p is a protective group;
or a salt or solvate thereof.

In one embodiment, the present invention relates to seco macrolide compound of Formula (I), wherein $X^{1p}$ is

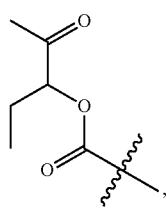

—C(=O)OH, C(=O)NH$_2$, —C(=S)NH$_2$, —C(=O)NHNH$_2$, —CH$_2$NH$_2$, —CH$_2$OH, —C(=O)H, —CN or NH$_2$, and $X^{2p}$ is hydrogen, CH(CH$_3$)C(=O)H, —C(=S)NH$_2$ or —C(=O)NH$_2$.

In another embodiment, the invention relates to a compound of formula (I), wherein:

(a) $X^{2p}$ is hydrogen, $X^{1p}$ is

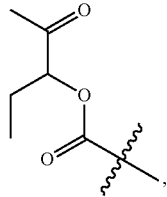

—C(=O)OH, C(=O)NH$_2$, —C(=S)NH$_2$, —C(=O)NHNH$_2$, —CH$_2$NH$_2$, —CH$_2$OH, —C(=O)H, —CN or NH$_2$;

(b) $X^{2p}$ is —C(=S)NH$_2$ or —C(=O)NH$_2$, $X^{1p}$ is —C(=O)OH; or (c) $X^{2p}$ is CH(CH$_3$)C(=O)H and $X^{1p}$ is

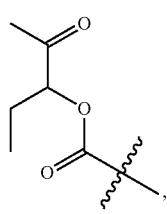 [SMILES: *C(=O)OC(CC)C(C)=O]

In a further embodiment, the invention relates to a compound of formula (I), wherein:

(a) $X^{2p}$ is hydrogen, $X^{1p}$ is

—C(=O)OH, C(=O)NH$_2$, —C(=S)NH$_2$, —C(=O)NHNH$_2$, —CH$_2$OH, —C(=O)H, —CN or NH$_2$; or (b) $X^{2p}$ is —C(=S)NH$_2$ or —C(=O)NH$_2$, $X^{1p}$ is —C(=O)OH.

In one further embodiment, the invention relates to a compound of formula (I), wherein:

(a) $X^{2p}$ is hydrogen, $X^{1p}$ is

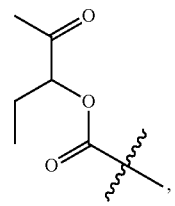

—C(=O)OH, C(=O)NH$_2$, —C(=O)NHNH$_2$, —CH$_2$NH$_2$ or —CH$_2$OH;

(b) $X^{2p}$ is —C(=S)NH$_2$ or —C(=O)NH$_2$, $X^{1p}$ is —C(=O)OH; or (c) $X^{2p}$ is CH(CH$_3$)C(=O)H and $X^1$ is

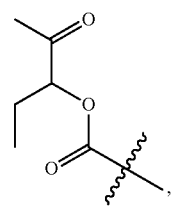 [SMILES: *C(=O)OC(CC)C(C)=O]

In even further embodiment, the invention relates to a compound of formula (I), wherein:

(a) $X^{2p}$ is hydrogen, $X^{1p}$ is

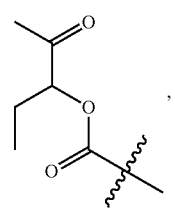 [SMILES: *C(=O)OC(CC)C(C)=O]

—C(=O)OH, C(=O)NH$_2$, —C(=O)NHNH$_2$, —CH$_2$NH$_2$ or —CH$_2$OH; or (b) $X^{2p}$ is —C(=S)NH$_2$ and $X^1$ is —C(=O)OH.

In another embodiment, the invention relates to a compound of formula (I), wherein:

(a) $X^{2p}$ is hydrogen, $X^{1p}$ is C(=O)NH$_2$, —C(=S)NH$_2$, —C(=O)NHNH$_2$, —CH$_2$NH$_2$, —CH$_2$OH, —C(=O)H, —CN or NH$_2$; or (b) $X^{2p}$ is —C(=S)NH$_2$ or —C(=O)NH$_2$, $X^{1p}$ is —C(=O)OH; or (c) $X^{2p}$ is CH(CH$_3$)C(=O)H and $X^1$ is

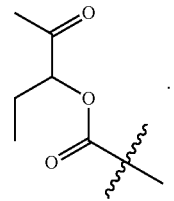 [SMILES: *C(=O)OC(CC)C(C)=O]

In a further embodiment, the invention relates to a compound of formula (I), wherein:

(a) $X^{2p}$ is hydrogen, $X^{1p}$ is C(=O)NH$_2$, —C(=S)NH$_2$, —C(=O)NHNH$_2$, —CH$_2$NH$_2$, —CH$_2$OH, —C(=O)H, —CN or NH$_2$; or (b) $X^{2p}$ is —C(=S)NH$_2$ or —C(=O)NH$_2$, $X^{1p}$ is —C(=O)OH.

In one further embodiment, the invention relates to a compound of formula (I), wherein:

(a) $X^{2p}$ is hydrogen, $X^{1p}$ is C(=O)NH$_2$, —C(=O)NHNH$_2$, —CH$_2$NH$_2$, —CH$_2$OH; or (b) $X^{2p}$ is —C(=S)NH$_2$ or —C(=O)NH$_2$, $X^{1p}$ is —C(=O)OH.

In another embodiment, the invention relates to a compound of formula (I), wherein $X^1$ is

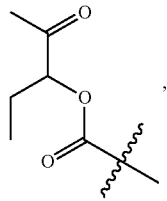 [SMILES: *C(=O)OC(CC)C(C)=O]

—C(=O)OH, C(=O)NH$_2$, —C(=S)NH$_2$, —C(=O)NHNH$_2$, —CH$_2$NH$_2$, —CH$_2$OH, —C(=O)H, —CN or NH$_2$, and $X^{2p}$ is hydrogen.

In another embodiment, the invention relates to a compound of formula (I), wherein $X^{1p}$ is

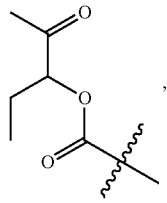 [SMILES: *C(=O)OC(CC)C(C)=O]

—C(=O)OH, C(=O)NH$_2$, —C(=O)NHNH$_2$, —CH$_2$NH$_2$ or —CH$_2$OH and $X^{2p}$ is hydrogen, CH(CH$_3$)C(=O)H, —C(=S)NH$_2$ or —C(=O)NH$_2$. In a further embodiment, the invention relates to a compound of formula (I), wherein $X^1$ is

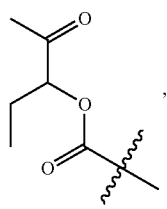

—C(=O)OH, C(=O)NH$_2$, —C(=O)NHNH$_2$, —CH$_2$NH$_2$ or —CH$_2$OH and $X^{2p}$ is hydrogen. In one further embodiment, the invention relates to a compound of formula (I), wherein $X^{1p}$ is

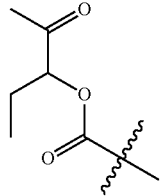 [SMILES: *C(=O)OC(CC)C(C)=O]

or —C(=O)OH and $X^{2p}$ is hydrogen.

In another embodiment, the invention relates to a compound of formula (I), wherein $X^{1p}$ is —C(=O)NH$_2$, —C(=S)NH$_2$, —C(=O)NHNH$_2$, —CH$_2$NH$_2$, —CH$_2$OH, —C(=O)H, —CN or —NH$_2$ and $X^{2p}$ is hydrogen, —C(=S)NH$_2$, or —C(=O)NH$_2$. In a further embodiment, the invention relates to a compound of formula (I), wherein $X^{1p}$ is —C(=O)NH$_2$, —C(=S)NH$_2$, —C(=O)NHNH$_2$, —CH$_2$NH$_2$, —CH$_2$OH, —C(=O)H, —CN or —NH$_2$ and $X^{2p}$ is hydrogen; or $X^{1p}$ is —COOH and $X^{2p}$ is —C(=S)NH$_2$ or —C(=O)NH$_2$. In one further embodiment, the invention relates to a compound of formula (I), wherein $X^{1p}$ is —C(=O)NH$_2$, —C(=O)NHNH$_2$, —CH$_2$NH$_2$ or —CH$_2$OH, and $X^{2p}$ is hydrogen; or $X^{1p}$ is —COOH and $X^{2p}$ is —C(=S)NH$_2$ or —C(=O)NH$_2$.

In another embodiment, the invention relates to compound of formula (I), wherein $X^1$ is —COOH and $X^{2p}$ is —C(=S)NH$_2$ or —C(=O)NH$_2$.

In another embodiment, the present invention relates to a compound of formula (I), wherein $X^{1p}$ is

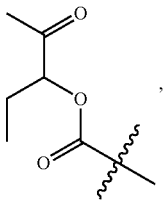 [SMILES: *C(=O)OC(CC)C(C)=O]

—C(=O)OH, —C(=O)NH$_2$, —C(=S)NH$_2$, —C(=O)NHNH$_2$, —CH$_2$NH$_2$, —CH$_2$OH, —C(=O)H, —CN, or —NH$_2$, $X^{2p}$ is hydrogen, —C(=S)NH$_2$ or —C(=O)NH$_2$ and $Z^1$ and $Z^2$ are both hydrogen. In a further embodiment, the invention relates to a compound of formula (I), wherein $X^{1p}$ is

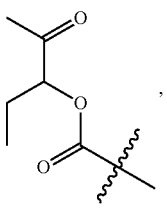 [SMILES: *C(=O)OC(CC)C(C)=O]

—C(=O)OH, —C(=O)NH$_2$, —C(=O)NHNH$_2$, —CH$_2$NH$_2$ or —CH$_2$OH, $X^{2p}$ is hydrogen or —C(=S)NH$_2$ and $Z^1$ and $Z^2$ are both hydrogen.

In another embodiment, the invention relates to a compound of formula (I), wherein $X^1$ is

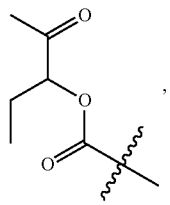

—C(=O)OH, —C(=O)NH$_2$, —C(=S)NH$_2$, —C(=O)NHNH$_2$, —CH$_2$NH$_2$, —CH$_2$OH, —C(=O)H, —CN, or —NH$_2$, $X^{2p}$ is hydrogen, —C(=S)NH$_2$ or —C(=O)NH$_2$, $Z^1$ and $Z^2$ are both hydrogen, and $R^N$ is $C_{1-6}$alkyl (preferably CH$_3$) or hydrogen. In a further embodiment, the invention relates to a compound of formula (I), wherein $X^{1p}$ is

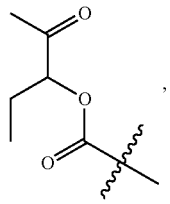 [SMILES: *C(=O)OC(CC)C(C)=O]

—C(=O)OH, C(=O)NH$_2$, —C(=O)NHNH$_2$, —CH$_2$NH$_2$ or —CH$_2$OH, $X^{2p}$ is hydrogen or —C(=S)NH$_2$, $Z^1$, $Z^2$ are both hydrogen, and $R^N$ is $C_{1-6}$alkyl (preferably CH$_3$) or hydrogen.

In another embodiment, the invention relates to a compound of formula (I), wherein:
(a) $X^{2p}$ is hydrogen, $X^{1p}$ is

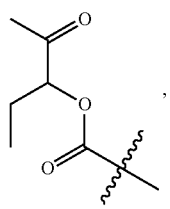

—C(=O)OH, C(=O)NH$_2$, —C(=S)NH$_2$, —C(=O)NHNH$_2$, —CH$_2$NH$_2$, —CH$_2$OH, —C(=O)H, —CN or NH$_2$; or
(b) $X^{2p}$ is —C(=S)NH$_2$ or —C(=O)NH$_2$, $X^{1p}$ is —C(=O)OH; and
$Z^1$ and $Z^2$ are both hydrogen. In a further embodiment, the invention relates to a compound of formula (I), wherein:

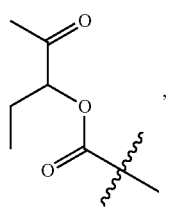

(a) $X^{2p}$ is hydrogen, $X^{1p}$ is —C(=O)OH, C(=O)NH$_2$, —C(=S)NH$_2$, —C(=O)NHNH$_2$, —CH$_2$NH$_2$, —CH$_2$OH, —C(=O)H, —CN or NH$_2$; or
(b) $X^{2p}$ is —C(=S)NH$_2$ or —C(=O)NH$_2$, $X^{1p}$ is —C(=O)OH;
$Z^1$ and $Z^2$ are both hydrogen, and $R^N$ is $C_{1-6}$alkyl (preferably CH$_3$) or hydrogen.

In another embodiment, the invention relates to a compound of formula (I), wherein: $X^{1p}$ is

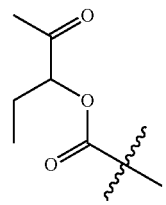 [SMILES: *C(=O)OC(CC)C(C)=O]

or —C(=O)OH, $X^{2p}$ is hydrogen, $Z^1$ and $Z^2$ are both hydrogen. In a further embodiment, the invention relates to a compound of formula (I), wherein: $X^{1p}$ is

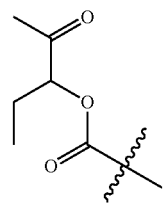

or —C(=O)OH, $X^{2p}$ is hydrogen, $Z^1$ and $Z^2$ are both hydrogen, and $R^N$ is $C_{1-6}$alkyl (preferably CH$_3$) or hydrogen.

In another embodiment, the present invention relates to a compound of formula (I), wherein $X^{1p}$ is

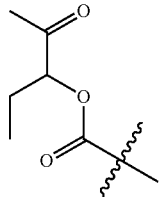 [SMILES: *C(=O)OC(CC)C(C)=O]

—C(=O)OH, C(=O)NH$_2$, —C(=S)NH$_2$, —C(=O)NHNH$_2$, —CH$_2$NH$_2$, —CH$_2$OH, —C(=O)H, —CN, or NH$_2$, $X^{2p}$ is CH(CH$_3$)C(=O)H, hydrogen, —C(=S)NH$_2$ or —C(=O)NH$_2$, $Z^1$ and $Z^2$ together with carbon atom to which they are attached form a keto group, $R^N$ is hydrogen and $A^1$ is —OC$_{1-6}$alkyl (preferably OCH$_3$). In a further embodiment, the invention relates to a compound of formula (I), wherein $X^{1p}$ is

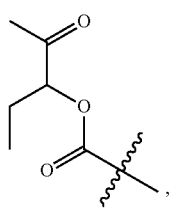 [SMILES: *C(=O)OC(CC)C(C)=O]
,

—C(=O)OH, C(=O)NH$_2$, —C(=O)NHNH$_2$, —CH$_2$NH$_2$ or —CH$_2$OH, X$^{2p}$ is CH(CH$_3$)C(=O)H, hydrogen or —C(=S)NH$_2$, Z$^1$ and Z$^2$ together with carbon atom to which they are attached form a keto group, R$^N$ is hydrogen and A$^1$ is —OC$_{1-6}$alkyl (preferably OCH$_3$).

In another embodiment, the invention relates to a compound of formula (I), wherein:

(a) X$^{2p}$ is CH(CH$_3$)C(=O)H, X$^{1p}$ is

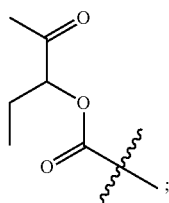 [SMILES: *C(=O)OC(CC)C(C)=O]
;

(b) X$^{2p}$ is hydrogen, X$^{1p}$ is —C(=O)OH, C(=O)NH$_2$, —C(=S)NH$_2$, —C(=O)NHNH$_2$, —CH$_2$NH$_2$, —CH$_2$OH, —C(=O)H, —CN or NH$_2$; or (c) X$^{2p}$ is —C(=S)NH$_2$ or —C(=O)NH$_2$, X$^{1p}$ is —C(=O)OH;

Z$^1$ and Z$^2$ together with carbon atom to which they are attached form a keto group, R$^N$ is hydrogen and A$^1$ is —OC$_{1-6}$alkyl (preferably OCH$_3$). In a further embodiment, the invention relates to a compound of formula (I), wherein:

(a) X$^{2p}$ is CH(CH$_3$)C(=O)H, X$^{1p}$ is

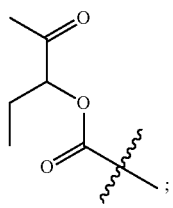 [SMILES: *C(=O)OC(CC)C(C)=O]
;

or (b) X$^{2p}$ is hydrogen, X$^{1p}$ is —C(=O)OH, C(=O)NH$_2$, —C(=S)NH$_2$, —C(=O)NHNH$_2$, —CH$_2$NH$_2$, —CH$_2$OH, —C(=O)H, —CN or NH$_2$;

Z$^1$ and Z$^2$ together with carbon atom to which they are attached form a keto group, R$^N$ is hydrogen and A$^1$ is —OC$_{1-6}$alkyl (preferably OCH$_3$). In one further embodiment, the invention relates to a compound of formula (I), wherein:

(a) X$^{2p}$ is CH(CH$_3$)C(=O)H, X$^{1p}$ is

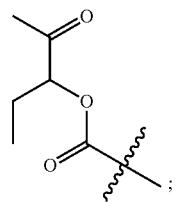 [SMILES: *C(=O)OC(CC)C(C)=O]
;

or (b) X$^{2p}$ is hydrogen, X$^{1p}$ is —C(=O)OH, C(=O)NH$_2$, —C(=O)NHNH$_2$, —CH$_2$NH$_2$, or —CH$_2$OH;

Z$^1$ and Z$^2$ together with carbon atom to which they are attached form a keto group, R$^N$ is hydrogen and A$^1$ is —OC$_{1-6}$alkyl (preferably OCH$_3$). In yet further embodiment, the invention relates to a compound of formula (I), wherein:

(a) X$^{2p}$ is CH(CH$_3$)C(=O)H, X$^{1p}$ is

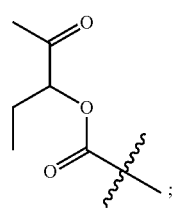 [SMILES: *C(=O)OC(CC)C(C)=O]
;

or (b) X$^{2p}$ is hydrogen, X$^{1p}$ is —C(=O)OH;

Z$^1$ and Z$^2$ together with carbon atom to which they are attached form a keto group, R$^N$ is hydrogen and A$^1$ is —OC$_{1-6}$alkyl (preferably OCH$_3$).

In another embodiment, the present invention relates to a compound of formula (I), wherein:

(a) X$^{1p}$ is

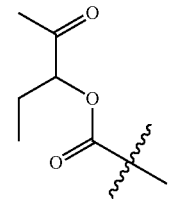 [SMILES: *C(=O)OC(CC)C(C)=O]

or —C(=O)OH, X$^{2p}$ is hydrogen, Z$^1$ and Z$^2$ are both hydrogen;

(b) X$^{1p}$ is

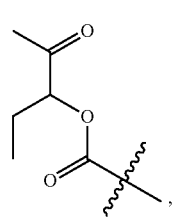 [SMILES: *C(=O)OC(CC)C(C)=O]
,

X$^{2p}$ is CH(CH$_3$)C(=O)H, Z$^1$ and Z$^2$ together with carbon atom to which they are attached form a keto group; or (c) $X^{1p}$ is —C(=O)OH, $X^{2p}$ is hydrogen, $Z^1$ and $Z^2$ together with carbon atom to which they are attached form a keto group.

In another embodiment, the invention relates to a compound of formula (I), wherein:

(a) $X^{1p}$ is

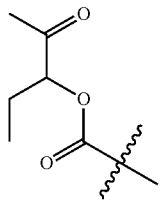 [SMILES: *C(=O)OC(CC)C(C)=O]

or —C(=O)OH, $X^{2p}$ is hydrogen, $Z^1$ and $Z^2$ are both hydrogen, $R^N$ is $C_{1-6}$ alkyl (preferably $CH_3$) or hydrogen;

(b) $X^{1p}$ is

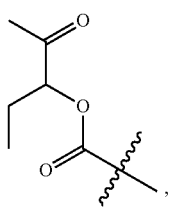 [SMILES: *C(=O)OC(CC)C(C)=O]

$X^{2p}$ is $CH(CH_3)C(=O)H$, $Z^1$ and $Z^2$ together with carbon atom to which they are attached form a keto group, $R^N$ is hydrogen and $A^1$ is —$OC_{1-6}$ alkyl (preferably $OCH_3$); or (c) $X^{1p}$ is —C(=O)OH, $X^{2p}$ is hydrogen, $Z^1$ and $Z^2$ together with carbon atom to which they are attached form a keto group, $R^N$ is hydrogen and $A^1$ is —$OC_{1-6}$ alkyl (preferably $OCH_3$).

In another embodiment, the invention relates to a compound of formula (I), wherein:

(a) $Z^1$ and $Z^2$ are both hydrogen, $R^N$ is $C_{1-6}$alkyl (preferably $CH_3$) or hydrogen, $A^1$ is OH or —$OC_{1-6}$ alkyl (preferably $OCH_3$), $X^{1p}$ is

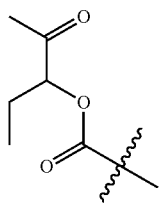 [SMILES: *C(=O)OC(CC)C(C)=O]

or —C(=O)OH and $X^{2p}$ is hydrogen; or (b) $Z^1$ and $Z^2$ together with carbon atom to which they are attached form a keto group, $R^N$ is hydrogen, $A^1$ is —$OC_{1-6}$alkyl (preferably $OCH_3$), $X^{1p}$ is

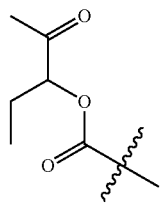 [SMILES: *C(=O)OC(CC)C(C)=O]

and $X^{2p}$ is —$CH(CH_3)C(=O)H$, or $X^{1p}$ is —C(=O)OH and $X^{2p}$ is hydrogen.

In one embodiment, seco macrolide compound of formula (I) is represented by formula (I-i):

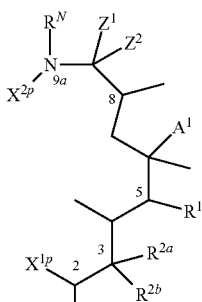

(I-i)

wherein, $X^{1p}$, $X^{2p}$, $R^N$, $Z^1$, $Z^2$, $A^1$, $R^1$, $R^{2a}$ and $R^{2b}$ are as defined in any particular embodiment. In a further embodiment, seco macrolide compound of formula (I) is represented by formula (I-ii):

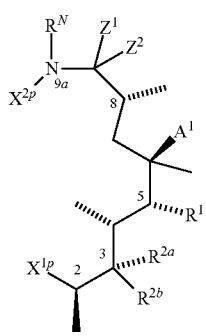

(I-ii)

wherein, $X^{1p}$, $X^{2p}$, $R^N$, $Z^1$, $Z^2$, $R^1$, $R^{2a}$ and $R^{2b}$ are as defined in any particular embodiment. In one further embodiment, seco macrolide compound of formula (I) is represented by formula (I-iii):

(I-iii)

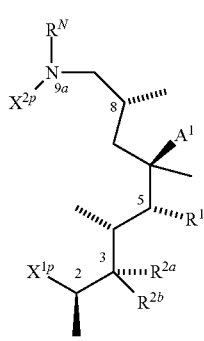

wherein, $X^{1p}$, $X^{2p}$, $R^N$, $A^1$, $R^1$, $R^{2a}$ and $R^{2b}$ are as defined in any particular embodiment. In one embodiment, the compound of formula (I) is represented by formula (I-i), wherein $A^1$ is OH, —O$C_{1-6}$alkyl (suitably OH or OCH$_3$) or OR$^p$; $R^1$ is S$^1$, OH, —O$C_{1-6}$alkyl, or OR$^p$; $R^{2a}$ is S$^2$, OH, H, or OR$^p$; $R^{2b}$ is H; $R^N$ is $C_{1-6}$alkyl (suitably CH$_3$) or H; $Z^1$ and $Z^2$ are both hydrogen; $X^{1p}$ is

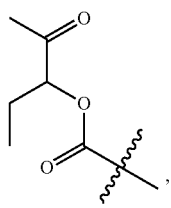 [SMILES: *C(=O)OC(CC)C(C)=O]

—C(=O)OH, C(=O)NH$_2$, —C(=S)NH$_2$, —C(=O)NHNH$_2$, —CH$_2$NH$_2$, —CH$_2$OH, —C(=O)H, —CN or NH$_2$; and $X^{2p}$ is hydrogen, —C(=S)NH$_2$ or C(=O)NH$_2$. In a further embodiment, the compound of formula (I) is represented by formula (I-i), wherein $A^1$ is OH, —O$C_{1-6}$alkyl (suitably OH or OCH$_3$); $R^1$ is S$^1$ or OH; $R^{2a}$ is S$^2$ or OH; $R^{2b}$ is H; $R^N$ is $C_{1-6}$alkyl (suitably CH$_3$) or H; $Z^1$ and $Z^2$ are both hydrogen; $X^{1p}$ is

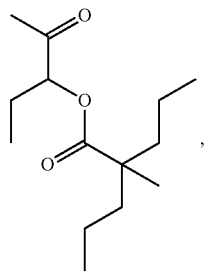 [SMILES: CCCC(C)(CCC)C(=O)OC(CC)C(C)=O]

—C(=O)OH, C(=O)NH$_2$, —C(=S)NH$_2$, —C(=O)NHNH$_2$, —CH$_2$NH$_2$, —CH$_2$OH, —C(=O)H, —CN or NH$_2$; and $X^{2p}$ is hydrogen, —C(=S)NH$_2$ or C(=O)NH$_2$.

In one embodiment, the compound of formula (I) is represented by formula (I-ii), wherein $A^1$ is OH, —O$C_{1-6}$ alkyl (suitably OH or OCH$_3$) or OR$^p$; $R^1$ is S$^1$, OH, —O$C_{1-6}$alkyl, or OR$^p$; $R^{2a}$ is S$^2$, OH, —O$C_{1-6}$ alkyl, H, or OR$^p$; $R^{2b}$ is H; $R^N$ is $C_{1-6}$alkyl (suitably CH$_3$) or H; $Z^1$ and $Z^2$ are both hydrogen; $X^{1p}$ is

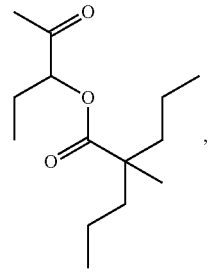 [SMILES: CCCC(C)(CCC)C(=O)OC(CC)C(C)=O]

—C(=O)OH, C(=O)NH$_2$, —C(=S)NH$_2$, —C(=O)NHNH$_2$, —CH$_2$NH$_2$, —CH$_2$OH, —C(=O)H, —CN or NH$_2$; and $X^{2p}$ is hydrogen, —C(=S)NH$_2$ or C(=O)NH$_2$. In a further embodiment, the compound of formula (I) is represented by formula (I-ii), wherein $A^1$ is OH, —O$C_{1-6}$alkyl (suitably OH or OCH$_3$); $R^1$ is S$^1$ or OH; $R^{2a}$ is S$^2$ or OH; $R^{2b}$ is H; $R^N$ is $C_{1-6}$alkyl (suitably CH$_3$) or H; $Z^1$ and $Z^2$ are both hydrogen; $X^{1p}$ is

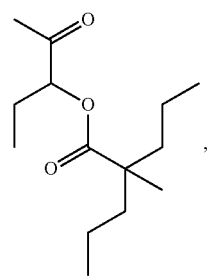 [SMILES: CCCC(C)(CCC)C(=O)OC(CC)C(C)=O]

—C(=O)OH, C(=O)NH$_2$, —C(=S)NH$_2$, —C(=O)NHNH$_2$, —CH$_2$NH$_2$, —CH$_2$OH, —C(=O)H, —CN or NH$_2$; and $X^{2p}$ is hydrogen, —C(=S)NH$_2$ or C(=O)NH$_2$.

In one embodiment, the compound of formula (I) is represented by formula (I-iii), wherein $A^1$ is OH, —O$C_{1-6}$ alkyl (suitably OH or OCH$_3$) or OR$^p$; $R^1$ is S$^1$, OH, —O$C_{1-6}$alkyl, or OR$^p$; $R^{2a}$ is S$^2$, OH, H, or OR$^p$; $R^{2b}$ is H; $R^N$ is $C_{1-6}$alkyl (suitably CH$_3$) or H; $X^{1p}$ is

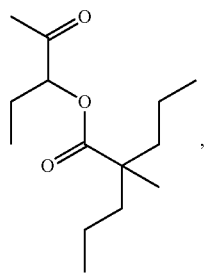 [SMILES: CCCC(C)(CCC)C(=O)OC(CC)C(C)=O]

—C(=O)OH, C(=O)NH₂, —C(=S)NH₂, —C(=O)NHNH₂, —CH₂NH₂, —CH₂OH, —C(=O)H, —CN or NH₂; and $X^{2p}$ is hydrogen, —C(=S)NH₂ or C(=O)NH₂.

In one embodiment, the compound of formula (I) is represented by formulae I-A, I-B, I-C, I-D, I-E, I-FA, I-FB, I-KA-a, I-KA, I-M, I-MN and I-RE as depicted in General synthetic procedures section below, wherein, $X^{1p}$, $X^{2p}$, $R^N$, $A^1$, $R^1$, $R^{2a}$ and $R^{2b}$ are as defined in any particular embodiment. In a further embodiment, the compound of formula (I) is represented by formula I-A or I-B. In a further embodiment, the compound of formula (I) is represented by formulae I-C, I-D, I-E, I-FA, I-FB, I-KA-a, I-KA, I-M, I-MN and I-RE.

In one embodiment, the compound of formula (I-iii) is represented by formula I-A1-iii. I-B1-iii, I-D1-iii, I-FA1-iii, I-FB1-iii, I-KA1-a-iii, I-KA1-iii, I-M1-iii, I-MN1-iii, and I-RE1-iii as depicted in General synthetic procedures section below, wherein $X^{1p}$, $X^{2p}$, $R^N$, $A^1$, $R^1$, $R^{2a}$ and $R^{2b}$ are as defined in any particular embodiment. In a further embodiment, the compound of formula (I) is represented by formula I-A1-iii. I-B1-iii, I-C1-iii, I-D1-iii, E1-iii, I-FA1-iii, I-FB1-iii, I-KA1-a-iii, I-KA1-iii, I-M1-iii, I-MN1-iii, and I-RE1-iii as depicted in General synthetic procedures section below, wherein $R^1$ is $S^1$ and $R^{2a}$ is $S^2$ or OH (suitably $R^1$ is b1-ii or b2-ii and $R^{2a}$ is d-i or OH). In one further embodiment, the compound of formula (I) is represented by formulae I-A1-iii. I-B1-iii, I-C1-iii, I-D1-iii, I-FA1-iii and I-KA1-a-iii, as depicted in General synthetic procedures section below, wherein $R^1$ is $S^1$ and $R^{2a}$ is $S^2$ or OH (suitably $R^1$ is b1-ii or b2-ii and $R^{2a}$ is d-i or OH). In one embodiment, seco macrolide compound of formula (I) is represented by formula (I-A2-iii) or (I-B2-iii):

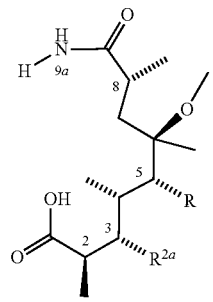

(I-B2-iii)

wherein, $R^1$ and $R^{2a}$ are as defined in any particular embodiment. In further embodiment, the compound of formula (I) is represented by formula (I-A2-iii) or (I-B2-iii), wherein $R^1$ is $S^1$ and $R^{2a}$ is $S^2$ or OH (suitably $R^1$ is b1-ii or b2-ii and $R^{2a}$ is d-i or OH).

In one embodiment, seco macrolide compound of formula (I) is represented by formulae selected from (I-iii), (I-A2-iii) and (I-B2-iii), wherein, $X^{1p}$, $X^{2p}$, $R^N$, $A^1$, $R^1$, $R^{2a}$ and $R^{2b}$ are as defined in any particular embodiment.

In one embodiment, the present invention relates to the process for preparation of seco (opened ring) macrolide compound of Formula (I), which comprises following steps:
(a) reacting a 9a-aza-9a-homoerythromycin compound of formula (II)

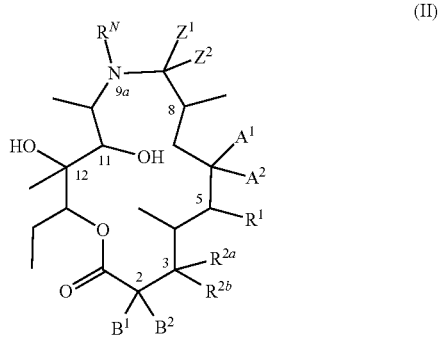

(II)

wherein,
$Z^1$, $Z^2$, $A^1$, $A^2$, $R^1$, $R^{2a}$, $R^{2b}$, $B^1$, $B^2$ and $R^N$ are as defined for formula (I) above, with a suitable oxidative cleavage reactant (suitably lead tetracaetate or periodic acid salts such as sodium periodate) in a suitable solvent or mixture of solvents to give:

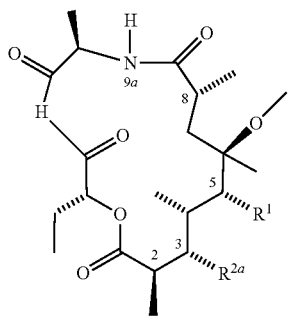

(I-A2-iii)

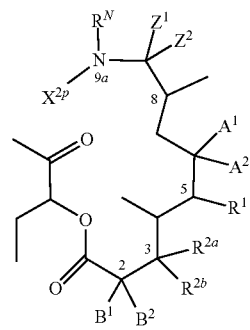

(I-A)

(i) a seco macrolide compound of formula (I-A), which is subset of formula (I), wherein $X^{1p}$ is

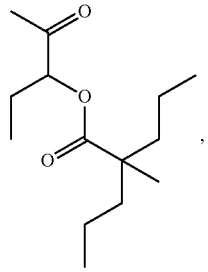 [SMILES: CCCC(C)(CCC)C(=O)OC(CC)C(C)=O]

$X^{2p}$ is hydrogen, $Z^1$ and $Z^2$ are both hydrogen, $A^1$, $A^2$, $R^1$, $R^{2a}$, $R^{2b}$, $B^1$, $B^2$ and $R^N$ are as defined for formula (I) when starting from compound of formula (II), wherein $Z^1$ and $Z^2$ are both hydrogen, or (ii) a seco macrolide compound of formula (I-A), which is subset of formula (I) wherein $X^{1p}$ is

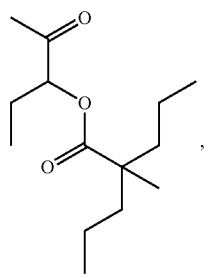 [SMILES: CCCC(C)(CCC)C(=O)OC(CC)C(C)=O]

$X^{2p}$ is $CH(CH_3)C(=O)H$, $Z^1$ and $Z^2$ together with carbon atom to which they are attached form a keto group, $R^N$ is hydrogen, $A^1$ is $-OC_{1-6}$alkyl, $A^2$, $R^1$, $R^{2a}$, $R^{2b}$, $B^1$ and $B^2$, are as defined for formula (I) when starting from compound of formula (II) wherein $Z^1$ and $Z^2$ together with carbon atom to which they are attached form a keto group;

(b) hydrolyzing a compound of formula (I-A) wherein $X^{1p}$ is

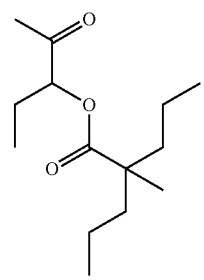 [SMILES: CCCC(C)(CCC)C(=O)OC(CC)C(C)=O]

obtained in step (a) to give compound of formula (I-B), which is subset of formula (I) wherein $X^{1p}$ is $-C(=O)OH$, $X^{2p}$ is hydrogen, $Z^1$, $Z^2$, $A^1$, $A^2$, $R^1$, $R^{2a}$, $R^{2b}$, $B^1$, $B^2$ and $R^N$ are as defined for formula (I) above; and optionally subjecting a compound of formula (I-B) wherein $X^{1p}$ is $-C(=O)OH$, $X^{2p}$ is hydrogen, $R^N$ is hydrogen and $Z^1$ and $Z^2$ together with carbon atom to which they are attached form a keto group to a further hydrolyzing conditions to give di-carboxylic acid of formula (XC), wherein $A^1$, $A^2$, $B^1$, $B^2$, $R^1$, $R^{2a}$ and $R^{2b}$ are as defined for formula (I); or

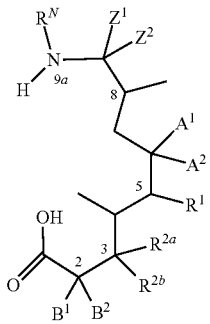

(I-B)

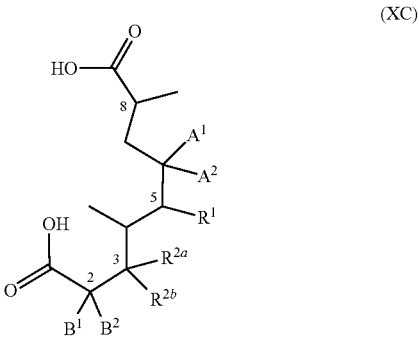

(XC)

(c) reacting a compound of formula (IA) wherein $X^{1p}$ is

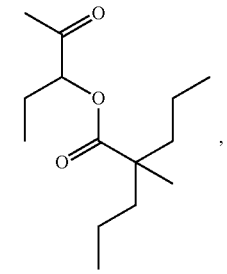 [SMILES: CCCC(C)(CCC)C(=O)OC(CC)C(C)=O]

$X^{2p}$ is hydrogen obtained in step (a) or compound of formula (I-B) wherein $X^{1p}$ is $-C(=O)OH$ and $X^{2p}$ is hydrogen obtained in step (b) with ammonium salt in the presence of base and coupling agent or with ammonia in organic solvents, or with ammonia hydroxide to give a compound of formula (I-C), which is subset of formula (I) wherein $X^{1p}$ is $-C(=O)NH_2$, $X^{2p}$ is hydrogen, $Z^1$, $Z^2$, $A^1$, $A^2$, $R^1$, $R^{2a}$, $R^{2b}$, $B^1$, $B^2$ and $R^N$ are as defined for formula (I) above; or

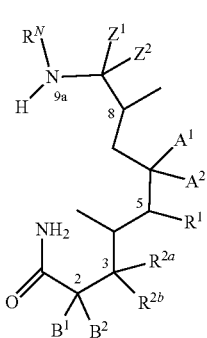
(I-C)

(d) reducing amide compound of formula (I-B) wherein $X^{1p}$ is —C(=O)NH$_2$, and $X^{2p}$ is hydrogen obtained in step (c) using suitable reducing agent (for example LiAlH$_4$, NaBH$_4$, LiEt$_3$BH, or borane-THF) to compound of formula (I-D), which is subset of formula (I) wherein $X^{1p}$ is —CH$_2$NH$_2$, $X^{2p}$ is hydrogen, $Z^1$, $Z^2$, $A^1$, $A^2$, $R^1$, $R^{2a}$, $R^{2b}$, $B^1$, $B^2$ and $R^N$ are as defined for formula (I) above; or

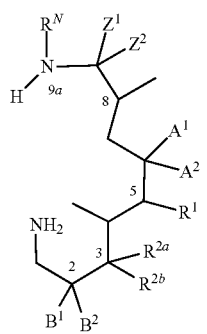
(I-D)

(e) reacting a compound of formula (I-A) obtained in step (a) wherein $X^{1p}$ is

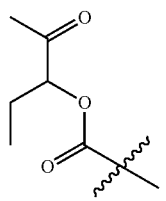 [SMILES: *C(=O)OC(CC)C(C)=O]

with hydrazine hydrate in a suitable solvent to give compound of formula (I-E), which is subset of formula (I) wherein $X^{1p}$ is —C(=O)—NH—NH$_2$ group, $X^{2p}$ is hydrogen, $Z^1$, $Z^2$, $A^1$, $A^2$, $R^1$, $R^{2a}$, $R^{2b}$, $B^1$, $B^2$ and $R^N$ are as defined for formula (I) above; or

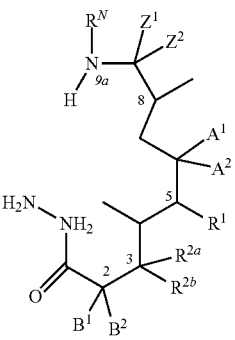
(I-E)

(f) reacting a compound of formula (I-A) obtained in step (a) wherein $X^{1p}$ is

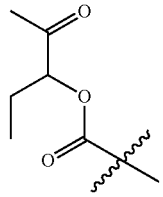 [SMILES: *C(=O)OC(CC)C(C)=O]

or a compound of formula (I-B) obtained in step (b) wherein $X^{1p}$ is —C(=O)OH with thiocarbonyldiimidazole followed by the amonolysis reaction conditions (provided when starting from compound of formula (I-A) then C/1-keto ester hydrolysis step (b) is usually performed prior amonolysis), or in alternative with thiocyanates or isothiocyanates to give compound of formula (I-FA), which is subset of formula (I) wherein $X^{1p}$ is —C(=O)OH group, $X^{2p}$ is C(=S)NH$_2$ group, $Z^1$, $Z^2$, $A^1$, $A^2$, $R^1$, $R^{2a}$, $R^{2b}$, $B^1$, $B^2$ and $R^N$ are as defined for formula (I) above; or

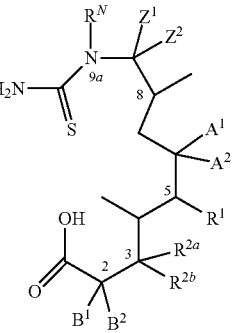
(I-FA)

(g) reacting a compound of formula (I-A) obtained in step (a) wherein $X^{1p}$ is

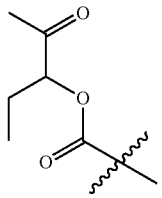 [SMILES: *C(=O)OC(CC)C(C)=O]

or a compound of formula (I-B) obtained in step (b) wherein $X^{1p}$ is —C(=O)OH with carbonyldiimidazole followed by the amonolysis reaction conditions (provided when starting from compound of formula (I-A) then C/1-keto ester hydrolysis step (b) is usually performed prior amonolysis), or in alternative with alkali metal cyanates or isocyanates to give compound of formula (I-FB), which is subset of formula (I) wherein $X^{1p}$ is —C(=O)OH group, $X^{2p}$ is C(=O)NH$_2$ group, $Z^1$, $Z^2$, $A^1$, $A^2$, $R^1$, $R^{2a}$, $R^{2b}$, $B^1$, $B^2$ and $R^N$ are as defined for formula (I) above; or

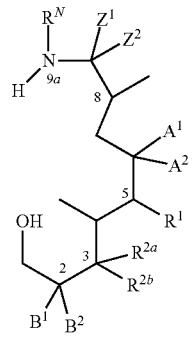

(i) reacting a compound of formula (I-KA-a) obtained in step (h) wherein $X^{1p}$ is —CH$_2$OH group and $X^{2p}$ is hydrogen with the standard oxidizing reagents to give compound of formula (I-KA), which is subset of formula (I) wherein $X^{1p}$ is —C(=O)H group, $X^{2p}$ is hydrogen, $Z^1$, $Z^2$, $A^1$, $A^2$, $R^1$, $R^{2a}$, $R^{2b}$, $B^1$, $B^2$ and $R^N$ are as defined for formula (I) above; or

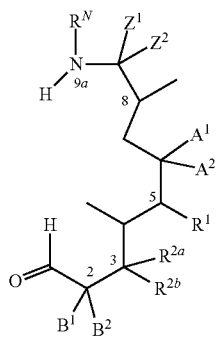

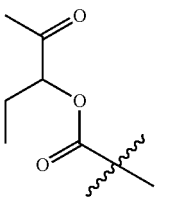 [SMILES: *C(=O)OC(CC)C(C)=O]

(h) subjecting a compound of formula (I-A) obtained in step (a) wherein $X^{1p}$ is (j) subjecting compound of formula (I-C) obtained in step (c) where $X^{1p}$ is —C(=O)NH$_2$ group and $X^{2p}$ is hydrogen to dehydration reaction (for example thionyl chloride, phosphorus pentoxide, thionyl chloride, phosphorus pentoxide, phosphorus oxychloride, titanium tetrachloride, pivaloyl chloride, ethyl dichlorophosphate, trichloroacetyl chloride, silanes/TBAF) to give compound of formula (I-MN), which is subset of formula (I) wherein $X^{1p}$ is —CN, $X^{2p}$ is hydrogen, $Z^1$, $Z^2$, $A^1$, $A^2$, $R^1$, $R^{2a}$, $R^{2b}$, $B^1$, $B^2$ and $R^N$ are as defined for formula (I) above; or

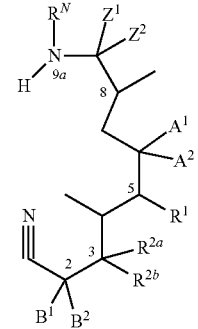

or a compound of formula (I-B) obtained in step (b) wherein $X^{1p}$ is —C(=O)OH to the standard carboxylic acid reduction conditions to give compound of formula (I-KA-a), which is subset of formula (I) wherein $X^{1p}$ is —CH$_2$OH group, $X^{2p}$ is hydrogen, $Z^1$, $Z^2$, $A^1$, $A^2$, $R^1$, $R^{2a}$, $R^{2b}$, $B^1$, $B^2$ and $R^N$ are as defined for formula (I) above; or (k) reacting
- a. a compound of formula (I-C) obtained in step (c) where $X^{1p}$ is —C(=O)NH$_2$, and $X^{2p}$ is hydrogen with Lawesson's or Bellau's reagents or with P$_4$S$_{10}$ alone or in combination with hexamethyldisiloxane, or in alternative
- b. a compound of formula (I-MN) obtained in step (j) where $X^{1p}$ —CN, and $X^{2p}$ is hydrogen using alkali metal hydrogen sulfide or ammonium sulfide under high pressure, phosphorus decasulfide, thioacids, thioacetic acid in combination with Lewis acid or benzylamine or calcium hydride, thioacetamide, DowexSH, O-dialkyldithiophosphates, 12 diphenylphosphinodithioacids, sodium trimethylsilanethiolate, sodium hydrosulfide hydrate and diethyl amine hydrochloride, sodium hydrosulfide hydrate and magnesium chloride hexahydrate, and (P$_4$S$_{11}$)Na$_2$ to give compound of formula (I-M), which is subset of formula (I) wherein $X^{1p}$ is —C(=S)NH$_2$, $X^{2p}$ is hydrogen, $Z^1$, $Z^2$, $A^1$, $A^2$, $R^1$, $R^{2a}$, $R^{2b}$, $B^1$, $B^2$ and $R^N$ are as defined for formula (I) above; or (I-M)

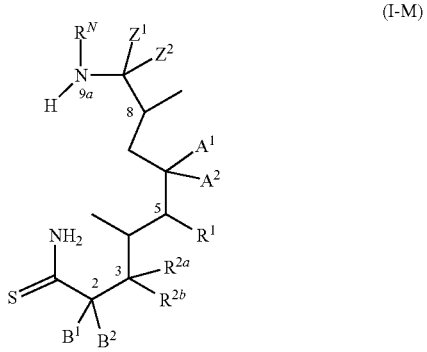

(l) subjecting
- a. a compound of formula (I-B) obtained in step (b) where $X^{1p}$ —C(=O)OH, and $X^{2p}$ is hydrogen to the modified Curtius rearrangement followed by mild acidic hydrolysis or hydrogenation of the carbamate group, or
- b. a compound of formula (I-A) obtained in step (a) where $X^{1p}$ is

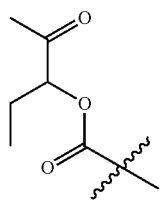 [SMILES: *C(=O)OC(CC)C(C)=O]

and $X^{2p}$ is hydrogen to the modified Lossen rearrangement followed by mild acidic hydrolysis or hydrogenation of the carbamate group, to give compound of formula (I-RE), which is subset of formula (I) wherein $X^1$ is NH$_2$, $X^{2p}$ is hydrogen, $Z^1$, $Z^2$, $A^1$, $A^2$, $R^1$, $R^{2a}$, $R^{2b}$, $B^1$, $B^2$ and $R^N$ are as defined for formula (I) above; and (I-RE)

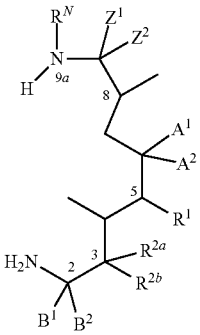

(m) if required after any of previous steps (a) (I), subjecting the resulting compound to one or more of the following operations:
  (i) removal of the protecting group $R^p$,
  (ii) removal of S$^2$ sugar group and/or S$^1$ sugar group,
  (iii) conversion of the resulting compound of formula (I) into a salt or solvate thereof.

In one embodiment, process steps (a) to (I) of the present invention for preparation of compound of formula (I) are performed according to general methods and procedures described in Methods A, B, C, D, E, FA, FB, K, M and RE, as well as KA, KB, KC, KD, KE, KF, KG-A, KG-B, KH, KI, KJ, KL-A, KL-B, KL-C, KM, KN, KO, KP, KR, KS and Schemes associated with these general methods in General synthetic procedures section below.

In one embodiment, process step (a) of the present invention for preparation of compound of formula (I) is performed according to general methods and procedures described in Method A and Scheme 1 as described in General synthetic procedures section below. In further embodiment in the process step (a) of the present invention Pb(OAc)$_4$ or NaIO$_4$ are used as suitable oxidative cleavage reactants with the appropriate 9a-aza-9a-homoerythromycin compound of formula (II) to give ring opened (seco) macrolide compound of formula (I-A), which is subset of formula (I) in a suitable solvent or mixture of solvents (such as glacial AcOH, DCM or chloroform) at 0° C. to 40° C.

In one embodiment, in the process step (a) of the present invention for preparation of compound of formula (I-A) lead tetracaetate (Pb(OAc)$_4$) is used as a suitable oxidative cleavage reactant with 9a-aza-9a-homoerythromycin compound of formula (II) to give ring opened (seco) macrolide compound of formula (I-A). In a further embodiment, in the process step (a) of the present invention for preparation of compound of formula (I-A) sodium periodate (NaIO$_4$) is used as a suitable oxidative cleavage reactant with 9a-aza-9a-homoerythromycin compound of formula (II) to give ring opened (seco) compound of formula (I-A).

In one embodiment, in the process step (a) of the present invention for preparation of compound of formula (I-A) 1-2.2 equivalents of oxidative cleavage reactant is used.

In one embodiment, in the process step (a) of the present invention for preparation of compound of formula (I-A) glacial AcOH, DCM or chloroform is used as a solvent or mixture of solvents. In a further embodiment, in the process step (a) of the present invention for preparation of compound of formula (I-A) glacial AcOH is used as a solvent.

In one embodiment, process step (a) of the present invention for preparation of compound of formula (I-A) is performed at 0° C. to 40° C. In a further embodiment, process step (a) of the present invention for preparation of compound of formula (I-A) is performed at room temperature.

In one embodiment, process step (b) of the present invention for preparation of compound of formula (I-B), which is subset of formula (I) is performed according to general methods and procedures described in Method B and Schemes 2A and 2B in General synthetic procedures section below. In a further embodiment process step (b) of the present invention for preparation of compound of formula (I-B) is performed by adding 1-10 equiv. of inorganic base such as sodium or lithium hydroxide to a solution of the appropriate intermediate of formula (I-A) obtained in step (a) in a suitable solvent or mixture of solvents (such as THF, MeCN or water (suitably mixture of THF/water or MeCN/water) at 0° C. to reflux temperature.

In one embodiment, in the process step (b) of the present invention for preparation of compound of formula (I-B) 1-10 equiv. of inorganic base is used for hydrolysis reaction. In one embodiment, in the process step (b) of the present invention for preparation of compound of formula (I-B) lithium hydroxide is used as a base for the hydrolysis reaction.

In one embodiment, in the process step (b) of the present invention for preparation of compound of formula (I-B) THF, MeCN or water are used as suitable solvents or mixture of solvents. In a further embodiment, in the process step (b) of the present invention for preparation of compound of formula (I-B) mixture of THF/water or MeCN/water is used as a solvent.

In one embodiment, process step (b) of the present invention for preparation of compound of formula (I-B) is performed at 0° C. to reflux temperature. In a further embodiment, process step (b) of the present invention for preparation of compound of formula (I-B) is performed at room temperature.

In one embodiment, process step (c) of the present invention for preparation of compound of formula (I-C) is performed according to general methods and procedures described in Method C and Scheme 3 in General synthetic procedures section below.

In one embodiment, process step (d) of the present invention for preparation of compound of formula (I-D) is performed according to general methods and procedures described in Method D and Scheme 4 in General synthetic procedures section below.

In one embodiment, process step (e) of the present invention for preparation of compound of formula (I-E) is performed according to general methods and procedures described in Method E and Scheme 5 in General synthetic procedures section below.

In one embodiment, process step (f) of the present invention for preparation of compound of formula (I-FA) is performed according to general methods and procedures described in Method FA and Scheme 6A in General synthetic procedures section below.

In one embodiment, process step (g) of the present invention for preparation of compound of formula (I-FB) is performed according to general methods and procedures described in Method FB and Scheme 6B in General synthetic procedures section below.

In one embodiment, process step (h) of the present invention for preparation of compound of formula (I-KA-a) is performed according to general methods and procedures described in Method K and Scheme 7, first step in General synthetic procedures section below.

In one embodiment, process step (i) of the present invention for preparation of compound of formula (I-KA) is performed according to general methods and procedures described in Method K and Scheme 7, second step in General synthetic procedures section below.

In one embodiment, process step (j) of the present invention for preparation of compound of formula (I-MN) is performed according to general methods and procedures described in Method M and Scheme 8, in General synthetic procedures section below.

In one embodiment, process step (k) of the present invention for preparation of compound of formula (I-M) is performed according to general methods and procedures described in Method M and Scheme 8, in General synthetic procedures section below.

In one embodiment, process step (l) of the present invention for preparation of compound of formula (I-RE) is performed according to general methods and procedures described in Method RE and Scheme 9, in General synthetic procedures section below.

In one embodiment, a 9a-aza-9a-homoerythromycin compound of formula (II) is represented by formula (II-i):

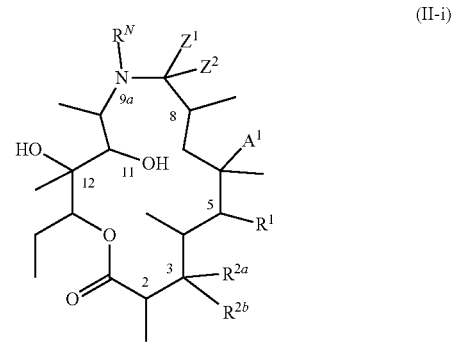

wherein, $Z^1$, $Z^2$, $R^N$, $A^1$, $R^1$, $R^{2a}$ and $R^{2b}$ are as defined in any particular embodiment. In a further embodiment, a 9a-aza-9a-homoerythromycin compound of formula (II) is represented by formula (II-ii):

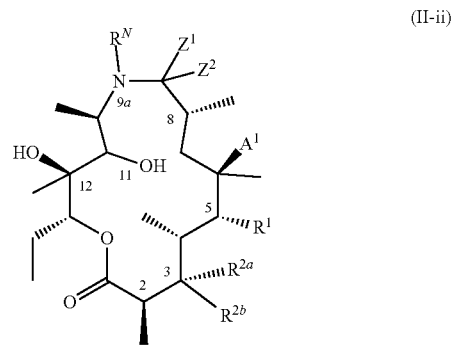

wherein, $Z^1$, $Z^2$, $R^N$, $A^1$, $R^1$, $R^{2a}$ and $R^{2b}$ are as defined in any particular embodiment. In one further embodiment, a 9a-aza-9a-homoerythromycin compound of formula (II) is represented by formula (II-iii):

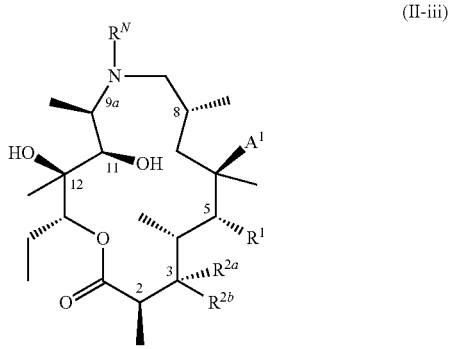

(II-iii)

wherein, $Z^1$, $Z^2$, $R^N$, $A^1$, $R^{2a}$ and $R^{2b}$ are as defined in any particular embodiment. In yet further embodiment, a 9a-aza-9a-homoerythromycin compound of formula (II) is represented by formula (II-iv):

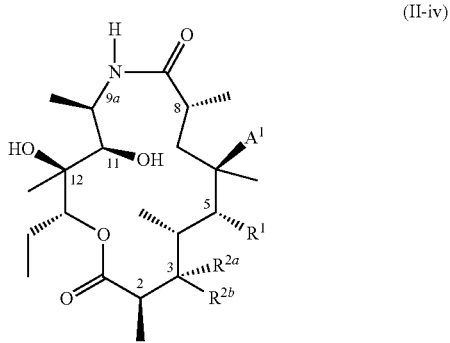

(II-iv)

wherein, $A^1$, $R^1$, $R^{2a}$ and $R^{2b}$ are as defined in any particular embodiment.

In a further embodiment, the compound of formula (II) is represented by formula (II-i), wherein $A^1$ is OH, —$OC_{1-6}$ alkyl (suitably OH or $OCH_3$) or $OR^p$; $R^1$ is $S^1$, OH, —$OC_{1-6}$alkyl, or $OR^p$; $R^{2a}$ is $S^2$, OH, H, or $OR^p$; $R^{2b}$ is H; $R^N$ is $C_{1-6}$alkyl (suitably $CH_3$) or H; $Z^1$ and $Z^2$ are as defined in any particular embodiment. In yet further embodiment, $Z^1$ and $Z^2$ are both hydrogen. In still further embodiment, $Z^1$ and $Z^2$ together with carbon atom to which they are attached form a keto group and $R^N$ is hydrogen.

In a further embodiment, the compound of formula (II) is represented by formula (II-ii), wherein $A^1$ is OH, —$OC_{1-6}$ alkyl (suitably OH or $OCH_3$) or $OR^p$; $R^1$ is $S^1$, OH, —$OC_{1-6}$alkyl, or $OR^p$; $R^{2a}$ is $S^2$, OH, H, or $OR^p$; $R^{2b}$ is H; $R^N$ is $C_{1-6}$alkyl (suitably $CH_3$) or H; and $Z^2$ are as defined in any particular embodiment. In yet further embodiment, $Z^1$ and $Z^2$ are both hydrogen. In still further embodiment, $Z^1$ and $Z^2$ together with carbon atom to which they are attached form a keto group and $R^N$ is hydrogen.

In a further embodiment, the compound of formula (II) is represented by formula wherein $A^1$ is OH, —$OC_{1-6}$alkyl (suitably OH or $OCH_3$) or $OR^p$; $R^1$ is $S^1$, OH, —$OC_{1-6}$alkyl, or $OR^p$; $R^{2a}$ is $S^2$, OH, H, or $OR^p$; $R^{2b}$ is H; and $R^N$ is $C_{1-6}$alkyl (suitably $CH_3$) or H. In a further embodiment, the compound of formula (II) is represented by formula (II-iv), wherein $A^1$ is —$OC_{1-6}$alkyl (suitably $OCH_3$); $R^1$ is $S^1$, OH, —$OC_{1-6}$alkyl, or $OR^p$; $R^{2a}$ is $S^2$, OH, H, or $OR^p$; and $R^{2b}$ is H. In yet further embodiment, $A^1$ is —$OC_{1-6}$alkyl (suitably $OCH_3$); $R^1$ is $S^1$, $R^{2a}$ is $S^2$; and $R^{2b}$ is H.

In one embodiment, the present invention relates to 9a-aza-9a-homoerythromycin compound of formula (II-X), as intermediate useful for the preparation of compounds of Formula (I).

In one embodiment, the present invention relates to 9a-aza-9a-homoerythromycin compound of formula (II-X), which is subset of compound of formula (II)

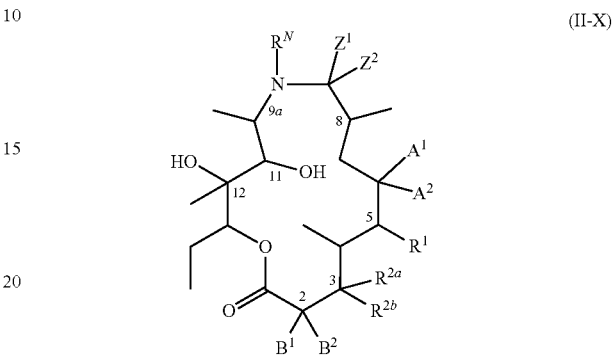

(II-X)

wherein,
$A^1$ is —$OC_{1-6}$ alkyl, —$OC_{2-6}$ alkenyl, —$OC_{2-6}$ alkynyl or $OR^p$;
$B^1$ and $B^2$ are independently H, $C_{1-6}$alkyl or halogen;
$R^1$ is OH, —$OC_{1-6}$ alkyl or $OR^p$;
$R^{2a}$ is OH, H, —$OC_{1-6}$alkyl or $OR^p$, provided $R^1$ and $R^{2a}$ are not simultaneously OH;
$R^{2b}$ is H;
$Z^1$, $Z^2$, $A^2$, $R^p$ and $R^N$ are as defined for formula (I) above; or a salt, solvate or prodrug thereof.

In one embodiment, a 9a-aza-9a-homoerythromycin compound of formula (II-X) is represented by formula (II-i), wherein, $Z^1$, $Z^2$, $R^N$, $A^1$, $R^1$, $R^{2a}$ and $R^{2b}$ are as defined in any particular embodiment. In a further embodiment, compound of formula (II-X) is represented by formula (II-i), wherein, $A^1$ is —$OC_{1-6}$alkyl (suitably $OCH_3$); $R^1$ is OH, —$OC_{1-6}$alkyl, or $OR^p$; $R^{2a}$ is OH, H, or $OR^p$; $R^{2b}$ is H; $R^N$ is $C_{1-6}$alkyl (suitably $CH_3$) or H; $Z^1$ and $Z^2$ are as defined in any particular embodiment. In yet further embodiment, compound of formula (II-X) is represented by formula (II-i), wherein, $A^1$ is —$OC_{1-6}$ alkyl (suitably $OCH_3$); $R^1$ is OH, —$OC_{1-6}$alkyl (suitably $OCH_3$); $R^{2a}$ is OH or —$OC_{1-6}$alkyl (suitably $OCH_3$); $R^{2b}$ is H; $R^N$ is $C_{1-6}$alkyl (suitably $CH_3$) or H; $Z^1$ and $Z^2$ are both hydrogen. In still further embodiment, compound of formula (II-X) is represented by formula (II-i), wherein, $R^N$ is $C_{1-6}$alkyl (suitably $CH_3$); $Z^1$ and $Z^2$ are both hydrogen; $R^{2b}$ is H; $A^1$ is —$OC_{1-6}$alkyl (suitably $OCH_3$); and $R^1$ and $R^{2a}$ are selected from: (i) $R^1$ is OH and $R^{2a}$ is-$OC_{1-6}$alkyl (suitably $OCH_3$); (ii) $R^1$ is —$OC_{1-6}$alkyl (suitably $OCH_3$) and $R^{2a}$ is OH; and (iii) $R^1$ and $R^{2a}$ are both —$OC_{1-6}$alkyl (suitably $OCH_3$). Suitably $R^1$ and $R^{2a}$ are both —$OC_{1-6}$alkyl (suitably $OCH_3$).

In one embodiment, a 9a-aza-9a-homoerythromycin compound of formula (II-X) is represented by formula (II-ii), wherein, $Z^1$, $Z^2$, $R^N$, $A^1$, $R^1$, $R^{2a}$ and $R^{2b}$ are as defined in any particular embodiment. In a further embodiment, compound of formula (II-X) is represented by formula (II-ii), wherein, $A^1$ is —$OC_{1-6}$alkyl (suitably $OCH_3$); $R^1$ is OH, —$OC_{1-6}$alkyl, or $OR^p$; $R^{2a}$ is OH, H, or $OR^p$; $R^{2b}$ is H; $R^N$ is $C_{1-6}$alkyl (suitably $CH_3$) or H; $Z^1$ and $Z^2$ are as defined in any particular embodiment. In yet further embodiment, compound of formula (II-X) is represented by formula (II-ii), wherein, $A^1$ is —$OC_{1-6}$ alkyl (suitably $OCH_3$); $R^1$ is OH, —OC$_{1-6}$alkyl (suitably OCH$_3$); R$^{2a}$ is OH or —OC$_{1-6}$alkyl (suitably OCH$_3$); R$^{2b}$ is H; R$^N$ is C$_{1-6}$alkyl (suitably CH$_3$) or H; Z$^1$ and Z$^2$ are both hydrogen. In still further embodiment, compound of formula (II-X) is represented by formula (II-ii), wherein, R$^N$ is C$_{1-6}$alkyl (suitably CH$_3$); Z$^1$ and Z$^2$ are both hydrogen; R$^{2b}$ is H; A$^1$ is —OC$_{1-6}$alkyl (suitably OCH$_3$); and R$^1$ and R$^{2a}$ are selected from: (i) R$^1$ is OH and R$^{2a}$ is —OC$_{1-6}$alkyl (suitably OCH$_3$); (ii) R$^1$ is —OC$_{1-6}$alkyl (suitably OCH$_3$) and R$^{2a}$ is OH; and (iii) R$^1$ and R$^{2a}$ are both —OC$_{1-6}$alkyl (suitably OCH$_3$). Suitably R$^1$ and R$^{2a}$ are both —OC$_{1-6}$alkyl (suitably OCH$_3$).

In one embodiment, a 9a-aza-9a-homoerythromycin compound of formula (II-X) is represented by formula (II-iii), wherein, R$^N$, A$^1$, R$^1$, R$^{2a}$ and R$^{2b}$ are as defined in any particular embodiment. In a further embodiment, compound of formula (II-X) is represented by formula (II-iii), wherein, A$^1$ is —OC$_{1-6}$alkyl (suitably OCH$_3$); R$^1$ is OH, —OC$_{1-6}$alkyl, or OR$^p$; R$^{2a}$ is OH, H, or OR$^p$; R$^{2b}$ is H; and R$^N$ is C$_{1-6}$alkyl (suitably CH$_3$) or H. In yet further embodiment, compound of formula (II-X) is represented by formula (II-iii), wherein, A$^1$ is —OC$_{1-6}$alkyl (suitably OCH$_3$); R$^1$ is OH, —OC$_{1-6}$alkyl (suitably OCH$_3$); R$^{2a}$ is OH or —OC$_{1-6}$alkyl (suitably OCH$_3$); R$^{2b}$ is H; and R$^N$ is C$_{1-6}$alkyl (suitably CH$_3$) or H. In still further embodiment, compound of formula (II-X) is represented by formula (II-iii), wherein, R$^N$ is C$_{1-6}$alkyl (suitably CH$_3$); R$^{2b}$ is H; A$^1$ is —OC$_{1-6}$alkyl (suitably OCH$_3$); and R$^1$ and R$^{2a}$ are selected from: (i) R$^1$ is OH and R$^{2a}$ is —OC$_{1-6}$alkyl (suitably OCH$_3$); (ii) R$^1$ is —OC$_{1-6}$alkyl (suitably OCH$_3$) and R$^{2a}$ is OH; and (iii) R$^1$ and R$^{2a}$ are both —OC$_{1-6}$alkyl (suitably OCH$_3$). Suitably R$^1$ and R$^{2a}$ are both —OC$_{1-6}$alkyl (suitably OCH$_3$).

In one embodiment, a 9a-aza-9a-homoerythromycin compound of formula (II-X) is represented by formula (II-iv), wherein A$^1$, R$^1$, R$^{2a}$ and R$^{2b}$ are as defined in any particular embodiment. In a further embodiment, compound of formula (II-X) is represented by formula (II-iv), wherein, A$^1$ is —OC$_{1-6}$alkyl (suitably OCH$_3$); R$^1$ is OH, —OC$_{1-6}$alkyl, or OR$^p$; R$^{2a}$ is OH, H, or OR$^p$; and R$^{2b}$ is H. In yet further embodiment, compound of formula (II-X) is represented by formula (II-iv), wherein, A$^1$ is —OC$_{1-6}$alkyl (suitably OCH$_3$); R$^1$ is OH, —OC$_{1-6}$alkyl (suitably OCH$_3$); R$^{2a}$ is OH or —OC$_{1-6}$alkyl (suitably OCH$_3$); and R$^{2b}$ is H. In still further embodiment, compound of formula (II-X) is represented by formula (II-iv), wherein R$^{2b}$ is H; A$^1$ is —OC$_{1-6}$alkyl (suitably OCH$_3$); and R$^1$ and R$^{2a}$ are selected from: (i) R$^1$ is OH and R$^{2a}$ is —OC$_{1-6}$alkyl (suitably OCH$_3$); (ii) R$^1$ is —OC$_{1-6}$alkyl (suitably OCH$_3$) and R$^{2a}$ is OH; and (iii) R$^1$ and R$^{2a}$ are both —OC$_{1-6}$alkyl (suitably OCH$_3$). Suitably R$^1$ and R$^{2a}$ are both —OC$_{1-6}$alkyl (suitably OCH$_3$).

In one embodiment, compound of formula (II) is (II-iii) or (II-iv), wherein R$^1$ is S$^1$, R$^{2a}$ is S$^2$ or OH (suitably R$^1$ is b1-ii or b2-ii and R$^{2a}$ is d-i or OH), R$^N$ is CH$_3$ or hydrogen.

In a further embodiment, the present invention also relates to macrolide based macrocycles of Formula (III)

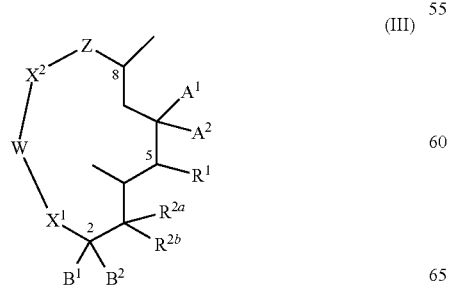

(III)

and pharmaceutically acceptable salts, solvates and prodrugs thereof, wherein

A$^1$, A$^2$, B$^1$, B$^2$, R$^1$, R$^{2a}$, R$^{2b}$, R$^N$ and R$^p$ are as defined for formula (I) above;

Z is —NR$^N$CH$_2$—, —NHC(=O)— or —OC(=O)— (left hand valence bond of these groups is attached to X$^2$ whereas right hand valence bond is attached to the C/8 carbon atom), provided when Z is —NHC(=O)— or —OC(=O)— then B$^1$ is CO$_{1-6}$alkyl;

X$^1$ is a bond, —C(=O)NR$^X$—, —NHC(=O)—, —NR$^u$—, —CH$_2$NR$^u$—, —CH$_2$O—, —C(=O)—, or —C(=O)O— (left hand valence bond of these groups is attached to the C/2 carbon atom whereas right hand valence bond is attached to W); wherein R$^u$ is H or C$_{1-6}$alkyl, R$^X$ is H, R$^Z$ or —CH(R$^Y$)—C(=O)NHR$^Z$;

R$^Y$ is H, C$_{1-6}$alkyl or phenyl; and

R$^Z$ is C$_{1-6}$alkyl, C$_{0-6}$alkyl-aryl or C$_{0-6}$alkyl-heteroaryl wherein aryl and heteroaryl independently from each other may be optionally substituted by one or more groups independently selected from halogen, CN, OH, NO$_2$, C$_{2-6}$alkenyl, C$_{2-6}$alkynyl, haloC$_{1-6}$alkyloxy, —C$_{1-6}$alkyl-OH, NH$_2$, N—(C$_{1-6}$-alkyl)amino, N,N-di(C$_{1-6}$alkyl)amino, —C(=O)C$_{1-6}$alkyl, —OC(=O)C$_{1-6}$alkyl, —C(=O)OH, —C(=O)OC$_{1-6}$ alkyl, —C(=O)NHC$_{1-6}$ alkyl and —NHC(=O)C$_{1-6}$ alkyl;

X$^2$ is a bond, —C(=O)— or —CH$_2$—;

W is —W$^1$—(CH$_2$)$_{m1}$—W$^2$—(CH$_2$)$_{m2}$—W$^3$— (left hand valence bond of W$^1$ is attached to X$^1$ whereas right hand valence bond of W$^3$ is attached to X$^2$), wherein:

m$^1$ is zero, 1, 2 or 3;

m$^2$ is zero, 1, 2 or 3;

W$^1$, W$^2$ and W$^3$ are:

(i) one of, two of or non of W$^1$, W$^2$ and W$^3$ are absent and the remaining of W$^1$, W$^2$ and W$^3$ are independently selected from:

a. 3-7 membered cycloalkyl which may be optionally substituted by one or more groups independently selected from OH, halogen, CN, NH$_2$, C$_{1-6}$alkyl, C$_{2-6}$ alkenyl, C$_{2-6}$alkynyl, haloC$_{1-6}$alkyloxy, —C(=O)C$_{1-6}$alkyl, —C(=O)OC$_{1-6}$alkyl, —C(=O)OH, —C(=O)NH$_2$, —C$_{0-6}$ alkyl-aryl or C$_{0-6}$alkyl-heteroaryl wherein aryl and heteroaryl independently from each other may be optionally substituted by one or more groups independently selected from halogen, CN, OH, NO$_2$, C$_{2-6}$alkenyl, C$_{2-6}$alkynyl, —OC$_{1-6}$ alkyl, haloC$_{1-6}$alkyloxy, —C$_{1-6}$ alkyl-OH, NH$_2$, N—(C$_{1-6}$-alkyl)amino, N,N-di(C$_{1-6}$ alkyl)amino, —C(=O)C$_{1-6}$ alkyl, —OC(=O)C$_{1-6}$ alkyl, —C(=O)OH, —C(=O)OC$_{1-6}$ alkyl, —C(=O)NHC$_{1-6}$ alkyl and —NHC(=O)C$_{1-6}$ alkyl;

b. 4-7 membered cycloalkenyl containing one or two double bonds which may be optionally substituted by one or more groups independently selected from OH, halogen, CN, NH$_2$, C$_{1-6}$alkyl, C$_{2-6}$alkenyl, C$_{2-6}$alkynyl, —OC$_{1-6}$ alkyl, haloC$_{1-6}$alkyloxy, —C(=O)C$_{1-6}$ alkyl, —C(=O)OC$_{1-6}$ alkyl, —C(=O)OH and —C(=O)NH$_2$;

c. 3-7 membered heterocycloalkyl containing one or two heteroatoms independently selected from N, O and S, where heterocycloalkyl may be optionally substituted by one or more groups independently selected from OH, halogen, CN, NH$_2$, C$_{1-6}$ alkyl, C$_{2-6}$alkenyl, C$_{2-6}$alkynyl, —OC$_{1-6}$ alkyl, —OC$_{1-6}$ alkyl, haloC$_{1-6}$alkyloxy, —OC$_{1-6}$ alkyl-OH, —C(=O)C$_{1-6}$ alkyl, —C(=O)OC$_{1-6}$ alkyl, —C(=O)OH, —C(=O)NH$_2$, —O$_{0-6}$alkyl-aryl, —O—C$_{0-6}$ alkyl-aryl, —O$_{0-6}$alkyl-heteroaryl, —O$_{0-6}$alkyl-cycloalkyl or —C$_{0-6}$ alkyl-heterocycloalkyl, wherein aryl, heteroaryl, cycloalkyl, and heterocycloalkyl independently from each other may be optionally substituted by one or more groups independently selected from halogen, CN, OH, NO$_2$, C$_{2-6}$alkenyl, C$_{2-6}$alkynyl, —OC$_{1-6}$alkyl, haloC$_{1-6}$alkyloxy, C$_{1-6}$alkyl-OH, NH$_2$, N—(O$_{1-6}$-alkyl)amino, N,N-di(C$_{1-6}$alkyl)amino, —C(=O)C$_{1-6}$ alkyl, —OC(=O)C$_{1-6}$ alkyl, —C(=O)OH, —C(=O)OC$_{1-6}$ alkyl, —C(=O)NHC$_{1-6}$ alkyl and —NHC(=O)C$_{1-6}$ alkyl;

d. 4-7 membered heterocycloalkenyl containing one or two heteroatoms independently selected from N, O and S and one or two double bonds where heterocycloalkenyl may be optionally substituted by one or more groups independently selected from OH, halogen, CN, NH$_2$, C$_{1-6}$alkyl, C$_{2-6}$alkenyl, C$_{2-6}$alkynyl, —OC$_{1-6}$alkyl, haloC$_{1-6}$alkyloxy, —C$_{1-6}$alkyl-OH, —C(=O)C$_{1-6}$ alkyl, —C(=O)OC$_{1-6}$ alkyl, —C(=O)OH and —C(=O)NH$_2$;

e. 6 membered aryl which may be optionally substituted by one or more groups independently selected from halogen, CN, OH, NO$_2$, C$_{1-6}$ alkyl, C$_{2-6}$ alkenyl, C$_{2-6}$alkynyl, haloC$_{1-6}$ alkyl, —OC$_{1-6}$ alkyl, haloC$_{1-6}$alkyloxy, —C$_{1-6}$ alkyl-OH, NH$_2$, N—(C$_{1-6}$-alkyl)amino, N,N-di(C$_{1-6}$ alkyl)amino, —C(=O)C$_{1-6}$ alkyl, —O(C=O)C$_{1-6}$ alkyl, —C(=O)OH, —C(=O)OC$_{1-6}$ alkyl, —C(=O)NHC$_{1-6}$ alkyl and —NHC(=O)C$_{1-6}$ alkyl;

f. 5-6 membered heteroaryl containing two or three heteroatoms independently selected from N, O and S, wherein heteroaryl may be optionally substituted by one or more groups independently selected from halogen, CN, OH, NO$_2$, C$_{2-6}$alkenyl, C$_{2-6}$alkynyl, haloC$_{1-6}$ alkyl, —OC$_{1-6}$ alkyl, haloC$_{1-6}$alkyloxy, —C$_{1-6}$alkyl-OH, NH$_2$, N—(C$_{1-6}$-alkyl)amino, N,N-di(C$_{1-6}$alkyl)amino, —C(=O)C$_{1-6}$ alkyl, —O(C=O)C$_{1-6}$ alkyl, —C(=O)OH, —C(=O)OC$_{1-6}$ alkyl, —C(=O)NHC$_{1-6}$ alkyl and —NHC(=O)C$_{1-6}$ alkyl;

g. —C(R$^{W1a}$)(R$^{W2a}$)—, wherein R$^{W1a}$ is hydrogen, and R$^{W2a}$ is C$_{1-6}$alkyl, C$_{2-6}$alkenyl, C$_{2-6}$alkynyl, halogen, OH, CN, —C(=O)OH, —C(=O)NH$_2$, haloC$_{1-6}$alkyl, OC$_{1-6}$alkyl, C$_{1-6}$alkyl-OH, —C$_{1-6}$alkylOC$_{1-6}$alkyl, —C$_{1-6}$alkylSC$_{1-6}$alkyl, —C$_{1-6}$alkyl-C(=O)OH, C$_{1-6}$alkyl-C(=O)OC$_{1-6}$alkyl, —C$_{1-6}$alkylOC(=O)C$_{1-6}$alkyl, —C$_{1-6}$alkylC(=O)NH$_2$, —C$_{1-6}$alkyl-NH$_2$, —C$_{1-6}$alkyl-NH(C$_{1-6}$alkyl), —C$_{1-6}$alkyl-N(C$_{1-6}$alkyl)$_2$, —C$_{1-6}$alkylNHC(=O)OC$_{1-6}$alkyl, —C$_{1-6}$alkyl-NHC(=O)C$_{2-6}$alkenyl, —C$_{1-6}$alkyl-NHC(=O)—C$_{0-4}$alkyl-heteroaryl, —C$_{1-6}$alkylNHSO$_2$C$_{1-6}$alkyl, —C$_{1-6}$alkylNHSO$_2$C$_{2-6}$alkenyl, —C$_{1-6}$alkylNHSO$_2$cycloalkyl, —C$_{0-6}$alkyl-aryl, —C$_{2-6}$alkenyl-aryl, —C$_{0-6}$alkyl-heteroaryl, —C$_{2-6}$alkenyl-heteroaryl, —C$_{0-6}$alkyl-cycloalkyl, or —C$_{0-6}$alkyl-heterocycloalkyl, wherein alkyl, alkenyl, alkynyl, aryl, heteroaryl, cycloalkyl, and heterocycloalkyl independently from each other may be optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, C$_{1-6}$alkyl-OH, NH$_2$, N—(C$_{1-6}$alkyl)amino, N,N-di(C$_{1-6}$alkyl)amino, —C(=O)C$_{1-6}$alkyl, —OC(=O)C$_{1-6}$alkyl, —C(=O)OH, —C(=O)OC$_{1-6}$alkyl, —C(=O)NHC$_{1-6}$alkyl, —NHC(=O)C$_{1-6}$alkyl, —C$_{1-6}$alkylNHSO$_2$C$_{1-6}$alkyl, and —C$_{1-6}$alkyl-NH(C=NH)NHR$^g$ wherein R$^g$ is H, amino protecting group, —C$_{0-6}$alkyl-aryl, —OC$_{0-6}$alkylaryl, —C$_{0-6}$alkyl-heteroaryl, —C$_{0-6}$alkyl-cycloalkyl or —C$_{0-6}$alkyl-heterocycloalkyl, wherein aryl, heteroaryl, cycloalkyl, and heterocycloalkyl independently from each other may be optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, C$_{1-6}$alkyl-OH, NH$_2$, N—(C$_{1-6}$-alkyl)amino, N,N-di(C$_{1-6}$alkyl)amino, —C(=O)C$_{1-6}$alkyl, —OC(=O)C$_{1-6}$alkyl, —C(=O)OH, —C(=O)OC$_{1-6}$alkyl, —C(=O)NHC$_{1-6}$alkyl and —NHC(=O)C$_{1-6}$alkyl;

h. —C(R$^{W1b}$)(R$^{W2b}$)— group wherein R$^{W1b}$ and R$^{W2b}$ together with carbon atom to which they are attached form:
   i. 3-7 membered spiro cycloalkyl group which may be optionally substituted by one or more groups independently selected from halogen, CN, keto (=O), OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, C$_{1-6}$alkyl-OH, NH$_2$, N—(C$_{1-6}$-alkyl)amino, N,N-di(C$_{1-6}$alkyl)amino, —C(=O)C$_{1-6}$alkyl, —OC(=O)C$_{1-6}$alkyl, —C(=O)OH, —C(=O)OC$_{1-6}$alkyl, —C(=O)NHC$_{1-6}$alkyl and —NHC(=O)C$_{1-6}$alkyl; or
   ii. 3-7 membered spiro heterocycloalkly group where heterocycloalkyl group may contain one or two heteroatoms selected form O, S and N;

i. —N(R$^{Wn}$)—, wherein R$^{Wn}$ is C$_{1-6}$alkyl, C$_{2-6}$alkenyl, C$_{2-6}$alkynyl, —C$_{1-6}$alkylOC$_{1-6}$alkyl, —C$_{1-6}$alkyl-C(=O)OH, —C$_{1-6}$alkyl-C(=O)OC$_{1-6}$alkyl, —C$_{1-6}$alkylOC(=O)C$_{1-6}$alkyl, —C$_{1-6}$alkyl-NH$_2$, —C$_{1-6}$alkylNHC(=O)OC$_{1-6}$alkyl, —C$_{1-6}$alkyl-aryl wherein aryl may be optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, OC$_{1-6}$alkyl, haloC$_{1-6}$alkyloxy, C$_{1-6}$alkyl-OH, NH$_2$, N—(C$_{1-6}$alkyl)amino, N,N-di(C$_{1-6}$alkyl)amino, —(C=O)C$_{1-6}$alkyl, —O(C=O)C$_{1-6}$alkyl, —C(=O)OH, —C(=O)OC$_{1-6}$alkyl, —C(=O)NHC$_{1-6}$alkyl and —NHC(=O)C$_{1-6}$alkyl;

j. —C(R$^{W1c}$)(R$^{W2c}$)— group wherein R$^{W1c}$ and R$^{W2c}$ together with carbon atom to which they are attached form:
   i. >C=C-aryl, or
   ii. >C=C-heteroaryl,
   wherein aryl and heteroaryl independently from each other may be optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, OC$_{1-6}$alkyl, haloC$_{1-6}$alkyloxy, C$_{1-6}$alkyl-OH, NH$_2$, N—(C$_{1-6}$alkyl)amino, N,N-di(C$_{1-6}$alkyl)amino, —(C=O)C$_{1-6}$alkyl, —O(C=O)C$_{1-6}$alkyl, —C(=O)OH, —C(=O)OC$_{1-6}$alkyl, —C(=O)NHC$_{1-6}$alkyl and —NHC(=O)C$_{1-6}$alkyl;

k. [—NHCH(R$^r$)C(=O)—]$_{t1}$ or

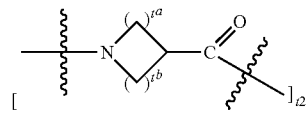

group,
wherein:
$t^1$ and $t^2$ independently are 1 to 5,
$t_a$ and $t_b$ independently are 0 to 3, provided the sum of $t^a$ and $t^b$ is 2 to 6,
$R^t$ is residue of natural amino acid selected from H, $C_{1-6}$alkyl, —C(=O)$C_{1-6}$alkyl, —C(=O)O$C_{1-6}$alkyl, —O$C_{1-6}$alkyl, —$C_{1-6}$alkyl-OH, —$C_{1-6}$alkyl-O$C_{1-6}$alkyl, —$C_{1-6}$alkyl-S$C_{1-6}$alkyl, CN, —C(=O)OH, —C(=O)NH$_2$, —$C_{0-6}$alkyl-aryl or —$C_{0-6}$alkyl-heteroaryl wherein aryl and heteroaryl may be mono or biyclic and each may be optionally substituted by one or more groups independently selected from halogen, CN, OH, NO$_2$, O$C_{1-6}$alkyl, NH$_2$, N—($C_{1-6}$alkyl)amino, N,N-di($C_{1-6}$alkyl)amino, —(C=O)$C_{1-6}$alkyl, —O(C=O)$C_{1-6}$alkyl, —C(=O)OH, —C(=O)O$C_{1-6}$alkyl, —C(=O)NH$C_{1-6}$alkyl and —NHC(=O)$C_{1-6}$alkyl;
l. —NHC($R^{W1d}$)($R^{W2d}$)C($R^{W1e}$)($R^{W2e}$)—NHC(=O)— group wherein $R^{W1d}$ and $R^{W1e}$ are hydrogen, and $R^{W2d}$ and $R^{W2e}$ are independently from each other $C_{0-4}$alkylaryl wherein aryl may be optionally substituted by one or more groups independently selected from halogen, CN, OH, NO$_2$, $C_{1-6}$alkyl, $C_{2-6}$alkenyl, $C_{2-6}$alkynyl, halo$C_{1-6}$alkyl, —O$C_{1-6}$alkyl, halo$C_{1-6}$alkyloxy, —$C_{1-6}$alkyl-OH, NH$_2$, N—($C_{1-6}$alkyl)amino, N,N-di($C_{1-6}$alkyl)amino, —C(=O)$C_{1-6}$alkyl, —O(C=O)$C_{1-6}$alkyl, —C(=O)OH, —C(=O)O$C_{1-6}$alkyl, —C(=O)NH$C_{1-6}$alkyl and —NHC(=O)$C_{1-6}$alkyl;

(ii) $W^1$ and $W^3$ are selected from (i-a) to (i-l), $W^2$ is —CH=CH—, —CH(OH)CH(OH)—, —CH=CH—CH(OH)—, or —CH=CH—CH=CH—, $X^2$ is —C(=O)— or —CH$_2$—, $X^1$ is —C(=O)NH— or —C(=O)O—;

(iii) $W^1$ is —CH=CH—, $X^1$ is a bond and $W^2$ and $W^3$ are independently selected from (i-a) to (i-l);

(iv) $W^2$ is >C(=O) or —C(=O)NH— and $W^1$ and $W^3$ are independently selected from (i-a) to (i-l), provided when $W^1$ is absent, $m^1$ cannot be zero; or (v) all absent.

In one embodiment, the present invention is directed to compounds of formula (III).

In one embodiment, the compound of formula (III) of the invention is represented by formula (III-i):

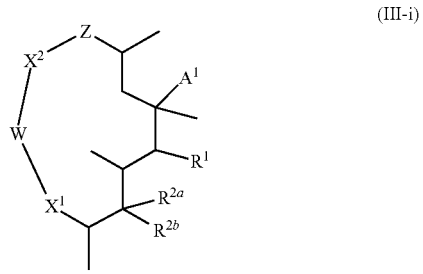

(III-i)

wherein Z, $A^1$, $R^1$, $R^{2a}$, $R^{2b}$, $X^1$, W and $X^2$ are as defined in any particular embodiment. In further embodiment, the compound of formula (III) of the invention is represented by formula (III-ii):

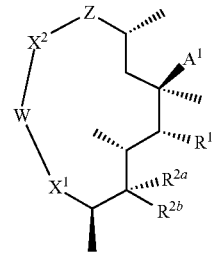

(III-ii)

wherein Z, $A^1$, $R^1$, $R^{1a}$, $R^{2b}$, $X^1$, W and $X^2$ are as defined in any particular embodiment.

For compounds of formulae (I), (II) and (III), if not already defined in particular embodiment in question, $R^N$, $Z^1$, $Z^2$, $A^1$, $R^1$, $R^{2a}$, $R^{2b}$, $X^1$, W and $X^2$ can have below specified subsets of meanings.

In one embodiment $R^N$ is hydrogen, $G^1$ (preferably CH$^3$), or $R^{12b}$ wherein $R^{12b}$ is $C_{1-4}$alkyl-G, —C(=O)G, —C(=O)NH—$C_{0-4}$alkyl-G, wherein G is $G^1$, $G^2$, $G^3$, $G^4$ or $G^5$. In further embodiment $R^N$ is hydrogen, $G^1$ (preferably CH$^3$), or $R^{12b}$ wherein $R^{12b}$ is $C_{1-4}$alkyl-G, —C(=O)G, —C(=O)NH—$C_{0-4}$alkyl-G, wherein G is $G^4$ or $G^5$ (suitably G is $G^4$, wherein $G^4$ is phenyl which may be optionally substituted by halogen). In even further embodiment $R^N$ is hydrogen, $G^1$ (preferably CH$^3$), or $R^{12b}$ wherein $R^{12b}$ is $C_{1-4}$alkyl-G (suitably CH$_2$-phenyl, —CH$_2$CH$_2$-phenyl, wherein phenyl may be optionally substituted, suitably by halogen), —C(=O)G (suitably C(=O)CH$_2$-phenyl, wherein phenyl may be optionally substituted, suitably by halogen), —C(=O)NH—$C_{0-4}$alkyl-G (suitably C(=O)NH-phenyl, —C(=O)NHCH$_2$-phenyl, wherein phenyl may be optionally substituted, suitably by halogen).

In one embodiment $R^N$ is CH$_3$. In further embodiment $R^N$ is hydrogen.

In one embodiment $Z^1$ and $Z^2$ are both hydrogen. In further embodiment $Z^1$ and $Z^2$ together with carbon atom to which they are attached form a keto (carbonyl) group.

In one embodiment $Z^1$ and $Z^2$ are both hydrogen and $R^N$ is CH$_3$ or hydrogen. In further embodiment, $Z^1$ and $Z^2$ together with carbon atom to which they are attached form a keto (carbonyl) group and $R^N$ is hydrogen.

In one embodiment $A^1$ is OH or OCH$_3$ and $A^2$ is CH$_3$. In a further embodiment, $A^1$ together with $R^{2b}$ forms cyclic hemiketal or cyclic ether and $A^2$ is CH$_3$.

In one embodiment, $R^1$ is $S^1$ or OH. In a further embodiment $R^1$ is $S^1$.

In one embodiment, $S^1$ sugar group is represented by formula (b1-i):

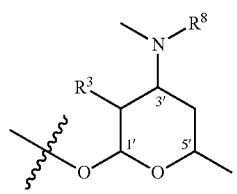

(b1-i)

wherein, $R^3$ and $R^8$ are as defined in any particular embodiment. In a further embodiment, $S^1$ sugar group is represented by formula (b1-ii):

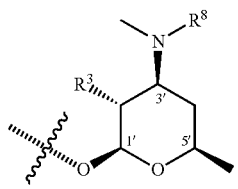

(b1-ii)

wherein, $R^3$ and $R^8$ are as defined in any particular embodiment.

In one embodiment, $R^3$ is OH, H or —O-$L^1$-G group. In further embodiment $R^3$ is OH or H. In even further embodiment $R^3$ is O-$L^1$-G group wherein $L^1$ is —$(CH_2)_{a1}$—$U^1$—$(CH_2)_{b1}$—, $U^1$ is —NHC(=O)—, $a^1$ is an integer from 2 to 6, $b^1$ is 0 to 6; and G is selected from $G^1$ ($C_{1-6}$ alkyl), $G^3$ (4-7 membered heterocycloalkyl) and $G^5$ (heteroaryl). In yet further embodiment $R^3$ is O-$L^1$-G group wherein $L^1$ is —$(CH_2)_{a1}$—$U^1$—$(CH_2)_{b1}$—, $U^1$ is —NHC(=O)—, $a^1$ is 3, $b^1$ is 0 or 1; and G is $C_{1-6}$alkyl (suitably ethyl), 6 membered heterocycloalkyl (suitably piperazinyl), or 5 membered heteroaryl (suitably 1H-piperazolyl). In one embodiment, $R^8$ is H or $G^1$ or —C(=O)$R^9$. In further embodiment, $R^8$ is H or $C_{1-4}$alkyl. In even further embodiment, $R^8$ is H, methyl, ethyl, or isopropyl. In yet further embodiment $R^8$ is —C(=O)$R^9$ and $R^9$ is $G^1$ ($C_{1-6}$alkyl). Suitably $G^1$ ($C_{1-6}$alkyl) is methyl or ethyl.

In one embodiment, $S^1$ sugar group is represented by formula (b2-i):

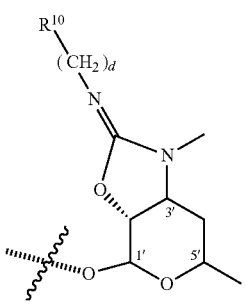

(b2-i)

wherein, $R^{10}$ and d are as defined in any particular embodiment. In a further embodiment, $S^1$ sugar group is represented by formula (b2-ii):

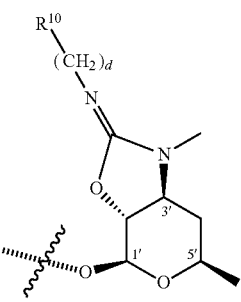

(b2-ii)

wherein, $R^{10}$ and d are as defined in any particular embodiment.

In one embodiment d is 0 and $R^{10}$ is $C_{1-6}$alkyl. In a further embodiment d is 0 and $R^{10}$ is isopropyl.

In one embodiment, $R^{2a}$ is OH or $S^2$. In a further embodiment $R^{2a}$ is $S^2$. In even further embodiment $R^{2a}$ is OH. In yet further embodiment, $R^{2a}$ together with $B^2$ forms a double bond or together with $R^{2b}$ forms a keto group. In even further embodiment $R^{2a}$ is OC(=O)$Y^1$, wherein $Y^1$ is $G^2$ (3-7 membered cycloalkyl) or $G^3$ (4-7 membered heterocycloalkyl). Suitably $G^2$ is cyclohexyl which may be optionally substituted (for example with halogen). Suitably $G^3$ is tetrahydropyranyl. In yet further embodiment $R^{2a}$ is —OC(=O)$Y^1$ wherein $Y^1$ is $G^1$ $C_{1-6}$alkyl (suitably methyl, ethyl or propyl), interrupted by N($R^{91}$), wherein $R^{91}$ is H or $C_{1-6}$alkyl (suitably methyl or ethyl). For example, $R^{2a}$ is OC(=O)—$CH_2N(CH_2CH_3)_2$.

In one embodiment, $S^2$ sugar group is represented by formula (d-i):

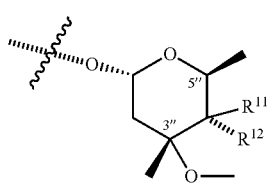

(d-i)

wherein, $R^{11}$ and $R^{12}$ are as defined in any particular embodiment.

In one embodiment $R^{11}$ is H and $R^{12}$ is OH. In a further embodiment $R^{11}$ together with $R^{12}$ and carbon atom to which they are attached forms keto or epoxy group. In even further embodiment, one of $R^{11}$ and $R^{12}$ is OH and the other is $CH_2N(R^{13})R^{14}$.

In one embodiment one of $R^{13}$ and $R^{14}$ is $C_{1-6}$alkyl (suitably methyl or ethyl) and the other is H or $C_{1-6}$alkyl (suitably methyl or ethyl). In a further embodiment both $R^{13}$ and $R^{14}$ are $C_{1-6}$alkyl (suitably methyl or ethyl). In even further embodiment $R^{13}$ and $R^{14}$ together with nitrogen to which they are attached form a heterocyclic ring (suitably morpholinyl).

In one embodiment, the compound of the invention is according to formula (III), wherein $X^1$ is bond, C(=O)NR$^x$—, C(=O)O—, C(=O)—, —NR$^u$—, —$CH_2$NR$^u$—, or —$CH_2$O—. In a further embodiment, $X^1$ is —C(=O)O—. In even further embodiment, $X^1$ is —C(=O)NR$^x$—, wherein R$^x$ is hydrogen. In yet further embodiment, $X^1$ is —C(=O)—. In yet further embodiment, $X^1$ is a bond. In additional embodiment, $X^1$ is NHC(=O)— or NH—. In a further embodiment $X^1$ is —NR$^u$—, —$CH_2$NR$^u$—, or —$CH_2$O—.

In one embodiment, the compound of the invention is according to formula (III), wherein $X^2$ is C(=O)— or a bond. In a further embodiment, $X^2$ is C(=O)— or $CH_2$—. In even further embodiment, $X^2$ is bond or $CH_2$—.

In one embodiment, the compound of the invention is according to formula (III), wherein $W^1$, $W^2$ and $W^3$ are absent. In a further embodiment, $W^1$, $W^2$ and $W^3$ are absent and one of $m^1$ and $m^2$ is zero and the other of $m^1$ and $m^2$ is 1, 2 or 3. In even further embodiment, $W^1$, $W^2$ and $W^3$ are absent and one of $m^1$ and $m^2$ is zero and the other is 2 or 3. In yet a further embodiment, $W^1$, $W^2$ and $W^3$ are absent and both $m^1$ and $m^2$ are zero.

In one embodiment, one of $W^1$, $W^2$ and $W^3$ is selected from any of $W^1$, $W^2$ and $W^3$ definitions specified for formula (III), list (i) and the other two are absent. In a further embodiment, two of $W^1$, $W^2$ and $W^3$ are selected from any of $W^1$, $W^2$ and $W^3$ definitions specified for formula (III), list (i) and the other one is absent. In even further embodiment, all three of $W^1$, $W^2$ and $W^3$ are selected from any of $W^1$, $W^2$ and $W^3$ definitions specified for formula (III), list (i).

In one embodiment, the compound of the invention is according to formula (III), wherein one of $W^1$, $W^2$ and $W^3$ is 3-7 membered cycloalkyl. In a further embodiment, one of $W^1$, $W^2$ and $W^3$ is cyclohexyl or cyclopentyl. In even further embodiment, one of $W^1$, $W^2$ and $W^3$ is 3-7 membered cycloalkyl one of $m^1$ and $m^2$ is zero and the other is 1 or both are zero.

In one embodiment, the compound of the invention is according to formula (III), wherein one of $W^1$, $W^2$ and $W^3$ is 4-7 membered cycloalkenyl. In a further embodiment, one of $W^1$, $W^2$ and $W^3$ is cyclohexenyl. In even further embodiment, one of $W^1$, $W^2$ and $W^3$ is 4-7 membered cycloalkenyl and both $m^1$ and $m^2$ are zero.

In one embodiment, the compound of the invention is according to formula (III), wherein one of $W^1$, $W^2$ and $W^3$ is 3-7 membered heterocycloalkyl. In a further embodiment, one of $W^1$, $W^2$ and $W^3$ is selected from azetidinyl, piperidinyl, pyrrolidinyl and piperazinyl. In even further embodiment, heterocycloalkyl may be optionally substituted by one or more groups independently selected from halogen and —$C_{0-6}$alkyl-aryl (suitably phenyl). In yet further embodiment, $W^1$ is 3-7 membered heterocycloalkyl, $W^2$ and $W^3$ are absent.

In one embodiment, the compound of the invention is according to formula (III), wherein one of $W^1$, $W^2$ and $W^3$ is aryl. In a further embodiment, one of $W^1$, $W^2$ and $W^3$ is phenyl. In even further embodiment, phenyl is 1,3- or 1,4-attached and unsubstituted.

In one embodiment, the compound of the invention is according to formula (III), wherein one of $W^1$, $W^2$ and $W^3$ is 5-6 membered heteroaryl. In a further embodiment, one of $W^1$, $W^2$ and $W^3$ is selected from oxazolyl, thiazolyl and triazolyl. In even further embodiment, heteroaryl is substituted by $C_{1-6}$alkyl, halo$C_{1-6}$alkyloxy, —C(=O)OH or —C(=O)O$C_{1-6}$alkyl. In even further embodiment, heteroaryl is substituted by $C_{1-6}$alkyl (suitably methyl).

In one embodiment, the compound of the invention is according to formula (III), wherein one of $W^1$, $W^2$ and $W^3$ is —C($R^{W1a}$)($R^{W2a}$)— wherein $R^{W1a}$ is hydrogen and $R^{W2a}$ is $C_{1-6}$alkyl, $C_{2-6}$alkenyl, $C_{2-6}$alkynyl, halogen, OH, CN, —C(=O)OH, —C(=O)NH$_2$, halo$C_{1-6}$alkyl, O$C_{1-6}$alkyl, $C_{1-6}$alkyl-OH, —$C_{1-6}$alkylO$C_{1-6}$alkyl, —$C_{1-6}$alkylS$C_{1-6}$alkyl, —$C_{1-6}$alkyl-C(=O)OH, $C_{1-6}$alkyl-C(=O)O$C_{1-6}$alkyl, —$C_{1-6}$alkylOC(=O)$C_{1-6}$alkyl, —$C_{1-6}$alkylC(=O)NH$_2$, —$C_{1-6}$alkyl-NH$_2$, —$C_{1-6}$alkyl-NH($C_{1-6}$alkyl), —$C_{1-6}$alkyl-N($C_{1-6}$alkyl)$_2$, —$C_{1-6}$alkylNHC(=O)O$C_{1-6}$alkyl, —$C_{1-6}$alkyl-NHC(=O)$C_{2-6}$alkenyl, —$C_{1-6}$alkyl-NHC(=O)—$C_{0-4}$alkyl-heteroaryl, —$C_{1-6}$alkyNHSO$_2$$C_{1-6}$alkyl, —$C_{1-6}$alkylNHSO$_2$$C_{2-6}$alkenyl, —$C_{1-6}$alkylNHSO$_2$cycloalkyl, —$C_{0-6}$alkyl-aryl, —$C_{2-6}$alkenyl-aryl, —$C_{0-6}$alkyl-heteroaryl, —$C_{2-6}$alkenyl-heteroaryl, —$C_{0-6}$alkyl-cycloalkyl, or —$C_{0-6}$alkyl-heterocycloalkyl, wherein alkyl, alkenyl, alkynyl, aryl, heteroaryl, cycloalkyl, and heterocycloalkyl independently from each other may be optionally substituted by one or more groups independently selected from halogen, CN, OH, NO$_2$, $C_{1-6}$alkyl, $C_{2-6}$alkenyl, $C_{2-6}$alkynyl, halo$C_{1-6}$alkyl, —O$C_{1-6}$alkyl, halo$C_{1-6}$alkyloxy, $C_{1-6}$alkyl-OH, NH$_2$, N—($C_{1-6}$-alkyl)amino, N,N-di($C_{1-6}$alkyl)amino, —C(=O)$C_{1-6}$alkyl, —OC(=O)$C_{1-6}$alkyl, —C(=O)OH, —C(=O)O$C_{1-6}$alkyl, —C(=O)NH$C_{1-6}$alkyl, —NHC(=O)$C_{1-6}$alkyl, —$C_{1-6}$alkylNHSO$_2$$C_{1-6}$alkyl, and —$C_{1-6}$alkyl-NH(C=NH)NHR$^g$ wherein R$^g$ is H, amino protecting group, —$C_{0-6}$alkyl-aryl, —O$C_{0-6}$alkylaryl, —$C_{0-6}$alkyl-heteroaryl, —$C_{0-6}$alkyl-cycloalkyl or —$C_{0-6}$alkyl-heterocycloalkyl, wherein aryl, heteroaryl, cycloalkyl, and heterocycloalkyl independently from each other may be optionally substituted by one or more groups independently selected from halogen, CN, OH, NO$_2$, $C_{1-6}$alkyl, $C_{2-6}$alkenyl, $C_{2-6}$alkynyl, halo$C_6$alkyl, —O$C_{1-6}$alkyl, halo$C_6$alkyloxy, $C_{1-6}$alkyl-OH, NH$_2$, N—($C_{1-6}$-alkyl)amino, N,N-di($C_{1-6}$alkyl)amino, —C(=O)$C_{1-6}$alkyl, —OC(=O)$C_{1-6}$alkyl, —C(=O)OH, —C(=O)O$C_{1-6}$alkyl, —C(=O)NH$C_{1-6}$alkyl and —NHC(=O)$C_{1-6}$ alkyl. In further embodiment, $R^{W1a}$ is hydrogen and $R^{W2a}$ is $C_{0-6}$alkyl-aryl, —$C_{0-6}$alkyl-heteroaryl or —$C_{0-6}$alkenyl-heteroaryl (suitably $C_{0-6}$alkyl-aryl is —CH$_2$-phenyl, —CH$_2$CH$_2$-phenyl or —CH$_2$CH$_2$CH$_2$-phenyl wherein phenyl is optionally substituted by halogen (Cl or Br), $C_{1-6}$alkyl or —O$C_{1-6}$alkyl; —$C_{0-6}$alkyl-heteroaryl is —CH$_2$-(1H-indol-3-yl) or —CH$_2$-benzothiophenyl, and —$C_{0-6}$alkenyl-heteroaryl is —CH=CH-indolyl).

In one embodiment, the compound of the invention is according to formula (III), wherein one of $W^1$, $W^2$ and $W^3$ is —C($R^{W1b}$)($R^{W2b}$)— group wherein $R^{W1b}$ and $R^{W2b}$ together with carbon atom to which they are attached form 3-7 membered spiro cycloalkyl group or 3-7 membered spiro heterocycloalkyl group. In further embodiment, 3-7 membered spiro cycloalkyl group is cyclohexyl or cyclopentyl. In even further embodiment, 3-7 membered spiro heterocycloalkly group is tetrahydro-pyranyl.

In one embodiment, the compound of the invention is according to formula (III), wherein one of $W^1$, $W^2$ and $W^3$ is —N($R^{Wn}$)—, wherein $R^{Wn}$ is —$C_{1-6}$alkyl-aryl wherein aryl may be optionally substituted (suitably by halogen). In further embodiment, aryl is phenyl.

In one embodiment, the compound of the invention is according to formula (III), wherein one of $W^1$, $W^2$ and $W^3$ is [—NHCH($R^t$)C(=O)—]$_{t1}$ or

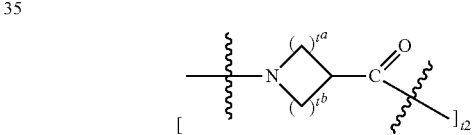

group, wherein $t^1$ and $t^2$ independently are 1 to 5, $t_a$ and $t_b$ independently are 0 to 3, provided sum of $t^a$ and $t^b$ is 2 to 6, $R^t$ is residue of natural amino acid selected from H, $C_{1-6}$alkyl, —$C_{1-6}$alkyl-S$C_{1-6}$alkyl, —$C_{0-6}$alkyl-aryl or —$C_{0-6}$alkyl-heteroaryl wherein aryl and heteroaryl may be mono or biyclic and each may be optionally substituted by one or more groups independently selected from halogen, CN, OH, NO$_2$, O$C_{1-6}$alkyl, NH$_2$, N—($C_{1-6}$alkyl)amino, N,N-di($C_{1-6}$alkyl)amino, —(C=O)$C_{1-6}$alkyl, —O(C=O)$C_{1-6}$alkyl, —C(=O)OH, —C(=O)O$C_{1-6}$alkyl, —C(=O)NH$C_{1-6}$alkyl and —NHC(=O)$C_{1-6}$alkyl. In further embodiment, $t^1$ and $t^2$ independently are 1 to 5 (suitably combination of $W^1$, $W^2$ and $W^3$ form di- or tripeptide), to is 3 and $t_b$ is zero, $R^t$ is residue of natural amino acid selected from H, $C_{1-6}$alkyl, —$C_{1-6}$alkyl-S$C_{1-6}$alkyl (suitably —CH$_2$CH$_2$S—CH$_3$), or —$C_{0-6}$alkyl-aryl (suitably —$C_{0-6}$alkyl-aryl is —CH$_2$-Ph).

In one embodiment, the compound of the invention is according to formula (III), wherein one of $W^1$, $W^2$ and $W^3$ is —NHC($R^{W1d}$)($R^{W2d}$)C($R^{W1e}$)($R^{W2e}$)—NHC(=O)— group wherein $R^{W1d}$ and $R^{W1e}$ are hydrogen, and $R^{W2d}$ and $R^{W2e}$ are independently from each other $C_{0-4}$alkylaryl wherein aryl (suitably $C_{0-4}$alkylaryl is phenyl) may be optionally substituted by one or more groups independently selected from halogen, CN, OH, NO$_2$, $C_{1-6}$alkyl, $C_{2-6}$alkenyl, $C_{2-6}$alkynyl, halo$C_{1-6}$alkyl, —O$C_{1-6}$alkyl, halo$C_{1-6}$alkyloxy, —$C_{1-6}$alkyl-OH, $NH_2$, N—($C_{1-6}$alkyl)amino, N,N-di($C_{1-6}$alkyl)amino, —C(=O)$C_{1-6}$alkyl, —O(C=O)$C_{1-6}$alkyl, —C(=O)OH, —C(=O)O$C_{1-6}$alkyl, —C(=O)NH$C_{1-6}$alkyl and —NHC(=O)$C_{1-6}$alkyl. In a further embodiment, the compound of the invention is according to formula (III), wherein one of $W^1$, $W^2$ and $W^3$ is —NHC($R^{W1d}$)($R^{W2d}$)C($R^{W1e}$)($R^{W2e}$)—NHC(=O)— group wherein $R^{W1d}$ and $R^{W1e}$ are hydrogen, and $R^{W2d}$ and $R^{W2e}$ are independently from each other phenyl substituted by halogen (suitably Cl).

In one embodiment, the compound of the invention is according to formula (III), wherein $W^2$ is >C(=O), provided $W^1$ is absent, m1 is 1 and $W^3$ is heterocycloalkyl. In further embodiment, heterocycloalkyl is pyrrolidinyl.

In one embodiment, the compound of the invention is according to formula (III), wherein $W^1$, $W^2$ and $W^3$ are selected from formula (III) list: (i): a, b, c, e, f, g, h, i, k, l, (ii), (iv) and (v). In a further embodiment, the compound of the invention is according to formula (III), wherein $W^1$, $W^2$ and $W^3$ are selected from formula (III) list: (i): a, b, c, e, f, g, h, i, k and l and (v). In even further embodiment, the compound of the invention is according to formula (III), wherein $W^1$, $W^2$ and $W^3$ are selected from formula (III) list: (i): g (C($R^{W1a}$)($R^{W2a}$)), i (—N($R^{Wn}$))—, and (v). In yet further embodiment, the compound of the invention is according to formula (III), wherein $W^1$, $W^2$ and $W^3$ are selected from formula (I) list: (i): g (—C($R^{W1a}$)($R^{W2a}$)).

In one embodiment, the compound of the invention is according to formula (III), wherein both m and n are zero. In a further embodiment, one of $m^1$ and $m^2$ is zero and the other is 1, 2 or 3. In even further embodiment, one of $m^1$ and $m^2$ is zero and the other is zero or 1. In yet further embodiment, $m^1$ is 2 and $m^2$ is 1. In additional embodiment, $m^1$ is 1 or 2 and $m^2$ is zero.

In one embodiment the compound and intermediate of the invention is not an isotopic variant.

In one aspect a compound and intermediate of the invention according to any one of the embodiments herein described is a free base.

In one aspect a compound and intermediate of the invention according to any one of the embodiments herein described is a salt.

In one aspect a compound of the invention according to any one of the embodiments herein described is a pharmaceutically acceptable salt.

In one aspect a compound and intermediate of the invention according to any one of the embodiments herein described is a solvate of the compound.

In one aspect a compound of the invention according to any one of the embodiments herein described is a solvate of a salt of a compound, in particular a solvate of a pharmaceutically acceptable salt.

Similarly, reference to intermediates of the invention, whether or not they themselves are claimed, is meant to embrace their salts, and solvates, where the context so permits.

With regard to stereoisomers, the compounds and intermediates of the invention have more than one asymmetric carbon atom. In the general formula(e) as drawn, the solid wedge shaped bond indicates that the bond is above the plane of the paper. The broken bond indicates that the bond is below the plane of the paper.

It will be appreciated that the substituents on the compounds and intermediates of the invention may also have one or more asymmetric carbon atoms. Thus, the compounds and intermediates of the invention may occur as individual enantiomers or diastereomers. All such isomeric forms are included within the present invention, including mixtures thereof.

Where a compound and intermediate of the invention contains an alkenyl group, cis (Z) and trans (E) isomerism may also occur. The present invention includes the individual stereoisomers of the compound and intermediate of the invention, and where appropriate the individual tautomeric forms thereof, together with mixtures thereof.

Separation of diastereoisomers or cis and trans isomers may be achieved by conventional techniques, e.g. by fractional crystallisation, chromatography or HPLC. A stereoisomeric mixture of the agent may also be prepared from a corresponding optically pure intermediate or by resolution, such as by HPLC, of the corresponding mixture using a suitable chiral support or by fractional crystallisation of the diastereoisomeric salts formed by reaction of the corresponding mixture with a suitable optically active acid or base, as appropriate.

Unless otherwise stated, in formulae disclosed herein a bond drawn without any attached group means a methyl group.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

While specified groups for each embodiment have generally been listed above separately, a compound and intermediate of the invention may be one for which one or more variables (R groups and/or integers) is selected from one or more embodiments according to any of the Formula(e) listed above. Therefore, the present invention is intended to include all combinations of variables from any of the disclosed embodiments within its scope.

Alternatively, the exclusion of one or more of the specified variables from a group or an embodiment, or combinations thereof is also contemplated by the present invention.

In certain aspects, the present invention provides prodrugs and derivatives of the compounds of the invention according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H. Design of Prodrugs, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy) alkyl esters or ((alkoxycarbonyl)oxy)alkylesters. Particularly useful are the $C_1$ to $C_8$ alkyl, $C_2$-$C_8$ alkenyl, aryl, substituted aryl, and arylalkyl esters of the compounds of the invention.

A person of skill in the art will appreciate that when administered in vivo compounds of the invention may be metabolised and that some of these biological metabolites may be active. In one aspect, the present invention therefore provides for biologically active metabolites of compounds of the invention.

In a further embodiment, the present invention also relates to process for preparation of compound of formula (III), which comprises following steps:
- (a-1) process steps from (a) to (m) for preparation of compound of formula (I) followed by:
- (b-1) reacting a compound of formula (I) obtained in step (a-1) with a compound of formula $X^{1m}$—$W^m$—$X^{2m}$, wherein $X^{1m}$ and km are the appropriate reactive or leaving groups or groups convertable to $X^1$ and $X^2$ as defined above for formula (III), and $W^m$ is W or the appropriate precursor convertable to W wherein W is as defined for formula (III) above;
- (c-1) cyclizing compound obtained in step (b-1) and thereafter, if required after any of steps (a-1) to (c-1), subjecting the resulting compound to one or more of the following operations:
  - (i) removal of the protecting group $R^p$,
  - (ii) conversion of $X^{1m}$, $X^{2m}$ and $W^m$ to $X^1$, $X^2$ and W,
  - (iii) removal of $S^2$ sugar group and/or Si sugar group,
  - (iv) conversion of the resulting compound of formula (III) into a pharmaceutically acceptable salt, solvate, or prodrug thereof.

In one embodiment, process steps (a-1) to (c-1) of the present invention for preparation of compound of formula (III) are performed according to general methods and procedures described in Methods A, B, C, D, E, FA, FB, K, M and RE, CY-1, CY-2, CY-3, CY-4G, CY-4H, CY-4I, CY-4J, CY-5, CY-6, CY-7A, CY-7B, CY-7C, CY-8, CY-9, CY-10A, CY-10B, CY-11, CY-12, CY-13, as well as KA, KB, KC, KD, KE, KF, KG-A, KG-B, KH, KI, KJ, KL-A, KL-B, KL-C, KM, KN, KO, KP, KR, KS and Schemes associated with these general methods in General synthetic procedures section below.

In one embodiment, process step (b-1) of the present invention for preparation of compound of formula (III) is performed by reacting a compound of formula (I) obtained in step (a-1) with a compound of formula $X^{1m}$—$W^m$—$X^{2m}$, wherein $X^{1m}$ and $X^{2m}$ are the appropriate reactive or leaving groups or groups convertable to $X^1$ and $X^2$ as defined above for formula (III), and $W^m$ is W or the appropriate precursor convertable to W wherein W is as defined for formula (III) above. In a further embodiment, process step (b-1) of the present invention for preparation of compound of formula (III) is performed by reacting a compound of formula 0-0 obtained in step (a-1) with a compound of formula $X^{1m}$—$W^m$—$X^{2m}$. In even further embodiment, process step (b-1) of the present invention for preparation of compound of formula (III) is performed by reacting a compound of formula (I-ii) obtained in step (a-1) with a compound of formula $X^{1m}$—$W^m$—$X^{2m}$. In yet further embodiment, process step (b-1) of the present invention for preparation of compound of formula (III) is performed by reacting a compound of formula (I-iii) obtained in step (a-1) with a compound of formula $X^{1m}$—$W^m$—$X^{2m}$.

In one embodiment, in the process of the present invention for preparation of compound of formula (III) identification of compound of formula $X^{1m}$—$W^m$—$X^{2m}$ used in step (b-1) is performed using fragment based drug discovery (FBDD) approach. In a further embodiment, in the process of the present invention for preparation of compound of formula (III) identification of precursor $W^m$ used in step (b-1) is performed using fragment based drug discovery (FBDD) approach.

Pharmaceutical Compositions

While it is possible that, for use in the methods of the invention, a compound of Formula (III) may be administered as the bulk substance, it is preferable to present the active ingredient in a pharmaceutical formulation as a pharmaceutical composition. Thus, when employed as a pharmaceutical, a compound of Formula (III) is typically administered in the form of a pharmaceutical composition. Such compositions can be prepared in a manner well known in the pharmaceutical art and comprise at least one active compound. Generally, a compound of Formula (III) is administered in a therapeutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the invention can be administered by a variety of routes including oral, rectal, transdermal, subcutaneous, intra-articular, intravenous, intramuscular, and intranasal. Depending on the intended route of delivery, a compound of Formula (III) is preferably formulated as either injectable or oral compositions or as salves, as lotions or as patches all for transdermal administration.

The compounds of the invention can be administered for immediate-, delayed-, modified-, sustained-, pulsed- or controlled-release applications.

The compositions for oral administration can take the form of bulk liquid solutions or suspensions, or bulk powders. More commonly, however, the compositions are presented in unit dosage forms to facilitate accurate dosing. The term 'unit dosage forms' refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampoules or syringes of the liquid compositions or pills, tablets, capsules or the like in the case of solid compositions. In such compositions, the compound of Formula (III) is usually a minor component (from about 0.1 to about 50% by weight or preferably from about 1 to about 40% by weight) with the remainder being various vehicles or carriers and processing aids helpful for forming the desired dosing form.

In one aspect, oral compositions are slow, delayed or positioned release (e.g., enteric especially colonic release) tablets or capsules. This release profile can be achieved for example, by use of a coating resistant to conditions within the stomach but releasing the contents in the colon or other portion of the GI tract wherein a lesion or inflammation site has been identified. Or a delayed release can be achieved by a coating that is simply slow to disintegrate. Or the two (delayed and positioned release) profiles can be combined in a single formulation by choice of one or more appropriate coatings and other excipients. Such formulations constitute a further feature of the present invention.

Suitable compositions for delayed or positioned release and/or enteric coated oral formulations include tablet formulations film coated with materials that are water resistant, pH sensitive, digested or emulsified by intestinal juices or sloughed off at a slow but regular rate when moistened. Suitable coating materials include, but are not limited to, hydroxypropyl methylcellulose, ethyl cellulose, cellulose acetate phthalate, polyvinyl acetate phthalate, hydroxypropyl methylcellulose phthalate, polymers of metacrylic acid and its esters, and combinations thereof. Plasticizers such as, but not limited to polyethylene glycol, dibutylphthalate, triacetin and castor oil may be used. A pigment may also be used to color the film. Suppositories are be prepared by using carriers like cocoa butter, suppository bases such as Suppocire C, and Suppocire NA50 (supplied by Gattefossé Deutschland GmbH, D-Weil am Rhein, Germany) and other Suppocire type excipients obtained by interesterification of hydrogenated palm oil and palm kernel oil ($C_8$-$C_{18}$ triglycerides), esterification of glycerol and specific fatty acids, or polyglycosylated glycerides, and whitepsol (hydrogenated plant oils derivatives with additives). Enemas are formulated by using the appropriate active compound according to the present invention and solvents or excipients for suspensions. Suspensions are produced by using micronized compounds, and appropriate vehicle containing suspension stabilizing agents, thickeners and emulsifiers like carboxymethylcellulose and salts thereof, polyacrylic acid and salts thereof, carboxyvinyl polymers and salts thereof, alginic acid and salts thereof, propylene glycol alginate, chitosan, hydroxypropylcellulose, hydroxypropylmethylcellulose, hydroxyethylcellulose, ethylcellulose, methylcellulose, polyvinyl alcohol, polyvinyl pyrrolidone, N-vinylacetamide polymer, polyvinyl methacrylate, polyethylene glycol, pluronic, gelatin, methyl vinyl ether-maleic anhydride copolymer, soluble starch, pullulan and a copolymer of methyl acrylate and 2-ethylhexyl acrylate lecithin, lecithin derivatives, propylene glycol fatty acid esters, glycerin fatty acid esters, sorbitan fatty acid esters, polyoxyethylene sorbitan fatty acid esters, polyethylene glycol fatty acid esters, polyoxyethylene hydrated caster oil, polyoxyethylene alkyl ethers, and pluronic and appropriate buffer system in pH range of 6.5 to 8. The use of preservatives, masking agents is suitable. The average diameter of micronized particles can be between 1 and 20 micrometers, or can be less than 1 micrometer. Compounds can also be incorporated in the formulation by using their water-soluble salt forms.

Alternatively, materials may be incorporated into the matrix of the tablet e.g. hydroxypropyl methylcellulose, ethyl cellulose or polymers of acrylic and metacrylic acid esters. These latter materials may also be applied to tablets by compression coating. Pharmaceutical compositions can be prepared by mixing a therapeutically effective amount of the active substance with a pharmaceutically acceptable carrier that can have different forms, depending on the way of administration. Pharmaceutical compositions can be prepared by using conventional pharmaceutical excipients and methods of preparation. The forms for oral administration can be capsules, powders or tablets where usual solid vehicles including lactose, starch, glucose, methylcellulose, magnesium stearate, di-calcium phosphate, mannitol may be added, as well as usual liquid oral excipients including, but not limited to, ethanol, glycerol, and water. All excipients may be mixed with disintegrating agents, solvents, granulating agents, moisturizers and binders. When a solid carrier is used for preparation of oral compositions (e.g., starch, sugar, kaolin, binders disintegrating agents) preparation can be in the form of powder, capsules containing granules or coated particles, tablets, hard gelatin capsules, or granules without limitation, and the amount of the solid carrier can vary (between 1 mg to 1 g). Tablets and capsules are the preferred oral composition forms.

Pharmaceutical compositions containing compounds of formula (III) may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

Examples of pharmaceutically acceptable disintegrants for oral compositions useful in the present invention include, but are not limited to, starch, pre-gelatinized starch, sodium starch glycolate, sodium carboxymethylcellulose, croscarmellose sodium, microcrystalline cellulose, alginates, resins, surfactants, effervescent compositions, aqueous aluminum silicates and crosslinked polyvinylpyrrolidone.

Examples of pharmaceutically acceptable binders for oral compositions useful herein include, but are not limited to, acacia; cellulose derivatives, such as methylcellulose, carboxymethylcellulose, hydroxypropylmethylcellulose, hydroxypropylcellulose or hydroxyethylcellulose; gelatin, glucose, dextrose, xylitol, polymethacrylates, polyvinylpyrrolidone, sorbitol, starch, pre-gelatinized starch, tragacanth, xanthane resin, alginates, magnesium-aluminum silicate, polyethylene glycol or bentonite.

Examples of pharmaceutically acceptable fillers for oral compositions include, but are not limited to, lactose, anhydrolactose, lactose monohydrate, sucrose, dextrose, mannitol, sorbitol, starch, cellulose (particularly microcrystalline cellulose), dihydro- or anhydro-calcium phosphate, calcium carbonate and calcium sulfate.

Examples of pharmaceutically acceptable lubricants useful in the compositions of the invention include, but are not limited to, magnesium stearate, talc, polyethylene glycol, polymers of ethylene oxide, sodium lauryl sulfate, magnesium lauryl sulfate, sodium oleate, sodium stearyl fumarate, and colloidal silicon dioxide.

Examples of suitable pharmaceutically acceptable flavourings for the oral compositions include, but are not limited to, synthetic aromas and natural aromatic oils such as extracts of oils, flowers, fruits (e.g., banana, apple, sour cherry, peach) and combinations thereof, and similar aromas. Their use depends on many factors, the most important being the organoleptic acceptability for the population that will be taking the pharmaceutical compositions.

Examples of suitable pharmaceutically acceptable dyes for the oral compositions include, but are not limited to, synthetic and natural dyes such as titanium dioxide, beta-carotene and extracts of grapefruit peel.

Suitable examples of pharmaceutically acceptable sweeteners for the oral compositions include, but are not limited to, aspartame, saccharin, saccharin sodium, sodium cyclamate, xylitol, mannitol, sorbitol, lactose and sucrose.

Suitable examples of pharmaceutically acceptable buffers include, but are not limited to, citric acid, sodium citrate, sodium bicarbonate, dibasic sodium phosphate, magnesium oxide, calcium carbonate and magnesium hydroxide.

Suitable examples of pharmaceutically acceptable surfactants include, but are not limited to, sodium lauryl sulfate and polysorbates.

Suitable examples of pharmaceutically acceptable preservatives include, but are not limited to, various antibacterial and antifungal agents such as solvents, for example ethanol, propylene glycol, benzyl alcohol, chlorobutanol, quaternary ammonium salts, and parabens (such as methyl paraben, ethyl paraben, propyl paraben, etc.).

Suitable examples of pharmaceutically acceptable stabilizers and antioxidants include, but are not limited to, ethylenediaminetetraacetic acid (EDTA), thiourea, tocopherol and butyl hydroxyanisole.

The compounds of the invention may also, for example, be formulated as suppositories e.g., containing conventional suppository bases for use in human or veterinary medicine or as pessaries e.g., containing conventional pessary bases.

The compounds of formula (III) may be formulated for topical administration, for use in human and veterinary medicine, in the form of ointments, creams, gels, hydrogels, lotions, solutions, shampoos, powders (including spray or dusting powders), pessaries, tampons, sprays, dips, aerosols, drops (e.g., eye ear or nose drops) or pour-ons.

For application topically to the skin, the compound of Formula (III) can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax, sorbitan monostearate, a polyethylene glycol, liquid paraffin, polysorbate 60, cetyl esters wax, cetearyl alcohol, 2-octyldodecanol, benzyl alcohol, and water. Such compositions may also contain other pharmaceutically acceptable excipients, such as polymers, oils, liquid carriers, surfactants, buffers, preservatives, stabilizers, antioxidants, moisturizers, emollients, colorants, and flavourings.

Examples of pharmaceutically acceptable polymers suitable for such topical compositions include, but are not limited to, acrylic polymers; cellulose derivatives, such as carboxymethylcellulose sodium, methylcellulose or hydroxypropylcellulose; natural polymers, such as alginates, tragacanth, pectin, xanthan and cytosan.

As indicated, the compound of Formula (III) can be administered intranasally or by inhalation and is conveniently delivered in the form of a dry powder inhaler or an aerosol spray presentation from a pressurized container, pump, spray or nebulizer with the use of a suitable propellant, e.g., a hydrofluoroalkane such as 1,1,1,2-tetrafluoroethane (HFA 134AT) or 1,1,1,2,3,3,3-heptafluoropropane (HFA 227EA), or a mixture thereof. In the case of a pressurized aerosol, the dosage unit may be determined by providing a valve to deliver a metered amount. The pressurized container, pump, spray or nebulizer may contain a solution or suspension of the active compound, e.g., using a mixture of ethanol and the propellant as the solvent, which may additionally contain a lubricant, e.g., sorbitan trioleate.

Capsules and cartridges (made, for example, from gelatin) for use in an inhaler or insufflator may be formulated to contain a powder mix of the compound and a suitable powder base such as lactose or starch.

For topical administration by inhalation the compounds of Formula (III) may be delivered for use in human or veterinary medicine via a nebulizer.

The pharmaceutical compositions of the invention may contain from 0.01 to 99% weight per volume of the active material. For topical administration, for example, the composition will generally contain from 0.01-10%, more preferably 0.01-1% of the active compound. A therapeutically effective amount of the compound of Formula (III) can be determined by methods known in the art. The therapeutically effective quantities will depend on the age and on the general physiological condition of the subject, the route of administration and the pharmaceutical formulation used. The therapeutic doses will generally be between about 10 and 2000 mg/day and suitably between about 30 and 1500 mg/day. Other ranges may be used, including, for example, 50-500 mg/day, 50-300 mg/day, 100-200 mg/day. The daily dose as employed for acute human treatment will range from 0.01 to 40 mg/kg body weight, suitably 2 to 20 mg/kg body weight, or suitably 5 to 10 mg/kg body weight, which may be administered in one to four daily doses, for example, depending on the route of administration and the condition of the subject. When the composition comprises dosage units, each unit will contain 10 mg to 2 g of active ingredient, suitably 200 mg to 1 g of active ingredient.

Administration may be once a day, twice a day, or more often, and may be decreased during a maintenance phase of treatment of the disease, e.g. once every second or third day instead of every day or twice a day. The dose and the administration frequency will depend on the clinical signs with the reduction or absence of at least one or more, preferably more than one, clinical signs of the acute phase known to the person skilled in the art. In one aspect of the present invention, administration is once daily oral dosing. The present invention is related to a pharmaceutical composition comprising a) 10 to 2000 mg of a compound of Formula (III) or a pharmaceutically acceptable salt thereof, and b) 0.1 to 2 g of one or more pharmaceutically acceptable excipients.

Methods of Treatment

In one embodiment, the present invention provides novel compounds of Formula (III), or pharmaceutical compositions comprising a compound of Formula (III), for use in medicine. In a particular embodiment, the present invention provides novel compounds of Formula (III) or pharmaceutical compositions comprising a compound of Formula (III), for use in the prophylaxis and/or treatment of conditions involving inflammation or immune responses and/or autoimmune diseases. Suitably, the present invention provides novel compounds of Formula (III) or pharmaceutical compositions comprising a compound of Formula (III), for use in the treatment of conditions involving inflammation or immune responses and/or autoimmune diseases.

In another embodiment, the present invention provides novel compounds of Formula (III), or pharmaceutical compositions comprising a compound of Formula (III) for use in the manufacture of a medicament for use in the prophylaxis and/or treatment of conditions involving inflammation or immune responses and/or autoimmune diseases.

In another embodiment, the present invention provides methods of prophylaxis and/or treatment of conditions involving inflammation or immune responses and/or autoimmune diseases, which methods comprise the administration of an effective amount of a compound of Formula (III) or one or more of the pharmaceutical compositions herein described for the treatment or prophylaxis of said condition. Suitably, the present invention provides methods of treatment of conditions involving inflammation or immune responses and/or autoimmune diseases, which methods comprise the administration of an effective amount of a compound of Formula (III) or one or more of the pharmaceutical compositions herein described for the treatment of said condition.

In another aspect the present invention provides a compound of Formula (III) or one or more of the pharmaceutical compositions for use in the prophylaxis and/or treatment of a condition involving inflammation or immune responses. In a specific embodiment, the condition involving inflammation or immune responses is selected from chronic obstructive pulmonary disease (COPD), cystic fibrosis (CF), diffuse panbronchiolitis (DPB), bronchiolitis obliterans (BOS), bronchitis, bronchiectasis, adult respiratory distress syndrome (ARDS), severe or steroid-resistant asthma, emphysema, chronic rhinosinusitis (with or without nasal polyposis), rheumatoid arthritis, gouty arthritis, inflammatory bowel disease (ulcerative colitis and Chron's disease), glomerulonephritis, damage from ischemic reperfusion, atherosclerosis, dermatoses such as psoriasis and vasculitis, systemic lupus erythematosus (SLE), systemic inflammatory response syndrome (SIRS), sepsis, ischemia-reperfusion injury, rosacea, periodontitis, gingival hyperplasia and prostatitis syndrome.

In further aspect the present invention provides the use of a compound of Formula (III) or one or more of the pharmaceutical compositions for use in the manufacture of a medicament for the prophylaxis and/or treatment of a condition involving inflammation or immune responses. In a specific embodiment, the condition involving inflammation or immune responses is selected from chronic obstructive pulmonary disease (COPD), cystic fibrosis (CF), diffuse panbronchiolitis (DPB), bronchiolitis obliterans (BOS), bronchitis, bronchiectasis, adult respiratory distress syndrome (ARDS), severe or steroid-resistant asthma, emphysema, chronic rhinosinusitis (with or without nasal polyposis), rheumatoid arthritis, gouty arthritis, inflammatory bowel disease (ulcerative colitis and Chron's disease), glomerulonephritis, damage from ischemic reperfusion, atherosclerosis, dermatoses such as psoriasis and vasculitis, systemic lupus erythematosus (SLE), systemic inflammatory response syndrome (SIRS), sepsis, ischemia-reperfusion injury, rosacea, periodontitis, gingival hyperplasia and prostatitis syndrome.

In additional method of treatment aspects, this invention provides methods of prophylaxis and/or treatment a subject susceptible to or afflicted with a condition involving inflammation or immune responses, which methods comprise the administration of an effective amount of a compound of Formula (III) or one or more of the pharmaceutical compositions herein described for the treatment or prophylaxis of said condition. In a specific embodiment, the condition involving inflammation or immune responses is selected from chronic obstructive pulmonary disease (COPD), cystic fibrosis (CF), diffuse panbronchiolitis (DPB), bronchiolitis obliterans (BOS), bronchitis, bronchiectasis, adult respiratory distress syndrome (ARDS), severe or steroid-resistant asthma, emphysema, chronic rhinosinusitis (with or without nasal polyposis), rheumatoid arthritis, gouty arthritis, inflammatory bowel disease (ulcerative colitis and Chron's disease), glomerulonephritis, damage from ischemic reperfusion, atherosclerosis, dermatoses such as psoriasis and vasculitis, systemic lupus erythematosus (SLE), systemic inflammatory response syndrome (SIRS), sepsis, ischemia-reperfusion injury, rosacea, periodontitis, gingival hyperplasia and prostatitis syndrome.

In another aspect the present invention provides a compound of Formula (III) or one or more of the pharmaceutical compositions for use in the prophylaxis and/or treatment of an autoimmune disease. In a specific embodiment, the autoimmune disease is selected from systemic lupus erythematosus (SLE), multiple sclerosis, diabetes (in particular type I diabetes mellitus), Sjogren syndrome, and inflammatory bowel diseases. In a further specific embodiment, the autoimmune disease is diabetes (in particular type I diabetes mellitus) and/or SLE. In a yet further specific embodiment, the autoimmune disease is multiple sclerosis. In an even further specific embodiment, the autoimmune disease is diabetes (particularly type I diabetes mellitus).

In yet another aspect the present invention provides the use of a compound of Formula (III) or one or more of the pharmaceutical compositions for use in the manufacture of a medicament for the prophylaxis and/or treatment of an autoimmune disease. In a specific embodiment, the autoimmune disease is selected from systemic lupus erythematosus (SLE), multiple sclerosis, diabetes (in particular type I diabetes mellitus), Sjogren syndrome, and inflammatory bowel diseases. In a further specific embodiment, the autoimmune disease is diabetes (in particular type I diabetes mellitus) and/or SLE. In a yet further specific embodiment, the autoimmune disease is multiple sclerosis. In an even further specific embodiment, the autoimmune disease is diabetes (particularly type I diabetes mellitus).

In additional method of treatment aspects, this invention provides methods of prophylaxis and/or treatment a subject susceptible to or afflicted with an autoimmune disease, which methods comprise the administration of an effective amount of a compound of Formula (III) or one or more of the pharmaceutical compositions herein described for the treatment or prophylaxis of said disease. In a specific embodiment, the autoimmune disease is selected from systemic lupus erythematosus (SLE), multiple sclerosis, diabetes (in particular type I diabetes mellitus), Sjogren syndrome, and inflammatory bowel diseases. In a further specific embodiment, the autoimmune disease is diabetes (in particular type I diabetes mellitus) and/or SLE. In a yet further specific embodiment, the autoimmune disease is multiple sclerosis. In an even further specific embodiment, the autoimmune disease is diabetes (particularly type I diabetes mellitus).

A compound of Formula (III) can be administered as the sole active agent or it can be administered in combination with other therapeutic agents, including other compounds that demonstrate the same or a similar therapeutic activity and that are determined to safe and efficacious for such combined administration. In a specific embodiment, co-administration of two (or more) agents allows for significantly lower doses of each to be used, thereby reducing the side effects seen.

In one embodiment, a compound of Formula (III) or a pharmaceutical composition comprising the compound of Formula (III) is administered as a medicament. In a specific embodiment, said pharmaceutical composition additionally comprises a further active ingredient.

In one embodiment, a compound of Formula (III) is co-administered with another therapeutic agent for the prophylaxis and/or treatment of conditions involving inflammation or immune responses; particular agents include, but are not limited to, immunoregulatory agents e.g. azathioprine, corticosteroids (e.g. prednisolone or dexamethasone), cyclophosphamide, cyclosporin A, tacrolimus, mycophenolate mofetil, muromonab-CD3 (OKT3, e.g. Orthocolone®), ATG, aspirin, acetaminophen, ibuprofen, naproxen, and piroxicam.

In one embodiment, a compound of Formula (III) is co-administered with another therapeutic agent for the prophylaxis and/or treatment of autoimmune diseases, particular agents include but are not limited to: corticosteroids, cytostatic agents (e.g. purine analogs), alkylating agents, (e.g. nitrogen mustards (cyclophosphamide), nitrosoureas, platinum compound of the inventions, and others), antimetabolites (e.g. methotrexate, azathioprine and mercaptopurine), cytotoxic antibiotics (e.g. dactinomycin anthracyclines, mitomycin C, bleomycin, and mithramycin), antibodies (e.g. anti-CD20, anti-CD25 or anti-CD3 (OTK3) monoclonal antibodies, Atgam® and Thymoglobuline®), cyclosporin, tacrolimus, rapamycin (sirolimus), interferons (e.g. IFN-β), TNF binding proteins (e.g. infliximab, etanercept, or adalimumab), mycophenolate, Fingolimod and Myriocin.

In one embodiment, a compound of Formula (III) is co-administered with another therapeutic agent for the prophylaxis and/or treatment of COPD, particular agents include but are not limited to: short-acting beta2-adrenoceptor agonists (e.g. salbutamol, fenoterol, levalbuterol, terbutaline and bitolterol), long-acting β2-agonists (e.g. salmeterol, formoterol, bambuterol, sustained-release oral albuterol, tulobuterol, indoacaterol and aformoterol), corticosteroids (oral/inhaled e.g. beclomethasone, budesonide, and fluticasone), combinations of inhaled steroids and long-acting bronchodilators (e.g. fluticasone/salmeterol, budesonide/formoterol), epinephrine (inhaled or tablets), anticholinergics (e.g. ipratropium bromide, oxitropium bromide and tiotropium), leukotriene antagonists and synthesis inhibitors (e.g. montelukast, zafirlukast and zileuton), inhibitors of mediator release (e.g. cromoglycate and ketotifen), biological regulators of IgE response (e.g. omalizumab), antihistamines (e.g. ceterizine, cinnarizine, fexofenadine), vasoconstrictors (e.g. oxymethazoline, xylomethazoline, nafazoline and tramazoline), methylxanthines (aminophylline and theophylline), and PDE-4 (roflumilast).

Additionally, a compound of Formula (III) may be administered in combination with emergency therapies for COPD, such therapies include oxygen or heliox administration, nebulized salbutamol or terbutaline (optionally combined with an anticholinergic (e.g. ipratropium), systemic steroids (oral or intravenous, e.g. prednisone, prednisolone, methylprednisolone, dexamethasone, or hydrocortisone), intravenous salbutamol, non-specific beta-agonists, injected or inhaled (e.g. epinephrine, isoetharine, isoproterenol, metaproterenol), anticholinergics (IV or nebulized, e.g. glycopyrrolate, atropine, ipratropium), methylxanthines (theophylline, aminophylline, bamiphylline), inhalation anesthetics that have a bronchodilatory effect (e.g. isoflurane, halothane, enflurane), ketamine and intravenous magnesium sulfate.

In one embodiment, a compound of Formula (III) is co-administered with another therapeutic agent for the treatment and/or prophylaxis of inflammatory bowel diseases (IBD), particular agents include but are not limited to: glucocorticoids (e.g. prednisone, budesonide) synthetic disease modifying, immunomodulatory agents (e.g. methotrexate, leflunomide, sulfasalazine, mesalazine, azathioprine, 6-mercaptopurine and cyclosporin) and biological disease modifying, immunomodulatory agents (infliximab, adalimumab, rituximab, and abatacept).

In one embodiment, a compound of Formula (III) is co-administered with another therapeutic agent for the treatment and/or prophylaxis of SLE, particular agents include but are not limited to: Disease-modifying antirheumatic drugs (DMARDs) such as antimalarials (e.g. plaquenil, hydroxychloroquine), immunosuppressants (e.g. methotrexate and azathioprine), cyclophosphamide and mycophenolic acid; immunosuppressive drugs and analgesics, such as nonsteroidal anti-inflammatory drugs, opiates (e.g. dextropropoxyphene and co-codamol), opioids (e.g. hydrocodone, oxycodone, MS Contin, or methadone) and the fentanyl duragesic transdermal patch.

By co-administration is included any means of delivering two or more therapeutic agents to the patient as part of the same treatment regime, as will be apparent to the skilled person. Whilst the two or more agents may be administered simultaneously in a single formulation, i.e. as a single pharmaceutical composition, this is not essential. The agents may be administered in different formulations and at different times.

General Synthetic Procedures

General

Compounds of Formula (I), (II) and (III) and salts thereof may be prepared by the general methods outlined hereinafter or any method known in the art, said methods constituting a further aspect of the invention. In the following description, the groups Z, $Z^1$, $Z^2$, $R^N$, $A^1$, $A^2$, $B^1$, $B^2$, $R^1$, $R^{2a}$, $R^{2b}$, $R^p$, W, $W^2$, $W^3$, $m^1$, $m^2$, and $R^3$ to $R^{15}$ have the meaning defined for the compounds of Formula (I), (II) and (III) unless otherwise stated.

A compound of the invention as well as intermediate of the invention can be prepared from readily available starting materials using the following general methods and procedures. It will be appreciated that where typical or preferred process conditions (i.e. reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures. Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, Protecting Groups in Organic Synthesis, Third Edition, Wiley, New York, 1999, and references cited therein.

The following methods are presented with details as to the preparation of a compound of the invention as well as intermediate of the invention as defined hereinabove and the comparative examples. A compound of the invention as well as intermediate of the invention may be prepared from known or commercially available starting materials and reagents by one skilled in the art of organic synthesis.

All reagents were of commercial grade and were used as received without further purification, unless otherwise stated. Commercially available anhydrous solvents were used for reactions conducted under inert atmosphere. Reagent grade solvents were used in all other cases, unless otherwise specified.

A compound of the invention as well as intermediate of the invention can be separated from a reaction mixture and further purified by a method such as column chromatography, high pressure liquid chromatography, or recrystallization.

Pharmaceutically acceptable acid addition salts, which also represent an object of the present invention, may be obtained by reaction of a compound of Formula (I), (II) and (III) with an at least equimolar amount of the corresponding inorganic or organic acid such as hydrochloric acid, hydroiodic acid, sulfuric acid, phosphoric acid, acetic acid, trifluoroacetic acid, propionic acid, benzoic acid, benzenesulfonic acid, methane sulfonic acid, laurylsulfonic acid, stearic acid, palmitic acid, succinic acid, ethylsuccinic acid, lactobionic acid, oxalic acid, salicylic acid and similar acid, in a solvent inert to the reaction. Addition salts are isolated by evaporating the solvent or, alternatively, by filtration after a spontaneous precipitation or a precipitation by the addition of a non-polar cosolvent. 9-Deoxo-9a-methyl-9a-aza-9a-homoerythromycin A, may be prepared by the procedure as described in *J. Chem. Res.* (S) 1988, page 152.

Compounds of Formula (II) wherein $R^N$ is hydrogen, $Z^1$ and $Z^2$ together with carbon atom to which they are attached form a keto group, and $A^1$ is $OCH_3$ are known compounds or they may be prepared from corresponding 6-O-methyl C/9-oximino compounds by Beckmann rearrangement according to the procedure described in WO99/51616.

Compounds of Formula (II) wherein $R^N$ is hydrogen, $Z^1$ and $Z^2$ are both hydrogen and $A^1$ is OH are known compounds or may be obtained by reduction of the corresponding 9a- or 8a-imino ether and than followed by reductive N-alkylation give analogues with $R^N$ is $C_{1-6}$alkyl according to the procedure described in *J. Chem. Soc. Perkin Trans* (1986) 1881-1890, *J. Chem Res. S* (1988) 152-153; (M) (1988) 1239-1261 and EP0508725.

Compounds of Formula (II) wherein $R^N$ is hydrogen, $Z^1$ and $Z^2$ are both hydrogen and $A^1$ is $OCH_3$ are known compounds or may be obtained by processes and methods described in *Bioorg. Med. Chem. Lett.* 8 (1998) 1321-1326.

Compounds of Formulae (II) or (III) wherein $R^N$ is other than hydrogen may be prepared by processes and methods described in WO2004101591, WO2006085228, WO2006087642, WO2007125414 international patent applications.

Compounds of Formulae (II) or (III) wherein C/3 is substituted may be prepared by processes and methods described in WO2006077501, WO2006087642, WO2004029067, and WO0063223.

Compounds of Formulae (II) or (III) wherein C/2'-O— is substituted may be prepared by processes and methods described in WO2009016142.

Compounds of formulae (II) or (III) wherein $R^3$ is O-$L^1$-G, $R^4$ is $N(CH_3)_2$, $R^5$ is H, and $L^1$ is —$(CH_2)_{a1}$—$U^1$—$(CH_2)_{b1}$ may be prepared by processes and methods described in WO2009016142 and WO2010086350 international patent applications.

Compounds of formulae (II) or (III) wherein both $R^4$ and $R^5$ are hydrogen or together form a bond may be prepared by processes and methods described in WO0042055 and WO2004005310.

Compounds of formulae (II) or (III) wherein $R^5$ is H and $S^1$ is sugar group of formula (b2) may be prepared by processes and methods described in WO2009130189.

Compounds of formulae (II) or (III) wherein $R^{2a}$ together with $R^{2b}$ forms a keto group (=O) or where $R^{2a}$ together with $B^2$ forms a double bond may be prepared by processes and methods described in WO2006087642.

Compounds of formulae (II) or (III) wherein $R^{2a}$ is —OC(=O)$Y^1$ may be prepared by processes and methods described in WO2006087642, WO2004029067, WO2004029067 and WO0063223.

Compounds of formulae (II) or (III) wherein $R^1$ is OH, $R^{2a}$ is OH and $R^{2b}$ is H, i.e. aglycone compounds may be prepared by processes and methods described in EP0283055.

List of abbreviations used in experimental section:

| | |
|---|---|
| AcOH | Acetic acid |
| Ac | acetic |
| anh. | anhydrous |
| AIBN | azobisisobutyronitrile |
| ABCN | 1,1'-azobis-cyclohexanecarbonitrile |
| CDI | carbonyldiimidazole |
| Cpd# | Compound number |
| DCC | Dicyclohexylcarbodiimide |
| DCE | 1,2-Dichloroethane |
| DBU | 1,8-Diazabicycloundec-7-ene |
| DABAL | Bis(trimethylaluminum)1,4-diazabicyclo[2.2.2]octane adduct |
| DCM | dichloromethane |
| DIPEA | diisopropyl N-ethylam |
| DMF | N,N-dinethylformamide |
| DMSO | dimethylsulfoxide |
| DPPA | diphenylphosphoryl azide |
| equiv./eq. | Equivalents |
| EDAC | 1-Ethyl-3-(3-dimethylaminopropyl)carbodiimide |
| EtOH | ethanol |
| Et3N | triethylamine |
| h | hour |
| HATU | (1-[Bis(dimethylamino)methylene]-1H-1,2,3-triazolo[4,5-b]pyridinium 3-oxid hexafluorophosphate) |
| HOAt | 1-Hydroxy-7-aza-benzotriazole |
| LiNTf2 | lithium bis(trifluoromethanesulfonimide) |
| LiEt3BH | Lithium triethylborohydride |
| MeCN | acetonitrile |
| Me-THF | 2-Methyl-tetrahydrofuran |
| MW | microwawe |
| NMO | N-methylmorpholine N-oxide |
| PS-CDI | Polymer supported carbonyl diimidazole |
| RCM | Ring Closing Metathesis |
| r.t. | room temperature |
| TEMPO | (2,2,6,6-tetramethylpiperidin-1-yl)oxidanyl |
| TEA | triethyl amine |
| T3P® | 1-Propanephosphonic acid cyclic anhydride |
| TFA | Trifluoroacetic acid |
| TFFH | Tetramethylfluoroformamidinium Hexafluorophosphate |
| THF | tetrahydrofuran |

The compounds and processes of the present invention will be better understood in connection with the following examples, which are intended as an illustration only and not limiting the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims. Where reactions are described as having been carried out in a similar manner to earlier, more completely described reactions, the general reaction conditions used were essentially the same. Work up conditions used were of the types standard in the art, but may have been adapted from one reaction to another. In the procedures that follow, reference to the product of a Description or Example by number is typically provided. This is provided merely for assistance to the skilled chemist to identify the starting material used. The starting material may not necessarily have been prepared from the batch referred to.

A compound of the invention as well as intermediate of the invention can be produced according to the following procedures.

Synthetic Preparation of the Seco Macrolide Compounds of Formula (I)

Method A: General Procedure for Preparation of Seco Macrolide Compound of Formula (I-A), Wherein $X^{1p}$ is

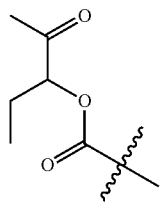 [SMILES: *C(=O)OC(CC)C(C)=O]

Group and $X^{2p}$ is H or $CH(CH_3)C(=O)H$ Group:

Scheme 1

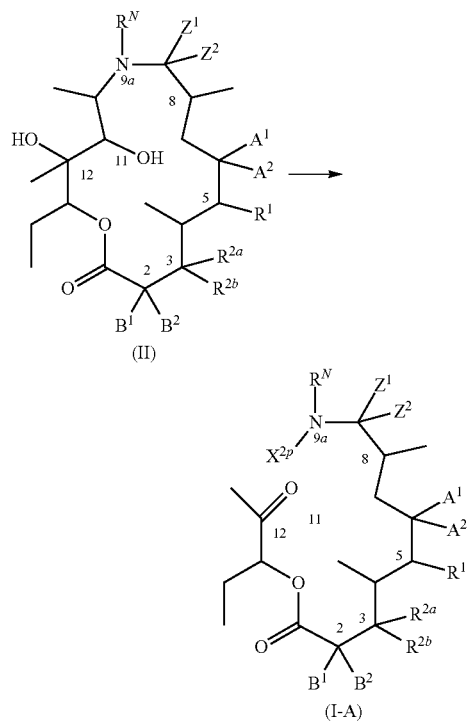

(I-A1): $X^{2p}$ = H;
(I-A2): $X^{2p}$ = —$CH(CH_3)C(=O)H$ and $R^N$=H

Scheme 1: illustrates ring cleavage reaction of compound of formula (II) using suitable oxidative cleavage reactant (suitably lead tetracaetate or sodium periodate), which in case when starting from compound of formula (II) where $Z^1$ and $Z^2$ are both hydrogen gives compound of formula (I-A$^1$), which is subset of compound of formula (I), wherein $X^{1p}$ is

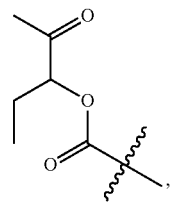 [SMILES: *C(=O)OC(CC)C(C)=O]

$X^{2p}$ is hydrogen, $Z^1$ and $Z^2$ are both hydrogen, $A^1$, $A^2$, $R^1$, $R^{2a}$, $R^{2b}$, $B^1$, $B^2$, and $R^N$ are as defined for formula (I); whereas in case when starting from compound of formula (II) where $Z^1$ and $Z^2$ together with carbon atom to which they are attached form a keto group gives compound of formula (I-A$^2$), which is subset of compound of formula (I), wherein $X^{1p}$ is

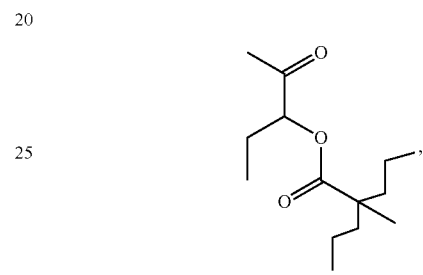

$X^{2p}$ is $CH(CH_3)C(=O)H$, $Z^1$ and $Z^2$ together with carbon atom to which they are attached form a keto group, $A^1$, $A^2$, $R^1$, $R^{2a}$, $R^{2b}$, $B^1$, $B^2$, and $R^N$ are as defined for formula (I).

The reaction is typically performed by adding 1-2.2 equiv. $Pb(OAc)_4$ or $NaIO_4$ to a solution of the appropriate compound of formula (II) in a suitable solvent or mixture of solvents such as glacial AcOH, DCM or chloroform (suitably glacial AcOH) at 0° C. to 40° C., suitably room temperature. The expected product may be isolated by methods known to one skilled in the art.

Compound I-A1-iii:

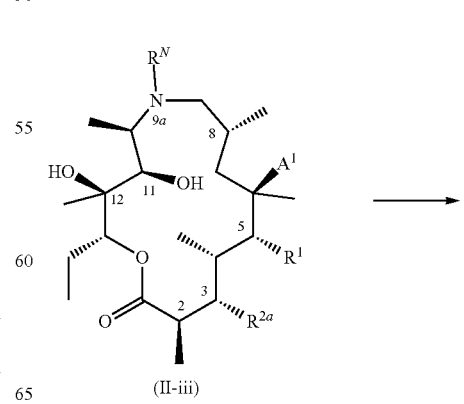

(II-iii)

75

-continued

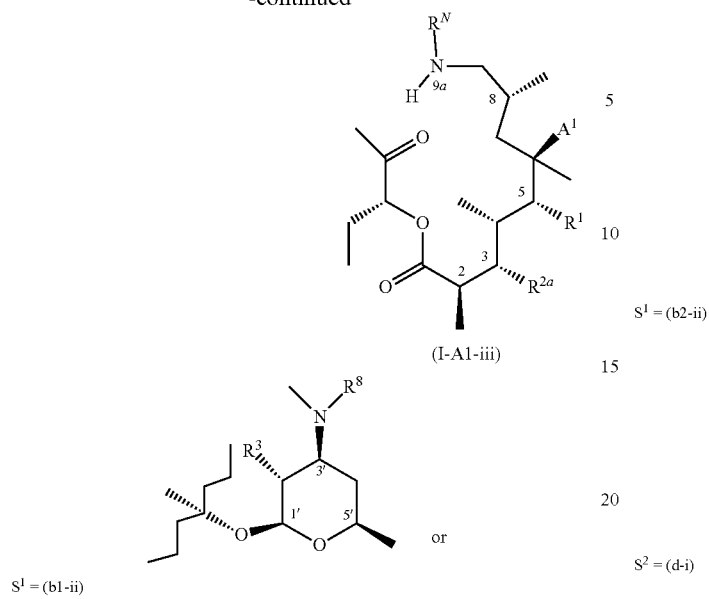

(I-A1-iii)

$S^1$ = (b1-ii)

76

-continued

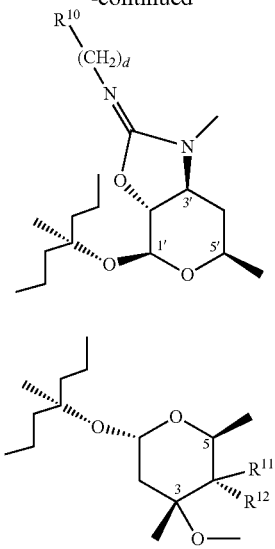

$S^1$ = (b2-ii)

$S^2$ = (d-i)

or

TABLE

Compound (I-A1-iii):

| I-A1-iii | $R^N$ | $A^1$ | $R^1$ | $R^3$ | $R^8$ | d | $R^{10}$ | $R^{2a}$ | $R^{11}$ | $R^{12}$ |
|---|---|---|---|---|---|---|---|---|---|---|
| 1 | CH$_3$ | OH | b1-ii | OH | CH$_3$ | NA | NA | d-i | H | OH |
| 2 | H | OH | b1-ii | OH | CH$_3$ | NA | NA | d-i | H | OH |
| 3 | CH$_3$ | OH | b1-ii | —O(CH$_2$)$_3$NHC(O)C$_2$H$_5$ | CH$_3$ | NA | NA | d-i | H | OH |
| 4 | CH$_3$ | OH | b1-ii | ![structure with pyrazole carboxamide] | CH$_3$ | NA | NA | d-i | H | OH |
| 5 | CH$_3$ | OH | b1-ii | ![structure with N-methylpiperazine acetamide] | CH$_3$ | NA | NA | d-i | H | OH |
| 6 | CH$_3$ | OH | b1-ii | ![structure with dimethylamino acetamide] | CH$_3$ | NA | NA | d-i | H | OH |
| 7 | CH$_3$ | OH | b1-ii | ![structure with isopropyl-methyl-thiazole carboxamide] | CH$_3$ | NA | NA | d-i | H | OH |
| 8 | CH$_3$ | OH | b1-ii | ![structure with N-tert-butyl azetidine carboxamide] | CH$_3$ | NA | NA | d-i | H | OH |

TABLE-continued

Compound (I-A1-iii):

| I-A1-iii | $R^N$ | $A^1$ | $R^1$ | $R^3$ | $R^8$ | d | $R^{10}$ | $R^{2a}$ | $R^{11}$ | $R^{12}$ |
|---|---|---|---|---|---|---|---|---|---|---|
| 9 | $CH_3$ | OH | b2-ii | NA | NA | 0 | isopropyl | d-i | H | OH |
| 10 | $CH_3$ | OH | b1-ii | OH | $CH_3$ | NA | NA | d-i | OH | $CH_2N(CH_3)_2$ |
| 11 | $CH_3$ | OH | b1-ii | OH | $CH_3$ | NA | NA | d-i | OH | CH₂-morpholine |
| 12 | $CH_3$ | OH | b1-ii | OH | $CH_3$ | NA | NA | OH | NA | NA |
| 13 | $CH_3$ | OH | b1-ii | OCb | Cb | NA | NA | d-i | H | OH |
| 14 | $CH_3$ | OH | b1-ii | —O(CH₂)₃NHC(O)OCH₂Ph | $CH_3$ | NA | NA | d-i | H | OH |
| 15 | $CH_3$ | OH | b1-ii | —O(CH₂)₃NHC(O)-(2-F-C₆H₄) | $CH_3$ | NA | NA | d-i | H | OH |
| 16 | $CH_3$ | OH | b1-ii | H | $CH_3$ | NA | NA | d-i | H | OH |
| 17 | $CH_3$ | $OCH_3$ | b1-ii | OH | $CH_3$ | NA | NA | d-i | H | OH |

NA = not applicable
Cb = —C(=O)OCH2—Ph, Ph is phenyl

Compound I-A1-iii-1: To a solution of 9-deoxo-9a-methyl-9a-aza-9a-homoerythromycin A (azithromycin) (20 g, 26.7 mmol) in glacial AcOH (150 mL), Pb(OAc)₄ (23.7 g, 53.45 mmol) was added and the reaction mixture was stirred at room temperature for 3 hours. The solvent was evaporated to dryness, DCM (200 mL) and water (200 mL) were added and pH was adjusted to 6.2 with 20% NaOH. The layers were separated, pH of water layer was adjusted to 8.7 and extracted with DCM (2×100 mL). The organic layers were dried over anhydrous Na₂SO₄ and evaporated to afford Compound I-A1-iii-1 (12.9 g); MS (ES⁺, m/z): 691.66 [MH]⁺.

¹H NMR (500 MHz, DMSO-d6): δ=1.09-1.16 (m, 6H, 8Me, 15), 1.28 (d, J=7.0 Hz, 3H, 4Me), 1.29-1.32 (m, 3H, 2Me), 1.32-1.37 (m, 13H, 4'<">, 6Me, 5'Me, 3"Me, 5"Me), 1.52 (dd, J=13.9, 9.3 Hz, 1H, 7<">), 1.63 (dd, J=15.1, 4.7 Hz, 1H, 2"<">), 1.78 (d, J=13.7 Hz, 1H, 7<>), 1.86 (d, J=13.1 Hz, 1H, 4'<>), 1.94 (dt, J=14.4, 7.3 Hz, 1H, 14<">), 2.02-2.12 (m, 2H, 8, 14<>), 2.37 (s, 3H, 11), 2.38-2.43 (m, 2H, 2"<>, 4), 2.46 (s, 6H, 3'NMe, 3'NMe), 2.50 (s, 3H, 9NMe), 2.52-2.58 (m, 1H, 9<">), 2.63-2.70 (m, 1H, 3'), 2.70-2.73 (m, 1H, 9<>), 3.09 (d, J=9.5 Hz, 1H, 4"), 3.19 (q, J=6.8 Hz, 1H, 2), 3.28-3.37 (m, 1H, 2'), 3.42 (s, 3H, 3"OMe), 3.76 (br. s., 2H, 5', 5), 4.22-4.34 (m, 2H, 5", 3), 4.54 (d, J=7.3 Hz, 1H, 1'), 4.86 (d, J=4.6 Hz, 1H, 1"), 5.15 (dd, J=7.5, 4.4 Hz, 1H, 13) ppm.

¹³C NMR (126 MHz, DMSO-d6): δ=9.3 (15), 9.8 (2Me), 11.8 (4Me), 17.9 (5"Me), 21.0 (5'Me, 3"Me), 21.6 (8Me), 23.0 (14), 26.1 (11, 6Me), 27.8 (8), 30.4 (4'), 35.3 (9NMe), 35.2 (2"), 35.8 (4), 40.4 (3'NMe, 3'NMe), 40.6 (2), 43.2 (7), 48.8 (3"OMe), 58.8 (9), 64.5 (5"), 64.7 (3'), 68.2 (5'), 70.3 (2'), 72.8 (3", 6), 77.4 (4"), 79.1 (13), 80.5 (3), 81.7 (5), 95.2 (1"), 102.3 (1'), 175.1 (1), 204.9 (12) ppm.

Compound I-A1-iii-2: To a solution of 9-deoxo-9a-aza-9a-homoerythromycin A (19.6 g, 26.7 mmol) in glacial AcOH (150 mL), Pb(OAc)₄ (23.7 g, 53.45 mmol) was added and the reaction mixture was stirred at room temperature for 1.5 hours. The solvent was evaporated to dryness, DCM (200 mL) and water (200 mL) were added and pH was adjusted to 6 with 20% NaOH. The layers were separated; pH of water layer was adjusted to 8 and extracted with DCM (2×100 mL). The layers were separated and water was liophylised. The organic layers were dried over anhydrous Na₂SO₄ and evaporated to afford Compound I-A1-iii-2 (12.9 g); MS (ES⁺, m/z): 691.66 [MH]⁺.

Compound I-A1-iii-3: According to Method A starting from 2'-O-{3-[(ethylacetyl)amino]propyl}-9-deoxo-9a-methyl-9a-aza-9a-homoerythromycin A (prepared according to WO2010086350 A1) (3.3 g, 3.8 mmol) the title compound was prepared (2 g); MS (ES⁺, m/z): 804.55 [MH]⁺.

Compound I-A1-iii-4: According to Method A starting from compound of formula (II-iii) wherein $R^N$ is $CH_3$, $R^1$ is $S^1$ of formula (MA), $R^3$ is

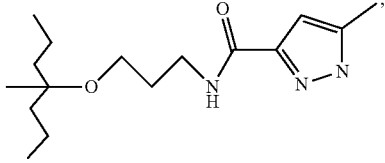 [SMILES: CCCC(C)(CCC)OCCCNC(=O)c1cc(C)[nH]n1]

$R^8$ is $CH_3$, $R^{2a}$ is $S^2$ of formula (d-i), $R^{11}$ is H, and $R^{12}$ is OH (prepared according to WO2010086350 A1) the title compound was prepared (0.96 g); MS (ES+, m/z): 856.56 [MH]+.

Compound I-A1-iii-5: According to Method A starting from compound of formula (II-iii) wherein $R^N$ is $CH_3$, $R^1$ is $S^1$ of formula (MA), $R^3$ is

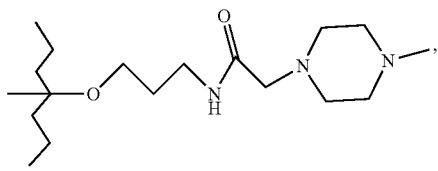 [SMILES: CCCC(C)(CCC)OCCCNC(=O)CN1CCN(C)CC1]

$R^8$ is $CH_3$, $R^{2a}$ is $S^2$ of formula (d-i), $R^{11}$ is H, and $R^{12}$ is OH (prepared according to WO2010086350 A1) the title compound was prepared (6 g); MS (ES+, m/z): 888.59 [MH]+.

Compound I-A1-iii-6: According to Method A starting from compound of formula (II-iii) wherein $R^N$ is $CH_3$, $R^1$ is $S^1$ of formula (MA), $R^3$ is

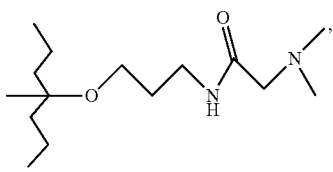 [SMILES: CCCC(C)(CCC)OCCCNC(=O)CN(C)C]

$R^8$ is $CH_3$, $R^{2a}$ is $S^2$ of formula (d-i), $R^{11}$ is H, and $R^{12}$ is OH (prepared according to WO2010086350 A1) the title compound was prepared (6.6 g); MS (ES+, m/z): 833.79 [MH]+.

Compound I-A1-iii-7: According to Method A starting from compound of formula (II-iii) wherein $R^N$ is $CH_3$, $R^1$ is $S^1$ of formula (MA), $R^3$ is

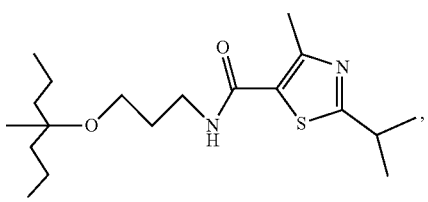 [SMILES: CCCC(C)(CCC)OCCCNC(=O)c1sc(C(C)C)nc1C]

$R^8$ is $CH_3$, $R^{2a}$ is $S^2$ of formula (d-i), $R^{11}$ is H, and $R^{12}$ is OH (prepared according to WO2010086350 A1) the title compound was prepared (6.6 g); MS (ES+, m/z): 915.90 [MH]+.

Compound I-A1-iii-8: According to Method A starting from compound of formula (II-iii) wherein $R^N$ is $CH_3$, $R^1$ is $S^1$ of formula (MA), $R^3$ is

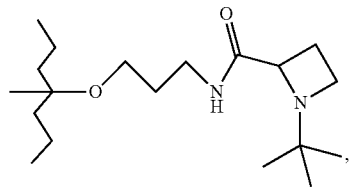 [SMILES: CCCC(C)(CCC)OCCCNC(=O)C1CCN1C(C)(C)C]

$R^8$ is $CH_3$, $R^{2a}$ is $S^2$ of formula (d-i), $R^{11}$ is H, and $R^{12}$ is OH (prepared according to WO2010086350 A1) the title compound was prepared (4.49 g); MS (ES+, m/z): 887.84 [MH]+.

Compound I-A1-iii-9: According to Method A starting from 2'-O,3'-N-(Carbonimidoyl)-3'-N-demethyl-9-deoxo-N'-isopropyl-9a-methyl-9a-aza-9a-homoerythromycin A (prepared according to WO2009130189 A1, example 3) the title compound was prepared (2.8 g); MS (ES+, m/z): 744.70 [MH]+.

$^1$H NMR (600 MHz, DMSO-d6): δ=0.84-0.88 (m, 6H, 8Me, 15), 0.89-0.92 (m, 6H, 4Me, 19), 0.95 (d, J=6.4 Hz, 3H, 19), 1.05-1.10 (m, 9H, 2Me, 3"Me, 5"Me), 1.12 (s, 3H, 6Me), 1.13 (d, J=6.1 Hz, 3H, 5'Me), 1.23 (q, J=11.7 Hz, 1H, 4'<">), 1.32 (dd, J=14.4, 9.1 Hz, 1H, 7<">), 1.39-1.47 (m, 2H, 7<>, 2"<">), 1.60-1.71 (m, 1H, 14<">), 1.73-1.80 (m, 1H, 14<>), 1.80-1.85 (m, 1H, 8), 1.96-2.01 (m, 1H, 4'<>), 2.07-2.09 (m, 3H, 11), 2.16-2.23 (m, 3H, 4, 9<">, 2"<>), 2.22 (s, 3H, 9NMe), 2.46 (dd, J=11.7, 3.9 Hz, 1H, 9<>), 2.49 (s, 3H, 3'NMe), 2.78-2.85 (m, 1H, 3'), 2.86-2.94 (m, 2H, 4", 2), 3.09-3.12 (m, 3H, 3"OMe), 3.39 (dd, J=10.5, 7.7 Hz, 1H, 2'), 3.43 (d, J=5.0 Hz, 1H, 5), 3.61 (dt, J=12.6, 6.4 Hz, 1H, 18), 3.75-3.86 (m, 1H, 5'), 3.98-4.03 (m, 2H, 5", 3), 4.32 (br. s., 1H, 4"OH), 4.66 (d, J=4.8 Hz, 1H, 1"), 4.83 (dd, J=7.7, 4.6 Hz, 1H, 13), 4.89 (d, J=7.9 Hz, 1H, 1') ppm.

$^{13}$C NMR (126 MHz, DMSO-d6): δ=9.4 (15), 10.1 (4Me), 12.2 (2Me), 17.9 (5"Me), 20.6 (5'Me), 21.0 (3"Me), 21.8 (8Me), 22.9 (14), 24.6 (19), 25.0 (19), 25.9 (11), 26.0 (6Me), 27.8 (8), 32.2 (3'NMe), 35.0 (2"), 35.3 (9NMe), 35.9 (4'), 36.8 (4), 41.5 (2), 42.9 (7), 45.9 (18), 48.6 (3"OMe), 59.0 (9), 61.9 (3'), 64.7 (5"), 69.3 (5'), 72.7 (6), 73.0 (3"), 77.1 (4"), 79.2 (3, 13), 79.5 (2'), 83.9 (5), 94.8 (1"), 99.1 (1'), 153.7 (16), 174.8 (1), 204.9 (12) ppm.

Compound III-A1-iii-10: According to Method A starting from compound of formula (II-iii) wherein $R^N$ is $CH_3$, $R^1$ is $S^1$ of formula (b1-ii), $R^3$ is OH, $R^8$ is $CH_3$, $R^{2a}$ is $S^2$ of formula (d-i), $R^{11}$ is OH, and $R^{12}$ is —$CH_2N(CH_3)_2$ (prepared according to WO9856801) the title compound was prepared (1.3 g); MS (ES+, m/z): 748.58 [MH]+.

Compound I-A1-iii-11: According to Method A starting from compound of formula (II-iii) wherein $R^N$ is $CH_3$, $R^1$ is $S^1$ of formula (b1-ii), $R^3$ is OH, $R^8$ is $CH_3$, $R^{2a}$ is $S^2$ of formula (d-i), $R^{11}$ is OH, and $R^{12}$ is

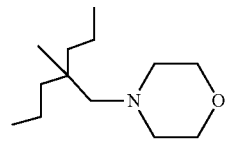

(prepared according to WO9856801) the title compound was prepared (1.5 g); MS (ES+, m/z): 790.52 [MH]+.

Compound I-A1-iii-12: According to Method A starting from compound of formula (II-iii) wherein $R^N$ is $CH_3$, $R^1$ is Si of formula (b1-ii), $R^3$ is OH, $R^8$ is $CH_3$, $R^{2a}$ is OH (prepared according to Method KA below) the title compound was prepared (0.41 g); MS (ES$^+$, m/z): 533.50 [MH]$^+$.

Compound I-A1-iii-13: According to Method A starting from compound of formula (II-iii) wherein $R^N$ is $CH_3$, $R^1$ is $S^1$ of formula (b1-ii), $R^3$ is —OCb, $R^8$ is Cb, $R^{2a}$ is $S^2$ of formula (d-i), $R^{11}$ is H and $R^{12}$ is OH (prepared according to Kobrehel et al, J. Antibiotics 45(4), 1992, 527-534) the title compound was prepared MS (ES$^+$, m/z): 945.57 [MH]$^+$.

Compound I-A1-iii-14: According to Method A starting from compound of formula (II-iii) wherein $R^N$ is $CH_3$, $R^1$ is Si of formula (b1-ii), $R^3$ is

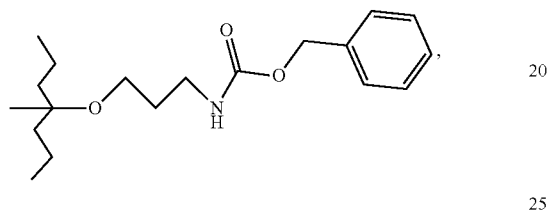

$R^8$ is $CH_3$, $R^{2a}$ is $S^2$ of formula (d-i), $R^{11}$ is H and $R^{12}$ is OH (prepared according to WO2010086350 A1) the title compound was prepared (0.130 g); MS (ES$^+$, m/z): 882.79 [MH]$^+$.

Compound I-A1-iii-15: According to Method A starting from compound of formula (II-iii) wherein $R^N$ is $CH_3$, $R^1$ is $S^1$ of formula (MA), $R^3$ is

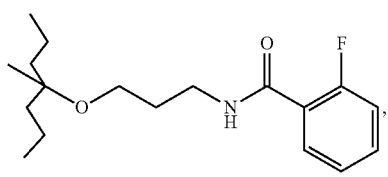 [SMILES: CCCC(C)(CCC)OCCCNC(=O)c1ccccc1F]

$R^8$ is $CH_3$, $R^{2a}$ is $S^2$ of formula (d-i), $R^{11}$ is H and $R^{12}$ is OH (prepared according to WO2010086350 A1) the title compound was prepared; MS (ES$^+$, m/z): 870.12 [MH]$^+$.

Compound I-A1-iii-16: According to Method A starting from 2'-deoxy-9-deoxo-9a-methyl-9a-aza-9a-homoerythromycin A (2'-deoxy azithromycin) (6.34 g, 8.64 mmol; prepared according to Method KH) the title compound was prepared; MS (ES$^+$, m/z): 675.47 [MH]$^+$.

$^1$H NMR (600 MHz, CDCl$_3$): δ=4.90 (dd), 4.72 (d), 4.48 (dd), 4.10 (dd), 4.00 (dd), 3.51 (t), 3.39 (m), 3.26 (s), 2.96 (m), 2.56 (dd), 2.39 (m), 2.35 (s), 2.28 (m), 2.23 (br.s, 3'NMe2), 2.21 (m), 2.13 (s), 2.11 (s), 2.06 (m), 1.88 (m), 1.81 (m), 1.74 (m), 1.65 (m), 1.55 (m), 1.48 (dd), 1.44 (m), 1.21 (m), 1.18 (m), 1.13 (d), 1.19 (t), 0.97 (d), 0.95 (d), 0.92 (d), 0.88 (t), 0.86 (t) ppm.

Compound I-A1-iii-17: According to Method A starting from 6-O-methyl-9a-methyl-9a-aza-9a-homoerythromycin A (0.992 g, 1.3 mmol; prepared according to Bioorg. Med. Chem. Lett. 8 (1998) 1321-1326) 0.42 g of title compound was prepared; MS (ES$^+$, m/z): 705 [MH]$^+$.

Compound I-A2-iii:

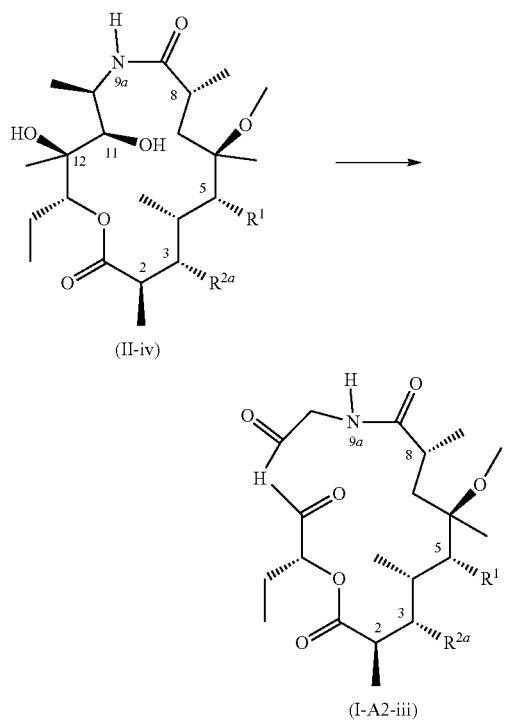

(II-iv)

(I-A2-iii)

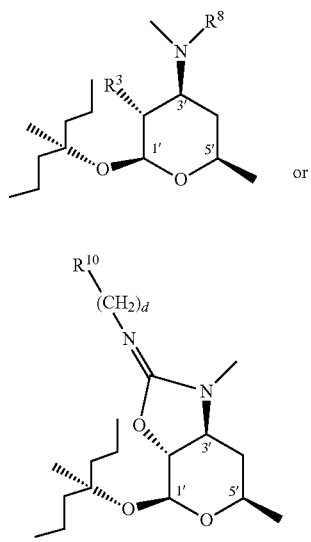

$S^1 =$ (b1-ii)

$S^1 =$ (b2-ii)

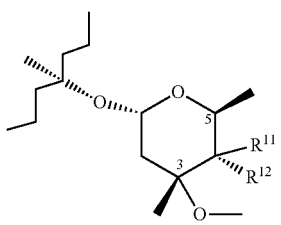

$S^2 =$ (d-i)

TABLE

Compound (I-A2-iii):

| I-A2-iii | $R^N$ | $R^1$ | $R^3$ | $R^8$ | d | $R^{10}$ | $R^{2a}$ | $R^{11}$ | $R^{12}$ |
|---|---|---|---|---|---|---|---|---|---|
| 1 | H | b1-ii | OH | $CH_3$ | NA | NA | d-i | H | OH |

NA = not applicable

Compound I-A2-iii-1: To a solution of 6-O-methyl-9a-aza-9a-homoerythromycin A (1 g, 1.31 mmol) in chloroform (60 mL) at 0° C., Pb(OAc)$_4$ (650 mg, 1.47 mmol) was added and the reaction mixture was stirred, allowing to reach room temperature, for 1 hour. Reaction mixture was extracted with saturated aqueous NaHCO$_3$, aqueous layer was extracted with chloroform, combined organic layers were dried over anhydrous Na$_2$SO$_4$ and evaporated to afford Compound I-A2-iii-1 (150 mg); MS (ES$^+$, m/z): 761.28 [MH]$^+$.

Method B: General Procedure for Preparation of Seco Macrolide Compound of Formula (I-B), Wherein $X^{1p}$ is —C(=O)OH, $X^{2p}$ is Hydrogen and Di-Carboxylic Acid Seco Macrolide (XC):

Scheme 2A

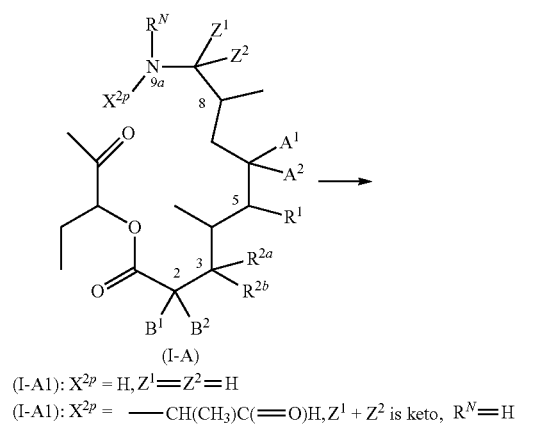

(I-A)
(I-A1): $X^{2p}$ = H, $Z^1$=$Z^2$=H
(I-A1): $X^{2p}$ = —CH(CH$_3$)C(=O)H, $Z^1$ + $Z^2$ is keto, $R^N$=H

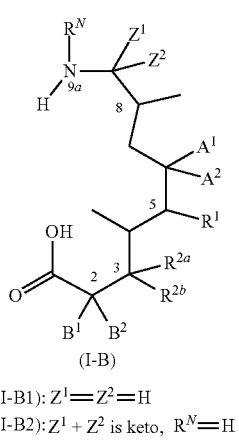

(I-B)
(I-B1): $Z^1$=$Z^2$=H
(I-B2): $Z^1$ + $Z^2$ is keto, $R^N$=H

Scheme 2B

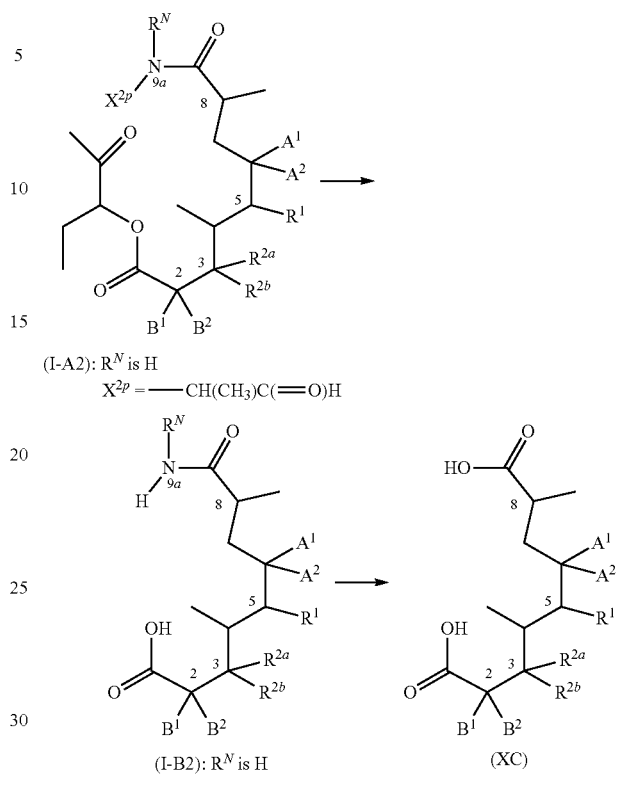

(I-A2): $R^N$ is H
$X^{2p}$ = —CH(CH$_3$)C(=O)H (I-B2): $R^N$ is H          (XC)

Scheme 2A: illustrates hydrolysis of C/1-keto ester of compound of formula (I-A) which in case when starting from compound of formula (I-A1) gives compound of formula (I-131), which is subset of compound of formula (I), wherein $X^{1p}$ is —C(=O)OH, $X^{2p}$ is hydrogen, $Z^1$ and $Z^2$ are both hydrogen, $A^1$, $A^2$, $R^1$, $R^{2a}$, $R^{2b}$, $B^1$, $B^2$, and $R^N$ are as defined for formula (I); whereas in case when starting from compound of formula (I-A2) gives compound of formula (I-B2), which is subset of compound of formula (I), wherein $X^{1p}$ is —C(=O)OH, $X^{2p}$ is hydrogen, $Z^1$ and $Z^2$ together with carbon atom to which they are attached form a keto group, $R^N$ is hydrogen, $A^1$, $A^2$, $R^1$, $R^{2a}$, $R^{2b}$, $B^1$, and $B^2$ are as defined for formula (I).

Scheme 2B: illustrates that when compound of formula (I-B2), wherein $R^N$ is hydrogen, $Z^1$ and $Z^2$ together with carbon atom to which they are attached form a keto group, $X^{1p}$ is C(=O)OH, $X^{2p}$ is hydrogen is further subjected to hydrolyzing conditions di-carboxylic acid seco macrolide (XC), wherein $A^1$, $A^2$, $B^1$, $B^2$, $R^1$, $R^{2a}$, $R^{2b}$ are as defined for formula (I) is obtained.

The reaction is typically performed by adding 1-10 equiv. of inorganic base such as sodium or lithium hydroxide to a solution of the appropriate compound of formula (I-A), obtained according to Method A in a suitable solvent or mixture of solvents such as THF, MeCN, water (suitably mixture of THF/water or MeCN/water) at 0° C. to reflux temperature, suitably room temperature. The expected product may be isolated by methods known to one skilled in the art.

Compound I-B1-iii
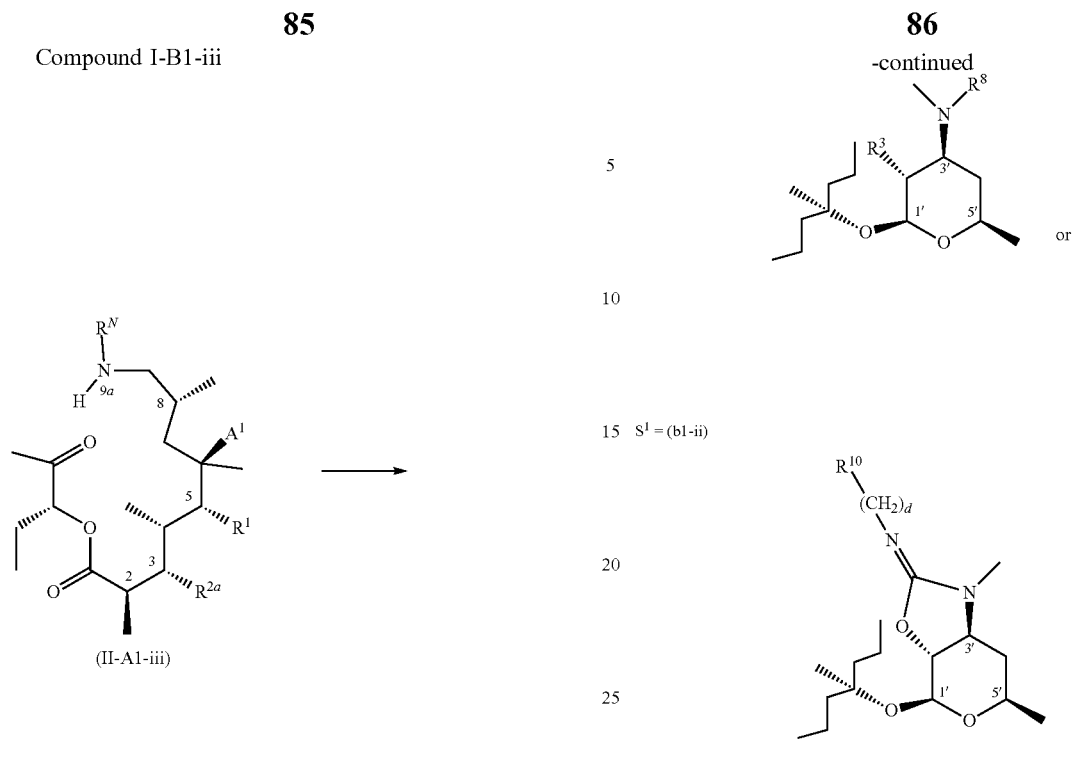
| I-B1-iii | $R^N$ | $A^1$ | $R^1$ | $R^3$ | $R^8$ | d | $R^{10}$ | $R^{2a}$ | $R^{11}$ | $R^{12}$ |
|---|---|---|---|---|---|---|---|---|---|---|
| 1 | $CH_3$ | OH | b1-ii | OH | $CH_3$ | NA | NA | d-i | H | OH |
| 2 | H | OH | b1-ii | OH | $CH_3$ | NA | NA | d-i | H | OH |
| 9 | $CH_3$ | OH | b2-ii | NA | NA | 0 | ![isopropyl] | d-i | H | OH |
| 13 | $CH_3$ | OH | b1-ii | OCb | Cb | NA | NA | d-i | H | OH |
NA = not applicable
Cb = —C(=O)OCH2—Ph, Ph is phenyl Compound I-B1-iii-1: To a solution of Compound I-A1-iii-1 (490 mg, 0.71 mmol) in acetonitrile (5 mL), LiOH (150 mg, 3.52 mmol) in water (5 mL) was added and the reaction mixture was stirred at room temperature for 2 hours. The acetonitrile was evaporated, DCM (10 mL) and water (10 mL) were added and pH was adjusted to 6.7 with 2M HCl. The layers were separated and water was liophylised. The crude residue was precipitated from iPrOH:diisopropylether to afford Compound I-B1-iii-1 (320 mg); MS (ES$^+$, m/z): 607.54 [MH]$^+$.

$^1$H NMR (500 MHz, DMSO-d6): δ=1.09 (d, J=6.7 Hz, 3H, 8Me), 1.15 (d, J=7.0 Hz, 3H, 4Me, 2Me), 1.20 (d, J=7.0 Hz, 3H), 1.22 (d, J=6.1 Hz, 3H, 5'Me), 1.26-1.33 (m, 10H, 4'<">, 6Me, 3"Me, 5"Me), 1.51 (dd, J=14.2, 4.7 Hz, 1H, 7<">), 1.57 (dd, J=15.4, 5.0 Hz, 1H, 2"<>), 1.65 (dd, J=14.3, 5.5 Hz, 1H, 7<'>), 1.78 (ddd, J=11.6, 4.3, 1.8 Hz, 1H, 4'<'>), 2.07 (d, J=5.5 Hz, 1H, 8), 2.19 (d, J=3.4 Hz, 1H, 4), 2.41 (s, 6H, 3'NMe, 3'NMe), 2.49 (dq, J=14.3, 7.6 Hz, 1H, 2), 2.50 (s, 3H, 9NMe), 2.58-2.67 (m, 2H, 3', 9<">), 2.69-2.73 (m, 1H, 9<'>), 3.01 (d, J=9.5 Hz, 1H, 4"), 3.25 (dd, J=9.6, 7.5 Hz, 2H, 2'), 3.37 (s, 3H, 3"OMe), 3.65 (d, J=6.7 Hz, 1H, 5), 3.69-3.71 (m, 1H, 5'), 4.16-4.26 (m, J=10.5, 6.7, 6.7, 6.7 Hz, 1H, 5"), 4.30 (dd, J=6.4, 2.7 Hz, 1H, 3), 4.51 (d, J=7.3 Hz, 1H, 1'), 4.85 (d, J=4.0 Hz, 1H, 1") ppm.

$^{13}$C NMR (126 MHz, DMSO-d6): δ=10.8 (4Me), 14.3 (2Me), 18.1 (5"Me), 21.1 (3"Me), 21.6 (8Me), 22.8 (5'Me), 26.0 (6Me), 27.0 (8), 30.6 (4'), 35.2 (9NMe), 35.4 (2"), 37.8 (4), 40.5 (3'NMe, 3'NMe), 40.7 (7), 46.5 (2), 48.8 (3"OMe), 58.3 (9), 64.3 (3'), 64.4 (5"), 67.8 (5'), 70.8 (2'), 72.8 (3"), 74.2 (6), 77.8 (4"), 81.5 (3), 83.6 (5), 96.2 (1"), 103.2 (1'), 179.1 (1) ppm.

Compound I-B1-iii-2: To a solution of Compound I-A1-iii-2 (1.28 g, 1.89 mmol) in acetonitrile (15 mL), LiOH (790 mg, 18.81 mmol) in water (15 mL) was added and the reaction mixture was stirred at room temperature for 16 hours. The acetonitrile was evaporated, DCM (10 mL) and water (10 mL) were added and pH was adjusted to 6.7 with 2M HCl. The layers were separated and water was lyophilised. The crude residue was suspended in DCM, filtered and precipitated with diisopropylether to afford Compound I-B1-iii-2 (700 mg); MS (ES$^+$, m/z): 593.63 [MH]$^+$.

$^1$H NMR (500 MHz, DMSO-d6): δ=0.81-0.91 (m, 3H, 8Me), 0.94-1.05 (m, 6H, 4Me, 2Me), 1.05-1.18 (m, 13H, 6Me, 3"Me, 5'Me, 5"Me, 4'<">), 1.19-1.30 (m, 1H, 7<">), 1.39 (dd, J=15.0, 4.3 Hz, 1H, 2"<>), 1.43-1.51 (m, 1H, 7<'>), 1.59 (d, J=11.0 Hz, 1H, 4'<'>), 1.70-1.81 (m, 1H, 8), 1.97-2.09 (m, 1H, 4), 2.21 (d, J=4.3 Hz, 6H, 3'NMe, 3'NMe), 2.27-2.33 (m, 2H, 2"<>, 2), 2.39-2.46 (m, 2H, 3', 9<">), 2.61-2.73 (m, 1H, 9<'>), 2.82 (d, J=9.2 Hz, 1H, 4"), 2.98-3.07 (m, 1H, 2'), 3.18 (s, 3H, 3"OMe), 3.48-3.53 (m, 2H, 5, 5'), 3.95-4.07 (m, 1H, 5"), 4.11 (d, J=7.0 Hz, 1H, 3), 4.31 (d, J=7.3 Hz, 1H, 1'), 4.64 (d, J=4.0 Hz, 1H, 1") ppm.

$^{13}$C NMR (126 MHz, DMSO-d6): δ=10.8 (4Me), 15.0 (2Me), 18.1 (5"Me), 21.1 (8Me, 5'Me, 3"Me), 25.8 (6Me), 29.0 (8), 30.5 (4'), 35.3 (2"), 38.0 (4), 38.9 (7), 40.4 (3'NMe, 3'NMe), 47.1 (2), 47.9 (9), 48.8 (3"OMe), 64.3 (3', 5"), 67.7 (5'), 71.0 (2'), 72.8 (3"), 75.0 (6), 77.9 (4"), 81.3 (3), 83.7 (5), 96.4 (1"), 103.3 (1'), 179.0 (1) ppm.

Compound I-B1-iii-9: According to Method B starting from Compound I-A1-iii-9 the title compound was prepared (380 mg); MS (ES$^+$, m/z): 660.60 [MH]$^+$.

Compound I-B1-iii-13: According to Method B starting from Compound I-A1-iii-13 the title compound was prepared (1.7 g); MS (ES$^+$, m/z): 861.50 [MH]$^+$.

Compounds I-B2-iii and XC-iii:

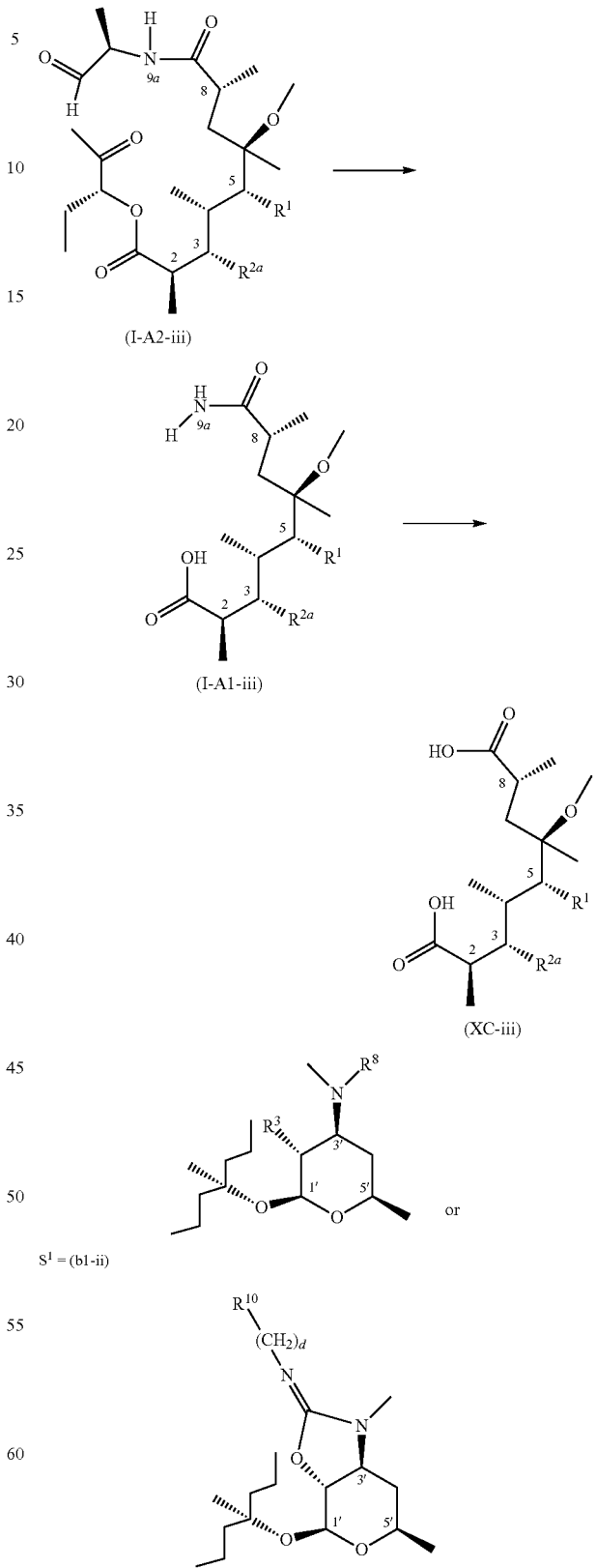

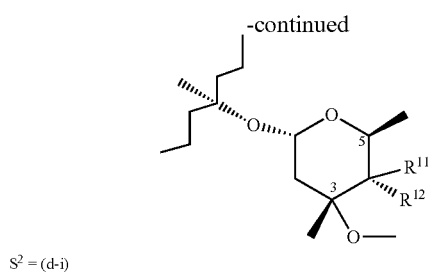

$S^2 = (d\text{-}i)$

Compound XC-iii-1: According to Method B starting from Compound I-A2-iii-1 the title compound was prepared (550 mg); MS (ES+, m/z): 621.77 [MH]+.

Method C: General procedure for preparation of seco macrolide compound of Formula (I-C), wherein $X^{1p}$ is —C(=O)NH$_2$ and $X^{2p}$ is hydrogen:

Scheme 3

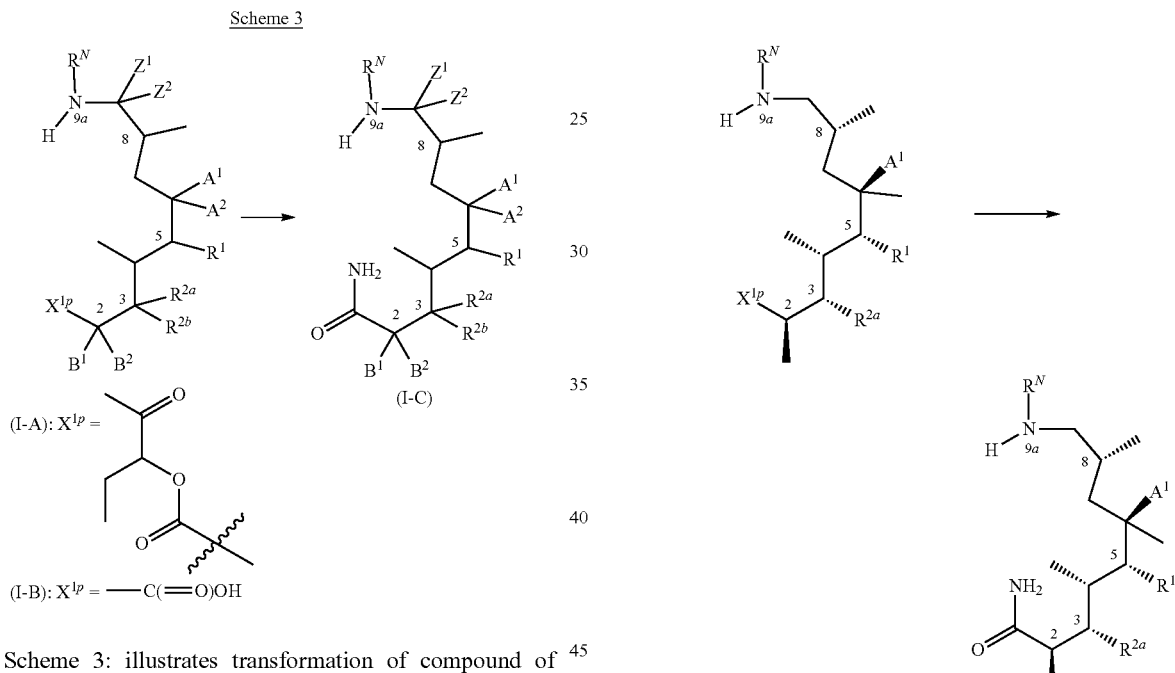

Scheme 3: illustrates transformation of compound of formula (I-A) wherein $X^1$ is

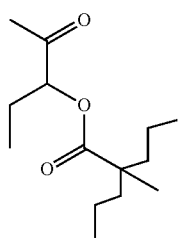 [SMILES: CCCC(C)(CCC)C(=O)OC(CC)C(C)=O]

or of formula (I-B), wherein $X^{1p}$ is —C(=O)OH, $X^{2p}$ is hydrogen, $Z^1$, $Z^2$, $A^1$, $A^2$, $R^1$, $R^{2a}$, $R^{2b}$, $B^1$, $B^2$, and $R^N$ are as defined for formula (I) above to compound of formula (I-C) which is subset of compounds of formula (I), wherein $X^{1p}$ is —C(=O)NH$_2$, $X^{2p}$ is hydrogen, $Z^1$, $Z^2$, $A^1$, $A^2$, $R^1$, $R^{2a}$, $R^{2b}$, $B^1$, $B^2$, and $R^N$ are as defined for formula (I). The reaction is suitably performed by reaction with ammonium salts, such as for example ammonium chloride and ammonium carbamate, in the presence of tertiary amine as a base and coupling agents typically used in peptide synthesis including, but not limited to, HATU, PyBOP, HBTU, EDAC, DCC. Preferred solvents for this reaction are DMF and DCM although other organic solvents and ionic liquids can be used. Typical reaction times range from 30 min to 24 h and reaction temperatures 0-60° C.

Alternatively, compound of formula (I-C) can be prepared from compound of formula (I-B) by reaction with ammonia in organic solvents, such as methanol, isopropanol, THF, diethylether, and dioxane, and with ammonium hydroxide. The reaction is typically performed by adding the appropriate compound of formula (I-B) to ammonium solution (suitably 7M ammonium solution in MeOH), and stirring at room to elevated temperature (suitably at 40° C.). The expected product may be isolated by methods known to one skilled in the art.

Compound I-C1-iii

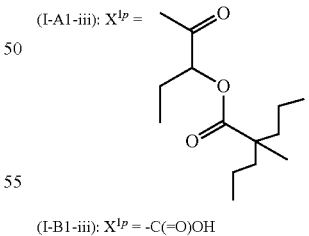

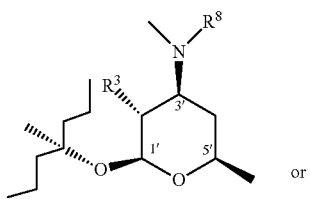

$S^1 = (b1\text{-}ii)$

-continued

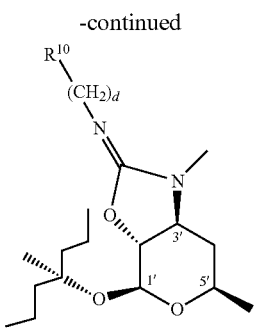

S¹ = (b2-ii)

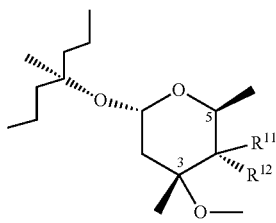

S² = (d-i)

TABLE

Compound (I-C1-iii):

| I-C1-iii | R$^N$ | A$^1$ | R$^1$ | R$^3$ | R$^8$ | d | R$^{10}$ | R$^{2a}$ | R$^{11}$ | R$^{12}$ |
|---|---|---|---|---|---|---|---|---|---|---|
| 1 | CH$_3$ | OH | b1-ii | OH | CH$_3$ | NA | NA | d-i | H | OH |

NA = not applicable

Compound I-C1-iii-1: Compound I-A1-iii-1 (1.0 g, 1.45 mmol) was dissolved in 7 M ammonium solution in methanol (30 mL) and stirred at 40° C. overnight. The solvent was evaporated to afford crude product that was purified by column chromatography (Biotage SP4, eluent 0-100% DCM:MeOH:NH$_4$OH (90:9:1.5) in DCM) to afford Compound I-C1-iii-1 (550 mg); MS (ES$^+$, m/z): 606.54 [MH]$^+$.

$^1$H NMR (500 MHz, DMSO-d6): δ=1.14 (d, 3H, J=6.5 Hz, 8Me), 1.20-1.26 (m, 6H, 4Me, 2Me), 1.50-1.70 (m, 13H, 6Me, 3"Me, 5'Me, 5"Me, 4'<">), 1.58-1.67 (m, 3H, 2", 7<">), 1.85 (d, J=11.5 Hz, 1H, 4'<">), 2.08-2.13 (m, 1H, 8), 2.20-2.26 (m, 1H, 4), 2.46 (s, 6H, 3'N(Me)$_2$), 2.50 (s, 3H, 9'NMe), 2.57-2.68 (m, 2H, 9<">), 2.74 (s, 1H, 3'), 2.78-2.82 (m, 1H, 2), 3.09 (d, J=9.5 Hz, 1H, 4"), 3.32-3.37 (dd, J=10 and 7.5 Hz, 1H, 2'), 3.44 (s, 3H, 3"OMe), 3.37 (d, J=5 Hz, 1H, 5), 3.81-3.85 (m, 1H, 5'), 4.21-4.24 (dd, J=4.5 and 4.5 Hz, 1H, 3), 4.25-4.30 (m, 1H, 5"), 4.61 (d, J=7.5 Hz, 1H, 1'), 4.97 (d, J=4.5 Hz, 1H, 1") ppm.

$^{13}$C NMR (126 MHz, DMSO-d6): δ=9.87 (4Me), 11.6 (2Me), 17.2 (5"Me), 20.2 and 20.3 (8Me, 3"Me), 20.7, (5"Me), 24.4 (6Me), 26.9 (8), 29.3 (4'), 34.4 (2"), 34.6 (9'NMe), 36.8 (4), 39.5 (3'N(Me)$_2$), 41.8 (2), 42.2 (7), 47.9 (3"OMe), 58.0 (9), 63.6 (3'), 63.7 (5"), 67.0 (5'), 69.7 (2'), 71.9 (3"), 72.8 (6), 76.7 (4"), 79.5 (3), 82.7 (5), 94.9 (1"), 101.8 (1'), 176.4 (1) ppm.

Method D: General Procedure for Preparation of Seco Macrolide Compound of Formula (I-D), Wherein X$^{1p}$ is —CH$_2$NH$_2$ and X$^{2p}$ is Hydrogen:

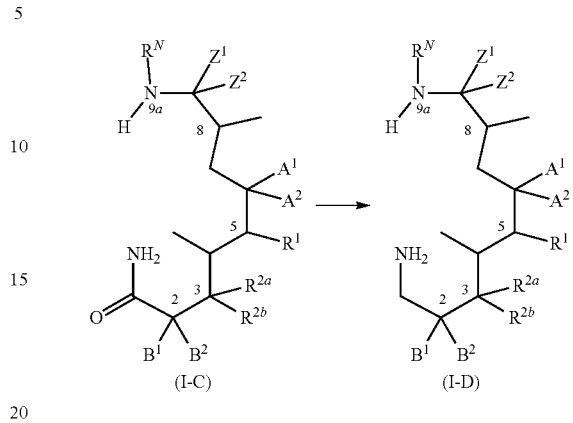

Scheme 4: illustrates reduction of C/1-amide compound of formula (I-C), wherein X$^{1p}$ is —C(=O)NH$_2$, X$^{2p}$ is hydrogen, Z$^1$, Z$^2$, A$^1$, A$^2$, R$^1$, R$^{2a}$, R$^{2b}$, B1, B2, and R$^N$ are as defined for formula (I) above, using suitable reducing agent to compound of formula (I-D) which is subset of compounds of formula (I), wherein X$^{1p}$ is —CH$_2$NH$_2$, X$^{2p}$ is hydrogen, Z$^1$, Z$^2$, A$^1$, A$^2$, R$^1$, R$^{2a}$, R$^{2b}$, B$^1$, B$^2$, and R$^N$ are as defined for formula (I) above.

The reduction is typically performed by adding 1-10 equiv. of reducing agent such as LiAlH$_4$, NaBH$_4$, LiEt$_3$BH, or borane-THF to a solution of the appropriate compound of formula (I-C) in suitable aprotic solvent preferably THF, dioxane or glyme at 0° C. to reflux temperature, suitably room temperature. The expected product may be isolated by methods known to one skilled in the art.

Compound I-D1-iii

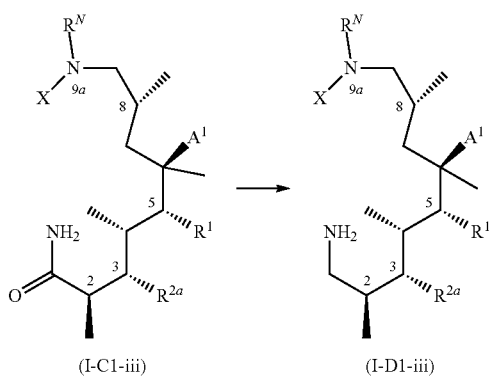

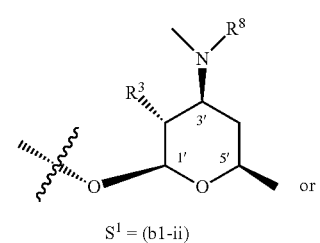

S¹ = (b1-ii)

-continued

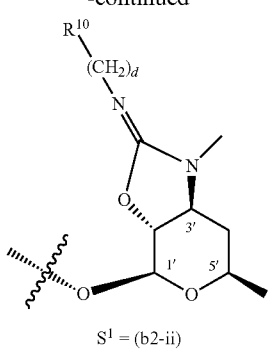

$S^1$ = (b2-ii)

Scheme 5

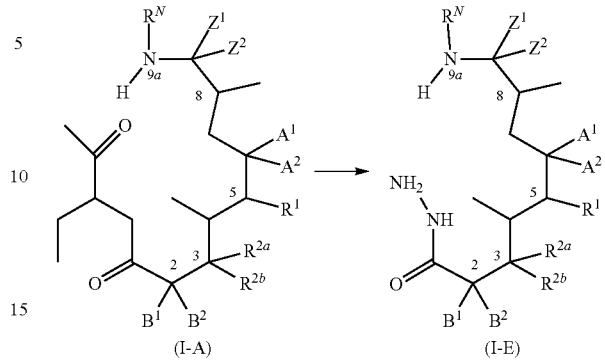

Scheme 5: illustrates transformation of compound of formula (I-A), wherein $X^1$ is

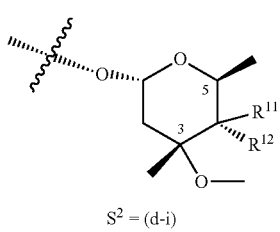

$S^2$ = (d-i)

$X^{2p}$ is hydrogen, $Z^1$, $Z^2$, $A^1$, $A^2$, $R^1$, $R^{2a}$, $R^{2b}$, $B^1$, $B^2$, and $R^N$ are as defined for formula (I) above, using hydrazine hydrate which gives compound of formula (I-E) which is subset of compounds of formula (I), wherein $X^{1p}$ is —C(=O)—NH—NH$_2$ group, $X^{2p}$ is hydrogen, $Z^1$, $Z^2$, $A^1$, $A^2$, $R^1$, $R^{2a}$, $R^{2b}$, $B^1$, $B^2$, and $R^N$ are as defined for formula (I) above.

The reaction is typically performed by adding 1-20 equiv. of hydrazine hydrate to a solution of the appropriate compound of formula (I-A) in a suitable solvent such as EtOH, with or without addition of base such as, for example, TEA and pyridine, at 0-120° C., suitably at room temperature. The expected product may be isolated by methods known to one skilled in the art.

Compound I-E1-iii

TABLE

Compound (I-D1-iii):

| I-D1-iii | $R^N$ | $A^1$ | $R^1$ | $R^3$ | $R^8$ | d | $R^{10}$ | $R^{2a}$ | $R^{11}$ | $R^{12}$ |
|---|---|---|---|---|---|---|---|---|---|---|
| 1 | CH$_3$ | OH | b1-ii | OH | CH$_3$ | NA | NA | d-i | H | OH |

NA = not applicable

Compound I-D1-iii-1: Compound I-C1-iii-1 (0.91 g, 1.50 mmol) was dissolved in dry THF (30 mL) and cooled to 0 C (ice-bath). 2 M THF solution of LiAlH$_4$ (7.51 mL, 15.0 mmol) was added dropwise during 15 minutes, the resulting mixture removed from the ice-bath and stirred at room temperature for 22 h. The reaction mixture was quenched at 0 C (ice-bath) by dropwise addition of water (0.57 mL). NaOH (20%, aq) (0.57 mL) was added dropwise, followed by more water (1.71 mL). The reaction mixture was removed from the ice-bath and further stirred at room temperature for 1 h. The precipitate was filtered off and further washed with THF (2×10 mL), all THF fractions combined and the solvent evaporated to afford crude Compound I-D1-iii-1 MS(m/z) 592.59 [MH]$^+$, which may be used in subsequent steps without further purification.

Method E: General Procedure for Preparation of Seco Macrolide Compound of Formula (I-E), Wherein $X^{1p}$ is —C(=O)—NH—NH$_2$ Group and $X^{2p}$ is Hydrogen:

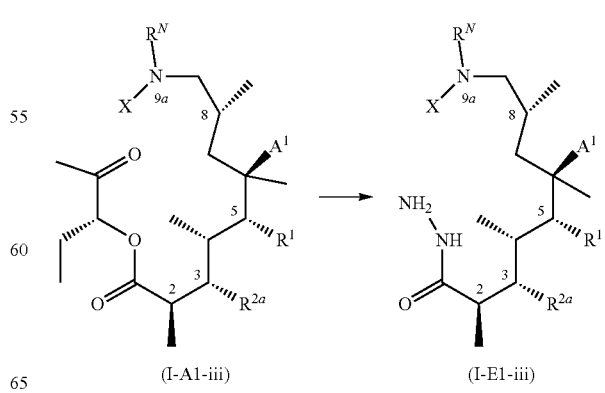

-continued

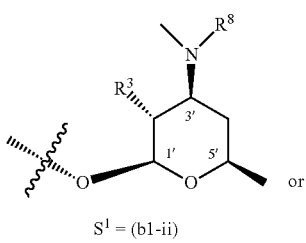

S¹ = (b1-ii)      or

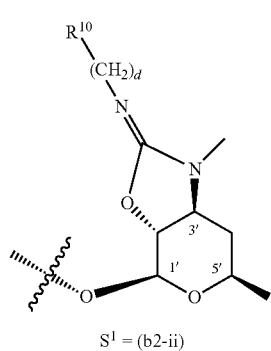

S¹ = (b2-ii)

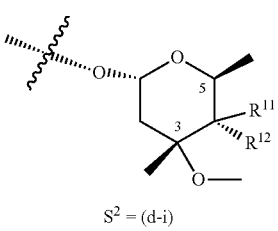

S² = (d-i)

TABLE

| Compound (I-E1-iii): | | | | | | | | | |
|---|---|---|---|---|---|---|---|---|---|
| I-E1-iii | $R^N$ | $A^1$ | $R^1$ | $R^3$ | $R^8$ | d | $R^{10}$ | $R^{2a}$ | $R^{11}$ | $R^{12}$ |
| 1 | $CH_3$ | OH | b1-ii | OH | $CH_3$ | NA | NA | d-i | H | OH |

NA = not applicable

Compound I-E1-iii-1: To a solution of Compound I-A1-iii-1 (500 mg, 0.72 mmol) in ethanol (1.5 mL), cooled to 0° C., hydrazine hydrate (3 mL) was added. Reaction mixture was allowed to gradually achieve room temperature and stirred overnight. The solvent was evaporated to afford crude product that was purified by column chromatography (Biotage SP4, eluent 0-100% DCM:MeOH:NH₄OH (90:9:1.5) in DCM) to afford Compound I-E1-iii-1 (190 mg); MS (ES⁺, m/z): 621.58 [MH]⁺.

Method FA: General Procedure for Preparation of Seco Macrolide Compound of Formula (I-FA), Wherein $X^{1p}$ is —C(=O)OH Group and $X^{2p}$ is C(=S)NH₂ Group:

Scheme 6A

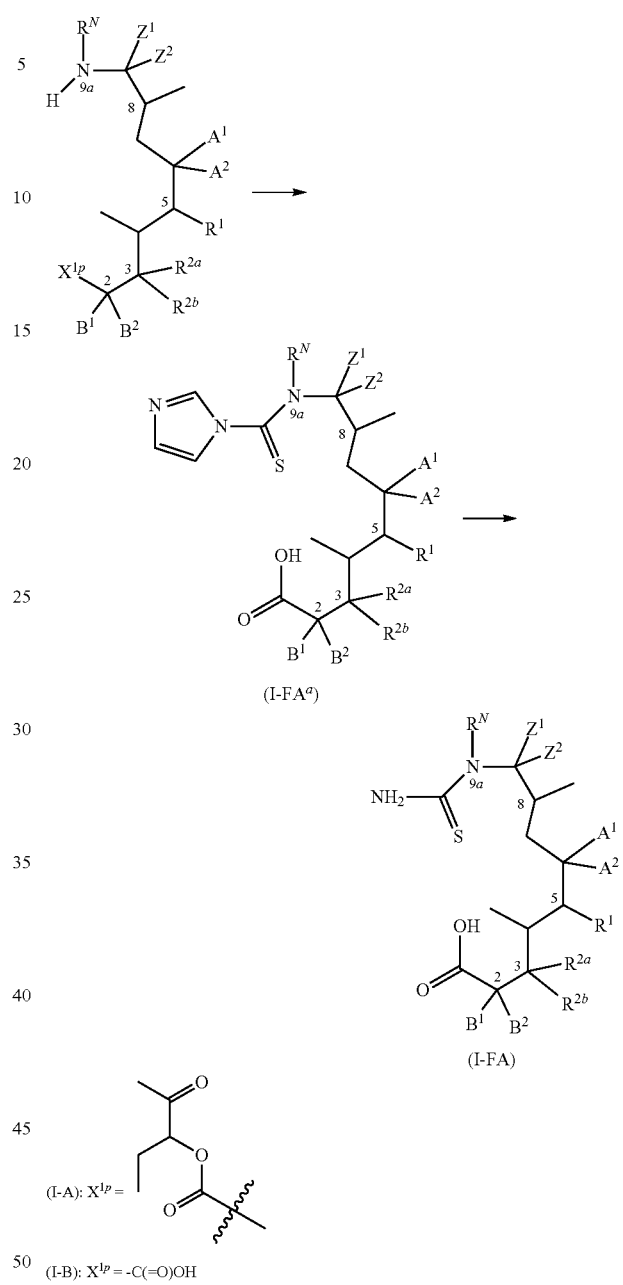

(I-A): $X^{1p}$ = 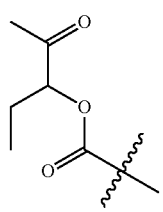 [SMILES: *C(=O)OC(CC)C(C)=O]

(I-B): $X^{1p}$ = -C(=O)OH

Scheme 6A: illustrates transformation of compound of formula (I-A) wherein $X^1$ is or formula (I-B), wherein $X^{1p}$ is —C(=O)OH, and $X^{2p}$ is hydrogen, $Z^1$, $Z^2$, $A^1$, $A^2$, $R^1$, $R^{2a}$, $R^{2b}$, $B^1$, $B^2$, and $R^N$ are as defined for formula (I) above to compound of formula (I-FA) which is subset of compounds of formula (I), wherein $X^{1p}$ is —C(=O)OH group. $X^{2p}$ is C(=S)NH$_2$ group, $Z^1$, $Z^2$, $A^1$, $A^2$, $R^1$, $R^{2a}$, $R^{2b}$, $B^1$, $B^2$, and $R^N$ are as defined for formula (I) above using in first step thiocarbonyldiimidazole, and in second step amonolysis reaction conditions. In case when method FA starts with compound of formula (I-A) then first step of Method FA is followed by C/1 ester hydrolysis Method B which is then followed by second (amonolysis) step of Method FA. If desired this can be performed as one pot reaction. The first step of Method FA is typically performed by adding 1.1-1.5 equiv. of thiocarbonyldiimidazole to a solution of the appropriate compound of formula (I-A) or (I-B) in a suitable solvent such as for example THF or MeCN at room temperature to elevated temperature (suitably at 60° C.) to give compound of formula (I-FA$^a$).

In case when the first step of Method FA starts from compound of formula (I-A) it is followed by hydrolysis of C/1 ester in the same pot by addition of base such as LiOH and water and stirring at 0 to 60° C. to give compound of formula (I-FA$^a$).

The second (amonolysis) step of Method FA is typically performed by adding amonia reagent including, but not limited to, NH$_3$/MeOH, NH$_4$OH, NH$_4$OH/MeCN, NH$_4$Cl/H$_2$O to solution of compound obtained in previous step, formula (I-FA$^a$), in suitable solvent (such as EtOH) at 0° C. to 60° C., suitably under cooling, suitably at 0° C. to room temperature. The expected product may be isolated by methods known to one skilled in the art.

Alternatively, compound of formula (I-A) or (I-B) may be subjected to reaction with thiocyanates, including KSCN and NH$_4$SCN, or isothiocyanates including, but not limited to, benzoyl isothiocyanate, trimethylsilyl isothiocyanate, and when starting from compound of formula (I-A) subsequently hydrolysed, to provide compound of formula (I-FA). The reaction with isothiocyanates requires stirring for 10 min to 24 h in organic solvents including, but not limited to, THF and acetonitrile, at 0-60° C.

Compound I-FA1-iii

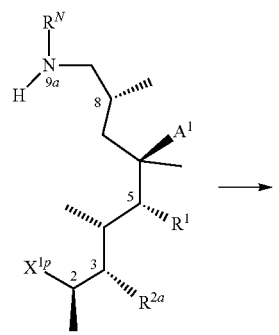

(I-A1-iii) or (I-B1-iii)

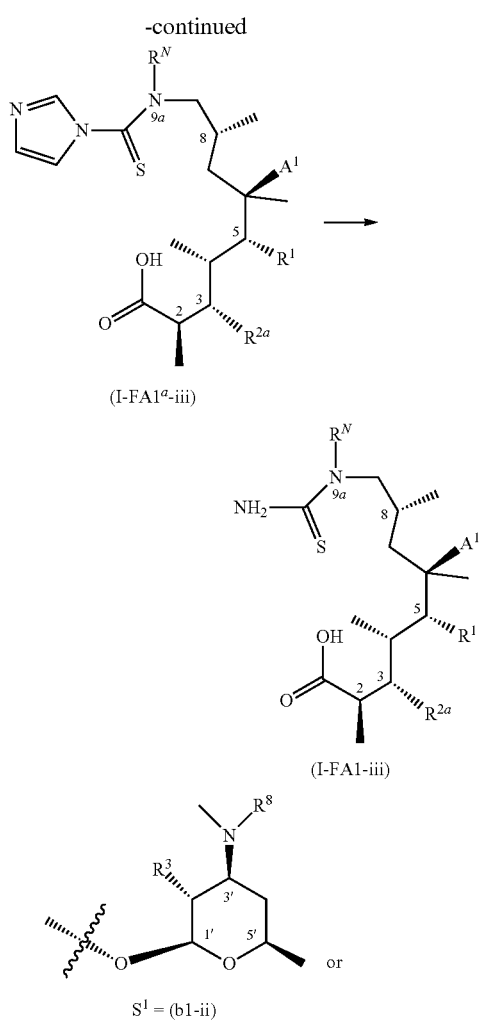

(I-FA1$^a$-iii)

(I-FA1-iii)

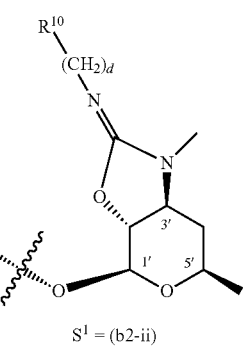

$S^1 = (b1\text{-}ii)$ or $S^1 = (b2\text{-}ii)$

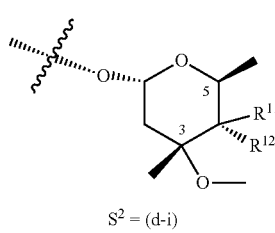

$S^2 = (d\text{-}i)$

TABLE compound (I-FA1-iii):

| I-FA1-iii | $R^N$ | $A^1$ | $R^1$ | $R^3$ | $R^8$ | d | $R^{10}$ | $R^{2a}$ | $R^{11}$ | $R^{12}$ |
|---|---|---|---|---|---|---|---|---|---|---|
| 1 | $CH_3$ | OH | b1-ii | OH | $CH_3$ | NA | NA | d-i | H | OH |
| 9 | $CH_3$ | OH | b2-ii | NA | NA | 0 | 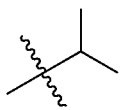 [SMILES: *C(C)C] | d-i | H | OH |

NA = not applicable

Compound I-FA1-iii-1: Step a) A solution of Compound I-B1-iii-1 (4.0 g, 6.6 mmol) and thiocarbonyldiimidazole (1.29 g, 7.2 mmol) in THF (80 mL) was stirred at 60° C. for 2 hours. The solvent was evaporated, the residue dissolved in DCM (150 mL), washed with sat. aq. $NaHCO_3$ (1×35 mL) and brine (1×35 mL), dried over anh. $Na_2SO_4$, and evaporated to afford crude product that was purified by column chromatography (Biotage SP4, eluent 0-100% DCM:MeOH:$NH_4OH$ (90:9:1.5) in DCM) to afford Compound I-FA1a-iii-1 (2.87 g); MS (ES+, m/z): 717.60 [MH]+.

Step b) To a solution of Compound I-FA1a-iii-1 from previous step (2.85 g, 4.0 mmol) in ethanol (10 mL), cooled to 0° C., $NH_4OH$ (50 mL, 25%-solution) was added. Reaction mixture was allowed to gradually achieve room temperature and stirred for 2 days. The solvent was partially evaporated and then lyophilized to afford crude Compound I-FA1-iii-1 (2.7 g) that was used without further purification in further reactions. MS (ES+, m/z): 666.59 [MH]+.

Compound I-FA1-iii-9:

Step a), Method FA:

Procedure 1, Step a, Method FA: Starting from Compound I-B1-iii-9:

A solution of Compound I-B1-iii-9 (2.4 g, 3.6 mmol) and thiocarbonyldiimidazole (0.72 g, 4.0 mmol) in THF (60 mL) was stirred at 60° C. for 1.5 hours. The solvent was evaporated and the residue purified by column chromatography (Biotage SP4, eluent 0-100% DCM:MeOH:$NH_4OH$ (90:9:1.5) in DCM) to afford Compound I-FA1a-iii-9 (1.9 g); MS (ES+, m/z): 770.54 [MH]+.

Procedure 2, Step a, Method FA: Starting from Compound I-A1-iii-9:

A solution of Compound I-A1-iii-9 (2.14 g, 2.88 mmol) and thiocarbonyldiimidazole (0.64 g, 3.6 mmol) in THF (60 mL) was stirred at 60° C. for 2 hours. Reaction mixture was cooled to room temperature, then LiOH (345 mg, 14.4 mmol) and water (114 uL, 6.3 mmol) were added. Reaction mixture was stirred at room temperature overnight and then at 40° C. for 24 hours. The solvent was evaporated and the residue purified by column chromatography (Biotage SP4, eluent 0-100% DCM:MeOH:$NH_4OH$ (90:9:1.5) in DCM) to afford Compound I-FA1a-iii-9 (1.95 g).

Step b) Amonolysis, Method FA:

To a solution of Compound I-FA1$^a$-iii-9 from previous step (1.9 g, 2.5 mmol) in ethanol (10 mL), cooled to 0° C., $NH_4OH$ (50 mL, 25%-solution) was added. Reaction mixture was allowed to gradually achieve room temperature and stirred overnight. The solvent was partially evaporated and then lyophilized to afford crude Compound I-FA1-iii-9 (1.85 g) that was used as is in further reactions. MS (ES+, m/z): 719.64 [MH]+.

Method FB: General Procedure for Preparation of Seco Macrolide Compound of Formula (I-FB), Wherein $X^{1p}$ is —C(=O)OH Group and $X^{2p}$ is C(=O)$NH_2$ Group

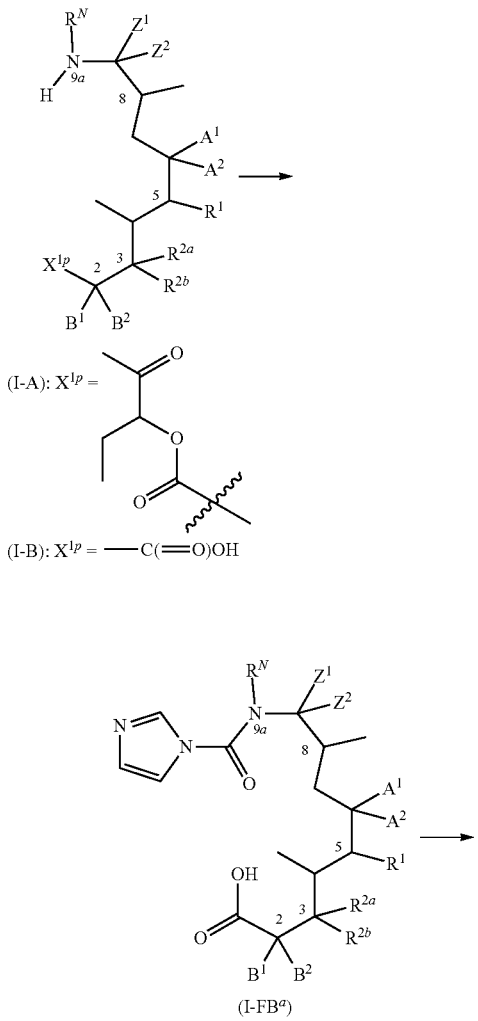

Scheme 6B

-continued

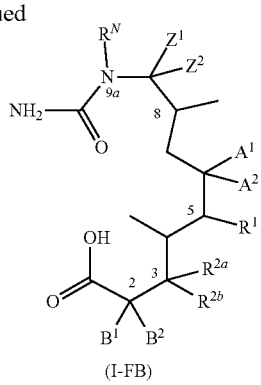

(I-FB)

Scheme 6B: illustrates transformation of compound of formula (I-A) wherein $X^1$ is

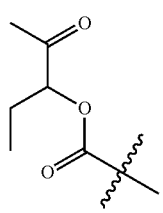 [SMILES: *C(=O)OC(CC)C(C)=O]

or of formula (I-B), wherein $X^{1p}$ is —C(═O)OH, and $X^{2p}$ is hydrogen, $Z^1$, $Z^2$, $A^1$, $A^2$, $R^1$, $R^{2a}$, $R^{2b}$, $B^1$, $B^2$, and $R^N$ are as defined for formula (I) above to compound of formula (I-FB) which is subset of compounds of formula (I), wherein $X^{1p}$ is —C(═O)OH group, and $X^{2p}$ is C(═O)NH$_2$ group, $Z^1$, $Z^2$, $A^1$, $A^2$, $R^1$, $R^{2a}$, $R^{2b}$, $B^1$, $B^2$, and $R^N$ are as defined for formula (I) above using in first step carbonyldiimidazole, and in second step amonolysis reaction conditions. In case when method FB starts with compound of formula (I-A) then first step of Method FB is followed by C/1 ester hydrolysis Method B which is then followed by second (amonolysis) step of Method FB. If desired this can be performed as a one pot reaction. The first step of Method FB is typically performed by adding 1.1-1.5 equiv. of carbonyldiimidazole to a solution of the appropriate compound of formula (I-A) or (I-B) in a suitable solvent such as for example THF or MeCN at 0° C. to 60° C. (suitably at room temperature to 60° C.) to give compound of formula (I-FB$^a$).

In case when first step of Method FB starts from compound of formula (I-A) it is followed by hydrolysis od C/1 ester in the same pot by addition of base such as LiOH and water and stirring at 0 to 60° C. to give compound of formula (I-FB$^a$).

The second (amonolysis) step of Method FB is typically performed as described above for Method FA.

Alternatively, compound of formula (I-A) or (I-B) may be subjected to reaction with alkali metal cyanates, including KOCN, or with isocyanates including, but not limited to, isocyanic acid, ammonium isocyanate, trimethylsilyl isocyanate, 2,2,2-trichloroacetyl isocyanate, sulfuryl chloride isocyanate, benzyl isocyanate and subsequently hydrolysed to provide compound of formula (I-FB). The reaction with isothiocyanates requires stirring for 10 min to 24 h in organic solvents including, but not limited to, DCM, THF, DMF, acetonitrile, isopropanol, and water at 0-60° C. Alternatively compound of formula (I-A) or (I-B) can react with carbamoyl chloride in organic solvents including, but not limited to, DCM, toluene, and water/MeCN preferably at temperatures 0-60° C. and in the presence or base such as TEA, morpholine, and disodium carbonate to provide compound of formula (I-FB). Alternatively compound of formula (I-A) or (I-B) can react with benzotriazole-1-carboxamide in organic solvents such as THF preferably at reflux to provide compound of formula (I-FB). Alternatively compound of formula (I-A) or (I-B) can react with 4-nitrophenyl-N-benzylcarbamate in organic solvent, such as dichloromethane, or dioxane/water in the presence of triethylamine. Subsequent hydrogenolysis provides compound of formula (I-FB). If starting from compound of formula (I-A), required ester hydrolysis can be achieved by LiOH/water and stirring at 0-60° C. for 1-48 h.

Compound I-FB1-iii

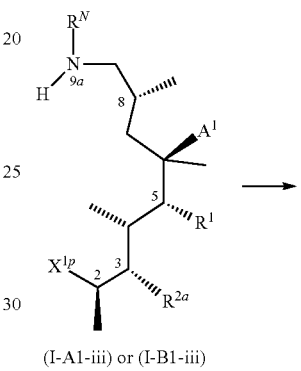

(I-A1-iii) or (I-B1-iii)

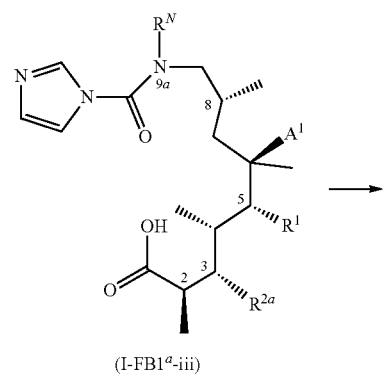

(I-FB1$^a$-iii)

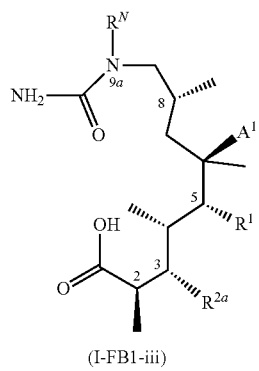

(I-FB1-iii)

-continued

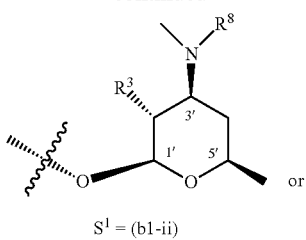

S¹ = (b1-ii) or

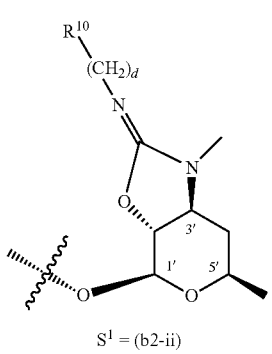

S¹ = (b2-ii)

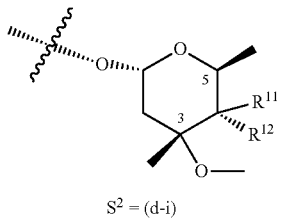

S² = (d-i)

TABLE

| compound (I-FB1-iii): | | | | | | | | | | |
|---|---|---|---|---|---|---|---|---|---|---|
| I-FA1-iii | R$^N$ | A¹ | R¹ | R³ | R⁸ | d | R¹⁰ | R$^{2a}$ | R¹¹ | R¹² |
| 1 | CH₃ | OH | b1-ii | OH | CH₃ | NA | NA | d-i | H | OH |

NA = not applicable

Compound I-FB1-iii-1: A solution of Intermediate I-A1-iii (100 mg, 0.165 mmol), CDI (40.1 mg, 0.247 mmol), and ammonium acetate (317.65 mg, 4.12 mmol) in DMF (1 mL) was shaken in a vial at room temperature for 2 days to afford crude Intermediate I-FB1-iii-1 (1.85 g) that was used as is in further reactions. MS (ES⁺, m/z): 650.60 [MH]⁺.

Method K: General Procedure for Preparation of Seco Macrolide Compound of Formula (I-KA-a), Wherein X$^{1p}$ is —CH₂OH Group and X$^{2p}$ is H; and of Seco Macrolide Compound of Formula (I-KA), Wherein X$^{1p}$ is —C(═O) OH Group and X$^{2p}$ is H:

Scheme 7

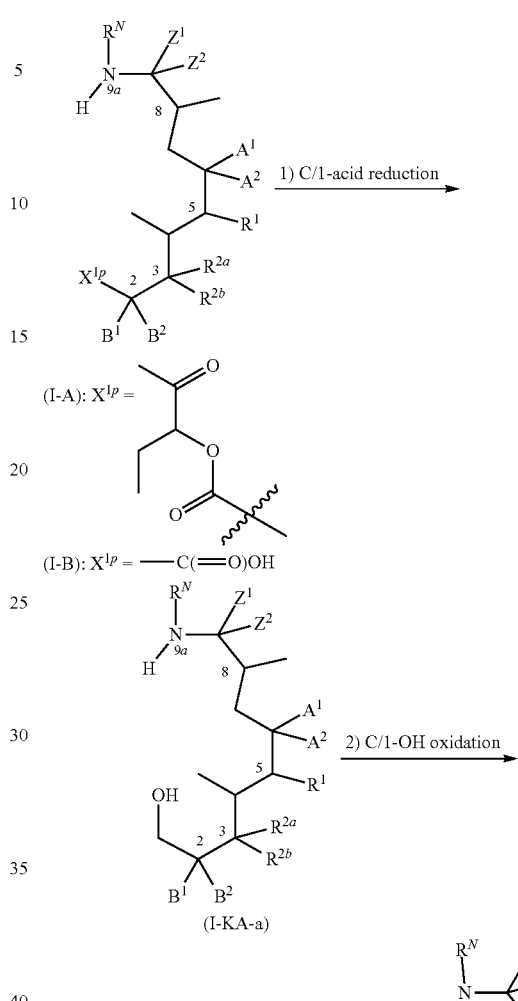

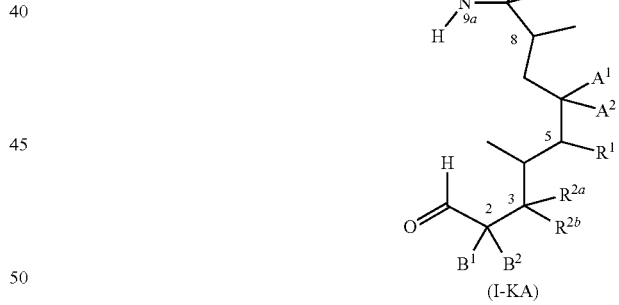

Scheme 7: illustrates transformation of compound of formula (I-A) wherein X¹ is

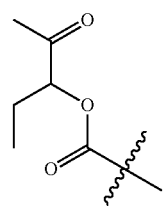 [SMILES: *C(=O)OC(CC)C(C)=O]

or of formula (I-B), wherein X$^{1p}$ is —C(═O)OH, and X$^{2p}$ is hydrogen, Z¹, Z², A¹, A², R¹, R$^{2a}$, R$^{2b}$, B¹, B², and R$^N$ are as defined for formula (I) above to compound of formula (I-KA-a), which is subset of compounds of formula (I), wherein $X^{1p}$ —$CH_2OH$ group, $X^{2p}$ is hydrogen, $Z^1$, $Z^2$, $A^1$, $A^2$, $R^1$, $R^{2a}$, $R^{2b}$, $B^1$, $B^2$, and $R^N$ are as defined for formula (I) above using in first step for C/1-ester (I-A) or C/1-acid (I-B) reduction standard carboxylic acid reduction conditions, typically $LiAlH_4$ or $LiEt_3BH$ in aprotic and inert solvent (suitably THF). Thus obtained alcohol intermediate (I-KA-a) is in second step subjected to oxidation using standard oxidizing reagents, typically using (2,2,6,6-tetramethylpiperidin-1-yl)oxidanyl (TEMPO) to give aldehid compound of formula (I-KA), which is subset of compounds of formula (I), wherein $X^{1p}$ is —C(=O)H group, $X^{2p}$ is hydrogen, $Z^1$, $Z^2$, $A^1$, $A^2$, $R^1$, $R^{2a}$, $R^{2b}$, $B^1$, $B^2$, and $R^N$ are as defined for formula (I) above.

Compound I-KA1-a-iii and I-KA1-iii

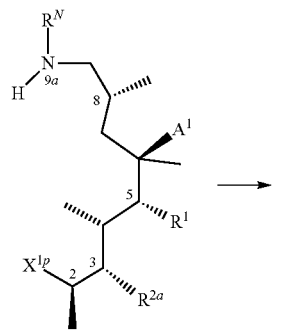

(I-A1-iii) or (I-B1-iii)

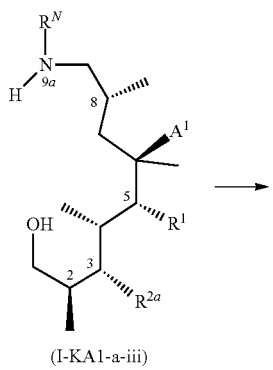

(I-KA1-a-iii)

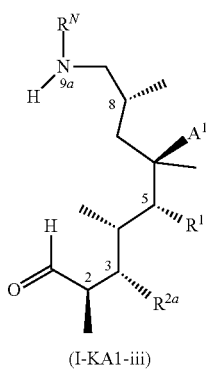

(I-KA1-iii)

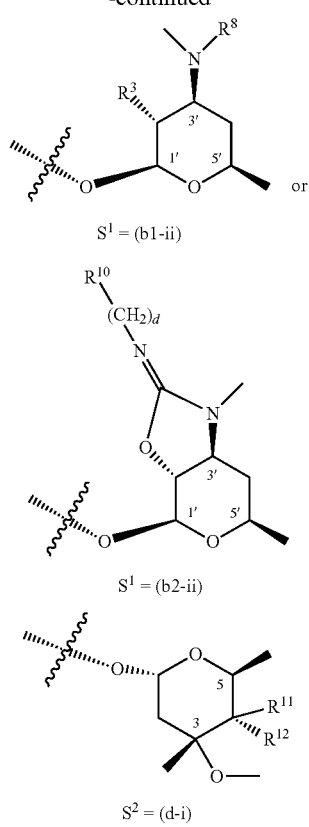

$S^1$ = (b1-ii)

$S^1$ = (b2-ii)

$S^2$ = (d-i)

TABLE

Compound (I-KA-a-iii) and (I-KA-iii):

| I-KA1-a-iii | $X^{1p}$ | $R^N$ | $A^1$ | $R^1$ | $R^3$ | $R^8$ | d | $R^{10}$ | $R^{2a}$ | $R^{11}$ | $R^{12}$ |
|---|---|---|---|---|---|---|---|---|---|---|---|
| 1 | —$CH_2OH$ | $CH_3$ | OH | b1-ii | OH | $CH_3$ | NA | NA | d-i | H | OH |

NA = not applicable

Compound I-KA1-a-iii-1: Compound I-A-iii-1 (0.6 g, 0.87 mmol) was dissolved in THF and solution was purged with argon and cooled to 0° C. Then $LiEt_3BH$ was added (1M in THF, 10 eq) and reaction mixture was stirred overnight at room temperature. Reaction was quenched with water, ethylacetate was added, layers were separated, aqueous layer was washed with ethylacetate, organics collected, dried and concentrated affording Compound I-KA1-a-iii-1 MS(m/z) 593.49 [MH]$^+$ which may be used in subsequent steps without further purification.

Method M: General Procedure for Preparation of Seco Macrolide Compound of Formula (I-MN), Wherein $X^{1p}$ is —C≡N and $X^{2p}$ is Hydrogen; and of Seco Macrolide Compound of Formula (I-M), Wherein $X^{1p}$ is —C(=S)$NH_2$ Group and $X^{2p}$ is Hydrogen:

Scheme 8

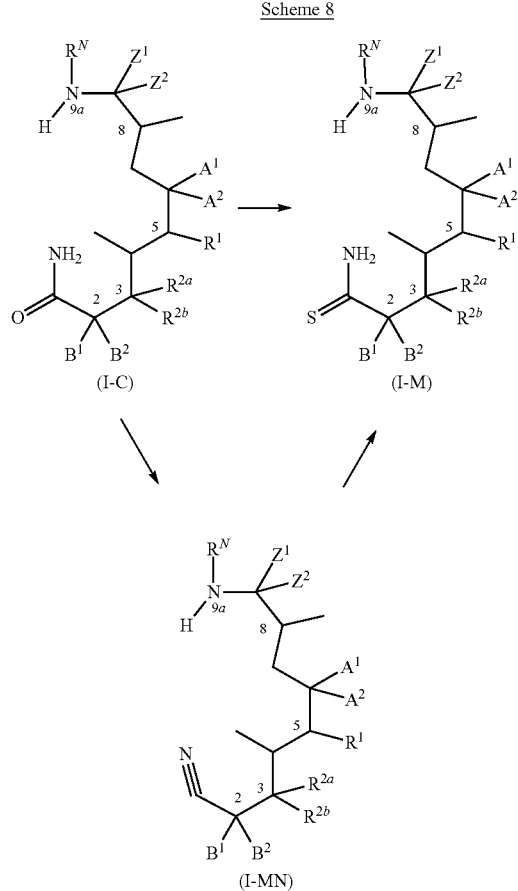

Scheme 8: illustrates transformation of compound of formula (I-C) wherein $X^{1p}$ C(=O)NH$_2$, $X^{2p}$ is hydrogen, $Z^1$, $Z^2$, $A^1$, $A^2$, $R^1$, $R^{2a}$, $R^{2b}$, $B^1$, $B^2$, and $R^N$ are as defined for formula (I) above to compound of formula (I-M), which is subset of compounds of formula (I) wherein $X^{1p}$ is —C(=S)NH$_2$, $X^{2p}$ is hydrogen, $Z^1$, $Z^2$, $A^1$, $A^2$, $R^1$, $R^{2a}$, $R^{2b}$, $B^1$, $B^2$, and $R^N$ are as defined for formula (I) above. The reaction is suitably performed in one step by reaction with Lawesson's or Bellau's reagents (0.5 or more equiv.) or with P$_4$S$_{10}$ (>0.25 equiv.) alone or in combination with hexamethyldisiloxane. Such reactions can be performed in various solvents including, but not limited to, toluene, THF, DCM, HMPA, chloroform. The reaction temperature is preferably in a range from room temperature to reflux of the corresponding solvent, and reaction time is usually 30 min to 48 h.

Alternatively, compound (I-M) can be prepared from compound of formula (I-C) in two steps via nitrile compound of formula (I-MN), which is subset of compounds of formula (I) wherein $X^{1p}$ is —CN, $X^{2p}$ is hydrogen, $Z^1$, $Z^2$, $A^1$, $A^2$, $R^1$, $R^{2a}$, $R^{2b}$, $B^1$, $B^2$, and $R^N$ are as defined for formula (I) above which can be prepared by dehydration reaction of compound of formula (I-C) using various reagents such as thionyl chloride, phosphorus pentoxide, phosphorus oxychloride, titanium tetrachloride, pivaloyl chloride, ethyl dichlorophosphate, trichloroacetyl chloride, and silanes/TBAF. Nitrile compound (I-MN) can be then converted to compound (I-M) using alkali metal hydrogen sulfide or ammonium sulfide under high pressure, phosphorus decasulfide, thioacids, thioacetic acid in combination with Lewis acid or benzylamine or calcium hydride, thioacetamide, DowexSH, O-dialkyldithiophosphates, 12 diphenylphosphinodithioacids, sodium trimethylsilanethiolate, sodium hydrosulfide hydrate and diethyl amine hydrochloride, sodium hydrosulfide hydrate and magnesium chloride hexahydrate, and (P$_4$S$_{11}$)Na$_2$.

Method RE: General Procedure for Preparation of Seco Macrolide Compound of Formula (I-RE), Wherein $X^{1p}$ is NH$_2$ and $X^{2p}$ is Hydrogen:

Scheme 9

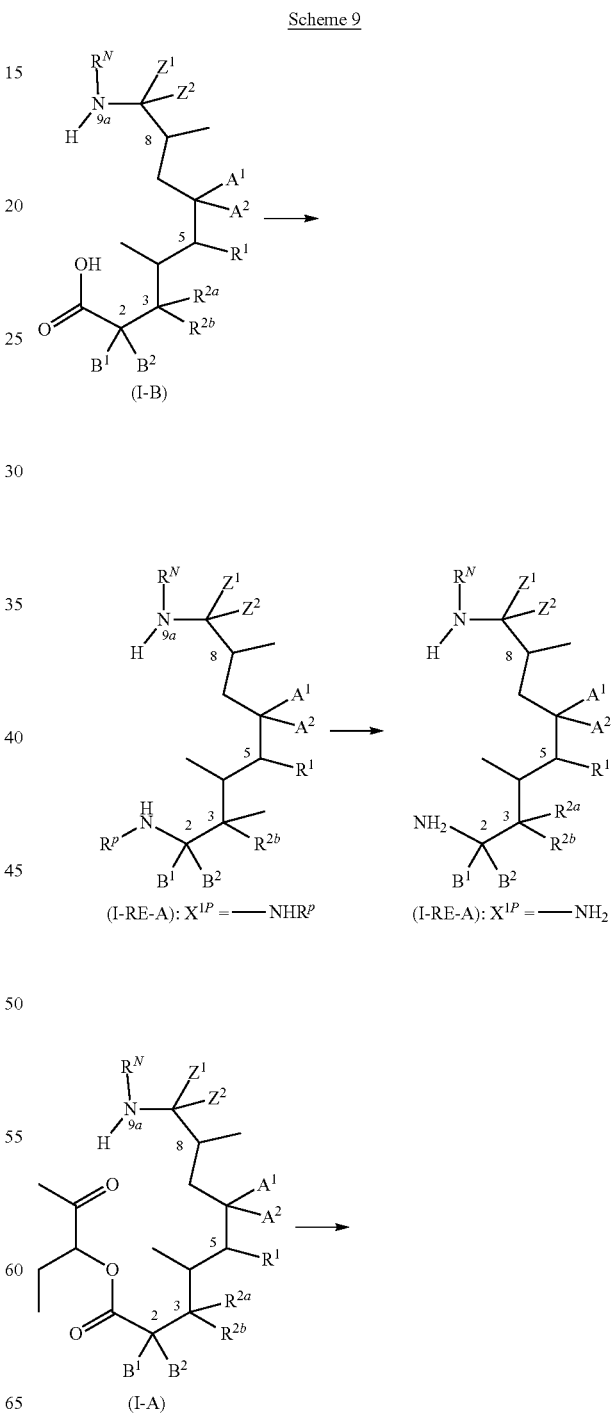

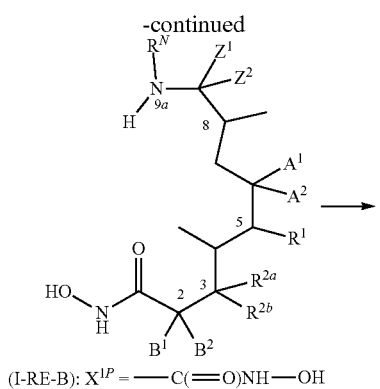

(I-RE-B): $X^{1P}$ = —C(=O)NH—OH

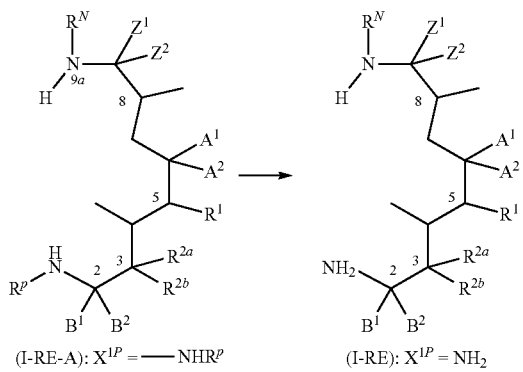

(I-RE-A): $X^{1P}$ = —NHR$^p$        (I-RE): $X^{1P}$ = NH$_2$

Scheme 9: illustrates transformation of compound of formula (I-B) wherein $X^{1p}$ C(=O)OH or of compound of formula (I-A) wherein $X^{1p}$ is

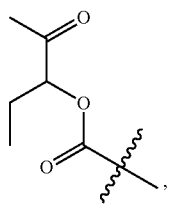 [SMILES: *C(=O)OC(CC)C(C)=O]

$X^{2p}$ is hydrogen, $Z^2$, $A^1$, $A^2$, $R^1$, $R^{2a}$, $R^{2b}$, $B^1$, $B^2$, and $R^N$ are as defined for formula (I) above to compound of formula (I-RE), which is subset of compounds of formula (I) wherein $X^{1p}$ is NH$_2$, $X^{2p}$ is hydrogen, $Z^1$, $Z^2$, $A^1$, $A^2$, $R^1$, $R^{2a}$, $R^{2b}$, $B^1$, and $R^N$ are as defined for formula (I) above. Said transformation can be prepared by modified Curtius rearrangement of compound of formula (I-B). Treatment of compound (I-B) with DPPA and excess of an alcohol in the presence of TEA in suitable solvent at elevated temperature gives the carbamate compound of formula (I-RE-A). Examples of alcohols that are commonly used, but are not limited to, are methanol, ethanol, t-butanol, benzyl alcohols. Suitable solvents used in these reactions, but not limited to, are dioxane, toluene, Me-THF, THF. Temperatures at which rearrangement is performed are usually boiling points of the solvents used (Shioiri, T., et al., J. Am. Chem. Soc. (1972) 94(17), 6203). Thus obtained (I-RE-A) can be transferred to (I-RE) after mild acidic hydrolysis or hydrogenation of the carbamate group. Acidic hydrolysis can be performed with, but not limited to, TFA or hydrochloric acid in aprotic solvents such as DCM, chloroform, dioxane, and a like. Hydrogenative transformation of (I-RE-A) to final amine of formula (I-RE) can be performed with gaseous hydrogen or hydrogen donors such as i-propanol, formic acid and its organic or inorganic salts, cyclohexene or cyclodienes in the presence of transition metal catalyst, most often palladium on carbon.

Alternatively, compound of formula (I-RE) can be prepared from compound (I-A) via modified Lossen rearrangement. Hydroxamic acid Intermediate (I-RE-B) can be prepared from the carboxylic acid (I-A) after treatment with hydroxyl amine in the presence of suitable coupling reagent, such as CDI, HATU, EDAC, DCC, T3P® or from the corresponding ester after treatment with hydroxyl amine in the presence of trimetylaluminium (Pirrung, M. et al., J. Org. Chem. (1995), 60(24), 8084) or its nonpyrophoric source DABAL (Dubois, N. et al., Tetrahedron (2013), 69(46), 9890). Thus obtained (I-RE-B) compound after treatment with CDI at elevated temepatures in aprotic solvent, such as acetonitrile, in the presence of alcohol forms the compound (I-RE-A) (Dube, P., et al. Org. Lett. (2009) 11(24) 5622). The compound (I-RE-A) can be transferred to desired compound of formula (I-RE) as described above.

Synthetic Procedure for O-Alkyl Aglycone Compounds of Formula (II)

Method O-ALKYL: General Procedure for Preparation of Macrolide Compound of Formula (II-X), Wherein $A^1$ is —OC$_{1-6}$Alkyl, $R^1$ is OH, $R^{2a}$ is —OC$_{1-6}$Alkyl (Formula II-XA); or $A^1$ is —OC$_{1-6}$Alkyl, $R^1$ is —OC$_{1-6}$Alkyl, $R^{2a}$ is OH (Formula II-XB); or $A^1$ is —OC$_{1-6}$Alkyl, $R^1$ is —OC$_{1-6}$Alkyl, $R^{2a}$ is —OC$_{1-6}$Alkyl (Formula II-XC):

Scheme 10: illustrates O-alkylation of hydroxyl groups at positions C/3 and C/5 of compound of formula (II) wherein position C/6 is already O-alkylated, i.e. $A^1$ is —OC$_{1-6}$ alkyl, and $Z^1$, $Z^2$, $A^2$, $B^1$, $B^2$, and $R^N$ are as defined for formula (II) above to give di-O-alkyl aglycone compounds of formula (II-XA) and (II-XB) and tri-O-alkyl aglycone compound of formula (II-XC), which are subset of compounds of formula (II-X), wherein $A^1$ is —OC$_{1-6}$alkyl, $R^1$ is OH, $R^{2a}$ is —OC$_{1-6}$alkyl (Formula II-XA); or $A^1$ is —OC$_{1-6}$alkyl, $R^1$ is —OC$_{1-8}$alkyl, $R^{2a}$ is OH (Formula II-XB); or $A^1$ is —OC$_{1-6}$alkyl, $R^1$ is —OC$_{1-6}$alkyl, $R^2$ is —OC$_{1-8}$alkyl (Formula II-XC), $Z^1$, $Z^2$, $A^2$, $R^1$, $R^{2a}$, $R^{2b}$, $B^1$, $B^2$, and $R^N$ are as defined for formula (II-X) above.

Scheme 10
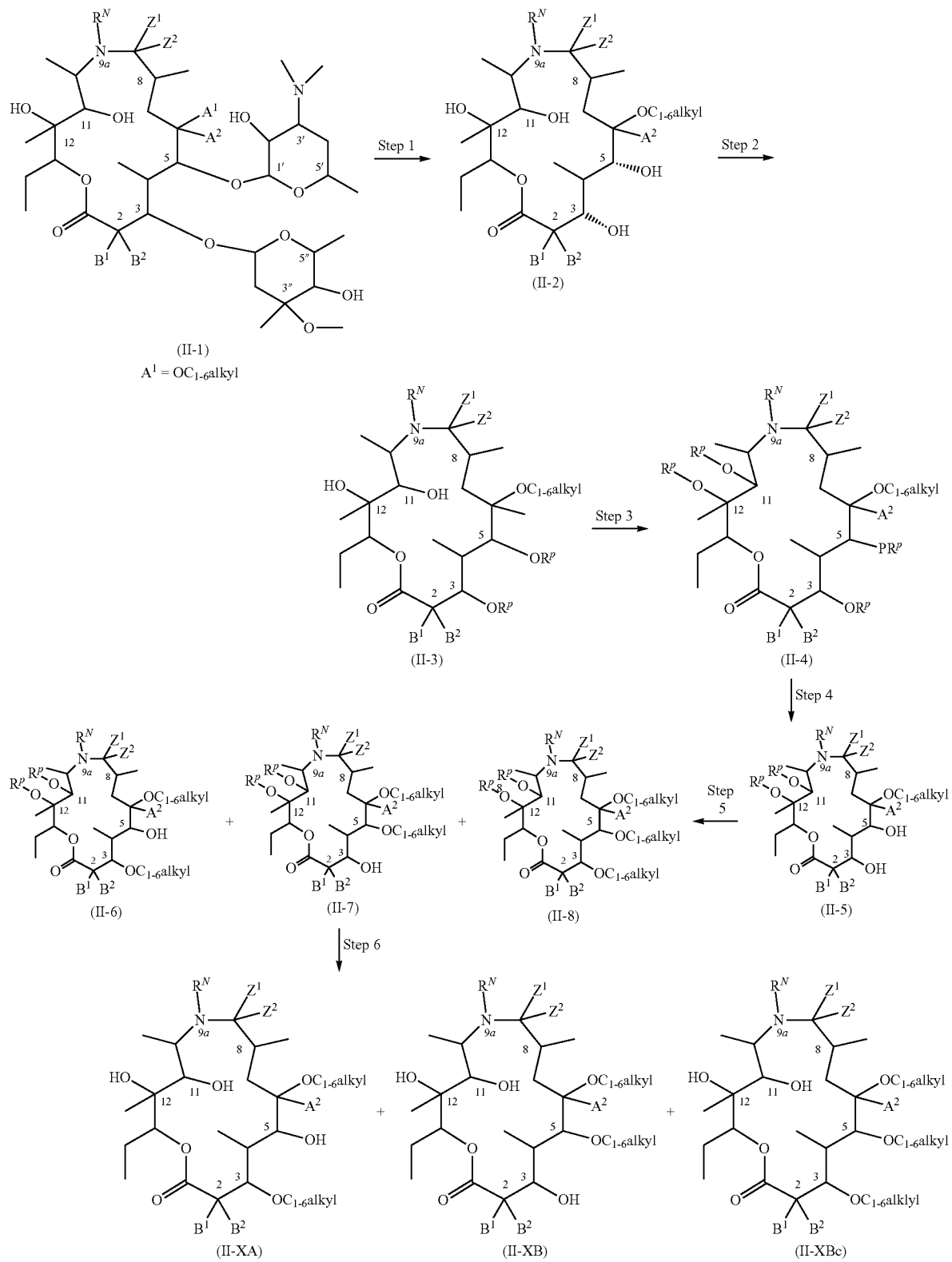
The reaction is usually conducted in several steps: in Step 1 both sugar groups are cleaved by treatment of starting macrolide compound of formula (II-1) with 6M HCl in organic solvent (suitably CHCl₃), for example following procedure described in EP0283055 to give compound of formula (II-2). In Step 2 hydroxyl groups at positions C/3 and C/5 are protected by processes and methods known to one skilled in the art (for example by 2,2-dimethoxypropane) to give compound of formula (II-3). In Step 3 hydroxyl groups at positions C/11 and C/12 are protected (suitably by cyclic carbonate) to give compound of formula (II-4). In Step 4 protective groups at positions C/3 and C/5 of compound of formula (II-4) are selectively removed (for example if C-11,12-cyclic carbonate protection was used by treatment with TFA) to give compound of formula (II-5), which is then in Step 5 subjected to O-alkylation reaction.

Step 5: O-alkylation reaction is performed using suitable diazoalkane of formula $R^q$—CH—$N_2$, wherein $R^q$ is hydrogen or $C_{1-6}$alkyl group in presence of transition metal halide catalyst or boric acid catalyst in an inert organic solvent as described in EP1633764 B1. Finally, In Step 6 protective groups form hydroxyl groups at positions C/11 and C/12 are removed to give desired di- and tri-O-alkyl compounds of formulae (II-XA), (II-XB) and (II-XC) respectively.

Compounds (II-XA-ii), (II-XB-ii) and (II-XC-ii)

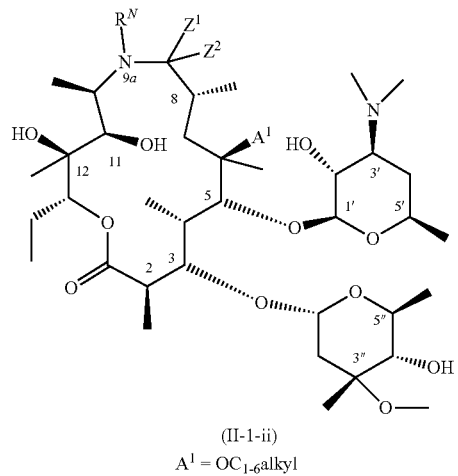

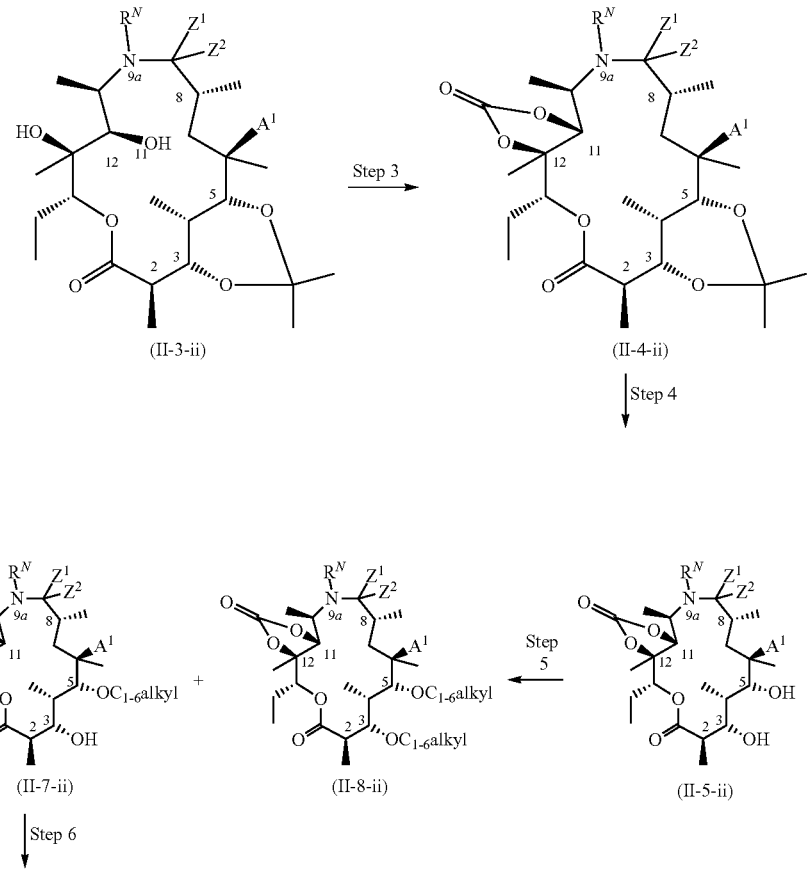

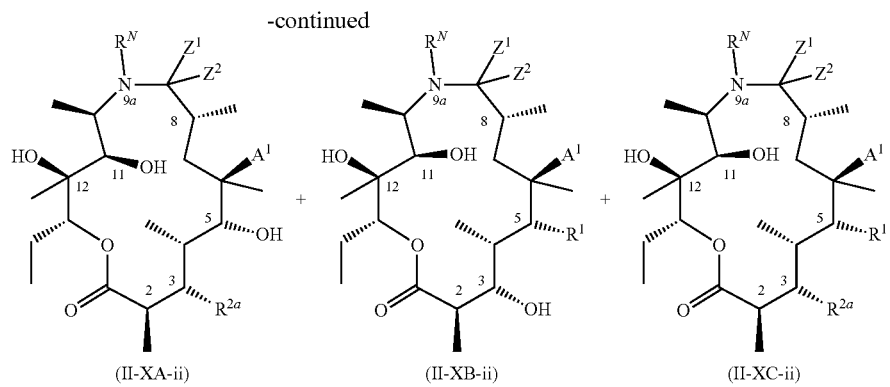

(II-XA-ii)  +  (II-XB-ii)  +  (II-XC-ii)

TABLE

Compounds (II-XA-ii), (II-XB-ii) and (I-XC-ii):

| Compound | $Z^1$ | $Z^2$ | $R^N$ | $A^1$ | $R^1$ | $R^{2a}$ |
|---|---|---|---|---|---|---|
| II-XA-ii-1 | H | H | $CH_3$ | $OCH_3$ | OH | $OCH_3$ |
| II-XB-ii-1 | H | H | $CH_3$ | $OCH_3$ | $OCH_3$ | OH |
| II-XC-ii-1 | H | H | $CH_3$ | $OCH_3$ | $OCH_3$ | $OCH_3$ |

NA = not applicable

Compounds II-XA-ii-1, II-XB-ii and II-XC-ii:

Step 1: Compound 11-2-ii-1: Compound 6-O-methyl-9-deoxo-9a-methyl-9a-aza-9a-homoerythromycin A (6-O-methyl azithromycin) (3.74 g, 0.05 mol) was treated with 6M HCl in $CHCl_3$ according to procedure described in EP0283055. After stirring for 16 hours the title compound (1.8 g) was obtained MS (m/z) 448.3 $[MH]^+$ which may be used in subsequent steps without further purification.

$^{13}C$ NMR (151 MHz, DMSO-d6): δ=7.3 (10Me), 7.8 (4Me), 12.1 (15), 15.7 (2Me), 18.2 (12Me), 19.9 (6Me), 21.0 (8Me), 21.7 (14), 28.0 (8), 35.9 (7, 4), 39.6 (9NMe), 43.7 (2), 48.6 (6OMe), 60.0 (10), 74.8 ppm.

Step 2: Compound II-3-ii-1: To a solution of Compound II-2-ii-1 (0.223 mmol) from Step 1 in DCM (2 mL) camphor sulfonic acid (1.5 eq) and 2,2-dimethoxypropane 84 eq) were added and reaction mixture stirred at room temperature for 18 hours. After that time reaction mixture was diluted with DCM and saturated aq. $NaHCO_3$ was added. Organic products were extracted with DCM, organic layers combined, dried over anhydrous $Na_2SO_4$ and solvent evaporated. Crude product was purified by column chromatography (silica gel; eluens DCM:MeOH:$NH_4OH$=10:1:0.1) giving Compound II-3-ii-1 (30 mg); MS m/z (ES$^+$): 488.3 $[MH]^+$.

$^{13}C$ NMR (151 MHz, DMSO-d6): δ=7.1 (10Me, 4Me), 10.7 (15), 14.7 (2Me), 17.7 (12Me), 19.0 (8Me), 19.1 (17), 20.2 (6Me), 21.1 (14), 29.8 (17), 32.0 (8), 33.6 (4), 37.0 (7), 40.9 (2), 44.9 (9NMe), 48.9 (6OMe), 59.0 (9, 10), 75.6 (12), 75.9 (3), 76.6 (13), 77.0 (11), 78.5 (6), 78.6 (5), 99.1 (16), 173.9 (1) ppm.

Step 3: Compound II-4-ii-1: To a solution of Compound II-3-ii-1 (1.05 mmol) in toluene (7.5 mL) carbodiimidazole (CDI, 1.5 eq) was added and reaction mixture stirred at 80° C. Additional amount od CDI (1.23 mmol) was added and after overall 48 hours reaction was cooled, concentrated in vacuo and residue dissolved in $H_2O$/DCM. Product was extracted with DCM, dried over anhydrous $Na_2SO_4$ and solvent evaporated to give crude Compound II-4-ii-1 (690 mg), which was used in following step without further purification; MS m/z (ES$^+$): 514.3 $[MH]^+$.

Step 4: Compound II-5-ii-1: To a solution of Compound II-4-ii-1 (0.98 mmol) in DCM (10 mL) trifluoroacetic acid (3 mL) was added and reaction mixture stirred at room temperature for 45 minutes. After that reaction mixture was diluted with DCM and water, layers separated and organic layer washed with $H_2O$, dried over anhydrous $Na_2SO_4$ and solvent evaporated to give Compound II-5-ii-1 (480 mg); MS m/z (ES$^+$): 474.26 $[MH]^+$. $^{13}C$ NMR (126 MHz, DMSO-d6): δ=8.0 (4Me), 8.1 (10Me), 9.9 (15), 15.2 (2Me), 16.0 (12Me), 19.3 (6Me), 20.4 (8Me), 21.3 (14), 25.5 (8), 34.3 (9NMe), 35.5 (4), 37.6 (7), 43.8 (2), 49.8 (6OMe), 58.6 (10), 65.1 (9), 75.2 (3), 75.9 (13), 77.7 (6), 81.9 (11), 82.2 (5), 87.4 (12), 152.7 (16), 174.6 (1) ppm.

Step 5: Compounds II-6-ii-1, II-7-ii-1 and II-8-ii-1: To a DCM solution of Compound 11-5-ii-1 (0.48 mmol) previously cooled at 0° C. fluoroboronic acid (FBA, 0.075 mL) was added followed with dropwise addition of TMS-$CHN_2$ (2 eq., 2M solution in diethylether). Reaction mixture was stirred at room temperature and mixture of unreacted starting material and Compounds II-6-ii-1, II-7-ii-1 and II-8-ii-1 was observed. Reaction mixture was flushed with $N_2$, diluted with DCM and $H_2O$, and products extracted with DCM. Crude products mixture was purified by column chromatography (EtOAc:n-hexane:diethylamine=10:10:2) giving mixture of di- and tri-O-methyl aglycone Compounds II-6-ii-1, II-7-ii-1 and II-8-ii-1 (125 mg); MS m/z (ES$^+$): 488.32 $[MH]^+$, MS m/z (ES$^+$): 488.27 $[MH]^+$ and MS m/z (ES$^+$): 502.37 $[MH]^+$.

Compound II-8-ii-1: In order to achieve complete tri-O-methylation, i.e. only Compound II-8-ii-1 to a DCM mixture of di- and tri-O-methyl aglycone Compounds II-6-ii-1, II-7-ii-1 and II-8-ii-1 (125 mg) under Ar atmosphere $Me_3OBF_4$ (5 eq) and 1,8-bis(dimethylamino)naphthalene (proton sponge; 5 eq) were added and reaction mixture stirred at room temperature for 20 hours. Then, reaction mixture was filtered through Celite and filtrate washed with 1M HCl. Organic layer was dried over anhydrous $Na_2SO_4$ and solvent evaporated. Crude product was purified by column chromatography (DCM:MeOH:$NH_4OH$=10:1:0.1) giving Compound II-8-ii-1 (35 mg); MS m/z (ES$^+$): 502.26 $[MH]^+$.

Step 6: Compounds II-XA-ii-1, II-XB-ii-1 and II-XC-ii-1: To a MeOH solution of Compounds II-6-ii-1, II-7-ii-1 and II-8-ii-1 mixture (48 mg), $K_2CO_3$ (10 eq) was added and reaction mixture stirred at 45° C. When all starting material was consumed reaction mixture was evaporated, residue dissolved in DCM, H2O and organic layers combined and dried over anhydrous $Na_2SO_4$ and solvent evaporated. Mixture of crude products was purified by column chromatography (EtOAc:n-Hex:diethylamine=10:10:2) to give di- and tri-O-methyl aglycone compounds II-XA-ii-1 (observed by MS and different retention time), II-XB-ii-1 (5 mg) and II-XC-ii-1 (8 mg):

Di-O-Methyl Aglycone Compound II-XB-ii-1: 5,6-Di-O-Methyl-3-O-Decladinosyl-5-O-Dedesosaminyl-9-Deoxo-9a-Methyl-9a-Aza-9a-Homoerythromycin A MS m/z (ES$^+$): 462.33 [MH]+

$^1$H NMR (600 MHz, DMSO-d6): δ=0.77 (t, J=7.4 Hz, 3H, 15), 0.79 (d, J=7.2 Hz, 3H, 4Me), 0.83 (d, J=7.2 Hz, 3H, 8Me), 0.84-0.87 (m, 1H, 7<">), 0.89 (d, J=6.8 Hz, 3H, 10Me), 1.00 (s, 3H, 12Me), 1.14 (d, J=6.6 Hz, 3H, 2Me), 1.16 (s, 3H, 6Me), 1.34-1.44 (m, 1H, 14<">), 1.63-1.69 (m, 1H, 8), 1.77-1.84 (m, 1H, 14<'>), 1.87 (q, J=7.0 Hz, 1H, 4), 1.89-1.94 (m, 1H, 7<'>), 2.22 (s, 3H, 9NMe), 2.46-2.48 (m, 1H, 2), 2.66-2.71 (m, 1H, 10), 3.03 (s, 3H, 6OMe), 3.07 (d, J=2.6 Hz, 1H, 5), 3.32 (s, 3H, 5OMe), 3.32-3.35 (m, 1H, 3), 3.40 (dd, J=6.6, 1.7 Hz, 1H, 11), 3.71 (br. s, 1H, 11OH), 4.27 (s, 1H, 12OH), 4.95 (d, J=7.0 Hz, 1H, 3OH), 5.06 (d, J=9.5 Hz, 1H, 13) ppm.

$^{13}$C NMR (151 MHz, DMSO-d6): δ=7.3 (10Me), 7.9 (4Me), 10.8 (15), 16.0 (2Me), 18.2 (12Me), 19.6 (6Me), 21.6 (14), 22.6 (8Me), 27.6 (8), 36.1 (7, 4), 44.1 (2), 49.5 (6OMe), 59.4 (5OMe), 60.8 (10), 74.8 (12), 75.5 (3), 76.3 (13), 77.4 (11), 79.7 (6), 86.1 (5), 174.8 (1) ppm.

Tri-O-Methyl Aglycone Compound II-XC-ii-1: 3,5,6-Tri-O-Methyl-3-O-Decladinosyl-5-O-Dedesosaminyl-9-Deoxo-9a-Methyl-9a-Aza-9a-Homoerythromycin A MS m/z (ES$^+$): 476 [MH]+

$^1$H NMR (600 MHz, DMSO-d6): δ=0.78 (t, J=6.5 Hz, 3H, 15), 0.80 (d, J=7.2 Hz, 3H, 4Me), 0.82-0.83 (m, 1H, 7<">), 0.84 (d, J=7.0 Hz, 3H, 7<">, 8Me), 0.89-0.91 (m, 3H, 10Me), 1.00 (s, 3H, 12Me), 1.18 (s, 3H, 6Me), 1.20 (d, J=7.0 Hz, 3H, 2Me), 1.36-1.45 (m, 1H, 14<">), 1.63-1.70 (m, 1H, 8), 1.77-1.83 (m, 1H, 14<>), 1.83-1.89 (m, 2H, 4, 7<'>), 2.20 (s, 3H, 9NMe), 2.63 (dd, J=9.8, 6.9 Hz, 1H, 2), 2.67 (br. s, 1H, 10), 3.09 (s, 3H, 6OMe), 3.12 (br. s., 1H, 5), 3.13-3.16 (m, 1H, 3), 3.34 (s, 3H, 5OMe), 3.36 (dd, J=6.7, 1.9 Hz, 1H, 11), 3.52 (s, 3H, 3OMe), 4.30 (br. s., 1H, 12OH), 5.05 (d, J=9.9 Hz, 1H, 13) ppm.

$^{13}$C NMR (151 MHz, DMSO-d6): δ=7.8 (10Me), 8.4 (4Me), 10.8 (15), 15.6 (2Me), 18.3 (12Me), 19.6 (6Me), 21.6 (14), 22.6 (8Me), 27.3 (8), 36.2 (7), 37.0 (4), 44.4 (2), 49.6 (6OMe), 58.9 (5OMe), 60.7 (10), 61.8 (3OMe), 74.7 (12), 76.0 (13), 77.1 (11), 80.6 (6), 85.6 (5), 86.7 (3), 175.0 (1) ppm.

Di-O-Methyl Aglycone Compound II-XA-ii-1: 3,6-Di-O-Methyl-3-O-Decladinosyl-5-O-Dedesosaminyl-9-Deoxo-9a-Methyl-9a-Aza-9a-Homoerythromycin A MS m/z (ES$^+$): 462.33 [MH]+

Di-O-methyl aglycone Compound II-XA-ii-1 (8 mg) together with additional amount of compound II-XB-ii-1 (7 mg) was isolated form another batch starting from compound 11-2-ii (200 mg) and following procedure as described above).

Synthetic Procedures for Macrolide Based Macrocycle Compounds of Formula (III) Cyclization (Ring Closure) Methods Method CY-1: General Procedure for C/1-Amide Linkage, Ring Closure for Compounds of Formula (III) Wherein $X^{1p}$ is —C(=O)NR$^x$— Group Scheme CY-1

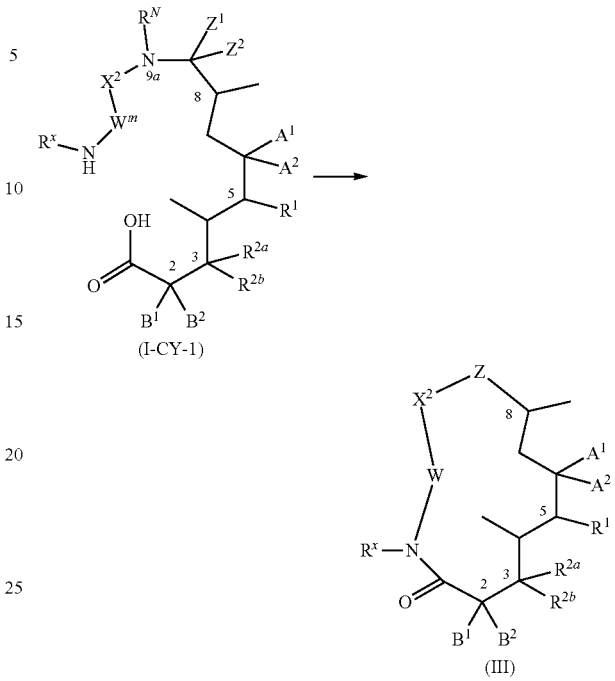

Scheme CY-1: illustrates macrocyclization of compound of formula (I-CY-1) wherein $X^{2p}$ is $X^2$—$W^m$—NH(R$^x$), wherein $W^m$ is W or the appropriate precursor convertable to W, wherein W, $X^2$, R$^x$, $Z^1$, $Z^2$, R$^N$, A$^1$, A$^2$, R$^1$, B$^1$, B$^2$, R$^{2a}$ and R$^{2b}$ are as defined for formula (III), to produce C/1-amide compound of formula (III), wherein XI is C(=O)NR$^x$—, and W, R$^x$, Z, A$^1$, A$^2$, R$^1$, B$^1$, B$^2$, R$^{2a}$ and R$^{2b}$ are as defined for formula (III) under standard amidation conditions as described above under the term "amidation" in more details. For example, it may be conducted in suitable solvent or mixture of solvents in presence of suitable coupling reagent. If desired suitable amidation additives may be used.

Method CY-1: Procedure 1 (CY-1.1): To a solution of Compound (l-CY-1) (for example compound (I-I) obtained by Method I) in dry DMF or DCM, DIPEA (1-1.5 equiv.) and HATU (1-1.5 equiv.) were added and the reaction mixture was stirred (if desired under argon) at 0° C. to room temperature for 1 to 24 hours. The expected product of formula (III) wherein $X^{1p}$ is —C(=O)NR$^x$— was isolated by methods known to one skilled in the art.

Method CY-1: Procedure 2 (CY-1.2): To a solution of Compound (l-CY-1) (for example compound (I-I) obtained by Method I) in dry DMF, DIPEA (1-1.5 equiv.) and propylphosphonic anhydride solution (50% in DMF, 1-1.5 equiv.) were added and the reaction mixture was stirred (if desired under argon) at 0° C. to room temperature for 1 to 24 hours. The expected product of formula (III) wherein $X^{1p}$ is —C(=O)NR$^x$— was isolated by methods known to one skilled in the art.

Method CY-1: Procedure 3 (CY-1.3): To a solution of Compound (I-CY-1) (for example compound (I-I) obtained by Method I) in dry DCM, TEA (20 equiv.), TBTU (10 equiv.) and HOAt (7 equiv.) were added and the reaction mixture was stirred, optionally under argon, at 0° C. to room temperature for 1 to 24 hours. The expected product of formula (III) wherein $X^{1p}$ is —C(=O)NR$^x$— was isolated by methods known to one skilled in the art.

Method CY-2: General Procedure for C/1-Ester Linkage, Ring Closure for Compounds of Formula (III) Wherein $X^1$ is —C(=O)O— Group Scheme CY-2

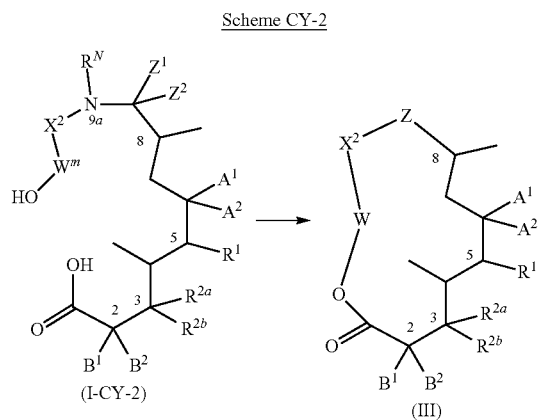

(I-CY-2) → (III)

Scheme CY-2: illustrates macrocyclization of compound of formula (I-CY-2) wherein $X^{2p}$ is $X^2$—$W^m$—OH, wherein $W^m$ is W or the appropriate precursor convertable to W, wherein W, $X^2$, $R^N$, $Z^1$, $Z^2$, $A^1$, $A^2$, $R^1$, $B^1$, $B^2$, $R^{2a}$ and $R^{2b}$ are as defined for formula (III) to produce C/1-ester compound of formula (III), wherein XI is C(=O)O—, and W, $X^2$, Z, $A^1$, $A^2$, $R^1$, $B^1$, $B^2$, $R^{2a}$ and $R^{2b}$ are as defined for formula (III), under standard esterification conditions as described above under the term "esterification" in more details. For example it may be conducted using 2,4,6-trichlorobenzoyl chloride as coupling reagent, TEA and DMAP as suitable bases and THF and toluene as suitable solvents at preferably temperature 75-110° C.

Method CY-2: Procedure 1 (CY-2.1): To a solution of Compound (I) (for example compound (I-J) obtained by Method J) in THF (5 mL) triethylamine (0.75 mmol, 3 eq) and 2,4,6-trichlorobenzoyl chloride (0.50 mmol, 2 eq) were added. After stirring at room temperature for 2 hours, the reaction mixture was added dropwise to a refluxed solution of DMAP (2.5 mmol, 10 eq) in toluene (25 mL) during 30 minutes. The expected product of formula (III) wherein $X^1$ is —C(=O)$NR^x$— was isolated by methods known to one skilled in the art.

Method CY-3: General Procedure for C/1-Amide Linkage, Ring Closure for Compounds of Formula (III) Wherein $X^1$ is —C(=O)$NR^x$— Group and $R^x$ is CH($R^Y$)—C(=O)$NHR^z$ Scheme CY-3

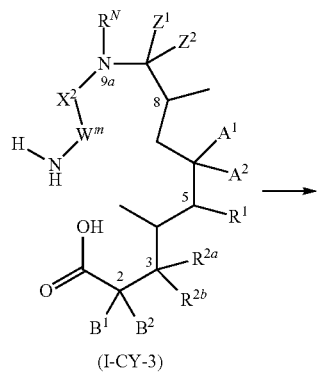

(I-CY-3)

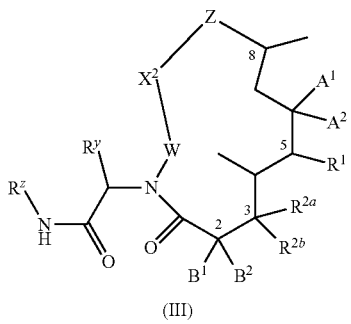

(III)

Scheme CY-3: illustrates macrocyclization of compound of formula (I-CY-3) wherein $X^{2p}$ is $X^2$—$W^m$—$NH_2$, wherein $W^m$ is W or the appropriate precursor convertible to W, wherein W, $R^x$, $Z^1$, $Z^2$, $R^N$, $A^1$, $A^2$, $B^1$, $B^2$, $R^{2a}$ and $R^{2b}$ are as defined for formula (III), to produce C/1-amide compound of formula (III), wherein $X^{1p}$ is —C(=O)$NR^x$—, wherein $R^x$ is CH($R^Y$)—C(=O)$NHR^z$, and Z, $X^2$, $R^y$, $R^z$, W, $A^1$, $A^2$, $B^1$, $B^2$, $R^{2a}$ and $R^{2b}$ are as defined for formula (III) using multicomponent reaction conditions with aldehydes and isonitriles in alcoholic media like, but not limited to, ethanol and methanol. Suitable aldehydes are, but not limited to, formaldehyde, acetaldehyde, propionaldehyde, benzaldehyde, while suitable isonitriles are, but not limited to, methyl isonitrile, ethyl isonitrile, i-propyl isonitrile and the like (Vercillo, O. E. et al., *Org. Lett.* (2008) 10(2), 205).

Method CY-4G: General Procedure for 9a-Amide Formation: Preparation of Seco 9a-Aza-Macrolide of Formula (I-CY-4G), Wherein $X^{2p}$ is C(=O)—$W^m$—$X^{1m}$ Group, $X^{1m}$ is —N($R^x$)$R^p$ or —$OR^p$, and $X^{1p}$ is C(=O)OH or

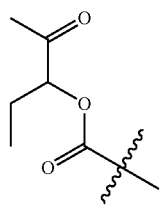 [SMILES: *C(=O)OC(CC)C(C)=O]

Group:

Scheme CY-4G

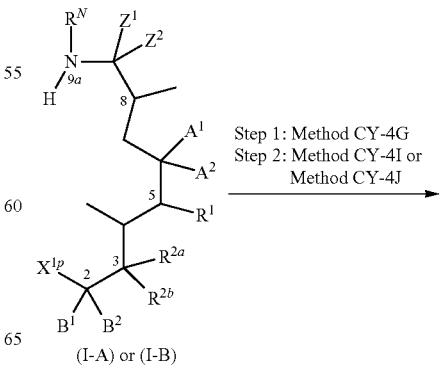

(I-A) or (I-B)

Step 1: Method CY-4G
Step 2: Method CY-4I or Method CY-4J

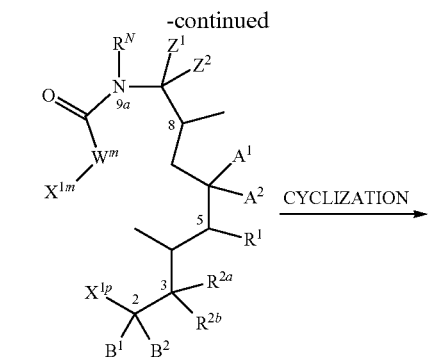

(I-CY-G) $X^2$ is —C(=O)—, $X^{1m}$ is —N($R^x$)—$R^p$ or

—$OR^p$ (I-CY-4GI) $X^2$ is —C(=O)—, $X^{1m}$ is —NH($R^x$)

(I-CY-4GJ) $X^2$ is —C(=O)—, $X^{1m}$ is OH

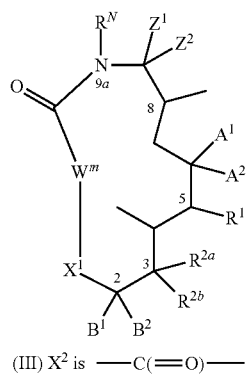

(III) $X^2$ is —C(=O)—

Scheme CY-4G, Step 1: Method CY-4G: illustrates amidation with 9a-nitrogen of compound of (I-A) wherein $X^{1p}$ is

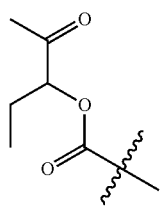

or of formula (I-B), wherein $X^{1p}$ is C(=O)OH, and $X^2$ is hydrogen, $Z^1$, $Z^2$, $A^1$, $A^2$, $R^1$, $R^{2a}$, $R^{2b}$, $B^1$, $B^2$, and $R^N$ are as defined for formula (I) above to compound of formula (l-CY-4G), wherein $X^{1p}$ is C(=O)OH group (such as for example compound (I-CY-1), (I-CY-2 or I-CY-3) or

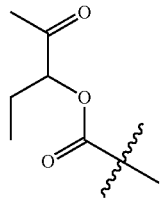 [SMILES: *C(=O)OC(CC)C(C)=O]

group, and $X^{2p}$ is C(=O)—$W^m$—$X^{1m}$ group, wherein km is —N($R^x$)$R^p$ or $OR^p$ using N-protected amino acid $R^p$—N($R^x$)—$W^m$—C(=O)OH or hydroxyl protected acid $R^p$—O—$W^m$—C(=O)OH, wherein $W^m$ is W or the appropriate precursor convertable to W, wherein W, $R^p$, and $R^x$ are as defined for formula (III), under standard amidation conditions as described above under the term "amidation" in more details. For example it may be conducted in suitable solvent or mixture of solvents in presence of suitable coupling reagent. If desired suitable amidation additives may be used.

Method CY-4G: Procedure 1 (CY-4G-1): Typically to a solution of N-protected amino acid $R^p$—N($R^x$)—$W^m$—C(=O)OH (1-2 equiv.) in suitable solvent or mixture of solvents (suitably DCM:DMF mixture), PS-CDI is added and the reaction mixture is stirred at room temperature for 5 to 15 minutes. Then, in reaction mixture compound of formula (I-A) or (I-B) in suitable solvent (such as DCM) is added and the reaction mixture is heated under MW irradiation at 60-100° C. for 10 to 30 minutes. The resin is filtered off and the expected product may be isolated form reaction mixture by methods known to one skilled in the art or it may be subjected to deprotection step without isolation of the obtained product.

Method CY-4G: Procedure 2 (CY-4G-2): Typically 9a-amidation may be conducted by adding to solution of N-protected amino acid $R^p$—N($R^x$)—$W^m$—C(=O)OH (1-2 equiv.) in suitable solvent or mixture of solvents (suitably DCM, or DCM:DMF mixture), HATU (1-1.5 equiv.), HOAt (1-2 equiv.), stirring at room temperature, and adding the appropriate compound of formula (I-A) or (I-B) in a suitable solvent such as DCM at room temperature to elevated temperature (suitably at room temperature). Suitably the expected product may be either isolated by methods known to one skilled in the art or may be subjected to following deprotection step without isolation of product obtained by method CY-4G.

Method CY-4G: Procedure 3 (CY-4G-3): Typically 9a-amidation may be conducted staring from appropriate compound of formula (I-A) or (I-B) using hydroxyl carboxylic acid HO—$W^m$—C(=O)OH or O-protected carboxylic acid $R^p$—O—$W^m$—C(=O)OH using HOBT and HOAt as coupling agents, and TMP as base in suitable solvent (such as DCM) at room temperature.

Method CY-4G: Procedure 4 (CY-4G-4): In alternative 9a-amidation may be conducted staring from the appropriate compound of formula (I-A) or (I-B) using appropriate lactone

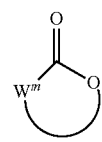

and aminolysis reaction conditions. For example it may be carried out using the appropriately substituted γ-butyrolactone in the presence of LiNTf2 as activator reagent and in suitable solvent such as for example THF, EtOH or chloroform (Synlett, 2008, 0189-0192).

Method CY-4H: General Procedure for 9a-Amine Formation (Reductive Amination): Preparation of Seco 9a-Aza-Macrolide of Formula (I-CY-4H), Wherein $X^{2p}$ is $CH_2$—$W^m$—$X^{1m}$ Group, $X^{1m}$ is $N(R^x)R^p$ or —$OR^p$, and $X^{1p}$ is —C(=O)OH Group or

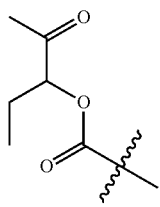 [SMILES: *C(=O)OC(CC)C(C)=O]

Group:

Scheme CY-4H

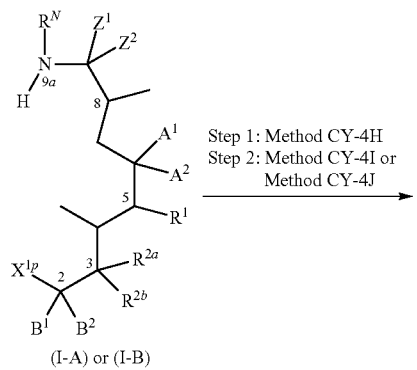

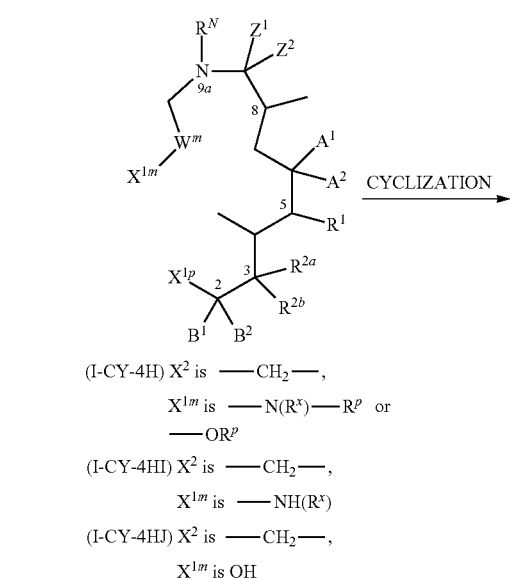

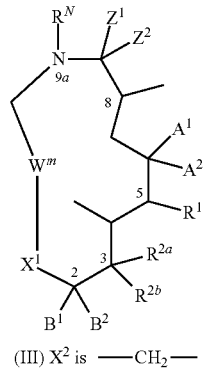

Scheme CY-4H, Step 1: Method CY-4H: illustrates reductive amination (reductive alkylation) with 9a-nitrogen of compound of formula (I-A) wherein $X^{1p}$ is

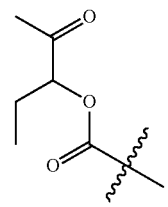 [SMILES: *C(=O)OC(CC)C(C)=O]

or of formula (I-B), wherein $X^{1p}$ is C(=O)OH, and $X^{2p}$ is hydrogen, $Z^1$, $Z^2$, $A^1$, $A^2$, $R^1$, $R^{2a}$, $R^{2b}$, $B^1$, $B^2$, and $R^N$ are as defined for formula (I) above to compound of formula (I-CY-4H) wherein $X^{1p}$ is C(=O)OH group (such as for example compound (I-CY-1), (I-CY-2 or I-CY-3) or

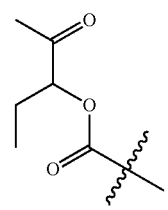 [SMILES: *C(=O)OC(CC)C(C)=O]

group, and $X^{2p}$ is $CH_2$—$W^m$—$X^{1m}$ group, wherein $X^{1m}$ is —$N(R^x)R^p$ or $OR^p$ using N-protected aldehyde $R^p$—N$(R^x)$—$W^m$—C(=O)H or hydroxyl protected aldehyde $R^p$—O—$W^m$—C(=O)H, wherein $W^m$ is W or the appropriate precursor convertable to W, wherein W, $R^p$, and $R^x$ are as defined for formula (III), under standard reductive amination (reductive alkylation) conditions as described above under the term "reductive amination (reductive alkylation)" in more details. For example it may be conducted in suitable solvent or mixture of solvents in presence of suitable reducing agent.

Method CY-4H: Procedure 1 (CY-4H-1): Typically to a solution of the appropriate compound of formula (I-A) or (I-B) in suitable solvent or mixture of solvents (suitably DCM, DCE or mixture of DCM or DCE and MeOH) the appropriate N-protected aldehyde $R^p$—N$(R^x)$—$W^m$—C(=O)H or hydroxyl protected aldehyde $R^p$—O—$W^m$—C(=O)H (1-2 equiv.), TEA (1.5-4 equiv.) and NaBH$_4$ (2-4 equiv.), NaCNBH$_3$ (2-4 equiv.) or Na(OAc)$_3$BH (2-4 equiv.) are added and the reaction mixture is stirred at room temperature for 6 to 24 hours. The expected product (I-4H-1) may be isolated by methods known to one skilled in the art or directly subjected to the deprotection step without isolation.

Method CY-4I: General Procedure for Removal of $R^p$ Group from Amino: Preparation of Seco 9a-Aza-Macrolide of Formula (I-CY-4G1) $X^{2p}$ is C(=O)—$W^m$—$X^{1m}$ Group or of Formula (I-CY-4H1) $X^{2p}$ is CH$_2$—$W^m$—$X^{1m}$ Group, and Wherein $X^{1m}$ is NH($R^x$) and $X^1$ is

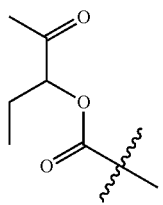 [SMILES: *C(=O)OC(CC)C(C)=O]

Group or C(=O)OH Group:

Scheme CY-4G and Scheme CY-4H, Step 2: Method CY-4I: illustrates removal of $R^p$ group from $X^{1m}$ is N($R^x$)$R^p$ of compound of formula (I-CY-4G) or (I-CY-4H), wherein $Z^1$, $Z^2$, $A^1$, $A^2$, $R^1$, $R^{2a}$, $R^{2b}$, $B^1$, $B^2$, and $R^N$ are as defined for formula (I) above giving compound of formula (I-CY-4I) wherein $X^1$ is

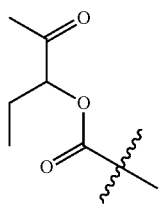 [SMILES: *C(=O)OC(CC)C(C)=O]

or C(=O)OH group, and $X^{2p}$ is C(=O)—$W^m$—$X^{1m}$ group compound of formula (I-CY-4G1) or $X^{2p}$ is CH$_2$—$W^m$—$X^{1m}$ group compound of formula (I-CY-4H1), and wherein $X^{1m}$ is —N($R^x$)H wherein $W^m$ is W or the appropriate precursor convertible to W, wherein W and $R^x$ are as defined for formula (III), under standard conditions.

Thus obtained compound of formula (I-CY-4G1) or (I-CY-4H1) can be cyclised to macrolide based macrocycle of formula (III) by methods known to one skilled in the art, for example by methods CY-1, CY-2, CY-3 and a like.

Method CY-4I: Procedure 1 (CY-4I-1): Typically to a solution of the appropriate compound of formula (I-CY-4G) or (I-CY-4H) isolated from Step 1., or to a reaction mixture from Step 1 in suitable solvent or mixture of solvents (suitably DCM or DMF) piperidine (5-10 equiv.) is added and the reaction mixture is stirred at room temperature for 2 to 48 hours. The expected product (I-CY-4G1) or (I-CY-4H1) may be isolated by methods known to one skilled in the art.

Method CY-4I: Procedure 2 (CY-4I-2): Typically to a solution of the appropriate compound of formula (I-CY-4G) or (I-CY-4H) isolated from Step 1., or to a reaction mixture from Step 1 in suitable solvent or mixture of solvents (suitably in THF or MeCN) LiOH or NaOH (2-10 equiv.) is added and the reaction mixture is stirred for 2 to 48 hours at room temperature to 50° C. to give (I-CY-4G1) or (I-CY-4H1) compound wherein $X^{1p}$ is —C(=O)OH group (if present at starting material C/1-ester is converted to C/1-acid under Method CY-4I, Procedure 2 conditions). The expected product (I-CY-4G1) or (I-CY-4H1) may be isolated by methods known to one skilled in the art.

Method CY-4I: Procedure 3 (CY-4I-3): Typically to a solution of the appropriate compound of formula (I-CY-4G) or (I-CY-4H) isolated from Step 1., or to a reaction mixture from Step 1 in suitable solvent or mixture of solvents (suitably in THF or MeCN) aqueous or dioxane, ether, or THF solution of HCl (5-50 equiv.) is added and the reaction mixture is stirred for 6 to 72 hours at room temperature to 50° C. to give (I-CY-4G1) or (I-CY-4HI) compound wherein $X^{1p}$ is C(=O)OH group and $R^{2a}$ is OH (if present at starting material C/1-ester is converted to C/1-acid and $S^2$ sugar is cleaved off under Method CY-4I, Procedure 3 conditions). The expected product (I-CY-4G1) or (I-CY-4H1) may be isolated by methods known to one skilled in the art.

Method CY-4I: Procedure 4 (CY-4I-4): Typically to a solution of the appropriate compound of formula (I-CY-4G) or (I-CY-4H) isolated from Step 1, or to a reaction mixture from Step 1; Scheme CY-4G or Scheme CY-4H in suitable solvent or mixture of solvents (suitably in DCM) TFA (2-10 equiv.) is added and reaction mixture stirred at room temperature for 30 min to give (I-CY-4G1) or (I-CY-4H1) compound wherein $X^{1p}$ is

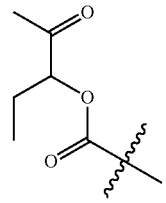 [SMILES: *C(=O)OC(CC)C(C)=O]

or C(=O)OH group (depending on starting material) and $R^{2a}$ is OH ($S^2$ sugar is cleaved off under Method CY-4I, Procedure 4 conditions). The expected product (I-CY-4G1) or (I-CY-4H1) may be isolated by methods known to one skilled in the art.

Method CY-4J: General Procedure for Removal of $R^p$ Group from Hydroxyl Group: Preparation of Seco 9a-Aza-Macrolide of Formula (I-CY-4GJ) $X^{2p}$ is C(=O)—$W^m$—$X^{1m}$ Group or of Formula (I-CY-4HJ) $X^{2p}$ is CF$_2$—$W^m$—$X^{1m}$ Group, and Wherein $X^{1m}$ is OH and $X^{1p}$ is

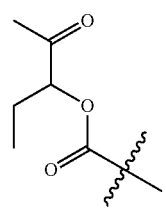 [SMILES: *C(=O)OC(CC)C(C)=O]

Or C(=O)OH Group:

Scheme CY-4G and Scheme CY-4H, Step 2: Method CY-4J: illustrates removal of $R^p$ group from $X^{1m}$ is O$R^p$ of formula (I-CY-4G) or (I-CY-4H), wherein $Z^1$, $Z^2$, $A^1$, $A^2$, $R^1$, $R^{2a}$, $R^{2b}$, $B^1$, $B^2$, and $R^N$ are as defined for formula (I) above giving compound of formula (I-CY-4J) wherein $X^{1p}$ is C(=O)OH group or

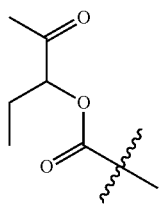 [SMILES: *C(=O)OC(CC)C(C)=O]

group, and $X^{2p}$ is C(=O)—$W^m$—$X^{1m}$ group compound of formula (I-CY-4GJ) or $X^{2p}$ is CH$_2$—$W^m$—$X^{1m}$ group compound of formula (I-CY-4HJ), and wherein $X^{1m}$ is OH wherein $W^m$ is W or the appropriate precursor convertable to W, wherein W and $R^x$ are as defined for formula (III), under standard conditions.

Thus obtained compound of formula (I-CY-4GJ) or (I-CY-4HJ) can be cyclised to macrolide based macrocycle of formula (III) by methods known to one skilled in the art, for example by methods CY-1, CY-2, CY-3 and a like.

Method CY-4J, Procedure 1 (CY-4J-1): Typically to a solution of the appropriate compound of formula (I-CY-4G) or (I-CY-4H) isolated from Step 1, or to a reaction mixture from Step 1; Scheme CY-4G and Scheme CY-4H in suitable solvent or mixture of solvents (suitably in MeOH), if desired purged with argon, 1,3-dimethylbarbituric acid (2-10 equiv.) is added followed by addition of Pd(Ph$_3$)$_4$ (0.1-2 equiv) and reaction mixture stirred at room temperature for 2 hours to give (I-CY-4GJ) or (I-CY-4HJ) compound wherein $X^1$ is

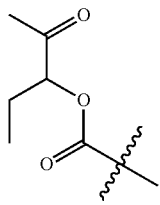 [SMILES: *C(=O)OC(CC)C(C)=O]

or C(=O)OH group (depending on starting material). The expected product (I-CY-4G1) or (I-CY-4H1) compound may be isolated by methods known to one skilled in the art.

Method CY-5: General Procedure for Formation of $X^1$ is Bond and $W^1$ is CH=CH-Compounds of Formula (III): Preparation of Seco 9a-Aza-Macrolide of Formula (I-CY-5) Wherein $X^{1p}$ is —CH=CH—$W^m$—$X^{2m}$ Group and $X^{2p}$ is Hydrogen Scheme CY-5

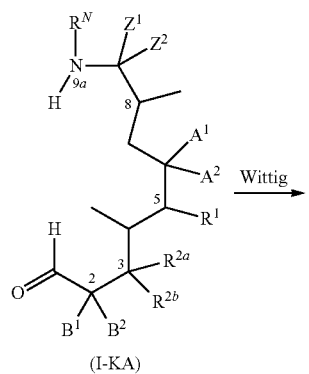

(I-KA)

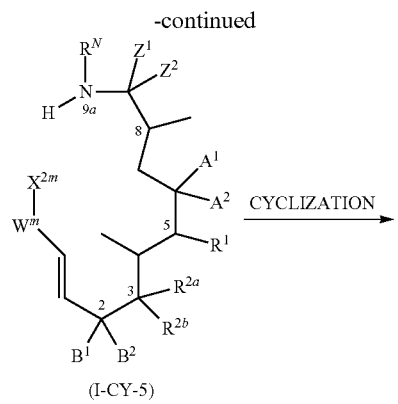

(I-CY-5)

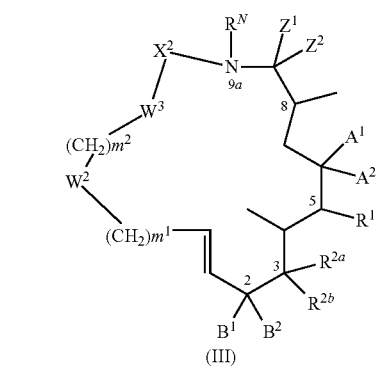

(III)

Scheme CY-5: Illustrates Wittig reaction of macrolide aldehid of formula (I-KA) with the appropriate phosphonium salt in the presence of base (Chem. Rev. 1989, 863-927, J. Org. Chem. 1985, 2624-2626) resulting in alkene compound of formula (I-CY-5), wherein $X^{1p}$ is —CH=CH—$W^m$—$X^{2m}$ group and $X^{2p}$ is hydrogen, $W^m$ is W or the appropriate precursor convertable to W, $X^{2m}$ is $X^2$ or the appropriate precursor convertable to $X^2$, wherein W, $X^2$, $R^N$, $Z^1$, $Z^2$, $A^1$, $A^2$, $R^1$, $B^1$, $B^2$, $R^{2a}$ and $R^{2b}$ are as defined for formula (III) above.

Thus obtained alkene compound of formula (I-CY-5) can be subsequently subjected to any cyclization method described herein or known in the art to give macrolide based macrocyle compound of formula (III). The type of cyclization method to be used for ring closure is known to one skilled in the art from the nature of $X^{2m}$ terminal group of specific (I-CY-5) compound.

Method CY-6: General Procedure for $X^2$ is Bond and $W^3$ is Thiazolyl or Oxazolyl Compounds of Formula (III): Preparation of Seco 9a-Aza-Macrolide of Formula (I-CY-6A) Wherein $X^{2p}$ is -Thiazolyl-$W^m$—$X^{1m}$; and of Seco 9a-Aza-Macrolide of Formula (I-CY-6B) Wherein $X^{2p}$ is -Oxazolyl-$W^m$—$X^{1m}$ Scheme CY-6

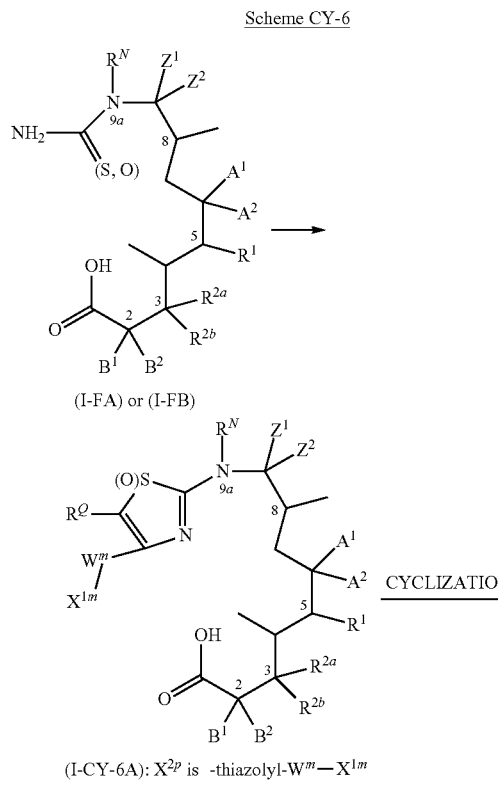

Compound of formula (III)

Scheme CY-6: illustrates reaction of compound of formula (I-FA) wherein $X^{1p}$ is —C(=O)OH group and $X^{2p}$ is C(=S)NH$_2$ group and (I-FB) wherein $X^{1p}$ is —C(=O)OH group and $X^{2p}$ is C(=O)NH$_2$ group, $Z^1$, $Z^2$, $R^N$, $A^1$, $A^2$, $R^1$, $B^1$, $B^2$, $R^{2a}$ and $R^{2b}$ are as defined for formula (I) above with bromomethyl- or chloromethyl ketone, which may be unprotected or suitably protected depending on the type of a side-chain —W$^m$—X$^{1m}$, to provide compound of formula (I-CY-6A) and compound of formula (I-CY-6B) respectively wherein $X^{1p}$ is —C(=O)H group and $X^{2p}$ is -thiazolyl-W$^m$—X$^{1m}$ (1-CY-6A) or -oxazolyl-W$^m$—X$^{1m}$ (1-CY-6B). The reaction can typically be performed with 1.1-5 equiv. of halogenomethyl ketone in organic solvents including, but not limited to, methanol, ethanol, MeCN, DCM, DCE, toluene, DMF, DMSO, glycerol, dioxane, NMP, and water with or without addition of base such as, for example, TEA, pyridine, and piperidine. The reaction temperature is suitably 0-180° C. and reaction time is suitably 5 min to 48 h.

Thus obtained thiazole compound of formula (I-CY-6A) and oxazole compound of formula (I-CY-6B) can be subsequently subjected to any cyclization method described herein or known in the art to give macrolide based macrocycle compound of formula (III).

The type of cyclization method to be used for ring closure is known to one skilled in the art from the nature of $X^{1m}$ terminal group of the specific I-CY-6A and I-CY-6B compound.

Method CY-7A: General Procedure for $X^1$ is Bond and $W^1$ is Oxazolyl or Thiazolyl Compounds of Formula (III): Preparation of Seco 9a-Aza-Macrolide of Formula (I-CY-7A-A), Wherein $X^1$ is -Oxazolyl-W$^m$—X$^{2m}$ and of Seco 9a-Aza-Macrolide of Formula (I-CY-7A-B) Wherein $X^{1p}$ is -Thiazolyl-W$^m$—X$^{2m}$ Scheme CY-7A

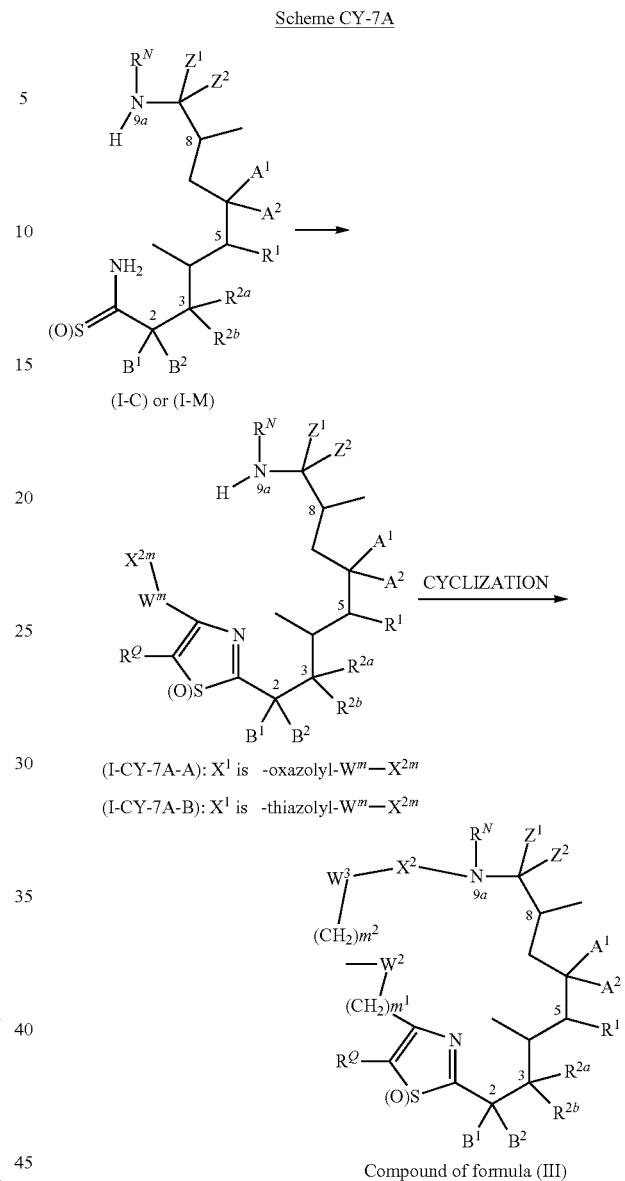

Compound of formula (III)

Scheme CY-7A: illustrates reaction of compound of formula (I-C) wherein $X^{1p}$ is —C(=O)NH$_2$ group and $X^{2p}$ is hydrogen and (I-M) wherein $X^{1p}$ is —C(=S)NH$_2$ group and $X^{2p}$ hydrogen, $Z^1$, $Z^2$, $R^N$, $A^1$, $A^2$, $R^1$, $B^1$, $B^2$, $R^{2a}$ and $R^{2b}$ are as defined for formula (I) above with bromomethyl- or chloromethyl ketone, which may be unprotected or suitably protected depending on the type of a side-chain —W$^m$—X$^{2m}$, to provide compound of formula (I-CY-7A-A) and compound of formula (I-CY-7A-B) respectively, wherein in (I-CY-7A-A) $X^{1p}$ is -oxazolyl-W$^m$—X$^{2m}$ group and $X^{2p}$ is hydrogen and in (I-CY-7A-B) $X^{1p}$ is -thiazolyl-W$^m$—X$^{2m}$ group and $X^{2p}$ is hydrogen.

The reaction can typically be performed with 1.1-5 equiv. of halogenomethyl ketone in organic solvents including, but not limited to, methanol, ethanol, MeCN, DCM, DCE, toluene, DMF, DMSO, glycerol, dioxane, NMP, and water with or without addition of base such as, for example, TEA, pyridine, and piperidine. The reaction temperature is suitably 0-180° C. and reaction time is suitably 5 min to 48 h.

Thus obtained oxazole compound of formula (I-CY-7A-A) and thiazole compound of formula (I-CY-7A-B) can be subsequently subjected to any cyclization method described herein or known in the art to give macrolide based macrocycle compound of formula (III). The type of cyclization method to be used for ring closure is known to one skilled in the art from the nature of $X^{2m}$ terminal group of the specific I-CY-7A-A and I-CY-7A-B compound.

Method CY-7B: General Procedure for $X^1$ is Bond and $W^1$ is Oxazolyl or Thiazolyl Compounds of Formula (III): Preparation of Seco 9a-Aza-Macrolide of Formula (I-CY-7B-A), Wherein $X^{1p}$ is —C(=O)NH$_2$ Group and $X^{2p}$ is —X$^2$—W$^m$—C(=O)—CH(R$^Q$)Br and of Seco 9a-Aza-Macrolide of Formula (I-CY-7B-B) Wherein $X^{1p}$ is —C(=S)NH$_2$ Group and $X^{2p}$ is —X$^2$—W$^m$—C(=O)—CH(R$^Q$)Br Scheme CY-7B

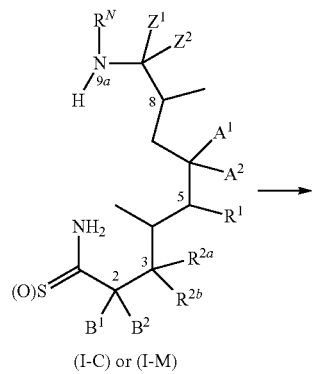

(I-C) or (I-M)

Scheme CY-7B: illustrates alternative method towards compound of formula (III) where $X^1$ is bond and $W^1$ is oxazolyl or thiazolyl starting from compound of formula (I-C) wherein $X^1$ is C(=O)NH$_2$ group or (I-M) wherein $X^{1p}$ is —C(=S)NH$_2$ group respectively and where $X^{2p}$ is hydrogen, $Z^1$, $Z^2$, $R^N$, $A^1$, $A^2$, $R^1$, $B^1$, $B^2$, $R^{2a}$ and $R^{2b}$ are as defined for formula (I). The alternative route includes synthesis of compounds of formula (I-CY-7B-A) and (I-CY-7B-B) that bear halogenomethyl ketones attached through —W$^m$—X$^{2m}$ precursor tail to secondary amine at position C-9. Compounds of formula (I-CY-7B-A), wherein $X^{1p}$ is —C(=O)NH$_2$ group and $X^{2p}$ is —X$^2$—W$^m$—C(=O)—CH(R$^Q$)Br and of formula (I-CY-7B-B), wherein $X^{1p}$ is —C(=S)NH$_2$ group and $X^{2p}$ is —X$^2$—W$^m$—C(=O)—CH(R$^Q$)Br can be prepared by various methods including, but not limited to, amidation, alkylation, and reductive alkylation. Final cyclization to macrolide based macrocycle compound of formula (III) wherein $X^1$ is bond and $W^1$ is oxazolyl or thiazolyl may be performed via intramolecular formation of oxazole or thiazole ring in suitable organic solvent including, but not limited to, methanol, ethanol, MeCN, DCM, DCE, toluene, DMF, DMSO, glycerol, dioxane, NMP, and water with or without addition of base such as, for example, TEA, pyridine, and piperidine. The reaction temperature is preferably 0-130° C. and reaction time is 5 min to 48 h.

Method CY-7C: General Procedure for $X^1$ is Bond and $W^1$ is Oxazolyl or Thiazolyl Compounds of Formula (III): Preparation of Seco 9a-Aza-Macrolide of Formula (I-CY-7C), Wherein $X^{1p}$ is —C(=O)NH—CH$_2$—C(=O)W$^m$—X$^{2m}$ and $X^{2p}$ is Hydrogen and its Conversion to (I-CY-7A-A) and (I-CY-7A-B) Seco Analogues Scheme CY-7C

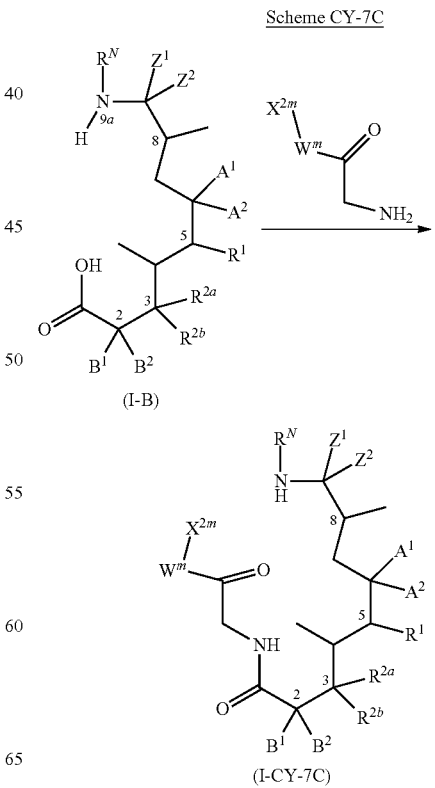

(I-B)

(I-CY-7C)

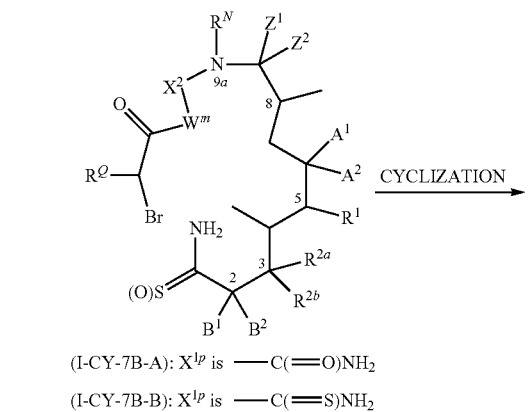

(I-CY-7B-A): $X^{1p}$ is —C(=O)NH$_2$
(I-CY-7B-B): $X^{1p}$ is —C(=S)NH$_2$

Compound of formula (III)

-continued

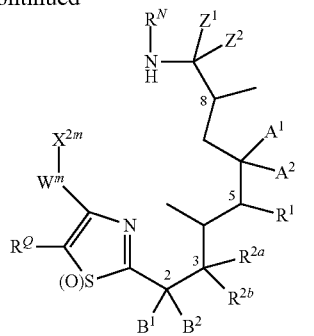

(I-CY-7A-A): $X^1$ is -oxazolyl-$W^m$—$X^{2m}$
(I-CY-7A-B): $X^1$ is -thiazolyl-$W^m$—$X^{2m}$

| CYCLIZATION

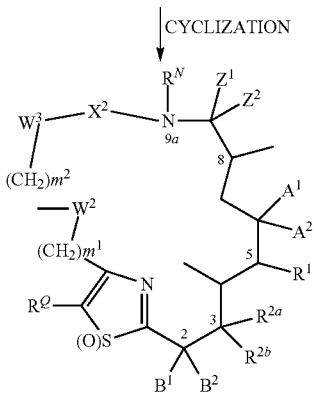

Compound of formula (III)

Scheme CY-7C: illustrates another alternative method towards compound of formula (III) where $X^1$ is bond and $W^1$ is oxazolyl or thiazolyl. In the first step compound of formula (I-CY-7C), wherein $X^{1p}$ is —C(=O)NH—$CH_2$— C(=O)$W^m$—$X^{2m}$ and $X^{2p}$ is hydrogen may be prepared by amidation of compound of formula (I-B) with suitable substituted a-aminoketone in the presence of tertiary amine as a base and coupling agents typically used in peptide synthesis including, but not limited to, HATU, PyBOP, HBTU, EDAC, DCC. Preferred solvents for this reaction are DMF and DCM although other organic solvents and ionic liquids can be used. Typical reaction times range from 30 min to 24 h and reaction temperatures 0-60° C. Cyclodehydration reaction of compound of formula (I-CY-7C) in the presence of dehydrating agent such as $POCl_3$, $P_2O_5$, $SOCl_2$, T3P, and Burgess reagent at elevated temperatures can provide oxazolyl compound (I-CY-7A-A). On the other hand, reaction of compound of formula (I-CY-7C) with for example Lawesson's reagent, Beallau's reagent (0.5 or more equiv.) or with $P_4S_{10}$ (>0.25 equiv.) alone or in combination with hexamethyldisiloxane can provide thiazolyl compound of formula (I-CY-7A-B). Such reactions can be performed in various solvents including, but not limited to, toluene, THF, DCM, HMPA, chloroform. The reaction temperature is preferably in a range from room temperature to reflux of the corresponding solvent, and reaction time is usually 30 min to 48 h.

Thus obtained oxazolyl compound of formula (I-CY-7A-A) and thiazolyl compound of formula (I-CY-7A-B) can be subsequently subjected to any cyclization method described herein or known in the art to give macrolide based macrocycle compound of formula (III). The type of cyclization method to be used for ring closure is known to one skilled in the art from the nature of $X^{2m}$ terminal group of the specific I-CY-7A-A and I-CY-7A-B compound. Method CY-8: General procedure for $X^1$ is bond and $W^1$ is oxadiazolyl or thiadiazolyl compounds of formula (III): Preparation of seco 9a-aza-macrolide of formula (I-CY-8A), wherein $X^{1p}$ is —C(=O)NH—NH—C(=O)—$W^m$—$X^{2m}$ and $X^{2p}$ is H, and its conversion to seco 9a-aza-macrolide of formula (I-CY-8B), wherein $X^1$ is oxadiazolyl-$W^m$—$X^{2m}$ or to seco 9a-aza-macrolide of formula (I-CY-8C), wherein $X^1$ is thiadiazolyl-$W^m$—$X^{2m}$ and $X^{2p}$ is hydrogen Scheme CY-8

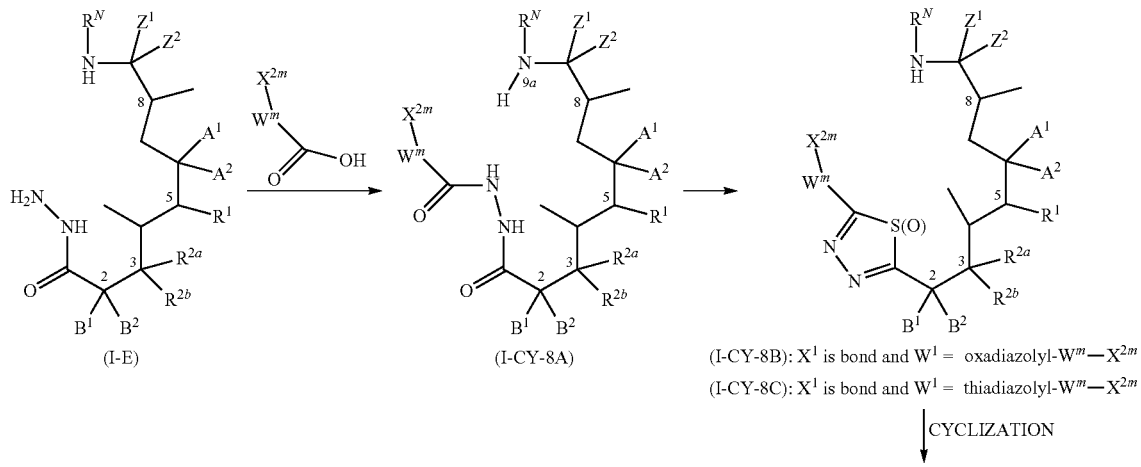

(I-CY-8B): $X^1$ is bond and $W^1$ = oxadiazolyl-$W^m$—$X^{2m}$
(I-CY-8C): $X^1$ is bond and $W^1$ = thiadiazolyl-$W^m$—$X^{2m}$

| CYCLIZATION

-continued

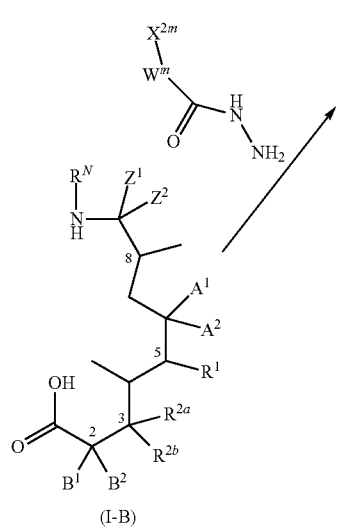

(I-B)

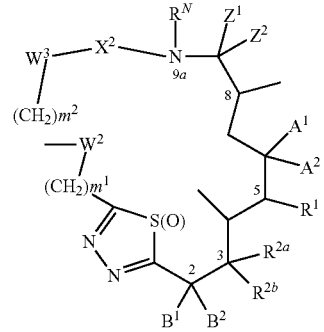

Compound of formula (III)

Scheme CY-8: illustrates method towards compound of formula (III) where $X^1$ is bond and $W^1$ is oxadiazolyl or thiadiazolyl. In the first step compound of formula (I-CY-8A), wherein $X^{1p}$ is —C(=O)NH—NH—C(=O)—$W^m$—$X^{2m}$ and $X^{2p}$ is H may be prepared by reaction of compound of formula (I-E) with suitable substituted carboxylic acids in the presence of tertiary amine as a base and coupling agents typically used in peptide synthesis including, but not limited to, HATU, PyBOP, HBTU, EDAC, and DCC to provide hydrazide compound of formula (I-CY-8A). Instead of carboxylic acids, derivatives thereof such as acyl chlorides, anhydrides, and esters can be used. Preferred solvents for this reaction are DMF and DCM although other organic solvents and ionic liquids can be used. Typical reaction times range from 30 min to 24 h and reaction temperatures 0-60° C. Alternatively, hydrazide compound of formula (I-CY-8A) can be prepared from compound of formula (III-B) by coupling reaction with suitable substituted hydrazides in the presence of tertiary amine as a base and coupling agents typically used in peptide synthesis including, but not limited to, HATU, PyBOP, HBTU, EDAC, and DCC. Cyclodehydration reactions of hydrazide compound (I-CY-8A) in the presence of dehydrating agents such as $POCl_3$, polyphosphoric acid, $P_2O_5$, $SOCl_2$, T3P, and Burgess reagent at elevated temperatures can provide oxadiazole compound of formula (I-CY-8B). Whereas reactions of hydrazide compound (I-CY-8A) with for example Lawesson's reagent, Beallau's reagent (0.5 or more equiv.) or with $P_4S_{10}$ (>0.25 equiv.) alone or in combination with hexamethyldisiloxane can provide thiadiazole compound of formula (I-CY-8C). Such reactions can be performed in various solvents including, but not limited to, toluene, xylene, THF, DCM, HMPA, chloroform. The reaction temperature is preferably in a range from room temperature to reflux of the corresponding solvent, and reaction time is usually 30 min to 48 h.

Thus obtained oxadiazolyl compound of formula (I-CY-8B) and thiadiazolyl compound of formula (I-CY-8C) can be subsequently subjected to any cyclization method described herein or known in the art to give macrolide based macrocycle compound of formula (III). The type of cyclization method to be used for ring closure is known to one skilled in the art from the nature of $X^{2m}$ terminal group of the specific compound of formula (I-CY-8B) and (I-CY-8O).

Method CY-9: General Procedure for Macrolide Based Macrocycle Compounds of Formula (III) Wherein $W^2$ is —CH=CH— or CH(OH)CH(OH)—, $X^2$ is C(=O)— or $CH_2$— and $X^{1p}$ is —C(=O)NH— or C(=O)O— and to their Seco 9a-Aza-Macrolide Precursors Derived from Compounds of Formula (I)

Scheme CY-9

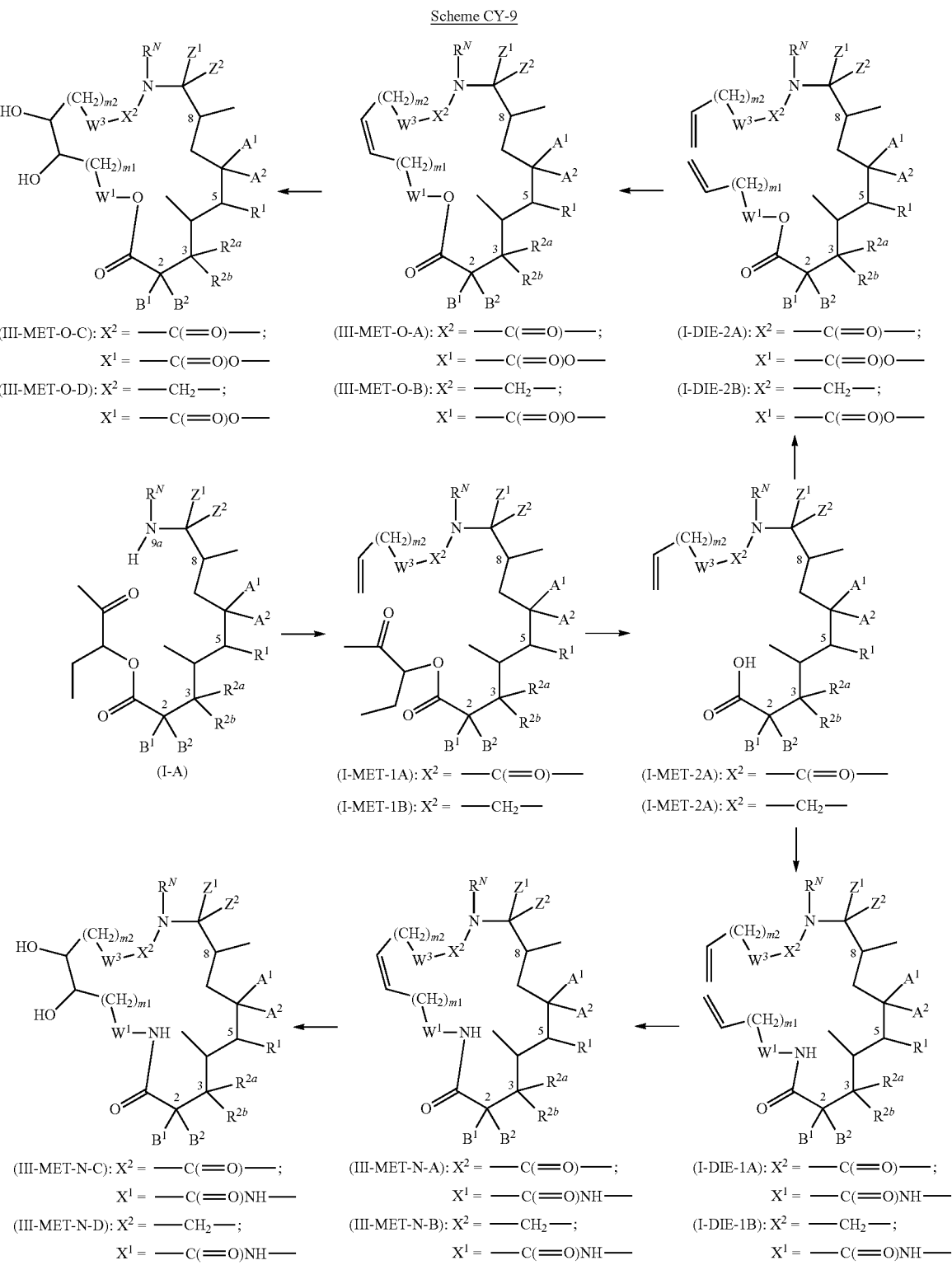

Scheme CY-9: illustrates a procedure for the formation of seco 9a-aza-macrolide diene compounds of formulae (I-DIE-1A), (I-DIE-1B), (I-DIE-2A) and (I-DIE-2B), starting from compound of formula (I-A). Amidation of the 9a-amino group of the compound (I-A) with unsaturated carboxylic acids gives compound (I-MET-1A), wherein $X^2$ is —C(=O)—. Selective hydrolysis of C/1-keto ester group in (I-MET-1A) by method B discussed above affords the compound (I-MET-2A) wherein $X^{1p}$ is —C(=O)OH and $X^2$ is —C(=O)—. Amidation of C/1-COOH of compound (I-MET-2A) with the appropriate unsaturated amine gives the diamide compound (I-DIE-1A), wherein $X^{1p}$ is —C(=O)NH— and $X^2$ is —C(=O)—. Alternatively, when compound (I-MET-2A) is subjected to esterification with unsaturated alcohols ester compound (I-DIE-2A), wherein $X^{1p}$ is —C(=O)O— and $X^2$ is —C(=O)— is obtained.

Accordingly, (I-MET-1B) analogues wherein $X^2$ is $CH_2$— can be obtained by reductive alkylation of the compound (I-A) with suitable unsaturated aldehyde.

Alkylation of the amino group of compound (I-A) can also be performed with unsaturated alkyl halides as previously described. Unsaturated alkyl halides are, but not limited to allyl bromide or chloride, homoallyl bromide or chloride.

Alternatively compound (I-A) can be alkylated with activated esters of allyl alcohols in the presence of palladium catalyst. Activated esters of allyl alcohols include, but not limited to allyl acetate, methyl, allyl carbonate, ally, t-butyl carbonate. Most palladium (0) catalysts are expected to produce alkylation (I-MET-1B) compound analogues. Similar results are expected from some palladium (II) salts in the presence of suitable ancillary ligands (Johansen, M., et al. *Chem. Rev.* (1998), 98(4), 1689). Typical palladium catalysts are, but not limited to, palladium(II)acetate, tetrakis(triphenylphosphine)palladium (0), tris(dibenzylidenacetone)dipalladium (0) and the like. Suitable phosphine ancillary ligands include, but are not limited to, triphenyl phosphine, tri-o-tolyl-phosphine, bis(diphenylphosphino)butane and the like.

Thus obtained (I-MET-1B) compound analogues wherein $X^2$ is $CH_2$— can be transformed to compounds (I-MET-2B), (I-DIE-1B) and (I-DIE-2B) wherein $X^2$ is $CH_2$— as described above for (I-MET-1A) compound.

Subset of compounds of formula (III) wherein $W^2$ is —CH=CH—: (III-MET-N-A), (III-MET-N-B), (III-MET-O-A) and (III-MET-O-B) can be prepared by RCM/Ring Closing Methathesis) reaction from the corresponding diene (I-DIE-1A), (I-DIE-1B), (I-DIE-2A), and (I-DIE-2B), respectively. Reaction is performed in aprotic solvents in the presence of suitably ligated ruthenium catalyst. As an additive in the reaction can be used but not obligatory Brønsted or Lewis acids like, but not limited to, monophenyl phosphoester, titanium(IV)isopropoxide (Furstner, A., et al., *J. Am. Chem. Soc.* (1997), 119(39), 9130) etc. Suitable solvents used as reaction media are, but not limited to, DCM, chloroform, DCE, diethyl ether. Most suitable catalysts that can be used are Grubbs G1, Grubbs G2, Hoveyda-Grubbs G1, Hoveyda-Grubbs G2. A more thorough discussion on RCM can be found in Kotha, S., *Tetrahedron* (2012), 68(2), 397 and Grubbs, R., *Tetrahedron* (2004), 60(34), 7117.

The double bond of compounds of formula (III) wherein $W^2$ is —CH=CH—: (III-MET-N-A), (III-MET-N-B), (III-MET-O-A) and (III-MET-O-B), may subsequently be oxidised to corresponding vicinal diole compounds of formula (III) wherein $W^2$ is —CH(OH)CH(OH)—, (III-MET-N-C), (III-MET-N-D), (III-MET-O-C) and (III-MET-O-D) using reagents such as osmium tetraoxide or potassium osmate in the presence of stoichiometric oxidants such as NMO (Borisova, S., et al., *Org. Lett.* (2010), 12(22), 5150).

Method CY-10: General Procedure for Macrolide Based Macrocycle Compounds of Formula (III) Wherein $W^2$ is -1,4- or 1,5-Attached Triazolyl, $X^2$ is C(=O)— or $CH_2$— and $X^{1p}$ is —C(=O)NH— or C(=O)O— and to their Seco 9a-Aza-Macrolide Precursors Derived from Compounds of Formula (I)

Scheme CY-10A

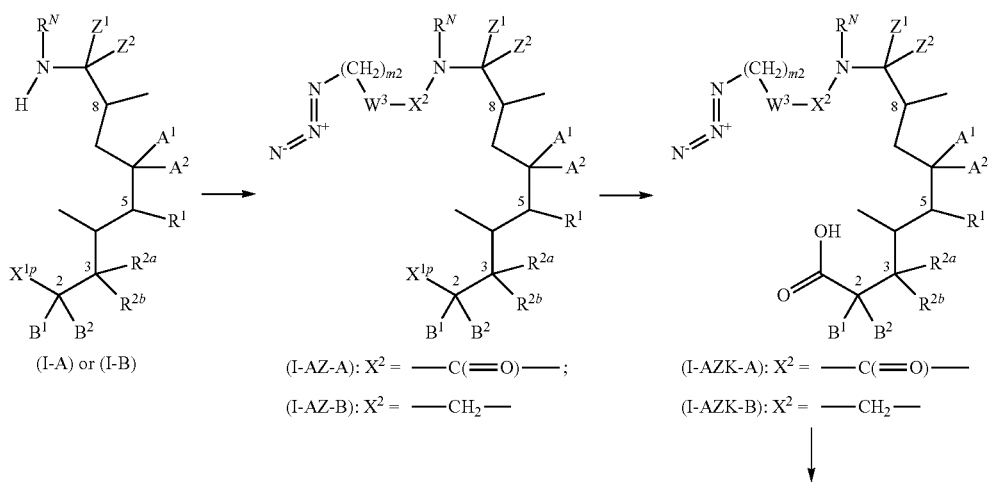

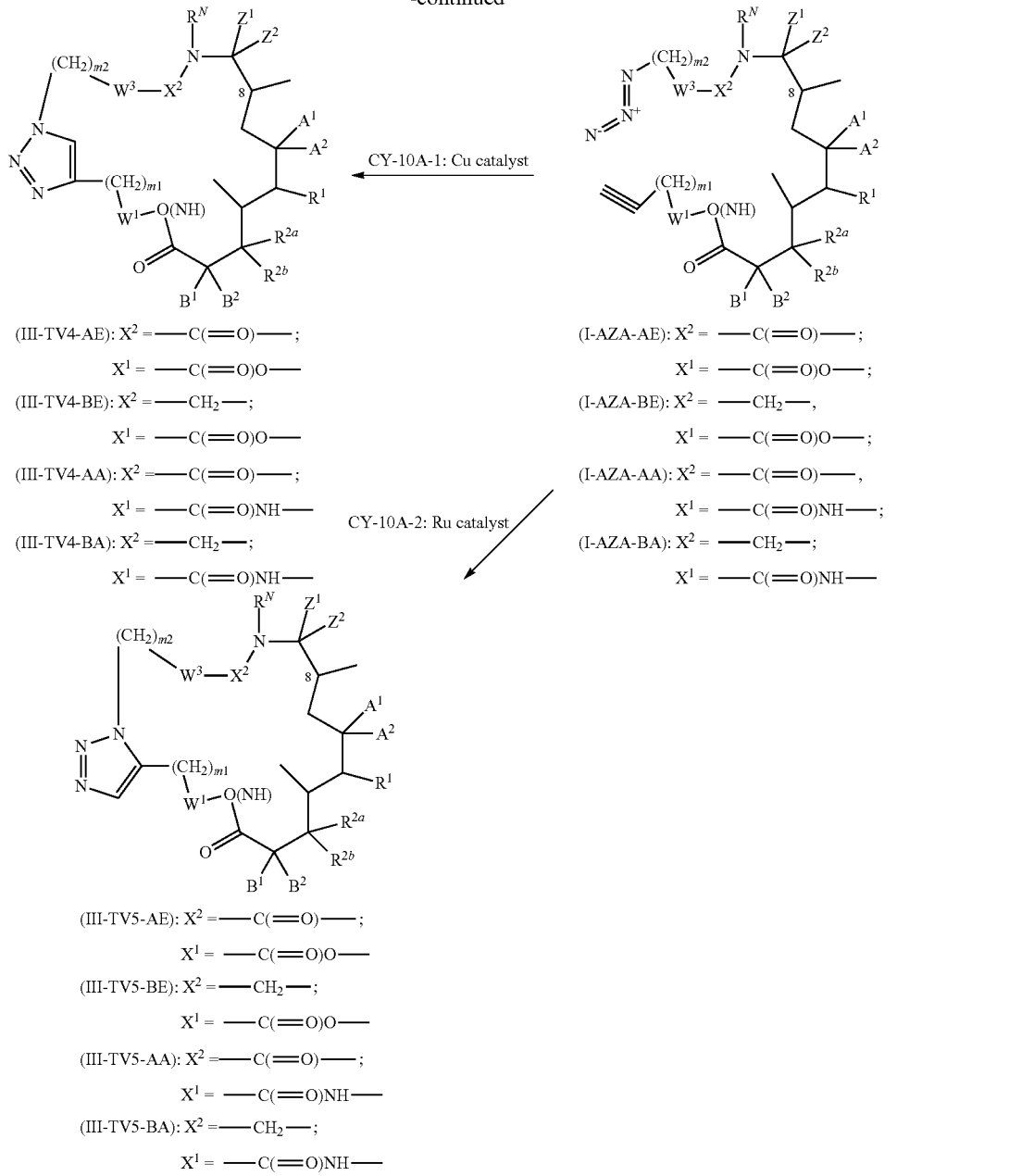

Scheme CY-10A and CY-10B: illustrate Method for the preparation of macrolide based macrocycles compounds of formulae (III), wherein $W^2$ is -1,4- or 1,5-attached triazolyl, $X^2$ is C(=O)— or CH$_2$— and $X^{1p}$ is —C(=O)NH— or C(=O)O—, and to their seco 9a-aza-macrolide precursors derived from compounds of formula (I).

Azide compound of formula (I-AZ-A), wherein $X^2$ is C(=O)— can be prepared by amidation of 9a-nitrogen from compound (IA) or from compound (I-B) with suitable azido acid. Azide compound analogue of formula (I-AZ-B), wherein $X^2$ is CH$_2$— can be prepared by reductive amination of 9a-nitrogen from compound (IA) or from compound of formula (I-B) with suitable azidoaldehyde in the presence of sodium cyanoborohydride, or by alkylation of 9a-nitrogen with azido-alkyl halides. Typical azidoaldehyde is, but not limited to, azidoacetaldehyde. Typical azido alkyl halides are, but not limited to, 2-azido-1-bromoethane, 3-azido-1-bromopropane, 4-azido-1-bromobutane.

In case when first step is performed starting from compound (IA) subsequent selective C/1-ester hydrolysis of azide compounds of formulae (I-AZ-A) and (I-AZ-B) to give their C/1-carboxylic acid analogues (I-AZK-A) and (I-AZK-B), respectively, wherein $X^{1p}$ is —C(=O)OH may be performed.

Thus obtained C/1-carboxylic acid compounds (I-AZK-A) and (I-AZK-B), can be further transformed to azido-alkyne compounds, wherein $X^{1p}$ is —C(=O)O—$W^1$—(CH$_2$)$_{m1}$—C≡CH (I-AZA-AE), wherein $X^2$ is —C(=O)— and (I-AZA-BE), wherein $X^2$ is CH$_2$—, by esterification using appropriate alkynyl alcohol.

Accordingly, C/1-carboxylic acid compounds (I-AZK-A) and (I-AZK-B), can be transformed to azidoalkyne analogues, wherein $X^{1p}$ is —C(=O)NH—$W^1$—(CH$_2$)$_m$—C=CH, (I-AZA-AA), wherein $X^2$ is —C(=O)— and (I-AZA-BA), wherein $X^2$ is CH$_2$—, by amidation with appropriate alkynylamines.

Thus obtained, azidoalkyne compounds (I-AZA-AE), (I-AZA-BE), (I-AZA-AA), and (I-AZA-BA) can be transformed to corresponding compounds of formulae (III), wherein $W^2$ is triazole by Huisgen cycloaddition in the presence of transition metal catalyst.

Method CY-10A-1: When using copper catalyst in the presence of reducing agents or bases compounds of formula (III) wherein $W^2$ is 1,4-attached triazole: (III-TV4-AE), (III-TV4-BE), (III-TV4-AA), and (III-TV4-BA), respectively may be obtained (Bock, V. D., et al. *Org. Lett.* (2006), 8(5), 919 and Turner, V. A. et al., *Org. Lett.* (2007), 9(24), 5011).

Method CY-10A-2:

Whereas when using ruthenium catalyst predominant formation of compounds of formula (III) wherein $W^2$ is 1,5-attached triazole: (III-TV5-AE), (III-TV5-BE), (III-TV5-AA), and (III-TV5-BA) (Zhang, L., et al. *J. Am. Chem. Soc.* (2005), 127(46), 15998) may be obtained. Typical copper catalyst are, but not limited to, copper (I) iodide and copper(I) bromide, copper(II)sulphate. Bases used in these processes are typically organic bases like, but not limited to DBU or 2,6-lutidine, while reducing agents are, but not limited to, ascorbic acid and its alkaline salts. Typical ruthenium catalyst is, but not limited to Cp*RuCl(PPh$_3$)$_2$ and the like.

Compound I-AZK-A1-iii-1: Azidoacetic acid (125 mg, 1.233 mmol) was dissolved in dry dichloromethane (10 mL), 2,2,6,6-tetramethylpiperidine (327 mg, 2.312 mmol) was added followed by HATU (469 mg, 1.233 mmol) and HOAt (168 mg, 1.233 mmol), stirring at room temperature for 45 min. Compound I-B1-iii-1 (500 mg, 0.771 mmol) was added, stirring continued at room temperature for 2 h when solvent was evaporated at reduced pressure to afford crude mixture which was used in the next step without purification MS(m/z) 732.66 [M+H]$^+$.

Compound I-AZA-AA1-iii-1: Crude compound I-AZK-A1-iii-1 (522 mg, 0.758 mmol assumed) was dissolved in dry DMF (7.5 mL), DIPEA (245 mg, 1.895 mmol) and HATU (288 mg, 0.758 mmol) were added, followed by propargylamine (42 mg, 0.758 mmol), stirred at room temperature for 15 min. Reaction mixture was evaporated at reduced pressure, the crude product purified by flash chromatography on a 15 g Merck Silica cartridge using a linear gradient of 0-7% MeOH:NH$_3$=10:1 in DCM to afford Compound I-AZA-AA1-iii-1 (308 mg) as light brown solid MS(m/z) 727.67 [M+H]$^+$.

Compound 128:

Compound I-AZA-AA1-iii-1 (258 mg, 0.355 mmol) was dissolved in degassed 96% ethanol (25 mL), degassed water (25 mL) was added followed by solution of copper(II) sulfate pentahydrate (3.57 mg, 0.014 mmol) in degassed water (0.200 mL) and freshly prepared 2 M aqueous (degassed water) solution of (+)-sodium 1-aspartate (0.040 mL, 0.080 mmol). The resulting clear solution was stirred at room temperature for 3 days. Reaction mixture was evaporated to dryness at reduced pressure and purified by preparative HPLC-MS to afford Compound 128, which is subset of Compound III-TV4-AA1-iii MS(m/z) 569.51 [M+H]$^+$.

Scheme CY-10B

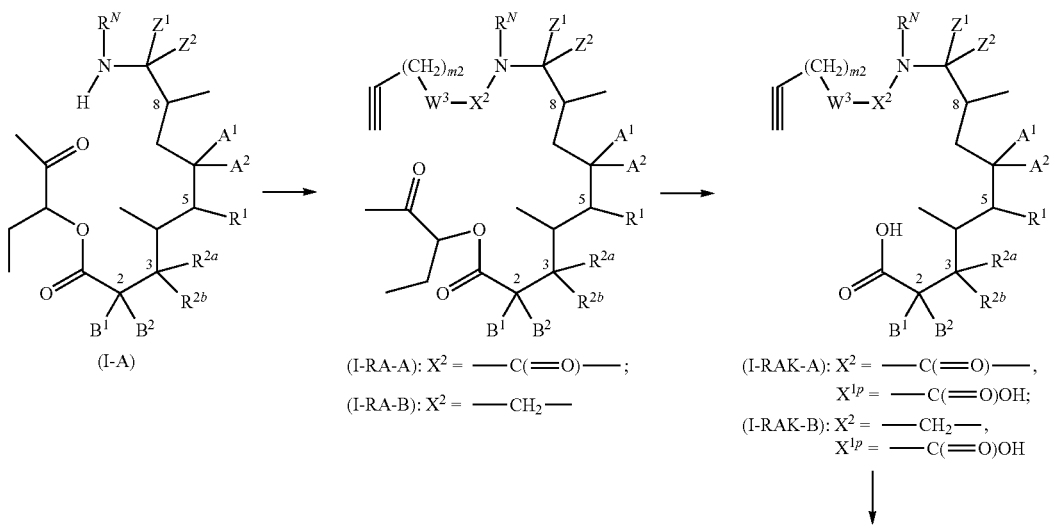

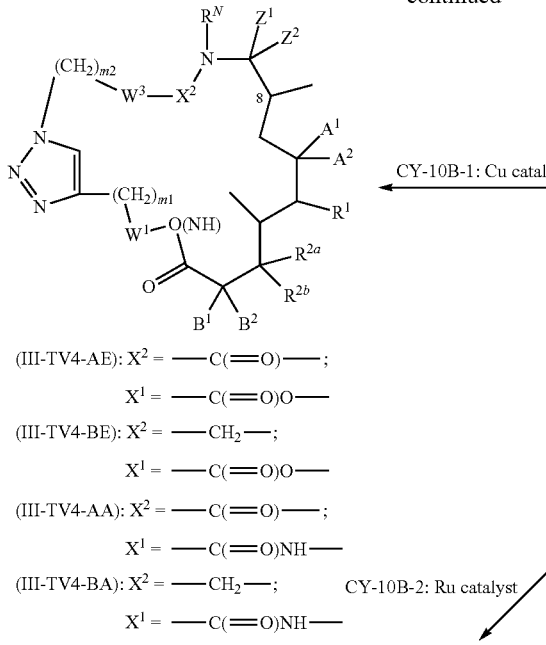

(III-TV4-AE): $X^2 =$ —C(=O)—;
$X^1 =$ —C(=O)O—
(III-TV4-BE): $X^2 =$ —CH$_2$—;
$X^1 =$ —C(=O)O—
(III-TV4-AA): $X^2 =$ —C(=O)—;
$X^1 =$ —C(=O)NH—
(III-TV4-BA): $X^2 =$ —CH$_2$—;
$X^1 =$ —C(=O)NH—

CY-10B-1: Cu catalyst

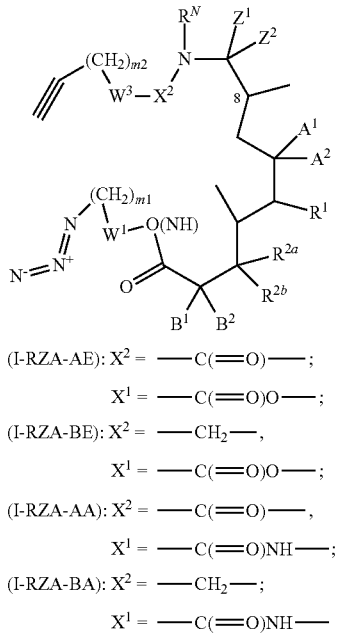

(I-RZA-AE): $X^2 =$ —C(=O)—;
$X^1 =$ —C(=O)O—;
(I-RZA-BE): $X^2 =$ —CH$_2$—,
$X^1 =$ —C(=O)O—;
(I-RZA-AA): $X^2 =$ —C(=O)—,
$X^1 =$ —C(=O)NH—;
(I-RZA-BA): $X^2 =$ —CH$_2$—;
$X^1 =$ —C(=O)NH—

CY-10B-2: Ru catalyst

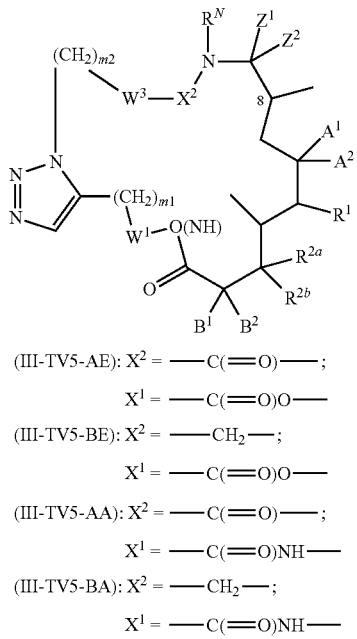

(III-TV5-AE): $X^2 =$ —C(=O)—;
$X^1 =$ —C(=O)O—
(III-TV5-BE): $X^2 =$ —CH$_2$—;
$X^1 =$ —C(=O)O—
(III-TV5-AA): $X^2 =$ —C(=O)—;
$X^1 =$ —C(=O)NH—
(III-TV5-BA): $X^2 =$ —CH$_2$—;
$X^1 =$ —C(=O)NH—

The alternative pathway towards macrolide based macrocycle compounds of formulae (III) wherein $W^2$ is triazole functionality which may be either 1,4- or 1,5-attached may be performed as follows.

Amidation of 9a-nitrogen of compounds (IA) with suitable propyolic acid analogue leads to compound of formulae (I-RA-A), wherein $X^2$ is C(O)O—, whereas alkylation with appropriate alkynyl halide or treatment with alkynly aldehyde under reductive amination conditions affords compound of formulae (I-RA-B), wherein $X^2$ is CH$_2$—.

Subsequent selective ester hydrolysis of compounds of formulae (I-RA-A) and (I-RA-B) affords their C/1-carboxylic acid analogues (I-RAK-A) and (I-RAK-B), respectively, wherein $X^{1p}$ is —C(=O)OH.

Following, C/1-carboxylic acid compounds (I-RAK-A) and (I-RAK-B), can be transformed to azido amide compounds, wherein $X^{1p}$ is —C(=O)NH—$W^1$—(CH$_2$)$_{m1}$—N$_3$, (I-RZA-AA), wherein $X^2$ is —C(=O)— and (I-RZA-BA), wherein $X^2$ is CH$_2$—, by amidation with appropriate azido amine.

Accordingly, esterification of C/1-carboxylic acid compounds (I-RAK-A) and (I-RAK-B), with the appropriate azido alcohol can give azido ester compounds, wherein $X^{1p}$ is C(=O)O—$W^1$—$(CH_2)_{m1}$—$N_3$, (I-RZA-AE), wherein $X^2$ is —C(=O)— and (I-RZA-BE), wherein $X^2$ is —$CH_2$—.

Thus obtained, azido amide and azido ester compounds (I-RZA-AA), (I-RZB-AA), (I-RZA-AE), (I-RZB-AE) can be transformed to corresponding compounds of formulae (III), wherein $W^2$ is triazole by Huisgen cycloaddition in the presence of transition metal catalyst as explained above giving compounds of formula (III) wherein $W^2$ is 1,4-attached triazole: (III-TV4-AE), (III-TV4-BE), (III-TV4-AA), and (III-TV4-BA), and compounds of formula (III) wherein $W^2$ is 1,5-attached triazole: (III-TV5-AE), (III-TV5-BE), (III-TV5-AA), and (III-TV5-BA).

Method CY-11: General Procedure for Macrolide Based Macrocycle Compounds of Formula (III) Wherein $W^3$ or $W^2$ is Pyridine and $X^1$ is —C(=O)NH—, and to their Seco 9a-Aza-Macrolide Precursors Derived from Compounds of Formula (I)

Scheme CY-11

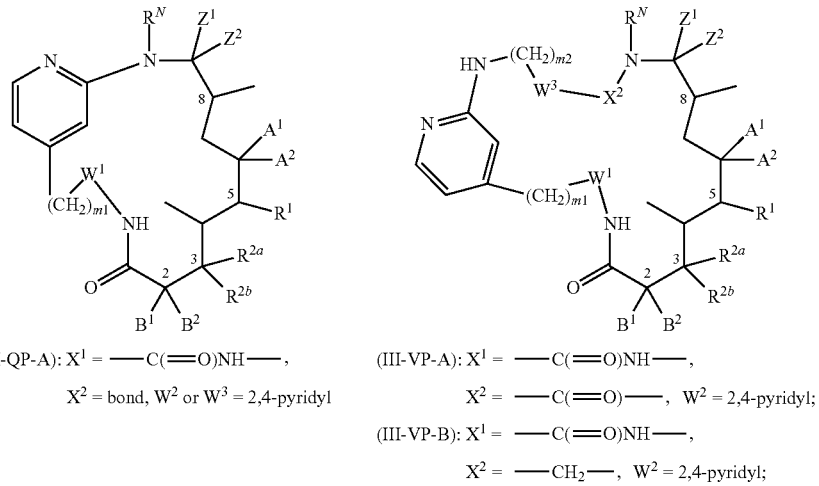

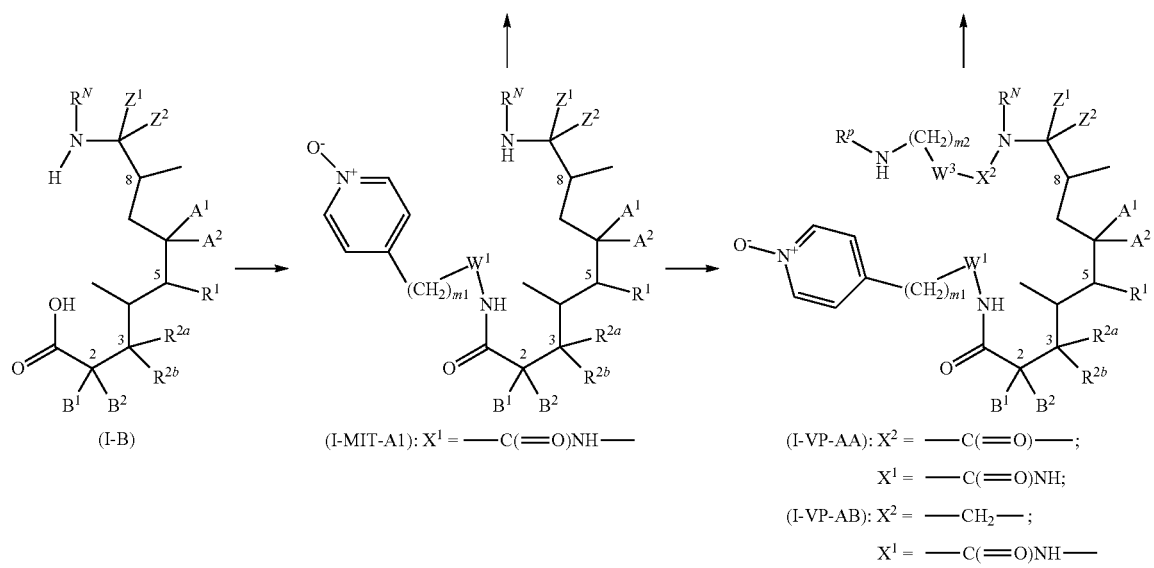

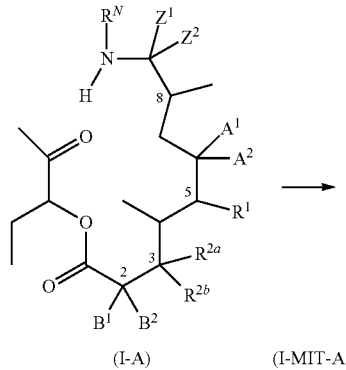
(I-A)

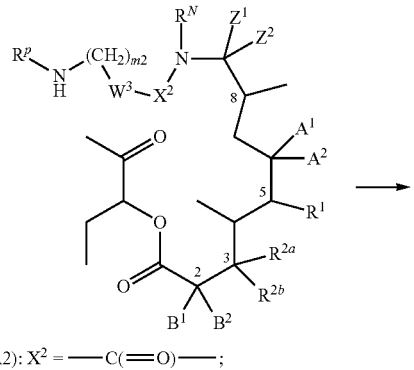
(I-MIT-A2): $X^2 = \text{—}C(\text{=}O)\text{—}$;
$X^{1p} = \text{—}C(\text{=}O)OCH(CH_2CH_3)C(\text{=}O)CH_3$;
(I-MIT-B2): $X^2 = \text{—}CH_2\text{—}$;
$X^{1p} = C(\text{=}O)OCH(CH_2CH_3)C(\text{=}O)CH_3$

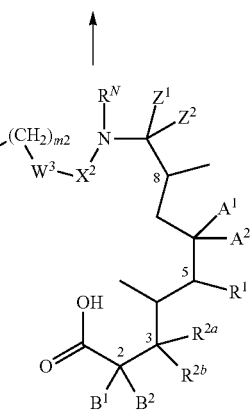
(I-MIT-A2): $X^2 = \text{—}C(\text{=}O)\text{—}$;
$X^{1p} = \text{—}C(\text{=}O)OH$;
(I-MIT-B2): $X^2 = \text{—}CH_2\text{—}$;
$X^{1p} = \text{—}C(\text{=}O)OH$ Scheme CY-11: illustrates method for the formation of macrolide based macrocycle compounds of formula (III) wherein $W^3$ or $W^2$ is pyridyl functionality which may be 2,4-attached and $X^1$ is —C(=O)NH—, and to their seco 9a-aza-macrolide precursors derived from compounds of formula (I).

Amidation of compound (IB) C/1-COOH group using ω-amino-alkylpyridine N-oxide affords (I-MIT-A¹) compound, wherein $X^{1p}$ is —C(=O)NH—$W^1$—$(CH_2)_{m1}$-(4-pyridyl N-oxide).

Treatment of (I-MIT-A¹) compound with electrophilic reagents gives compound of formula (III-QP-A), wherein $W^3$ is 2,4-pyridy, $X^2$ is a bond and $X^1$ is —C(=O)NH—. Suitable electrophilic reagents are, but are not limited to, oxalyl chloride, tosyl anhydride, mesyl anhydride, PyBroP, BroP (Londregan, A., et al., *Org. Lett.* (2010), 12(22), 5254, Londregan, A., et al. *Org. Lett.* (2012), 14(11) 2890).

9a-Nitrogen amidation of compound (I-MIT-A) using suitable protected co-amino acid gives compound (I-VP-AA), wherein $X^2$ is C(=O)— and $X^{1p}$ is —C(=O)NH—$W^1$—$(CH_2)_{m1}$-(4-pyridyl N-oxide).

Whereas, alkylation of 9a-nitrogen of compound (I-MIT-A) using protected co-amino aldehyde under reductive alkylation conditions or with protected co-amino alkyl halide gives (I-VP-AB), wherein $X^2$ is $CH_2$— and $X^{1p}$ is —C(=O)NH—$W^1$—$(CH_2)_{m1}$-(4-pyridyl N-oxide).

Deprotection of (I-VP-AA) and subsequent treatment with electrophilic reagents like, but not limited to, oxalyl chloride, tosyl anhydride, mesyl anhydride, PyBroP, BroP affords compound of formula (III-VP-A), wherein $X^1$ is —C(=O)NH—, $X^2$ is —C(=O)—, and $W^2$ is 2,4-pyridyl. Whereas, deprotection a and subsequent treatment with electrophilic reagents of (I-VP-AB) analogue gives compound of formula (III-VP-A), wherein $X^1$ is —C(=O)NH—, $X^2$ is $CH_2$—, and $W^2$ is 2,4-pyridyl.

Alternatively, compound of formula (III-VP-A), wherein $X^1$ is —C(=O)NH—, $X^2$ is —C(=O)—, and $W^2$ is 2,4-pyridyl can be prepared from compound (I-A) by amidation of 9a-nitrogen using protected ω-amino acid, followed by selective ester hydrolisysis to give compound (I-MIT-A²), wherein $X^{2m}$ is —C(=O)—$W^3$—$(CH_2)_{m1}$—$NHR^P$; $X^{1p}$ is —C(=O)OH, which after amidation with ω-amino-alkylpyridine N-oxide gives (I-VP-AA), which may be cyclised as described above.

Accordingly, compound of formula (III-VP-B), wherein $X^1$ is —C(=O)NH—, $X^2$ is —C(=O)—, and $W^2$ is 2,4-pyridyl can be prepared from compound (I-A) by alkylation of 9a-nitrogen using protected co-amino aldehydes or protected co-amino alkyl halides as previously described to give compound (I-MIT-B²), wherein $X^{2m}$ is —$CH_2$—$W^3$—$(CH_2)_{m1}$—$NHR^P$; $X^{1p}$ is —C(=O)OH, which after amidation with ω-amino-alkylpyridine N-oxide gives (I-VP-AB), which may be cyclised as described above.

Method CY-12: General Procedure for Macrolide Based Macrocycle Compounds of Formula (III) Wherein $W^2$ is —CH=CH—CH(OH)—, $X^2$ is C(=O)— or $CH_2$—, $X^1$ is —C(=O)NH— or C(=O)O—, and to their Seco 9a-Aza-Macrolide Precursors Derived from Compounds of Formula (I)

Scheme CY-12

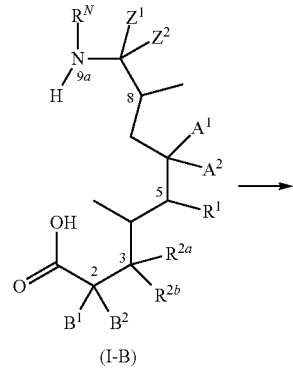
(I-B)

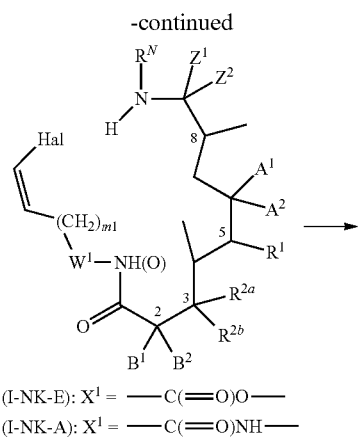

(I-NK-E): X¹ = —C(═O)O—
(I-NK-A): X¹ = —C(═O)NH—

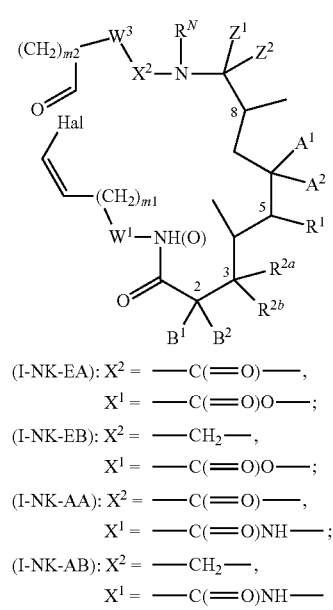

(I-NK-EA): X² = —C(═O)—,
X¹ = —C(═O)O—;
(I-NK-EB): X² = —CH₂—,
X¹ = —C(═O)O—;
(I-NK-AA): X² = —C(═O)—,
X¹ = —C(═O)NH—;
(I-NK-AB): X² = —CH₂—,
X¹ = —C(═O)NH—

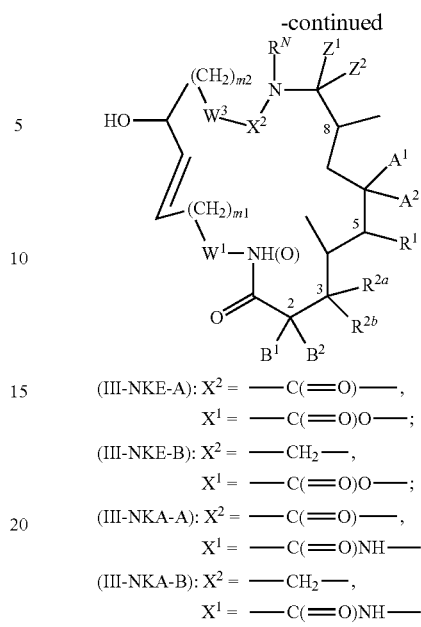

(III-NKE-A): X² = —C(═O)—,
X¹ = —C(═O)O—;
(III-NKE-B): X² = —CH₂—,
X¹ = —C(═O)O—;
(III-NKA-A): X² = —C(═O)—,
X¹ = —C(═O)NH—;
(III-NKA-B): X² = —CH₂—,
X¹ = —C(═O)NH—

Scheme CY-12: illustrates method for the formation of alkene compounds of formulae (I) and their macrolide based macrocycle closed ring analogues of formulae (III) wherein $W^2$ is —CH═CH—CH(OH)— functionality.

Esterification of compound (IB) C/1-COOH group using the appropriate vinyl halide alcohol can give (I-NK-E) compound, wherein $X^{1p}$ is —C(═O)O—$W^1$—$(CH_2)_{m1}$—CH═CH-hal (hal stands for halogen). Whereas, amidation of compound (IB) C/1-COOH group using the appropriate vinyl halide amine affords (I-NK-A) compound, wherein $X^{1p}$ is —C(═O)NH—$W^1$—$(CH_2)_{m1}$—CH═CH-halogen.

Subsequent amidation or alkylation of 9a-nitrogen of (I-NK-E) compound with protected ω-formyl carboxylic acid or monoprotected dialdehyde gives corresponding $X^1$ is —C(═O)O— compounds (I-NK-EA), wherein $X^2$ is —C(═O)— or (I-NK-EB), wherein $X^2$ is —CH₂—, whereas amidation or alkylation of 9a-nitrogen of (I-NK-A) gives $X^1$ is —C(═O)NH— compounds (I-NK-AA), wherein $X^2$ is —C(═O)— or (I-NK-AB), wherein wherein $X^2$ is —CH₂—.

Macrolide based macrocycle allyl alcohols which are subset of formula (III): (III-NKE-A), (III-NKE-B), (III-NKA-A) or (III-NKA-B), wherein $W^2$ is —CH═CH—CH(OH)—, can be produced from (I-NK-EA), (I-NK-EB), (I-NK-AA), and (I-NK-AB) compounds after aldehyde deprotection and treatment with chromium salts in the presence of nickel catalyst (Nozaki-Kishi method).

Method CY-13: General Procedure for Macrolide Based Macrocycle Compounds of Formula (III) Wherein $W^2$ is —CH═CH—CH═CH—, and to their Seco 9a-Aza-Macrolide Precursors Derived from Compounds of Formula (I)

Scheme CY-13

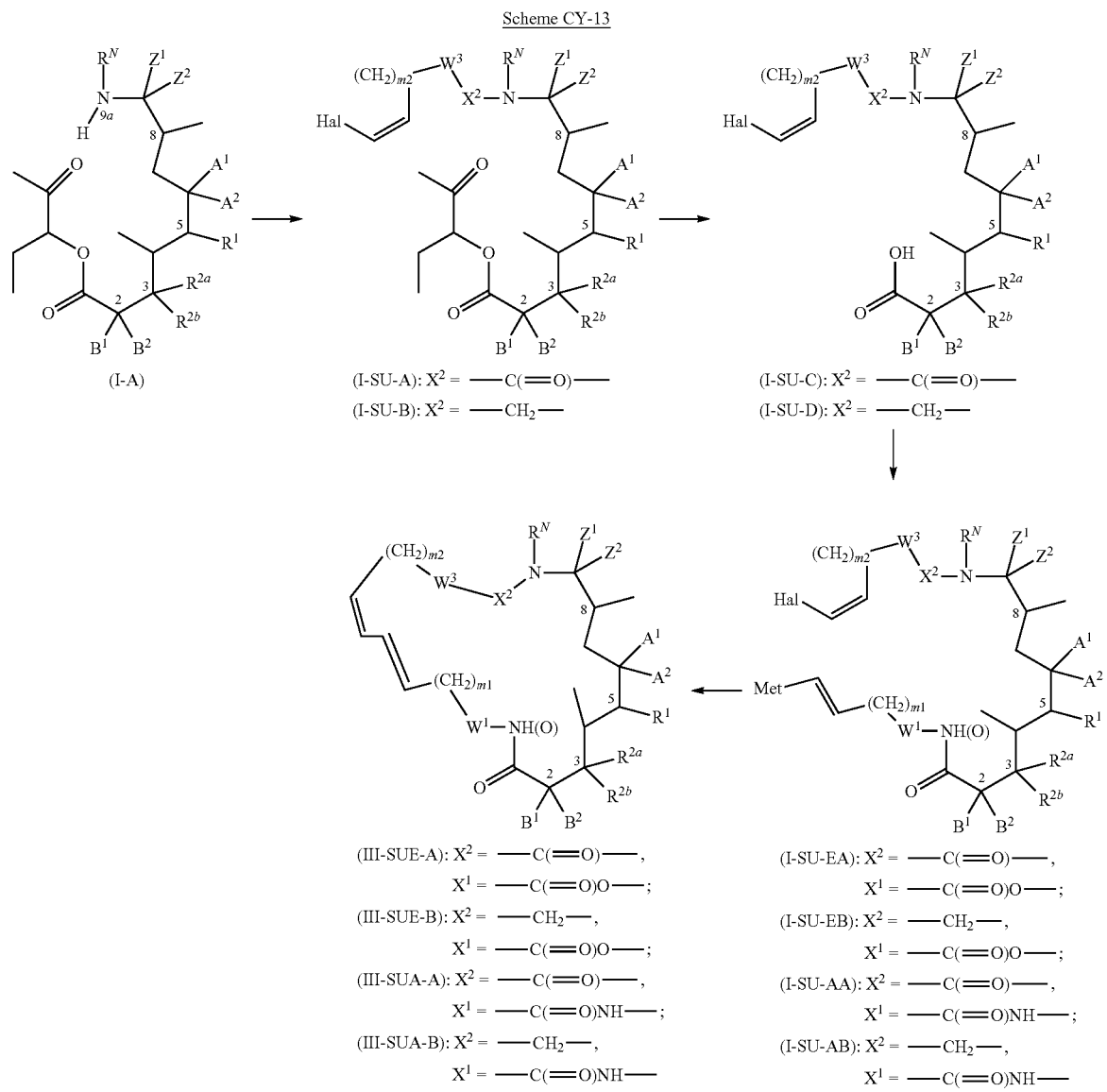

Scheme CY-13: illustrates method for the formation of alkene compounds and their macrolide based macrocycle closed ring analogues of formulae (III) wherein $W^2$ is —CH=CH—CH=CH-functionality.

9a-Nitrogen of compound (I-A) can be amidated or alkylated to compound (I-SU-A), wherein $X^2$ is —C(=O)— or (I-SU-B), wherein $X^2$ is —CH$_2$— using the appropriate vinyl carboxylic acid or vinyl aldehyde respectively.

Subsequent hydrolysis of C/1-ester provides corresponding (I-SU-C), wherein $X^2$ is —C(=O)— or (I-SU-D), wherein $X^2$ is —CH$_2$—.

Esterification of compound (I-SU-C) and (I-SU-D) C/1-COOH group using the appropriate vinyl metalated alcohol can give (I-SU-EA) and (I-SU-EB) compounds, wherein $X^{1p}$ is —C(=O)O—$W^1$—(CH$_2$)$_{m1}$—CH=CH-Met (Met stands for metal). Whereas, amidation of compound (I-SU-C) and (I-SU-D) C/1-COOH group using the appropriate vinyl metalated amine affords (I-SU-AA) and (I-SU-AB) compound, wherein $X^{1p}$ is —C(=O)NH—$W^1$—(CH$_2$)$_{m1}$—CH=CH-Met, where Met can be (R$^x$)$_3$Sn, or (Pin)B, and Hal can be bromine, iodine or pseudohalide like OTf or ONf. Macrolide based macrocycle compound of formulae (III-SUE-A), (III-SUE-B), (III-SUA-A) and (III-SUA-B), wherein $W^2$ is —CH=CH—CH=CH— can be prepared from compounds (I-SU-EA), (I-SU-EB), (I-SU-AA) and (I-SU-AB) after intramolecular cross coupling reaction in the presence of transition metal catalyst. Most palladium (0) catalysts are expected to produce the product. Similar results are expected from some palladium (II) salts in the presence of suitable ancillary ligands (Njardarson, J., et al. Chem. Commun. (2002), 2759 and Nicolaou, K. C., et al, Angew. Chem. int. Ed. (2005), 44, 4442). Typical palladium catalysts are, but not limited to, palladium(I1)acetate, tetrakis (triphenylphosphine)palladium (0), tris(dibenzylidenacetone)dipalladium (0) and the like. Suitable phosphine ancillary ligands include, but are not limited to, triphenyl phosphine, tri-o-tolyl-phosphine, BINAP, XPhos, SPhos, RuPhos, BrettPhos and the like, as well as arsene ligands like triphenyl arsene and the like.

Synthetic Procedures for Further Modifications of Compounds of Formulae (I), (II) and (III)

Method KA: General Procedure for Sugar Moiety Removal from $R^{2a}$ Position: Conversion of $S^2$ Sugar to OH Group at Position $R^{2a}$ Compounds of formula (I), (II) and (III) wherein $R^1$ is $S^1$, $R^{2a}$ is OH and $R^{2b}$ is H can be prepared starting from compounds of formula (I), (II) or (III) respectively wherein $R^1$ is $S^1$, $R^{2a}$ is $S^2$ and $R^{2b}$ is H using standard methods and procedures for removal of cladinose. Typically it is conducted under mild acid-catalyzed hydrolysis conditions. Representative acids include, but not limited to, dilut hydrochloric acid, sulphuric acid, chloroacetic acid, perchloric acid or trifluoroacetic acid. Suitable solvents for the reaction include, but not limited to, methanol, ethanol, isopropanol, dichloromethane, water or mixtures thereof. Reaction times are typically 30 min. to 24 hours. Reaction temperature is suitably 0° to 80° C. For example acid-catalyzed cleavage of the cladinose sugar may be performed as described in J. Chem. Soc. Perkin. Trans. 1 (1986) 1881-1890 and WO9951616.

In alternative, Method CY-4I-3 and CY-4I-4 reaction conditions as described herein can be used for conversion of $S^2$ sugar to OH group at position $R^{2a}$.

Typically, reaction may be performed by adding to a solution of the appropriate compound of formula (I), (II) or (III) in suitable solvent or mixture of solvents (suitably in THF or MeCN) aqueous or dioxane, ether, or THF solution of HCl (5-50 equiv.) is added and the reaction mixture is stirred for 6 to 72 hours at room temperature to 50° C. The expected product may be isolated by methods known to one skilled in the art.

Below are further alternative reaction conditions used for conversion of $S^2$ sugar to OH group at position $R^{2a}$.

Method KA1: To a solution of compound of formula (III) in THF or MeCN water solution of LiOH (2-10 equiv.) is added and the reaction mixture is stirred for 2 to 48 hours at room temperature. Reaction mixture is isolated by evaporation of organic solvent, then extraction with organic solvents as DCM. The crude compound was dissolved in H2O 2O at pH 2 to remove cladinose. Reaction mixture was isolated by extraction and purified by column chromatography or precipitation from DCM:diisopropylether to afford compound of formula (III) wherein $R^1$ is S1, $R^{2a}$ is OH and $R^{2b}$ is H.

Method KA2: A compound of formula (III) was dissolved in water at pH 2 to remove cladinose. Reaction mixture was isolated by extraction and purified by column chromatography or precipitation from DCM:diisopropylether to afford compound of formula (III) wherein $R^1$ is $S^1$, $R^{2a}$ is OH and $R^{2b}$ is H.

Method KB: General Procedure for Acylation of C/3-OH Group ($R^{2a}$ Hydroxyl Group)

Compounds of formula (II) and (III) wherein $R^{2a}$ is OC(=O)-substituted may be prepared from compounds of formula (II) and (III) respectively wherein $R^1$ is $S^1$, $R^{2a}$ is OH and $R^{2b}$ is H using standard methods and procedures for hydroxyl group acylation such as those described in WO2006087642, WO2004029067, WO0063223, and WO2006077501.

Suitably C/3-OH acylation may be performed under basic conditions using a suitable acylated agent in aprotic solvent. Typical acylating agents include, but not limited to, acid chlorides, acid anhydrides and chloroformates. Typical bases include, but not limited to, pyridine, triethylamine, diisopropyl amine, N-methyl morpholine, N-methylpyrrolidine, 1,8-diazabicyclo (5.4.0)undec-7-ene.

For compounds of formula (II) and (III) wherein $R^3$ is OH suitable protecting group $R^p$ (for example acetyl) may be introduced prior $R^{2a}$ hydroxyl group acylation. Such $R^p$ group may be subsequently removed after acylation of $R^{2a}$ hydroxyl group by processes known to one skilled in the art.

Method KB1: In a solution of EDCxHCl (3-6 equiv.) and DMAP (3-6 equiv.) in DCM, the appropriate carboxylic acid (3-6 equiv.) is added and the reaction mixture is stirred at room temperature for 20 to 30 minutes. Then, compound of formula (I) is added and stirring continued at room temperature for 4 to 24 hours. The $R^p$ group, if present may be removed by processes known in the art, for example when $R^3$ is OAc then Ac protection may be removed by stirring in MeOH at room temperature to 50° C. for 4-72 hours. The expected product of formula (I) wherein $R^{2a}$ is —OC(=O)-substituted is isolated by methods known to one skilled in the art.

Method KC: General Procedure for Mono-Demethylation of the 3'-NMe2 Group

Compounds of Formula (II) wherein $R^4$ is $NHCH_3$ are either known compounds or they as well as compounds of formula (III) wherein $R^4$ is $NHCH_3$ may be prepared by conventional techniques for mono-demethylation of the 3'-$NMe_2$ group, for example by reaction of compound of Formula (II) or (III) respectively wherein $R^4$ is $N(CH_3)_2$ by irradiation with 500 W lamp in the presence of suitable halogen such is iodine or bromine, in the presence of a suitable base such as sodium acetate trihydrate (U.S. Pat. No. 3,725,385 and WO2004/013153), and in a suitable inert solvent such us MeOH, THF, DMF or dioxane; or by reaction with triphenylphosphine-diethyl azocarboxylate (DEAD) in acetone followed by hydolisis of formed adduct in mixture of MeOH and saturated ammonium chloride solution; or by reaction of compound of Formula (II) or (III) respectively with iodine in the presence of an ammine (suitably 2-amino-2(hydroxylmethyl)-1,3-propanediol, known as Trizma® base) (as described in WO2007/067281 and *Tetrahedron* Lett. (2008), 49: 598-600), or by reaction of compound of Formula (II) or (III) respectively with N-iodosuccinimide in acetonitrile at room temperature (*J. Org. Chem*. (2000), 65: 3875-3876) or with benzylchloroformate, followed by elimination of benzyloxycarbonyl groups at position 2' and 3' as described in U.S. Pat. No. 5,250,518.

Below is exemplary reaction conditions used for mono-demethylation of the 3'-$NMe_2$ group.

Method KC1: To a solution of compound of formula (III) wherein $R^4$ is $N(CH_3)_2$ in anhydrous acetonitrile, N-iodosuccinimide is added (1.2 eq) in small portions at 0° C. under $N_2$. The reaction mixture is stirred at room temperature for 24 h. The expected product of formula (III) wherein $R^4$ is $NHCH_3$ is isolated by methods known to one skilled in the art.

Method KD: General Procedure for Acylation of C/3'-$NHCH_3$ Group

Compounds of Formula (II) wherein $R^4$ is $N(R^8)CH_3$, wherein $R^8$ is —C(=O)—$R^9$, wherein $R^9$ is $C_{1-6}$alkyl or H are either known compounds or they as well as compounds of formula (III) wherein $R^4$ is $N(R^8)CH_3$, wherein $R^8$ is —C(=O)—$R^9$, wherein $R^9$ is $C_{1-6}$alkyl or H may be prepared by conventional techniques for amine acylation, for example by reactions of compound of Formula (II) or (III) respectively wherein $R^4$ is $NHCH_3$ with the appropriate carboxylic acid anhydride or carboxylic acid hydride.

Method KD1: To a solution of compound of formula (III) wherein $R^4$ is $NHCH_3$ in DCM, $Et_3N$ (1.5 eq) and carboxylic acid anhydride (1 eq) were added. The reaction mixture was stirred at room temperature for 24 h. The expected product of formula (III) wherein $R^4$ is $N(R^8)CH_3$, wherein $R^8$ is —C(=O)—$R^9$, wherein $R^9$ is $C_{1-8}$alkyl or H was isolated by methods known to one skilled in the art.

Method KE: General Procedure for Alkylation of C/3'-NHCH$_3$ Group

Compounds of Formula (II) wherein $R^4$ is $N(R^8)CH_3$, wherein $R^8$ is $C_{1-6}$alkyl are either known compounds or they as well as compounds of formula (III) wherein $R^4$ is $N(R^8)CH_3$, wherein $R^8$ is $C_{1-6}$alkyl may be prepared by conventional techniques for amine alkylation, for example by reactions of compound of Formula (II) or (III) respectively wherein $R^4$ is $NHCH_3$ with the appropriate alkyl halide.

Method KE-1: To a solution of compound of formula (III) wherein $R^4$ is $NHCH_3$ in anhydrous acetonitrile DIPEA (1.25-5 eq) and alkyl iodide (2.5-10 eq) were added and reaction mixture was stirred at room temperature for 24-48 h. The expected product of formula (III) wherein $R^4$ is $N(R^8)CH_3$, wherein $R^8$ is $C_{1-8}$alkyl was isolated by methods known to one skilled in the art.

Method KF: General Procedures for C/4"-OH Group Acylation

Compounds of Formula (II) wherein $R^{12}$ is —OC(=O)$Y^3$ are either known compounds or they as well as their C/4"-analogues of formula (III) may be prepared by conventional techniques for hydroxyl group acylation from compounds of Formula (II) or (III) respectively wherein $R^{12}$ is OH and $R^{11}$ is H. For example by processes and methods described in WO2006087644A2 and WO2005108412A1.

Method KF-1: To a solution of compound of formula (III) wherein $R^3$ is OH, $R^{11}$ is H, and $R^{12}$ is OH in DCM, DMAP (5 eq) and acetic anhydride (5 eq) were added. The reaction mixture was stirred at room temperature for 24 h, crude product isolated by extraction, dissolved in MeOH and stirred at room temperature for 24 h (in order to remove Ac from $R^3$ hydroxyl). The expected product of formula (III) wherein $R^3$ is OH, $R^{11}$ is H, and $R^{12}$ is OC(=O)—CH$_3$ was isolated by methods known to one skilled in the art.

Method KG-A: General Procedure for C/3-OH Oxidation to Keto Compounds of Formula (II) wherein $R^{2a}$ and $R^{2b}$ together form a keto group provided $A^1$ is $OR^p$ or $OC_{1-6}$alkyl are either known compounds or they as well as their C/3-keto analogues of formula (III) may be prepared from corresponding compound of formula (II) or compound of formula (III) respectively wherein $A^1$ is $OR^p$ or $OC_{1-6}$alkyl, $R^{2a}$ is OH and $R^{2b}$ is H, by well known processes and methods for C/3-OH oxidation. For example by processes and methods described in WO2006087642.

Method KG-B: General Procedure for C/3-C/6-Cyclichemiketal Preparation Compounds of Formula (II) wherein $R^{2b}$ together with $A^1$ forms cyclic hemiketal group and $R^{2a}$ is OH are either known compounds or they as well as their C/3-C/6-cyclic hemiketal analogues of formula (III) may be prepared from corresponding compound of formula (II) or compound of formula (III) respectively wherein $A^1$ is OH, $R^{2a}$ is OH and $R^{2b}$ is H, by well known processes and methods for C/3-0H oxidation. For example by processes and methods described in WO2006087642.

Method KG-B-1: To a solution of compound of formula (III) wherein $A^1$ is OH, $R^{2a}$ is OH and $R^{2b}$ is H, in DCM, Dess Martin periodinane (2 eq) was added at 0° C. The reaction mixture was stirred at room temperature for 2 h. Crude product was isolated by extraction, then dissolved in MeOH and stirred at room temperature for 24 h. (in order to remove Ac from $R^3$ hydroxyl). The expected product of formula (III) wherein $R^{2b}$ together with $A^1$ forms cyclic hemiketal group and $R^{2a}$ is OH was isolated by methods known to one skilled in the art.

Method KH: General Procedure for Removal of C/2'-OH Group

Compounds of formula (II) or (III) wherein $R^3$ is H may be obtained starting from compounds of formula (II) or (III) respectively wherein $R^3$ is OH by reaction with O-phenylchlorothioformate to produce C/2'-O-thiocarbonate which is then submitted to the radical deoxygenation reaction using Bu$_3$SnH or (TMS)$_3$SH as hydrogen donors and AIBN or ABCN as radical initiators. This reaction may cause C/5"-CH$_3$ group epimerisation giving both C/5"-CH$_3$ epimers of the end product, wherein $R^3$ is H. For example removal of C/2'-OH group may be performed according to procedure described in *J. Chem. Soc. Perkin Trans* 1 (1975), 1574-1585.

Method KI: General Procedure for Heck Reaction

Typically DMF solution of the appropriate compound of formula (I), (II) or (III) wherein exocyclic double bond functionality is present Pd(OAc)$_2$ (0.2 eq) and tri-o-tolylphosphin (0.4 eq) were added under argon atmosphere. The reaction mixture was stirred at room temperature for 30 min. followed by addition of aryl halide (2.5 eq) and Et$_3$N (1.6 eq). The reaction mixture was stirred at 65° C. for 2 h and at 75° for additional 18 h. The expected product was isolated by methods known to one skilled in the art.

Method KJ: General Procedure for Double Bond Reduction

To a EtOH solution of compound of formula (I), (II) or (III) wherein double bond functionality is present Pd/C (10 wt %) was added and hydrogenated at 2-5 barr for 24 h. The expected product was isolated by methods known to one skilled in the art.

Method KL: General Procedure for Nitrogen Substitution:

Method KL-A: General Procedure for N-Alkylation

Typically to a solution of the appropriate compound of formula (II) or (III) wherein $R^N$ is H in suitable solvent or mixture of solvents (suitably DCM, DCE or mixture of DCM or DCE and MeOH) the appropriate aldehyde $R^N$—C(=O)H (1-2 equiv.), TEA (1.5-4 equiv.) and NaBH$_4$ (2-4 equiv.), NaCNBH$_3$ (2-4 equiv.) or Na(OAc)$_3$BH (2-4 equiv.) are added and the reaction mixture is stirred at room temperature for 6 to 24 hours. The expected product of formula (II) or (III) may be isolated by methods known to one skilled in the art or directly subjected to the deprotection step without isolation.

Method KL-B: General Procedure for N-Acylation

To a cooled (0-5° C.) solution of compound of formula (II) or (III) in DCM, Et$_3$N (2 eq) and corresponding acid chloride or DIPEA (1 to 2 eq) were added. The reaction mixture was stirred at room temperature for 30 min. The expected product was isolated by methods known to one skilled in the art.

Method KL-C: General Procedure for N-Urea Formation

To a solution of compound of formula (II) or (III) in $CH_3CN$, $Et_3N$ (3 eq) and corresponding isothiocyanate (3 eq) were added. The reaction mixture was stirred at room temperature for 24 h. The expected product was isolated by methods known to one skilled in the art.

Method KM: General Procedure for Ts Deprotection:

To a solution of approptiate compound of formula (I), (II) or (III) wherein nitrogen atom is Ts protected in DMF, TASF (tris(dimethylamino)sulfonium difluorotrimethylsilicate) was added. Reaction mixture was stirred at r.t. for 24 h. The expected compound of formula (I), (II) or (III) may be isolated by methods known to one skilled in the art.

Method KN: General Procedure for C/2'-O and C/3'-N Cb-Deprotection

To a solution of approptiate compound of formula (II) or (III), wherein C/2'-O and C/3'-N are Cb protected in EtOH, Pd/C (10 wt %) was added and hydrogenated at (2-5) barr for 24 h. The expected compound of formula (II) or (III), $R^3$ is OH and $R^4$ is $NHCH_3$ may be isolated by methods known to one skilled in the art.

Method KO: General Procedure for Bn-Deprotection

To a solution of approptiate compound of formula (II) or (III), wherein benzyl protecting group is present at OH functionality in isopropanol, ammonium formate (5 equiv.) and Pd/C (10 wt %) were added and heated in microwave reactor for 10 min at 90° C. The expected compound of formula (II) or (III), wherein OH group is deprotected may be isolated by methods known to one skilled in the art.

Method KP: General Procedure for Allyl Deprotection

A solution of O-allyl protected compound of formula (II) or (III), (1 eq.) and 1,3-dimethylbarbituric acid (2.15 eq.) in MeOH was degassed with Ar bubbling for 5 min. and Pd(PPh3)4 was added. Reaction mixture was stirred at r. t. The expected product was isolated by methods known to one skilled in the art.

Method KR: General Procedure for Sonogashira Coupling

To a solution of compound of formula (II) or (III) having alkyne functionality (1 eq.), aryl halide (2 eq.) in $CH_3CN$ and $Et_3N$ (10 eq.) were added and solution bubbled with Ar for 5 min. Then CuI (0.2 eq.) and $Pd(Ph_3)_2Cl_2$ (0.05 eq.) were added and reaction mixture was stirred at 70-80° C. for 3-4 hours. The expected product was isolated by methods known to one skilled in the art.

Method KS: General Procedure for Removal of C/3-OH Group: Preparation of C/3-Deoxy Compounds Compounds of formula (II) or (III) wherein $R^{2a}$ and $R^{2b}$ are both hydrogen may be obtained starting from compounds of formula (II) or (III) respectively wherein $R^{2a}$ is OH, $R^{2b}$ is H, $R^1$ is $S^1$, OC1-6alkyl, or $OR^p$, $A^1$ is OC1-6alkyl, OC-1-6alkenyl, OC1-6alkynyl or ORp.

In the first step protection of C/2'-OH group is introduced (suitably for example by acetyl), then suitable protection of hydroxyl groups C/11-0H and C/12-OH is introduced (for example C/11,12-cyclic carbonate protective group). In thus obtained analogue where C/2'-OH and C/11-OH and C/12-OH are protected and $R^{2a}$ is OH deoxygenation of C/3-OH may be conducted by converting C/3-OH to the appropriate ester (such as for example dithiocarbonic acid-2-yl methyl ester) by reaction with base such as sodium hydride, potassium hexamethyldisilazide, and a like (suitably NaH) in a solution of a suitable solvent such as DMF, tetrahydrofuran, ether, dioxane and a like (suitably DMF) at temperatures ranging from −20° C. to room temperature followed by reaction of the resulting alkoxide with excess carbon disulfide and iodomethane a C/3-O-methyl xantate. Thus obtained C/-3-O-methyl xantate is then subjected to the radical deoxygenation procedure by treatment with a radical initiator suc as azobis-isobutyrylnitrile (AIBN), triethylborane, and a like (suitably AIBN) and in excess of a hydride source such as tributyltin, hydride, triphenyltin hydride, and a like (suitably tributyltin) in suitable solvent such as benzene, toluene, and a like (suitably benzene) at a temperature ranging from room to solvent boling temperature. From thus obtained C/3-deoxy analogue hydroxyl protective groups from C/2', C/11 and C/12 may be removed by standard techniques known to one skilled in the art.

For example removal of C/3-OH group may be performed according to procedure described in WO9900124.

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 1 | 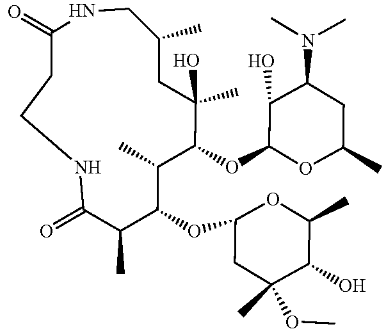 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CNC(=O)CCNC(=O)[C@@H]2C)O[C@@H](C)[C@@H]1O] | 646.65 | I-B1-iii-2 | CY-4G-2 (using Fmoc-β-alanine), CY-4I-1 and CY-1.1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 2 | 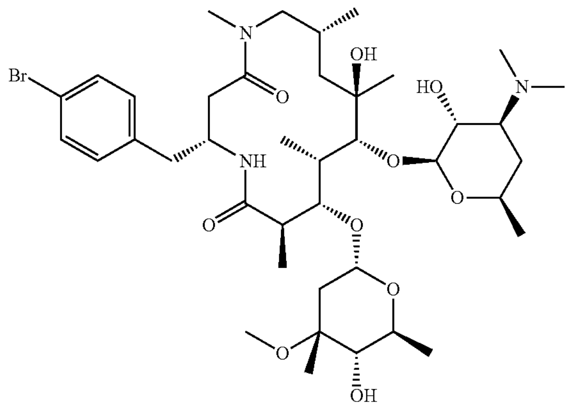 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C[C@@H](Cc3ccc(Br)cc3)NC(=O)[C@@H]2C)O[C@@H](C)[C@@H]1O] | 646.65 | I-A1-iii-1 | CY-4G-2 (using Fmoc-(R)-3-amino-(4-bromophenyl)butyric acid), CY-4I-2 and CY-1.1 |
| 3 | 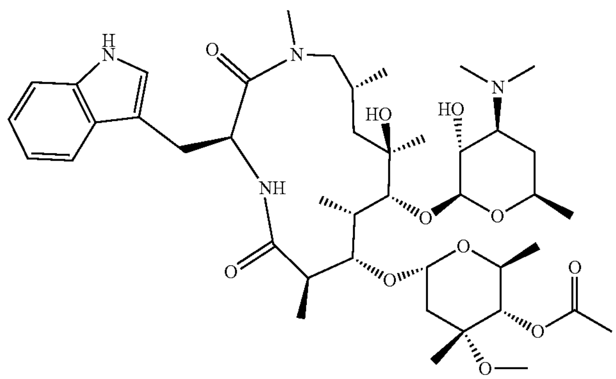 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)[C@H](Cc3c[nH]c4ccccc34)NC(=O)[C@@H]2C)O[C@@H](C)[C@@H]1OC(C)=O] | 817.74 | I-B1-iii-1 | CY-4G-2 (using N-Fmoc-(S)-2-Amino-3-(1H-indol-3-yl)-propionic acid), CY-4I-1 and CY-1.1 |
| 4 | 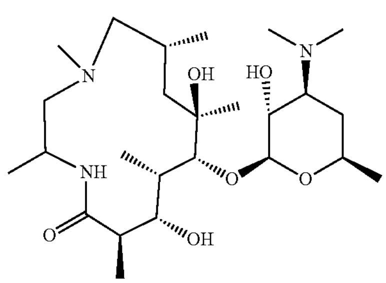 | 488.46 | I-B1-iii-1 | CY-4H-1 (using N-Boc-2-Amino-propionaldehyde), CY-4I-4 and CY-1.1 |
| 5 | 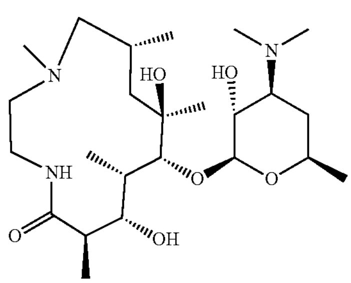 [SMILES: C[C@H]1CN(C)CCNC(=O)[C@H](C)[C@@H](O)[C@H](C)[C@@H](O[C@@H]2O[C@H](C)C[C@H](N(C)C)[C@H]2O)[C@](C)(O)C1] | 474.46 | I-B1-iii-1 | CY-4H-1 (using t-Bu-(1-oxopropan-2-yl)carbamate), CY-4I-3 and CY-1.1 |

-continued

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 6 | 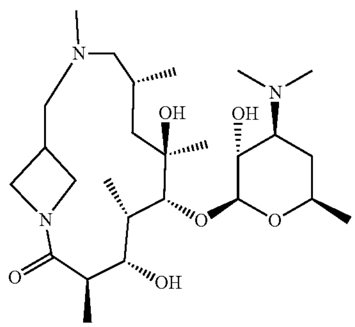 [SMILES: C[C@H]1CN(C)CC2CN(C2)C(=O)[C@H](C)[C@@H](O)[C@H](C)[C@@H](O[C@@H]2O[C@H](C)C[C@H](N(C)C)[C@H]2O)[C@](C)(O)C1] | 500.43 | I-A1-iii-1 | CY-4H-1 (using 1-Boc-3-azetidine carboxaldehyde), CY-4I-3 and CY-1.1 |
| 7 | 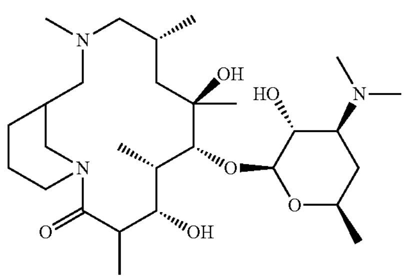 [SMILES: CC1C(=O)N2CCCC(CN(C)C[C@H](C)C[C@@](C)(O)[C@H](O[C@@H]3O[C@H](C)C[C@H](N(C)C)[C@H]3O)[C@@H](C)[C@@H]1O)C2] | 528.52 | I-A1-iii-1 | CY-4H-1 (using N-Boc-piperidine-3-carbaldehyde), CY-4I-3 and CY-1.1 |
| 8 | 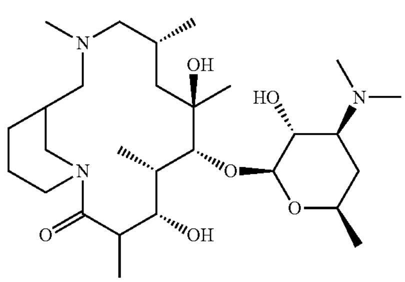 [SMILES: CC1C(=O)N2CCCC(CN(C)C[C@H](C)C[C@@](C)(O)[C@H](O[C@@H]3O[C@H](C)C[C@H](N(C)C)[C@H]3O)[C@@H](C)[C@@H]1O)C2] | 528.51 | I-A1-iii-1 | CY-4H-1 (using N-Boc-piperidine-3-carbaldehyde), CY-4I-3 and CY-1.1 |
| 9 | 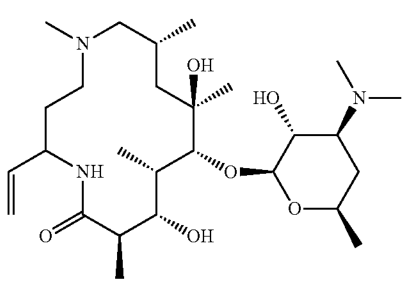 [SMILES: C=CC1CCN(C)C[C@H](C)C[C@@](C)(O)[C@H](O[C@@H]2O[C@H](C)C[C@H](N(C)C)[C@H]2O)[C@@H](C)[C@H](O)[C@@H](C)C(=O)N1] | 514.4 | I-A1-iii-1 | CY-4H-1 (using N-Boc-(+/−)-3-aminopentana-4-enal), CY-4I-3 and CY-1.1 |

-continued

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 10 | 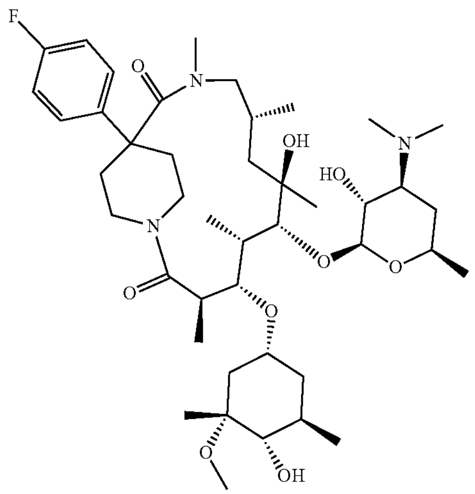 | 794.73 | I-A1-iii-1 | CY-4G-2 (using Fmoc-4-(4-Fluoro-phenyl)-piperidine-4-carboxylic acid, CY-4I-2 and CY-1.1 |
| 11 | 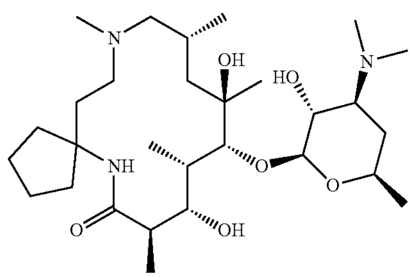 [SMILES: C[C@H]1CN(C)CCC2(CCCC2)NC(=O)[C@H](C)[C@@H](O)[C@H](C)[C@@H](O[C@@H]2O[C@H](C)C[C@H](N(C)C)[C@H]2O)[C@](C)(O)C1] | 556.5 | I-A1-iii-1 | CY-4G-2 (using N-Boc-(1-Amino-cyclopentyl)-acetic acid), CY-4I-3 and CY-1.1 |
| 12 | 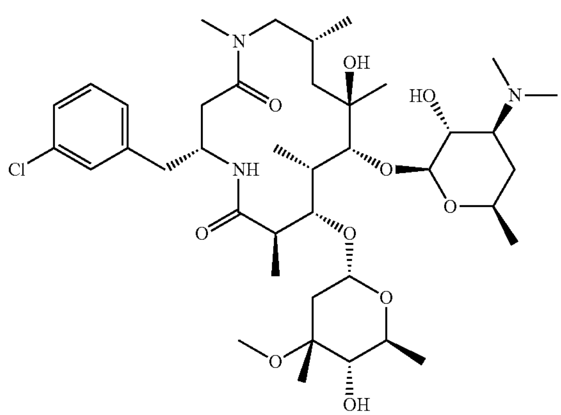 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C[C@@H](Cc3cccc(Cl)c3)NC(=O)[C@@H]2C)O[C@@H](C)[C@@H]1O] | 784.67 | I-A1-iii-1 | CY-4G-2 (using N-Fmoc-(R)-3-Amino-4-(3-chloro-phenyl)-butiric acid), CY-4I-2 and CY-1.1 |
| 13 | 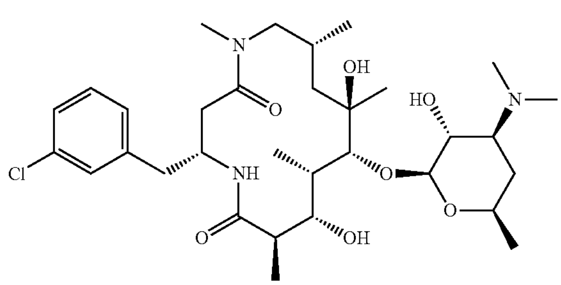 [SMILES: C[C@H]1CN(C)C(=O)C[C@@H](Cc2cccc(Cl)c2)NC(=O)[C@H](C)[C@@H](O)[C@H](C)[C@@H](O[C@@H]2O[C@H](C)C[C@H](N(C)C)[C@H]2O)[C@](C)(O)C1] | 626.49 | 12 | KA-2 |

-continued

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 14 | 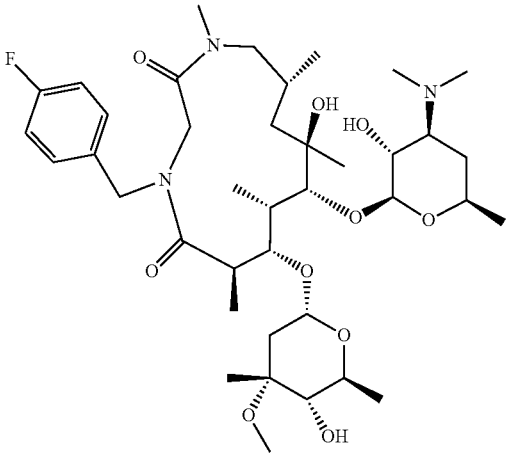 | 754.68 | I-A1-iii-1 | CY-4G-2 (using Fmoc-(4-Fluoro-benzylamino)-acetic acid), CY-4I-2 and CY-1.1 |
| 15 | 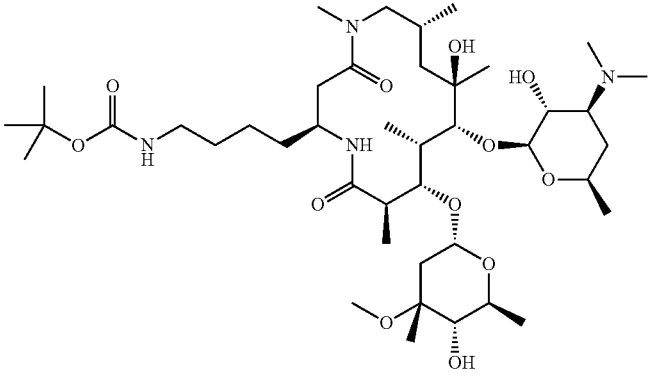 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C[C@H](CCCCNC(=O)OC(C)(C)C)NC(=O)[C@@H]2C)O[C@@H](C)[C@@H]1O] | 831.8 | I-A1-iii-1 | CY-4G-2 (using (S)-3-Amino-7-tert-butoxycarbonylamino-heptanoic acid), CY-4I-2 and CY-1.1 |
| 16 | 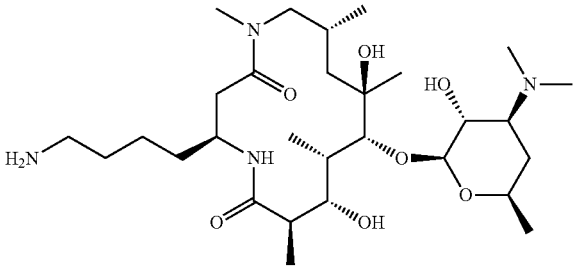 [SMILES: C[C@H]1CN(C)C(=O)C[C@H](CCCCN)NC(=O)[C@H](C)[C@@H](O)[C@H](C)[C@@H](O[C@@H]2O[C@H](C)C[C@H](N(C)C)[C@H]2O)[C@](C)(O)C1] | 573.5 | 15 | CY-4I-4 |
| 17 | 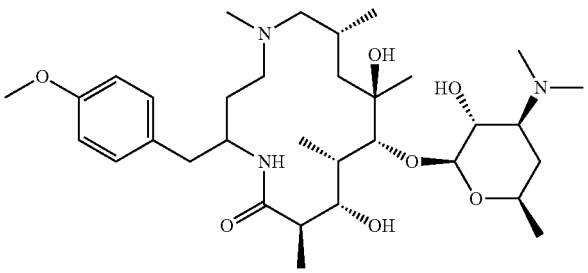 | 608.6 | I-B1-iii-1 | CY-4H-2 (using N-Boc-3-Amino-4-(4-methoxy-phenyl)-butyraldehyde), CY-4I-3 and CY-1.1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 18 | 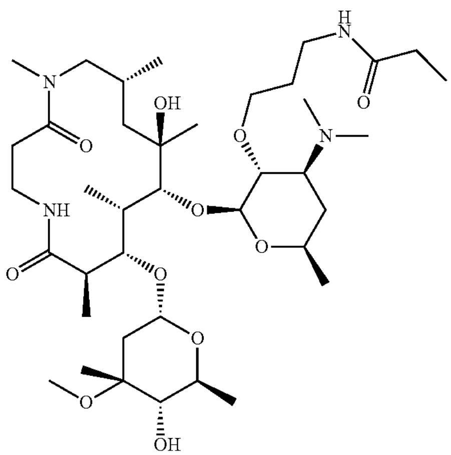 [SMILES: CCC(=O)NCCCO[C@H]1[C@H](O[C@@H]2[C@@H](C)[C@H](O[C@H]3C[C@@](C)(OC)[C@@H](O)[C@H](C)O3)[C@@H](C)C(=O)NCCC(=O)N(C)C[C@H](C)C[C@@]2(C)O)O[C@H](C)C[C@@H]1N(C)C] | 773.71 | I-A1-iii-3 | CY-4G-2 (using Fmoc-β-alanine), CY-4I-2 and CY-1.1 |
| 19 | 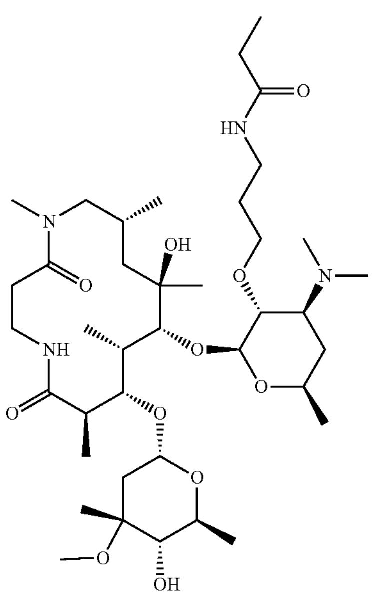 [SMILES: CCC(=O)NCCCO[C@H]1[C@H](O[C@@H]2[C@@H](C)[C@H](O[C@H]3C[C@@](C)(OC)[C@@H](O)[C@H](C)O3)[C@@H](C)C(=O)NCCC(=O)N(C)C[C@H](C)C[C@@]2(C)O)O[C@H](C)C[C@@H]1N(C)C] | 773.95 | I-A1-iii-3 | CY-4G-2 (using Fmoc-β-alanine), CY-4I-2 and CY-1.1 |

Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 20 | 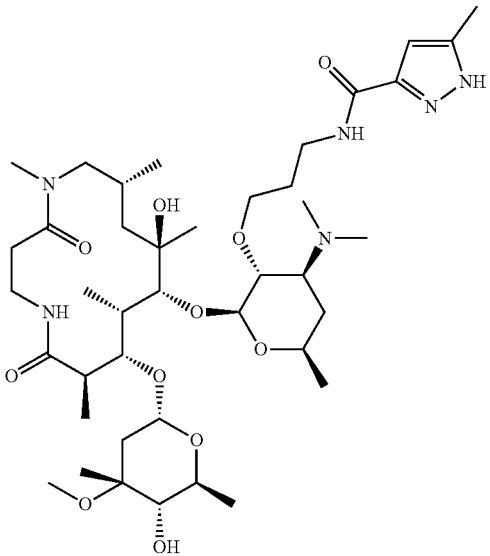 [SMILES: CO[C@]1(C)C[C@H](O[C@H]2[C@H](C)[C@@H](O[C@@H]3O[C@H](C)C[C@H](N(C)C)[C@H]3OCCCNC(=O)c3cc(C)[nH]n3)[C@](C)(O)C[C@@H](C)CN(C)C(=O)CCNC(=O)[C@@H]2C)O[C@@H](C)[C@@H]1O] | 825.81 | I-A1-iii-4 | CY-4G-2 (using Fmoc-β-alanine), CY-4I-2 and CY-1.1 |
| 21 | 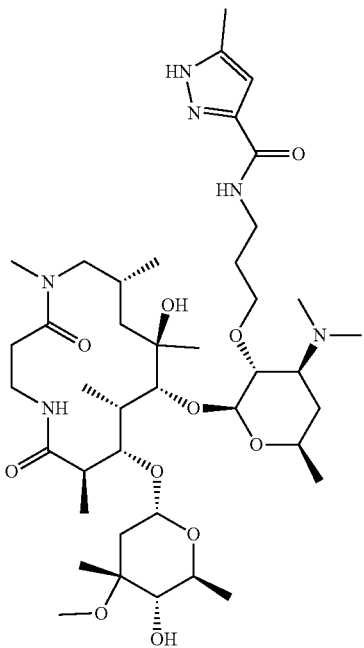 [SMILES: CO[C@]1(C)C[C@H](O[C@H]2[C@H](C)[C@@H](O[C@@H]3O[C@H](C)C[C@H](N(C)C)[C@H]3OCCCNC(=O)c3cc(C)[nH]n3)[C@](C)(O)C[C@@H](C)CN(C)C(=O)CCNC(=O)[C@@H]2C)O[C@@H](C)[C@@H]1O] | 826.07 | I-A1-iii-4 | CY-4G-2 (using Fmoc-β-alanine), CY-4I-2 and CY-1.1 |

Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 22 | 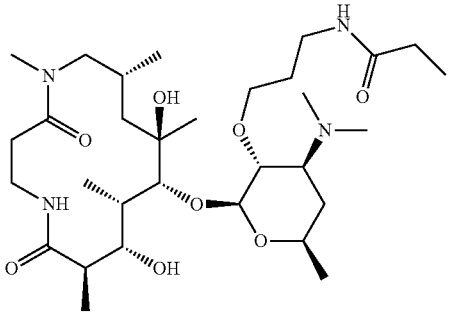 [SMILES: CCC(=O)NCCCO[C@H]1[C@H](O[C@@H]2[C@@H](C)[C@H](O)[C@@H](C)C(=O)NCCC(=O)N(C)C[C@H](C)C[C@@]2(C)O)O[C@H](C)C[C@@H]1N(C)C] | 615.59 | 18 | KA2 |
| 23 | 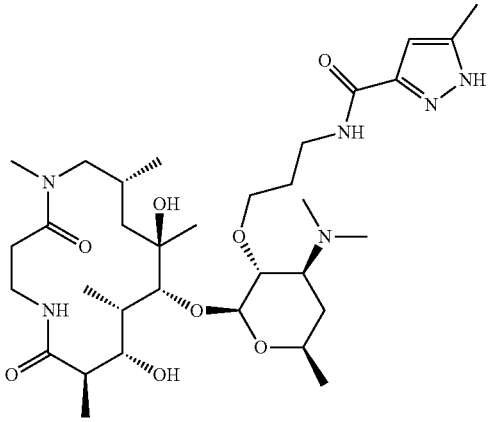 [SMILES: Cc1cc(C(=O)NCCCO[C@H]2[C@H](O[C@@H]3[C@@H](C)[C@H](O)[C@@H](C)C(=O)NCCC(=O)N(C)C[C@H](C)C[C@@]3(C)O)O[C@H](C)C[C@@H]2N(C)C)n[nH]1] | 667.61 | 20 | KA2 |
| 24 | 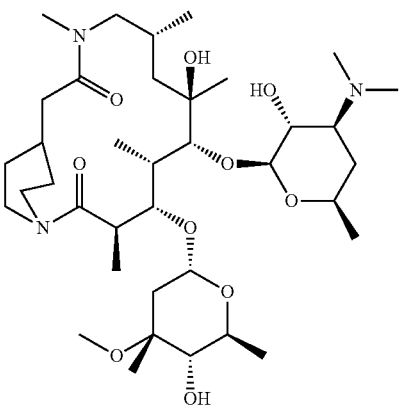 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)CC3CCN(CC3)C(=O)[C@@H]2C)O[C@@H](C)[C@@H]1O] | 714.61 | I-A1-iii-1 | CY-4G-2 (using Fmoc-piperidin-4-yl-acetic acid), CY-4I-2 and CY-1.1 |

-continued
Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 25 | 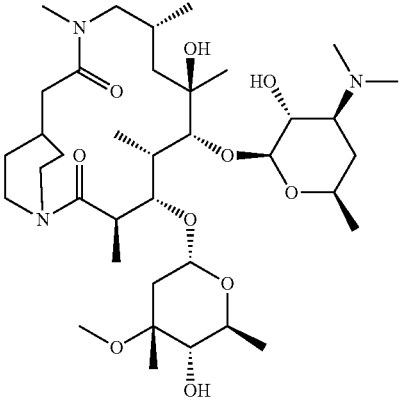 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)CC3CCN(CC3)C(=O)[C@@H]2C)O[C@@H](C)[C@@H]1O] | 714.99 | I-A1-iii-1 | CY-4G-2 (using Fmoc-piperidin-4-yl-acetic acid), CY-4I-2 and CY-1.1 |
| 26 | 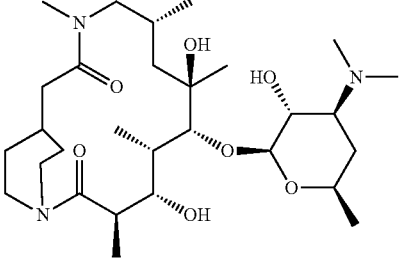 | 556.6 | 24 | KA2 |
| 27 | 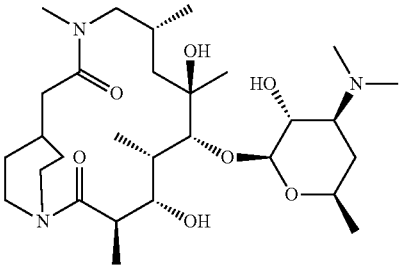 [SMILES: C[C@H]1CN(C)C(=O)CC2CCN(CC2)C(=O)[C@H](C)[C@@H](O)[C@H](C)[C@@H](O[C@@H]2O[C@H](C)C[C@H](N(C)C)[C@H]2O)[C@](C)(O)C1] | 556.36 | 25 | KA2 |
| 28 | 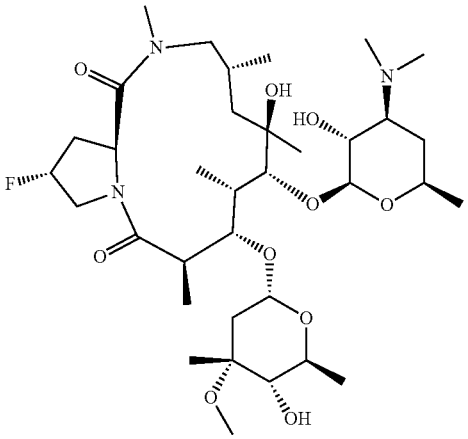 | 704.4 | I-A1-iii-1 | CY-4G-2 (using (2S,4R)-4-Fluoro-pyrrolidine-2-carboxylic acid), CY-4I-2 and CY-1.1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 29 | 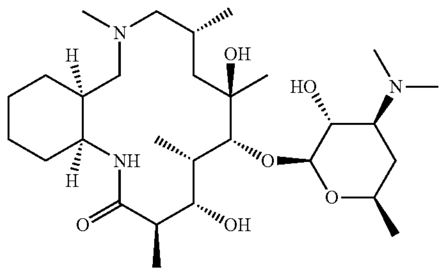 [SMILES: C[C@H]1CN(C)C[C@@H]2CCCC[C@@H]2NC(=O)[C@H](C)[C@@H](O)[C@H](C)[C@@H](O[C@@H]2O[C@H](C)C[C@H](N(C)C)[C@H]2O)[C@](C)(O)C1] | 542.4 | I-B1-iii-1 | CY-4H-1 (using N-Boc-(1R,2S)-2-Amino-cyclohexanecarbaldehide), CY-4I-3 and CY-1.1 |
| 30 | 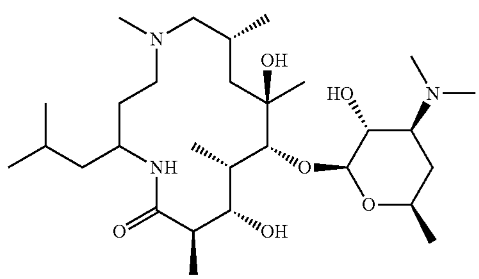 [SMILES: CC(C)CC1CCN(C)C[C@H](C)C[C@@](C)(O)[C@H](O[C@@H]2O[C@H](C)C[C@H](N(C)C)[C@H]2O)[C@@H](C)[C@H](O)[C@@H](C)C(=O)N1] | 544.5 | I-B1-iii-1 | CY-4H-1 (using N-Boc-3-Amino-5-methyl-hexanal), CY-4I-3 and CY-1.1 |
| 31 | 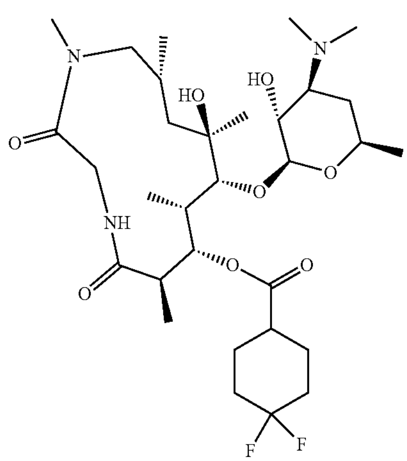 [SMILES: C[C@H]1CN(C)C(=O)CNC(=O)[C@H](C)[C@@H](OC(=O)C2CCC(F)(F)CC2)[C@H](C)[C@@H](O[C@@H]2O[C@H](C)C[C@H](N(C)C)[C@H]2O)[C@](C)(O)C1] | 634.22 | 50 | KB1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 32 | 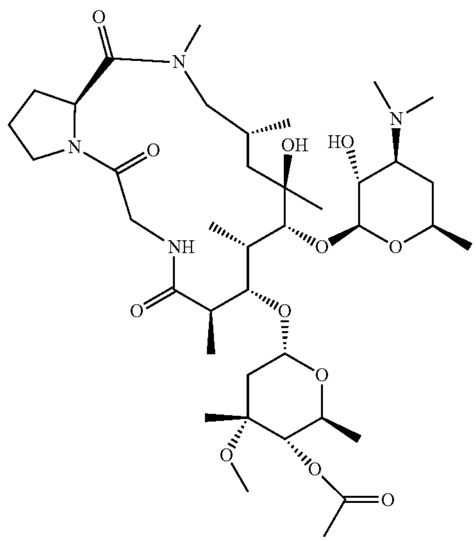 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)[C@@H]3CCCN3C(=O)CNC(=O)[C@@H]2C)O[C@@H](C)[C@@H]1OC(C)=O] | 785.62 | I-B1-iii-1 | CY-4G-2 (using (S)-1-(2-Amino-acetyl)-pyrrolidine-2-carboxylic acid), CY-4I-1 and CY-1.1 |
| 33 | 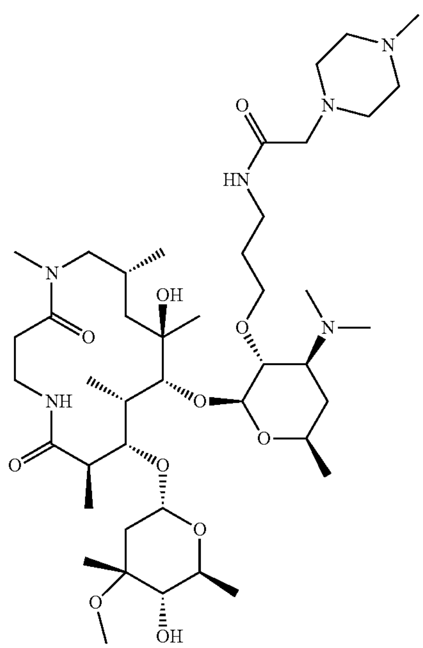 [SMILES: CO[C@]1(C)C[C@H](O[C@H]2[C@H](C)[C@@H](O[C@@H]3O[C@H](C)C[C@H](N(C)C)[C@H]3OCCCNC(=O)CN3CCN(C)CC3)[C@](C)(O)C[C@@H](C)CN(C)C(=O)CCNC(=O)[C@@H]2C)O[C@@H](C)[C@@H]1O] | 857.8 | I-A1-iii-5 | CY-4G-2 (using Fmoc-β-alanine), CY-4I-2 and CY-1.1 |

Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 34 | 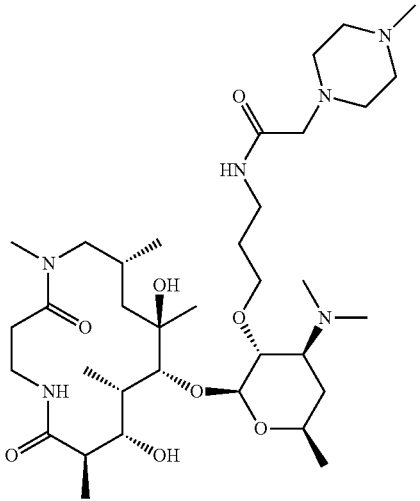 [SMILES: C[C@H]1CN(C)C(=O)CCNC(=O)[C@H](C)[C@@H](O)[C@H](C)[C@@H](O[C@@H]2O[C@H](C)C[C@H](N(C)C)[C@H]2OCCCNC(=O)CN2CCN(C)CC2)[C@](C)(O)C1] | 699.7 | 33 | KA2 |
| 35 | 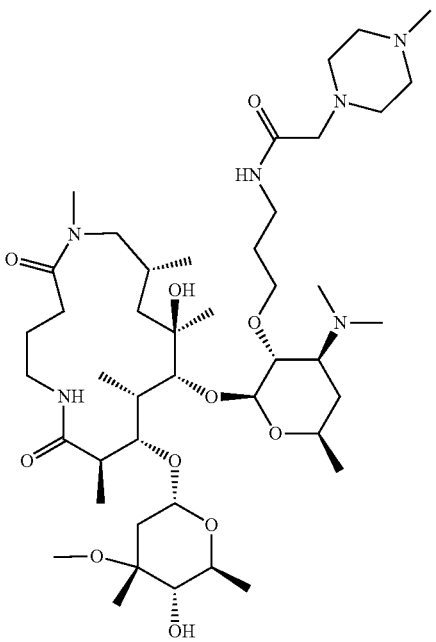 [SMILES: CO[C@]1(C)C[C@H](O[C@H]2[C@H](C)[C@@H](O[C@@H]3O[C@H](C)C[C@H](N(C)C)[C@H]3OCCCNC(=O)CN3CCN(C)CC3)[C@](C)(O)C[C@@H](C)CN(C)C(=O)CCCNC(=O)[C@@H]2C)O[C@@H](C)[C@@H]1O] | 871.78 | I-A1-iii-5 | CY-4G-2 (using Fmoc-4-aminobutyric acid), CY-4I-2 and CY-1.1 |

-continued

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 36 | 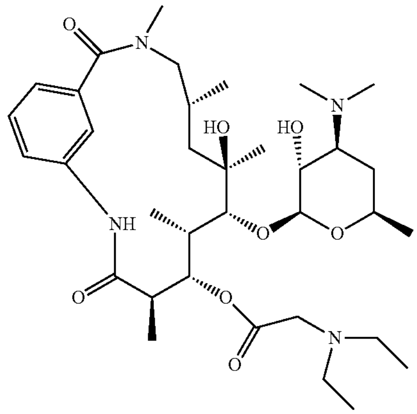 [SMILES: CCN(CC)CC(=O)O[C@H]1[C@H](C)[C@@H](O[C@@H]2O[C@H](C)C[C@H](N(C)C)[C@H]2O)[C@](C)(O)C[C@@H](C)CN(C)C(=O)c2cccc(c2)NC(=O)[C@@H]1C] | 663.53 | 49 | KB1 |
| 37 | 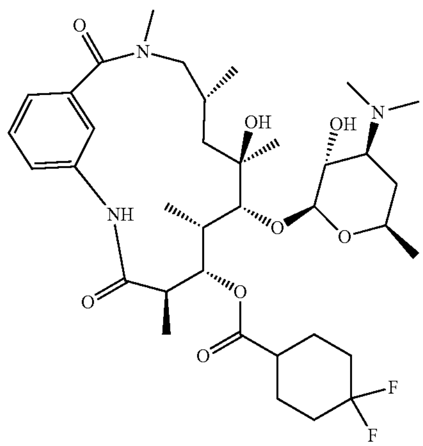 [SMILES: C[C@H]1CN(C)C(=O)c2cccc(c2)NC(=O)[C@H](C)[C@@H](OC(=O)C2CCC(F)(F)CC2)[C@H](C)[C@@H](O[C@@H]2O[C@H](C)C[C@H](N(C)C)[C@H]2O)[C@](C)(O)C1] | 696.58 | 49 | KB1 |
| 38 | 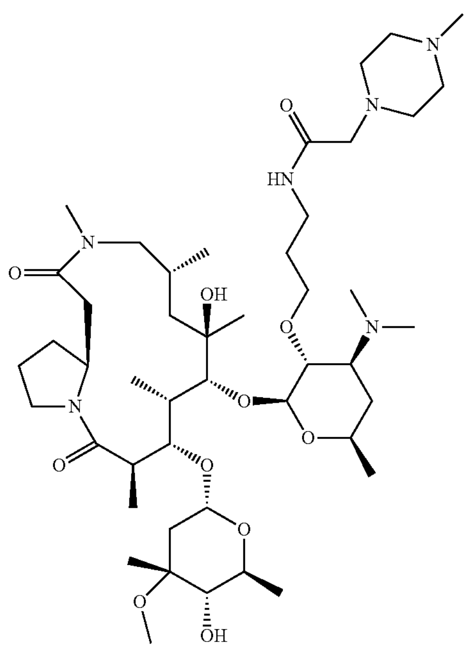 [SMILES: CO[C@]1(C)C[C@H](O[C@H]2[C@H](C)[C@@H](O[C@@H]3O[C@H](C)C[C@H](N(C)C)[C@H]3OCCCNC(=O)CN3CCN(C)CC3)[C@](C)(O)C[C@@H](C)CN(C)C(=O)C[C@@H]3CCCN3C(=O)[C@@H]2C)O[C@@H](C)[C@@H]1O] | 897.85 | I-A1-iii-5 | CY-4G-2 (using N-Fmoc-(S)-Pyrrolidin-2-yl-acetic acid), CY-4I-2 and CY-1.1 |

Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 39 | 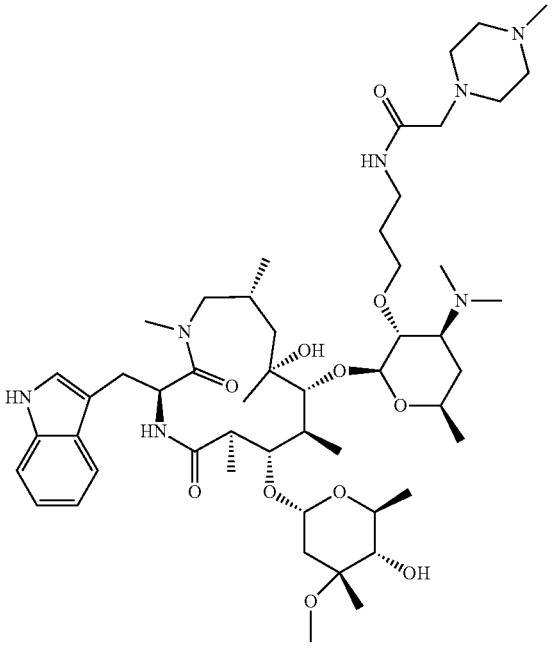 [SMILES: CO[C@]1(C)C[C@H](O[C@H]2[C@H](C)[C@@H](O[C@@H]3O[C@H](C)C[C@H](N(C)C)[C@H]3OCCCNC(=O)CN3CCN(C)CC3)[C@](C)(O)C[C@@H](C)CN(C)C(=O)[C@H](Cc3c[nH]c4ccccc34)NC(=O)[C@@H]2C)O[C@@H](C)[C@@H]1O] | 972.92 | I-A1-iii-5 | CY-4G-2 (using (N-Fmoc-(S)-2-Amino-3-(1H-indol-3-yl)-propionic acid), CY-4I-2 and CY-1.1 |
| 40 | 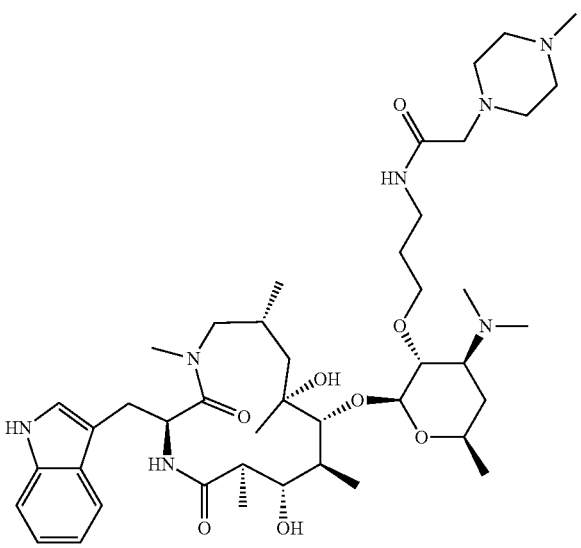 [SMILES: C[C@H]1CN(C)C(=O)[C@H](Cc2c[nH]c3ccccc23)NC(=O)[C@H](C)[C@@H](O)[C@H](C)[C@@H](O[C@@H]2O[C@H](C)C[C@H](N(C)C)[C@H]2OCCCNC(=O)CN2CCN(C)CC2)[C@](C)(O)C1] | 814.7 | 39 | KA2 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 41 | 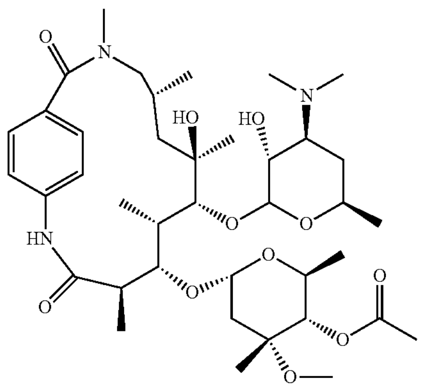 [SMILES: CO[C@]1(C)C[C@H](O[C@H]2[C@H](C)[C@@H](OC3O[C@H](C)C[C@H](N(C)C)[C@H]3O)[C@](C)(O)C[C@@H](C)CN(C)C(=O)c3ccc(cc3)NC(=O)[C@@H]2C)O[C@@H](C)[C@@H]1OC(C)=O] | 750.74 | I-B1-iii-1 | CY-4G-2 (using N-Fmoc-4-Amino-benzoic acid), CY-4I-1 and CY-1.1 |
| 42 | 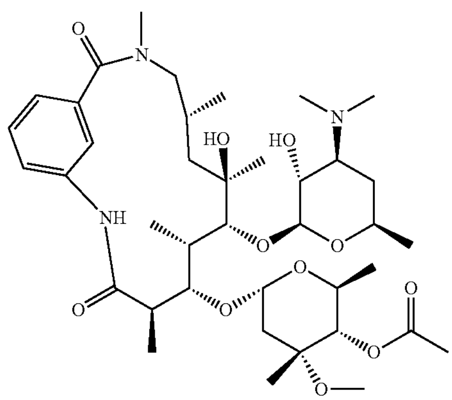 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)c3cccc(c3)NC(=O)[C@@H]2C)O[C@@H](C)[C@@H]1OC(C)=O] | 750.76 | I-B1-iii-1 | CY-4G-2 (using N-Fmoc-3-Amino-benzoic acid), CY-4I-1 and CY-1.1 |
| 43 | 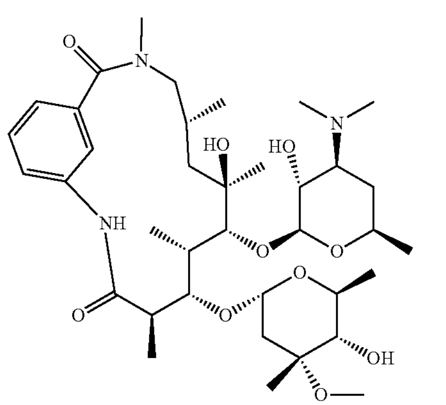 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)c3cccc(c3)NC(=O)[C@@H]2C)O[C@@H](C)[C@@H]1O] | 708.63 | I-B1-iii-1 | CY-4G-2 (using N-Fmoc-3-Amino-benzoic acid), CY-4I-1 and CY-1.1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 44 | 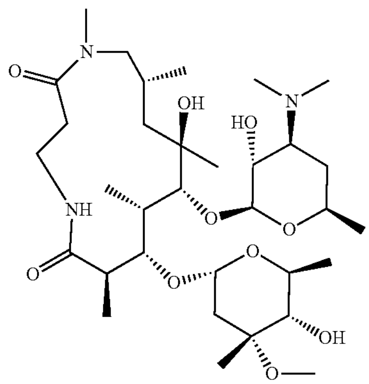 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)CCNC(=O)[C@@H]2C)O[C@@H](C)[C@@H]1O] | 660.62 | I-B1-iii-1 | CY-4G-2 (using N-Fmoc-3-Amino-propionic acid), CY-4I-1 and CY-1.1 |
| 45 | 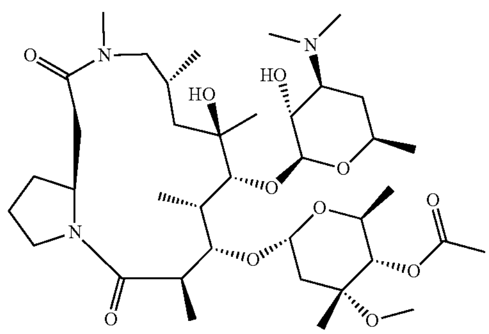 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C[C@@H]3CCCN3C(=O)[C@@H]2C)O[C@@H](C)[C@@H]1OC(C)=O] | 742.76 | I-B1-iii-1 | CY-4G-2 (using N-Fmoc-(S)-Pyrrolidin-2-yl-acetic acid), CY-4I-1 and CY-1.1 |
| 46 | 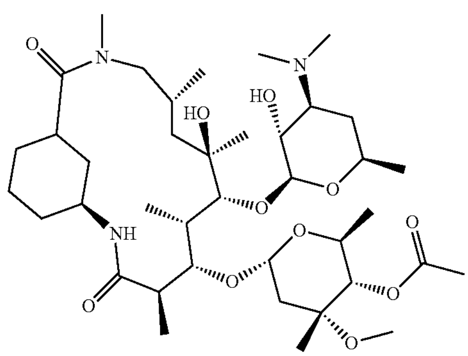 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C3CCC[C@@H](C3)NC(=O)[C@@H]2C)O[C@@H](C)[C@@H]1OC(C)=O] | 756.75 | I-B1-iii-1 | CY-4G-2 (using N-Fmoc-(1R,3S)-3-Amino-cyclohexanecarboxylic acid), CY-4I-1 and CY-1.1 |
| 47 | 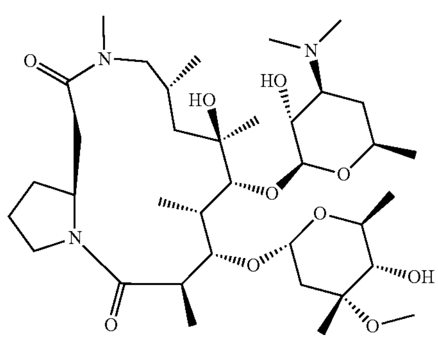 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C[C@@H]3CCCN3C(=O)[C@@H]2C)O[C@@H](C)[C@@H]1O] | 700.7 | I-B1-iii-1 | CY-4G-2 (using (S)-Pyrrolidin-2-yl-acetic acid), CY-4I-1 and CY-1.1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 48 | 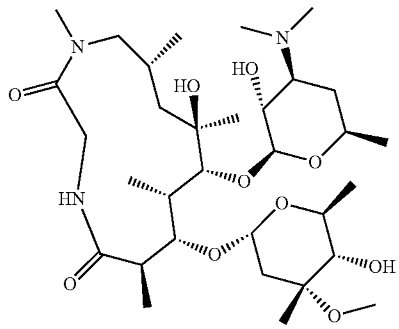 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)CNC(=O)[C@@H]2C)O[C@@H](C)[C@@H]1O] | 646.68 | I-B1-iii-1 | CY-4G-2 (using N-Fmoc-Amino-acetic acid), CY-4I-1 and CY-1.1 |
| 49 | 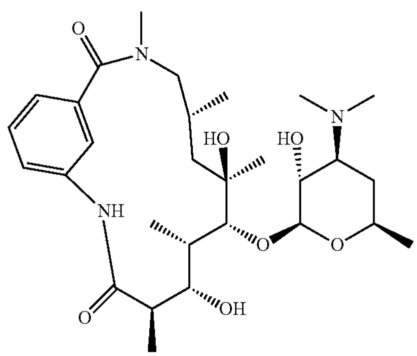 [SMILES: C[C@H]1CN(C)C(=O)c2cccc(c2)NC(=O)[C@H](C)[C@@H](O)[C@H](C)[C@@H](O[C@@H]2O[C@H](C)C[C@H](N(C)C)[C@H]2O)[C@](C)(O)C1] | 550.56 | 43 | KA1 |
| 50 | 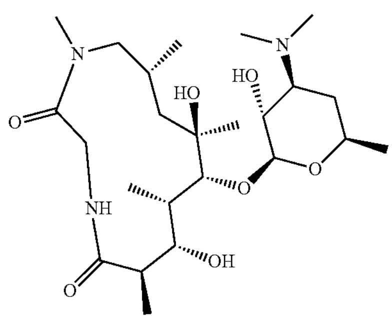 [SMILES: C[C@H]1CN(C)C(=O)CNC(=O)[C@H](C)[C@@H](O)[C@H](C)[C@@H](O[C@@H]2O[C@H](C)C[C@H](N(C)C)[C@H]2O)[C@](C)(O)C1] | 488.51 | 48 | KA1 |
| 51 | 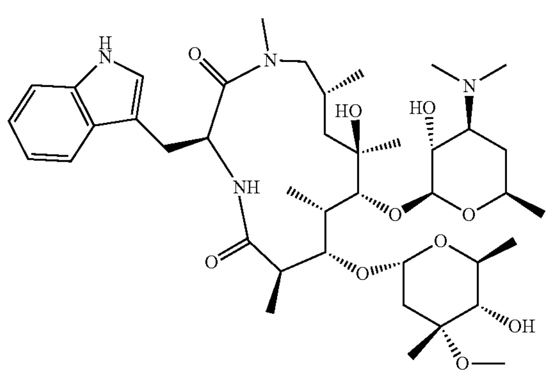 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)[C@H](Cc3c[nH]c4ccccc34)NC(=O)[C@@H]2C)O[C@@H](C)[C@@H]1O] | 776 | I-A1-iii-1 | CY-4G-2 (using (S)-2-Amino-3-(1H-indol-3-yl)-propionic acid), CY-4I-2 and CY-1.1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 52 | 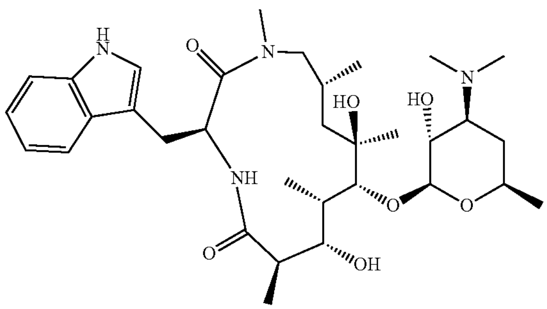 [SMILES: C[C@H]1CN(C)C(=O)[C@H](Cc2c[nH]c3ccccc23)NC(=O)[C@H](C)[C@@H](O)[C@H](C)[C@@H](O[C@@H]2O[C@H](C)C[C@H](N(C)C)[C@H]2O)[C@](C)(O)C1] | 618 | 51 | KA1 |
| 53 | 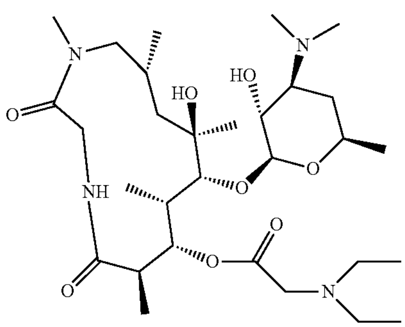 [SMILES: CCN(CC)CC(=O)O[C@H]1[C@H](C)[C@@H](O[C@@H]2O[C@H](C)C[C@H](N(C)C)[C@H]2O)[C@](C)(O)C[C@@H](C)CN(C)C(=O)CNC(=O)[C@@H]1C] | 601.48 | 48 | KB1 |
| 54 | 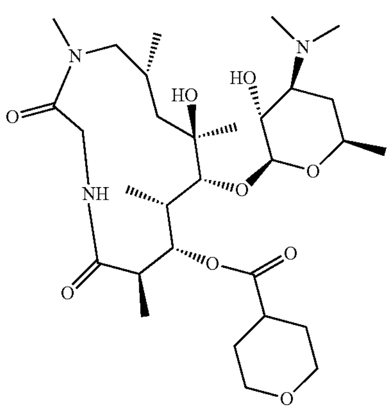 [SMILES: C[C@H]1CN(C)C(=O)CNC(=O)[C@H](C)[C@@H](OC(=O)C2CCOCC2)[C@H](C)[C@@H](O[C@@H]2O[C@H](C)C[C@H](N(C)C)[C@H]2O)[C@](C)(O)C1] | 600.54 | 48 | KB1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 55 | 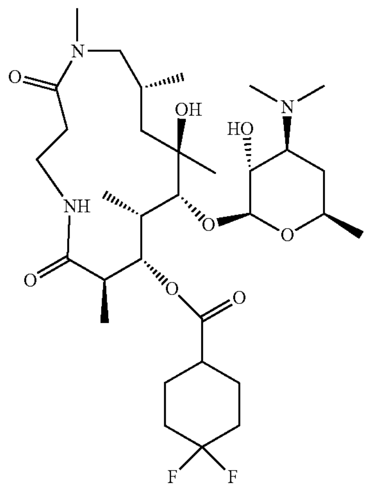 [SMILES: C[C@H]1CN(C)C(=O)CCNC(=O)[C@H](C)[C@@H](OC(=O)C2CCC(F)(F)CC2)[C@H](C)[C@@H](O[C@@H]2O[C@H](C)C[C@H](N(C)C)[C@H]2O)[C@](C)(O)C1] | 648.54 | 91 | KB1 |
| 56 | 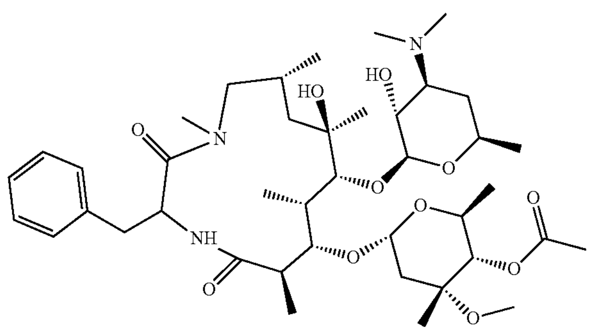 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C(Cc3ccccc3)NC(=O)[C@@H]2C)O[C@@H](C)[C@@H]1OC(C)=O] | 778.67 | I-B1-iii-1 | CY-4G-2 (using N-Fmoc-(S)-2-Amino-3-phenyl-propionic acid), CY-4I-1 and CY-1.1 |
| 57 | 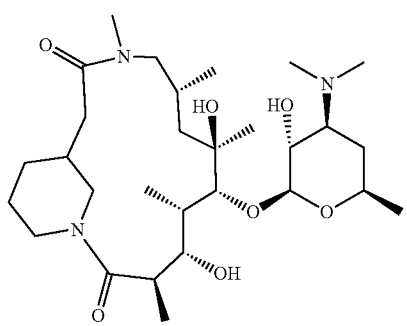 [SMILES: C[C@H]1CN(C)C(=O)CC2CCCN(C2)C(=O)[C@H](C)[C@@H](O)[C@H](C)[C@@H](O[C@@H]2O[C@H](C)C[C@H](N(C)C)[C@H]2O)[C@](C)(O)C1] | 556.50 | 112 | KA1 |
| 58 | 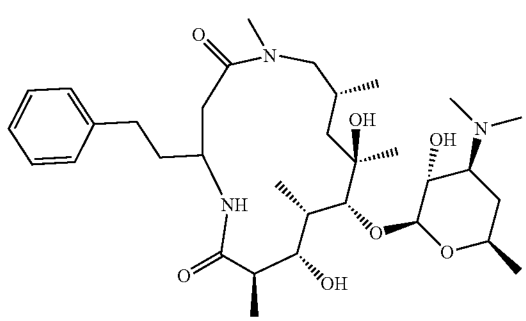 [SMILES: C[C@H]1CN(C)C(=O)CC(CCc2ccccc2)NC(=O)[C@H](C)[C@@H](O)[C@H](C)[C@@H](O[C@@H]2O[C@H](C)C[C@H](N(C)C)[C@H]2O)[C@](C)(O)C1] | 606.55 | I-A1-iii-1 | CY-4G-2 (using N-Boc-3-Amino-5-phenyl-pentanal), CY-4I-4 and CY-1.3 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 59 | 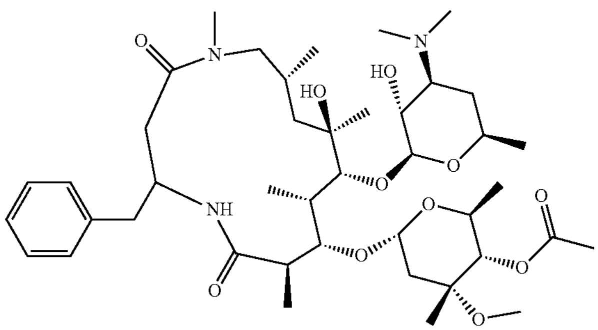 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)CC(Cc3ccccc3)NC(=O)[C@@H]2C)O[C@@H](C)[C@@H]1OC(C)=O] | 792.62 | I-B1-iii-1 | CY-4G-2 (using N-Fmoc-3-Amino-4-phenyl-butyric acid), CY-4I-1 and CY-1.1 |
| 60 | 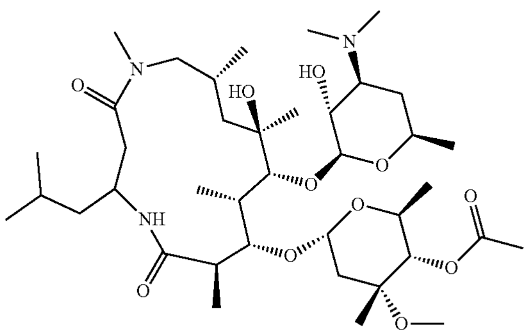 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)CC(CC(C)C)NC(=O)[C@@H]2C)O[C@@H](C)[C@@H]1OC(C)=O] | 758.66 | I-B1-iii-1 | CY-4G-2 (using 3-Amino-5-methyl-hexanoic acid), CY-4I-1 and CY-1.1 |
| 61 | 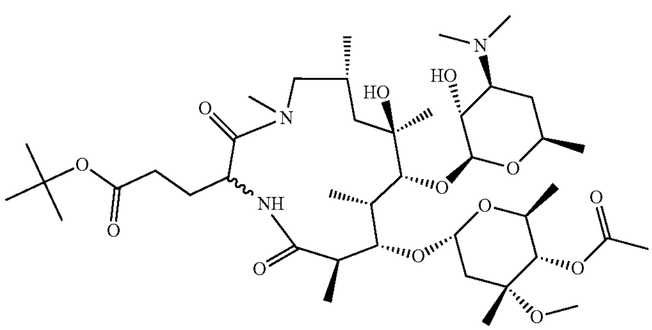 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C(CCC(=O)OC(C)(C)C)NC(=O)[C@@H]2C)O[C@@H](C)[C@@H]1OC(C)=O] | 816.84 | I-B1-iii-1 | CY-4G-2 (using 2-Amino-pentanedioic acid 5-tert-butyl ester), CY-4I-1 and CY-1.1 |
| 62 | 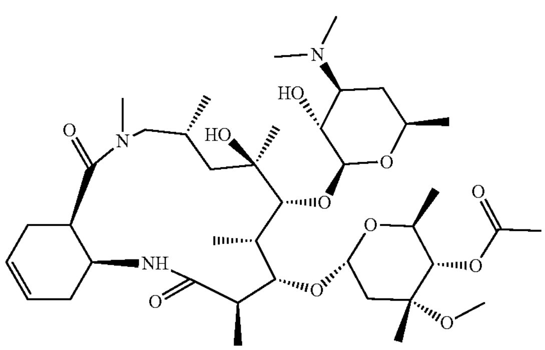 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)[C@@H]3CC=CC[C@@H]3NC(=O)[C@@H]2C)O[C@@H](C)[C@@H]1OC(C)=O] | 754.62 | I-B1-iii-1 | CY-4G-2 (using N-Fmoc-(1R,6S)-6-Amino-cyclohex-3-enecarboxylic acid), CY-4I-1 and CY-1.1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 63 | 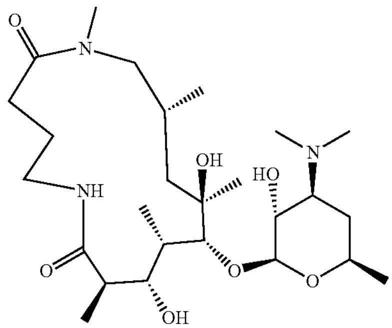 [SMILES: C[C@H]1CN(C)C(=O)CCCNC(=O)[C@H](C)[C@@H](O)[C@H](C)[C@@H](O[C@@H]2O[C@H](C)C[C@H](N(C)C)[C@H]2O)[C@](C)(O)C1] | 516.43 | 76 | KA1 |
| 64 | 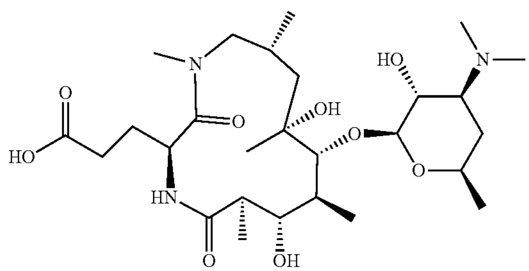 [SMILES: C[C@H]1CN(C)C(=O)[C@H](CCC(=O)O)NC(=O)[C@H](C)[C@@H](O)[C@H](C)[C@@H](O[C@@H]2O[C@H](C)C[C@H](N(C)C)[C@H]2O)[C@](C)(O)C1] | 560.48 | I-A1-iii-1 | CY-4G-1 (using Boc protected 2-Amino-pentanedioic acid), CY-4I-2, CY-1.1 and CY-4I-4 |
| 65 | 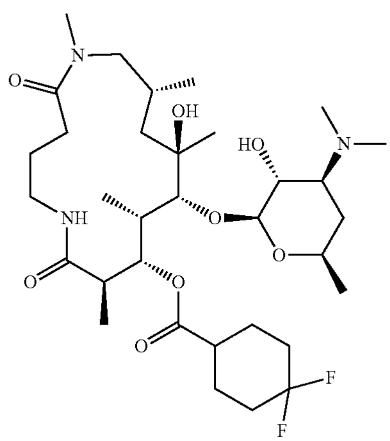 [SMILES: C[C@H]1CN(C)C(=O)CCCNC(=O)[C@H](C)[C@@H](OC(=O)C2CCC(F)(F)CC2)[C@H](C)[C@@H](O[C@@H]2O[C@H](C)C[C@H](N(C)C)[C@H]2O)[C@](C)(O)C1] | 662.60 | 63 | KB1 |
| 66 | 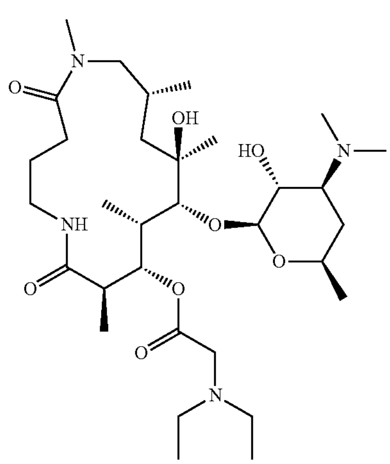 [SMILES: CCN(CC)CC(=O)O[C@H]1[C@H](C)[C@@H](O[C@@H]2O[C@H](C)C[C@H](N(C)C)[C@H]2O)[C@](C)(O)C[C@@H](C)CN(C)C(=O)CCCNC(=O)[C@@H]1C] | 630.53 | 63 | KB1 |

Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 67 | 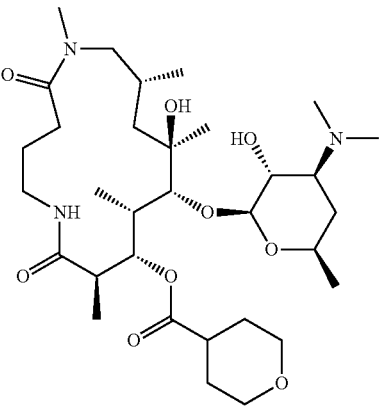 [SMILES: C[C@H]1CN(C)C(=O)CCCNC(=O)[C@H](C)[C@@H](OC(=O)C2CCOCC2)[C@H](C)[C@@H](O[C@@H]2O[C@H](C)C[C@H](N(C)C)[C@H]2O)[C@](C)(O)C1] | 628.48 | 63 | KB1 |
| 68 | 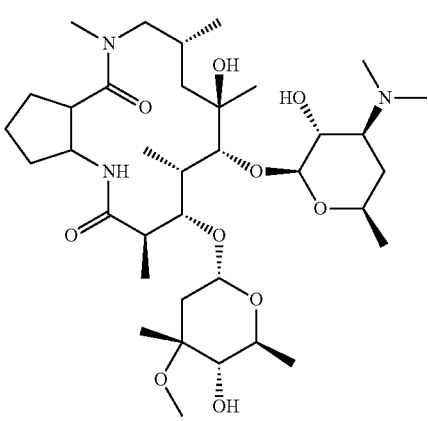 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C3CCCC3NC(=O)[C@@H]2C)O[C@@H](C)[C@@H]1O] | 742.63 | I-A1-iii-1 | CY-4G-1 (using N-Fmoc-2-Amino-cyclopentanecarboxylic acid), CY-4I-1 and CY-1.1 |
| 69 | 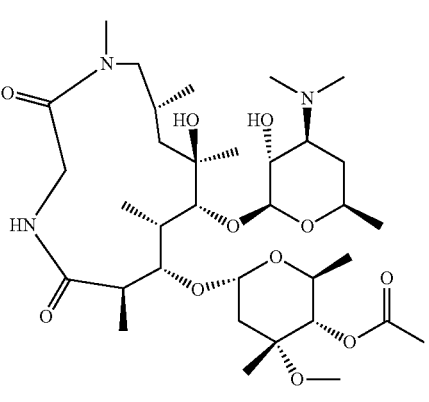 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)CNC(=O)[C@@H]2C)O[C@@H](C)[C@@H]1OC(C)=O] | 688.50 | I-B1-iii-1 | CY-4G-2 (using N-Fmoc-Amino-acetic acid), CY-4I-1 and CY-1.1 |

-continued

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 70 | 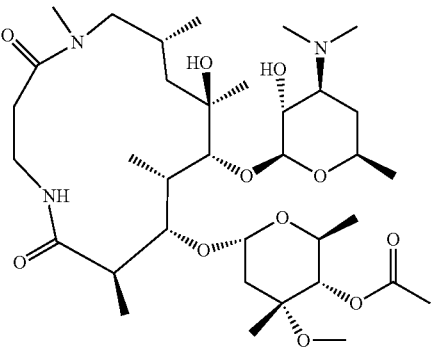 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)CCNC(=O)[C@@H]2C)O[C@@H](C)[C@@H]1OC(C)=O] | 702.50 | I-B1-iii-1 | CY-4G-2 (using N-Fmoc-3-Amino-propionic acid), CY-4I-1 and CY-1.1 |
| 71 | 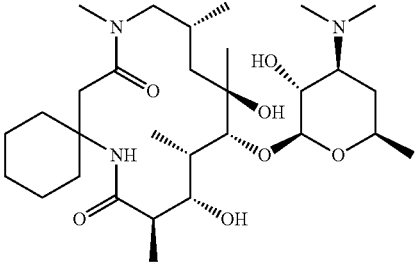 [SMILES: C[C@H]1CN(C)C(=O)CC2(CCCCC2)NC(=O)[C@H](C)[C@@H](O)[C@H](C)[C@@H](O[C@@H]2O[C@H](C)C[C@H](N(C)C)[C@H]2O)[C@](C)(O)C1] | 570.56 | I-A1-iii-1 | CY-4G-2 (using N-Boc-(1-Amino-cyclohexyl)-acetic acid), CY-4I-2, CY-4I-3 and CY-1.1 |
| 72 | 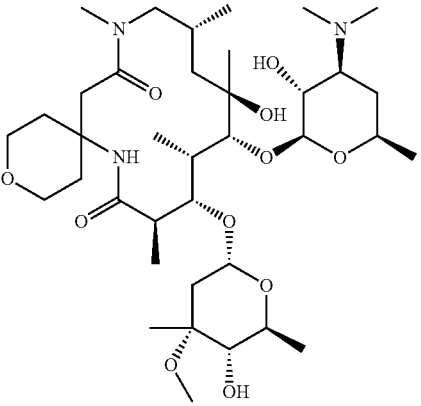 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)CC3(CCOCC3)NC(=O)[C@@H]2C)O[C@@H](C)[C@@H]1O] | 730.70 | I-A1-iii-1 | CY-4G-2 (using N-Fmoc-(4-Amino-tetrahydro-pyran-4-yl)-acetic acid), CY-4I-2 and CY-1.1 |
| 73 | 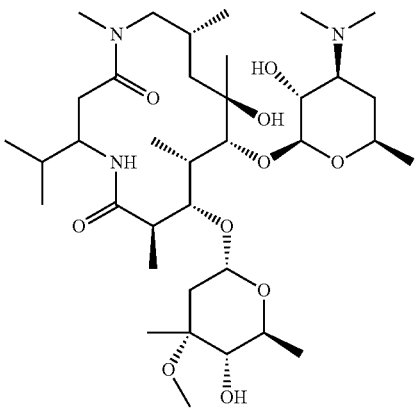 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)CC(C(C)C)NC(=O)[C@@H]2C)O[C@@H](C)[C@@H]1O] | 702.68 | I-A1-iii-1 | CY-4G-2 (using N-Fmoc-3-Amino-4-methyl-pentanoic acid), CY-4I-2 and CY-1.1 |

-continued
Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 74 | 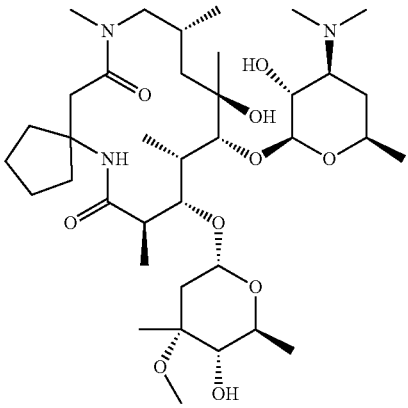 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)CC3(CCCC3)NC(=O)[C@@H]2C)O[C@@H](C)[C@@H]1O] | 714.50 | I-A1-iii-1 | CY-4G-2 (using N-Fmoc-(1-Amino-cyclopentyl)-acetic acid), CY-4I-2 and CY-1.1 |
| 75 | 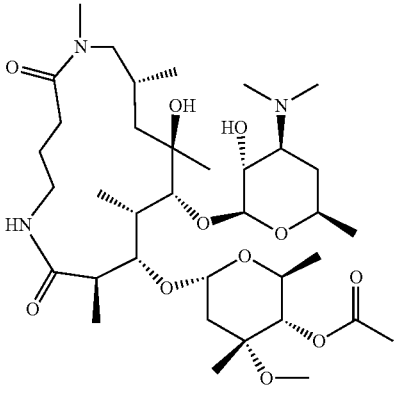 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)CCCNC(=O)[C@@H]2C)O[C@@H](C)[C@@H]1OC(C)=O] | 716.66 | I-B1-iii-1 | CY-4G-2 (using N-Fmoc-4-Amino-butyric acid), CY-4I-1 and CY-1.1 |
| 76 | 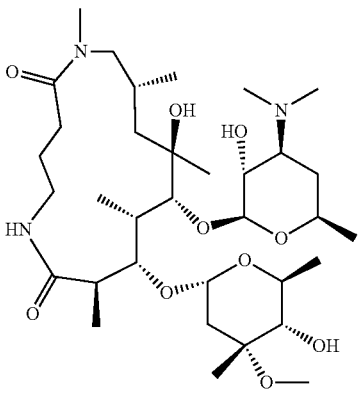 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)CCCNC(=O)[C@@H]2C)O[C@@H](C)[C@@H]1O] | 674.59 | I-A1-iii-1 | CY-4G-2 (using N-Fmoc-4-Amino-butyric acid), CY-4I-2 and CY-1.1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 77 | 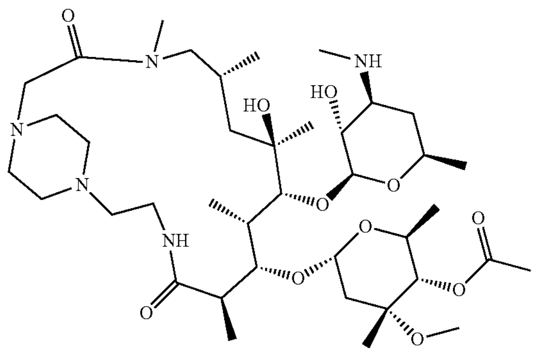 | 801 | I-B1-iii-1 | CY-4G-2 (using N-Fmoc-[4-(2-Amino-ethyl)-piperazin-1-yl]-acetic acid), CY-4I-1 and CY-1.1 |
| 78 | 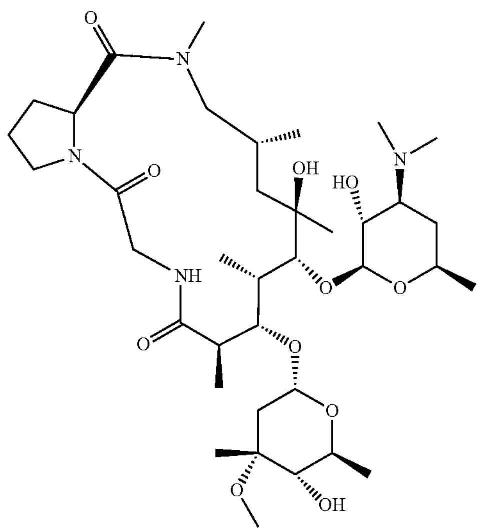 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)[C@@H]3CCCN3C(=O)CNC(=O)[C@@H]2C)O[C@@H](C)[C@@H]1O] | 743.62 | I-A1-iii-1 | CY-4G-2 (using Fmoc-Gly-Pro-OH), CY-4I-2 and CY-1.1 |
| 79 | 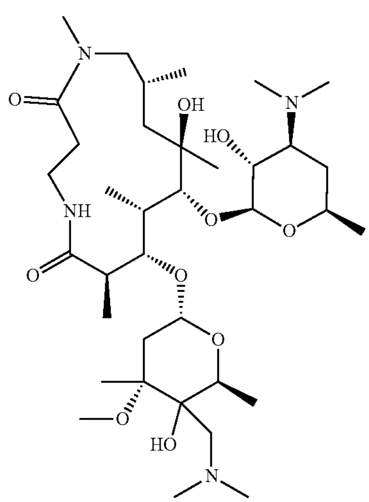 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)CCNC(=O)[C@@H]2C)O[C@@H](C)C1(O)CN(C)C] | 717.15 | I-A1-iii-10 | CY-4G-2 (using N-Fmoc-3-Amino-propionic acid), CY-4I-2 and CY-1.1 |

Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 80 | 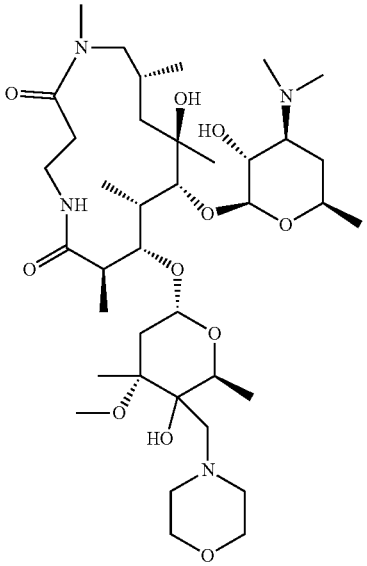 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)CCNC(=O)[C@@H]2C)O[C@@H](C)C1(O)CN1CCOCC1] | 759.71 | I-A1-iii-11 | CY-4G-2 (using N-Fmoc-3-Amino-propionic acid), CY-4I-2 and CY-1.1 |
| 81 | 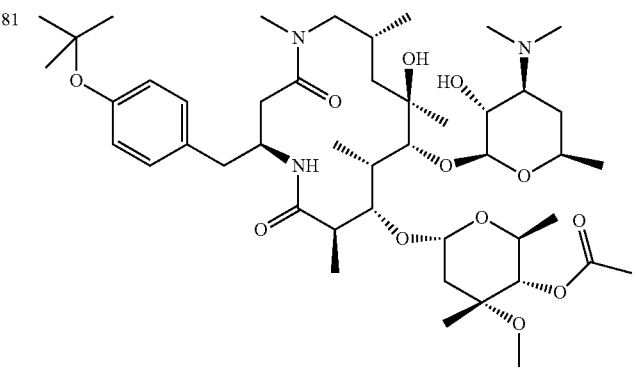 | 864.71 | I-B1-iii-1 | CY-4G-2 (using N-Fmoc-(S)-3-Amino-4-(4-tert-butoxy-phenyl)-butyric acid), CY-4I-1 and CY-1.1 |
| 82 | 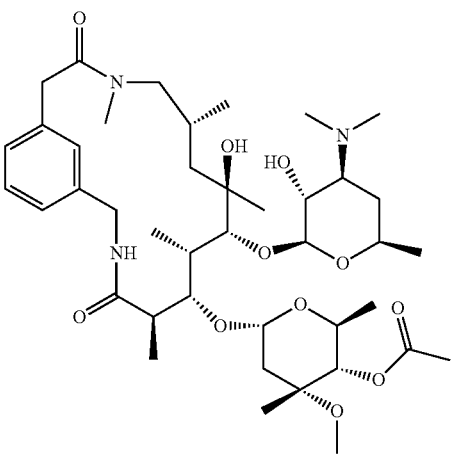 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)Cc3cccc(c3)CNC(=O)[C@@H]2C)O[C@@H](C)[C@@H]1OC(C)=O] | 778.60 | I-B1-iii-1 | CY-4G-2 (using N-Fmoc-(3-aminomethyl-phenyl)-acetic acid), CY-4I-1 and CY-1.1 |

Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 83 | 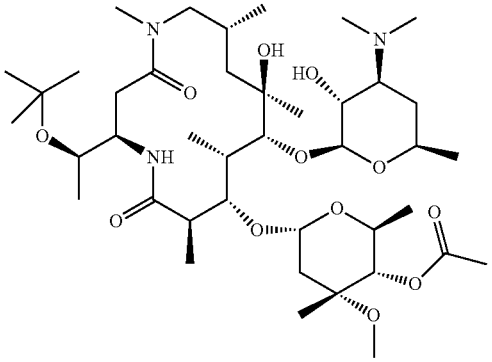 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C[C@H]([C@@H](C)OC(C)(C)C)NC(=O)[C@@H]2C)O[C@@H](C)[C@@H]1OC(C)=O] | 802.72 | I-B1-iii-1 | CY-4G-2 (using N-Fmoc-(3R,4R)-3-Amino-4-tert-butoxy-pentanoic acid), CY-4I-1 and CY-1.1 |
| 84 | 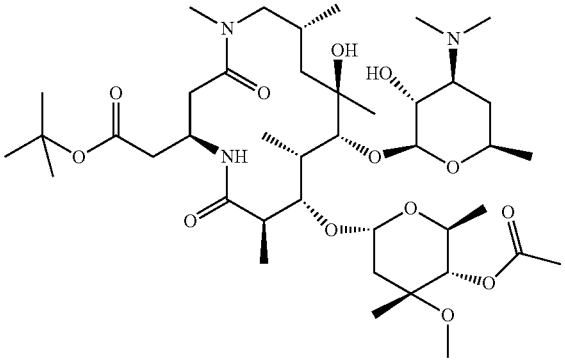 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C[C@H](CC(=O)OC(C)(C)C)NC(=O)[C@@H]2C)O[C@@H](C)[C@@H]1OC(C)=O] | 816.71 | I-B1-iii-1 | CY-4G-2 (using N-Fmoc-(R)-3-Amino-pentanedioic acid mono-tert-butyl ester), CY-4I-1 and CY-1.1 |
| 85 | 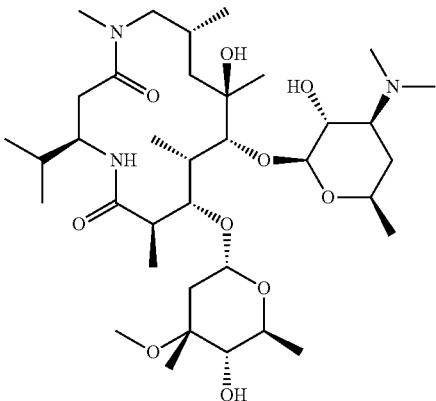 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C[C@H](C(C)C)NC(=O)[C@@H]2C)O[C@@H](C)[C@@H]1O] | 702.59 | I-A1-iii-1 | CY-4G-2 (using N-Fmoc-(R)-3-Amino-4-methyl-pentanoic acid), CY-4I-2 and CY-1.1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 86 | 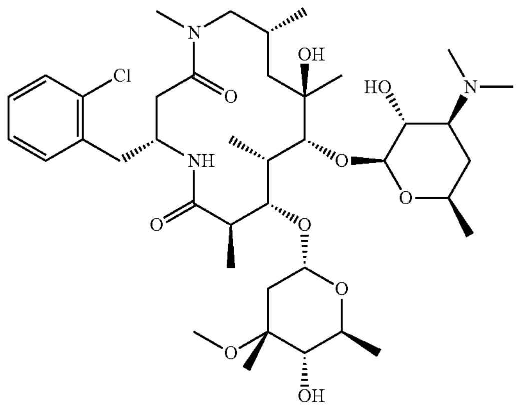 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C[C@@H](Cc3ccccc3Cl)NC(=O)[C@@H]2C)O[C@@H](C)[C@@H]1O] | 784.64 | I-A1-iii-1 | CY-4G-2 (using N-Fmoc-(R)-3-Amino-4-(2-chloro-phenyl)-butyric acid), CY-4I-2 and CY-1.1 |
| 87 | 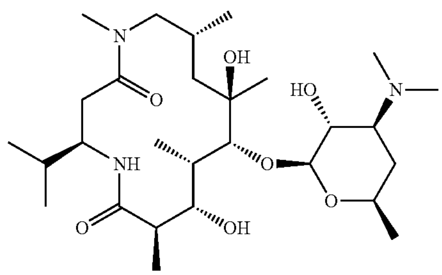 [SMILES: CC(C)[C@H]1CC(=O)N(C)C[C@H](C)C[C@@](C)(O)[C@H](O[C@@H]2O[C@H](C)C[C@H](N(C)C)[C@H]2O)[C@@H](C)[C@H](O)[C@@H](C)C(=O)N1] | 544.47 | 85 | KA2 |
| 88 | 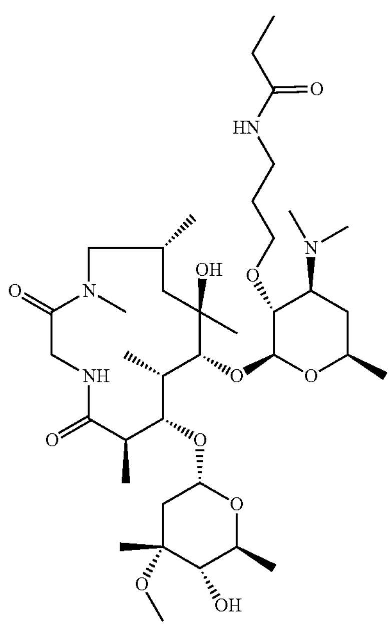 [SMILES: CCC(=O)NCCCO[C@H]1[C@H](O[C@@H]2[C@@H](C)[C@H](O[C@H]3C[C@@](C)(OC)[C@@H](O)[C@H](C)O3)[C@@H](C)C(=O)NCC(=O)N(C)C[C@H](C)C[C@@]2(C)O)O[C@H](C)C[C@@H]1N(C)C] | 759.68 | I-A1-iii-3 | CY-4G-2 (using N-Fmoc-Amino-acetic acid), CY-4I-2 and CY-1.1 |

Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 89 | 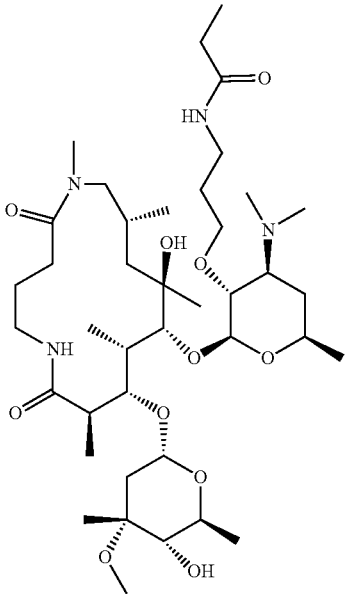 [SMILES: CCC(=O)NCCCO[C@H]1[C@H](O[C@@H]2[C@@H](C)[C@H](O[C@H]3C[C@@](C)(OC)[C@@H](O)[C@H](C)O3)[C@@H](C)C(=O)NCCCC(=O)N(C)C[C@H](C)C[C@@]2(C)O)O[C@H](C)C[C@@H]1N(C)C] | 787.75 | I-A1-iii-3 | CY-4G-2 (using N-Fmoc-4-Amino-butyric acid), CY-4I-2 and CY-1.1 |
| 90 | 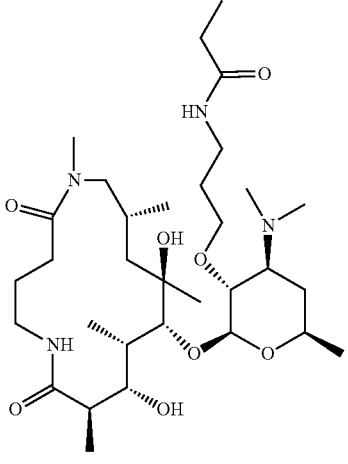 [SMILES: CCC(=O)NCCCO[C@H]1[C@H](O[C@@H]2[C@@H](C)[C@H](O)[C@@H](C)C(=O)NCCCC(=O)N(C)C[C@H](C)C[C@@]2(C)O)O[C@H](C)C[C@@H]1N(C)C] | 625.51 | 89 | KA2 |
| 91 | 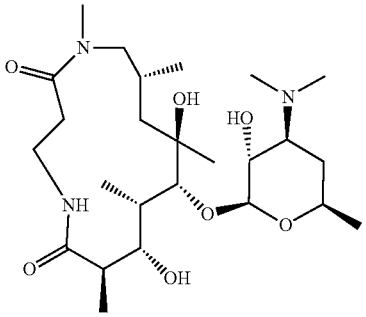 [SMILES: C[C@H]1CN(C)C(=O)CCNC(=O)[C@H](C)[C@@H](O)[C@H](C)[C@@H](O[C@@H]2O[C@H](C)C[C@H](N(C)C)[C@H]2O)[C@](C)(O)C1] | 502.28 | 44 | KA1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 92 | 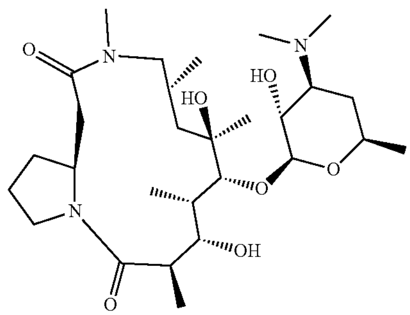 [SMILES: C[C@@H]1CN(C)C(=O)C[C@@H]2CCCN2C(=O)[C@H](C)[C@@H](O)[C@H](C)[C@@H](O[C@@H]2O[C@H](C)C[C@H](N(C)C)[C@H]2O)[C@](C)(O)C1] | 542.60 | 78 | KA1 |
| 93 | 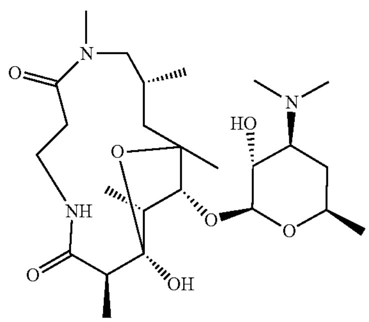 [SMILES: C[C@H]1CN(C)C(=O)CCNC(=O)[C@H](C)[C@@]2(O)OC(C)(C1)[C@H](O[C@@H]1O[C@H](C)C[C@H](N(C)C)[C@H]1O)[C@H]2C] | 500.61 | 91 | KG-B1 |
| 94 | 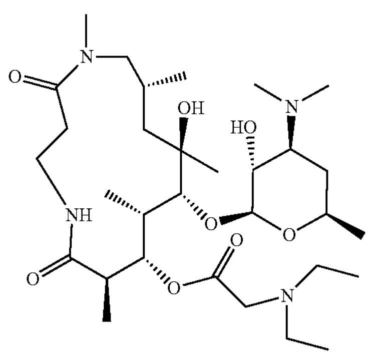 [SMILES: CCN(CC)CC(=O)O[C@H]1[C@H](C)[C@@H](O[C@@H]2O[C@H](C)C[C@H](N(C)C)[C@H]2O)[C@](C)(O)C[C@@H](C)CN(C)C(=O)CCNC(=O)[C@@H]1C] | 615.61 | 91 | KB1 |
| 95 | 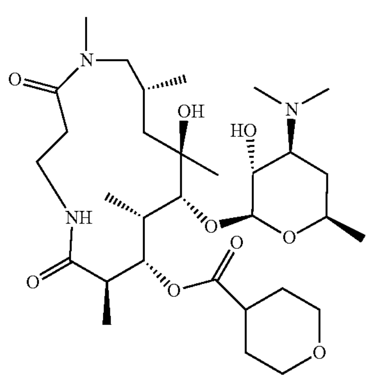 [SMILES: C[C@H]1CN(C)C(=O)CCNC(=O)[C@H](C)[C@@H](OC(=O)C2CCOCC2)[C@H](C)[C@@H](O[C@@H]2O[C@H](C)C[C@H](N(C)C)[C@H]2O)[C@](C)(O)C1] | 614.61 | 91 | KB1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 96 | 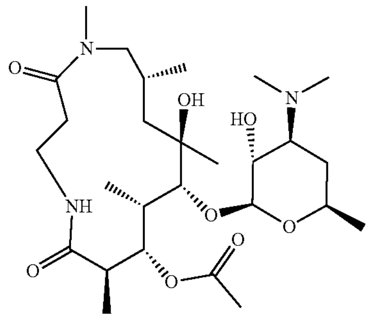 [SMILES: CC(=O)O[C@H]1[C@H](C)[C@@H](O[C@@H]2O[C@H](C)C[C@H](N(C)C)[C@H]2O)[C@](C)(O)C[C@@H](C)CN(C)C(=O)CCNC(=O)[C@@H]1C] | 544.53 | 91 | KB1 |
| 97 | 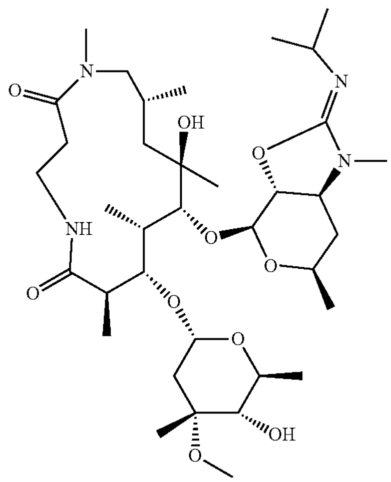 [SMILES: CO[C@]1(C)C[C@H](O[C@H]2[C@H](C)[C@@H](O[C@@H]3O[C@H](C)C[C@H]4[C@H]3O/C(=N\C(C)C)N4C)[C@](C)(O)C[C@@H](C)CN(C)C(=O)CCNC(=O)[C@@H]2C)O[C@@H](C)[C@@H]1O] | 713.57 | I-A1-iii-9 | CY-4G-2 (using N-Fmoc-3-Amino-propionic acid), CY-4I-2 and CY-1.1 |
| 98 | 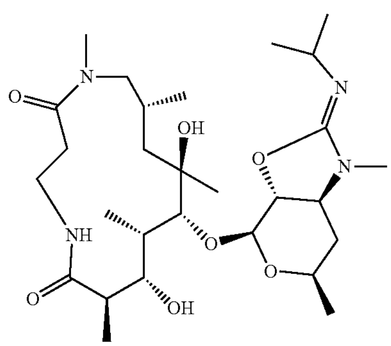 [SMILES: CC(C)/N=C1\O[C@H]2[C@H](O[C@@H]3[C@@H](C)[C@H](O)[C@@H](C)C(=O)NCCC(=O)N(C)C[C@H](C)C[C@@]3(C)O)O[C@H](C)C[C@@H]2N1C] | 556.57 | 97 | KA2 |
| 99 | 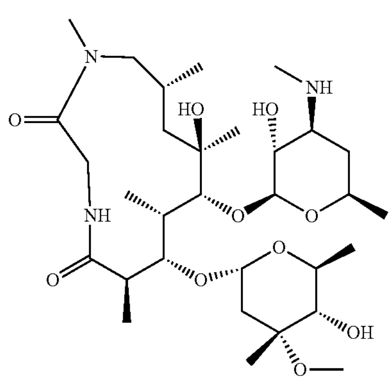 [SMILES: CN[C@H]1C[C@@H](C)O[C@@H](O[C@@H]2[C@@H](C)[C@H](O[C@H]3C[C@@](C)(OC)[C@@H](O)[C@H](C)O3)[C@@H](C)C(=O)NCC(=O)N(C)C[C@H](C)C[C@@]2(C)O)[C@@H]1O] | 632.57 | 48 | KC1 |

Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 100 | 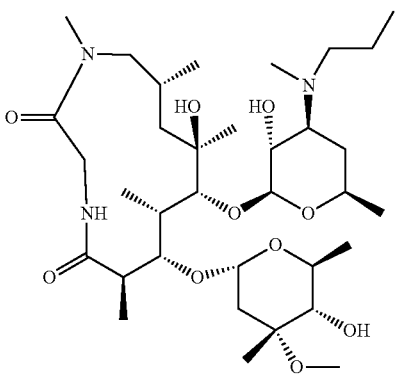 [SMILES: CCCN(C)[C@H]1C[C@@H](C)O[C@@H](O[C@@H]2[C@@H](C)[C@H](O[C@H]3C[C@@](C)(OC)[C@@H](O)[C@H](C)O3)[C@@H](C)C(=O)NCC(=O)N(C)C[C@H](C)C[C@@]2(C)O)[C@@H]1O] | 675.41 | 99 | KE1 |
| 101 | 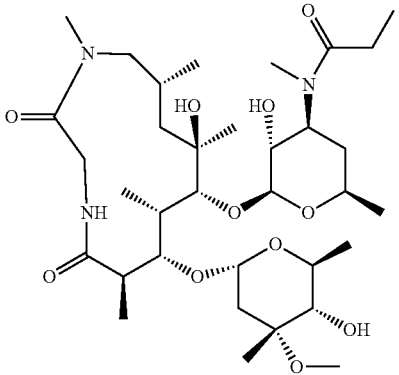 [SMILES: CCC(=O)N(C)[C@H]1C[C@@H](C)O[C@@H](O[C@@H]2[C@@H](C)[C@H](O[C@H]3C[C@@](C)(OC)[C@@H](O)[C@H](C)O3)[C@@H](C)C(=O)NCC(=O)N(C)C[C@H](C)C[C@@]2(C)O)[C@@H]1O] | 688.32 | 99 | KD1 |
| 102 | 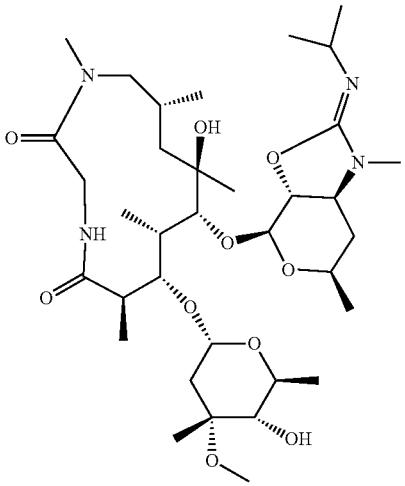 [SMILES: CO[C@]1(C)C[C@H](O[C@H]2[C@H](C)[C@@H](O[C@@H]3O[C@H](C)C[C@H]4[C@H]3O/C(=N\C(C)C)N4C)[C@](C)(O)C[C@@H](C)CN(C)C(=O)CNC(=O)[C@@H]2C)O[C@@H](C)[C@@H]1O] | 699.53 | I-A1-iii-9 | CY-4G-2 (using N-Fmoc-Amino-acetic acid), CY-4I-2 and CY-1.1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 103 | 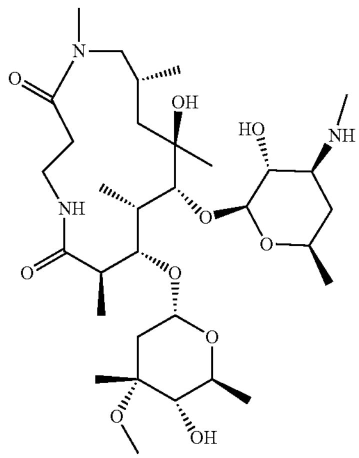 [SMILES: CN[C@H]1C[C@@H](C)O[C@@H](O[C@@H]2[C@@H](C)[C@H](O[C@H]3C[C@@](C)(OC)[C@@H](O)[C@H](C)O3)[C@@H](C)C(=O)NCCC(=O)N(C)C[C@H](C)C[C@@]2(C)O)[C@@H]1O] | 646.48 | 1 | KC1 |
| 104 | 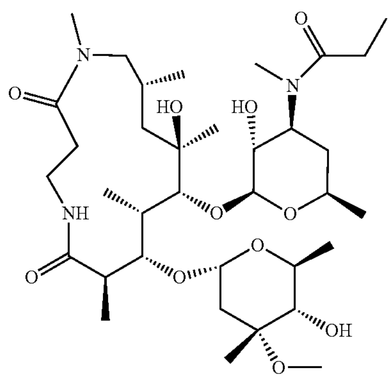 [SMILES: CCC(=O)N(C)[C@H]1C[C@@H](C)O[C@@H](O[C@@H]2[C@@H](C)[C@H](O[C@H]3C[C@@](C)(OC)[C@@H](O)[C@H](C)O3)[C@@H](C)C(=O)NCCC(=O)N(C)C[C@H](C)C[C@@]2(C)O)[C@@H]1O] | 702.57 | 103 | KD1 |
| 105 | 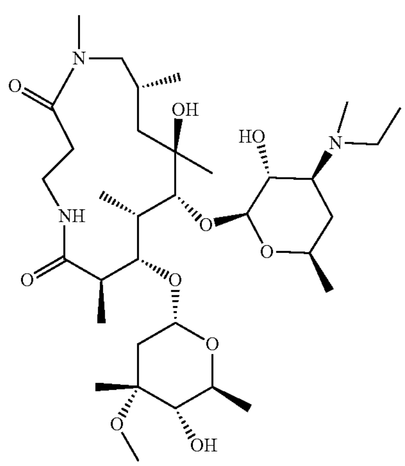 [SMILES: CCN(C)[C@H]1C[C@@H](C)O[C@@H](O[C@@H]2[C@@H](C)[C@H](O[C@H]3C[C@@](C)(OC)[C@@H](O)[C@H](C)O3)[C@@H](C)C(=O)NCCC(=O)N(C)C[C@H](C)C[C@@]2(C)O)[C@@H]1O] | 674.95 | 103 | KE1 |

-continued

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 106 | 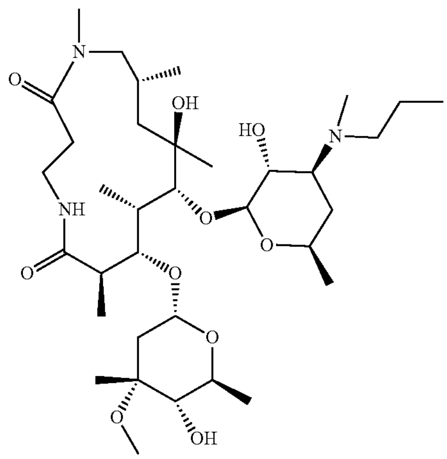 [SMILES: CCCN(C)[C@H]1C[C@@H](C)O[C@@H](O[C@@H]2[C@@H](C)[C@H](O[C@H]3C[C@@](C)(OC)[C@@H](O)[C@H](C)O3)[C@@H](C)C(=O)NCCC(=O)N(C)C[C@H](C)C[C@@]2(C)O)[C@@H]1O] | 688.63 | 103 | KE1 |
| 107 | 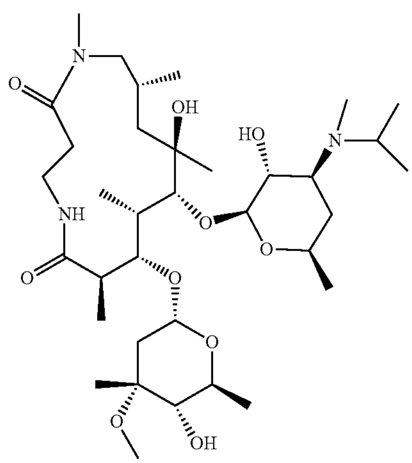 [SMILES: CO[C@]1(C)C[C@H](O[C@H]2[C@H](C)[C@@H](O[C@@H]3O[C@H](C)C[C@H](N(C)C(C)C)[C@H]3O)[C@](C)(O)C[C@@H](C)CN(C)C(=O)CCNC(=O)[C@@H]2C)O[C@@H](C)[C@@H]1O] | 688.57 | 103 | KE1 |
| 108 | 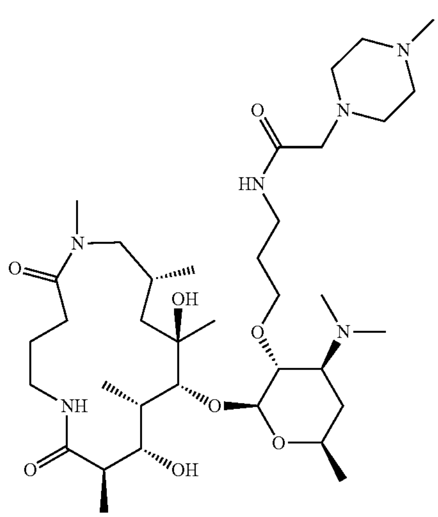 [SMILES: C[C@H]1CN(C)C(=O)CCCNC(=O)[C@H](C)[C@@H](O)[C@H](C)[C@@H](O[C@@H]2O[C@H](C)C[C@H](N(C)C)[C@H]2OCCCNC(=O)CN2CCN(C)CC2)[C@](C)(O)C1] | 713.68 | I-A1-iii-5 | CY-4G-2 (using Fmoc-4-Amino-butyric acid), CY-4I-2 and CY-1.1, KA2 |

TABLE-continued

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 109 | 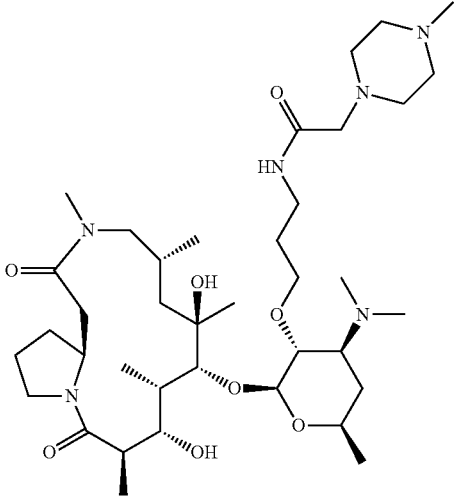 [SMILES: C[C@H]1CN(C)C(=O)C[C@@H]2CCCN2C(=O)[C@H](C)[C@@H](O)[C@H](C)[C@@H](O[C@@H]2O[C@H](C)C[C@H](N(C)C)[C@H]2OCCCNC(=O)CN2CCN(C)CC2)[C@](C)(O)C1] | 739.74 | I-A1-iii-5 | CY-4G-2 (using N-Fmoc-(S)-Pyrrolidin-2-yl-acetic acid), CY-4I-2 and CY-1.1, KA2 |
| 110 | 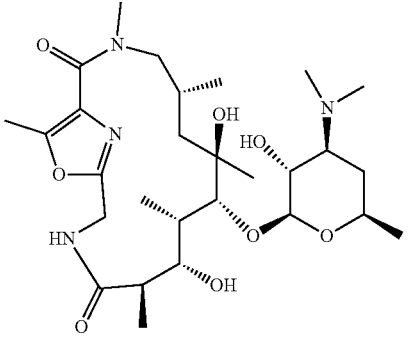 | 569.38 | I-A1-iii-1 | CY-4G-2 (using N-Boc-2-Aminomethyl-5-methyl-oxazole-4-carboxylic acid), CY-4I-2, CY-4I-3, CY-1.1 |
| 111 | 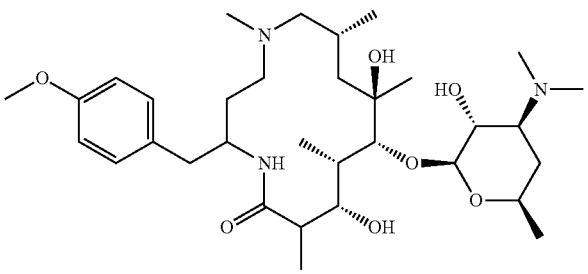 | 608.51 | I-B1-iii-1 | CY-4H-1 (using N-Boc-3-Amino-4-(4-methoxy-phenyl)-butyraldehyde); CY-4I-3; CY-1.1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 112 | 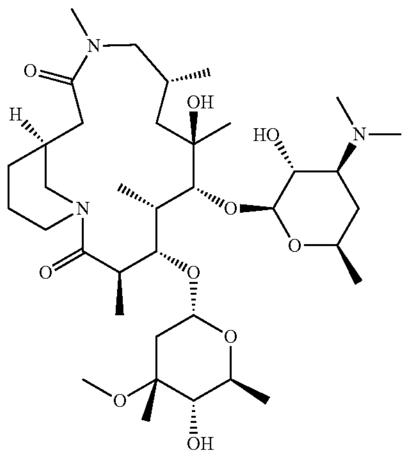 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C[C@@H]3CCCN(C3)C(=O)[C@@H]2C)O[C@@H](C)[C@@H]1O] | 714.60 | I-A1-iii-1 | CY-4G-2 (using N-Fmoc-(S)-Piperidin-3-yl-acetic acid); CY-4I-2; CY-1.1 |
| 113 | 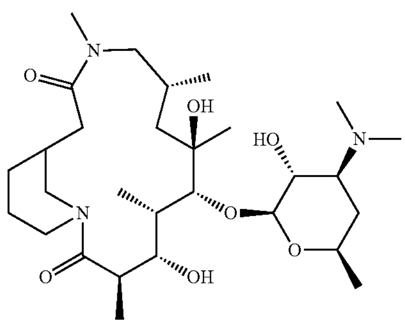 [SMILES: C[C@H]1CN(C)C(=O)CC2CCCN(C2)C(=O)[C@H](C)[C@@H](O)[C@H](C)[C@@H](O[C@@H]2O[C@H](C)C[C@H](N(C)C)[C@H]2O)[C@](C)(O)C1] | 556.32 | 112 | KA2 |
| 114 | 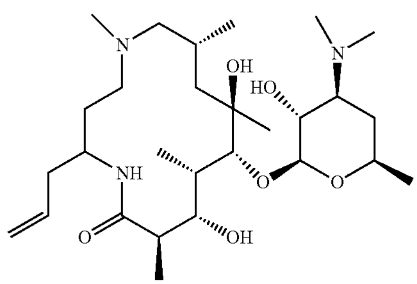 [SMILES: C=CCC1CCN(C)C[C@H](C)C[C@@](C)(O)[C@H](O[C@@H]2O[C@H](C)C[C@H](N(C)C)[C@H]2O)[C@@H](C)[C@H](O)[C@@H](C)C(=O)N1] | 528.54 | I-A1-iii-1 | CY-4H-1 (using N-Boc-3-Amino-hex-5-enal); CY-4I-4; CY-1.1 |
| 115 | 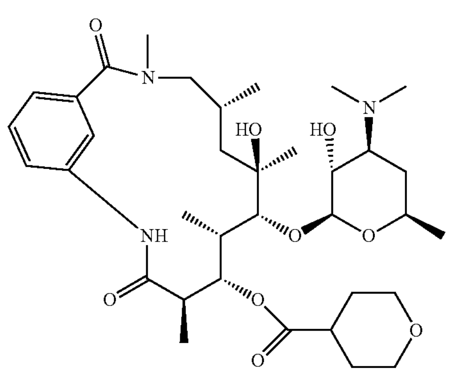 [SMILES: C[C@H]1CN(C)C(=O)c2cccc(c2)NC(=O)[C@H](C)[C@@H](OC(=O)C2CCOCC2)[C@H](C)[C@@H](O[C@@H]2O[C@H](C)C[C@H](N(C)C)[C@H]2O)[C@](C)(O)C1] | 662.56 | 49 | KB1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 116 | 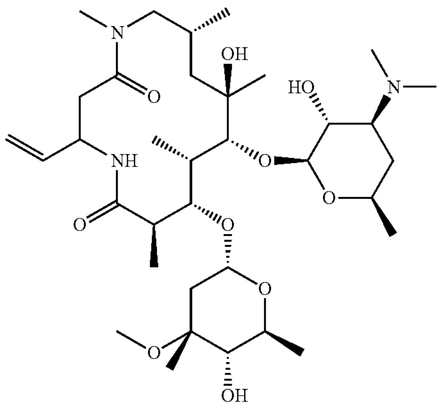 [SMILES: C=CC1CC(=O)N(C)C[C@H](C)C[C@@](C)(O)[C@H](O[C@@H]2O[C@H](C)C[C@H](N(C)C)[C@H]2O)[C@@H](C)[C@H](O[C@H]2C[C@@](C)(OC)[C@@H](O)[C@H](C)O2)[C@@H](C)C(=O)N1] | 686.55 | I-A1-iii-1 | CY-4G-2 (using N-Fmoc-3-Amino-pent-4-enoic acid); CY-4I-2; CY-1.1 |
| 117 | 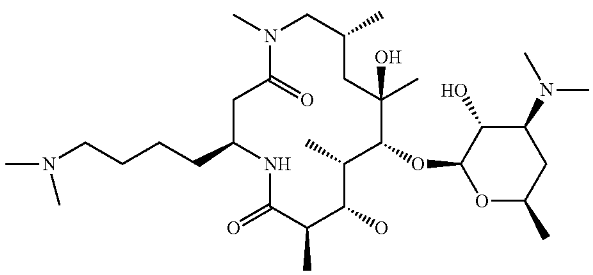 | 601.42 | 16 | reductive amination (CHO, NaCHBH3) |
| 118 | 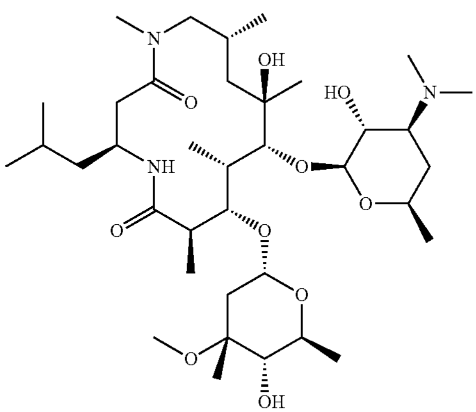 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C[C@H](CC(C)C)NC(=O)[C@@H]2C)O[C@@H](C)[C@@H]1O] | 716.51 | I-A1-iii-1 | CY-4G-2 (using N-Fmoc-(S)-3-Amino-5-methyl-hexanoic acid); CY-4I-2; CY-1.1 |
| 119 | 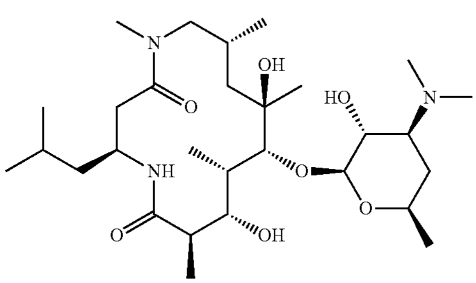 [SMILES: CC(C)C[C@H]1CC(=O)N(C)C[C@H](C)C[C@@](C)(O)[C@H](O[C@@H]2O[C@H](C)C[C@H](N(C)C)[C@H]2O)[C@@H](C)[C@H](O)[C@@H](C)C(=O)N1] | 558.38 | 118 | KA2 |

233 234
-continued
Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 120 | 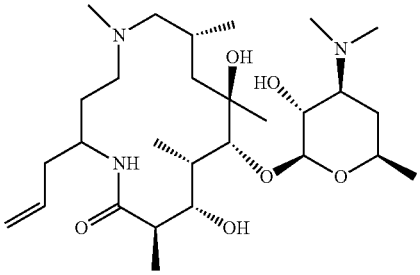 [SMILES: C=CCC1CCN(C)C[C@H](C)C[C@@](C)(O)[C@H](O[C@@H]2O[C@H](C)C[C@H](N(C)C)[C@H]2O)[C@@H](C)[C@H](O)[C@@H](C)C(=O)N1] | 528.52 | I-A1-iii-1 | CY-4H-1 (using N-Boc-3-Amino-hex-5-enal); CY-4I-4; CY-1.1 |
| 121 | 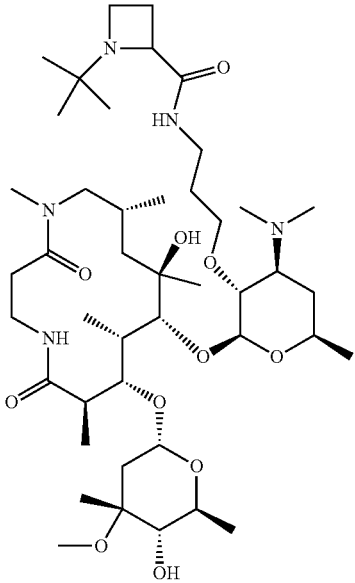 [SMILES: CO[C@]1(C)C[C@H](O[C@H]2[C@H](C)[C@@H](O[C@@H]3O[C@H](C)C[C@H](N(C)C)[C@H]3OCCCNC(=O)C3CCN3C(C)(C)C)[C@](C)(O)C[C@@H](C)CN(C)C(=O)CCNC(=O)[C@@H]2C)O[C@@H](C)[C@@H]1O] | 856.82 | I-A1-iii-8 | CY-4G-2 (using N-Fmoc-3-Amino-propionic acid); CY-4I-2; CY-1.1 |
| 122 | 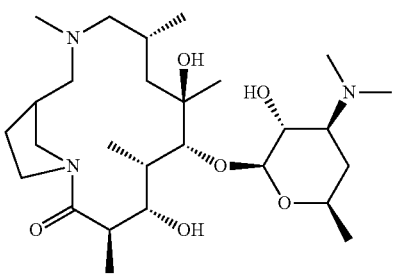 [SMILES: C[C@H]1CN(C)CC2CCN(C2)C(=O)[C@H](C)[C@@H](O)[C@H](C)[C@@H](O[C@@H]2O[C@H](C)C[C@H](N(C)C)[C@H]2O)[C@](C)(O)C1] | 514.03 | I-A1-iii-1 | CY-4H-1 (using N-Boc-pyrrolidine-3-carbaldehyde); CY-4I-4; CY-1.1 |

Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 123 | 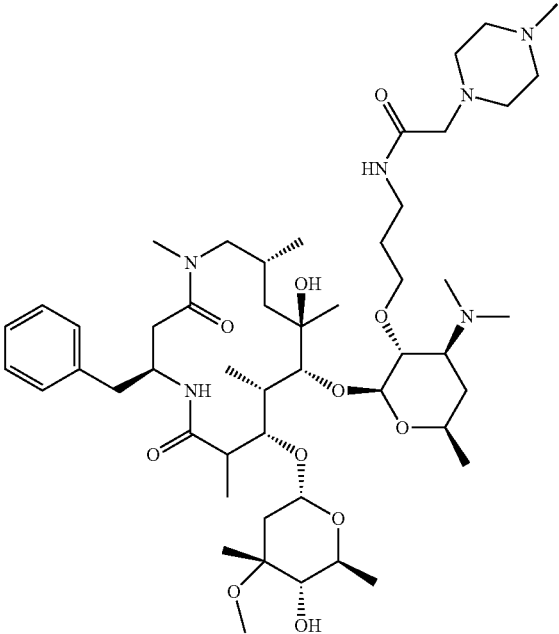 [SMILES: CO[C@]1(C)C[C@H](O[C@@H]2C(C)C(=O)N[C@@H](Cc3ccccc3)CC(=O)N(C)C[C@H](C)C[C@@](C)(O)[C@H](O[C@@H]3O[C@H](C)C[C@H](N(C)C)[C@H]3OCCCNC(=O)CN3CCN(C)CC3)[C@H]2C)O[C@@H](C)[C@@H]1O] | 789.76 | I-A1-iii-5 | CY-4G (N-Fmoc-(S)-3-Amino-4-phenyl-butyric acid); CY-4I-2; CY-1.1 |
| 124 | 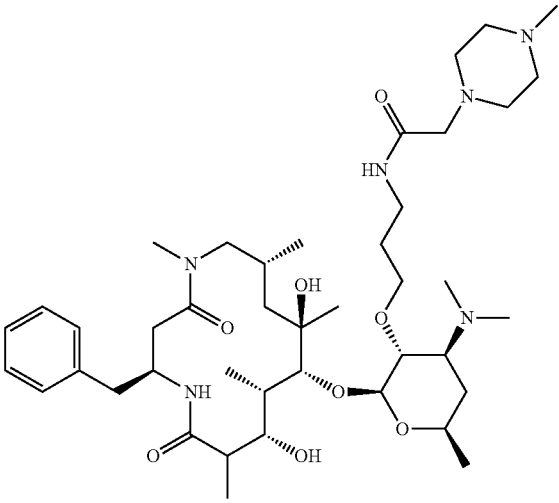 [SMILES: CC1C(=O)N[C@@H](Cc2ccccc2)CC(=O)N(C)C[C@H](C)C[C@@](C)(O)[C@H](O[C@@H]2O[C@H](C)C[C@H](N(C)C)[C@H]2OCCCNC(=O)CN2CCN(C)CC2)[C@@H](C)[C@@H]1O] | 631.72 | 123 | KA2 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 125 | 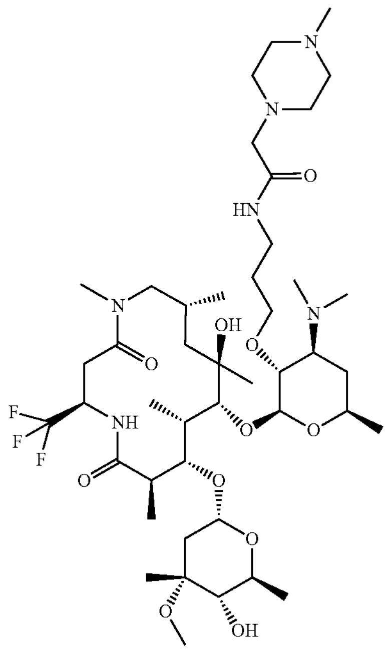 [SMILES: CO[C@]1(C)C[C@H](O[C@H]2[C@H](C)[C@@H](O[C@@H]3O[C@H](C)C[C@H](N(C)C)[C@H]3OCCCNC(=O)CN3CCN(C)CC3)[C@](C)(O)C[C@@H](C)CN(C)C(=O)C[C@H](C(F)(F)F)NC(=O)[C@@H]2C)O[C@@H](C)[C@@H]1O] | 925.68 | I-A1-iii-5 | CY-4G-2 (N-Fmoc-(R)-3-Amino-4,4,4-trifluoro-butyric acid); CY-4I-2; CY-1.1 |
| 126 | 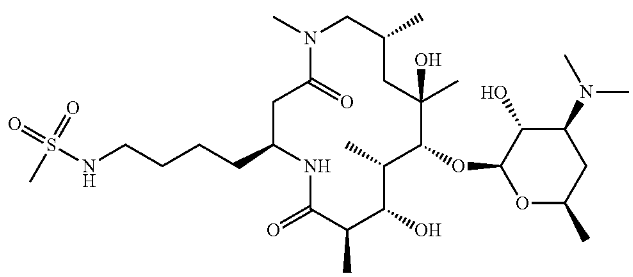 [SMILES: C[C@H]1CN(C)C(=O)C[C@H](CCCCNS(C)(=O)=O)NC(=O)[C@H](C)[C@@H](O)[C@H](C)[C@@H](O[C@@H]2O[C@H](C)C[C@H](N(C)C)[C@H]2O)[C@](C)(O)C1] | 651.36 | 16 | Sulfonyl chloride |
| 127 | 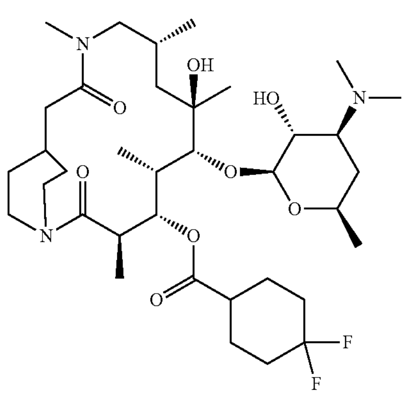 [SMILES: C[C@H]1CN(C)C(=O)CC2CCN(CC2)C(=O)[C@H](C)[C@@H](OC(=O)C2CCC(F)(F)CC2)[C@H](C)[C@@H](O[C@@H]2O[C@H](C)C[C@H](N(C)C)[C@H]2O)[C@](C)(O)C1] | 702.75 | 113 | KB1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 128 | 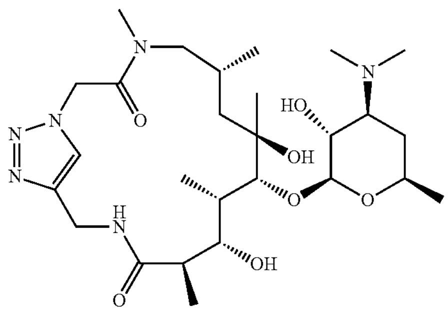 [SMILES: C[C@H]1CN(C)C(=O)Cn2cc(nn2)CNC(=O)[C@H](C)[C@@H](O)[C@H](C)[C@@H](O[C@@H]2O[C@H](C)C[C@H](N(C)C)[C@H]2O)[C@](C)(O)C1] | 569.51 | I-B1-iii-1 | CY-10A-1 |
| 129 | 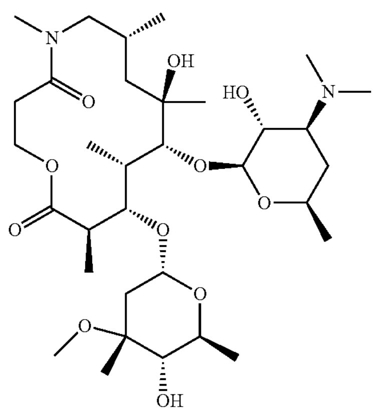 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)CCOC(=O)[C@@H]2C)O[C@@H](C)[C@@H]1O] | 661.48 | I-A1-iii-1 | CY-4G-2 (using 3-Allyloxy-propionic acid); CY-4J; CY-2.1 |
| 130 | 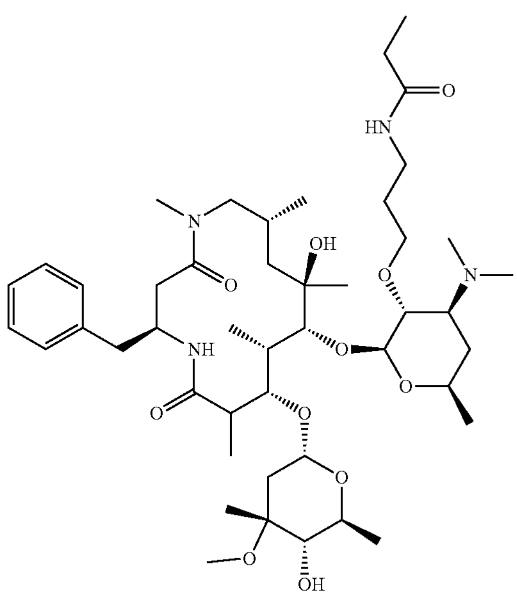 [SMILES: CCC(=O)NCCCO[C@H]1[C@H](O[C@@H]2[C@@H](C)[C@H](O[C@H]3C[C@@](C)(OC)[C@@H](O)[C@H](C)O3)C(C)C(=O)N[C@@H](Cc3ccccc3)CC(=O)N(C)C[C@H](C)C[C@@]2(C)O)O[C@H](C)C[C@@H]1N(C)C] | 863.88 | I-A1-iii-3 | CY-4G-2 (using Fmoc-L-beta-homoleucine); CY-4I-2; CY-1.1 |

-continued

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 131 | 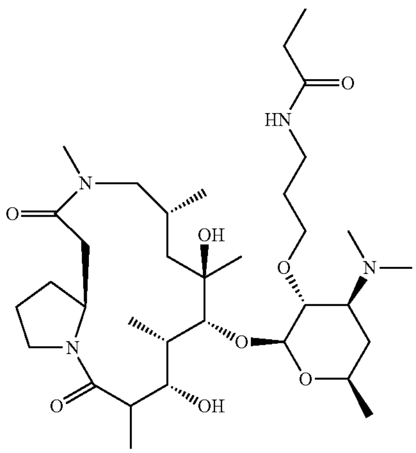 [SMILES: CCC(=O)NCCCO[C@H]1[C@H](O[C@@H]2[C@@H](C)[C@H](O)C(C)C(=O)N3CCC[C@H]3CC(=O)N(C)C[C@H](C)C[C@@]2(C)O)O[C@H](C)C[C@@H]1N(C)C] | 655.73 | I-A1-iii-3 | CY-4G-2 (using Fmoc-betahomoproline; CY-4I-2; CY-1.1 |
| 132 | 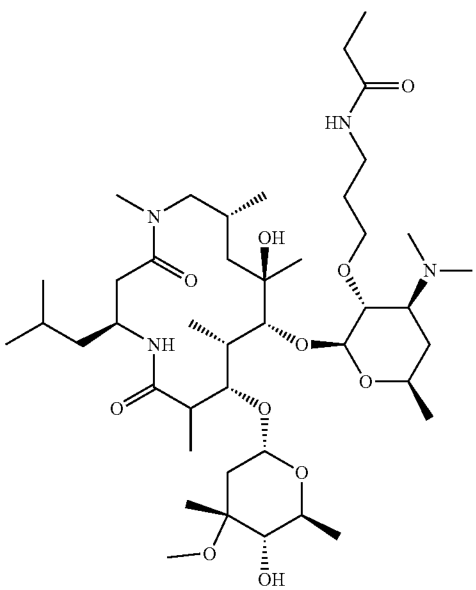 [SMILES: CCC(=O)NCCCO[C@H]1[C@H](O[C@@H]2[C@@H](C)[C@H](O[C@H]3C[C@@](C)(OC)[C@@H](O)[C@H](C)O3)C(C)C(=O)N[C@@H](CC(C)C)CC(=O)N(C)C[C@H](C)C[C@@]2(C)O)O[C@H](C)C[C@@H]1N(C)C] | 829.65 | I-A1-iii-1 | CY-4G-2 (using Fmoc-L-b-homophenylalanine); CY-4I-2; CY-1.1; |
| 133 | 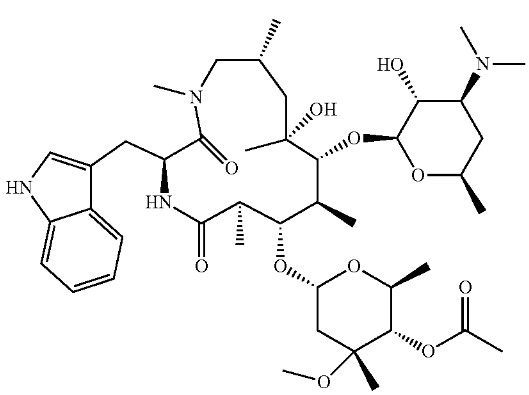 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)[C@H](Cc3c[nH]c4ccccc34)NC(=O)[C@@H]2C)O[C@@H](C)[C@@H]1OC(C)=O] | 817.76 | I-A1-iii-1 | CY-4G-2 (using Fmoc-Trp-OH); CY-4I-2; CY-1.1; KF-1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 134 | 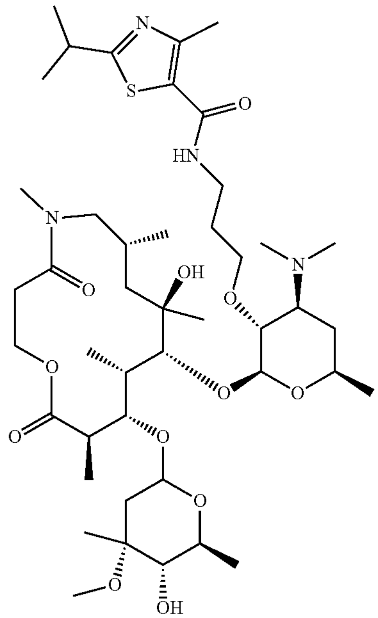 [SMILES: CO[C@]1(C)CC(O[C@H]2[C@H](C)[C@@H](O[C@@H]3O[C@H](C)C[C@H](N(C)C)[C@H]3OCCCNC(=O)c3sc(C(C)C)nc3C)[C@](C)(O)C[C@@H](C)CN(C)C(=O)CCOC(=O)[C@@H]2C)O[C@@H](C)[C@@H]1O] | 885.18 | I-A1-iii-7 | CY-4G-2 (using Fmoc-β-alanine), CY-4I-2 and CY-1.1 |
| 135 | 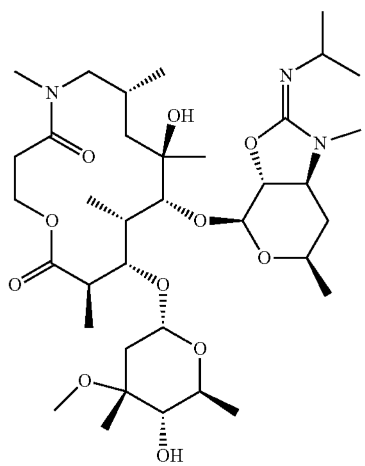 [SMILES: CO[C@]1(C)C[C@H](O[C@H]2[C@H](C)[C@@H](O[C@@H]3O[C@H](C)C[C@H]4[C@H]3O/C(=N/C(C)C)N4C)[C@](C)(O)C[C@@H](C)CN(C)C(=O)CCOC(=O)[C@@H]2C)O[C@@H](C)[C@@H]1O] | 713.92 | I-A1-iii-9 | CY-4G-2 (using 3-allyl(oxy-propionic acid), CY-4I-2 and CY-1.1 |
| 136 | 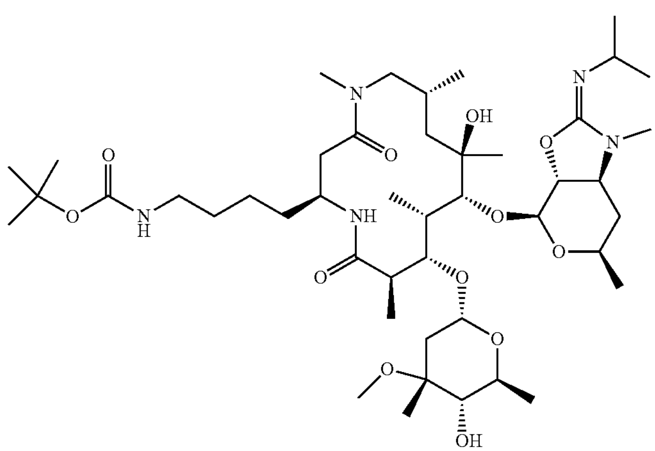 [SMILES: CO[C@]1(C)C[C@H](O[C@H]2[C@H](C)[C@@H](O[C@@H]3O[C@H](C)C[C@H]4[C@H]3O/C(=N/C(C)C)N4C)[C@](C)(O)C[C@@H](C)CN(C)C(=O)C[C@H](CCCCNC(=O)OC(C)(C)C)NC(=O)[C@@H]2C)O[C@@H](C)[C@@H]1O] | 884.17 | I-A1-iii-9 | CY-4G-2 (using (S)-3-Amino-7-tert-butoxycarbonylamino-heptanoic acid), CY-4I-2 and CY-1.1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 137 | 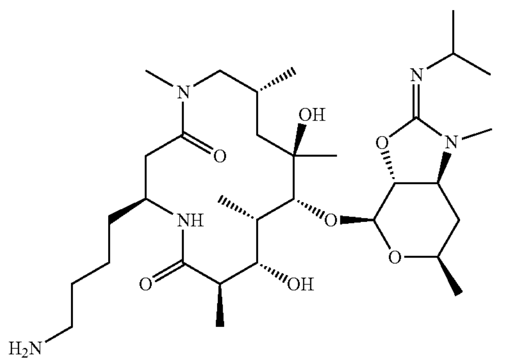 [SMILES: CC(C)/N=C1/O[C@H]2[C@H](O[C@@H]3[C@@H](C)[C@H](O)[C@@H](C)C(=O)N[C@@H](CCCCN)CC(=O)N(C)C[C@H](C)C[C@@]3(C)O)O[C@H](C)C[C@@H]2N1C] | 784.06 | 136 | CY-4I-4 |
| 138 | 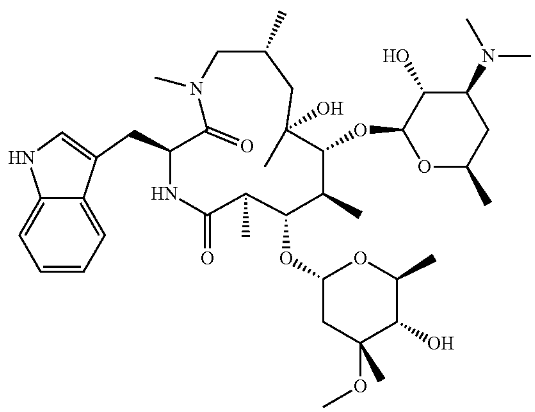 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)[C@H](Cc3c[nH]c4ccccc34)NC(=O)[C@@H]2C)O[C@@H](C)[C@@H]1O] | 775.68 | I-A1-iii-1 | CY-4G-2 (using Fmoc-Trp-OH); CY-4I-2; CY-1.1 |
| 139 | 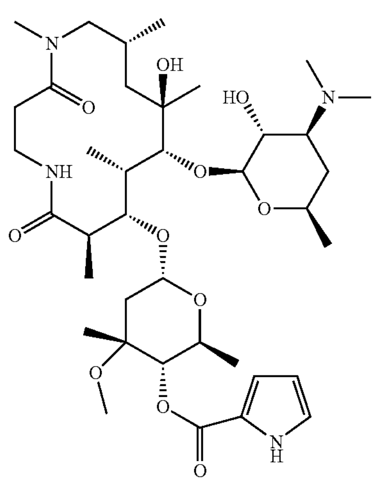 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)CCNC(=O)[C@@H]2C)O[C@@H](C)[C@@H]1OC(=O)c1ccc[nH]1] | 753.72 | 44 | KF (using N-Ts-pyrrole-1-carboxylic acid) method described for acylation C/3-OH group used for C/4''-OH; KM |

Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 140 | 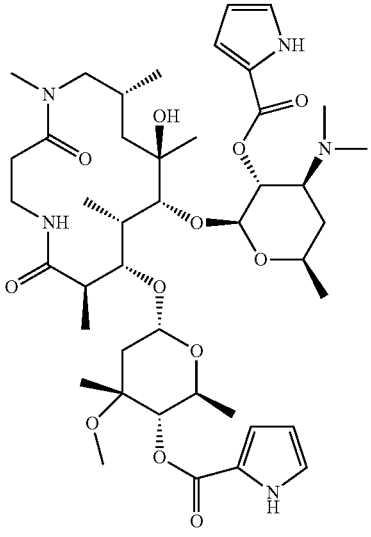 [SMILES: CO[C@]1(C)C[C@H](O[C@H]2[C@H](C)[C@@H](O[C@@H]3O[C@H](C)C[C@H](N(C)C)[C@H]3OC(=O)c3ccc[nH]3)[C@](C)(O)C[C@@H](C)CN(C)C(=O)CCNC(=O)[C@@H]2C)O[C@@H](C)[C@@H]1OC(=O)c1ccc[nH]1] | 846.80 | 44 | KF (using N-Ts-pyrrole-1-carboxylic acid) method described for acylation C/3-OH group used for C/4″-OH; KM |
| 141 | 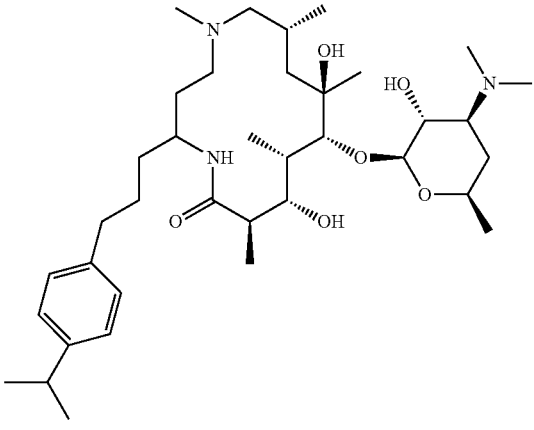 [SMILES: CC(C)c1ccc(CCCC2CCN(C)C[C@H](C)C[C@@](C)(O)[C@H](O[C@@H]3O[C@H](C)C[C@H](N(C)C)[C@H]3O)[C@@H](C)[C@H](O)[C@@H](C)C(=O)N2)cc1] | 648.66 | 114 | KI (using 1-iodo-4-isopropyl-benzene), KJ |
| 142 | 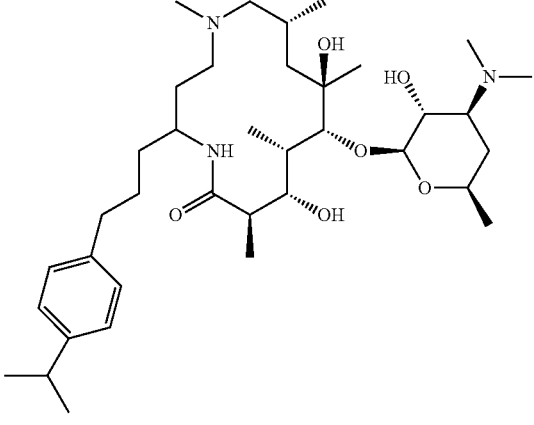 [SMILES: CC(C)c1ccc(CCCC2CCN(C)C[C@H](C)C[C@@](C)(O)[C@H](O[C@@H]3O[C@H](C)C[C@H](N(C)C)[C@H]3O)[C@@H](C)[C@H](O)[C@@H](C)C(=O)N2)cc1] | 648.66 | 114 | KI (using 1-iodo-4-isopropyl-benzene), KJ |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 143 | 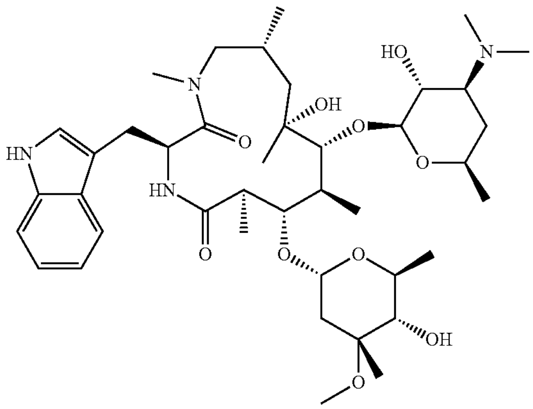 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)[C@H](Cc3c[nH]c4ccccc34)NC(=O)[C@@H]2C)O[C@@H](C)[C@@H]1O] | 775.71 | I-A1-iii-1 | CY-4G-2 (using (S)-2-Amino-3-(1H-indol-3-yl)-propionic acid), CY-4I-2 and CY-1.1 |
| 144 | 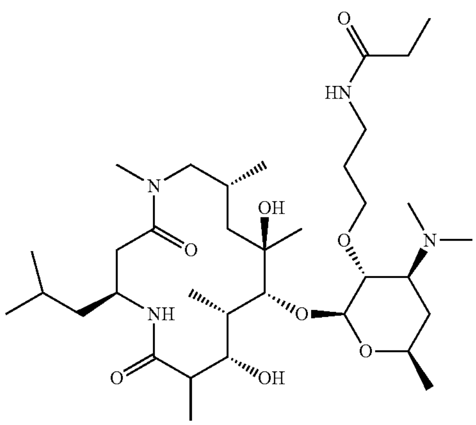 [SMILES: CCC(=O)NCCCO[C@H]1[C@H](O[C@@H]2[C@@H](C)[C@H](O)C(C)C(=O)N[C@@H](CC(C)C)CC(=O)N(C)C[C@H](C)C[C@@]2(C)O)O[C@H](C)C[C@@H]1N(C)C] | 671.67 | 132 | KA-2 |
| 145 | 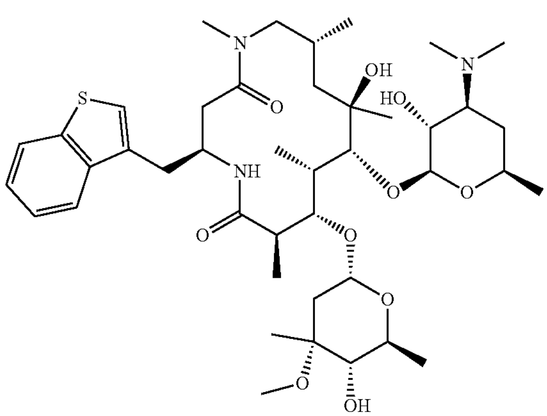 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C[C@H](Cc3csc4ccccc34)NC(=O)[C@@H]2C)O[C@@H](C)[C@@H]1O] | 806.08 | I-A1-iii-1 | CY-4G-2 (using Fmoc-(R)-3-amino-4-(3-benzothienyl)butyric acid), CY-4I-2 and CY-1.1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 146 | 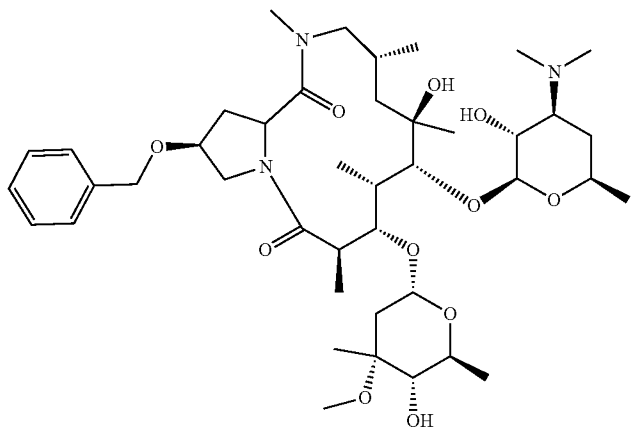 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C3C[C@H](OCc4ccccc4)CN3C(=O)[C@@H]2C)O[C@@H](C)[C@@H]1O] | 792.03 | I-A1-iii-1 | CY-4G-2 (using Fmoc-O-benzyl-L-4-hydroxyproline), CY-4I-2 and CY-1.1 |
| 147 | 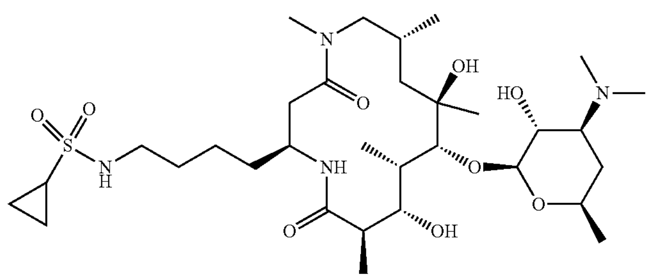 [SMILES: C[C@H]1CN(C)C(=O)C[C@H](CCCCNS(=O)(=O)C2CC2)NC(=O)[C@H](C)[C@@H](O)[C@H](C)[C@@H](O[C@@H]2O[C@H](C)C[C@H](N(C)C)[C@H]2O)[C@](C)(O)C1] | 676.90 | 16 | KL-B |
| 148 | 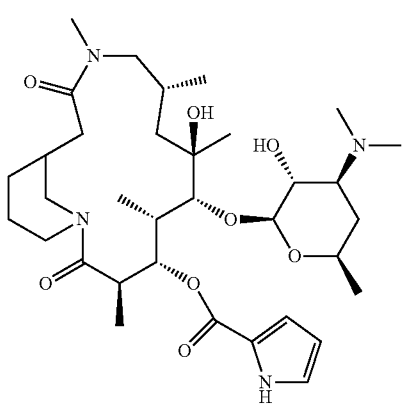 [SMILES: C[C@H]1CN(C)C(=O)CC2CCCN(C2)C(=O)[C@H](C)[C@@H](OC(=O)c2ccc[nH]2)[C@H](C)[C@@H](O[C@@H]2O[C@H](C)C[C@H](N(C)C)[C@H]2O)[C@](C)(O)C1] | 649.71 | 113 | KB1 (using N-Ts-pyrrole-1-carboxylic acid), KM |

Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 149 | 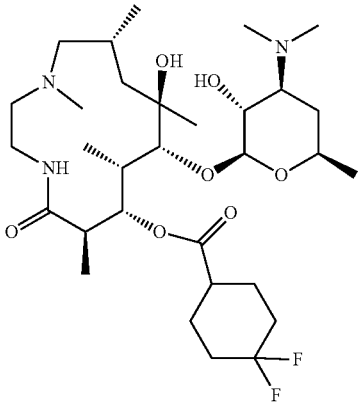 [SMILES: C[C@H]1CN(C)CCNC(=O)[C@H](C)[C@@H](OC(=O)C2CCC(F)(F)CC2)[C@H](C)[C@@H](O[C@@H]2O[C@H](C)C[C@H](N(C)C)[C@H]2O)[C@](C)(O)C1] | 619.80 | 5 | KB1 (using 4,4-difluoro cyclohexane carboxylic acid) |
| 150 | 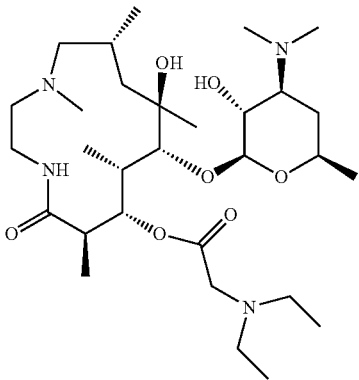 [SMILES: CCN(CC)CC(=O)O[C@H]1[C@H](C)[C@@H](O[C@@H]2O[C@H](C)C[C@H](N(C)C)[C@H]2O)[C@](C)(O)C[C@@H](C)CN(C)CCNC(=O)[C@@H]1C] | 586.82 | 5 | KB1 (using N,N-diethyl glycine) |
| 151 | 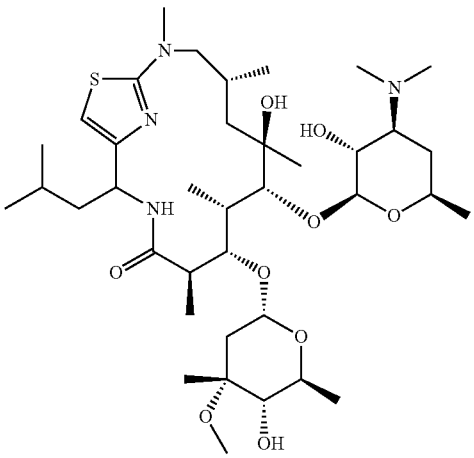 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)c3nc(cs3)C(CC(C)C)NC(=O)[C@@H]2C)O[C@@H](C)[C@@H]1O] | 768.46 | I-B1-iii-1 | FA, CY-6A (using Fmoc-chloromethy-Leu) and CY-1.1 |
| 152 | 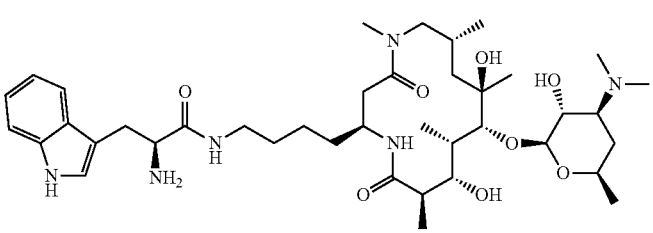 [SMILES: C[C@H]1CN(C)C(=O)C[C@H](CCCCNC(=O)[C@@H](N)Cc2c[nH]c3ccccc23)NC(=O)[C@H](C)[C@@H](O)[C@H](C)[C@@H](O[C@@H]2O[C@H](C)C[C@H](N(C)C)[C@H]2O)[C@](C)(O)C1] | 759.71 | 16 | CY-4G-1 (using Fmoc-Trp-OH), CY-4I-1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 153 | 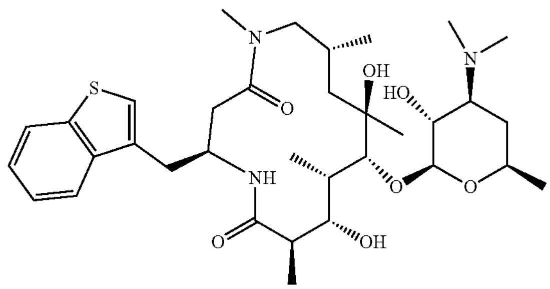 [SMILES: C[C@H]1CN(C)C(=O)C[C@H](Cc2csc3ccccc23)NC(=O)[C@H](C)[C@@H](O)[C@H](C)[C@@H](O[C@@H]2O[C@H](C)C[C@H](N(C)C)[C@H]2O)[C@](C)(O)C1] | 647.88 | 145 | KA2 |
| 154 | 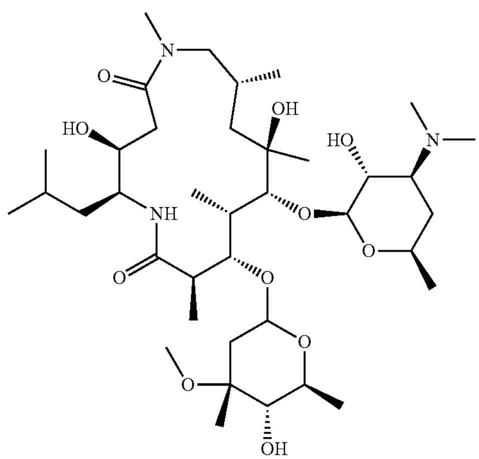 [SMILES: CO[C@]1(C)CC(O[C@H]2[C@H](C)[C@@H](O[C@@H]3O[C@H](C)C[C@H](N(C)C)[C@H]3O)[C@](C)(O)C[C@@H](C)CN(C)C(=O)C[C@H](O)[C@H](CC(C)C)NC(=O)[C@@H]2C)O[C@@H](C)[C@@H]1O] | 746 | I-A1-iii-1 | CY-4G-2 (using Fmoc-L-statine), CY-4I-2 and CY-1.1 |
| 155 | 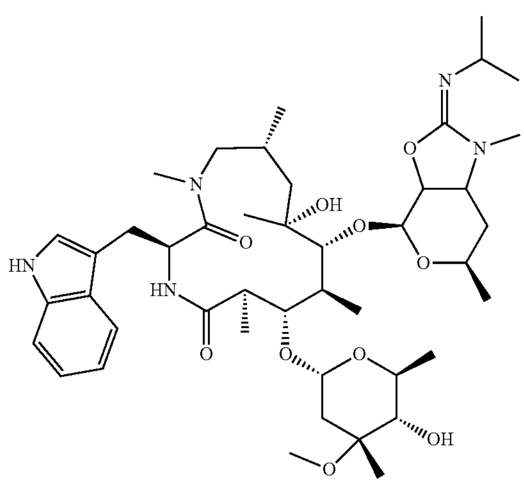 [SMILES: CO[C@]1(C)C[C@H](O[C@H]2[C@H](C)[C@@H](O[C@@H]3O[C@H](C)CC4C3O/C(=N/C(C)C)N4C)[C@](C)(O)C[C@@H](C)CN(C)C(=O)[C@H](Cc3c[nH]c4ccccc34)NC(=O)[C@@H]2C)O[C@@H](C)[C@@H]1O] | 828.07 | I-A1-iii-9 | CY-4G-2 (using (N-Fmoc-(S)-2-Amino-3-(1H-indol-3-yl)-propionic acid), CY-4I-2 and CY-1.1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 156 | 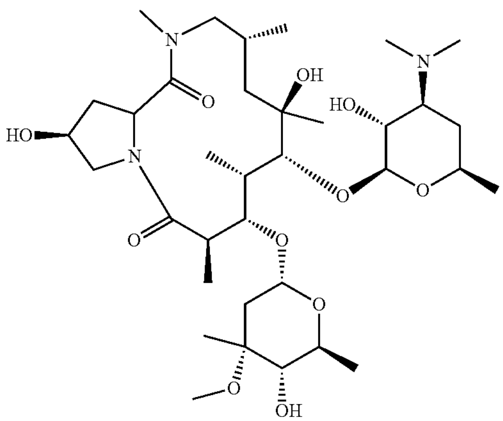 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C3C[C@H](O)CN3C(=O)[C@@H]2C)O[C@@H](C)[C@@H]1O] | 701.91 | 146 | KO |
| 157 | 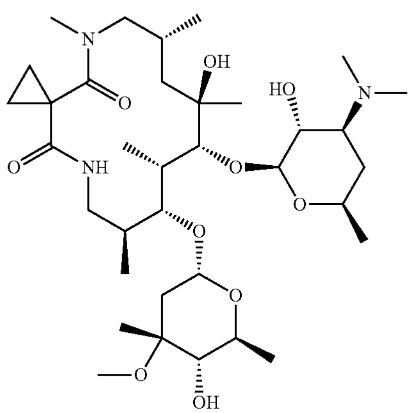 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C3(CC3)C(=O)NC[C@@H]2C)O[C@@H](C)[C@@H]1O] | 685.89 | I-D1-iii-1 | CY-4G-2 (using cyclopropane-1,1-dicarboxylic acid methyl ester); CY-4I-2; CY-1.1 |
| 158 | 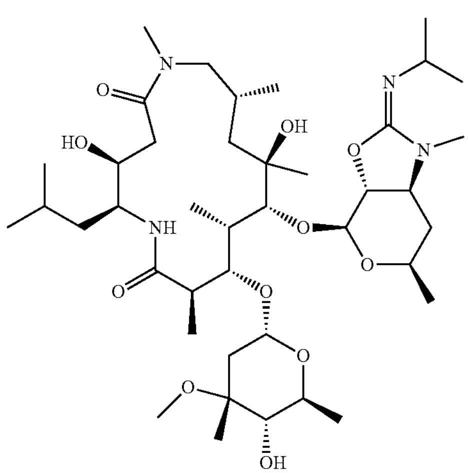 [SMILES: CO[C@]1(C)C[C@H](O[C@H]2[C@H](C)[C@@H](O[C@@H]3O[C@H](C)C[C@H]4[C@H]3O/C(=N/C(C)C)N4C)[C@](C)(O)C[C@@H](C)CN(C)C(=O)C[C@H](O)[C@H](CC(C)C)NC(=O)[C@@H]2C)O[C@@H](C)[C@@H]1O] | 799.07 | I-A1-iii-9 | CY-4G-2 (using Fmoc-L-statine), CY-4I-2 and CY-1.1 |

-continued

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 159 | 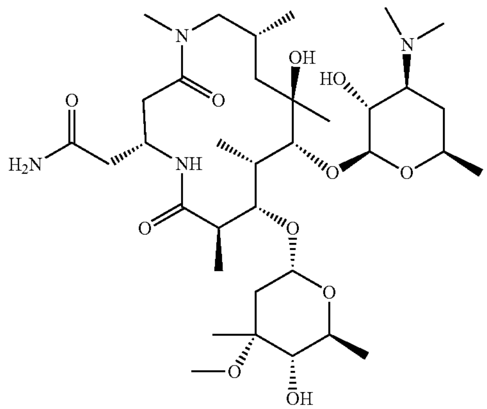 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C[C@@H](CC(N)=O)NC(=O)[C@@H]2C)O[C@@H](C)[C@@H]1O] | 716.92 | I-A1-iii-1 | CY-4G-2 (using Fmoc-β-Gln-OH), CY-4I-2 and CY-1.1 |
| 160 | 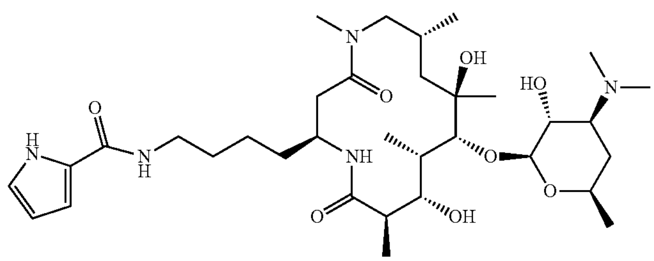 [SMILES: C[C@H]1CN(C)C(=O)C[C@H](CCCCNC(=O)c2ccc[nH]2)NC(=O)[C@H](C)[C@@H](O)[C@H](C)[C@@H](O[C@@H]2O[C@H](C)C[C@H](N(C)C)[C@H]2O)[C@](C)(O)C1] | 666.77 | 16 | CY-4G-1 (using Fmoc-Trp-OH), KM |
| 161 | 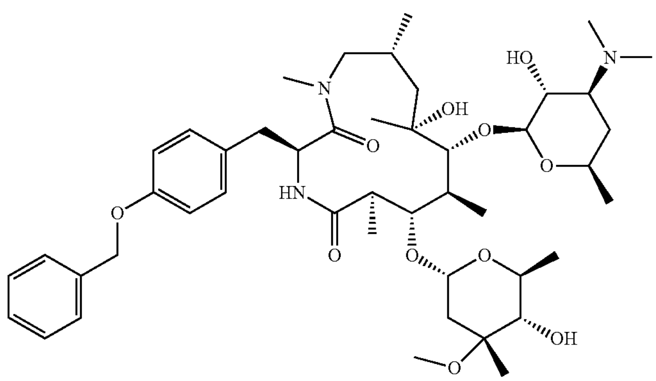 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)[C@H](Cc3ccc(OCc4ccccc4)cc3)NC(=O)[C@@H]2C)O[C@@H](C)[C@@H]1O] | 842.09 | I-A1-iii-1 | CY-4G-2 (using Fmoc-Tyr(Bz)-OH), CY-4I-2 and CY-1.1 |
| 162 | 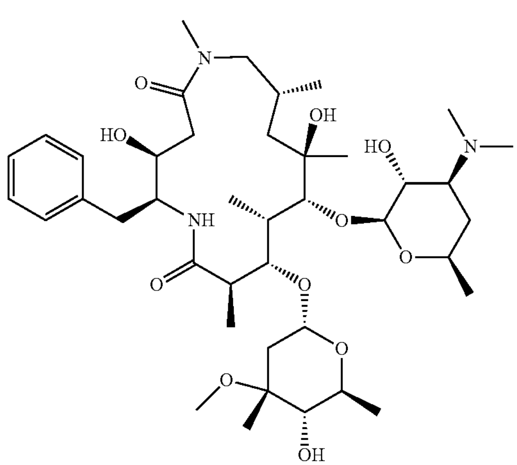 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C[C@H](O)[C@H](Cc3ccccc3)NC(=O)[C@@H]2C)O[C@@H](C)[C@@H]1O] | 780.02 | I-A1-iii-1 | CY-4G-2 (using CAS: 198542-01-7), CY-4I-2 and CY-1.1 |

Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 163 | 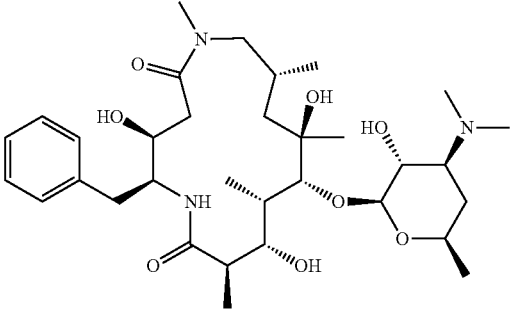 [SMILES: C[C@H]1CN(C)C(=O)C[C@H](O)[C@H](Cc2ccccc2)NC(=O)[C@H](C)[C@@H](O)[C@H](C)[C@@H](O[C@@H]2O[C@H](C)C[C@H](N(C)C)[C@H]2O)[C@](C)(O)C1] | 621.82 | 162 | KA2 |
| 164 | 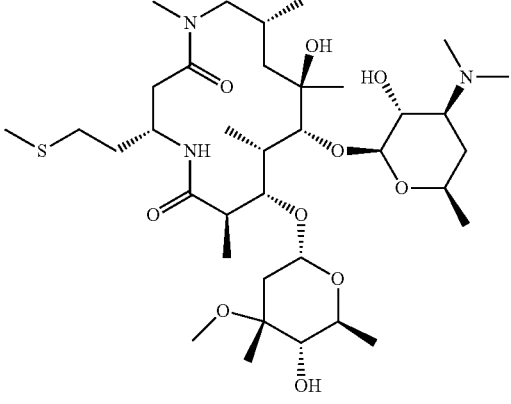 | 734.01 | I-A1-iii-1 | CY-4G-2 (using Fmoc-L-beta-homomethionine), CY-4I-2 and CY-1.1 |
| 165 | 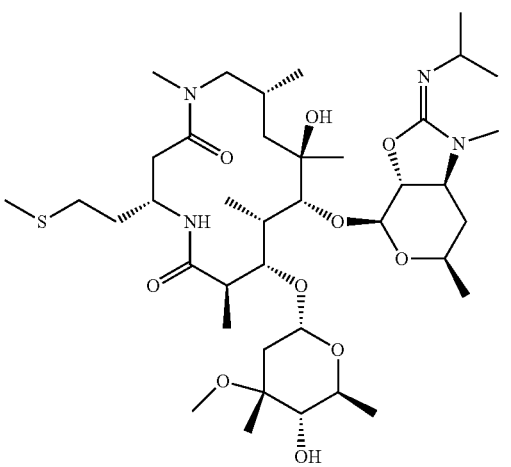 | 787.08 | I-A1-iii-9 | CY-4G-2 (using Fmoc-L-beta-homomethionine), CY-4I-2 and CY-1.1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 166 | 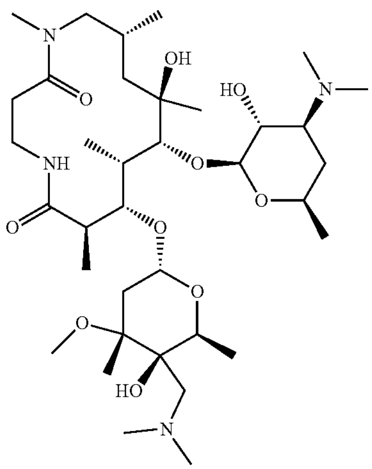 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)CCNC(=O)[C@@H]2C)O[C@@H](C)[C@]1(O)CN(C)C] | 716.99 | I-A1-iii-10 | CY-4G-2 (using 3-(9H-fluoren-9-yl-methoxycarbonylamino methylene), CY-4I-2 and CY-1.1 |
| 167 | 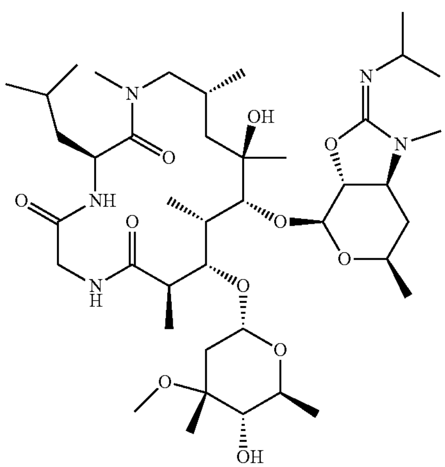 [SMILES: CO[C@]1(C)C[C@H](O[C@H]2[C@H](C)[C@@H](O[C@@H]3O[C@H](C)C[C@H]4[C@H]3O/C(=N/C(C)C)N4C)[C@](C)(O)C[C@@H](C)CN(C)C(=O)[C@H](CC(C)C)NC(=O)CNC(=O)[C@@H]2C)O[C@@H](C)[C@@H]1O] | 812.04 | I-B1-iii-9 | CY-4G-2 (using Fmoc-Leu-OH), CY-4G-2 (using L-glycine methyl ester hydrochloride), CY-4I-2 and CY-1.1 |
| 168 | 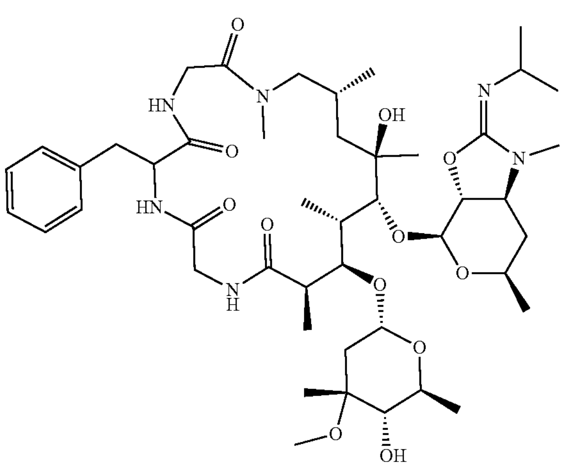 [SMILES: CO[C@]1(C)C[C@H](O[C@@H]2[C@H](C)[C@@H](O[C@@H]3O[C@H](C)C[C@H]4[C@H]3O/C(=N/C(C)C)N4C)[C@](C)(O)C[C@@H](C)CN(C)C(=O)CNC(=O)C(Cc3ccccc3)NC(=O)CNC(=O)[C@@H]2C)O[C@@H](C)[C@@H]1O] | 903.14 | I-B1-iii-9 | CY-4G-2 (using Fmoc-Phe-Gly-OH), CY-4G-2 (using L-glycine methyl ester hydrochloride), CY-4I-2 and CY-1.1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 169 | 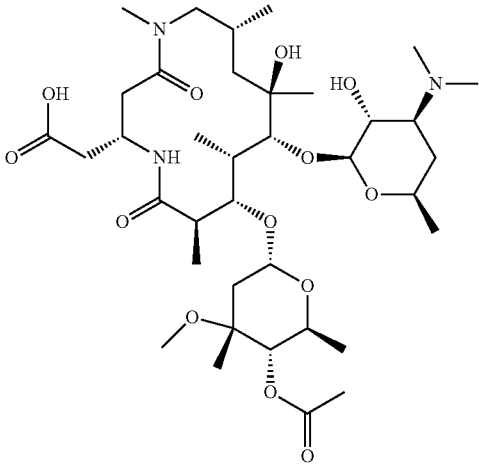 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C[C@@H](CC(=O)O)NC(=O)[C@@H]2C)O[C@@H](C)[C@@H]1OC(C)=O] | | I-B1-iii-1 | CY-4G-1 (using Fmoc-(S)-3-Amino-pentanedioic acid monoallyl ester), CY-4I-1; CY-1.1; KF; KP |
| 170 | 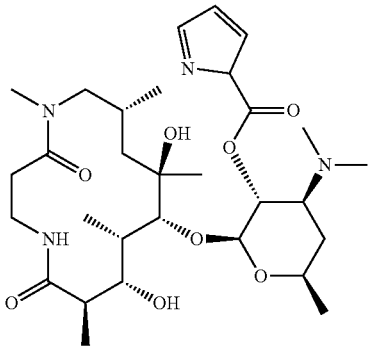 [SMILES: C[C@H]1CN(C)C(=O)CCNC(=O)[C@H](C)[C@@H](O)[C@H](C)[C@@H](O[C@@H]2O[C@H](C)C[C@H](N(C)C)[C@H]2OC(=O)C2C=CC=N2)[C@](C)(O)C1] | 595.55 | 91 | KB1 (using N-Ts-pyrrole-1-carboxylic acid), KM (2'-protection was partially removed in reaction conditions and C/2'-mono acyl compound 170 isolated together with C/3-acyl compound 171 in same reaction) |
| 171 | 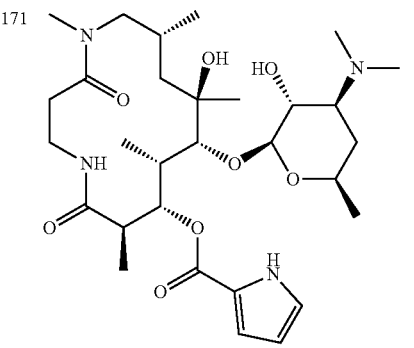 | 595.53 | 91 | KB1 (using N-Ts-pyrrole-1-carboxylic acid), KM |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 172 | 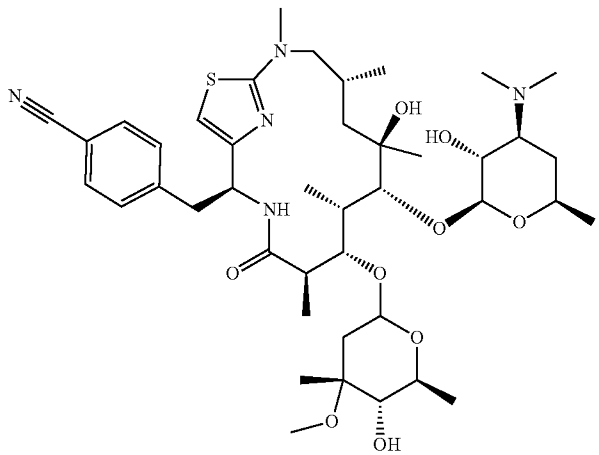 [SMILES: CO[C@]1(C)CC(O[C@H]2[C@H](C)[C@@H](O[C@@H]3O[C@H](C)C[C@H](N(C)C)[C@H]3O)[C@](C)(O)C[C@@H](C)CN(C)c3nc(cs3)[C@H](Cc3ccc(C#N)cc3)NC(=O)[C@@H]2C)O[C@@H](C)[C@@H]1O] | 816.08 | I-B1-iii-1 | FA, CY-6 ( using 4-(2-Fmoc-amino-4-chloro-3-oxo-butyl)benzonitrile), CY-4I-1, CY-1.1 |
| 173 | 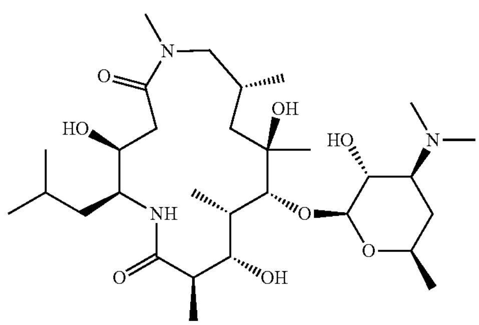 [SMILES: CC(C)C[C@@H]1NC(=O)[C@H](C)[C@@H](O)[C@H](C)[C@@H](O[C@@H]2O[C@H](C)C[C@H](N(C)C)[C@H]2O)[C@](C)(O)C[C@@H](C)CN(C)C(=O)C[C@@H]1O] | 587.80 | 154 | KA2 |
| 174 | 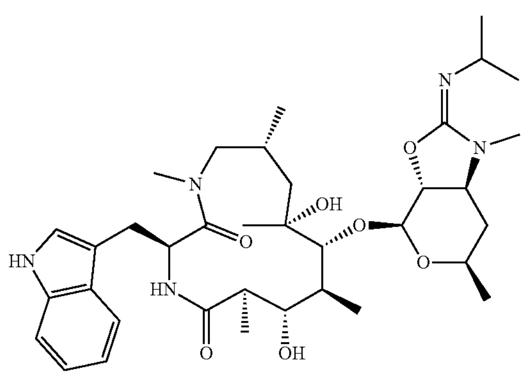 [SMILES: CC(C)/N=C1/O[C@H]2[C@H](O[C@@H]3[C@@H](C)[C@H](O)[C@@H](C)C(=O)N[C@@H](Cc4c[nH]c5ccccc45)C(=O)N(C)C[C@H](C)C[C@@]3(C)O)O[C@H](C)C[C@@H]2N1C] | 669.87 | 155 | KA2 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 175 | 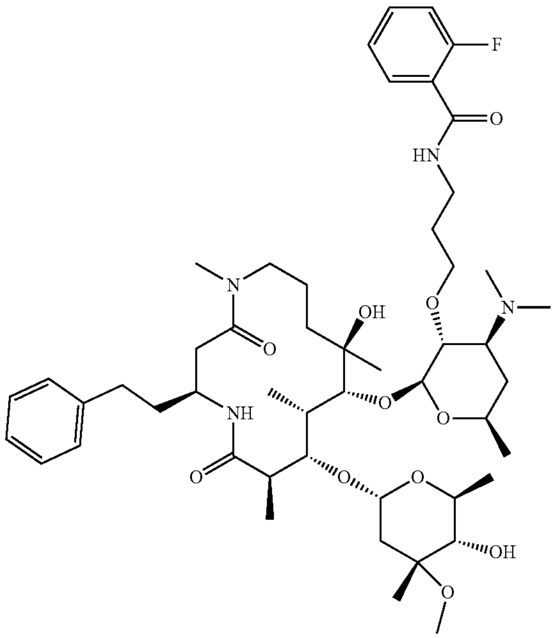 [SMILES: CO[C@]1(C)C[C@H](O[C@H]2[C@H](C)[C@@H](O[C@@H]3O[C@H](C)C[C@H](N(C)C)[C@H]3OCCCNC(=O)c3ccccc3F)[C@](C)(O)CCCN(C)C(=O)C[C@H](CCc3ccccc3)NC(=O)[C@@H]2C)O[C@@H](C)[C@@H]1O] | 929.16 | I-A1-iii-15 | CY-4G-2 (using (R)-3-(Fmoc-amino)-5-phenyl-pentanoic acid; CY-4I-2; CY-1.1 |
| 176 | 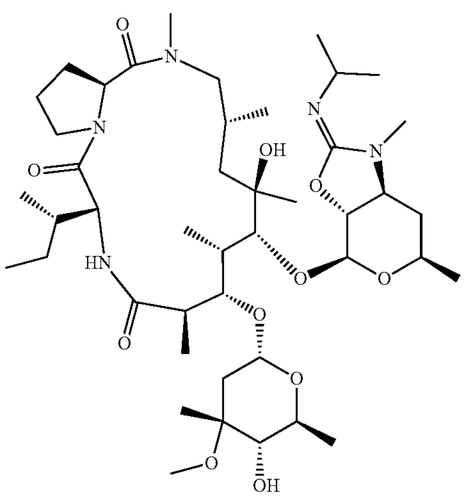 [SMILES: CC[C@H](C)[C@H]1NC(=O)[C@H](C)[C@@H](O[C@H]2C[C@@](C)(OC)[C@@H](O)[C@H](C)O2)[C@H](C)[C@@H](O[C@@H]2O[C@H](C)C[C@H]3[C@H]2O/C(=N/C(C)C)N3C)[C@](C)(O)C[C@@H](C)CN(C)C(=O)[C@@H]2CCCN2C1=O] | 852.64 | I-B1-iii-9 | CY-4G-1 (Fmoc-Ile-Pro-OH), CY-4I-1, CY-1.1 |
| 177 | 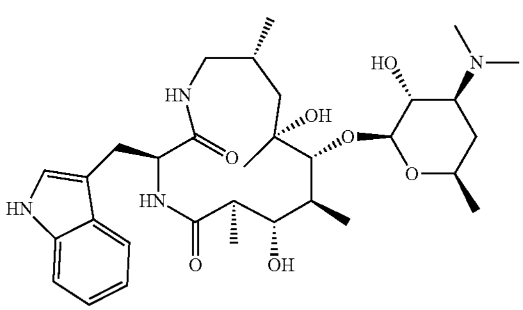 [SMILES: C[C@H]1CNC(=O)[C@H](Cc2c[nH]c3ccccc23)NC(=O)[C@H](C)[C@@H](O)[C@H](C)[C@@H](O[C@@H]2O[C@H](C)C[C@H](N(C)C)[C@H]2O)[C@](C)(O)C1] | 603.37 | 182 | KA-2 |

Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 178 | 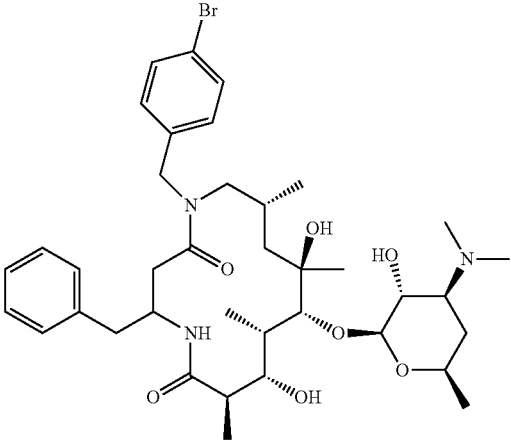 [SMILES: C[C@H]1CN(Cc2ccc(Br)cc2)C(=O)CC(Cc2ccccc2)NC(=O)[C@H](C)[C@@H](O)[C@H](C)[C@@H](O[C@@H]2O[C@H](C)C[C@H](N(C)C)[C@H]2O)[C@](C)(O)C1] | 734.35 | 216 | KL-A (using 4-Bromo-benzaldehyde) |
| 179 | 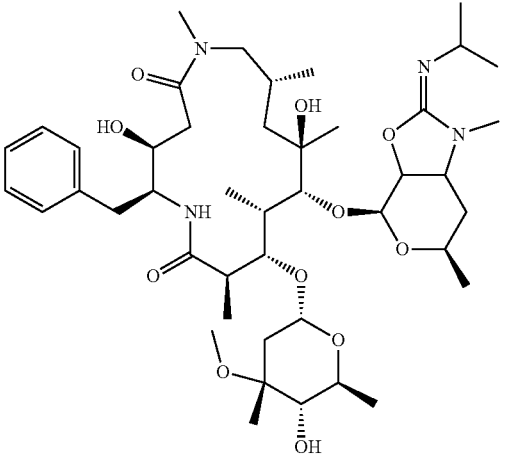 [SMILES: CO[C@]1(C)C[C@H](O[C@H]2[C@H](C)[C@@H](O[C@@H]3O[C@H](C)CC4C3O/C(=N/C(C)C)N4C)[C@](C)(O)C[C@@H](C)CN(C)C(=O)C[C@H](O)[C@H](Cc3ccccc3)NC(=O)[C@@H]2C)O[C@@H](C)[C@@H]1O] | 833.08 | I-A1-iii-9 | CY-4G-2 (using CAS: 198542-01-7), CY-4I-2 and CY-1.1 |
| 180 | 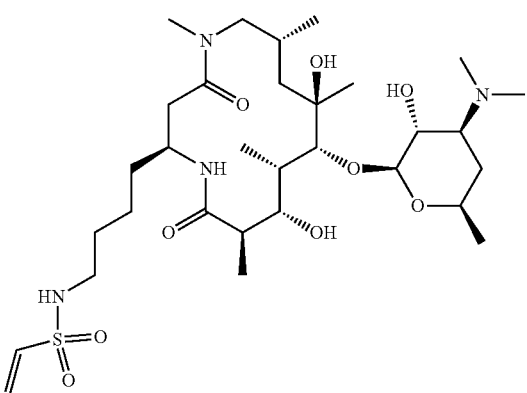 [SMILES: C=CS(=O)(=O)NCCCC[C@H]1CC(=O)N(C)C[C@H](C)C[C@@](C)(O)[C@H](O[C@@H]2O[C@H](C)C[C@H](N(C)C)[C@H]2O)[C@@H](C)[C@H](O)[C@@H](C)C(=O)N1] | 662.89 | 16 | KL-B (using sulfonyl chloride) |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 181 | 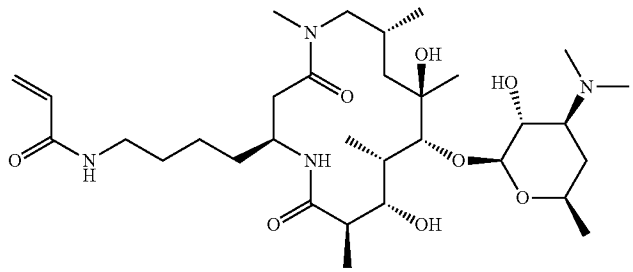 [SMILES: C=CC(=O)NCCCC[C@H]1CC(=O)N(C)C[C@H](C)C[C@@](C)(O)[C@H](O[C@@H]2O[C@H](C)C[C@H](N(C)C)[C@H]2O)[C@@H](C)[C@H](O)[C@@H](C)C(=O)N1] | 626.84 | 16 | CY-4G-1 (using acrylic acid) |
| 182 | 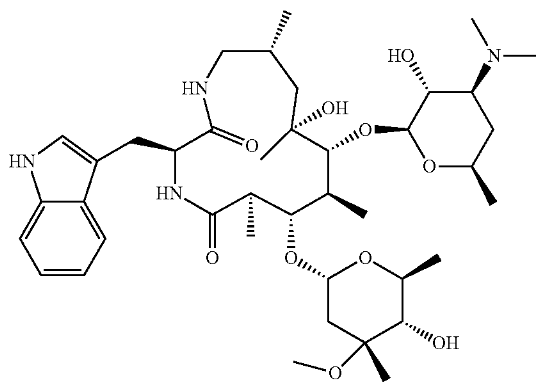 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CNC(=O)[C@H](Cc3c[nH]c4ccccc34)NC(=O)[C@@H]2C)O[C@@H](C)[C@@H]1O] | 761.49 | I-B1-iii-2 | CY-4G-2 (using (S)-2-Amino-3-(1H-indol-3-yl)-propionic acid), CY-4I-2 and CY-1.1 |
| 183 | 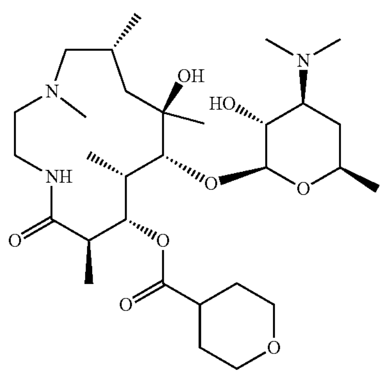 [SMILES: C[C@H]1CN(C)CCNC(=O)[C@H](C)[C@@H](OC(=O)C2CCOCC2)[C@H](C)[C@@H](O[C@@H]2O[C@H](C)C[C@H](N(C)C)[C@H]2O)[C@](C)(O)C1] | 585.77 | 5 | KB1 (using tetrahydro-2H-pyran-4-carb. acid) |
| 184 | 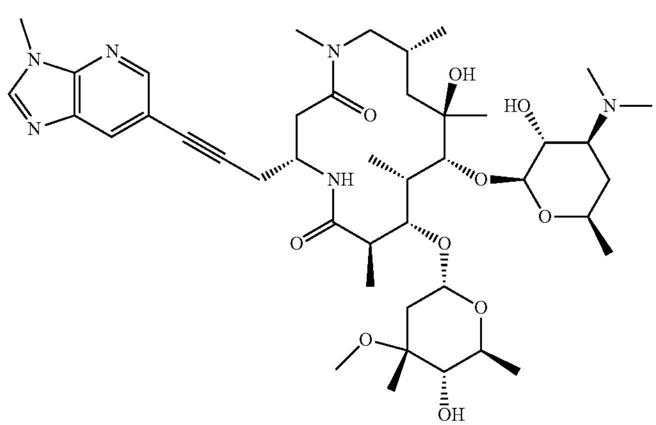 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C[C@@H](CC#Cc3cnc4c(c3)ncn4C)NC(=O)[C@@H]2C)O[C@@H](C)[C@@H]1O] | 829.06 | 244 | KR (using 6-iodo-3-methyl-1H-imidazo[4,5-b]pyridine) |

Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 185 | 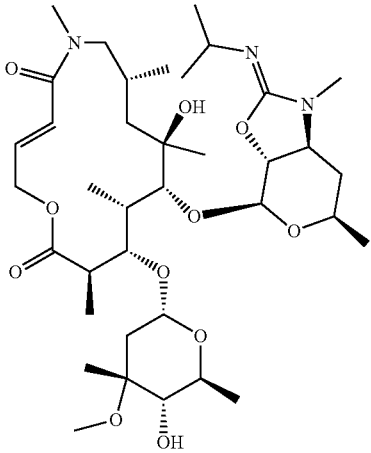 [SMILES: CO[C@]1(C)C[C@H](O[C@H]2[C@H](C)[C@@H](O[C@@H]3O[C@H](C)C[C@H]4[C@H]3O/C(=N\C(C)C)N4C)[C@](C)(O)C[C@@H](C)CN(C)C(=O)/C=C/COC(=O)[C@@H]2C)O[C@@H](C)[C@@H]1O] | 725.91 | I-A1-iii-9 | CY-9: I-MET-1A; I-MET-2A; I-DIE-2A; III-MET-O-A |
| 186 | 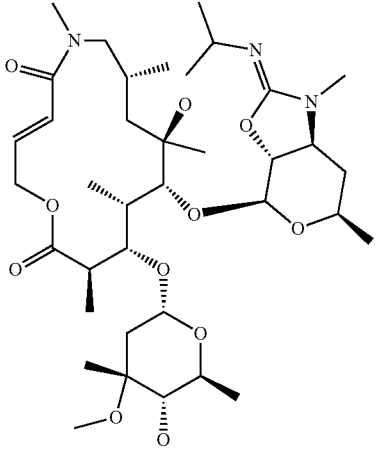 [SMILES: CO[C@]1(C)C[C@H](O[C@H]2[C@H](C)[C@@H](O[C@@H]3O[C@H](C)C[C@H]4[C@H]3O/C(=N\C(C)C)N4C)[C@](C)(O)C[C@@H](C)CN(C)C(=O)/C=C/COC(=O)[C@@H]2C)O[C@@H](C)[C@@H]1O] | 725.91 | I-A1-iii-9 | CY-9: I-MET-1A; I-MET-2A; I-DIE-2A; III-MET-O-A |
| 187 | 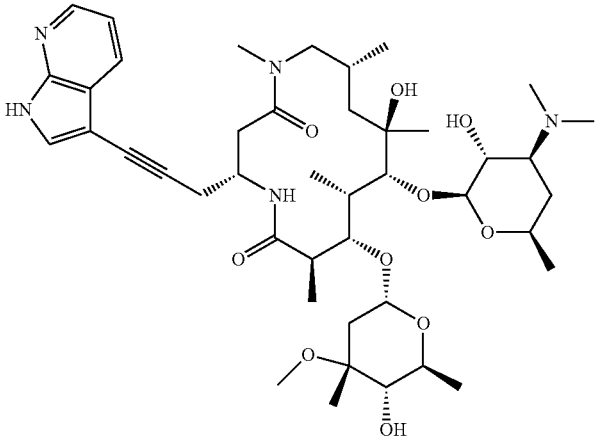 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C[C@@H](CC#Cc3c[nH]c4ncccc34)NC(=O)[C@@H]2C)O[C@@H](C)[C@@H]1O] | 814.04 | 244 | KR (using CAS192189-18-7), Deprotection: K2CO3 (2.5 eq) in MeOH at r.t. |

Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 188 | 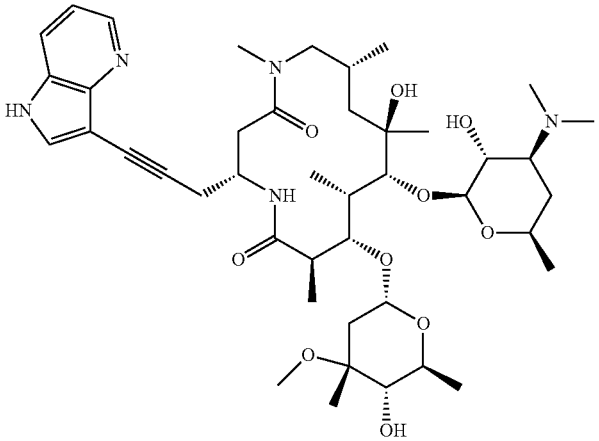 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C[C@@H](CC#Cc3c[nH]c4cccnc34)NC(=O)[C@@H]2C)O[C@@H](C)[C@@H]1O] | 814.04 | 244 | KR (using CAS1316228-21-3), Deprotection: K2CO3 (2.5 eq) in MeOH at r.t. |
| 189 | 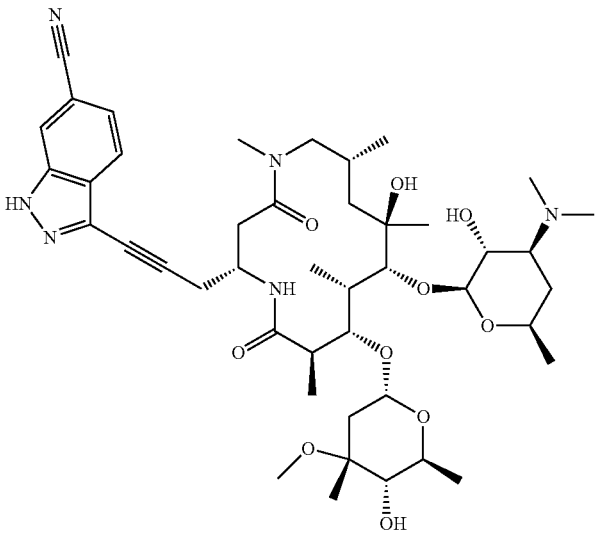 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C[C@@H](CC#Cc3n[nH]c4cc(C#N)ccc34)NC(=O)[C@@H]2C)O[C@@H](C)[C@@H]1O] | 839.05 | 244 | KR (using CAS811451-19-1), Deprotection: K2CO3 (2.5 eq) in MeOH at r.t. |

Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 190 | 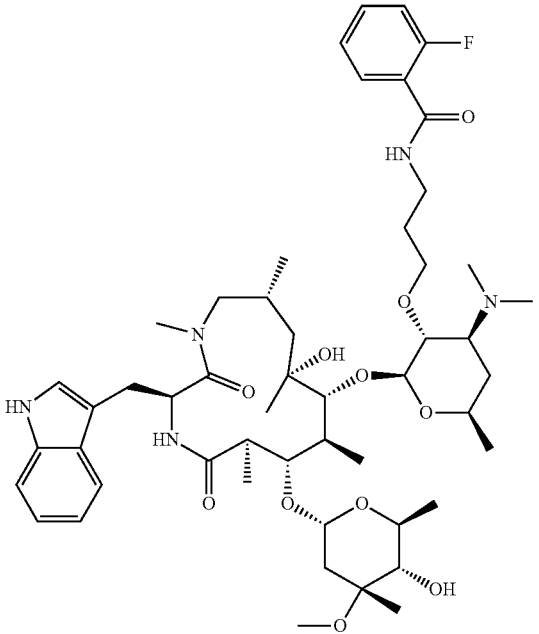 [SMILES: CO[C@]1(C)C[C@H](O[C@H]2[C@H](C)[C@@H](O[C@@H]3O[C@H](C)C[C@H](N(C)C)[C@H]3OCCCNC(=O)c3ccccc3F)[C@](C)(O)C[C@@H](C)CN(C)C(=O)[C@H](Cc3c[nH]c4ccccc34)NC(=O)[C@@H]2C)O[C@@H](C)[C@@H]1O] | 954.17 | I-A1-iii-15 | CY-4G-2 (using (N-Fmoc-(S)-2-Amino-3-(1H-indol-3-yl)-propionic acid), CY-4I-2 and CY-1.1 |
| 191 | 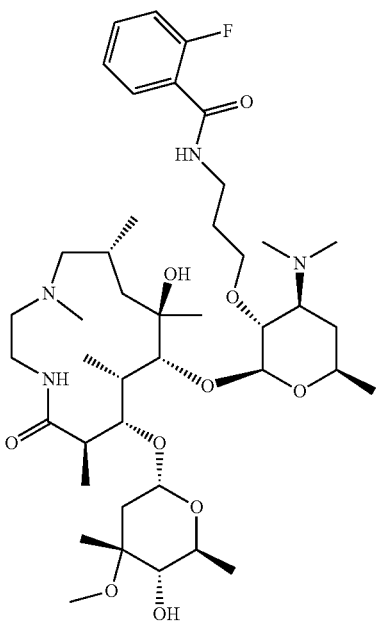 [SMILES: CO[C@]1(C)C[C@H](O[C@H]2[C@H](C)[C@@H](O[C@@H]3O[C@H](C)C[C@H](N(C)C)[C@H]3OCCCNC(=O)c3ccccc3F)[C@](C)(O)C[C@@H](C)CN(C)CCNC(=O)[C@@H]2C)O[C@@H](C)[C@@H]1O] | 811.03 | I-A1-iii-15 | CY-4H-1 (using N-Fmoc-β-2-acetaldehyde), CY-4I-2 and CY-1.1 |

Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 192 | 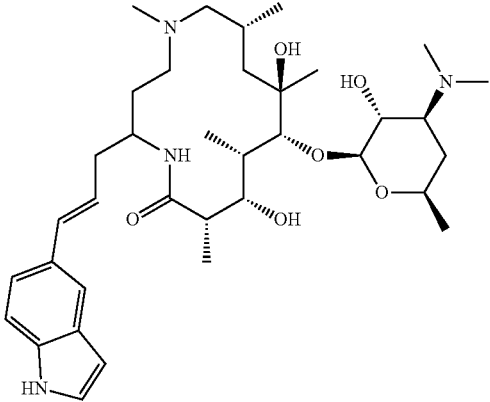 [SMILES: C[C@H]1CN(C)CCC(C/C=C/c2ccc3[nH]ccc3c2)NC(=O)[C@@H](C)[C@@H](O)[C@H](C)[C@@H](O[C@@H]2O[C@H](C)C[C@H](N(C)C)[C@H]2O)[C@](C)(O)C1] | 643.49 | 114 | KI (using 5-iodo indole) |
| 193 | 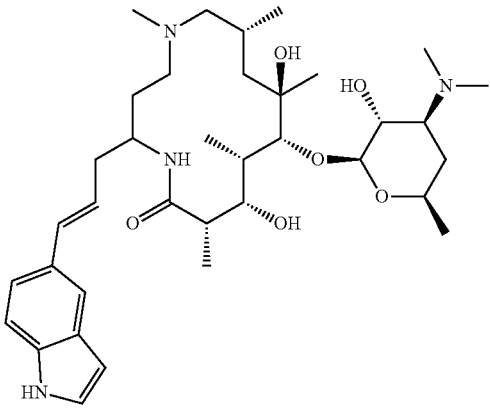 [SMILES: C[C@H]1CN(C)CCC(C/C=C/c2ccc3[nH]ccc3c2)NC(=O)[C@@H](C)[C@@H](O)[C@H](C)[C@@H](O[C@@H]2O[C@H](C)C[C@H](N(C)C)[C@H]2O)[C@](C)(O)C1] | 643.52 | 114 | KI (using 5-iodo indole) |
| 194 | 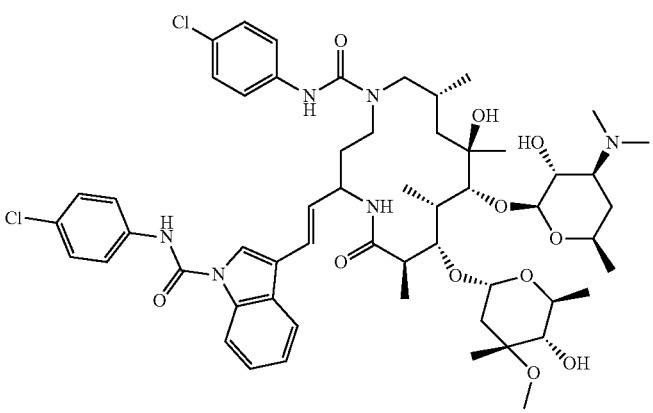 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C(=O)Nc3ccc(Cl)cc3)CCC(/C=C/c3cn(C(=O)Nc4ccc(Cl)cc4)c4ccccc34)NC(=O)[C@@H]2C)O[C@@H](C)[C@@H]1O] | 1080.14 | I-A1-iii-1 | CY-4H-1 (using N-fmoc-(+/−)-3-amino-pent-enal), CY-4I-2, CY-1.1, KI (using 5-iodo indole), KL-C (using 4-chorophenyl isocyanate) |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 195 | 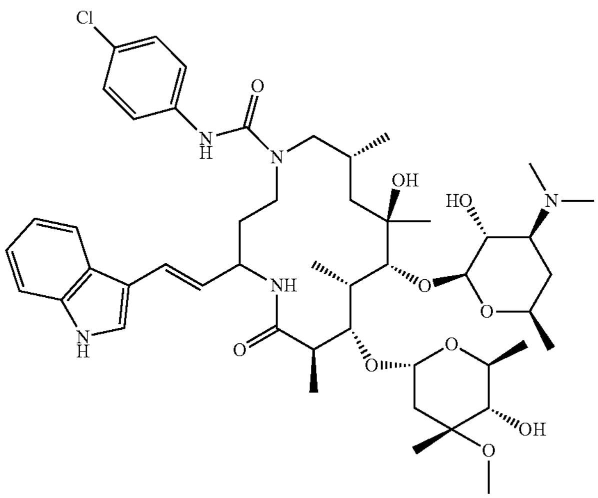 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C(=O)Nc3ccc(Cl)cc3)CCC(/C=C/c3c[nH]c4ccccc34)NC(=O)[C@@H]2C)O[C@@H](C)[C@@H]1O] | 926.58 | I-A1-iii-1 | CY-4H-1 (using N-fmoc-(+/−)-3-amino-pent-enal), CY-4I-2, CY-1.1, KL-C (using 4-chorophenyl isocyanate), KI (using 5-iodo indole) |
| 196 | 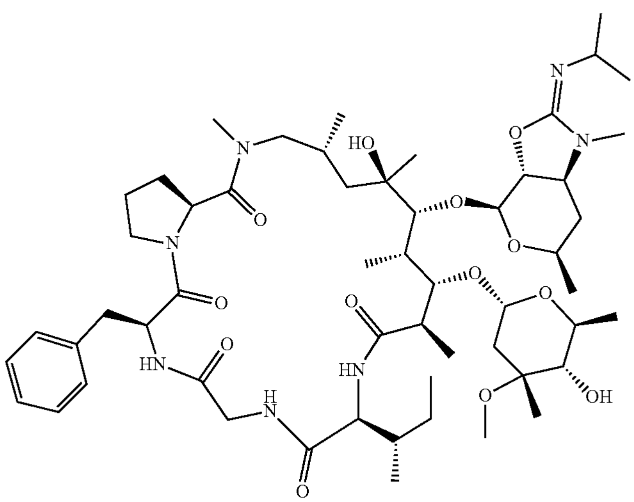 | 1056.33 | I-A1-iii-9 | CY-4G-2 (using Fmoc-Phe-Pro-OH), CY-4I-1, CY-4G-2 (using Fmoc-Ile-Gly-OH), CY-4I-2 and CY-1.1 |
| 197 | 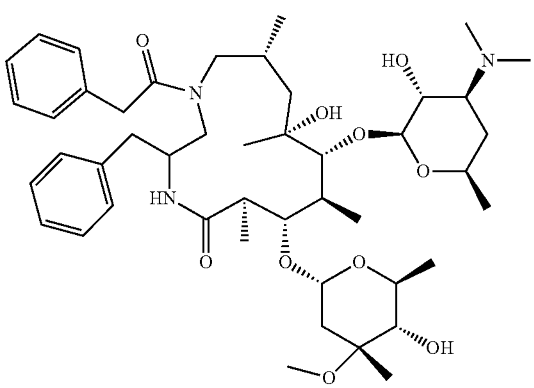 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C(=O)Cc3ccccc3)CC(Cc3ccccc3)NC(=O)[C@@H]2C)O[C@@H](C)[C@@H]1O] | 826.09 | 206 | KL-B (using phenylacetyl chloride) |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 198 | 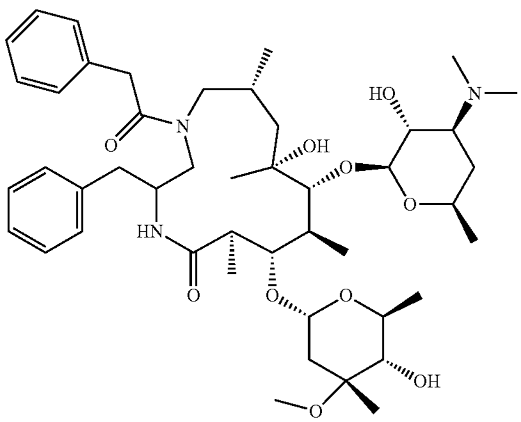 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C(=O)Cc3ccccc3)CC(Cc3ccccc3)NC(=O)[C@@H]2C)O[C@@H](C)[C@@H]1O] | 826.09 | 206 | KL-B (using phenylacetyl chloride) |
| 199 | 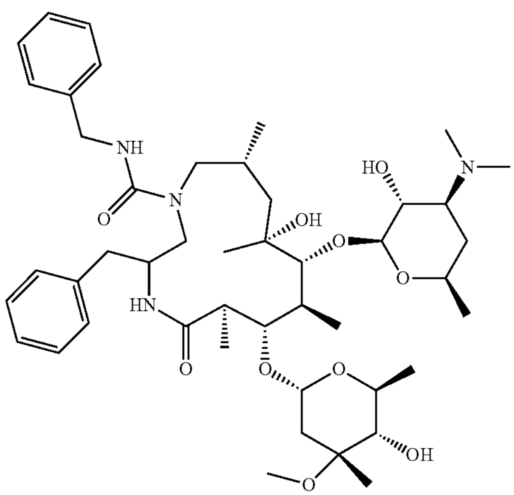 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C(=O)NCc3ccccc3)CC(Cc3ccccc3)NC(=O)[C@@H]2C)O[C@@H](C)[C@@H]1O] | 841.08 | 206 | KL-C (using benzyl isocyanate) |
| 200 | 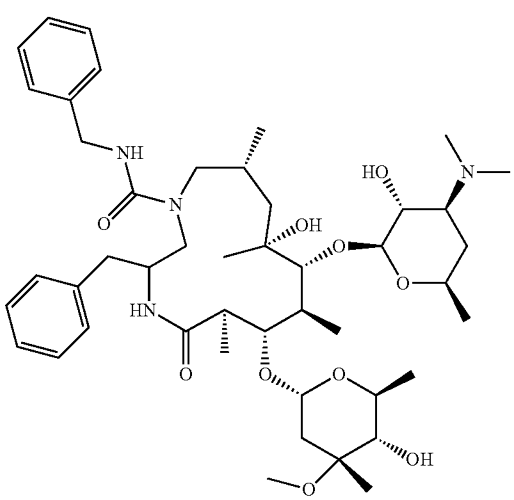 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C(=O)NCc3ccccc3)CC(Cc3ccccc3)NC(=O)[C@@H]2C)O[C@@H](C)[C@@H]1O] | 841.08 | 206 | KL-C (using benzyl isocyanate) |

Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 201 | 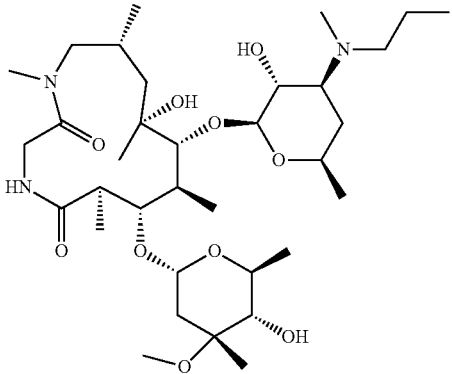 [SMILES: CCCN(C)[C@H]1C[C@@H](C)O[C@@H](O[C@@H]2[C@@H](C)[C@H](O[C@H]3C[C@@](C)(OC)[C@@H](O)[C@H](C)O3)[C@@H](C)C(=O)NCC(=O)N(C)C[C@H](C)C[C@@]2(C)O)[C@@H]1O] | 673.88 | I-B1-iii-13 | CY-4G-2 (using Fmoc β glycine), CY-4I-1, CY-1-1, KN, KE-1 (using iodopropane) |
| 202 | 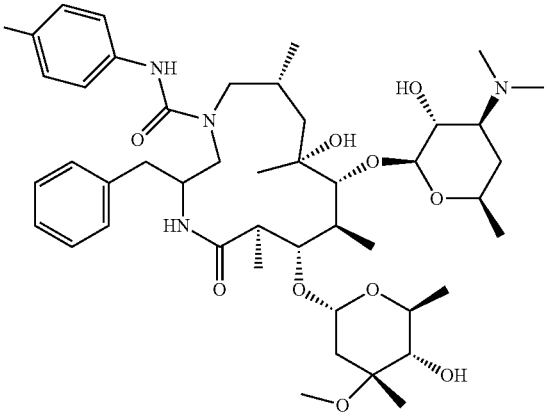 | 861.50 | 206 | KL-C (using 4-chlorophenyl isocyanate) |
| 203 | 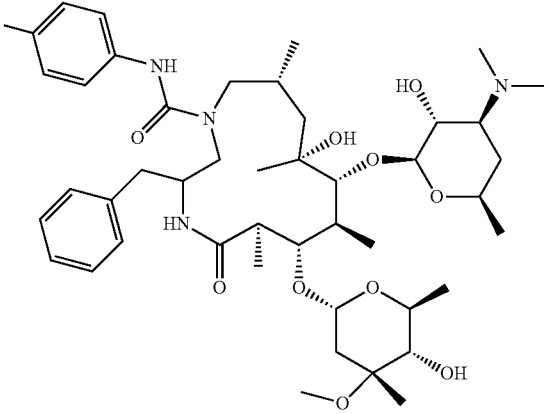 | 861.50 | 206 | KL-C (using 4-chlorophenyl isocyanate) |

-continued
Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 204 | 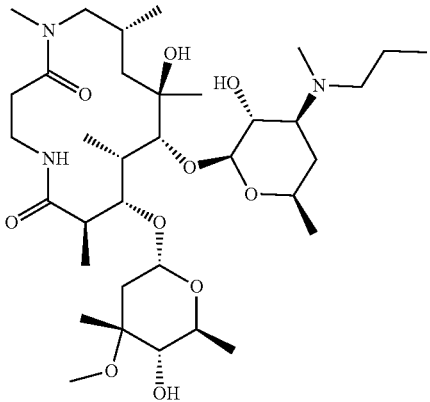 [SMILES: CCCN(C)[C@H]1C[C@@H](C)O[C@@H](O[C@@H]2[C@@H](C)[C@H](O[C@H]3C[C@@](C)(OC)[C@@H](O)[C@H](C)O3)[C@@H](C)C(=O)NCCC(=O)N(C)C[C@H](C)C[C@@]2(C)O)[C@@H]1O] | 687.92 | I-B1-iii-13 | CY-4G-2 (using Fmoc β alanine), CY-4I-1, CY-1-1, KN, KE-1 using iodopropane) |
| 205 | 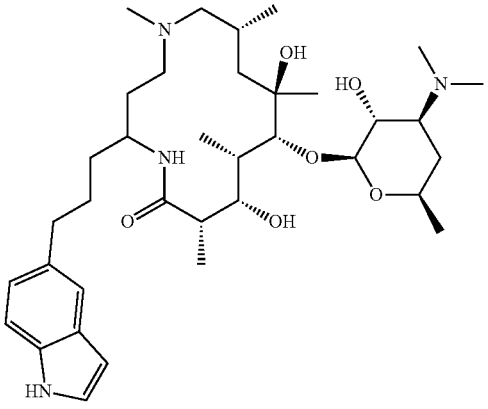 [SMILES: C[C@H]1CN(C)CCC(CCCc2ccc3[nH]ccc3c2)NC(=O)[C@@H](C)[C@@H](O)[C@H](C)[C@@H](O[C@@H]2O[C@H](C)C[C@H](N(C)C)[C@H]2O)[C@](C)(O)C1] | 645.46 | 193 | KJ |
| 206 | 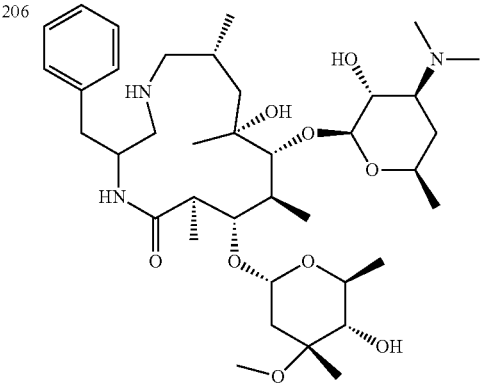 | 708.47/708.56 mixture of isomers 2:1 | I-B1-iii-2 | CY-4H-1 (using N-Fmoc-(+/−)-3-aminopent-4-enal), CY-4I-2, CY-1.1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 207 | 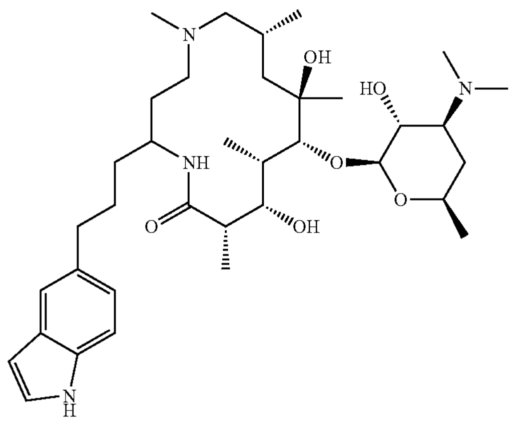 [SMILES: C[C@H]1CN(C)CCC(CCCc2ccc3[nH]ccc3c2)NC(=O)[C@@H](C)[C@@H](O)[C@H](C)[C@@H](O[C@@H]2O[C@H](C)C[C@H](N(C)C)[C@H]2O)[C@](C)(O)C1] | 645.25 | 193 | KJ |
| 208 | 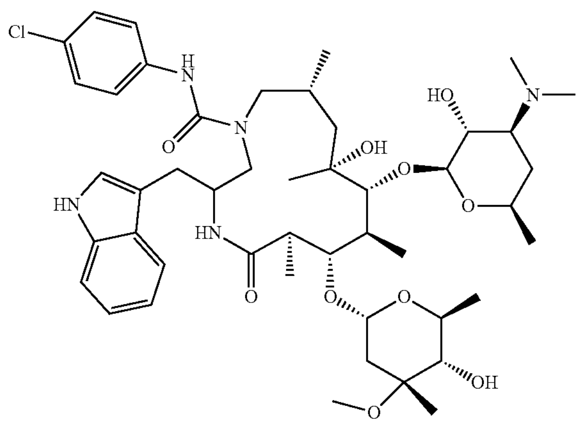 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C(=O)Nc3ccc(Cl)cc3)CC(Cc3c[nH]c4ccccc34)NC(=O)[C@@H]2C)O[C@@H](C)[C@@H]1O] | 900.56 | I-B1-iii-2 | CY-4H-1 (using 9H-fluoren-9-ylmethyl N-[(2S)-1-(1H-indol-3-yl)-3-oxopropan-2-yl]carbamate), CY-4I-2, CY-1.1, KL-C (using 4-chlorophenyl isocyanate) |
| 209 | 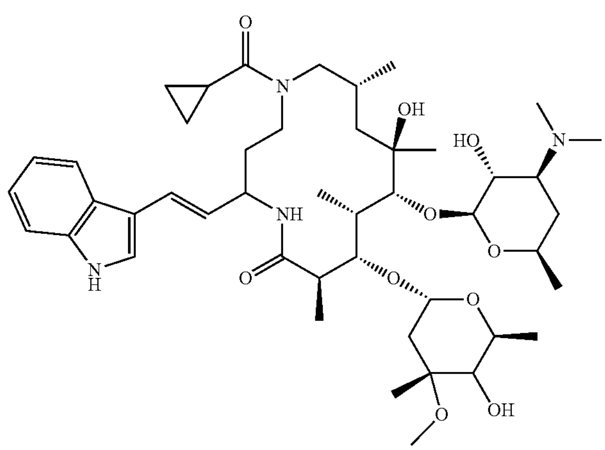 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C(=O)C3CC3)CCC(/C=C/c3c[nH]c4ccccc34)NC(=O)[C@@H]2C)O[C@@H](C)C1O] | 841.08 | I-A1-iii-1 | CY-4H-1 (using N-fmoc-(+/−)-3-amino-pent-enal), CY-4I-2, CY-1.1, KL-B (using cyclopropanecarbonyl chloride), KI (using 5-iodo indole), |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 210 | 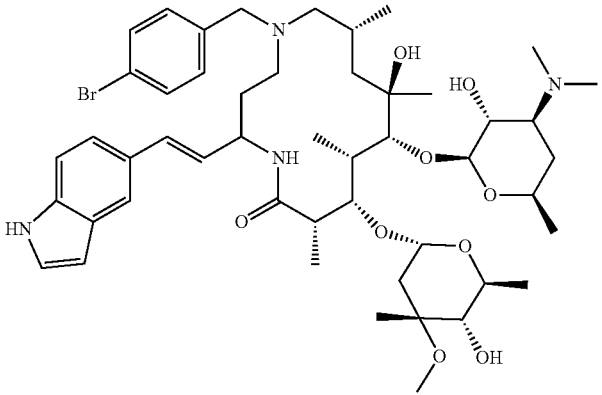 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(Cc3ccc(Br)cc3)CCC(/C=C/c3ccc4[nH]ccc4c3)NC(=O)[C@H]2C)O[C@@H](C)[C@@H]1O] | 942.0 | I-A1-iii-1 | CY-4H-1 (using 4-bromo-benzaldehyde), H1 (using N-fmoc-(+/−)-3-amino-pent-enal), CY-4I-2, CY-1.1, KI (using 5-iodo indole), |
| 211 | 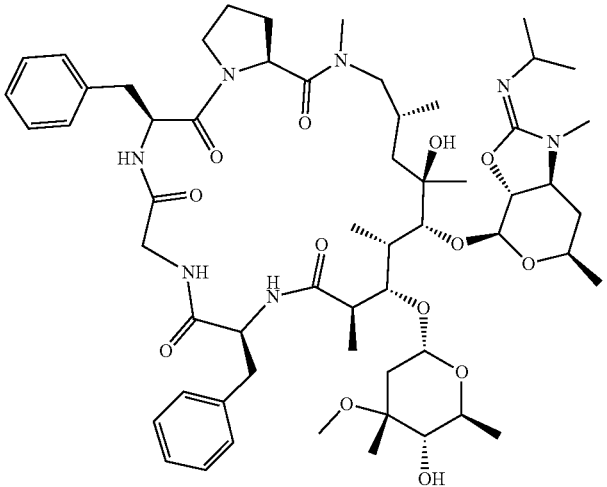 | 1090.35 | I-A1-iii-9 | CY-4G-2 (using Fmoc-Phe-Pro-OH), CY-4I-1, CY-4G (using Fmoc-Phe-Gly-OH), CY-4I-2 and CY-1.1 |
| 212 | 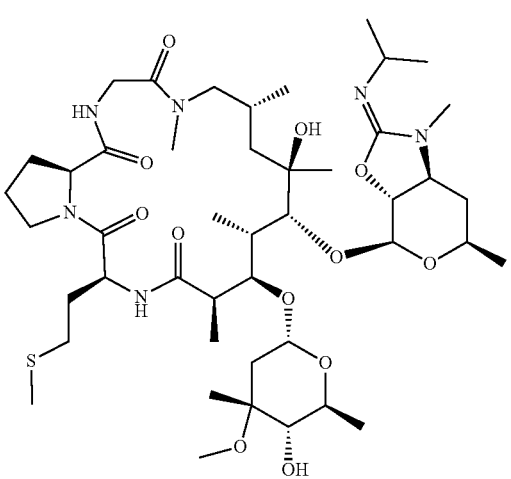 [SMILES: CO[C@]1(C)C[C@H](O[C@@H]2[C@H](C)[C@@H](O[C@@H]3O[C@H](C)C[C@H]4[C@H]3O/C(=N/C(C)C)N4C)[C@](C)(O)C[C@@H](C)CN(C)C(=O)CNC(=O)[C@@H]3CCCN3C(=O)[C@H](CCSC)NC(=O)[C@@H]2C)O[C@@H](C)[C@@H]1O] | 927.20 | I-B1-iii-9 | CY-4G-2 (using Fmoc-Pro-Gly-OH), CY-4I-1, CY-4G (using L-Methionine methyl ester HCl), CY-4I-2 and CY-1.1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 213 | 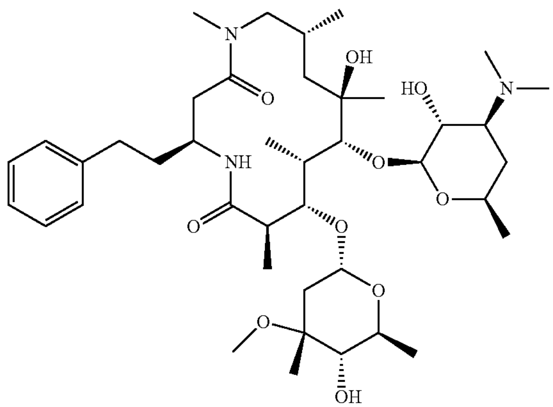 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C[C@H](CCc3ccccc3)NC(=O)[C@@H]2C)O[C@@H](C)[C@@H]1O] | 764.00 | I-A1-iii-1 | CY-4G-2 (using (R)-3-(Fmoc-amino)-5-phenyl-pentanoic acid), CY-4I-2 and CY-1.1 |
| 214 | 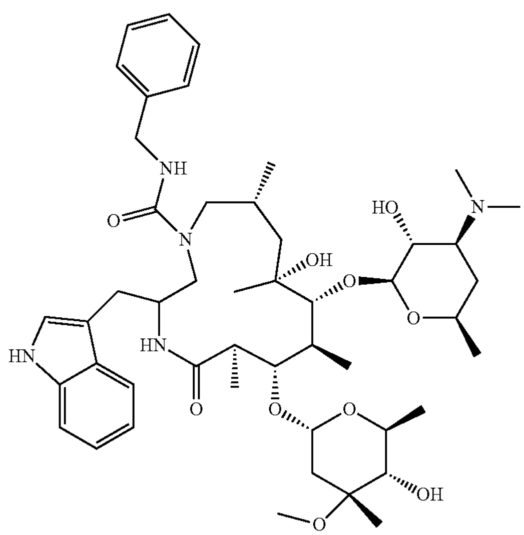 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C(=O)NCc3ccccc3)CC(Cc3c[nH]c4ccccc34)NC(=O)[C@@H]2C)O[C@@H](C)[C@@H]1O] | 880.1 | I-B1-iii-2 | CY-4H-1 (using 9H-fluoren-9-ylmethyl N-[(2S)-1-(1H-indol-3-yl)-3-oxopropan-2-yl]carbamate), CY-4I-2, CY-1.1, KL-C (using benzyl isocyanate) |
| 215 | 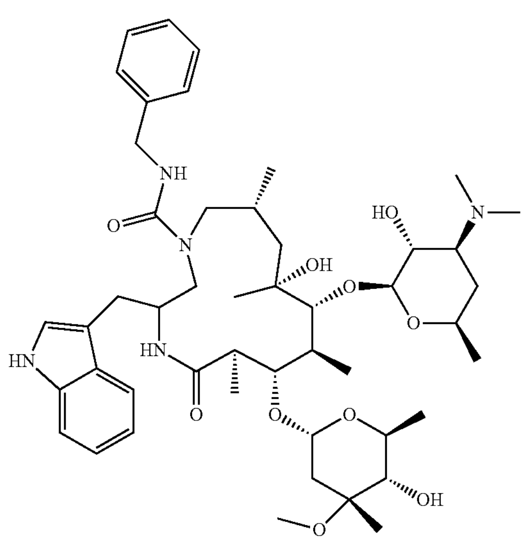 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C(=O)NCc3ccccc3)CC(Cc3c[nH]c4ccccc34)NC(=O)[C@@H]2C)O[C@@H](C)[C@@H]1O] | 880.1 | I-B1-iii-2 | CY-4H-1 (using 9H-fluoren-9-ylmethyl N-[(2S)-1-(1H-indol-3-yl)-3-oxopropan-2-yl]carbamate), CY-4I-2, CY-1.1, KL-C (using benzyl isocyanate) |

Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 216 | 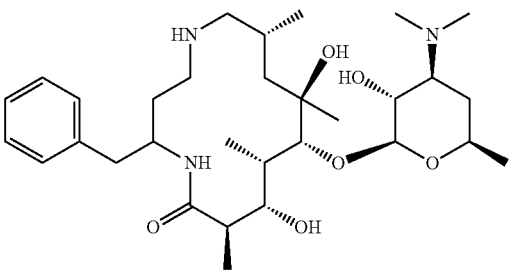 [SMILES: C[C@H]1CNCCC(Cc2ccccc2)NC(=O)[C@H](C)[C@@H](O)[C@H](C)[C@@H](O[C@@H]2O[C@H](C)C[C@H](N(C)C)[C@H]2O)[C@](C)(O)C1] | 563.77 | I-A1-iii-1 | CY-4H-1 (using N-boc-(+/−)-3-amino-4-phenylbutanal), CY-4I-3 and CY-1.1 |
| 217 | 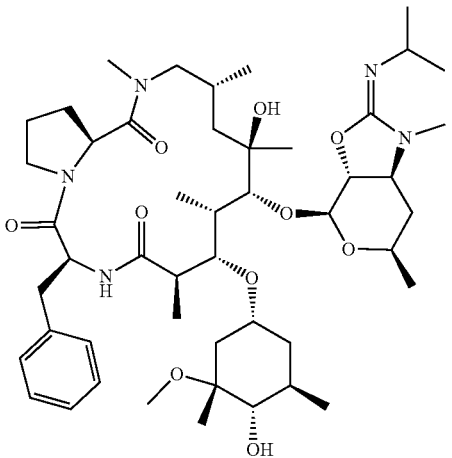 [SMILES: CO[C@]1(C)C[C@H](O[C@H]2[C@H](C)[C@@H](O[C@@H]3O[C@H](C)C[C@H]4[C@H]3O/C(=N/C(C)C)N4C)[C@](C)(O)C[C@@H](C)CN(C)C(=O)[C@@H]3CCCN3C(=O)[C@H](Cc3ccccc3)NC(=O)[C@@H]2C)C[C@@H](C)[C@@H]1O] | 886.12 | I-A1-iii-9 | CY-4G-2 (using Fmoc-Phe-Pro-OH), CY-4I-1, CY-4I-2 and CY-1.1 |
| 218 | 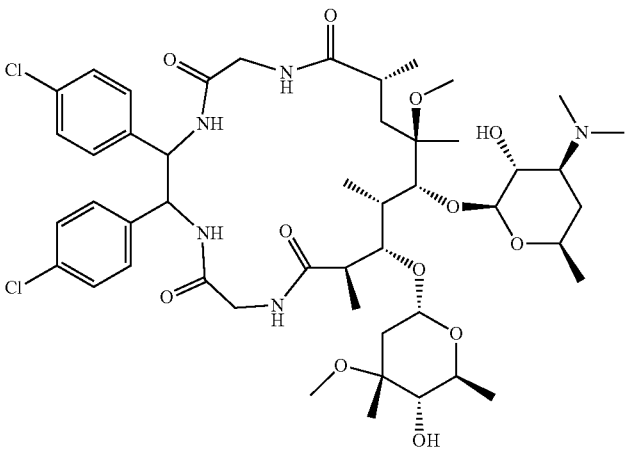 [SMILES: CO[C@]1(C)C[C@@H](C)C(=O)NCC(=O)NC(c2ccc(Cl)cc2)C(c2ccc(Cl)cc2)NC(=O)CNC(=O)[C@H](C)[C@@H](O[C@H]2C[C@@](C)(OC)[C@@H](O)[C@H](C)O2)[C@H](C)[C@H]1O[C@@H]1O[C@H](C)C[C@H](N(C)C)[C@H]1O] | 981.03 | XC-iii-1 | Step 1: CY-4G-1 Using 1,2-bis (4-chlorophenyl)ethane-1,2-diamine and Fmoc-Glycine; CY-4I-1 Step 2: product from Step 1 and CY-1.1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 219 | 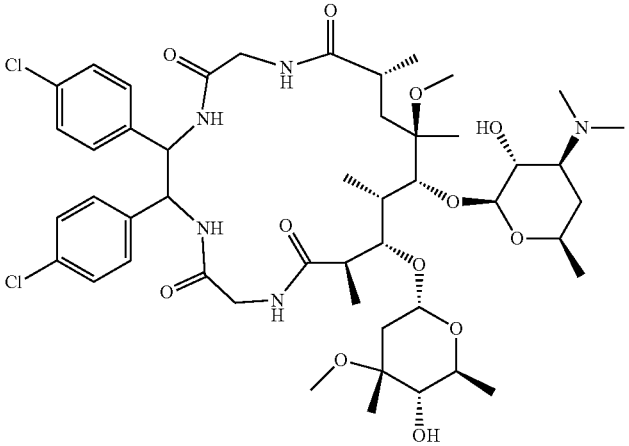 [SMILES: CO[C@]1(C)C[C@@H](C)C(=O)NCC(=O)NC(c2ccc(Cl)cc2)C(c2ccc(Cl)cc2)NC(=O)CNC(=O)[C@H](C)[C@@H](O[C@H]2C[C@@](C)(OC)[C@@H](O)[C@H](C)O2)[C@H](C)[C@H]1O[C@@H]1O[C@H](C)C[C@H](N(C)C)[C@H]1O] | 981.03 | XC-iii-1 | Step 1: CY-4G-1 Using 1,2-bis (4-chlorophenyl)ethane-1,2-diamine and Fmoc-Glycine; CY-4I-1 Step 2: product from Step 1 and CY-1.1 |
| 220 | 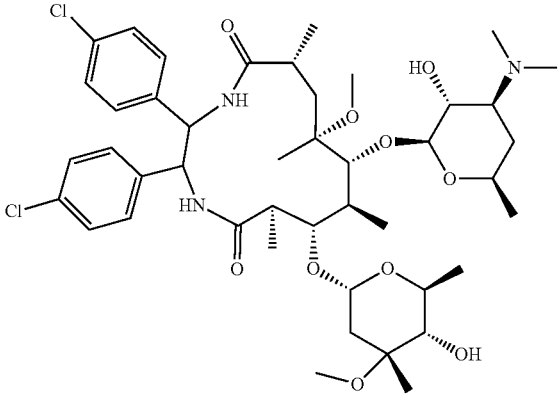 [SMILES: CO[C@]1(C)C[C@@H](C)C(=O)NC(c2ccc(Cl)cc2)C(c2ccc(Cl)cc2)NC(=O)[C@H](C)[C@@H](O[C@H]2C[C@@](C)(OC)[C@@H](O)[C@H](C)O2)[C@H](C)[C@H]1O[C@@H]1O[C@H](C)C[C@H](N(C)C)[C@H]1O] | 866.93 | XC-iii-1 | CY-1.1 Using 1,2-bis (4-chlorophenyl)-ethane-1,2-diamine |
| 221 | 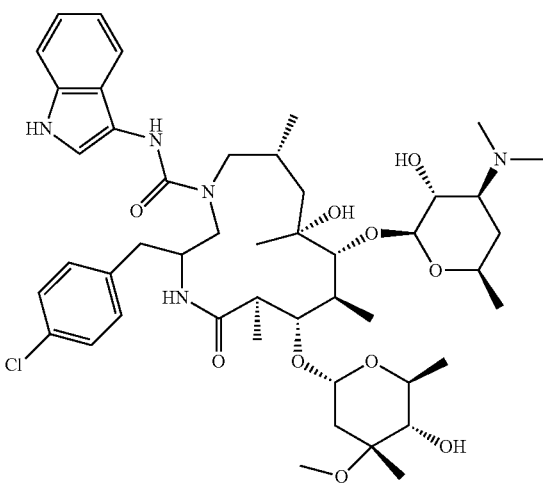 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C(=O)Nc3c[nH]c4ccccc34)CC(Cc3ccc(Cl)cc3)NC(=O)[C@@H]2C)O[C@@H](C)[C@@H]1O] | 900.56 | I-B1-iii-2 | CY-4H-1 (using [(S)-1-(4-chloro-phenyl)-3-oxo-propyl]carbamic acid 9H-fluoren-9-yl methylester), CY-4I-2, CY-1.1, KL-C (using 3-isocyanato-1-H-indole) |

-continued

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 222 | 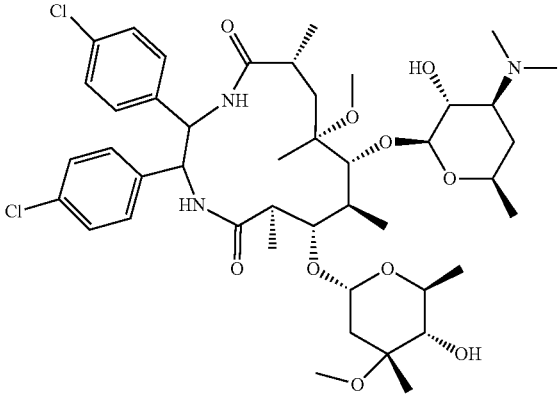 [SMILES: CO[C@]1(C)C[C@@H](C)C(=O)NC(c2ccc(Cl)cc2)C(c2ccc(Cl)cc2)NC(=O)[C@H](C)[C@@H](O[C@H]2C[C@@](C)(OC)[C@@H](O)[C@H](C)O2)[C@H](C)[C@H]1O[C@@H]1O[C@H](C)C[C@H](N(C)C)[C@H]1O] | 866.93 | XC-iii-1 | CY-1.1 Using 1,2-bis (4-chlorophenyl)-ethane-1,2-diamine |
| 223 | 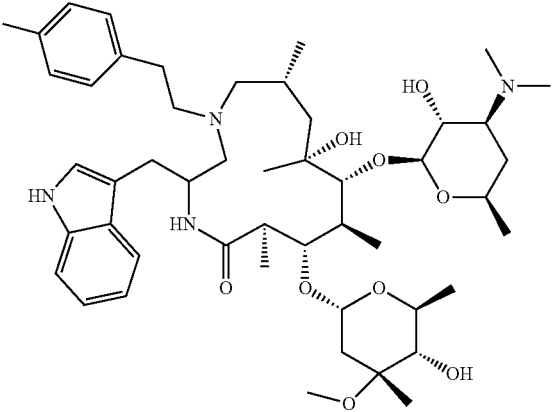 | 885.57 | I-B1-iii-2 | CY-4H-1 (using 9H-fluoren-9-ylmethyl N-[(2S)-1-(1H-indol-3-yl)-3-oxopropan-2-yl]carbamate), CY-4I-2, CY-1.1, KL-B (using 4-chlorophenylacetaldehyde) |
| 224 | 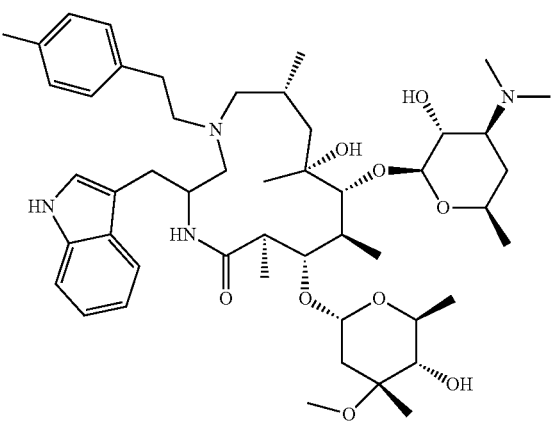 | 885.57 | I-B1-iii-2 | CY-4H-1 (using 9H-fluoren-9-ylmethyl N-[(2S)-1-(1H-indol-3-yl)-3-oxopropan-2-yl]carbamate), CY-4I-2, CY-1.1, KL-B (using 4-chlorophenylacetaldehyde) |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 225 | 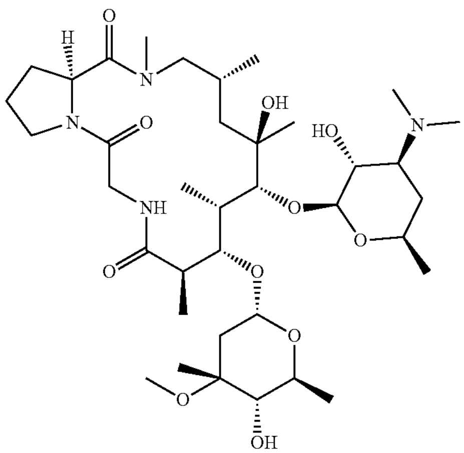 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)[C@@H]3CCCN3C(=O)CNC(=O)[C@@H]2C)O[C@@H](C)[C@@H]1O] | 742.96 | I-A1-iii-1 | CY-4G-1 (using Fmoc-Gly-Pro-OH); CY-4I-2 and CY-1.1 |
| 226 | 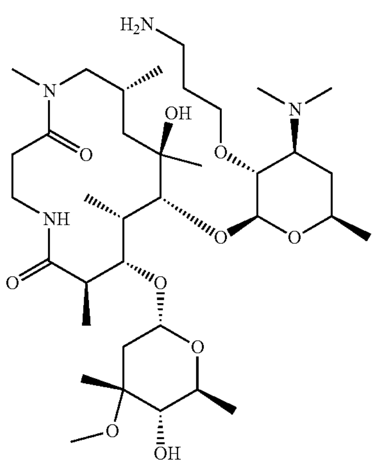 [SMILES: CO[C@]1(C)C[C@H](O[C@H]2[C@H](C)[C@@H](O[C@@H]3O[C@H](C)C[C@H](N(C)C)[C@H]3OCCCN)[C@](C)(O)C[C@@H](C)CN(C)C(=O)CCNC(=O)[C@@H]2C)O[C@@H](C)[C@@H]1O] | 716.96 | I-A1-iii-14 | CY-4G-1 (using Fmoc-beta-alanine), CY-4I-2, CY 1.1, KN |

Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 227 | 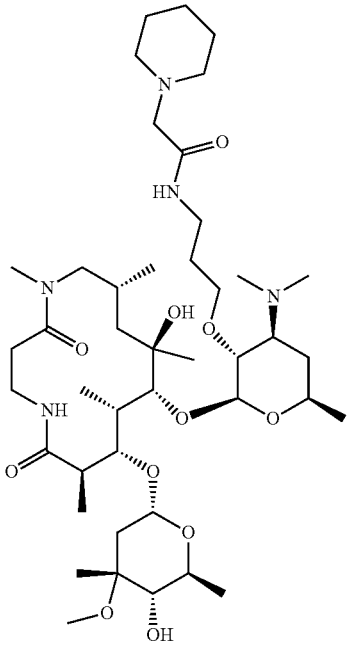 [SMILES: CO[C@]1(C)C[C@H](O[C@H]2[C@H](C)[C@@H](O[C@@H]3O[C@H](C)C[C@H](N(C)C)[C@H]3OCCCNC(=O)CN3CCCCC3)[C@](C)(O)C[C@@H](C)CN(C)C(=O)CCNC(=O)[C@@H]2C)O[C@@H](C)[C@@H]1O] | 842.14 | 226 | CY-4G-1 (using 2-(1-piperidyl)acetic acid) |
| 228 | 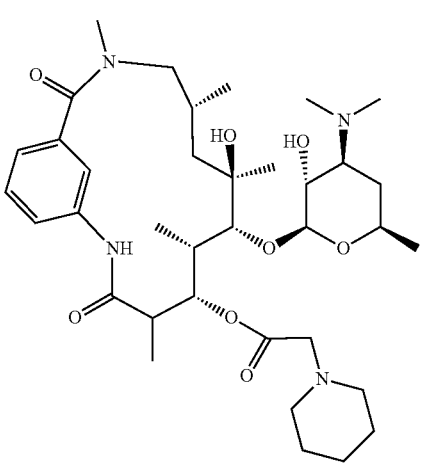 [SMILES: CC1C(=O)Nc2cccc(c2)C(=O)N(C)C[C@H](C)C[C@@](C)(O)[C@H](O[C@@H]2O[C@H](C)C[C@H](N(C)C)[C@H]2O)[C@@H](C)[C@@H]1OC(=O)CN1CCCCC1] | 674.89 | 49 | KB1 (using Piprridin-1-yl-acetic acid) |

Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 229 | 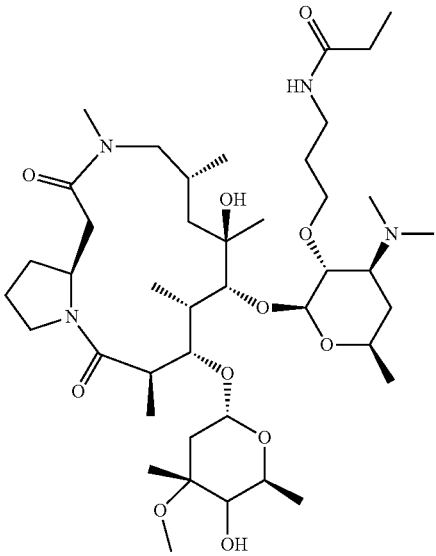 | 813.09 | I-A1-iii-3 | CY-4G-2 (using Fmoc-betahomoPro-OH); CY-4I-2 and CY-1.1 |
| 230 | 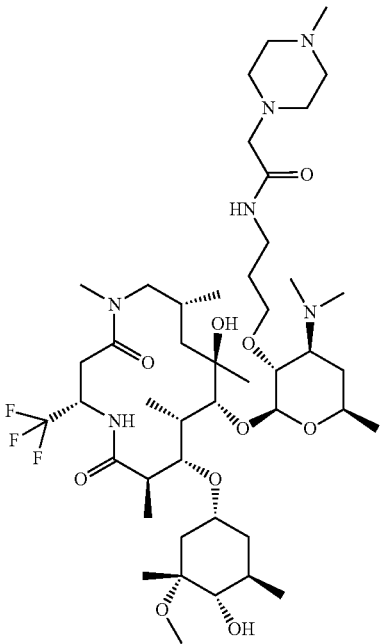 [SMILES: CO[C@]1(C)C[C@H](O[C@H]2[C@H](C)[C@@H](O[C@@H]3O[C@H](C)C[C@H](N(C)C)[C@H]3OCCCNC(=O)CN3CCN(C)CC3)[C@](C)(O)C[C@@H](C)CN(C)C(=O)C[C@@H](C(F)(F)F)NC(=O)[C@@H]2C)C[C@@H](C)[C@@H]1O] | 925.15 | I-A1-iii-5 | CY-4G-2 (using (S)-Fmoc-3-amino-4,4,4 trifluoro butiric acid); CY-4I-2; and CY-1.1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 231 | 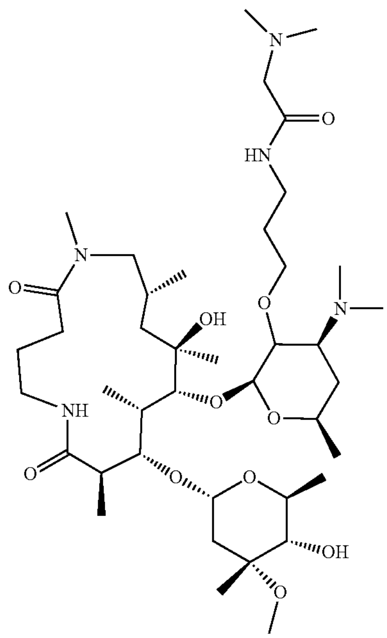 [SMILES: CO[C@]1(C)C[C@H](O[C@H]2[C@H](C)[C@@H](O[C@@H]3O[C@H](C)C[C@H](N(C)C)C3OCCCNC(=O)CN(C)C)[C@](C)(O)C[C@@H](C)CN(C)C(=O)CCCNC(=O)[C@@H]2C)O[C@@H](C)[C@@H]1O] | 816.10 | I-A1-iii-6 | CY-4G-2 (using 4-(Fmoc-amino)-butiric acid); CY-4I-2; CY-1.1 |
| 232 | 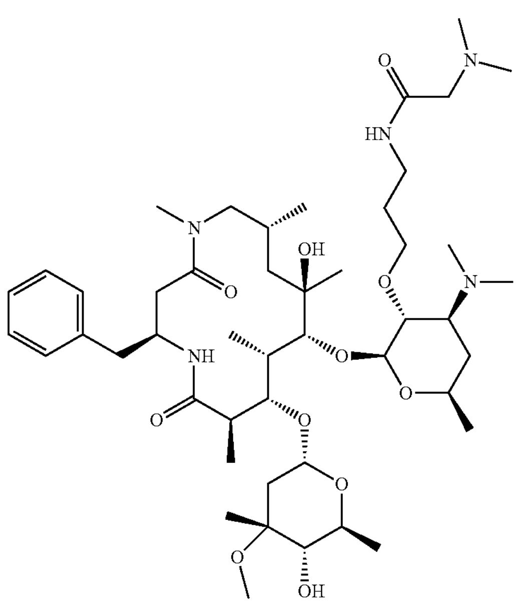 [SMILES: CO[C@]1(C)C[C@H](O[C@H]2[C@H](C)[C@@H](O[C@@H]3O[C@H](C)C[C@H](N(C)C)[C@H]3OCCCNC(=O)CN(C)C)[C@](C)(O)C[C@@H](C)CN(C)C(=O)C[C@H](Cc3ccccc3)NC(=O)[C@@H]2C)O[C@@H](C)[C@@H]1O] | 892.20 | I-A1-iii-6 | CY-4G-2 (using Fmoc-L-beta-homophenylalanine); CY-4I-2; CY-1.1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 233 | 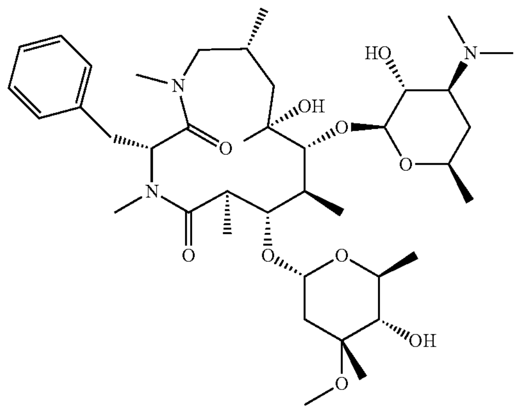 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)[C@@H](Cc3ccccc3)N(C)C(=O)[C@@H]2C)O[C@@H](C)[C@@H]1O] | 749.99 | I-A1-iii-1 | CY-4G-2 (using CAS138775-05-0), CY-4I-2 and CY-1.1 |
| 234 | 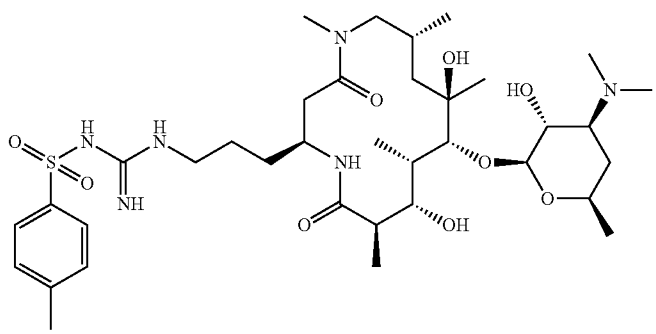 [SMILES: Cc1ccc(S(=O)(=O)NC(=N)NCCC[C@H]2CC(=O)N(C)C[C@H](C)C[C@@](C)(O)[C@H](O[C@@H]3O[C@H](C)C[C@H](N(C)C)[C@H]3O)[C@@H](C)[C@H](O)[C@@H](C)C(=O)N2)cc1] | 754.99 | I-A1-iii-1 | CY-4G-2 (CAS136271-81-3), CY-4I-2; I4 and CY-1.1 |
| 235 | 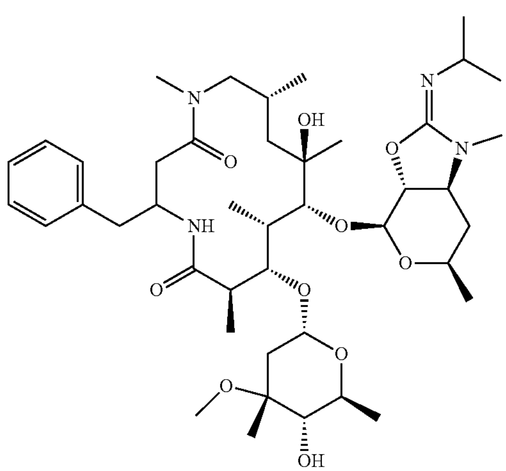 [SMILES: CO[C@]1(C)C[C@H](O[C@H]2[C@H](C)[C@@H](O[C@@H]3O[C@H](C)C[C@H]4[C@H]3O/C(=N/C(C)C)N4C)[C@](C)(O)C[C@@H](C)CN(C)C(=O)CC(Cc3ccccc3)NC(=O)[C@@H]2C)O[C@@H](C)[C@@H]1O] | 802.07 | I-A1-iii-9 | CY-4G-2 (using N-Fmoc-L-beta-homophenylalanine acid), CY-4I-2 and CY-1.1 |

-continued
Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 236 | 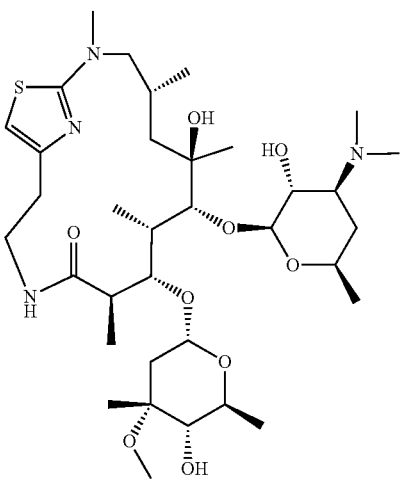 | 714.97 | I-B1-iii-1 | FA, CY-6 (using 4-bromo-1-aminobutan-2-one) and CY-1.1 |
| 237 | 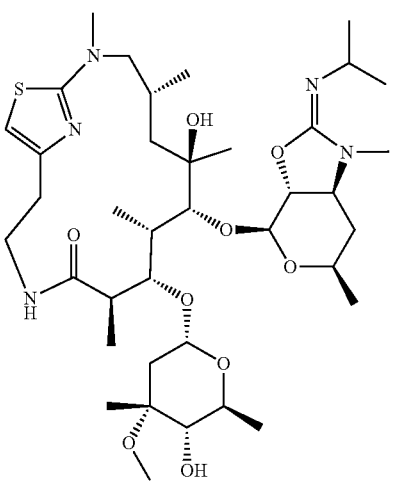 | 768.46 | I-B1-iii-9 | FA, CY-6 (using 4-bromo-1-aminobutan-2-one) and CY-1.1 |
| 238 | 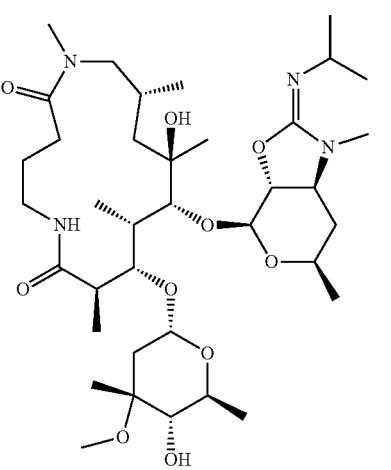 [SMILES: CO[C@]1(C)C[C@H](O[C@H]2[C@H](C)[C@@H](O[C@@H]3O[C@H](C)C[C@H]4[C@H]3O/C(=N/C(C)C)N4C)[C@](C)(O)C[C@@H](C)CN(C)C(=O)CCCNC(=O)[C@@H]2C)O[C@@H](C)[C@@H]1O] | 726.94 | I-A1-iii-9 | CY-4G-2 (using 4-Fmoc-aminobutiric acid), CY-4I-2 and CY-1.1 |

-continued

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 239 | 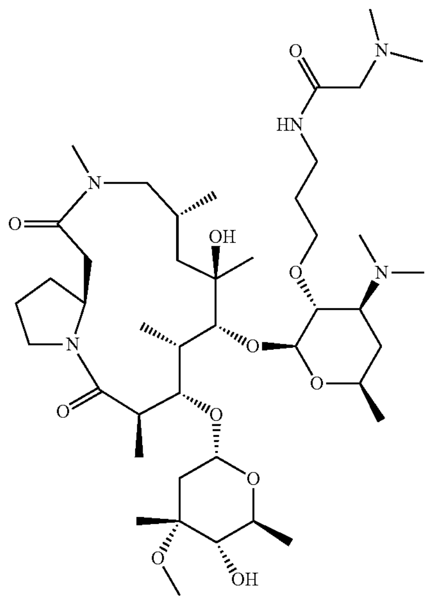 [SMILES: CO[C@]1(C)C[C@H](O[C@H]2[C@H](C)[C@@H](O[C@@H]3O[C@H](C)C[C@H](N(C)C)[C@H]3OCCCNC(=O)CN(C)C)[C@](C)(O)C[C@@H](C)CN(C)C(=O)C[C@@H]3CCCN3C(=O)[C@@H]2C)O[C@@H](C)[C@@H]1O] | 842.14 | I-A1-iii-6 | CY-4G-2 (using Fmoc-L-beta-homoPro-OH); CY-4I-2; CY-1.1 |
| 240 | 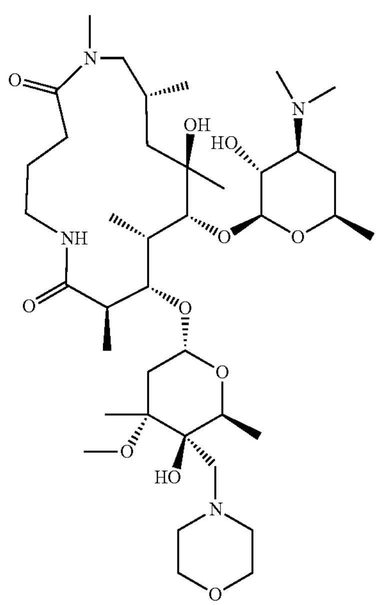 | 773.03 | I-A1-iii-11 | CY-4G-2 (using 4-(Fmoc-amino)butyric acid); CY-4I-2; CY-1.1 |

-continued

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 241 | 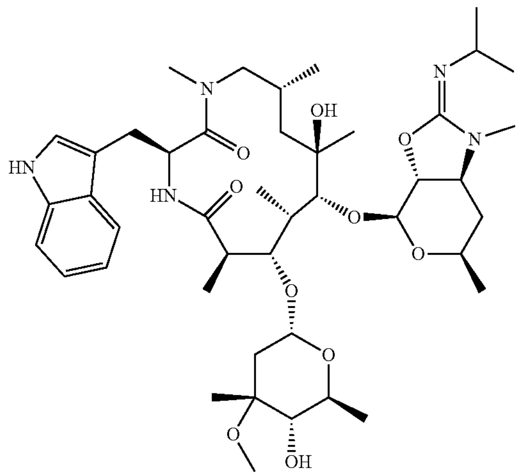 [SMILES: CO[C@]1(C)C[C@H](O[C@H]2[C@H](C)[C@@H](O[C@@H]3O[C@H](C)C[C@H]4[C@H]3O/C(=N/C(C)C)N4C)[C@](C)(O)C[C@@H](C)CN(C)C(=O)[C@H](Cc3c[nH]c4ccccc34)NC(=O)[C@@H]2C)O[C@@H](C)[C@@H]1O] | 828.05 | I-A1-iii-9 | CY-4G-2 (using 4-Fmoc-aminobutiric acid), CY-4I-2 and CY-1.1 |
| 242 | 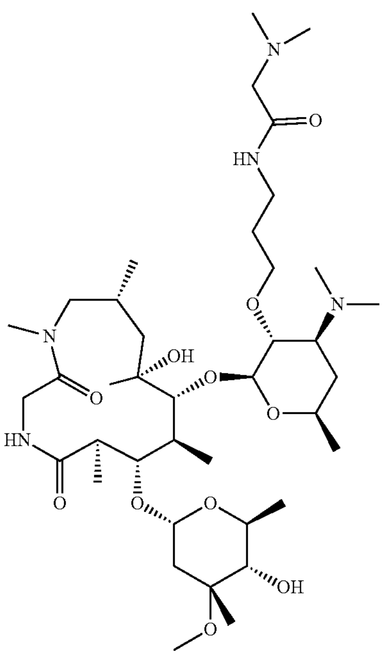 | 788.04 | I-A1-iii-6 | CY-4G-2 (using Fmoc-beta-glicine); CY-4I-2; CY-1.1 |

Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 243 | 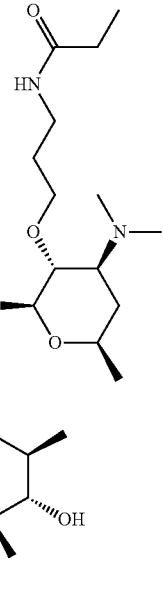 | 888.16 | I-A1-iii-3 | CY-4G-2 (using Fmoc-Trp-OH); CY-4I-2 and CY-1.1 |
| 244 | 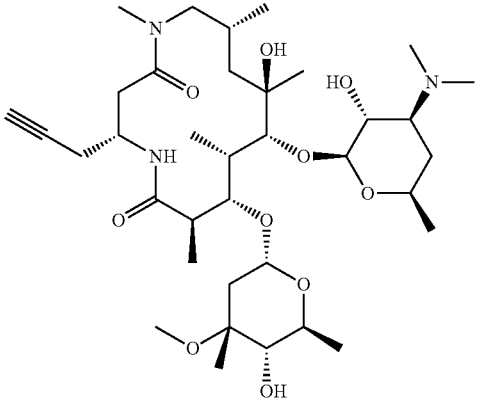 [SMILES: C#CC[C@@H]1CC(=O)N(C)C[C@H](C)C[C@@](C)(O)[C@H](O[C@@H]2O[C@H](C)C[C@H](N(C)C)[C@H]2O)[C@@H](C)[C@H](O[C@H]2C[C@@](C)(OC)[C@@H](O)[C@H](C)O2)[C@@H](C)C(=O)N1] | 697.92 | I-A1-iii-1 | CY-4G-2, using Fmoc-(R)-3-amino-5-hexanoic acid; CY-4I-2, CY-1.1 |
| 245 | 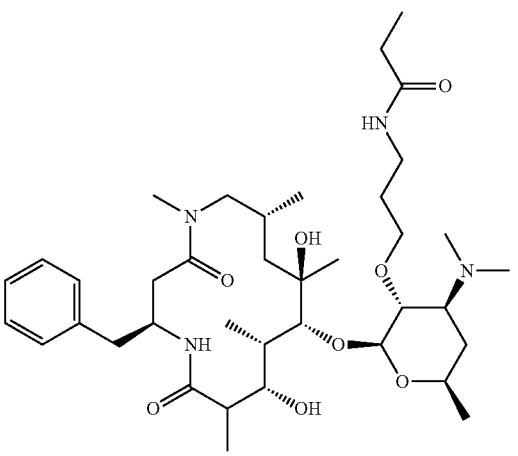 [SMILES: CCC(=O)NCCCO[C@H]1[C@H](O[C@@H]2[C@@H](C)[C@H](O)C(C)C(=O)N[C@@H](Cc3ccccc3)CC(=O)N(C)C[C@H](C)C[C@@]2(C)O)O[C@H](C)C[C@@H]1N(C)C] | 704.96 | I-A1-iii-3 | CY-4G-2 (using Fmoc-L-beta-homoleucine); CY-4I-2; CY-1.1 and KA2 |

Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 246 | 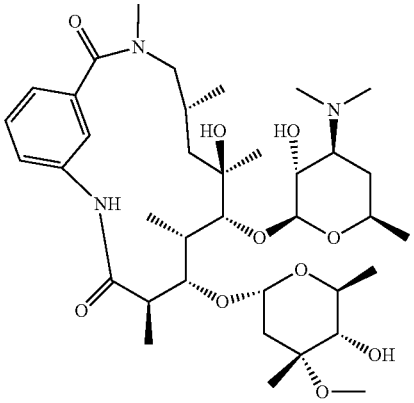 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)c3cccc(c3)NC(=O)[C@@H]2C)O[C@@H](C)[C@@H]1O] | 707.91 | I-B1-iii-1 | CY-4G-2 (using 3-(Fmoc-amino)benzoic acid), CY-4I-1 and CY-1.1 |
| 247 | 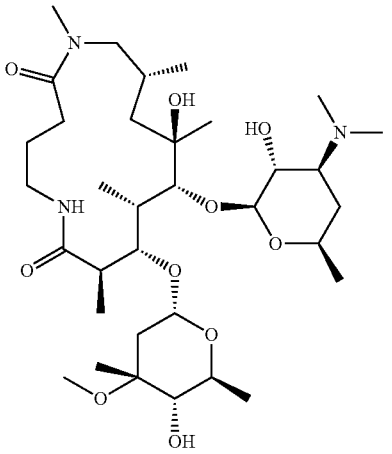 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)CCCNC(=O)[C@@H]2C)O[C@@H](C)[C@@H]1O] | 673.90 | I-B1-iii-1 4˘Ac | CY-4G-2 (using 4-(Fmoc-amino)butiric acid), CY-4I-1 and CY-1.1 |
| 248 | 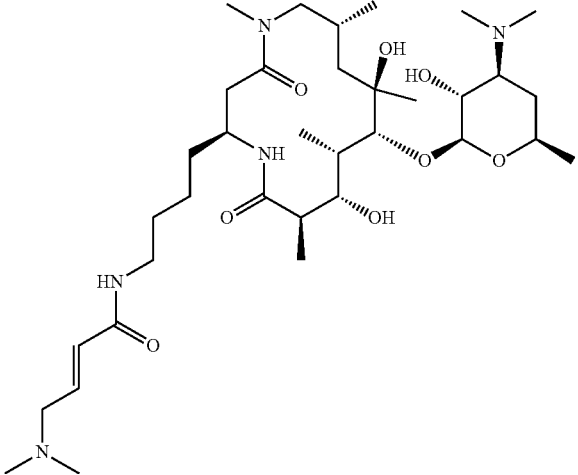 | 683.94 | 16 | CY-4G-1 (using (E)-4-(dimethylamino)but-2-enonic acid) |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 249 | 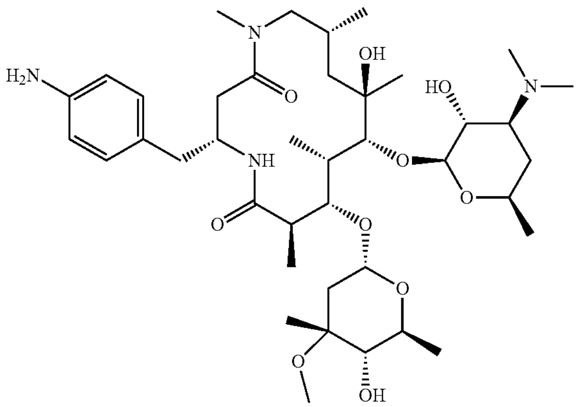 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C[C@@H](Cc3ccc(N)cc3)NC(=O)[C@@H]2C)O[C@@H](C)[C@@H]1O] | 765.03 | 250 | KJ. |
| 250 | 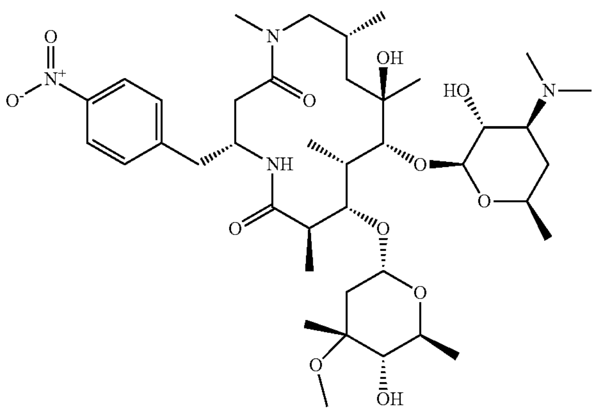 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)C[C@@H](Cc3ccc([N+](=O)[O-])cc3)NC(=O)[C@@H]2C)O[C@@H](C)[C@@H]1O] | 794.99 | I-A1-iii-1 | CY-4G-2 (using Fmoc-(R)-3-amino-4-(4-nitrophenyl butyric acid), CY-4I-2 and CY-1.1 |
| 251 | 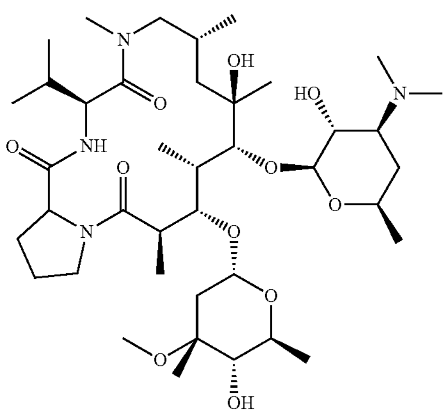 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)[C@H](C(C)C)NC(=O)C3CCCN3C(=O)[C@@H]2C)O[C@@H](C)[C@@H]1O] | 785.0 | I-A1-iii-1 | CY-4G-2 (using Fmoc-L-Val-OH), CY-4I-1, CY-4G-2 (using Fmoc-D-Pro-OH), CY-4I-2 and CY-1.1 |
| 252 | 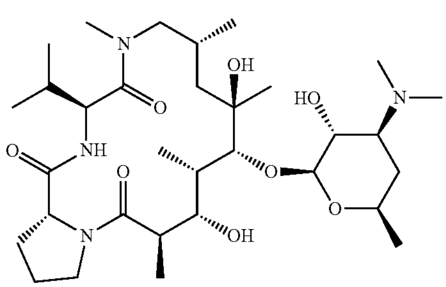 [SMILES: CC(C)[C@@H]1NC(=O)[C@H]2CCCN2C(=O)[C@H](C)[C@@H](O)[C@H](C)[C@@H](O[C@@H]2O[C@H](C)C[C@H](N(C)C)[C@H]2O)[C@](C)(O)C[C@@H](C)CN(C)C1=O] | 626.8 | 251 | KA2 |

Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 253 | 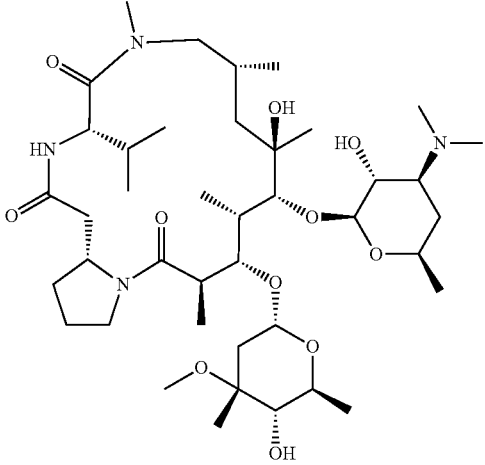 | 799.0 | I-A1-iii-1 | CY-4G-2 (using Fmoc-L-Val-OH), CY-4I-1, CY-4G-2 (using Fmoc-D-beta-homoPro-OH), CY-4I-2 and CY-1.1 |
| 254 | 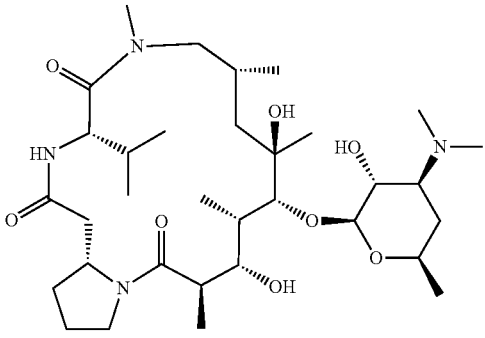 [SMILES: CC(C)[C@@H]1NC(=O)C[C@H]2CCCN2C(=O)[C@H](C)[C@@H](O)[C@H](C)[C@@H](O[C@@H]2O[C@H](C)C[C@H](N(C)C)[C@H]2O)[C@](C)(O)C[C@@H](C)CN(C)C1=O] | 640.8 | 253 | KA2 |
| 255 | 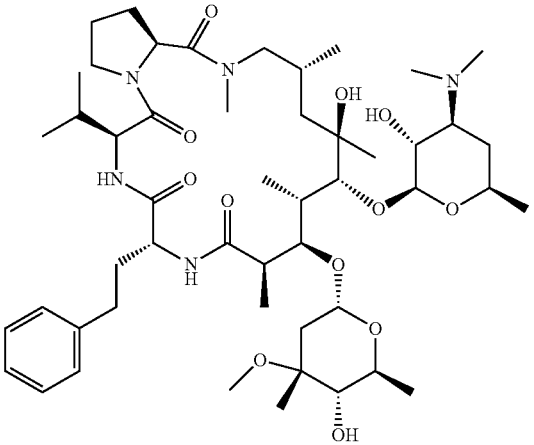 [SMILES: CO[C@]1(C)C[C@H](O[C@@H]2[C@H](C)[C@@H](O[C@@H]3O[C@H](C)C[C@H](N(C)C)[C@H]3O)[C@](C)(O)C[C@@H](C)CN(C)C(=O)[C@@H]3CCCN3C(=O)[C@H](C(C)C)NC(=O)[C@@H](CCc3ccccc3)NC(=O)[C@@H]2C)O[C@@H](C)[C@@H]1O] | 946.22 | I-A1-iii-1 | CY-4G-2 (using Fmoc-L-Pro-OH), CY-4I-1, CY-4G-2 (using Fmoc-L-Val-OH), CY-4I-1, CY-4G-2 (using Fmoc-D-homphenylalanine), CY-4I-2 and CY-1.1 |

Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 256 | 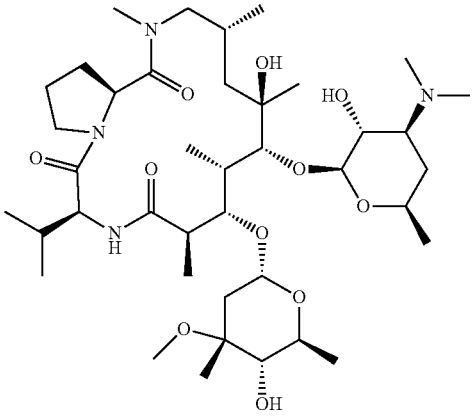 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)[C@@H]3CCCN3C(=O)[C@H](C(C)C)NC(=O)[C@@H]2C)O[C@@H](C)[C@@H]1O] | 785.02 | I-A1-iii-1 | CY-4G-2 (using Fmoc-L-Pro-OH), CY-4I-1, CY-4G-2 (using Fmoc-L-Val-OH), CY-4I-1, CY-4I-2 and CY-1.1 |
| 257 | 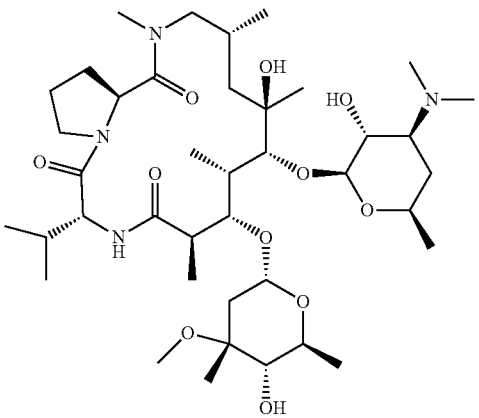 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)[C@@H]3CCCN3C(=O)[C@@H](C(C)C)NC(=O)[C@@H]2C)O[C@@H](C)[C@@H]1O] | 785.02 | I-A1-iii-1 | CY-4G-2 (using Fmoc-L-Pro-OH), CY-4I-1, CY-4G-2 (using Fmoc-D-Val-OH), CY-4I-1, CY-4I-2 and CY-1.1 |
| 258 | 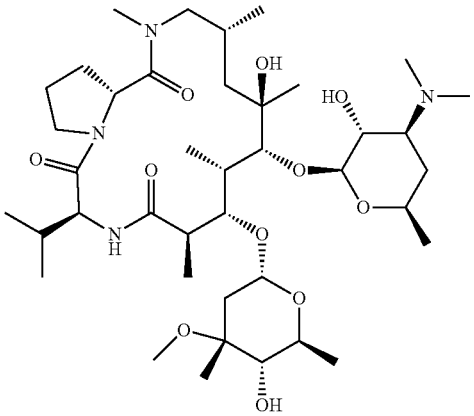 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)[C@H]3CCCN3C(=O)[C@H](C(C)C)NC(=O)[C@@H]2C)O[C@@H](C)[C@@H]1O] | 785.02 | I-A1-iii-1 | CY-4G-2 (using Fmoc-D-Pro-OH), CY-4I-1, CY-4G-2 (using Fmoc-L-Val-OH), CY-4I-1, CY-4I-2 and CY-1.1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 259 | 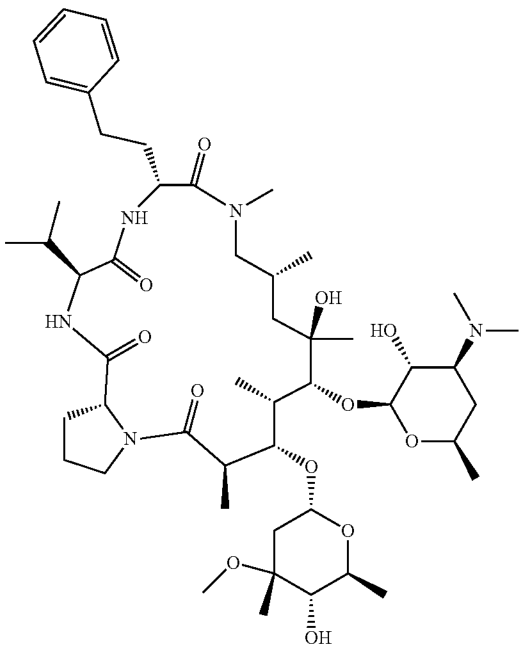 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)[C@@H](CCc3ccccc3)NC(=O)[C@H](C(C)C)NC(=O)[C@H]3CCCN3C(=O)[C@@H]2C)O[C@@H](C)[C@@H]1O] | 946.2 | I-A1-iii-1 | CY-4G-2 (using Fmoc-D-homoPhe-OH), CY-4I-1, CY-4G-2 (using Fmoc-L-Val-OH), CY-4I-1, CY-4G-2 (using Fmoc-D-Pro-OH), CY-4I-2 and CY-1.1 |
| 260 | 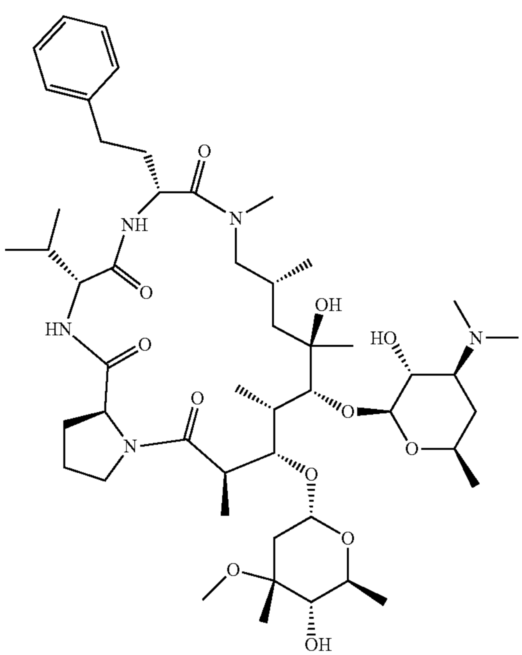 [SMILES: CO[C@]1(C)C[C@H](O[C@H]2[C@H](C)[C@@H](O[C@@H]3O[C@H](C)C[C@H](N(C)C)[C@H]3O)[C@](C)(O)C[C@@H](C)CN(C)C(=O)[C@@H](CCc3ccccc3)NC(=O)[C@@H](C(C)C)NC(=O)[C@@H]3CCCN3C(=O)[C@@H]2C)O[C@@H](C)[C@@H]1O] | 946.2 | I-A1-iii-1 | CY-4G-2 (using Fmoc-D-homoPhe-OH), CY-4I-1, CY-4G-2 (using Fmoc-D-Val-OH), CY-4I-1, CY-4G-2 (using Fmoc-L-Pro-OH), CY-4I-2 and CY-1.1 |

Table with Representative Compounds of Macrolide Based Macrocycles of Formula (III):
| Cpd # (III) | Structure | MS (m/z, ES+) | Starting Cpd# | Sequence of Methods |
|---|---|---|---|---|
| 261 | 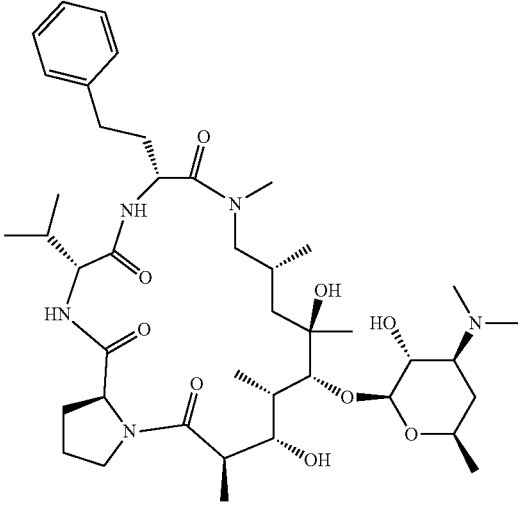 [SMILES: CC(C)[C@H]1NC(=O)[C@@H]2CCCN2C(=O)[C@H](C)[C@@H](O)[C@H](C)[C@@H](O[C@@H]2O[C@H](C)C[C@H](N(C)C)[C@H]2O)[C@](C)(O)C[C@@H](C)CN(C)C(=O)[C@@H](CCc2ccccc2)NC1=O] | 788.0 | 260 | KA2 |
| 262 | 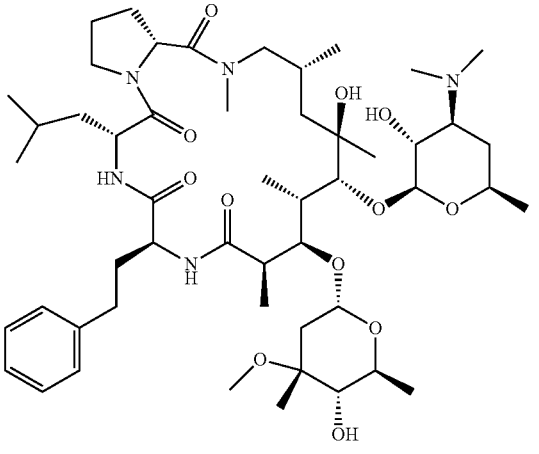 [SMILES: CO[C@]1(C)C[C@H](O[C@@H]2[C@H](C)[C@@H](O[C@@H]3O[C@H](C)C[C@H](N(C)C)[C@H]3O)[C@](C)(O)C[C@@H](C)CN(C)C(=O)[C@H]3CCCN3C(=O)[C@@H](CC(C)C)NC(=O)[C@H](CCc3ccccc3)NC(=O)[C@@H]2C)O[C@@H](C)[C@@H]1O] | 960.2 | I-A1-iii-1 | CY-4G-2 (using Fmoc-D-Pro-OH), CY-4I-1, CY-4G-2 (using Fmoc-L-Leu-OH), CY-4I-1, CY-4G-2 (using Fmoc-D-homoPhe-OH), CY-4I-2 and CY-1.1 |
| 263 | 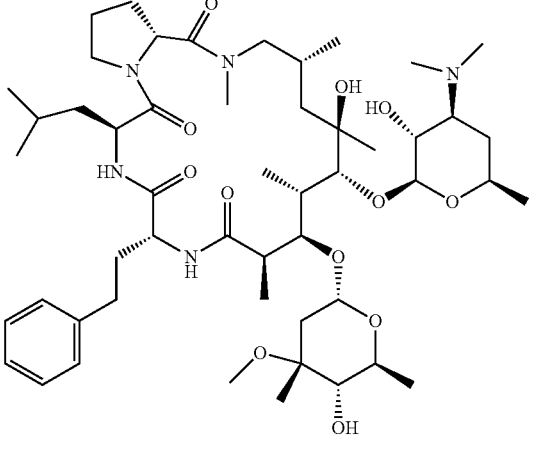 [SMILES: CO[C@]1(C)C[C@H](O[C@@H]2[C@H](C)[C@@H](O[C@@H]3O[C@H](C)C[C@H](N(C)C)[C@H]3O)[C@](C)(O)C[C@@H](C)CN(C)C(=O)[C@H]3CCCN3C(=O)[C@H](CC(C)C)NC(=O)[C@@H](CCc3ccccc3)NC(=O)[C@@H]2C)O[C@@H](C)[C@@H]1O] | 960.2 | I-A1-iii-1 | CY-4G-2 (using Fmoc-D-Pro-OH), CY-4I-1, CY-4G-2 (using Fmoc-L-Leu-OH), CY-4I-1, CY-4G-2 (using Fmoc-L-homoPhe-OH), CY-4I-2 and CY-1.1 |

Table with Representative Compounds of Macrolide Based Macrocycles of Formula (III):

| Cpd # (III) | Structure | MS (m/z, ES+) | Starting Cpd# | Sequence of Methods |
|---|---|---|---|---|
| 264 | 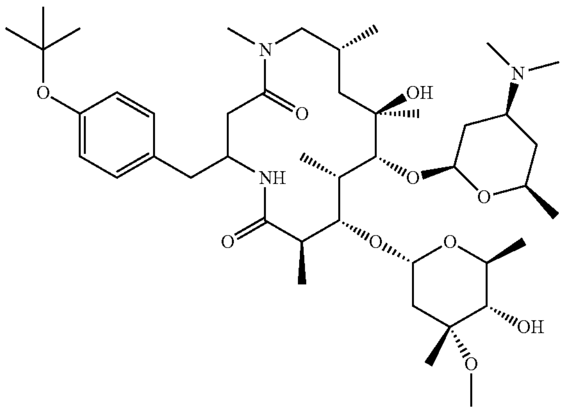 [SMILES: CO[C@]1(C)C[C@H](O[C@H]2[C@H](C)[C@@H](O[C@H]3C[C@@H](N(C)C)C[C@@H](C)O3)[C@](C)(O)C[C@@H](C)CN(C)C(=O)CC(Cc3ccc(OC(C)(C)C)cc3)NC(=O)[C@@H]2C)O[C@@H](C)[C@@H]1O] | 806.48 | I-A1-iii-16 | CY-4G-2 (using N-Fmoc-(S)-3-Amino-4-(4-tert-butoxy-phenyl)-butyric acid), CY-4I-1 and CY-1.1 |
| 265 | 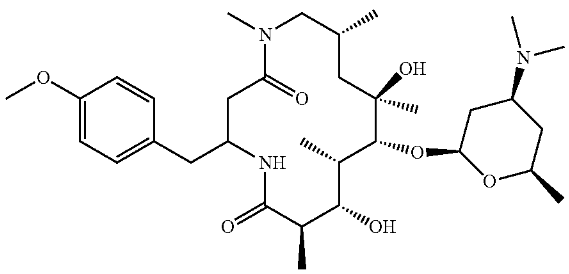 | 592.58 | I-A1-iii-16 | CY-4H-1 (using N-Boc-3-Amino-4-(4-methoxy-phenyl)-butyraldehyde), CY-4I-2, CY-4I-4 and CY-1.1 |
| 266 | 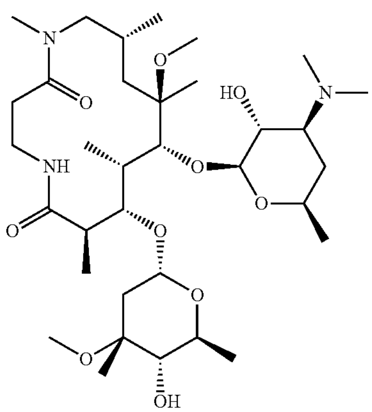 [SMILES: CO[C@]1(C)C[C@@H](C)CN(C)C(=O)CCNC(=O)[C@H](C)[C@@H](O[C@H]2C[C@@](C)(OC)[C@@H](O)[C@H](C)O2)[C@H](C)[C@H]1O[C@@H]1O[C@H](C)C[C@H](N(C)C)[C@H]1O] | 674.55 | I-A1-iii-17 | CY-4G-2 (using N-Fmoc-β-alanine, CY-4I-2, and CY-1.1 |

MS Ms'd = Measured molecular weight by mass spectrometry

Table with NMR Data of Representative Compounds of Formula (I):

| Cpd# | δ NMR Data |
|---|---|
| 1 | $^{13}$C NMR (151 MHz, DMSO-d6): δ = 9.4 (4Me), 14.6 (2Me), 18.3 (5"Me), 21.0 (3"Me), 21.3 (5'Me), 21.3 (8Me), 26.0 (6Me), 27.1 (8), 30.1 (4'), 34.8 (2"), 35.9 (12), 36.2 (11), 39.5 (7), 40.2 (4, 3'NMe, 3'NMe), 44.9 (2), 47.3 (9), 48.7 (3"OMe), 64.3 (3'), 64.6 (5"), 67.1 (5), 70.5 (2'), 72.7 (3"), 74.4 (6), 77.5 (4"), 78.1 (3), 82.2 (5), 95.1 (1"), 101.9 (1'), 169.3 (10), 175.8 (1) ppm. |
| 2 | $^{13}$C NMR (126 MHz, DMSO-d6): δ = 9.9 (4Me), 15.2 (2Me), 18.1 (5"Me), 21.0 (8Me, 5'Me, 3"Me), 26.9 (6Me), 29.8 (4'), 34.8 (2"), 36.0 (9NMe), 37.8 (7), 38.5 (4), 40.2 (14), 45.5 (2), 47.0 (12), 48.7 (3"OMe), 64.6 (5"), 67.2 (5), 69.9 (2'), 72.6 (3"), 74.5 (6), 77.6 (4"), 78.3 (3), 82.8 (5), 96.1 (1"), 102.8 (1'), 119.2 (18), 130.9 (19, 17), 131.5 (20, 16), 138.0 (15), 169.5 (10), 176.0 (1) ppm. |

-continued

Table with NMR Data of Representative Compounds of Formula (I):

| Cpd# | δ NMR Data |
|---|---|

3  $^{13}$C NMR (151 MHz, DMSO-d6): δ = 9.4 (4Me), 16.5 (2Me), 17.7 (5"Me), 20.6 (3'Me), 20.7 (24), 21.2 (8Me), 21.4 (5'Me), 23.8 (8), 26.5 (12), 27.4 (6Me), 30.1 (4'), 35.0 (2"), 36.1 (7), 38.5 (4), 40.0 (9NMe), 40.2 (3'NMe, 3'NMe), 46.7 (2), 49.1 (3"OMe), 49.6 (11), 57.7 (9), 62.3 (5"), 64.7 (3'), 67.6 (5'), 70.6 (2'), 72.3 (3"), 74.9 (6), 78.2 (4"), 78.3 (3), 82.3 (5), 96.1 (1"), 103.0 (1'), 110.7 (13), 111.3 (17), 118.3 (19), 118.5 (20), 120.8 (18), 123.6 (14), 127.5 (21), 136.1 (16), 170.4 (10), 170.5 (23), 173.5 (1) ppm.

4  $^{13}$C NMR (151 MHz, DMSO-d6): δ = 7.5 (4Me), 13.8 (2Me), 18.9 (11Me), 19.8 (8Me), 20.4 (5'Me), 26.8 (6Me), 27.7 (8), 29.8 (4'), 36.1 (4), 39.8 (3'NMe, 3'NMe), 41.6 (11), 42.6 (7), 44.5 (2), 44.9 (9NMe), 64.0 (3'), 65.7 (10), 67.7 (9), 68.3 (5), 69.8 (2'), 73.1 (6), 76.0 (3), 90.8 (5), 104.7 (1'), 173.9 (1) ppm.

5  $^{1}$H NMR (600 MHz, DMSO-d6): δ = 0.88 (d, J = 7.2 Hz, 3 H, 4Me), 0.92 (d, J = 6.6 Hz, 3 H, 8Me), 1.06 (d, J = 6.8 Hz, 3 H, 2Me), 1.13 (s, 3 H, 6Me), 1.16 (d, J = 6.1 Hz, 3 H, 5'Me), 1.17-1.23 (m, J = 12.5, 11.6, 11.6 Hz, 1 H, 4'<AX>), 1.20 (dd, J = 14.0, 7.5 Hz, 1 H, 7<">), 1.54 (qd, J = 6.8, 3.1 Hz, 1 H, 8), 1.68 (ddd, J = 12.8, 4.2, 2.0 Hz, 1 H, 4'<EQ>), 1.72 (dd, J = 14.7, 1.5 Hz, 1 H, 7<'>), 1.91-1.98 (m, J = 12.7, 10.3 Hz, 1 H, 9<">), 2.01 (dd, J = 12.0, 2.9 Hz, 1 H, 9<'>), 2.04 (qd, J = 7.0, 3.3 Hz, 1 H, 4), 2.15 (br. s., 1 H, 10<">), 2.18 (s, 3 H, 9aNMe), 2.23-2.30 (m, J = 13.8, 10.6, 6.8 Hz, 1 H, 2), 2.25-2.28 (m, 6 H, 3'NMe, 3'NMe), 2.55 (ddd, J = 12.1, 10.1, 4.2 Hz, 1 H, 3'<AX>), 2.77 (t, J = 10.3 Hz, 1H, 10<'>), 2.97 (dddd, J = 13.9, 8.6, 5.9, 2.6 Hz, 1 H, 11<">), 3.16 (dd, J =1 0.0, 7.4 Hz, 1 H, 2'<AX>), 3.19 (dddd, J = 12.0, 8.8, 6.2, 2.8 Hz, 1 H, 11<'>), 3.59 (d, J = 3.5 Hz, 1 H, 5), 3.62 (dd, J = 10.4, 4.3 Hz, 2 H, 5'<AX>, 3), 4.29 (d, J = 7.3 Hz, 1 H, 1'<AX>), 4.35 (d, J = 3.1 Hz, 1 H, 3OH), 4.56 (br. s., 1 H,), 5.08 (br. s., 1 H,), 7.37 (br. s., J = 2.5, 2.5 Hz, 1 H, 12) ppm.

6  $^{13}$C NMR (151 MHz, DMSO-d6): δ = 8.7 (4Me), 13.9 (2Me), 20.7 (8Me), 21.0 (5'Me), 26.9 (11), 27.0 (6Me), 27.2 (8), 30.3 (4'), 38.2 (4), 38.9 (2), 40.4 (3'NMe, 3'NMe), 45.1 (9aNMe), 50.2 (12), 51.1 (14), 57.4 (10), 64.4 (3'), 68.6 (5), 68.6 (9), 70.2 (2'), 73.8 (6), 75.8 (3), 89.5 (5), 103.8 (1'), 174.8 (1) ppm.

7  $^{13}$C NMR (126 MHz, DMSO-d6): δ = 7.9 (4Me), 15.3 (2Me), 20.7 (5'Me), 21.0 (8Me), 21.9 (15), 26.8 (16), 28.0 (6Me, 8), 29.8 (4'), 31.0 (11), 37.9 (4), 40.3 (3'NMe, 3'NMe), 40.4 (2), 43.1 (12), 44.2 (9NMe), 44.4 (7), 45.8 (14), 57.4 (10), 63.7 (3'), 69.2 (5), 69.9 (2'), 70.1 (9), 73.9 (6), 76.5 (3), 93.3 (5), 105.9 (1'), 173.6 (1) ppm.

8  $^{13}$C NMR (126 MHz, DEUTERIUM OXIDE): δ = 7.2 (4Me), 14.5 (2Me), 19.7 (5'Me), 20.1 (8Me), 22.1 (15), 26.6 (16), 27.0 (6Me), 27.1 (8), 29.8 (4'), 30.8 (11), 37.9 (4), 39.1 (2), 39.4 (3'NMe, 3'NMe), 43.2 (9NMe), 43.9 (7), 45.0 (14), 47.3 (12), 56.3 (10), 63.5 (3'), 69.3 (9), 70.2 (2'), 70.6 (5), 75.8 (6), 78.0 (3), 93.4 (5), 105.9 (1'), 175.6 (1) ppm.

9  $^{13}$C NMR (126 MHz, DMSO-d6): δ = 8.0 (4Me), 15.4 (2Me), 20.6 (8Me), 20.7 (5'Me), 27.5 (6Me, 8), 30.2 (4'), 33.0 (11), 36.8 (4), 40.3 (3'NMe, 3'NMe), 42.9 (9NMe), 43.5 (7), 44.5 (2), 48.4 (12), 52.8 (10), 63.7 (3'), 68.5 (9), 68.9 (5), 69.7 (2'), 73.7 (6), 76.5 (3), 92.0 (5), 105.0 (1'), 114.0 (15), 138.8 (14), 174.1 (1) ppm.

10  $^{13}$C NMR (151 MHz, DMSO-d6): δ = 9.4 (4Me), 14.6 (2Me), 17.9 (5"Me), 20.9 (8Me), 21.0 (3"Me), 21.0 (5'Me), 25.4 (6Me), 25.7 (8), 31.4 (4'), 33.8 (15), 35.2 (2"), 35.5 (12), 36.4 (9NMe), 36.8 (14), 39.0 (7), 39.9 (4), 40.4 (3'NMe, 3'NMe), 41.3 (2), 42.4 (13), 48.9 (3"OMe), 56.0 (9), 64.1 (3'), 65.3 (5"), 67.7 (5'), 71.0 (2'), 72.5 (3"), 73.8 (6), 77.3 (4"), 79.7 (3), 85.4 (5), 96.0 (1"), 102.9 (1'), 115.4 (18, 20), 126.6 (21, 17), 141.3 (16), 160.4 (19), 172.9 (10), 174.7 (1) ppm.

11  $^{13}$C NMR (151 MHz, DMSO-d6): δ = 8.0 (4Me), 8.3 (4Me), 15.4 (2Me), 16.5 (2Me), 18.8 (8Me), 19.4 (8Me), 20.7 (5'Me), 20.9 (5'Me), 22.1 (15), 22.5 (15), 23.0 (16), 23.1 (16), 24.7 (6Me), 26.1 (8), 28.1 (6Me), 29.5 (4'), 30.1 (4'), 31.0 (8), 34.5 (9NMe), 36.3 (4), 36.9 (17), 37.4 (17), 37.5 (4), 37.8 (14), 38.2 (9NMe), 38.2 (14), 38.5(11), 39.5 (7), 39.6(11), 40.1 (3'NMe, 3'NMe), 40.3 (3'NMe, 3'NMe), 42.5 (7), 44.1 (2), 53.2 (9), 58.0 (9), 61.5 (12), 61.9 (12), 63.7 (3'), 64.2 (3'), 68.7 (5), 69.2 (5), 69.6 (2'), 69.9 (2'), 71.7 (6), 74.0 (6), 75.4 (3), 76.7 (3), 94.3 (5), 105.0 (1'), 106.0 (1'), 170.2 (10), 170.5 (10), 175.1 (1) ppm.

12  $^{13}$C NMR (151 MHz, DMSO-d6): δ = 9.3 (4Me), 14.1 (2Me), 17.7 (5"Me), 20.3 (8Me), 20.7 (5'Me, 3"Me), 25.6 (6Me), 26.0 (8), 30.1 (4'), 34.8 (2"), 35.6 (9NMe), 38.0 (7), 39.5 (11), 39.8 (3'NMe, 3'NMe), 40.0 (14), 40.0 (4), 45.2 (2), 46.6 (12), 48.4 (3"OMe), 55.0 (9), 63.9 (3'), 64.5 (5"), 67.2 (5'), 70.4 (2'), 72.3 (3"), 73.9 (6), 77.2 (4"), 78.0 (3), 83.4 (5), 95.3 (1"), 102.0 (1'), 125.7 (18), 127.3 (16), 128.5 (20), 129.3 (19), 132.4 (17), 140.9 (15), 169.2 (10), 174.5 (1) ppm.

13  $^{13}$C NMR (151 MHz, DMSO-d6): δ = 8.3 (4Me), 15.1 (2Me), 15.4 (2Me), 18.7 (8Me), 20.5 (5'Me), 20.9 (8Me), 25.5 (6Me), 27.9 (6Me), 29.4 (4'), 29.9 (4'), 31.2 (8), 37.2 (4, 9NMe), 38.3 (14), 40.3 (3'NMe, 3'NMe), 42.1 (7), 43.9 (2), 44.5 (2), 48.3 (12), 57.9 (9), 63.9 (3'), 68.7 (5), 68.9 (5), 69.8 (2'), 73.5 (6), 75.4 (3), 75.9 (3), 94.3 (5), 104.8 (1'), 105.7 (1'), 125.6 (18), 127.7 (16), 128.9 (20), 129.8 (19), 131.4 (17), 141.5 (15), 142.5 (15), 170.6 (10), 174.6 (1) ppm.

14  $^{13}$C NMR (151 MHz, DMSO-d6): δ = 10.4 (4Me), 15.2 (2Me), 18.1 (5"Me), 20.9 (3"Me), 21.2 (8Me), 21.3 (5'Me), 25.0 (8), 26.3 (6Me), 29.8 (4'), 35.0 (2"), 35.6 (9NMe), 36.3 (7), 38.1 (4), 40.4 (3'NMe, 3'NMe), 40.6 (2), 47.0 (11), 48.7 (3"OMe), 52.5 (13), 53.8 (9), 64.2 (3'), 64.5 (5"), 67.5 (5'), 70.6 (2'), 72.6 (3"), 75.3 (6), 77.7 (4"), 80.6 (3), 82.4 (5), 96.7 (1"), 102.8 (1'), 115.5 (16, 16), 128.9 (15, 15), 133.3 (14), 161.1 (17), 169.2 (10), 177.0 (1) ppm.

15  $^{13}$C NMR (126 MHz, DMSO-d6): δ = 9.4 (4Me), 14.5 (2Me), 18.1 (5"Me), 21.0 (3"Me), 21.2 (8Me, 5'Me), 23.1 (15), 25.3 (6Me), 26.6 (8), 28.2 (22, 23, 21), 29.1 (16), 30.4 (4'), 34.7 (2"), 35.1 (9NMe), 35.2 (11), 39.9 (17), 40.4 (3'NMe, 3'NMe), 45.5 (2), 48.6 (3"OMe), 49.5 (12), 54.2 (9), 64.1 (3'), 64.8 (5"), 67.4 (5), 70.8 (2'), 72.6 (3"), 74.8 (6), 77.1 (20), 77.4 (4"), 81.2 (5), 95.0 (1"), 102.3 (1'), 155.5 (19), 170.7 (10), 175.5 (1) ppm.

-continued

Table with NMR Data of Representative Compounds of Formula (I):

| Cpd# | δ NMR Data |
|---|---|
| 16 | $^{13}$C NMR (126 MHz, DMSO-d6): δ = 7.6 (4Me), 7.9 (4Me), 15.5 (2Me), 16.1 (2Me), 18.6 (8Me), 19.4 (8Me), 20.7 (5'Me), 20.9 (5'Me), 23.7 (15), 25.3 (6Me), 27.0 (8), 27.9 (6Me), 29.6 (4'), 30.3 (4'), 31.1 (8), 31.2 (14), 32.7 (16), 32.9 (16), 34.0 (9NMe), 35.0 (11), 35.6 (4), 37.0 (4), 37.8 (9NMe), 40.3 (3'NMe, 3'NMe), 40.4 (3'NMe, 3'NMe), 41.6 (17), 42.3 (7), 44.5 (2), 45.9 (2), 49.0 (12), 57.8 (9), 63.9 (3'), 64.2 (3'), 68.8 (5'), 69.2 (5'), 69.7 (2'), 70.0 (2'), 71.0 (3), 71.9 (3), 94.8 (5), 105.0 (1'), 106.0 (1'), 170.9 (10), 174.0 (1), 174.9 (1) ppm. |
| 17 | $^{13}$C NMR (126 MHz, DMSO-d6): δ = 8.0 (4Me), 15.2 (2Me), 20.4 (8Me), 20.8 (5'Me), 25.0 (8), 27.4 (6Me), 30.1 (4'), 33.4 (11), 36.6 (4), 39.7 (14), 40.4 (3'NMe, 3'NMe), 42.7 (9NMe), 43.1 (7), 44.5 (2), 48.3 (12), 52.6 (10), 54.7 (19), 63.9 (3'), 66.7 (9), 68.8 (5), 69.9 (2'), 73.8 (6), 76.5 (3), 97.1 (5), 104.9 (1'), 113.4 (17, 17), 129.9 (16, 16), 131.0 (15), 157.5 (18), 174.2 (1) ppm. |
| 18 | $^{13}$C NMR (151 MHz, DMSO-d6): δ = 8.5 (4Me), 9.3 (20), 12.7 (2Me), 17.6 (5''Me), 20.3 (8Me, 5'Me), 20.7 (3''Me), 24.4 (6Me), 26.2 (8), 28.1 (19), 29.8 (15), 29.9 (4'), 31.4 (11), 34.4 (2''), 34.5 (16), 34.6 (9NMe), 34.8 (12), 37.3 (3'NMe), 38.1 (7), 40.0 (4), 42.3 (3'NMe), 43.7 (2), 48.3 (3''OMe), 53.6 (9), 64.4 (3'), 64.7 (5''), 66.4 (5), 68.9 (14), 72.5 (3''), 73.7 (6), 76.5 (2'), 76.9 (4''), 78.1 (3), 82.2 (5), 94.5 (1''), 100.4 (1'), 170.3 (10), 173.8 (18), 175.2 (1) ppm. |
| 19 | $^{13}$C NMR (151 MHz, DMSO-d6): δ = 9.2 (20), 9.1 (4Me), 12.9 (2Me), 14.9 (2Me), 17.6 (5''Me), 20.2 (8Me), 20.6 (3''Me, 5'Me), 23.5 (6Me), 25.9 (8), 27.0 (8), 28.2 (19), 29.6 (15), 31.6 (9NMe), 32.1 (11), 34.3 (9NMe), 34.8 (2'', 16, 12), 38.7 (4), 40.4 (7), 42.9 (2), 44.0 (2), 48.3 (3''OMe), 53.9 (9), 55.0 (9), 64.7 (5''), 67.0 (5), 68.2 (14), 72.4 (3''), 74.2 (6), 77.1 (4''), 78.2 (3), 78.3 (3), 82.4 (5), 95.4 (1''), 101.1 (1'), 101.5 (1'), 174.9 (1) ppm. |
| 20 | $^{13}$C NMR (126 MHz, DMSO-d6): δ = 8.9 (4Me), 10.3 (24), 12.6 (2Me), 18.2 (5'Me), 20.6 (8Me), 20.7 (3''Me), 21.1(5'Me), 24.9 (6Me), 26.6 (8), 29.8 (15), 30.0 (4'), 31.5(11), 34.5 (16, 2''), 34.9 (9NMe), 35.2 (12), 37.2 (3'NMe), 37.5 (7), 40.0 (4), 41.9 (3'NMe), 42.8 (2), 48.6 (3''OMe), 53.7 (9), 64.4 (3'), 64.8 (5''), 66.6 (5), 69.0 (14), 72.8 (3''), 73.9 (6), 76.0 (2'), 77.1 (4''), 78.0 (3), 82.4 (5), 94.5 (1''), 100.6 (1'), 104.1 (23), 140.0 (22), 147.0 (19), 170.6 (10), 175.6 (1) ppm. |
| 21 | $^{13}$C NMR (126 MHz, DMSO-d6): δ = 9.4 (4Me), 10.3 (24), 15.3 (2Me), 18.1 (5'Me), 19.1 (8Me), 20.6 (3''Me), 21.0 (5'Me), 25.0 (6Me), 27.4 (8), 29.7 (4'), 30.0 (15), 32.3 (9NMe), 32.5 (11), 34.4 (16), 35.0 (2''), 35.4 (12), 37.2 (3'NMe), 38.9 (4), 41.5 (7), 42.7 (3'NMe), 43.8 (2), 48.7 (3''OMe), 55.9 (9), 64.4 (3'), 65.0 (5''), 67.0 (5), 68.8 (14), 72.9 (3''), 73.8 (6), 75.9 (2'), 77.2 (4''), 77.9 (3), 82.9 (5), 95.7 (1''), 101.4 (1'), 104.3 (23), 140.0 (22), 170.0 (10), 174.9 (1) ppm. |
| 25 | $^{13}$C NMR (126 MHz, DMSO-d6): δ = 9.9 (4Me), 10.2 (4Me), 14.9 (2Me), 15.2 (2Me), 18.1 (5''Me), 19.2 (8Me), 20.9 (3''Me), 21.1 (5'Me), 26.5 (6Me), 27.7 (8), 31.0 (4'), 32.0 (13, 17), 32.7 (9NMe), 33.3 (12), 33.7 (17, 13), 35.6 (2''), 36.0 (9NMe), 38.3 (11), 39.9 (4, 2), 40.0 (7), 40.3 (3'NMe, 3'NMe), 41.8 (16, 14), 45.5 (16, 14), 48.8 (3''OMe), 56.0 (9), 64.3 (3'), 64.7 (5''), 67.7 (5'), 70.6 (2'), 72.7 (3''), 74.9 (6), 77.6 (4''), 79.7 (3), 80.2 (3), 83.2 (5), 96.1 (1''), 102.7 (1'), 170.9 (10), 172.0 (10), 173.0 (1) ppm. |
| 28 | $^{13}$C NMR (126 MHz, DMSO-d6): δ = 11.8 (4Me), 12.6 (2Me), 18.0 (5'Me), 20.6 (8Me, 5'Me), 21.1 (3''Me), 26.2 (6Me), 27.8 (8), 29.6 (4'), 35.5 (2''), 37.0 (15), 38.5 (9NMe), 40.2 (4), 41.5 (2), 48.7 (3''OMe), 53.3 (13), 55.2 (11), 57.2 (9), 64.1 (5''), 66.1 (5''), 67.3 (5), 68.5 (2'), 73.0 (3''), 74.4 (6), 76.6 (4''), 76.8 (3), 82.9 (5), 91.9 (14), 95.5 (1''), 101.0 (1'), 171.7 (10), 174.7 (1) ppm. |
| 29 | $^{13}$C NMR (151 MHz, DMSO-d6): δ = 7.8 (4Me), 16.7 (2Me), 20.9 (8Me, 5'Me), 23.0 (16), 26.3 (6Me), 26.7 (15), 27.0 (8), 31.1 (4'), 35.2 (11), 37.0 (4), 40.5 (3'NMe, 3'NMe), 43.9 (7), 44.3 (9NMe), 47.3 (2), 58.9 (10), 64.2 (3'), 67.7 (9), 69.0 (5'), 70.5 (2'), 74.3 (6, 3), 90.0 (5), 105.3 (1'), 173.7 (1) ppm. |
| 30 | $^{13}$C NMR (151 MHz, DMSO-d6): δ = 7.8 (4Me), 15.6 (2Me), 20.5 (8Me), 20.9 (5'Me), 21.5 (16), 23.0 (16), 24.4 (15), 26.8 (8), 27.6 (6Me), 30.2 (4'), 34.3 (11), 36.5 (4), 40.3 (3'NMe, 3'NMe), 42.8 (9NMe), 43.2 (14), 43.4 (7), 44.3 (2), 44.6 (12), 52.5 (10), 64.1 (3'), 68.5 (9), 68.9 (5), 70.0 (2'), 73.0 (6), 76.6 (3), 92.2 (5), 104.9 (1'), 174.2 (1) ppm. |
| 31 | $^{13}$C NMR (101 MHz, DMSO-d6): δ = 9.2 (4Me), 14.0 (2Me), 21.0 (5'Me), 21.2 (8Me), 24.8 (8), 25.2 (26), 25.3 (22), 25.4 (6Me), 30.4 (4'), 32.0 (25, 23), 35.6 (9aNMe), 35.9 (7), 35.9 (4), 39.8 (11), 40.0 (21), 40.4 (3'NMe, 3'NMe), 42.4 (2), 53.6 (9), 64.7 (3'), 68.6 (5), 70.3 (2'), 74.5 (6), 78.5 (3), 83.1 (5), 103.3 (1'), 123.6(24), 169.7 (10), 173.6 (20), 173.9 (1) ppm. |
| 32 | $^{13}$C NMR (151 MHz, DMSO-d6): δ = 9.3 (4Me), 12.1 (2Me), 18.0 (5''Me), 20.0 (24), 20.3 (8Me, 3''Me), 20.8 (5'Me), 23.4 (17), 24.0 (18), 27.4 (6Me), 30.1 (4'), 35.1 (2''), 39.9 (3'NMe, 3'NMe), 41.5 (14), 44.4 (2), 45.1 (16), 48.5 (3''OMe), 55.9 (11), 62.1 (5''), 64.5 (3'), 67.0 (5), 70.6 (2'), 71.7 (3''), 75.0 (6), 78.0 (4''), 80.0 (3), 84.0 (5), 96.1 (1''), 103.1 (1'), 169.9 (23), 176.0 (1) ppm. |
| 35 | $^{13}$C NMR (151 MHz, DMSO-d6): δ = 8.0 (4Me), 17.7 (5'Me), 19.2 (8Me), 20.6 (5'Me), 21.1 (3''Me), 24.0 (8), 25.0 (6Me), 28.9 (12), 29.6 (16), 31.8 (4'), 34.0 (9NMe), 34.1 (11), 35.1 (2''), 36.0 (17), 40.3 (3'NMe, 3'NMe), 40.9 (4), 43.8 (2), 44.9 (25), 47.9 (3''OMe), 52.1 (22, 22), 54.0 (23, 23), 61.0 (20), 63.5 (3'), 64.8 (5''), 67.5 (5), 69.0 (15), 72.3 (3''), 73.0 (6), 77.0 (2'), 77.9 (3), 78.8 (4''), 82.4 (5), 168.0 (10), 175.0 (1) ppm. |
| 36 | $^{13}$C NMR (126 MHz, DMSO-d6): δ = 9.0 (4Me), 12.6 (22, 22), 14.5 (2Me), 21.0 (5'Me), 22.3 (8Me), 26.9 (6Me), 28.9 (8), 30.6 (4'), 35.1 (9NMe), 36.2 (4), 40.3 (3'NMe, 3'NMe), 44.8 (2), 47.1 (21, 21), 53.6 (19), 64.3 (3'), 68.5 (5), 70.5 (2'), 74.0 (6), 78.2 (3), 82.9 (5), 102.6 (1'), 122.7 (15), 124.5 (17), 129.4 (16), 136.9 (11), 137.7 (13), 170.3 (10), 171.0 (18), 171.9 (1) ppm. |

Table with NMR Data of Representative Compounds of Formula (I):

| Cpd# | δ NMR Data |
|---|---|
| 39 | $^{13}$C NMR (126 MHz, DMSO-d6): δ = 8.9 (4Me), 16.1 (2Me), 18.3 (5"Me), 20.9 (5'Me), 21.1 (8Me), 30.0 (16), 32.7 (4'), 35.1 (2"), 35.9 (17), 39.0 (4), 39.4 (9NMe), 40.7 (3'NMe, 3'NMe), 45.6 (25), 48.4 (3"OMe), 52.7 (22, 22), 54.4 (23, 23), 57.5 (9), 61.5 (20), 63.4 (3'), 64.7 (5"), 67.4 (5), 70.0 (15), 72.6 (3"), 75.1 (6), 77.6 (4"), 79.2 (3), 80.5 (2'), 82.3 (5), 96.9 (1"), 102.7 (1'), 111.1 (31), 118.1 (33), 118.4 (34), 120.7 (32), 123.5 (28), 127.4 (35), 136.1 (30), 168.8 (19), 170.4 (10) ppm. |
| 41 | $^{13}$C NMR (101 MHz, DMSO-d6): δ = 9.2 (2Me), 11.3 (4Me), 16.7 (5"Me), 19.5 (8Me), 20.1 (3"Me), 20.4 (21), 20.8 (5'Me), 25.0(6Me),28.6 (8)32.0 (4'), 35.2 (2"), 36.7 (9NMe), 37.5 (4), 37.6 (2), 40.0 (3'NMe, 3'NMe), 45.1 (7), 48.2 (3"OMe), 58.3 (9), 62.3 (5"), 63.4 (3'), 68.2 (5'), 71.2 (2'), 72.1 (3"), 73.9 (6), 77.8 (5), 78.0 (4"), 80.6 (3), 97.1 (1"), 99.9 (1'), 125.5 (16), 125.7 (15), 126.5 (13), 128.0 (12), 135.4 (11), 137.9 (14), 169.8 (20), 170.1 (10), 175.5 (1) ppm. |
| 42 | $^{13}$C NMR (151 MHz, MeOD): δ = 8.1, 13.6, 16.5, 18.9, 19.4, 19.9, 20.5, 24.4, 24.6, 30.6, 33.5, 34.4, 36.8, 38.8, 39.7, 39.9, 48.1, 52.9, 62.1, 62.8, 66.1, 70.5, 72.3, 74.3, 75.9, 77.8, 82.3, 93.1, 101.3, 124.7, 125.3, 125.8, 129.7, 136.6, 170.4, 171.1, 179 ppm.<br>$^{13}$C NMR (126 MHz, DMSO-d6): δ = 9.0 (4Me), 9.6 (4Me), 14.5 (2Me), 17.4 (5"), 17.6 (5"Me), 20.6 (21), 20.7 (5'Me), 20.7 (14), 20.8 (3"Me), 20.9 (3"Me), 21.5 (8Me), 25.3 (8Me), 26.3 (6Me), 26.6 (6Me), 30.5 (4'), 31.8 (13), 32.0 (13), 34.3 (2"), 35.0 (9NMe), 35.3 (9NMe), 37.7 (7), 37.9 (7), 40.1 (11), 40.4 (3'NMe, 3'NMe), 42.0 (2, 4), 42.3 (2), 45 43.7 (4), 44.4 (15), 45.4 (15), 48.8 (3"OMe), 49.0 (3"OMe), 53.5 (12), 54.0 (9), 54.7 (12), 55.5 (9), 61.9 (5"), 65.1 (3'), 69.7 (5'), 70.5 (2'), 72.6 (3"), 74.2 (6), 74.9 (6), 75.9 (3), 76.9 (3), 78.3 (4"), 81.9 (5), 82.6 (5), 93.4 (1"), 102.0 (1'), 170.3 (20), 171.0 (10), 174.4 (1), 174.7 (1) ppm. |
| 46 | $^{13}$C NMR (151 MHz, DMSO-d6): δ = 10.3 (4Me), 15.8 (2Me), 17.2 (5"Me), 20.0 (24), 20.4 (3"Me), 20.8 (8Me, 5'Me), 24.8 (8, 6Me), 25.9 (16), 29.3 (14), 30.3 (4'), 33.8 (9NMe), 35.1 (2"), 37.4 (7), 38.1 (4), 40.2 (3'NMe, 3'NMe), 46.1 (13), 46.8 (2), 48.6 (3"OMe), 52.1 (9), 62.3 (5"), 64.1 (3'), 67.2 (5'), 70.4 (2'), 72.3 (3"), 74.6 (6), 78.0 (4"), 80.6 (3), 82.9 (5), 95.8 (1"), 102.3 (1'), 170.5 (23), 174.2 (1), 176.5 (10) ppm. |
| 48 | $^{13}$C NMR (151 MHz, DMSO-d6): δ = 10.0 (4Me), 14.9 (2Me), 18.1 (5"Me), 21.0 (8Me), 21.2 (3"Me, 5'Me), 24.9 (8), 26.3 (6Me), 29.9 (4), 34.8 (2"), 35.8 (9NMe), 36.2 (7), 37.6 (4), 39.9 (11), 40.3 (3'NMe, 3'NMe), 44.6 (2), 48.8 (3"OMe), 53.5 (9), 63.9 (3), 64.3 (5"), 67.5 (5), 70.7 (2), 72.7 (3"), 75.2 (6), 77.7 (4"), 79.4 (3), 82.1 (5), 96.7 (1"), 102.9 (1), 169.6 (10), 176.7 (1) ppm. |
| 49 | $^{13}$C NMR (151 MHz, DMSO-d6): δ = 7.6 (4Me), 14.2 (2Me), 20.0(8Me), 20.7 (5'Me), 24.9 (6Me), 27.7 (8), 29.5 (4), 33.3 (9NMe), 36.7 (4), 40.3 (3'NMe, 3'NMe), 42.5 (7), 45.3 (2), 58.7 (9), 63.9 (3'), 69.1 (5'), 69.7 (2'), 72.9 (6), 78.0 (3), 96.2 (5), 105.7 (1), 119.0 (12), 120.7 (14, 16), 129.2 (15), 137.1 (13), 137.8 (11), 171.1 (10), 174.6 (1) ppm. |
| 51 | $^{13}$C NMR (101 MHz, DMSO-d6): δ = 9.0 (4Me), 15.6 (2Me), 17.9 (5"Me), 20.4 (8Me), 20.6 (5'Me, 3"Me), 23.7 (8), 26.1 (13), 27.3 (6Me), 29.8 (4), 35.2 (2"), 35.6 (7), 38.2 (4), 38.7 (9NMe), 39.8 (3'NMe, 3'NMe), 46.8 (2), 48.5 (3"OMe), 49.2 (11), 57.3 (9), 64.3 (3), 64.7 (5"), 67.3 (5'), 70.5 (2'), 72.3 (3"), 75.0 (6), 77.4 (4"), 78.8 (3), 82.6 (5), 96.6 (1"), 103.0 (1), 110.8 (14, 18), 117.7 (20), 117.9 (21), 120.3 (19), 123.0 (15), 127.3 (22), 135.9 (17), 170.2 (10) ppm. |
| 52 | $^{13}$C NMR (151 MHz, DMSO-d6): δ = 6.7 (4Me), 8.0 (4Me), 13.9 (2Me), 18.7 (8Me), 20.7 (5'Me), 26.3 (6Me), 27.9 (6Me), 28.3 (13, 4), 30.6 (4), 31.6 (8), 35.5 (4), 36.5 (4), 37.5 (9NMe), 38.9 (9NMe), 40.3 (3'NMe, 3'NMe), 40.5 (3'NMe, 3'NMe), 43.3 (7), 44.3 (2), 47.7 (2), 50.0 (11), 56.3 (9), 56.9 (9), 63.9 (3), 68.2 (5), 69.2 (2), 70.1 (2), 75.9 (3), 78.8 (3), 94.4 (5), 106.5 (1'), 111.1 (18), 118.0 (20), 118.6 (21), 120.7 (19), 123.6 (15), 169.5 (10), 170.2 (10), 173.1 (1) ppm. |
| 53 | $^{13}$C NMR (151 MHz, DMSO-d6): δ = 9.2 (4Me), 12.7 (15, 15), 14.1 (2Me), 21.1 (8Me), 21.2 (5'Me), 24.8 (8), 25.4 (6Me), 30.4 (4), 35.6 (9NMe), 35.8 (4), 36.0 (7), 39.4 (11), 40.4 (3'NMe, 3'NMe), 42.0 (2), 46.9 (14, 14), 53.4 (17), 53.6 (9), 64.5 (3), 68.4 (5'), 70.2 (2), 74.5 (6), 78.0 (3), 83.3 (5), 103.4 (1), 169.6 (10), 170.9 (18), 174.1 (1) ppm. |
| 54 | $^{13}$C NMR (151 MHz, DMSO-d6): δ = 9.1 (4Me), 13.9 (2Me), 21.1 (5'Me), 21.2 (8Me), 24.8 (8), 25.5 (6Me), 28.8 (15, 15), 30.5 (4), 35.6 (4, 9NMe), 35.9 (7), 39.5 (4, 11), 40.5 (3'NMe, 3'NMe), 42.4 (2), 53.5 (9), 64.6 (3), 66.1 (16, 16), 68.5 (5), 70.2 (2), 74.5 (6), 77.9 (3), 83.1 (5), 103.2 (1), 169.6 (10), 173.7 (13), 174.0 (1) ppm. |
| 55 | $^{13}$C NMR (151 MHz, DMSO-d6): δ = 9.1 (4Me), 14.3 (2Me), 21.2 (3'Me), 21.6 (8Me), 24.7 (6Me), 25.0 (15), 25.2 (8), 25.4 (15), 30.2 (4), 31.2 (11), 32.0 (16, 16), 34.8 (9NMe), 35.0 (4), 35.2 (12), 36.6 (7), 39.9 (14), 40.4 (3'NMe, 3'NMe), 42.3 (2), 53.8 (9), 64.8 (3), 68.3 (5), 70.1 (2), 73.9 (6), 79.8 (3), 85.0 (5), 102.7 (1), 123.6 (17), 171.0 (10), 171.9 (1), 173.5 (18) ppm. |
| 56 | $^{13}$C NMR (151 MHz, Pyr): δ = 10.5 (4Me), 18.5 (2Me), 19.2 (5"Me), 21.3 (3"Me), 21.6 (24), 22.1 (8Me), 22.5 (5'Me), 24.3 (8), 28.2 (6Me), 31.3 (4), 36.1 (2"), 37.6 (7), 39.0 (13), 40.2 (4), 40.3 (9NMe), 41.0 (3'NMe, 3'NMe), 48.6 (2), 50.3 (3"OMe), 51.3 (11), 58.9 (9), 63.9 (5"), 66.0 (3'), 68.9 (5'), 72.3 (2'), 73.3 (3"), 76.7 (6), 79.5 (4"), 83.6 (5), 97.3 (1"), 104.6 (1), 126.5 (17), 128.9 (16, 16), 130.8 (15, 15), 139.8 (14), 171.3 (23, 10), 174.5 (1) ppm. |
| 57 | $^{13}$C NMR (151 MHz, DMSO-d6): δ = 7.5 (4Me), 7.6 (4Me), 14.2 (2Me), 14.9 (2Me), 19.2 (8Me), 19.9 (8Me), 20.8 (5'Me), 22.7 (17), 24.5 (6Me), 25.6 (6Me), 25.9 (8), 26.7 (17), 28.2 (8), 28.7 (12), 29.3 (4), 29.5 (4), 29.9 (13), 30.6 (9NMe), 31.3 (13), 32.7 (11), 34.0 |

Table with NMR Data of Representative Compounds of Formula (I):

| Cpd# | δ NMR Data |
|---|---|
| | (9NMe), 36.5 (12), 37.1 (4), 37.9 (4), 38.6 (11), 40.0 (2), 40.3 (3'NMe, 3'NMe), 41.8 (7), 42.1 (7), 44.2 (14), 45.7 (14), 45.9 (16), 47.1 (16), 56.8 (9), 63.9 (3), 63.9 (3), 69.2 (2), 69.2 (2'), 69.6 (5'), 72.2 (6), 72.4 (6), 75.5 (3), 77.1 (3), 96.6 (5), 97.8 (5), 105.9 (1), 106.1 (1), 170.8 (10), 171.2 (10), 173.5 (1), 173.7 (1) ppm. |
| 58 | $^{13}$C NMR (101 MHz, DMSO-d6): δ = 8.2 (4Me), 8.3 (4Me), 16.0 (2Me), 18.9 (8Me), 20.7 (8Me), 20.9 (5'Me), 27.8 (6Me), 29.6 (4), 31.3 (8), 32.0 (14), 32.6 (14), 35.1 (13), 37.3 (4), 38.3 (9NMe), 40.2 (3'NMe, 3'NMe), 40.4 (3'NMe, 3'NMe), 42.3 (7), 43.9 (2), 44.6 (2), 46.3 (12), 47.5 (11), 58.0 (9), 63.8 (3), 64.2 (3), 69.3 (5), 69.8 (2), 70.1 (2), 73.5 (6), 75.9 (3), 94.5 (5), 105.0 (1), 106.0 (1), 125.6 (18), 125.7 (18), 128.2 (17, 17), 128.3 (16, 16), 141.8 (15), 142.0 (15), 170.7 (10), 174.7 (1) ppm. |
| 59 | $^{13}$C NMR (151 MHz, DMSO-d6): δ = 9.0 (4Me), 13.6 (2Me), 17.5 (5"Me), 20.5 (24), 20.7 (3"Me), 21.1 (8Me), 21.3 (5'Me), 24.8 (6Me), 26.8 (8), 30.8 (4), 34.2 (2"), 34.8 (11), 35.2 (9NMe), 38.4 (14), 40.0 (7), 40.5 (3'NMe, 3'NMe), 44.8 (2), 48.7 (3"OMe), 51.4 (12), 54.3 (9), 62.2 (5"), 63.6 (3'), 67.1 (5'), 70.7 (2'), 72.3 (3"), 74.6 (6), 77.9 (3, 4"), 80.3 (5), 94.6 (1"), 101.3 (1), 125.9 (18), 128.0 (19, 17), 128.9 (20, 16), 139.6 (15), 170.1 (23), 170.6 (10), 175.6 (1) ppm. |
| 60 | $^{13}$C NMR (151 MHz, DMSO-d6): δ = 9.2 (4Me), 14.1 (2Me), 17.5 (5"Me), 20.6 (24), 20.7 (3"Me), 21.2 (8Me), 21.3 (5'Me), 21.8 (17), 23.1 (16), 24.5 (15), 25.0 (6Me), 26.9 (8), 30.8 (4), 34.3 (2"), 35.2 (9NMe), 35.4(11), 38.8 (4), 39.1 (7), 40.4 (3'NMe, 3'NMe), 41.8 (14), 45.1 (2), 47.7 (12), 48.7 (3"OMe), 54.4 (9), 62.3 (5"), 64.2 (3), 67.2 (5'), 70.7 (2), 72.3 (3"), 74.7 (6), 77.9 (3, 4"), 80.4 (5), 94.7 (1"), 101.5 (1), 170.2 (24), 170.8 (10), 175.6 (1) ppm. |
| 61 | $^{13}$C NMR (151 MHz, DMSO-d6): δ = 9.3 (4Me), 17.2 (2Me), 17.7 (5"Me), 20.5 (3"Me), 20.7 (24), 21.1 (8Me), 21.4 (5'Me), 23.4 (8), 26.6 (12), 27.0 (6Me), 27.7 (16, 16, 16), 29.9 (4), 31.1 (13), 34.9 (2"), 36.1 (7), 38.4 (4), 39.9 (9NMe), 40.2 (3'NMe, 3'NMe), 46.9 (2), 47.3 (11), 49.1 (3"OMe), 57.4 (9), 62.2 (5"), 64.6 (3), 67.5 (5), 70.5 (2), 72.2 (3"), 74.9 (6), 77.7 (3), 78.1 (4"), 79.5 (15), 82.0 (5), 95.8 (1"), 102.9 (1), 170.0 (10), 170.3 (23), 172.0 (14), 173.4 (1 )ppm. |
| 62 | $^{13}$C NMR (151 MHz, DMSO-d6): δ = 9.6 (4Me), 14.2 (2Me), 17.2 (5"Me), 20.6 (8Me), 20.6 (24), 20.7 (3"Me), 21.2 (5'Me), 24.3 (17), 26.2 (6Me), 26.8 (8), 29.4 (14), 30.8 (4), 34.5 (2"), 34.8 (9NMe), 37.0 (11), 38.0 (7), 40.1 (4), 40.3 (3'NMe, 3'NMe), 43.2 (12), 44.1 (2), 48.8 (3"OMe), 54.3 (9), 62.3 (5"), 64.2 (3), 67.6 (5), 70.7 (2), 72.4 (3"), 73.9 (6), 77.8 (4", 3), 81.5 (5), 95.3 (1"), 102.4 (1), 124.0 (15), 124.7 (16), 170.3 (23), 171.8 (10), 175.9 (1) ppm. |
| 63 | $^{13}$C NMR (126 MHz, DMSO-d6): δ = 8.5 (4Me), 16.1 (2Me), 19.0 (8Me), 20.7 (5'Me), 23.8 (12), 25.7 (6Me), 27.9 (11), 28.5 (8), 29.7 (4), 34.4 (9NMe), 36.9 (13), 37.3 (4), 40.1 (3'NMe, 3'NMe), 42.1 (7), 45.2 (2), 56.8 (9), 64.0 (3'), 69.1 (5'), 69.6 (2'), 72.6 (6), 75.5 (3), 95.8 (5), 105.7 (1), 171.3 (10), 175.1 (1) ppm. |
| 64 | $^{13}$C NMR (126 MHz, DMSO-d6): δ = 7.5 (4Me), 13.9 (2Me), 14.7 (2Me), 18.7 (8Me), 20.7 (8Me, 5'Me), 26.1 (13), 26.2 (8), 28.5 (6Me), 29.8 (14), 31.2 (4), 37.6 (4), 38.8 (9NMe), 40.3 (3'NMe, 3'NMe), 43.4 (7), 46.0 (2), 47.4 (11), 53.9 (9), 56.8 (9), 64.9 (3), 69.8 (5), 70.1 (2), 74.3 (6), 77.0 (3), 92.9 (5), 105.4 (1), 173.9 (1, 15), 175.0 (10) ppm. |
| 65 | $^{13}$C NMR (151 MHz, DMSO-d6): δ = 9.2 (4Me), 10.0 (4Me), 15.2 (2Me), 15.9 (2Me), 20.7 (8Me), 20.9 (5'Me), 21.0 (8Me), 23.1 (17, 17), 24.0 (17, 17), 25.0 (12), 25.8 (8, 6Me), 29.6 (8), 30.2 (11, 4), 32.0 (11, 18, 18), 34.9 (9NMe), 36.4 (4), 37.2 (4), 37.4 (13, 7), 38.2 (13), 39.5 (7), 39.9 0, 40.2 (16, 3'NMe, 3'NMe), 44.0 (2), 56.5 (9), 64.1 (3), 68.3 (5), 69.9 (2), 72.9 (3), 84.9 (5), 103.0 (1), 123.0 (19), 171.5 (10), 172.3 (10), 173.0 (1), 173.4 (15) ppm. |
| 66 | $^{13}$C NMR (151 MHz, DMSO-d6): δ = 9.2 (4Me), 9.7 (4Me), 12.4 (19, 19), 12.5 (19, 19), 15.5 (2Me), 15.9 (2Me), 20.7 (8Me), 21.1 (5'Me), 21.3 (5'Me), 23.9 (12), 24.8 (12), 25.3 (6Me), 26.0 (8), 26.8 (6Me), 28.5 (8), 29.1 (11), 30.3 (4), 30.9 (11), 35.0 (9NMe), 36.5 (4), 36.9 (4), 38.0 (13), 39.9 (7), 40.4 (3'NMe, 3'NMe), 43.9 (2), 46.8 (18, 18), 53.8 (16, 9), 56.5 (9), 64.7 (3'), 68.0 (5'), 70.2 (2'), 72.9 (6), 77.0 (3), 78.0 (3), 83.0 (5), 85.0 (5), 103.3 (1), 170.4 (15), 171.5 (10), 172.3 (10), 172.7 (1), 173.4 (1) ppm. |
| 67 | $^{13}$C NMR (126 MHz, DMSO-d6): δ = 9.3 (4Me), 9.9 (4Me), 15.3 (2Me), 15.9 (2Me), 20.7 (8Me), 20.9 (5'Me), 21.1 (5'Me), 21.3 (8Me), 23.7 (12), 24.5 (12), 25.6 (6Me), 25.9 (8, 6Me), 28.5 (16), 28.7 (8), 28.9 (16), 29.0 (16), 29.1 (11), 30.3 (4), 30.5 (4), 30.7 (11), 34.9 (9NMe), 35.4 (9NMe), 36.5 (4), 37.2 (4), 37.5 (7), 37.7 (13), 38.1 (13), 39.9 (15), 40.1 (7), 40.4 (3'NMe, 3'NMe), 43.7 (2), 43.9 (2), 53.9 (9), 56.5 (9), 64.5 (3'), 64.7 (3'), 66.0 (17), 66.1 (17), 66.3 (17), 68.5 (5), 68.7 (5), 70.2 (2), 73.2 (6), 73.2 (6), 77.5 (3), 77.8 (3), 83.9 (5), 85.0 (5), 102.7 (1), 103.1 (1), 171.7 (10), 173.3 (10), 173.6 (1), 173.8 (1) ppm. |
| 68 | $^{13}$C NMR (126 MHz, DMSO-d6): δ = 9.7 (4Me), 13.5 (2Me), 17.7 (5"Me), 20.9 (24), 21.1 (3"Me), 21.4 (5'Me), 21.5 (8Me), 22.4 (15), 25.5 (6Me), 26.9 (8), 28.8 (16), 31.2 (4), 32.4 (14), 34.5 (2"), 34.9 (9NMe), 40.9 (3'NMe, 3'NMe), 41.8 (4), 43.8 (11), 44.3 (2), 49.0 (3"OMe), 51.8 (12), 56.3 (9), 62.5 (5"), 64.7 (3), 67.7 (5), 71.1 (2), 72.7 (3"), 75.0 (6), 77.5 (3), 78.4 (4"), 81.1 (5), 94.9 (1"), 101.4 (1), 170.5 (23), 172.6 (10), 176.1 (1) ppm. |
| 69 | $^{13}$C NMR (151 MHz, DMSO-d6): δ = 9.8 (4Me), 17.4 (5"Me), 20.6 (3"Me, 5'Me, 2Me, 13), 21.2 (8Me), 21.3 (6Me), 26.2 (8), 30.3 (4'), 34.7 (2"), 35.6 (9NMe), 36.4 (7), 37.6 (4), 40.0 (11), 40.2 (3'NMe, 3'NMe), 44.4 (2), 48.8 (3"OMe), 53.5 (9), 62.0 (5"), 64.4 (3), 67.5 (5), 70.4 (2'), 72.3 (3"), 75.0 (6), 78.0 (4"), 78.9 (3), 81.9 (5), 95.8 (1"), 102.6 (1'), 169.6 (10), 170.3 (12), 176.2 (1) ppm. |
| 70 | $^{13}$C NMR (151 MHz, DMSO-d6): δ = 9.3 (4Me), 12.8 (2Me), 17.4 (5"Me), 20.6 (8Me), 20.7 (14, 3"Me), 21.3 (5'Me), 24.4 (6Me), 26.7 (8), 30.7 (4'), 31.5 (11), 34.2 (2"), 34.6 (9NMe), 35.0 (12), 37.7 (7), 40.1 (4), 40.4 (3'NMe, 3'NMe), 43.2 (2), 48.8 (3"OMe), 53.3 |

-continued

Table with NMR Data of Representative Compounds of Formula (I):

| Cpd# | δ NMR Data |
|---|---|
| | (9), 62.3 (5''), 64.2 (3'), 67.2 (5'), 70.7 (2'), 72.4 (3''), 73.8 (6), 77.9 (4''), 78.5 (3), 82.5 (5), 94.4 (1''), 101.1 (1'), 170.1 (10), 170.6 (13), 175.2 (1) ppm. |
| 71 | $^{13}$C NMR (126 MHz, DMSO-d6): δ = 8.1 (4Me), 8.3 (4Me), 15.9 (2Me), 16.7 (2Me), 18.8 (8Me), 19.2 (8Me), 20.7 (5'Me), 20.8 (17), 20.9 (5'Me), 21.2 (17), 21.3 (15), 21.5 (15), 24.8 (6Me), 25.6 (16), 26.4 (6Me), 28.2 (8), 29.4 (4'), 30.1 (4'), 30.9 (8), 34.2 (18), 34.7 (18), 35.5 (14), 36.4 (9NMe), 37.7 (4), 38.3 (9NMe, 4), 40.2 (3'NMe, 3'NMe), 40.3 (3'NMe, 3'NMe), 42.5 (7), 43.1 (7), 44.2 (2), 44.9 (2), 53.3 (9), 58.1 (9), 63.9 (3'), 64.0 (3'), 68.7 (5'), 69.1 (5'), 69.7 (2'), 70.0 (2'), 72.3 (6), 73.7 (6), 75.2 (3), 76.3 (3), 94.0 (5), 96.0 (5), 105.2 (1'), 106.0 (1'), 169.9 (10), 175.0 (1) ppm. |
| 72 | $^{13}$C NMR (126 MHz, DMSO-d6): δ = 9.3 (4Me), 14.2 (2Me), 18.3 (5'Me), 21.0 (3''Me), 21.1 (5'Me), 21.3 (8Me), 24.9 (6Me), 27.1 (8), 30.5 (4'), 34.5 (2'', 16), 35.5 (9NMe), 36.6 (13), 39.0 (11), 40.0 (7), 40.1 (4), 40.5 (3'NMe, 3'NMe), 44.8 (2), 48.5 (3''OMe), 51.7 (12), 54.7 (9), 62.6 (14), 62.9 (15), 64.1 (3'), 64.7 (5''), 67.3 (5), 70.8 (2'), 72.7 (3''), 74.8 (6), 77.4 (4'', 3), 80.3 (5), 94.6 (1''), 101.6 (1'), 169.9 (10), 176.2 (1) ppm. |
| 73 | $^{13}$C NMR (151 MHz, DMSO-d6): δ = 8.9 (4Me), 13.9 (2Me), 17.7 (5''Me), 18.1 (15, 15), 18.7 (15, 15), 20.3 (8Me), 20.5 (3''Me), 20.6 (5'Me), 25.0 (6Me), 25.5 (6Me), 25.8 (8), 27.0 (8), 30.2 (4'), 31.1 (14), 31.7 (14), 31.9 (11), 34.6 (9NMe), 34.8 (2''), 36.7 (9NMe), 36.9 (11), 38.0 (7), 39.1 (4), 39.9 (3'NMe, 3'NMe), 45.7 (2), 48.3 (3''OMe), 51.1 (12), 53.9 (9), 54.9 (12), 55.4 (9), 64.1 (3'), 64.6 (5''), 67.2 (5), 67.4 (5), 70.6 (2'), 70.7 (2'), 72.2 (3''), 74.0 (6), 74.4 (3), 77.2 (4''), 81.2 (5), 83.6 (5), 95.4 (1''), 102.0 (1'), 170.9 (10), 174.2 (1), 174.4 (1) ppm. |
| 74 | $^{13}$C NMR (126 MHz, DMSO-d6): δ = 9.2 (4Me), 14.0 (2Me), 18.1 (5''Me), 21.0 (3''Me), 21.1 (5'Me), 21.2 (8Me), 22.2 (16), 22.8 (15), 24.9 (6Me), 26.9 (8), 30.5 (4'), 34.6 (2''), 35.3 (9NMe), 38.1 (14, 17), 39.1 (11), 39.9 (7), 40.1 (4), 40.3 (3'NMe, 3'NMe), 44.7 (2), 48.6 (3''OMe), 54.9 (9), 62.2 (12), 64.2 (3'), 64.6 (5''), 66.9 (5), 70.7 (2'), 72.6 (3''), 74.8 (6), 77.3 (4'', 3), 81.1 (5), 94.8 (1''), 101.6 (1'), 170.4 (10), 175.8 (1) ppm. |
| 75 | $^{13}$C NMR (126 MHz, DMSO-d6): δ = 9.6 (4Me), 12.9 (2Me), 17.0 (5''Me), 20.1 (8Me), 20.6 (24), 20.7 (3''Me), 21.3 (5'Me), 23.1 (6Me), 24.1 (12), 28.7 (8), 29.5 (11), 30.7 (4'), 33.7 (9NMe), 34.3 (2''), 37.2 (13), 40.0 (7), 40.5 (3'NMe, 3'NMe), 41.2 (4), 44.0 (2), 48.7 (3'OMe), 56.7 (9), 62.1 (5''), 64.0 (3'), 67.4 (5), 70.7 (2'), 72.5 (3''), 73.4 (6), 77.8 (4''), 78.6 (3), 83.5 (5), 94.4 (1''), 101.2 (1'), 169.0 (23), 170.1 (10), 175.9 (1) ppm. |
| 77 | $^{13}$C NMR (151 MHz, DMSO-d6): δ = 9.4 (4Me), 14.5 (2Me), 17.0 (5''Me), 19.2 (8Me), 20.6 (3''Me, 24), 21.2 (5'Me), 22.8 (6Me), 26.3 (8), 26.6 (8), 30.2 (4'), 32.6 (9NMe), 34.2 (2''), 34.7 (9NMe), 36.0 (17), 39.4 (4), 40.4 (3'NMe, 3'NMe), 41.2 (7), 44.2 (2), 52.6 (13, 13, 14, 14), 53.0 (9), 55.2 (9), 56.8 (16), 60.2(11), 62.1 (5''), 64.3 (3'), 67.4 (5), 70.3 (2'), 72.4 (3''), 74.5 (6), 78.0 (3, 4''), 83.0 (5), 95.2 (1''), 102.1 (1'), 168.5 (10), 168.9 (10), 170.1 (23), 174.7 (1) ppm. |
| 78 | $^{13}$C NMR (151 MHz, CHLOROFORM-d): δ = 9.9 (4Me), 15.5 (2Me), 16.5 (2Me), 18.3 (5''Me), 21.4 (3''Me, 8Me), 21.7 (5'Me), 23.3 (17), 23.6 (6Me), 26.0 (17), 27.2 (6Me), 27.7 (8), 28.2 (18), 29.4 (4'), 32.0 (18), 33.5 (9NMe), 35.6 (2''), 37.9 (4), 38.7 (7), 40.5 (3'NMe, 3'NMe), 40.6 (3'NMe, 3'NMe), 41.8 (14), 43.0 (7), 44.1 (14), 46.3 (16), 46.8 (2), 47.5 (16), 49.5 (3''OMe), 51.0 (2), 56.5 (9), 57.5 (11), 59.1 (11), 64.0 (3'), 65.8 (3'), 66.7 (5''), 68.9 (5), 69.2 (5), 71.3 (2'), 71.6 (2'), 73.1 (3''), 78.9 (4''), 79.2 (4''), 82.6 (3), 84.9 (5), 87.7 (5), 96.9 (1''), 99.2 (1''), 105.2 (1'), 108.1 (1'), 169.8 (13), 171.9 (10), 175.2 (1) ppm. |
| 79 | $^{13}$C NMR (126 MHz, DMSO-d6): δ = 9.4 (4Me), 13.3 (2Me), 14.5 (5''Me), 18.3 (3''Me), 20.6 (8Me), 21.1 (5'Me), 24.8 (6Me), 26.5 (8), 30.4 (4'), 31.0 (2''), 31.8 (11), 34.7 (9NMe), 35.1 (12), 37.8 (7), 40.2 (4), 40.4 (3'NMe, 3'NMe), 43.7 (2), 47.2 (14NMe, 14NMe), 48.9 (3''OMe), 53.6 (9), 58.6 (14), 64.6 (3'), 66.6 (5''), 67.8 (5), 70.4 (2'), 71.3 (4''), 73.9 (6), 75.7 (3), 78.6 (3), 83.2 (5), 94.5 (1''), 102.0 (1'), 170.5 (10), 175.8 (1) ppm. |
| 80 | $^{13}$C NMR (151 MHz, DMSO-d6): δ = 9.5 (4Me), 11.6 (2Me), 14.7 (5''Me), 18.5 (3''Me), 20.6 (8Me), 21.2 (5'Me), 24.5 (6Me), 26.5 (8), 30.4 (4'), 31.0 (2''), 31.9 (11), 35.1 (12), 35.3 (9NMe), 37.0 (7), 40.5 (3'NMe, 3'NMe), 40.7 (4), 43.8 (2), 48.9 (3''OMe), 53.9 (9), 55.0 (16, 16), 57.9 (14), 64.3 (3'), 66.3 (17, 17), 66.6 (5''), 68.0 (5), 70.6 (2'), 71.9 (4''), 74.0 (6), 76.1 (3''), 78.5 (3), 83.3 (5), 93.9 (1''), 102.1 (1'), 169.9 (10), 175.9 (1) ppm. |
| 81 | $^{13}$C NMR (126 MHz, DMSO-d6): δ = 8.9 (4Me), 14.1 (2Me), 17.5 (5''Me), 20.6 (24), 20.7 (3''Me), 21.1 (8Me), 21.3 (5'Me), 24.7 (6Me), 26.5 (8), 28.7 (20, 20, 20), 30.8 (4'), 34.2 (2''), 34.8 (11), 35.3 (9NMe), 37.9 (14), 39.4 (7), 40.1 (4), 40.5 (3'NMe, 3'NMe), 44.9 (2), 48.7 (3''OMe), 51.9 (12), 54.5 (9), 62.3 (5''), 64.2 (3'), 67.2 (5), 70.7 (2'), 72.3 (3''), 74.7 (6), 77.5 (19), 78.0 (4'', 3), 80.3 (5), 94.5 (1''), 101.3 (1'), 123.5 (17, 17), 129.6 (16, 16), 134.2 (15), 153.2 (18), 170.1 (23), 170.6 (10), 175.6 (1) ppm. |
| 82 | $^{13}$C NMR (151 MHz, DMSO-d6): δ = 9.7 (4Me), 14.7 (2Me), 15.9 (2Me), 17.3 (5''Me), 17.5 (5''Me), 20.2 (3''Me), 20.6 (24), 21.2 (5'Me), 21.3 (8Me), 25.8 (6Me), 26.9 (8), 29.7 (8), 30.5 (4'), 30.7 (4'), 34.5 (2''), 35.5 (9NMe), 35.8 (11), 36.7 (11), 39.4 (7), 39.9 (4), 40.4 (3'NMe), 41.5 (14), 42.0 (14), 44.6 (2), 45.1 (2), 48.9 (3''OMe), 48.9 (3''OMe), 54.9 (9), 57.6 (9), 62.3 (5''), 64.2 (3'), 67.5 (5'), 70.6 (2'), 70.7 (2'), 72.3 (3''), 73.7 (6), 77.6 (3), 77.9 (4'', 3), 82.0 (5), 83.8 (5), 95.1 (1''), 95.3 (1''), 102.2 (1'), 102.3 (1'), 126.6 (), 126.7 (16), 127.7 (19), 129.2 (18), 130.2 (20), 130.7 (20), 135.2 (17), 135.4 (17), 136.2 (15), 136.3 (15), 170.2 (23), 170.5 (10), 171.0 (10), 174.7 (1), 175.5 (1) ppm. |
| 83 | $^{13}$C NMR (151 MHz, DMSO-d6): δ = 9.0 (4Me), 14.8 (2Me), 17.1 (5''Me), 17.8 (15), 20.0 (24), 20.4 (3''Me), 20.7 (8Me), 20.8 (5'Me), 24.9 (6Me), 25.8 (8), 27.9 (17, 17, 17), 29.3 (11), 30.4 (4'), 34.7 (9NMe), 34.8 (2''), 37.7 (7), 38.1 (4), 39.9 (3'NMe, 3'NMe), 46.1 (2), 48.5 (3''OMe), 53.6 (12), 53.8 (9), 62.2 (5''), 64.2 (3'), 67.0 (14), 67.2 (5), 70.6 (2'), 71.7 (3''), 72.6 (16), 74.5 (6), 78.1 (4''), 78.7 (3), 81.0 (5), 95.4 (1''), 101.9 (1'), 169.6 (23), 170.4 (10), 173.9 (1) ppm. |

-continued

Table with NMR Data of Representative Compounds of Formula (I):

Cpd# δ NMR Data

84 $^{13}$C NMR (151 MHz, DMSO-d6): δ = 9.2 (4Me), 14.0 (2Me), 17.5 (5"Me), 20.6 (24), 20.7 (3"Me), 21.2 (8Me), 21.3 (5'Me), 24.9 (6Me), 26.6 (8), 27.8 (17, 17, 17), 30.8 (4'), 34.2 (2"), 34.5 (11), 35.2 (9NMe), 38.9 (7, 14), 39.9 (4), 40.5 (3'NMe, 3'NMe), 44.8 (2), 46.8 (12), 48.9 (3"OMe), 54.4 (9), 62.2 (5"), 64.5 (3'), 67.2 (5), 70.7 (2'), 72.3 (3"), 74.6 (6), 78.0 (3, 4"), 79.7 (16), 80.6 (5), 94.5 (1"), 101.5 (1'), 170.2 (23, 10, 15), 170.4 (1) ppm.

85 $^{13}$C NMR (151 MHz, DMSO-d6): δ = 9.0 (4Me), 14.6 (2Me), 17.7 (5"Me), 18.7 (16), 19.0 (15), 20.6 (3"Me, 5'Me, 8Me), 24.9 (6Me), 25.8 (8), 30.2 (4'), 30.8 (14), 32.3 (11), 34.7 (9NMe), 34.9 (2"), 38.2 (7), 39.1 (4), 39.9 (3'NMe, 3'NMe), 45.8 (2), 48.4 (3"OMe), 53.9 (9), 54.9 (12), 64.1 (3'), 64.6 (5"), 67.3 (5), 70.7 (2'), 72.2 (3"), 74.6 (6), 77.2 (4"), 78.6 (3), 81.4 (5), 96.1 (1"), 102.0 (1'), 170.0 (10), 174.9 (1) ppm.

86 $^{13}$C NMR (101 MHz, DMSO-d6): δ = 9.2 (4Me), 14.2 (2Me), 17.7 (5"Me), 20.2 (8Me), 20.6 (3"Me, 5'Me), 25.7 (6Me), 26.3 (8), 30.1 (4'), 34.8 (2"), 35.7 (9NMe), 38.2 (14, 7), 38.8 (11), 38.9 (4), 39.5 (3'NMe, 3'NMe), 45.1 (12, 2), 48.3 (3"OMe), 55.2 (9), 64.3 (3'), 64.6 (5"), 67.2 (5'), 70.5 (2'), 72.3 (3"), 74.0 (6), 77.0 (4"), 78.3 (3), 83.2 (5), 94.6 (1"), 102.3 (1'), 126.3 (19), 127.6 (18), 128.6 (17), 131.1 (20), 133.1 (16), 135.8 (15), 169.8 (10), 175.3 (1) ppm.

87 $^{13}$C NMR (126 MHz, DMSO-d6): δ = 7.4 (4Me), 8.0 (4Me), 15.9 (2Me), 18.7 (8Me), 19.3 (8Me), 20.2 (14Me), 20.5 (14Me), 20.7 (5'Me), 20.9 (5'Me), 24.9 (6Me), 27.8 (6Me), 29.7 (4'), 30.4 (4'), 31.0 (14), 32.8(11), 35.5 (4), 37.0 (4), 37.8 (9NMe), 38.9 (7), 40.4 (3'NMe, 3'NMe), 42.2 (7), 44.4 (2), 45.0 (2), 55.5 (12), 57.7 (9), 63.8 (3'), 64.1 (3'), 68.8 (5), 69.1 (5), 69.7 (5', 2'), 70.0 (2'), 76.0 (3), 76.6 (3), 94.4 (5), 104.9 (1'), 106.0 (1'), 170.6 (10), 171.2 (10), 175.2 (1) ppm.

88 $^{13}$C NMR (151 MHz, DMSO-d6): δ = 9.5 (4Me), 10.0 (19), 15.0 (2Me), 18.3 (5"Me), 21.0 (3"Me), 21.1 (5'Me), 21.2 (8Me), 24.8 (8), 26.6 (6Me), 28.6 (18), 29.8 (14), 30.7 (4'), 34.8 (2"), 35.7 (9NMe), 36.1 (7), 36.5 (15), 38.7 (4), 40.1 (11), 40.5 (3'NMe, 3'NMe), 44.7 (2), 48.7 (3"OMe), 53.4 (9), 63.4 (3'), 64.6 (5"), 65.1 (5), 70.3 (13), 72.6 (3"), 75.1 (6), 77.5 (4"), 78.0 (3), 79.9 (2'), 81.8 (5), 96.0 (1"), 102.8 (1'), 169.6 (10), 172.4 (17), 176.4 (1) ppm.

89 $^{13}$C NMR (151 MHz, DMSO-d6): δ = 8.0 (4Me, 21), 14.8 (2Me), 17.8 (5"Me), 20.5 (8Me, 3"Me,5'Me), 24.9 (8), 25.9(6Me), 28.2(20), 29.5 (16),31.8(4'), 34.8 (2"), 35.2 (9NMe), 35.9 (17), 37.0 (7), 37.9 (4), 40.2 (3'NMe, 3'NMe), 40.5 (13), 43.9 (2), 48.4 (3"OMe), 52.9 (9), 63.4 (3'), 64.5 (5"), 66.9 (5'), 68.9 (15), 72.2 (3"), 75.0 (6), 77.3 (4"), 78.3 (3), 79.7 (2'), 82.0 (5), 95.9 (1"), 102.0 (1'), 170.0 (10), 172.1 (19), 175.0 (1) ppm.

91 $^{13}$C NMR (151 MHz, DMSO-d6): δ = 8.0 (4Me), 14.5 (2Me), 15.5 (2Me), 18.7 (8Me), 20.0 (8Me), 20.7 (5'Me), 21.0 (5'Me), 24.8 (6Me), 25.5 (8), 27.7 (6Me), 29.7 (4'), 30.3 (4'), 30.7 (11), 31.7 (8), 34.4(9NMe), 35.1(12),35.6 (4), 36.8(4), 37.2 (9NMe), 38.3 (7), 40.3 (3'NMe, 3'NMe), 40.4 (3'NMe, 3'NMe), 42.0 (7), 43.9 (2), 53.3 (9), 57.6 (9), 63.9 (3'), 64.2 (3'), 68.4 (5'), 69.2 (5'), 69.8 (2'), 70.1 (2'), 73.4 (6), 76.0 (3), 76.9 (3), 93.0 (5), 94.3 (5), 104.2 (1'), 105.9 (1'), 170.5 (10), 174.1 (1), 175.0 (1) ppm.

92 $^{13}$C NMR (151 MHz, DMSO-d6): δ = 9.3 (4Me), 9.9 (4Me), 11.5 (2Me), 11.9 (2Me), 19.6 (8Me), 20.6 (8Me), 20.8 (5'Me), 21.1 (14), 21.5 (14), 25.5 (6Me), 26.3 (6Me), 30.3 (8), 31.0 (4'), 31.1 (13), 33.0 (13), 35.6 (9NMe), 37.6 (9NMe), 38.5 (4), 39.2 (11, 4), 40.5 (3'NMe, 3'NMe), 41.3 (7), 41.5 (2), 41.9 (7), 44.5 (15), 45.2 (15), 53.2(12), 53.8 (12), 55.4 (9), 56.3 (9), 64.1 (3'), 68.9 (5'), 70.2 (2'), 73.9 (6), 74.5 (3), 87.8 (5), 90.2 (5), 104.6 (1'), 169.7 (10), 174.8 (1) ppm.

93 $^{13}$C NMR (151 MHz, DMSO-d6): δ = 11.0 (4Me), 11.8 (4Me), 12.1 (2Me), 12.4 (2Me), 20.7 (8Me), 21.0 (5'Me), 21.2 (8Me), 26.5 (6Me), 26.5 (8), 27.0 (6Me), 30.4 (8), 30.6 (4'), 30.7 (11), 31.3 (4'), 34.9 (11), 35.9 (9NMe), 36.3 (12), 37.5 (9NMe), 37.7 (12), 39.2 (7), 40.5 (3'NMe, 3'NMe), 40.6 (3'NMe, 3'NMe), 41.0 (7), 46.1 (4), 47.0 (4), 47.9 (2), 48.7 (2), 52.7 (9), 57.7 (9), 64.1 (3'), 64.4 (3'), 68.3 (5'), 69.6 (2'), 69.7 (2'), 80.7 (6), 83.3 (6), 94.2 (5), 94.7 (5), 101.9 (3), 103.4 (3), 106.4 (1'), 107.2 (1'), 171.7 (10), 172.5 (1), 172.9 (10), 175.1 (1) ppm.

94 $^{13}$CNMR (151 MHz, DMSO-d6): δ = 9.1 (4Me), 12.4 (18, 18), 14.3 (2Me), 21.1 (5'Me), 21.6 (8Me), 24.7 (6Me), 25.3 (8), 30.3 (4'), 31.3 (11), 34.8 (9NMe, 4), 35.2 (12), 36.7 (7), 40.4 (3'NMe, 3'NMe), 42.2 (2), 46.8 (17, 17), 53.9 (9), 54.1 (15), 64.9 (3'), 68.3 (5'), 70.3 (2'), 73.9 (6), 79.6 (3), 84.7 (5), 102.6 (1'), 170.9 (14), 171.1 (10), 172.1 (1) ppm.

98 $^{13}$C NMR (151 MHz, DMSO-d6): δ = 8.0 (4Me), 14.0 (2Me), 20.7 (5'Me), 21.7 (8Me), 24.8 (6Me), 25.0 (8), 25.0 (18, 18), 31.2 (11), 32.1 (3'NMe), 34.8 (9NMe), 35.1 (4), 35.8 (12), 36.2 (4'), 36.4 (7), 43.4 (2), 45.9 (17), 53.9 (9), 62.0 (3'), 69.4 (5'), 73.5 (6), 76.1 (3), 79.3 (2'), 86.1 (5), 96.7 (1'), 154.0 (15), 171.9 (10), 174.0 (1) ppm.

99 $^{13}$C NMR (151 MHz, DMSO-d6): δ = 9.9 (4Me), 14.9 (2Me), 18.3 (5"Me), 21.0 (3"Me), 21.1 (5'Me), 21.1 (8Me), 25.0 (8), 26.5 (6Me),32.9 (3'NMe), 34.9 (2"), 35.6 (9NMe), 36.2 (7), 37.2 (4'), 37.7 (4), 40.1 (11), 44.6 (2), 48.8 (3"OMe), 53.4 (9), 60.2 (3'), 64.4 (5"), 67.2 (5), 72.6 (3"), 73.6 (2'), 75.1 (6), 77.6 (4"), 79.2 (3), 82.2 (5), 96.4 (1"), 102.5 (1'), 169.5 (10), 176.4 (1) ppm.

100 $^{13}$C NMR (151 MHz, DMSO-d6): δ = 10.0 (4Me), 11.4 (15), 15.1 (2Me), 18.1 (5"Me), 20.9 (14), 21.1 (5'Me, 3"Me, 8Me), 25.0 (8), 26.4 (6Me), 30.8 (4'), 34.9 (2"), 35.7 (9NMe), 36.1 (7), 36.4 (3'NMe), 37.7 (4), 40.1 (11), 44.6 (2), 48.7 (3"OMe), 53.5 (9), 55.3 (13), 64.3 (3'), 64.4 (5"), 67.6 (5), 70.4 (2'), 72.7 (3"), 75.1 (6), 77.6 (4"), 79.5 (3), 82.6 (5), 96.9 (1"), 102.9 (1'), 169.6 (10), 176.5 (1) ppm.

101 $^{13}$C NMR (151 MHz, DMSO-d6): δ = 9.2 (15), 9.5 (15), 10.0 (4Me), 15.2 (2Me), 18.2 (5"Me), 20.9 (3"Me), 20.9 (3"Me), 21.0 (5'Me), 21.2 (8Me), 25.7 (14), 26.3 (3'NMe), 26.5 (14), 26.5 (6Me), 28.9 (3'NMe), 35.0 (2"), 35.4 (4'), 35.7 (9NMe), 35.8 (9NMe), 36.3 (7), 36.9 (4), 40.1 (11), 44.5 (2), 48.7 (3"OMe), 53.5 (9), 54.0 (3'),

-continued

Table with NMR Data of Representative Compounds of Formula (I):

| Cpd# | δ NMR Data |
|---|---|
| | 57.4 (3'), 64.6 (5"), 67.0 (5), 67.2 (5), 69.8 (2'), 69.9 (2'), 72.7 (3"), 75.1 (6), 75.1 (6), 77.6 (4"), 77.7 (4"), 79 (3), 82.4 (5), 96.6 (1"), 102.9 (1'), 169.6 (10), 173.0 (13), 176.5 (1) ppm. |
| 102 | $^{13}$C NMR (151 MHz, DMSO-d6): δ = 9.5 (4Me), 15.0 (2Me),17.8 (5"Me), 20.4 (3"Me), 20.9 (5'Me), 21.1 (8Me), 24.5 (14), 24.8 (8), 25.1 (14), 26.1 (6Me), 31.9 (3'NMe), 34.8 (2"), 35.7 (4'), 35.8 (9NMe, 7), 36.7 (4), 40.0 (11), 45.4 (2), 46.0 (13), 48.7 (3"OMe), 53.4 (9), 61.6 (3'), 64.6 (5"), 69.6 (5), 73.1 (3"), 74.6 (6), 77.5 (4"), 79.4 (2'), 79.8 (3), 84.2 (5), 96.5 (1"), 100.3 (1'), 153.5 (15), 169.3 (10), 176.2 (1) ppm. |
| 103 | $^{13}$C NMR (101 MHz, DMSO-d6): δ = 9.4 (4Me), 13.1 (2Me), 18.0 (5"Me), 20.6 (8Me), 21.0 (3"Me), 21.1 (5'Me), 25.0 (6Me), 25.6 (8), 32.3 (11), 33.1 (3'NMe), 34.7 (9NMe, 2"), 35.2 (12), 36.4 (4'), 38.0 (7), 40.1 (4), 43.7 (2), 48.6 (3"OMe), 53.4 (9), 59.2 (3'), 64.8 (5"), 66.9 (5), 72.6 (3"), 73.7 (2', 6), 77.2 (4"), 78.5 (3), 82.6 (5), 94.8 (1"), 101.0 (1'), 170.5 (10), 175.4 (1) ppm. |
| 105 | $^{1}$H NMR (600 MHz, DMSO-d6): δ = 0.90 (d, J = 7.3 Hz, 3 H, 4Me), 0.91 (d, J = 7.0 Hz, 3 H, 2Me), 0.95 (t, J = 6.4 Hz, 1 H, 7<">), 0.96-1.00 (m, 6 H, 8Me, 15), 1.01 (q, J = 10.1 Hz, 1 H, 4'<">), 1.05 (d, J = 6.1 Hz, 3 H, 5'Me), 1.07 (s, 3 H, 6Me), 1.11 (d, J = 6.1 Hz, 3 H, 5"Me), 1.11 (s, 3 H, 3"Me), 1.41-1.49 (m, 2 H, 2"<">, 7<'>), 1.56 (ddd, J = 12.7, 3.9, 1.5 Hz, 1 H, 4'<'>), 1.87 (quind, J = 7.3, 2.1 Hz, 1 H, 4), 1.98 (br. s., 1 H, 8), 2.07 (d, J = 14.5 Hz, 1 H, 11<">), 2.16 (s, 3 H, 3'NMe), 2.26 (d, J = 15.0 Hz, 1 H, 2"<5), 2.34 (br. s., 1 H, 9<">), 2.41 (dq, J = 12.5, 7.0 Hz, 1 H, 14<">), 2.48 (dq, J = 14.1, 7.2 Hz, 1 H, 2), 2.54 (dq, J = 12.4, 7.5 Hz, 1 H, 14<>), 2.56 (ddd, J = 11.9, 10.5, 3.9 Hz, 1 H, 3'), 2.82 (br. s., 1 H, 11<'>), 2.88 (s, 3 H, 9NMe), 2.90 (dd, J = 9.4, 7.5 Hz, 1 H, 4"), 3.00 (tt, J = 12.0, 3.5 Hz, 1 H, 12<">), 3.07 (ddd, J = 9.5, 8.5, 1.5 Hz, 1 H, 2'), 3.21 (s, 3 H, 3"OMe), 3.43 (d, J = 6.1 Hz, 1 H, 5), 3.46 (br. s., 1 H, 12<'>), 3.62 (br. s., 1 H, 3), 3.69 (s, 1 H, 60H), 3.73 (dq, J = 10.5, 6.0 Hz, 1 H, 5), 3.94 (d, J = 1.8 Hz, 1 H, 2'OH), 3.97-4.05 (m, 2 H, 9<'>, 5"), 4.28 (d, J = 7.2 Hz, 1 H, 4"OH), 4.55 (d, J = 7.3 Hz, 1 H, 1'), 4.88 (d, J = 4.0 Hz, 1 H, 1"), 7.88 (t, J = 3.7 Hz, 1 H, 13) ppm. |
| 106 | $^{13}$C NMR (151 MHz, DMSO-d6): δ = 9.5 (4Me), 11.6 (15), 13.0 (2Me), 18.0 (5"Me), 20.5 (8Me), 20.9 (14), 21.1 (3"Me), 21.2 (5'Me), 24.6 (6Me), 26.7 (8), 31.1 (4'), 31.7 (11), 34.5 (2"), 34.8 (9NMe), 35.1 (12), 36.5 (3'NMe), 38.1 (7), 40.4 (4), 43.4 (2), 48.7 (3"OMe), 54.9 (9), 55.4 (16), 63.4 (3'), 64.7 (5"), 67.5 (5), 70.4 (2'), 72.7 (3"), 73.8 (6), 77.3 (4"), 78.2 (3), 82.4 (5), 94.4 (1"), 101.1 (1'), 170.2 (10), 176.1 (1) ppm. |
| 107 | $^{13}$C NMR (151 MHz, DMSO-d6): δ = 3.4 (), 9.4 (4Me), 12.9 (2Me), 18.0 (5"Me), 20.3 (15), 20.6 (8Me), 21.0 (15), 21.1 (3"Me), 21.2 (5'Me), 24.6 (6Me), 26.8 (8), 30.9 (3'NMe), 31.6 (11), 33.4 (4'), 34.5 (2"), 34.6 (9NMe), 35.1 (12), 38.1 (7), 39.6 (4), 43.3 (2), 48.7 (3"OMe), 52.1 (14), 53.5 (9), 60.8 (3'), 64.6 (5"), 67.4 (5), 69.9 (2'), 72.7 (3"), 73.8 (6), 77.6 (4"), 78.5 (3), 82.3 (5), 94.6 (1"), 101.2 (1'), 170.5 (10), 175.8 (1) ppm. |
| 110 | $^{13}$C NMR (126 MHz, DMSO-d6): δ = 7.2 (4Me), 11.0 (13), 14.3 (2Me), 20.7 (5'Me), 20.9 (8Me), 23.3 (6Me), 25.4 (8), 29.7 (4'), 32.8 (9NMe), 36.2 (16), 36.4 (4), 40.3 (3'NMe, 3'NMe), 41.6 (7), 44.7 (2), 56.8 (9), 64.0 (3'), 68.9 (5'), 69.8 (2'), 72.9 (6), 76.1 (3), 96.2 (5), 105.2 (1'), 130.2(11), 149.9 (12), 158.3 (15), 163.1 (10), 174.6 (1) ppm. |
| 111 | $^{13}$C NMR (126 MHz, DMSO-d6): δ = 7.7 (4Me), 15.3 (2Me), 20.4 (8Me), 21.0 (5'Me), 27.0 (8), 27.3 (6Me), 30.8 (4'), 31.4 (11), 36.3 (4), 38.9 (14), 40.5 (3'NMe, 3'NMe), 42.4 (9NMe), 43.4 (7), 46.3 (2), 50.3 (12), 52.0 (10), 54.8 (19), 64.3 (3'), 67.0 (9), 68.7 (5), 70.3 (2'), 73.6 (6), 77.2 (3), 90.0 (5), 105.1 (1'), 113.3 (17, 17), 130.1 (16, 16), 131.7 (15), 158.3 (18), 174.1 (1) ppm. |
| 112 | $^{13}$C NMR (126 MHz, DMSO-d6): δ = 10.7 (4Me), 12.7 (2Me), 18.0 (5"Me), 21.2 (3"Me, 5'Me), 22.7 (8Me), 24.6 (6Me), 24.9 (16), 25.9 (8), 28.8 (12), 30.5 (4'), 30.8 (4'), 31.7 (17), 34.8 (2"), 35.4 (9NMe), 40.1 (4, 2), 40.3 (3'NMe, 3'NMe), 41.6 (15), 42.3 (15), 48.6 (3"OMe), 48.9 (3"OMe), 51.1 (13), 56.1 (9), 57.5 (9), 62.8 (5), 64.1 (3'), 64.2 (3'), 64.5 (5"), 64.6 (5"), 70.6 (2'), 72.9 (3"), 73.8 (6), 77.2 (3), 77.5 (4"), 77.7 (4"), 82.9 (5), 93.7 (1"), 94.9 (1"), 101.8 (1'), 171.0 (10), 174.1 (1) ppm. |
| 114 | $^{13}$C NMR (126 MHz, DMSO-d6): δ = 7.6 (4Me), 15.7 (2Me), 20.5 (8Me), 20.8 (5'Me), 27'0 (8)' 27.6 (6Me), 30.2 (4'), 32.9 (11), 36.7 (4), 38.3 (14), 40.3 (3'NMe, 3'NMe), 42.9 (9NMe), 43.5 (7), 44.6 (2), 46.4 (12), 52.5 (10), 64.5 (3'), 68.5 (9), 69.3 (5), 70.1 (2'), 73.8 (6), 76.5 (3), 92.1 (5), 104.7 (1'), 116.6 (16), 136.3 (15), 174.2 (1) ppm. |
| 116 | $^{13}$C NMR (151 MHz, DMSO-d6): δ = 8.6 (4Me), 14.1 (2Me), 18.3 (5"Me), 20.3 (8Me), 20.6 (3"Me), 20.6 (5'Me), 25.0 (6Me), 27.1 (8), 30.3 (4'), 34.7 (2"), 36.0 (9NMe), 38.4 (11), 38.7 (7), 39.9 (3'NMe, 3'NMe), 40.1 (4), 44.9 (2), 47.5 (12), 48.3 (3"OMe), 55.4 (9), 63.6 (3'), 63.9 (5"), 67.0 (5'), 70.6 (2'), 72.4 (3"), 74.1 (6), 77.2 (4"), 77.9 (3), 82.9 (5), 95.2 (1"), 102.5 (1'), 112.7 (15), 139.1 (14), 169.0 (10), 175.0 (1) ppm. |
| 120 | $^{13}$C NMR (126 MHz, DMSO-d6): δ = 7.6 (4Me), 15.7 (2Me), 20.5 (8Me), 20.8 (5'Me), 27.0 (8) 27.6 (6Me), 30.2 (4'), 32.9 (11), 36.7 (4), 38.3 (14), 40.3 (3'NMe, 3'NMe), 42.9 (9NMe), 43.5 (7), 44.6 (2), 46.4 (12), 52.5 (10), 64.5 (3'), 68.5 (9), 69.3 (5), 70.1 (2'), 73.8 (6), 76.5 (3), 92.1 (5), 104.7 (1'), 116.6 (16), 136.3 (15), 174.2 (1) ppm. |
| 128 | $^{13}$C NMR (126 MHz, DMSO-d6): δ = 7.9 (4Me), 8.2 (4Me), 15.7 (2Me), 16.5 (2Me), 20.3 (8Me), 20.7 (5'Me), 21.4 (8Me), 24.2 (6Me), 26.0 (8), 26.6 (6Me, 8), 30.8 (4'), 32.1 (4'), 35.1 (4) 36.1 (4), 37.1 (7), 38.2 (7), 40.2 (3'NMe, 3'NMe), 40.4 (3'NMe, 3'NMe), 44.0 (2), 54.9 (9)', 55.2 (9), 64.5 (3'), 68.3 (5'), 68.6 (5'), 69.9 (2'), 71.0 (2'), 73.0 (6), 73.9 (6), 75.7 (3), 77.4 (3), 93.4 (5), 104.5 (1'), 123.2 (13), 146.5 (14), 148.3 (14), 166.9 (10), 174.7 (1) ppm. |
| 138 | $^{13}$C NMR (101 MHz, DMSO-d6): δ = 9.0 (4Me), 15.6 (2Me), 17.9 (5"Me), 20.4 (8Me), 20.6 (5'Me, 3"Me), 23.7 (8), 26.1 (13), 27.3 (6Me), 29.8 (4), 35.2 (2"), 35.7 (4), 38.2 (4), 38.7 (9NMe), 39.8 (3'NMe, 3'NMe), 46.8 (2), 48.5 (3"OMe), 49.2 (11), 57.3 (9), 64.3 (3), 64.7 (5"), 67.3 (5), 70.5 (2), 72.3 (3"), 75.0 (6), 77.4 (4"), 78.8 (3), 82.6 (5), 96.6 (1"), |

-continued

Table with NMR Data of Representative Compounds of Formula (I):

| Cpd# | δ NMR Data |
|---|---|
| | 103.0 (1), 110.8 (14, 18), 117.7 (20), 117.9 (21), 120.3 (19), 123.0 (15), 127.3 (22), 135.9 (17), 170.2 (10) ppm |
| 141 | $^{13}$C NMR (126 MHz, DMSO-d6): δ = 7.9 (4Me), 15.7 (2Me), 20.4 (8Me), 21.0 (5'Me), 24.0 (22, 22), 26.9 (8), 27.3 (6Me), 27.9 (15), 30.8 (11, 4), 33.0 (21), 33.8 (14), 34.4 (16), 36.2 (4), 40.5 (3NMe, 3'NMe), 42.2 (9NMe), 43.4 (7), 46.7 (2), 47.3 (12), 52.3 (10), 64.3 (3), 66.4 (9), 68.7 (5), 70.4 (2), 73.5 (6), 76.8 (3), 89.9 (5), 104.4 (1), 126.1 (19, 19), 128.0 (18, 18), 139.5 (17), 145.5(20), 173.7 (1) ppm |
| 142 | $^{13}$C NMR (126 MHz, DMSO-d6): δ = 7.9 (4Me), 15.7 (2Me), 20.6(8Me), 20.9 (5'Me), 23.9 (22, 22), 26.9 (8), 27.7 (6Me), 28.0 (15), 30.2 (4), 32.9 (21), 33.6 (11, 14), 34.5 (16), 36.7 (4), 40.0 (3NMe, 3'NMe), 42.8 (9NMe), 43.4 (7), 44.4 (2), 46.3 (12), 52.6 (10), 64.0 (3), 68.5 (9), 68.9 (5), 70.0 (2), 73.8 (6), 76.3 (3), 92.1(5), 104.9 (1), 126.1 (19, 19), 128.1 (18, 18), 139.4 (17), 145.6(20), 174.2 (1) ppm |
| 148 | $^{13}$C NMR (151 MHz, DMSO-d6): δ = 9.4 (2Me), 11.4 (4Me), 19.3(8Me), 21.0 (8Me, 5'Me), 23.1 (5'Me), 24.9 (8), 26.9 (6Me), 28.0 (12), 28.5 (8, 6Me), 30.6 (4), 31.7 (4), 34.5 (9NMe), 35.2 (4), 37.2 (7, 4), 37.5 (4), 37.8 (2), 38.0 (7), 39.1 (2, 4, 9NMe), 40.2(3NMe, 3'NMe), 40.5 (3'NMe, 3'NMe), 40.6 (7), 41.7 (13), 43.4 (13), 45.0 (13), 45.6 (15), 47.0 (15), 50.3 (15), 51.6 (9), 56.1 (9), 57.4 (9), 64.5 (3), 65.8 (3), 69.0 (5), 70.0 (2), 74.0 (3), 78.0 (3), 83.9 (5), 85.1 (5), 86.0 (5), 103.3 (1), 104.0 (1), 109.5 (20), 115.3 (21), 121.9 (19), 124.0 (22), 160.0 (18), 169.9 (10), 170.9(10), 172.3 (1), 173.6 (1) ppm |
| 153 | $^{13}$C NMR (126 MHz, DMSO-d6): δ = 9.4 (4Me), 13.3 (2Me), 14.5 (5"Me), 18.3 (3Me), 20.6 (8Me), 21.1 (5'Me), 24.8 (6Me), 26.5 (8), 30.4 (4), 31.0 (2"), 31.8 (11), 34.7 (9NMe), 35.1 (12), 37.8 (7), 40.2 (4), 40.4 (3'NMe, 3'NMe), 43.7 (2), 47.2 (14NMe, 14NMe), 48.9 (3"OMe), 53.6 (9), 58.6 (14), 64.6 (3), 66.6 (5"), 67.8 (5), 70.4 (2), 71.3 (4"), 73.9 (6), 75.7 (3"), 78.6 (3), 83.2 (5), 94.5 (1"), 102.0 (1), 170.5 (10), 175.8 (1) ppm |
| 154 | $^{13}$C NMR (101 MHz, DMSO-d6): δ = 9.0 (4Me), 14.9 (2Me), 17.7 (5"Me), 19.3 (8Me), 20.6 (3"Me, 5'Me), 21.0 (16), 22.5 (17), 24.1 (15), 26.0 (6Me), 30.1 (4), 34.9 (9aNMe, 2"), 37.1 (11), 38.1 (14), 39.6 (4), 39.7 (3'NMe, 3'NMe), 46.0 (2), 48.4 (3"OMe), 52.1 (13), 64.2 (3), 65.0 (5"), 67.2 (5), 68.8 (12), 70.2 (2), 72.3 (3"), 73.9(6), 77.0 (4"), 79.4 (3), 83.2 (5), 95.6 (1"), 102.0 (1), 171.0 (10), 174.1 (1) ppm |
| 157 | $^{13}$C NMR (151 MHz, DMSO-d6): δ = 9.1 (4Me), 9.9 (4Me), 14.5 (14, 15), 15.0 (15, 14), 15.9 (2Me), 16.2 (2Me), 18.2 (5"Me), 18.4 (5Me), 21.1 (3"Me), 21.2 (8Me), 21.3 (5'Me), 24.1 (8), 26.1 (6Me), 30.1 (4), 34.8 (9NMe), 34.9 (2"), 36.8 (7), 38.0 (2), 40.0 (4), 40.3 (3'NMe, 3'NMe), 46.9 (1), 48.8 (3"OMe), 54.2 (9), 58.7(9), 64.1 (3), 64.8 (5"), 67.3 (5), 67.5 (5), 70.7 (2), 72.6 (3), 74.8 (6), 77.5 (4"), 82.1 (3), 83.0 (5), 95.9 (1"), 103.6 (1), 168.3 (10), 168.8 (12) ppm |
| 160 | $^{13}$C NMR (151 MHz, DMSO-d6): δ = 7.6 (4Me), 8.0 (4Me), 15.6(2Me), 16.1 (2Me), 18.7 (8Me), 19.4 (8Me), 20.8 (5'Me), 20.9 (5Me), 23.3 (15), 23.8 (15), 24.9 (6Me), 25.7 (8), 27.9 (6Me), 29.1 (16), 29.6 (4), 30.4 (4), 30.7 (8), 31.1 (14), 33.1 (14), 34.0 (9NMe), 35.1 (11), 35.6 (4), 37.0 (4), 37.8 (9NMe), 38.5 (17), 38.9 (7), 40.2 (3'NMe, 3'NMe), 40.5 (3'NMe, 3'NMe), 42.3 (7), 44.5 (2), 45.9 (2), 49.1 (2), 53.1 (9), 57.8 (9), 63.9 (3), 64.2 (3), 68.8 (5), 69.2 (5), 69.7 (2), 70.1 (2), 73.9 (6), 76.1 (3), 76.8 (3), 94.4 (5), 94.9 (5), 105.0 (1), 106.0 (1), 108.4 (22), 109.5 (21), 120.9 (23), 126.4 (20), 160.5 (19), 170.5 (10), 170.8 (10), 173.9(1), 175.2 (1) ppm |
| 169 | $^{13}$C NMR (151 MHz, DMSO-d6): δ = 9.0 (4Me), 13.9 (2Me), 16.9 (5"Me), 19.9 (17), 20.2 (8Me), 20.4 (3"Me), 20.7 (5'Me), 25.2 (6Me), 25.9 (8), 30.5 (4), 34.7(2), 35.5 (9NMe), 37.9 (11), 38.2 (7), 39.4 (4), 39.9 (3'NMe, 3'NMe), 40.5 (14), 43.4 (12), 44.8 (2), 48.4 (3"OMe), 54.8 (9), 62.1 (5"), 64.2 (3), 67.0 (5), 70.6 (2), 72.1 (3"), 73.9 (6), 77.9 (4"), 78.3 (3), 83.1 (5), 95.0 (1"), 101.8 (1), 169.6 (16,10), 172.4 (15), 174.7 (1) ppm |
| 170 | $^{13}$C NMR (126 MHz, DMSO-d6): δ = 8.4 (4Me), 14.5 (2Me), 21.1(5Me), 21.6 (8Me), 24.9 (86Me) 30.9 (4), 31.1 (11), 34.6(9NMe), 34.9 (12), 35.0 (4), 36.1 (7), 40.4 (3'NMe, 3'NMe), 43.5 (2), 53.8 (9), 62.8 (3), 67.6 (5), 70.5 (2), 73.7 (6), 76.5 (3), 84.1(5), 98.4 (1), 109.1 (17), 114.7 (16), 122.6 (15), 123.3 (18), 159.6 (14), 170.9 (10), 173.6 (1) ppm |
| 184 | $^{13}$C NMR (151 MHz, DMSO-d6): δ = 9.1 (4Me), 9.8 (4Me), 11.8 (2Me), 18.1 (5"Me), 20.8 (8Me), 21.0 (3"Me), 21.2 (5'Me), 23.1 (6Me), 25.5 (14), 26.4 (6Me), 27.4 (8), 29.5 (23), 30.1 (4'), 32.1 (9NMe), 34.9 (2"), 35.7 (9NMe), 37.6 (7), 37.9 (7), 39.1 (4), 40.4 (3NMe, 3'NMe), 41.6 (4), 45.2 (11), 45.4 (12, 2), 48.7 (3"OMe), 55.4 (9), 64.1 (3'), 64.7 (5"), 67.5 (5'), 70.7 (2'), 72.7 (3"), 73.5 (6), 74.4 (6), 77.7 (4"), 78.4 (3), 79.3 (16), 84.9 (5), 88.5 (15), 94.4 (1"), 95.7 (1"), 101.3 (1'), 102.7 (1'), 113.7 (17), 129.4 (18), 134.2 (19), 146.3 (26), 146.5 (24), 147.3 (21), 169.4 (10), 176.1 (1) ppm |
| 185 | $^{13}$C NMR (151 MHz, DMSO-d6): δ = 9.0 (4Me), 14.1 (2Me), 17.9 (5Me), 20.5 (5'Me, 3"Me), 20.9 (8Me), 24.4 (17), 25.0 (16), 26.5 (6Me), 30.4 (8), 32.2 (3'NMe), 34.7 (2"), 35.8 (4'), 36.0 (9NMe), 39.9 (7), 40.0 (4), 43.1 (2), 45.9 (15), 48.4 (3"OMe), 57.7 (9), 61.5 (3'), 62.3 (13), 65.2 (5"), 69.4 (5), 72.8 (3"), 73.1 (6), 77.0 (4), 78.2 (3), 79.5 (2'), 83.2 (5), 95.1 (1"), 98.5 (1'), 120.3 (11), 137.1 (12), 153.7 (14), 165.0 (10), 174.7 (1) ppm |
| 197 | $^{13}$C NMR (126 MHz, DMSO-d6): δ = 9.3 (4Me), 14.3 (2Me), 17.6 (5Me), 19.4 (8Me), 20.7 (3"Me, 5'Me), 28.1 (6Me, 8), 31.0 (4), 35.3 (2"), 37.7 (15), 39.7 (3'NMe, 3'NMe), 40.0 (23), 40.5 (4), 41.7 (7), 47.2 (2), 48.8 (3"OMe), 50.3 (13), 63.7 (3'), 65.3 (5), 67.9 (5), 71.8 (2'), 72.8 (3"), 74.4 (6), 77.4 (4"), 79.8 (3), 85.4 (5),96.3 (1"), 104.4 (1'), 125.6 (27, 19), 127.6 (20, 18, 28, 26), 128.6 (29, 25, 21, 17), 135.9 (24), 138.3 (16), 174.7 (1) ppm |
| 208 | $^{13}$C NMR (151 MHz, DMSO-d6): δ = 10.0 (4Me), 14.8 (2Me), 17.5 (5"Me), 20.8 (3"Me), 20.9 (8Me), 21.0 (5'Me), 24.9 (8), 27.1 (14), 28.6 (6Me), 30.3 (4'), 35.3 (2"), 38.7 (4), 40.2 (3'NMe, 3'NMe), 46.6 (2), 48.7 (3"OMe), 49.7 (12), 54.9 (9), 64.3 (3'), 64.9 (5"), 68.3 (5), 70.4 (2'), 72.6 (3"), 75.1 (6), 77.2 (4"), 82.8(3), 98.4 (1"), 104.6 (1'), 110.2 (15), 111.1 (19), 118.2 (21), 118.6(22), 120.8 (20), 121.3 (31, 27), 123.6 (16), 125.2 (29), 127.6 (30, 28), 127.8 (23), 136.0 (18), 139.2 (26), 174.0 (1) ppm |

Table with NMR Data of Representative Compounds of Formula (I):

| Cpd# | δ NMR Data |
|---|---|
| 212 | $^{13}$C NMR (126 MHz, DMSO-d6): δ = 8.9 (4Me), 14.9 (2Me, 25), 17.7 (5″Me), 20.3 (5′Me), 20.9 (8Me, 3″Me), 21.6 (17), 24.1 (27), 24.5 (27, 6Me), 27.1 (8), 29.7 (23), 31.0 (18), 31.2 (22), 31.6 (3′NMe), 34.1 (9NMe), 35.2 (2″), 35.8 (4′), 38.8 (4), 41.2 (11), 43.7 (2), 45.7 (26), 47.1 (16), 48.3 (3″OMe), 51.4 (20), 54.0 (9), 59.8 (14), 61.8 (3′), 64.8 (5″), 69.5 (5), 73.3 (3″), 74.3 (6), 77.2 (4″), 79.3 (3), 80.0 (2′), 84.6 (5), 95.3 (1″), 99.2 (1′), 154.0 (28), 176.2 (1) ppm |
| 218 | $^{13}$C NMR (126 MHz, DMSO-d6): δ = 10.2 (4Me), 12.7 (2Me), 18.6 (5″Me), 20.0 (8Me), 20.2 (6Me), 21.0 (3″Me), 21.3 (5Me), 30.3 (4′), 34.9 (2″), 34.9 (8), 38.5 (7), 40.2 (4), 40.4 (3′NMe, 3′NMe), 42.6 (10), 43.0 (17), 44.2 (2), 48.6 (3″OMe), 50.2 (6″OMe), 54.7 (13), 56.0 (14), 64.4 (3′), 64.7 (5″), 67.3 (5), 70.7 (2), 72.8 (3″), 77.5 (4″), 77.7 (3), 77.9 (5), 79.2 (6), 95.0 (1),101.9 (1′), 127.8 (27, 29), 128.0 (23, 21), 129.3 (24, 20), 129.5 (30, 26), 131.9 (22), 132.1 (28), 135.6 (25), 136.2 (19), 169.5 (16), 170.3 (11), 175.6 (1), 177.0 (9) ppm |
| 219 | $^{13}$C NMR (151 MHz, DMSO-d6): δ = 10.4 (4Me), 13.7 (2Me),18.3 (5″Me), 20.2 (6Me, 8Me), 21.2 (3″Me, 5′Me), 30.2 (4′), 34.5 (8), 34.9 (2″), 38.1 (7), 39.9 (4), 40.4 (3′NMe, 3′NMe), 42.6 (17, 10), 44.7 (2), 48.6 (3″OMe), 50.2 (6″OMe), 55.3 (13, 14), 64.3 (3), 64.6 (5″), 67.2 (5), 70.9 (2′), 72.6 (3″), 77.4 (4″), 77.6 (3), 78.0(5), 79.2 (6), 95.2 (1″), 102.1 (1′), 127.7 (27, 29, 23, 21), 129.4 (24, 20, 30, 26), 131.8 (28, 22), 136.6 (19, 25), 170.7 (16, 11), 175.9 (1), 177.0 (9) ppm |
| 220 | $^{13}$C NMR (151 MHz, DMSO-d6): δ = 9.7 (4Me), 13.9 (2Me), 18.2 (5Me), 18.5 (8Me), 20.6 (6Me), 20.9 (3″Me), 21.1 (5′Me), 30.1 (4), 33.0 (8), 35.0 (2″), 37.9 (4), 40.0 (7), 40.3 (3′NMe, 3NMe), 47.9 (2), 48.7 (3″OMe), 50.7 (6″OMe), 54.0(11), 54.9 (12), 64.2 (3), 64.9 (5″), 67.8 (5), 70.7 (2′), 72.7 (3″), 76.7 (5), 77.7 (4), 80.3 (3), 81.2 (5), 97.5 (1″), 103.5 (1′), 127.8 (18, 16), 128.1 (24, 22), 128.7 (21, 25), 129.2 (19, 15), 131.7 (23, 17), 136.1 (14), 138.2 (20), 174.3 (1), 175.2 (9) ppm |
| 222 | $^{13}$C NMR (151 MHz, DMSO-d6): δ = 9.1 (4Me), 14.7 (2Me), 18.4(8Me), 18.7 (5″Me), 19.8 (6Me), 20.9 (3″Me), 21.3 (5′Me), 30.5(4), 32.0 (8), 34.8 (2″), 39.1 (4), 40.4 (3′NMe, 3′NMe), 41.0 (7),44.8 (2), 49.0 (3″OMe), 51.6 (6″OMe), 52.8 (12), 58.4(11), 64.3(3), 64.9 (5″), 67.2 (5), 70.8 (2′), 72.6 (3″), 77.2 (4″), 77.4 (3),78.8 (5), 79.0 (6), 95.7 (1″), 102.7 (1′), 127.5 (18, 16), 127.8 (24,22), 128.5 (17), 128.6 (23), 128.7 (19, 15), 129.1 (25, 21), 136.8 (14), 137.9 (20), 175.2 (1), 175.5 (9) ppm |
| 223 | $^{13}$C NMR (151 MHz, DMSO-d6): δ = 9.4 (4Me), 14.1 (2Me), 18.2 (5Me), 21.0 (3″Me), 21.3 (5′Me), 22.0 (8Me), 25.5 (8), 25.7 (24), 26.1 (6Me), 29.7 (13), 29.9 (4), 34.8 (2″), 39.1 (4), 40.3 (3′NMe, 3′NMe), 41.8 (7), 45.5 (2), 46.3 (11), 48.8 (3″OMe), 50.8 (23), 59.3 (10), 64.4 (5″, 3), 64.5 (9), 67.2 (5), 70.6 (2), 72.6 (3″), 73.4(6), 77.5 (4″), 78.5 (3), 82.6 (5), 95.2 (1″), 102.7 (1), 111.5 (18), 111.5 (14), 118.3 (20), 118.5 (21), 120.9 (19), 123.1 (15), 127.2 (22), 128.0 (27, 29), 130.1 (28), 130.2 (30, 26), 136.3 (17), 139.2 (25), 174.1 (1) ppm |
| 224 | $^{13}$C NMR (151 MHz, DMSO-d6): δ = 9.7 (4Me), 18.2 (5Me), 21.1 (3″Me), 21.2 (5′Me), 22.0 (8Me), 25.1 (8), 28.1 (6Me), 29.8 (24, 4), 30.0 (13), 35.3 (2″), 37.8 (4), 40.1 (3′NMe, 3′NMe), 46.6 (11), 48.0 (2), 48.6 (3″OMe), 55.8 (23), 64.3 (3), 64.5 (5″), 67.5(5), 70.7 (2), 72.7 (3″), 73.9 (6), 77.7 (4″), 79.8 (3), 82.3 (5), 96.7(1), 103.3 (1), 111.0 (14), 111.3 (18), 118.2 (20), 118.7 (21),120.8 (19), 123.3 (15), 127.5 (22), 128.1 (29, 27), 130.3 (30, 26),136.2 (17), 139.4 (25), 173.8 (1) ppm |
| 238 | $^{13}$C NMR (151 MHz, DMSO-d6): δ = 9.1 (4Me), 14.0 (2Me), 15.6 (2Me), 16.1 (19, 19), 16.6 (5′Me), 17.3 (19, 19), 17.9 (5″Me), 20.9 (3″Me, 8Me), 22.0 (3″Me, 8Me), 23.9 (5′Me), 24.7 (12), 25.0 (12), 26.0 (6Me), 27.0 (8), 29.2 (8), 30.0 (11, 3′NMe), 34.8 (2″, 9NMe), 35.9 (3′NMe), 37.4 (13), 38.9 (4, 7), 45.0 (2), 46.6 (18), 48.7 (3″OMe), 57.5 (9), 65.0 (5″), 70.0 (5), 76.9 (4″), 79.8 (3), 80.9 (3), 85.0 (5), 96.0 (1″), 96.8 (1″), 98.0 (1), 172.9 (10), 176.0 (1) ppm |
| 255 | $^{13}$C NMR (126 MHz, DMSO-d6): δ = 9.2 (4Me), 13.2 (2Me), 14.0 (2Me), 18.9 (5″Me, 20, 19, 8Me), 20.7 (5′Me, 3″Me), 21.9 (14), 26.9 (6Me), 29.9 (9NMe, 4, 8), 30.7 (15), 31.4 (26), 32.9 (18), 35.3 (9NMe, 2″), 36.9 (25), 40.4 (3′NMe, 3′NMe), 42.9 (4), 45.0 (2), 46.6 (13), 48.0 (3″OMe), 51.4 (23), 53.9 (17), 54.9 (17), 56.0 (11), 57.0 (11, 9), 65.2 (3′, 5″), 67.1 (5), 72.9 (3″), 74.9 (6), 76.4 (3), 77.3 (4″), 81.8 (5), 95.0 (1″), 101.9 (1), 125.7 (30), 127.9 (32,28), 128.4 (29, 31), 142.0 (27), 169.8 (16), 171.2 (10), 175.9 (1) ppm |
| 256 | $^{13}$C NMR (126 MHz, DMSO-d6): δ = 10.5 (4Me), 15.9 (2Me), 18.7 (21, 20), 18.9 (5″Me), 21.1 (3″Me), 21.3 (8Me), 21.7 (5Me),24.8 (14), 25.5 (6Me), 26.6 (8), 28.5 (15), 29.6 (19), 30.1 (4), 35.3 (2″), 35.4 (9NMe), 35.8 (4), 37.4 (7), 40.3 (3′NMe, 3NMe), 47.1 (13), 47.9 (2), 48.8 (3″OMe), 54.0 (9), 55.2 (11), 55.2 (17), 64.5 (3), 64.8 (5″), 66.5 (5), 71.1 (2), 72.6 (3″), 74.8 (6), 77.4 (4″), 79.5 (3), 81.8 (5), 95.4 (1″), 101.2 (1), 171.1 (16), 171.7 (10), 173.2 (1) ppm |
| 257 | $^{13}$C NMR (126 MHz, DMSO-d6): δ = 9.9 (4Me), 15.1 (5Me),18.8 (21, 20), 21.0 (8Me, 3″Me, 5′Me), 24.9 (14), 27.5 (15), 29.4(19), 29.9 (8), 30.2 (4), 34.6 (2″), 36.9 (9NMe), 40.4 (3′NMe, 3′NMe), 43.7 (2), 46.8 (13), 48.7 (3″OMe), 51.4 (17), 64.5 (3), 64.7 (5″), 67.3 (5), 70.7 (2), 72.8 (3″), 74.1 (6), 77.3 (4″), 83.9 (5), 95.1 (1″), 102.0 (1′) ppm |
| 258 | $^{13}$C NMR (126 MHz, DMSO-d6): δ = 10.5 (4Me), 15.9 (2Me),18.7 (21, 20), 18.9 (5″Me), 21.1 (3″Me), 21.3 (8Me), 21.7 (5Me),24.8 (14), 25.5 (6Me), 26.6 (8), 28.5 (15), 29.6 (19), 30.1 (4),35.3 (2″), 35.4 (9NMe), 35.8 (4), 37.4 (7), 40.3 (3′NMe, 3NMe), 47.1 (13), 47.9 (2), 48.8 (3″OMe), 54.0 (9), 55.2 (11), 55.2 (17), 64.5 (3), 64.8 (5″), 66.5 (5), 71.1 (2), 72.6 (3″), 74.8 (6), 77.4(4″), 79.5 (3), 81.8 (5), 95.4 (1″), 101.2 (1), 171.1 (16), 171.7 (10), 173.2 (1) ppm |
| 259 | $^{13}$C NMR (151 MHz, DMSO-d6): δ = 9.7 (4Me), 10.1 (4Me), 14.9 (2Me), 18.0 (17, 16), 18.1 (5″Me, 17), 19.0 (16), 19.2 (8Me), 20.9 (3Me), 21.2 (5′Me), 24.9 (6Me), 25.4 (8), |

-continued

Table with NMR Data of Representative Compounds of Formula (I):

| Cpd# | δ NMR Data |
|---|---|
| | 28.9 (4), 30.4 (24),30.6 (15), 31.2 (15), 31.4 (26), 32.1 (26), 33.1 (25), 34.1 (9NMe), 35.1 (9NMe, 2"), 35.8 (2"), 36.6 (4), 40.1 (3'NMe, 3'NMe), 40.5(7), 40.7 (3'NMe, 3'NMe), 42.8 (2, 7), 47.0 (22), 48.7 (3"OMe), 53.7 (9), 54.3 (9), 56.8(11), 58.7 (20), 64.2 (3), 64.7 (5"), 67.5 (5), 70.6 (2), 71.9 (3"), 75.0 (6), 77.5 (4"), 82.3 (5), 82.7 (5), 94.4(1), 96.4 (1"), 101.6 (1), 102.5 (1), 103.9 (1), 125.9 (30), 128.3(31, 29, 32, 28), 140.9 (27), 170.0 (19, 10), 172.4 (1), 174.0 (1) ppm. |
| 260 | $^{13}$C NMR (126 MHz, DMSO-d6): δ = 10.2 (4Me), 15.0 (2Me), 18.2 (5"Me), 19.1 (17, 16), 21.4 (8Me, 5'Me, 3"Me), 24.9 (23), 25.8 (6Me), 26.9 (6Me), 27.7 (8), 29.1 (24), 29.6 (15), 30.2 (4), 31.4 (26), 33.0 (25), 35.3 (9NMe, 2"), 37.1 (9NMe), 38.2 (7, 4),40.4 (3'NMe, 3'NMe), 41.9 (2), 42.6 (2), 43.4 (22), 48.7 (3"OMe),49.8 (11), 50.9(11), 57.2 (9), 59.6 (14, 20), 64.7 (5", 3), 68.1 (5),70.8 (2), 76.0 (3), 77.5 (4"), 83.1 (5), 83.8 (5), 92.5 (1"), 96.9 (1), 98.1 (1"), 101.6 (1), 103.2 (1), 103.7 (1), 125.7 (30), 128.0 (32, 31, 29, 28), 141.8 (27), 170.2 (19), 170.7 (10), 174.8 (1) ppm. |
| 262 | $^{13}$C NMR (126 MHz, DMSO-d6): δ = 9.6 (4Me), 15.4 (2Me), 18.6 (5Me), 20.1 (8Me), 20.9 (3"Me), 21.4 (5'Me), 21.6 (20), 21.9 (14), 22.9 (21), 23.7 (19), 24.9 (6Me), 28.8 (8), 30.1 (4'), 31.7(27), 32.1 (15), 34.0 (26), 34.8 (2"), 36.9 (9NMe), 39.0 (7), 39.8 (4), 40.3 (3'NMe, 3'NMe), 41.1 (18), 44.3 (2), 46.7 (13), 47.8 (17), 48.7 (3"OMe), 52.2 (24), 55.5 (11), 57.2 (9), 64.5 (3'), 64.8(5), 67.1 (5), 70.6 (2'), 72.7 (3"), 74.9 (6), 77.4 (4"), 78.0 (3), 82.8 (5), 95.1 (1"), 102.1 (1'), 125.7 (31), 128.2 (33, 29), 128.3 (32, 30), 141.4 (28), 169.3 (16), 171.3 (23), 172.8 (10), 175.6 (1) ppm. |
| 264 | $^{1}$H NMR (500 MHz, DMSO) δ = 7.79 (br.$), 7.04 (d), 6.86 (d), 4.85 (br.$), 4.59 (br.$), 4.30 (d), 3.96 (m), 3.60 (br.s, N CH$_3$), 3.49 (s), 3.17 (s), 2.90 (s) 2.73 (d), 2.37 (m), 2.26 (d), 2.14 (br.s, N(CH$_3$)$_2$), 2.01 (d), 1.87 (d), 1.80 (t), 1.60 (d), 1.48 (m), 1.26 (br.s, —OtBu), 1.14 (m), 1.07 (m), 0.95 (m), 0.76 (d) ppm. |
| 265 | Two diastereoisomeres: $^{1}$H NMR (600 MHz, DMSO) δ = 7.22 (br.$), 7.04 (d), 6.78 (d), 4.64 (d), 4.57 (d), 3.68 (N-CH$_3$), 3.47 (s), 2.78 (m) 2.57 (dd), 2.48 (m), 2.32 (m),2.24 (m), 2.13 (s, N(CH$_3$)2), 2.12 (m), 2.04 (s), 1.94 (t), 1.86 (m), 1.69 (m), 1.63 (d), 1.56 (m), 1.47 (m), 1.22 (m), 1.12 (d), 1.04 (s), 1.02 (m), 0.95 (d), 0.84 (d), 0.74 (d) ppm. .$^{1}$H NMR (600 MHz, DMSO) δ = 7.82 (d), 7.12 (d), 6.83 (d), 4.64 (d), 4.55 (d), 3.79 (m), 3.71 (N—CH$_3$), 3.42 (s), 2.64 (m) 2.53 (m), 2.39 (m), 2.36 (m), 2.30 (m), 2.22 (m), 2.13 (s, N(CH$_3$)$_2$), 2.06 (m), 2.00 (m), 1.96 (s), 1.88 (m), 1.65 (m), 1.57 (m), 1.28 (m), 1.17 (dd), 1.12 (d), 1.03 (s), 1.02 (m), 0.89 (d), 0.85 (d), 0.83 (d) ppm. |

Biological Assays

The potential for a compound of formula (II) obtained by the process of the present invention to have an advantageous profile for providing therapeutic benefit in the prophylaxis and/or treatment of conditions involving inflammation or immune responses, and/or autoimmune diseases may be demonstrated, for example using the in vitro protocols for Inhibition of IL-6 production in LPS-stimulated murine spleenocytes in vitro, as well as using the in vivo protocol for TNF-alpha overproduction induced by bacterial lipopolysaccharide (LPS) in male BALB/cJ mice, as well as using in vitro and in vivo protocols described in international patent applications WO2010086349 A1 and WO2009130189.

The following abbreviations are used in the text: DMSO for dimethyl sulfoxide, DMEM for Dulbecco's modified Eagle medium, LPS for bacterial lipopolysaccharide, PBS for phosphate buffered saline and BALF for bronchoalveolar lavage fluid.

In Vitro Screening Protocol

Compound Preparation

Test and reference substances used in an in vitro assay are dissolved in dimethyl sulfoxide (DMSO) (Sigma Chemical Co., USA) at a concentration of 50 mM and are further diluted to final concentrations of 50 μM, 25 μM, 12.5 μM, 6.3 μM and 3.1 μM in Dulbecco's modified Eagle medium (DMEM) (Gibco, USA) supplemented with 1% heat inactivated fetal bovine serum (FBS) (BioWest, Ringmer, United Kingdom).

Inhibition of IL-6 Production in LPS-Stimulated Murine Splenocytes In Vitro

After cervical dislocation, mouse spleens were removed using sterile dissection tools. Spleens were transferred to a pre-wetted cell strainer in a 50 mL sterile conical tube and cell suspension was made by gentle puddle. Cells were centrifuged (20 min, 300×g) and resuspended in 2 mL of sterile phosphate buffered saline (PBS) (Sigma Chemical Co., USA). Red blood cells were lysed by addition of 3 mL of sterile water and occasional gentle shaking for 1 minute. Afterwards, the tube was filled to 40 mL with DMEM medium and centrifuged (20 min, 300×g). Cells were resuspended in DMEM supplemented with 1% FBS and seeded in a 24-well plate, 1×10$^6$ cells per mL medium. Cells were pre-incubated with the test compounds for 3 h at 37° C., in an atmosphere of 5% CO$_2$ and 90% humidity. Afterwards, cells were stimulated with 1 μg/mL lipopolysaccharide (LPS, E. coli 0111:B4, Sigma Chemical Co., USA) and incubated overnight. Concentration of IL-6 was determined in cell supernatants by sandwich ELISA using capture and detection antibodies (R&D Systems, USA) according to the manufacturer's recommendations. Inhibition (as percentage) was calculated using the following formula:

% inhibition=[1−(concentration of IL-6 in sample−concentration of IL-6 in negative control)/(concentration of IL-6 in positive control−concentration of IL-6 in negative control)]×100.

The positive control refers to LPS-stimulated samples that were not preincubated with the compounds.

The negative control refers to unstimulated and untreated samples.

| Table with IL-6 production assay Values of Compounds of Formula (III) | |
|---|---|
| A | ≤0-29% |
| B | 30-59% |
| C | 60-79% |
| D | 80-100% |
| Cpd# | IL6/IC$_{50}$ (µM) |
| 2 | A |
| 3 | A |
| 10 | A |
| 12 | A |
| 13 | A |
| 14 | A |
| 17 | A |
| 28 | A |
| 31 | A |
| 37 | B |
| 46 | B |
| 51 | B |
| 58 | A |
| 59 | B |
| 62 | C |
| 65 | A |
| 69 | B |
| 70 | A |
| 81 | A |
| 84 | A |
| 85 | B |
| 86 | A |
| 87 | A |
| 90 | A |
| 106 | A |
| 122 | A |
| 130 | A |
| 132 | B |
| 133 | A |
| 135 | A |
| 136 | B |
| 138 | A |
| 141 | A |
| 142 | A |
| 143 | A |
| 148 | A |
| 151 | A |
| 153 | A |
| 155 | A |
| 158 | D |
| 175 | A |
| 186 | A |
| 192 | B |
| 231 | A |
| 232 | A |
| 233 | A |
| 235 | A |
| 241 | A |
| 243 | B |

In Vivo Screening Protocols

TNF-Alpha Overproduction Induced by Bacterial Lipopolysaccharide (LPS) in Male BALB/cJ Mice For intraperitoneal administration (i.p.) compounds are dissolved in a final concentration of 10 mg/mL. The required amount of compound is first dissolved in dimethylsulfoxide (DMSO, Sigma) and then diluted with 0.5% (w/v) methylcellulose so that the final DMSO concentration is 5% (v/v).

Male BALB/cJ mice (Charles River, France), with an average weight of ~30 g are randomly grouped (n=8 in testing group, 10 in positive control and 8 in negative control). Mice receive intraperitoneally (i.p.) a single dose of 25 mg/kg or 50 mg/kg of test compound. Two hours after administration, 1 µg of LPS (from *Escherichia coli* serotype 0111:B4, Sigma), dissolved in sterile PBS in a volume of 60 µL, is intranasally administered to all experimental groups except the negative control group, which receive the same volume of vehicle (PBS). Blood samples are taken from animals 0.5 hours after application of LPS in order to measure TNF-alpha levels. Results are expressed as percentage decrease in total TNF-alpha level of treated animals compared to positive control (LPS challenged, but untreated animals).

Tested compounds of Formula (III) exhibited 40% or more inhibition of TNF-alpha overproduction at doses of 25 mg/kg. Suitably, compounds of Formula (III) exhibit 50% or more inhibition of TNF-alpha overproduction at doses of 25 mg/kg. For example, compounds of Formula (III) of examples 17, 65, 232 and 233 showed more than 70% inhibition at doses of 25 mg/kg, whereas compounds of Formula (III) of examples 59, 235 and 241, showed more than 40% inhibition at 25 mg/kg.

We claim:

1. A macrolide based macrocycle compound of Formula (III)

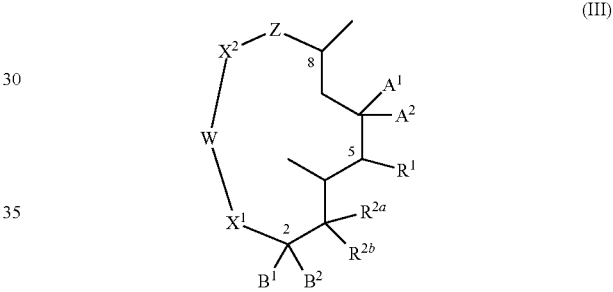

and pharmaceutically acceptable salts, solvates and prodrugs thereof, wherein $A^1$ is OH, $OC_{1-6}$alkyl, $OC_{2-6}$alkenyl, $OC_{2-6}$alkynyl, $OR^p$, or $A^1$ together with $R^{2b}$ forms cyclic hemiketal or ether;

$A^2$ is $CH_3$ or H;

$B^1$ and $B^2$ are independently H, $C_{1-6}$alkyl or halogen, or $B^2$ together with $R^{2a}$ forms a double bond;

$R^1$ is $S^1$, OH, $OC_{1-6}$alkyl or $OR^p$;

$S^1$ is sugar group of formula (b1):

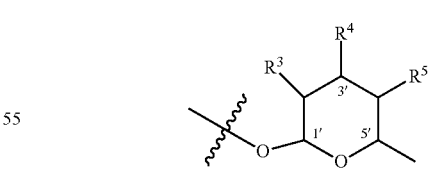

wherein, $R^3$ is OH, H, $OR^p$, —O-$L^1$-G or —OC(=O)G, provided when $R^3$ is —O-$L^1$-G or —OC(=O)G group then $R^4$ is —N(CH$_3$)$_2$ and $R^5$ is H, wherein $L^1$ —(CH$_2$)$_{a1}$—$U^1$—(CH$_2$)$_{b1}$—;

$U^1$ is —N(R$^6$)—, —NHC(=O)— or —C(=O)NH—;

$R^6$ is H or $C_{1-3}$alkyl;

$a^1$ is an integer from 2 to 6;

$b^1$ is an integer from 0 to 6;

G is selected from:
(i) $G^1$, wherein $G^1$ is $C_{1-8}$alkyl, wherein alkyl may be optionally interrupted by 1 to 3 bivalent radical groups selected from —O—, —S— and —N($R^{g1}$)—, where $R^{g1}$ is H or $C_{1-6}$alkyl, and where alkyl may be optionally substituted by one or more groups independently selected from halogen, OH, keto, $C_{1-6}$alkyl, $C_{2-6}$alkenyl, $C_{2-6}$alkynyl, $OC_{1-6}$alkyl, halo$C_{1-6}$alkyl, halo$C_{1-6}$alkyloxy, —C(=O)O$C_{1-6}$alkyl, —$C_{1-6}$alkyl-OH, $NH_2$, N—($C_{1-6}$-alkyl)amino, N,N-di($C_{1-6}$alkyl)amino; aryl or heteroaryl wherein said aryl and heteroaryl may be mono or biyclic and independently each may be optionally substituted by one or more groups independently selected from halogen, CN, OH, $NO_2$, $OC_{1-6}$alkyl, $NH_2$, N—($C_{1-6}$-alkyl)amino, N,N-di($C_{1-6}$alkyl)amino, —C(=O)$C_{1-6}$-alkyl, —OC(=O)$C_{1-6}$-alkyl, —C(=O)OH, —C(=O)O$C_{1-6}$-alkyl, —C(=O)NH$C_{1-6}$alkyl, and —NHC(=O) $C_{1-6}$-alkyl;
(ii) $G^2$, wherein $G^2$ is 3-7 membered cycloalkyl which may be optionally substituted by one or more groups independently selected from OH, halogen, CN, $NH_2$, $C_{1-6}$alkyl, $C_{2-6}$alkenyl, $C_{2-6}$ alkynyl, halo$C_{1-6}$alkyl, —O$C_{1-6}$alkyl, halo$C_{1-6}$alkyloxy, —$C_{1-6}$alkyl-OH, —C(=O)$C_{1-6}$-alkyl, —C(=O)O$C_{1-6}$-alkyl, —C(=O)OH, —C(=O)$NH_2$, —$C_{0-6}$alkyl-aryl or —$C_{0-6}$alkyl-heteroaryl wherein aryl and heteroaryl independently from each other may be optionally substituted by one or more groups independently selected from halogen, CN, OH, $NO_2$, $C_{1-6}$ alkyl, $C_{2-6}$alkenyl, $C_{2-6}$alkynyl, halo$C_{1-6}$alkyl, —O$C_{1-6}$alkyl, halo$C_{1-6}$alkyloxy, —$C_{1-6}$alkyl-OH, $NH_2$, N—($C_{1-6}$alkyl)amino, N,N-di($C_{1-6}$alkyl)amino, —C(=O)$C_{1-6}$alkyl, —OC(=O)$C_{1-6}$alkyl, —C(=O)OH, —C(=O)O$C_{1-6}$alkyl, —C(=O)NH$C_{1-6}$alkyl and —NHC(=O)$C_{1-6}$alkyl;
(iii) $G^3$, wherein $G^3$ is 3-7 membered heterocycloalkyl containing one or two heteroatoms independently selected from N, O and S, where heterocycloalkyl may be optionally substituted by one or more groups independently selected from OH, halogen, CN, $NH_2$, $C_{1-6}$alkyl, $C_{2-6}$alkenyl, $C_{2-6}$alkynyl, halo$C_{1-6}$alkyl, —O$C_{1-6}$alkyl, halo$C_{1-6}$alkyloxy, —$C_{1-6}$alkyl-OH, —C(=O) $C_{1-6}$alkyl, —C(=O)O$C_{1-6}$alkyl, —C(=O)OH and —C(=O)$NH_2$;
(iv) $G^4$, wherein $G^4$ is aryl wherein aryl may be optionally substituted by one or more groups independently selected from halogen, CN, OH, $NO_2$, $C_{1-6}$alkyl, $C_{2-6}$alkenyl, $C_{2-6}$alkynyl, halo$C_{1-6}$alkyl, —O$C_{1-6}$alkyl, halo$C_{1-6}$alkyloxy, —$C_{1-6}$alkyl-OH, $NH_2$, N—($C_{1-6}$alkyl) amino, N,N-di($C_{1-6}$alkyl)amino, —C(=O)$C_{1-6}$alkyl, —O(C=O)$C_{1-6}$alkyl, —C(=O)OH, —C(=O) O$C_{1-6}$alkyl, —C(=O)NH$C_{1-6}$alkyl and —NHC(=O) $C_{1-6}$alkyl;
(v) $G^5$, wherein $G^5$ is heteroaryl wherein heteroaryl may be optionally substituted by one or more groups independently selected from halogen, CN, OH, $NO_2$, $C_{1-6}$alkyl, $C_{2-6}$alkenyl, $C_{2-6}$alkynyl, halo$C_{1-6}$alkyl, —O$C_{1-6}$alkyl, halo$C_{1-6}$alkyloxy, —$C_{1-6}$alkyl-OH, $NH_2$, N—($C_{1-6}$alkyl)amino, N,N-di($C_{1-6}$alkyl)amino, —C(=O)$C_{1-6}$alkyl, —O(C=O) $C_{1-6}$alkyl, —C(=O) OH, —C(=O)O$C_{1-6}$alkyl, —C(=O)NH$C_{1-6}$alkyl and —NHC(=O)$C_{1-6}$alkyl;
$R^4$ is —N($R^7$)$R^8$, wherein
$R^7$ is $CH_3$;
$R^8$ is $C_{1-6}$alkyl, H, —C(=O)$R^9$ or $R^p$ wherein $R^9$ is $C_{1-6}$alkyl or H;
$R^5$ is hydrogen;
or both $R^4$ and $R^5$ are hydrogen or together form a bond;
or $S^1$ is sugar group of formula (b2):

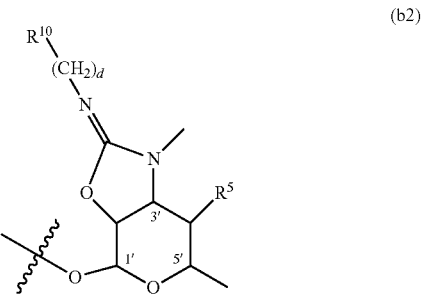

(b2)

wherein:
$R^5$ is H;
d is an integer from zero to 3;
$R^{10}$ is $C_{1-4}$alkyl;
$R^{2a}$ is:
(i) $S^2$;
(ii) —OH;
(iii) —O$C_{1-6}$alkyl,
(iv) H;
(v) together with $R^{2b}$ forms a keto group (=O);
(vi) together with $B^2$ forms a double bond;
(vii) —OC(=O)$Y^1$, wherein $Y^1$ $G^1$, $G^2$, $G^3$, $G^4$, $G^5$ or H; or
(viii) —O$R^p$;
$R^{2b}$ is H, together with $R^{2a}$ forms a keto group, together with $A^1$ forms cyclic hemiketal and $R^{2a}$ is OH, or together with $A^1$ forms cyclic ether group and $R^{2a}$ is H;
$S^2$ is sugar group of formula (d)

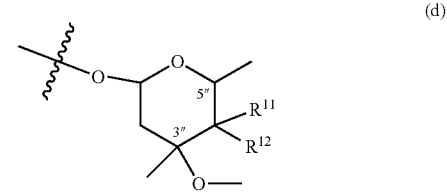

(d)

wherein,
$R^{11}$ is:
(i) H;
(ii) together with $R^{12}$ and carbon atom to which they are attached forms a keto or epoxy group;
(iii) one of $R^{11}$ and $R^{12}$ is OH and the other is —$CH_2$N ($R^{13}$)$R^{14}$, wherein one of $R^{13}$ and $R^{14}$ is $C_{1-6}$alkyl and the other is H, $G^1$, $G^2$, $G^3$, $G^4$, $G^5$ or $R^p$, or wherein $R^{13}$ and $R^{14}$ taken together with the nitrogen atom to which they are attached form a non-aromatic heterocyclic ring containing between 2 and 6 carbon atoms which is:
a. saturated or unsaturated and contains zero or 1 additional heteroatom selected from O, S and N; and/or
b. unsubstituted or substituted by from 1 to 2 groups selected from $C_{1-5}$alkanoyl; $C_{1-6}$alkyl wherein alkyl is uninterrupted or is interrupted by 1-3 bivalent radical groups selected from —O—, —S— and —N($R^{18}$)—, and/or wherein $C_{1-6}$alkyl is unsubstituted or substituted by from 1 to 2 groups selected from OH, NH$_2$, a non-aromatic heterocyclic ring containing between 2 and 6 carbon atoms which is unsubstituted or is substituted by a group selected form C$_{1-4}$alkyl, halogen, NH$_2$, OH, SH, C$_{1-6}$alkoxy and C$_{1-4}$hydroxyalkyl, and C$_{3-7}$cycloalkyl which is unsubstituted or is substituted by a group selected from C$_{1-4}$alkyl, halogen, NH$_2$, OH, SH, C$_{1-6}$alkoxy, C$_{1-4}$hydroxyalkyl; and C$_{1-4}$dialkylamino;

R$^{12}$ is:
 (i) OH,
 (ii) together with R$^{11}$ and carbon atom to which they are attached forms a keto or epoxy group;
 (iii) —OC(=O)Y$^3$, wherein Y$^3$ is H, G$^1$, G$^2$, G$^3$, G$^4$, or G$^5$, or
 (iv) QR$^p$;

R$^N$ is hydrogen, G$^1$, G$^2$, G$^3$, G$^4$, G$^5$, R$^p$, or R$^{15}$ wherein R$^{15}$ is —C$_{1-4}$alkyl-G, —C(=O)G, —C(=O)NH—C$_{0-4}$alkyl-G, wherein G is G$^1$, G$^2$, G$^3$, G$^4$ or G$^5$;

R$^p$ is a protective group;

Z is —NR$^N$CH$_2$—, —NHC(=O)— or —OC(=O)— (left hand valence bond of these groups is attached to X$^2$ whereas right hand valence bond is attached to the C/8 carbon atom), provided when Z is —NHC(=O)— or —OC(=O)— then B$^1$ is OC$_{1-6}$alkyl;

X$^1$ is a bond, —C(=O)NR$^x$—, —NHC(=O)—, —NR$^u$—, —CH$_2$NR$^u$—, —CH$_2$O—, —C(=O)—, or —C(=O)O— (left hand valence bond of these groups is attached to the C/2 carbon atom whereas right hand valence bond is attached to W); wherein
R$^u$ is H or C$_{1-6}$alkyl,
R$^X$ is H, R$^Z$ or —CH(R$^Y$)—C(=O)NHR$^Z$;
R$^Y$ is H, C$_{1-6}$alkyl or phenyl; and
R$^Z$ is C$_{1-6}$alkyl, C$_{0-6}$alkyl-aryl or C$_{0-6}$alkyl-heteroaryl wherein aryl and heteroaryl independently from each other may be optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, NH$_2$, N—(C$_{1-6}$alkyl)amino,N,N-di(C$_{1-6}$alkyl)amino, —C(=O)C$_{1-6}$alkyl, —OC(=O)C$_{1-6}$alkyl, —C(=O)OH, —C(=O)OC$_{1-6}$alkyl, —C(=O)NHC$_{1-6}$alkyl and —NHC(=O)C$_{1-6}$alkyl;

X$^2$ is a bond, —C(=O)— or —CH$_2$—;

W is —W$^1$—(CH$_2$)$_{m1}$—W$^2$—(CH$_2$)$_{m2}$—W$^3$— (left hand valence bond of W$^1$ is attached to X$^1$ whereas right hand valence bond of W$^3$ is attached to X$^2$), wherein:
m$^1$ is zero, 1, 2 or 3;
m$^2$ is zero, 1, 2 or 3;
W$^1$ W$^2$ and W$^3$ are:
 (i) one of, two of or none of W$^1$, W$^2$ and W$^3$ are absent and the remaining of W$^1$, W$^2$ and W$^3$ are independently selected from:
  a. 3-7 membered cycloalkyl which may be optionally substituted by one or more groups independently selected from OH, halogen, CN, NH$_2$, C$_{1-6}$ alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, —C(=O) C$_{1-6}$alkyl, —C(=O)OC$_{1-6}$alkyl, —C(=O)OH, —C(=O) NH$_2$, —C$_{0-6}$alkyl-aryl or C$_{0-6}$alkyl-heteroaryl wherein aryl and heteroaryl independently from each other may be optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, NH$_2$, N—(C$_{1-6}$-alkyl)amino, N,N-di(C$_{1-6}$alkyl)amino, —C(=O)C$_{1-6}$alkyl, —OC(=O) C$_{1-6}$alkyl, —C(=O)OH, —C(=O)OC$_{1-6}$alkyl, —C(=O)NHC$_{1-6}$alkyl and —NHC(=O)C$_{1-6}$alkyl;
  b. 4-7 membered cycloalkenyl containing one or two double bonds which may be optionally substituted by one or more groups independently selected from OH, halogen, CN, NH$_2$, C$_{1-6}$ alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, —C(=O) C$_{1-6}$alkyl, —C(=O)OC$_{1-6}$alkyl, —C(=O)OH and —C(=O)NH$_2$;
  c. 3-7 membered heterocycloalkyl containing one or two heteroatoms independently selected from N, O and S, where heterocycloalkyl may be optionally substituted by one or more groups independently selected from OH, halogen, CN, NH$_2$, C$_{1-6}$ alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, —C(=O)C$_{1-6}$alkyl, —C(=O)OC$_{1-6}$alkyl, —C(=O)OH, —C(=O)NH$_2$, —C$_{0-6}$alkyl-aryl, —O—C$_{0-6}$alkyl-aryl, —C$_{0-6}$alkyl-heteroaryl, —C$_{0-6}$alkyl-cycloalkyl or —C$_{0-6}$alkyl-heterocycloalkyl, wherein aryl, heteroaryl, cycloalkyl, and heterocycloalkyl independently from each other may be optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, C$_{1-6}$alkyl-OH, NH$_2$, N—(C$_{1-6}$-alkyl)amino, N,N-di(C$_{1-6}$alkyl) amino, —C(=O)C$_{1-6}$alkyl, —OC(=O)C$_{1-6}$alkyl, —C(=O)OH, —C(=O)OC$_{1-6}$alkyl, —C(=O)NHC$_{1-6}$alkyl and —NHC(=O)C$_{1-6}$alkyl;
  d. 4-7 membered heterocycloalkenyl containing one or two heteroatoms independently selected from N, O and S and one or two double bonds where heterocycloalkenyl may be optionally substituted by one or more groups independently selected from OH, halogen, CN, NH$_2$, C$_{1-6}$ alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, —C(=O) C$_{1-6}$alkyl, —C(=O)OC$_{1-6}$alkyl, —C(=O)OH and —C(=O)NH$_2$;
  e. 6 membered aryl which may be optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, NH$_2$, N—(C$_{1-6}$-alkyl) amino, N,N-di(C$_{1-6}$alkyl) amino, —C(=O)C$_{1-6}$alkyl, —O(C=O) C$_{1-6}$alkyl, —C(=O)OH, —C(=O)OC$_{1-6}$alkyl, —C(=O)NHC$_{1-6}$alkyl and —NHC(=O)C$_{1-6}$alkyl;
  f. 5-6 membered heteroaryl containing two or three heteroatoms independently selected from N, O and S, wherein heteroaryl may be optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, —OC$_{1-6}$alkyl, haloC$_{1-6}$alkyloxy, —C$_{1-6}$alkyl-OH, NH$_2$, N—(C$_{1-6}$-alkyl)amino, N,N-di(C$_{1-6}$alkyl) amino, —C(=O)C$_{1-6}$alkyl, —O(C=O)C$_{1-6}$alkyl, —C(=O)OH, —C(=O)OC$_{1-6}$alkyl, —C(=O) NHC$_{1-6}$alkyl and —NHC(=O)C$_{1-6}$alkyl;
  g. —C(R$^{w1a}$)(R$^{w2a}$)—, R$^{w1a}$ is hydrogen, and R$^{w2a}$ is C$_{1-6}$alkyl, C$_{2-6}$alkenyl, C$_{2-6}$ alkynyl, halogen, OH, CN, —C(=O)OH, —C(=O)NH$_2$, halo C$_{1-6}$alkyl, OC$_{1-6}$alkyl, C$_{1-6}$alkyl-OH, —C$_{1-6}$alkylOC$_{1-6}$alkyl, —C$_{1-6}$alkylSC$_{1-6}$alkyl, —C$_{1-6}$alkyl-C(=O)OH, —C$_{1-6}$alkyl-C(=O)OC$_{1-6}$alkyl, —C$_{1-6}$alkylOC(=O)C$_{1-6}$alkyl, —C$_{1-6}$alkylC(=O)NH$_2$, —C$_{1-6}$alkyl-NH$_2$, —C$_{1-6}$ alkyl-NH(C$_{1-6}$alkyl), —C$_{1-6}$alkyl-N(C$_{1-6}$alkyl)$_2$, —C$_{1-6}$alkylNHC(=O)OC$_{1-6}$alkyl, —C$_{1-6}$alkyl-NHC(=O)C$_{2-6}$alkenyl, —C$_{1-6}$alkyl-NHC(=O)—C$_{0-4}$alkyl-heteroaryl, —C$_{1-6}$alkylNHSO$_2$C$_{1-6}$alkyl, —C$_{1-6}$alkylNHSO$_2$C$_{2-6}$alkenyl, —C$_{1-6}$alkylNHSO$_2$cycloalkyl, —C$_{0-6}$alkyl-aryl, —C$_{2-6}$alkenyl-aryl, —C$_{0-6}$alkyl-heteroaryl, —C$_{2-6}$alkenyl-heteroaryl, —C$_{0-6}$alkyl-cycloalkyl, or —C$_{0-6}$alkyl-heterocycloalkyl, wherein alkyl, alkenyl, alkynyl, aryl, heteroaryl, cycloalkyl, and heterocycloalkyl independently from each other may be optionally substituted by one or more groups independently selected from halogen, CN, OH, NO$_2$, C$_{1-6}$alkyl, C$_{2-6}$alkenyl, C$_{2-6}$ alkynyl, haloC$_{1-6}$alkyl, —OC$_{1-6}$alkyl, haloC$_{1-6}$alkyloxy, C$_{1-6}$alkyl-OH, NH$_2$, N—(C$_{1-6}$-alkyl)amino, N,N-di(C$_{1-6}$alkyl)amino, —C(=O)C$_{1-6}$alkyl, —OC(=O)C$_{1-6}$alkyl, —C(=O)OH, —C(=O)OC$_{1-6}$alkyl, —C(=O)NHC$_{1-6}$alkyl, —NHC(=O)C$_{1-6}$alkyl, —C$_{1-6}$alkylNHSO$_2$C$_{1-6}$ alkyl, and —C$_{1-6}$alkyl-NH(C=NH)NHR$^g$ wherein R$^g$ is H, amino protecting group, —C$_{0-6}$alkyl-aryl, —OC$_{0-6}$alkylaryl, —C$_{0-6}$alkyl-heteroaryl, —C$_{0-6}$alkyl-cycloalkyl or —C$_{0-6}$alkyl-heterocloalkyl, wherein aryl, heteroaryl, cycloalkyl, and heterocycloalkyl independently from each other may be optionally substituted by one or more groups independently selected from halogen, CN, OH, NO$_2$, C$_{1-6}$ alkyl, C$_{2-6}$alkenyl, C$_{2-6}$alkynyl, haloC$_{1-6}$alkyl, —OC$_{1-6}$alkyl, haloC$_{1-6}$alkyloxy, C$_{1-6}$alkyl-OH, NH$_2$, N—(C$_{1-6}$-alkyl) amino, N,N-di(C$_{1-6}$alkyl) amino, —C(=O)C$_{1-6}$alkyl, —OC(=O)C$_{1-6}$alkyl, —C(=O)OH, —C(=O)OC$_{1-6}$alkyl, —C(=O)NHC$_{1-6}$alkyl, —NHC(=O)C$_{1-6}$alkyl, —C$_{1-6}$alkylNHSO$_2$C$_{1-6}$ alkyl, and —C$_{1-6}$alkyl-NH(C=NH)NHR$^g$ wherein R$^g$ is H, amino protecting group, —C$_{0-6}$alkyl-aryl, —OC$_{0-6}$alkylaryl, —C$_{0-6}$alkyl-heteroaryl, —C$_{0-6}$alkyl-cycloalkyl or —C$_{0-6}$alkyl-heterocloalkyl, wherein aryl, heteroaryl, cycloalkyl, and heterocycloalkyl independently from each other may be optionally substituted by one or more groups independently selected from halogen, CN, OH, NO$_2$, C$_{1-6}$ alkyl, C$_{2-6}$alkenyl, C$_{2-6}$alkynyl, haloC$_{1-6}$alkyl, —OC$_{1-6}$alkyl, haloC$_{1-6}$alkyloxy, C$_{1-6}$alkyl-OH, NH$_2$, N—(C$_{1-6}$alkyl)amino, N,N-di(C$_{1-6}$alkyl)amino, —C(=O)C$_{1-6}$alkyl, —OC(=O)C$_{1-6}$ alkyl, —C(=O)OH, —C(=O)OC$_{1-6}$alkyl, —C(=O)NHC$_{1-6}$alkyl and —NHC(=O)C$_{1-6}$alkyl;

h. —C(R$^{W1b}$)(R$^{W2b}$)— group wherein R$^{W1b}$ and R$^{W2b}$ together with carbon atom to which they are attached form:
 i. 3-7 membered spiro cycloalkyl group which may be optionally substituted by one or more groups independently selected from halogen, CN, keto (=O), OH, NO$_2$, C$_{1-6}$alkyl, C$_{2-6}$alkenyl, C$_{2-6}$alkynyl, haloC$_{1-6}$alkyloxy, —OC$_{1-6}$alkyl, haloC$_{1-6}$alkyloxy, C$_{1-6}$alkyl-OH, NH$_2$, N—(C$_{1-6}$-alkyl)amino, N,N-di(C$_{1-6}$alkyl) amino, —C(=O)C$_{1-6}$alkyl, —OC(=O)C$_{1-6}$alkyl, —C(=O)OH, —C(=O)OC$_{1-6}$alkyl, —C(=O)NHC$_{1-6}$alkyl and —NHC(=O)C$_{1-6}$alkyl; or
 ii. 3-7 membered spiro heterocycloalkyl group where heterocycloalkyl group may contain one or two heteroatoms selected form O, S and N;

i. —N(R$^{Wn}$)—, wherein R$^{Wn}$ is C$_{1-6}$alkyl, C$_{2-6}$alkenyl, C$_{2-6}$alkynyl, —C$_{1-6}$alkylOC$_{1-6}$alkyl, —C$_{1-6}$alkyl-C(=O)OH, —C$_{1-6}$alkyl-C(=O)OC$_{1-6}$alkyl, —C$_{1-6}$alkylOC(=O) C$_{1-6}$alkyl, —C$_{1-6}$alkyl-NH$_2$, —C$_{1-6}$alkylNHC(=O)OC$_{1-6}$alkyl, —C$_{1-6}$alkyl-aryl wherein aryl may be optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, OC$_{1-6}$alkyl, haloC$_{1-6}$alkyloxy, C$_{1-6}$alkyl-OH, NH$_2$, N—(C$_{1-6}$-alkyl)amino, N,N-di(C$_{1-6}$alkyl)amino, —(C=O)C$_{1-6}$alkyl, —O(C=O)C$_{1-6}$alkyl, —C(=O)OH, —C(=O)OC$_{1-6}$alkyl, —C(=O)NHC$_{1-6}$alkyl and —NHC(=O)C$_{1-6}$alkyl;

j. —C(R$^{w1c}$)(R$^{w2c}$)- group wherein R$^{W1c}$ and R$^{w2c}$ together with carbon atom to which they are attached form:
 i. >C=C-aryl, or
 ii. >C=C-heteroaryl,
 wherein aryl and heteroaryl independently from each other may be optionally substituted by one or more groups independently selected from halogen, CN, OH, NO$_2$, C$_{1-6}$alkyl, C$_{2-6}$alkenyl, C$_{2-6}$alkynyl, haloC$_{1-6}$alkyl, OC$_{1-6}$alkyl, haloC$_{1-6}$alkyloxy, C$_{1-6}$alkyl-OH, NH$_2$, N—(C$_{1-6}$-alkyl) amino, N,N-di(C$_{1-6}$alkyl) amino, —(C=O)C$_{1-6}$alkyl, —O(C=O) C$_{1-6}$alkyl, —C(=O)OH, —C(=O)OC$_{1-6}$alkyl, —C(=O)NHC$_{1-6}$alkyl and —NHC(=O)C$_{1-6}$alkyl;

k. [—NHCH(R$^t$)C(=O)]$_{t1}$ or

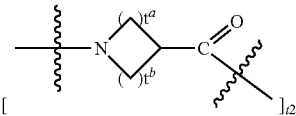

group,
 wherein:
 t$^1$ and t$^2$ independently are 1 to 5,
 t$_a$ and t$_b$ independently are 0 to 3, provided the sum of t$_a$ and t$_b$ is 2 to 6, R$^t$ is residue of natural ammo acid selected from H, C$_{1-6}$alkyl, —C(=O)C$_{1-6}$alkyl, —C(=O)OC$_{1-6}$ alkyl, —OC$_{1-6}$alkyl, —C$_{1-6}$alkyl-OH, —C$_{1-6}$alkyl-OC$_{1-6}$alkyl, —C$_{1-6}$alkyl-SC$_{1-6}$alkyl, CN, —C(=O)OH, —C(=O)NH$_2$, —C$_{0-6}$alkyl-aryl or —C$_{0-6}$alkyl-heteroaryl wherein aryl and heteroaryl may be mono or biyclic and each may be optionally substituted by one or more groups independently selected from halogen, CN, OH, NO$_2$, OC$_{1-6}$alkyl, NH$_2$, N—(C$_{1-6}$-alkyl)amino, N,N-di(C$_{1-6}$alkyl)amino, —(C=O)C$_{1-6}$ alkyl, —O(C=O)C$_{1-6}$alkyl, —C(=O)OH, —C(=O)OC$_{1-6}$alkyl, —C(=O)NHC$_{1-6}$alkyl and —NHC(=O)C$_{1-6}$alkyl;

l. —NHC(R$^{W1d}$)(R$^{W2d}$)C(R$^{W1e}$)(R$^{W2e}$)-NHC(=O)— group wherein R$^{W1d}$ and R$^{W1e}$ are hydrogen, and R$^{W2d}$ and R$^{W2e}$ are independently from each other $C_{0-4}$alkylaryl wherein aryl may be optionally substituted by one or more groups independently selected from halogen, CN, OH, $NO_2$, $C_{1-6}$alkyl, $C_{2-6}$ alkenyl, $C_{2-6}$alkynyl, halo$C_{1-6}$alkyl, —O$C_{1-6}$alkyl, halo$C_{1-6}$alkyloxy, —$C_{1-6}$alkyl-OH, $NH_2$, N—($C_{1-6}$-alkyl)amino, N,N-di($C_{1-6}$alkyl)amino, —C(=O)$C_{1-6}$alkyl, —O(C=O)$C_{1-6}$alkyl, —C(=O)OH, —C(=O)O$C_{1-6}$alkyl, —C(=O)NH$C_{1-6}$alkyl and —NHC(=O)$C_{1-6}$alkyl;

(ii) $W^1$ and $W^3$ are selected from (i-a) to (i-l), $W^2$ is —CH=CH—, —CH(OH)CH(OH)—, —CH=CH—CH(OH)—, or —CH=CH—CH=CH—, $X^2$ is —C(=O)— or —$CH_2$—, $X^1$ is —C(=O)NH— or —C(=O)O—;

(iii) $w^1$ is —CH=CH—, $x^1$ is a bond and $W^2$ and $W^3$ are independently selected from (i-a) to (i-l);

(iv) $W^2$ is >C(=O) or —C(=O)NH— and $W^1$ and $W^3$ are independently selected from (i-a) to (i-l), provided when $W^1$ is absent, $m^1$ cannot be zero; or (v) all absent.

2. The compound according to claim 1, wherein $R^N$ is $C_{1-6}$alkyl or hydrogen.

3. The compound according to claim 1, wherein $A^1$ is OH or —O$C_{1-6}$alkyl.

4. The compound according to claim 1, wherein $R^1$ is $S^1$ or OH.

5. The compound according to claim 1, wherein $R^{2a}$ is $S^2$, OH or —OC(=O)$Y^1$, wherein $S^2$ and $Y^1$ are as defined in claim 1 above.

6. The compound according to claim 1, wherein $R^{2b}$ is H.

7. The compound according to claim 1, wherein $B^1$ and $B^2$ independently are H or $C_{1-6}$alkyl.

8. The compound according to claim 1, wherein $S^1$ is sugar group of formula

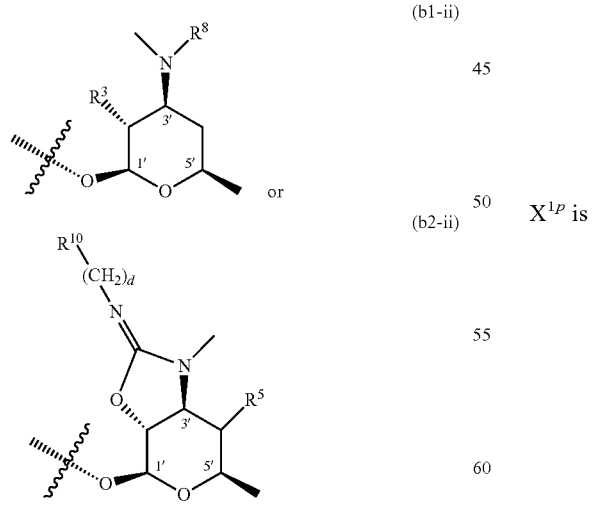

wherein $R^3$, $R^8$, d, and $R^{10}$ are as defined in claim 1 above.

9. The compound according to claim 8, wherein $R^3$ is OH, H or —O— $L^1$-G group, $R^{10}$ is $C_{1-6}$alkyl, and $L^1$, G and d are as defined above.

10. The compound according to claim 1, wherein $S^2$ is sugar group of formula

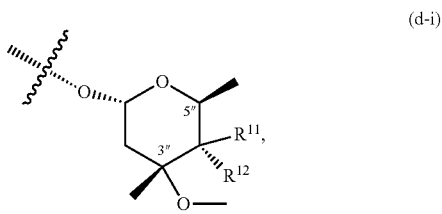

and wherein $R^{11}$ and $R^{12}$ are as defined in claim 1 above.

11. The compound according to claim 10, wherein
(i) $R^{11}$ is H and $R^{12}$ is OH; or
(ii) one of $R^{11}$ and $R^{12}$ is OH and the other is —$CH_2$N($R^{13}$)$R^{14}$, wherein $R^{13}$ and $R^{14}$ are as defined above.

12. The compound according to claim 11, wherein
(i) one of $R^{13}$ and $R^{14}$ is $C_{1-6}$alkyl and the other is H or $C_{1-6}$alkyl; or
(ii) $R^{13}$ and $R^{14}$ together with nitrogen to which they are attached form a heterocyclic ring.

13. A process for preparation of compound of formula (III), or pharmaceutically acceptable salt, solvate or prodrug thereof as defined in claim 1, wherein the process comprises following steps:

(a-1) providing a seco (opened ring) macrolide compound of Formula (I) or a salt or solvate thereof wherein,

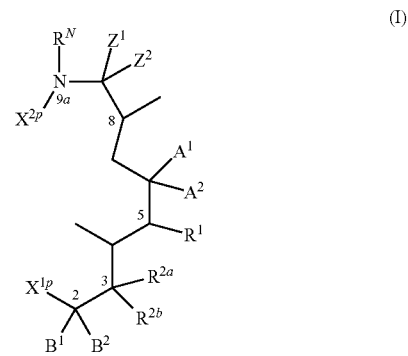

$X^{1p}$ is

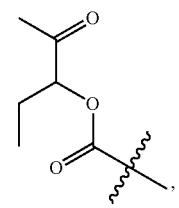 [SMILES: *C(=O)OC(CC)C(C)=O]

—C(=O)OH, —C(=O)$NH_2$, —C(=S)$NH_2$ —C(=O)NH$NH_2$, —$CH_2NH_2$, —$CH_2OH$, —C(=O)H, —CN or —$NH_2$;

$X^{2p}$ is hydrogen, —CH($CH_3$)C(=O)H, —C(=S)$NH_2$, or —C(=O)$NH_2$;

$Z^1$ and $Z^2$
(i) are both hydrogen, or
(ii) together with carbon atom to which they are attached form a keto group provided $R^N$ is hydrogen and $A^1$ is $OC_{1-6}$alkyl;

and $A^1, A^2, B^1, B^2, R^1, R^{2a}, R^{2b}, R^N$, and $R^P$ are as defined in claim 1;

(b-1) reacting the compound of formula (I) obtained in step (a-1) with a compound of formula $X^{1m}\text{-}W^m\text{-}X^{2m}$, wherein $X^{1m}$ and $X^{2m}$ are the appropriate reactive or leaving groups or groups convertable to $X^1$ and $X^2$ as defined above for formula (III), and $W^m$ is W or the appropriate precursor convertable to W wherein W is as defined for formula (III) above;

(c-1) cyclizing compound obtained in step (b-1) and thereafter, if required after any of steps (a-1) to (c-1), subjecting the resulting compound to one or more of the following operations:
(i) removal of the protecting group $R^P$,
(ii) conversion of $X^{1m}, X^{2m}$ and $W^m$ to $X^1, X^2$ and W,
(iii) removal of $S^2$ sugar group and/or $S^1$ sugar group,
(iv) conversion of the resulting compound of formula (III) into a pharmaceutically acceptable salt, solvate, or prodrug thereof.

14. The process according to claim 13, wherein step (a-1) comprises process steps (a) to (m) for preparation of the compound of formula (I) as follows:

(a) reacting a 9a-aza-9a-homoerythromycin compound of formula (II)

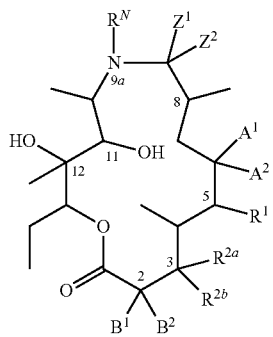

(II)

wherein,
$Z^1, Z^2, A^1, A^2, R^1, R^{2a}, R^{2b}, B^1, B^2$ and $R^N$ are as defined for formula (I) in claim 13, with a suitable oxidative cleavage reactant in a suitable solvent or mixture of solvents to give:

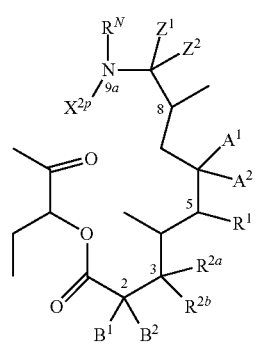

(I-A)

(i) a seco macrolide compound of formula (I-A), which is subset of formula (I), wherein $X^{1p}$ is

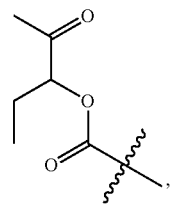 [SMILES: *C(=O)OC(CC)C(C)=O]

$X^{2p}$ is hydrogen, $Z^1$ and $Z^2$ are both hydrogen, $A^1, A^2, R^1, R^{2a}, R^{2b}, B^1, B^2$ and $R^N$ are as defined for formula (I) when starting from compound of formula (II), wherein $Z^1$ and $Z^2$ are both hydrogen, or (ii) a seco macrolide compound of formula (I-A), which is subset of formula (I) wherein $X^{1p}$ is

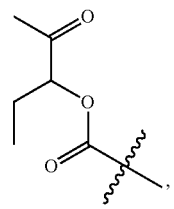 [SMILES: *C(=O)OC(CC)C(C)=O]

$X^{2p}$ is $-CH(CH_3)C(=O)H$, $Z^1$ and $Z^2$ together with carbon atom to which they are attached form a keto group, $R^N$ is hydrogen, $A^1$ is $-OC_{1-6}$alkyl, $A^2, R^1, R^{2a}, R^{2b} B^1$ and $B^2$, are as defined for formula (I) when starting from compound of formula (II) wherein $Z^1$ and $Z^2$ together with carbon atom to which they are attached from keto group;

(b) hydrolyzing a compound of formula (I-A) wherein $X^{1p}$ is

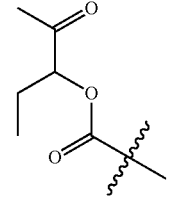 [SMILES: *C(=O)OC(CC)C(C)=O]

obtained in step (a) to give compound of formula (I-B), which is subset of formula (I) wherein $X^{1p}$ is $-C(=O)OH$, $X^{2p}$ is hydrogen, $Z^1, Z^2, A^1, A^2, R^1, R^{2a}, R^{2b}, B^1, B^2$ and $R^N$ are as defined for formula (I) above; and optionally subjecting a compound of formula (I-B) wherein $X^{1p}$ is $-C(=O)OH$, $X^{2p}$ is hydrogen, $R^N$ is hydrogen and $Z^1$ and $Z^2$ together with carbon atom to which they are attached form a keto group to a further hydrolyzing conditions to give di-carboxylic acid of formula (XC), wherein $A^1, A^2, B^1, B^2, R^1, R^{2a}$ and $R^{2b}$ are as defined for formula (I); or

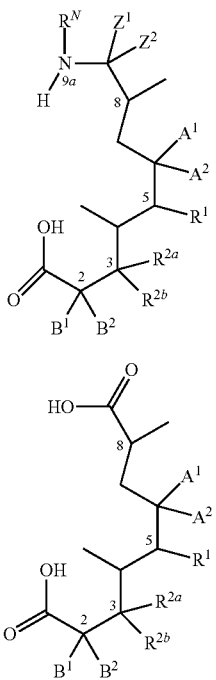 (I-B)

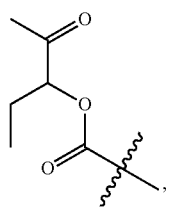 [SMILES: *C(=O)OC(CC)C(C)=O] (XC)

(c) reacting a compound of formula (IA) wherein $X^{1p}$ is

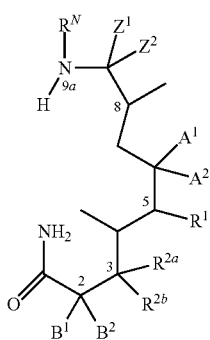

$X^{2p}$ is hydrogen obtained in step (a) or compound of formula (I-B) wherein $X^{1p}$ is —C(=O)OH and $X^{2p}$ is hydrogen obtained in step (b) with ammonium salt in the presence of base and coupling agent or with ammonia in organic solvents, or with ammonia hydroxide to give a compound of formula (I-C), which is subset of formula (I) wherein $X^{1p}$ is —C(=O)NH$_2$, $X^{2p}$ is hydrogen, $Z^1$, $Z^2$, $A^1$, $A^2$, $R^1$, $R^{2a}$, $R^{2b}$, $B^1$, $B^2$ and $R^N$ are as defined for formula (I) above; or

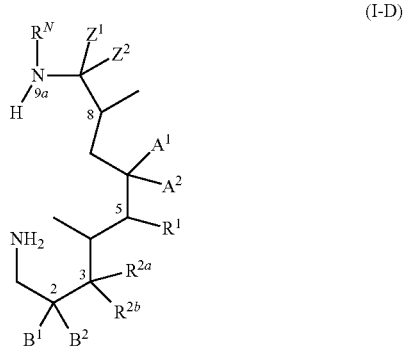 (I-C)

(d) reducing amide compound of formula (I-B) wherein $X^{1p}$ is —C(=O)NH$_2$, and $X^{2p}$ is hydrogen obtained in step (c) using suitable reducing agent to compound of formula (I-D), which is subset of formula (I) wherein $X^{1p}$ is —CH$_2$NH$_2$, $X^{2p}$ is hydrogen, $Z^1$, $Z^2$, $A^1$, $A^2$, $R^1$, $R^{2a}$, $R^{2b}$, $B^1$, $B^2$ and $R^N$ are as defined for formula (I) above; or

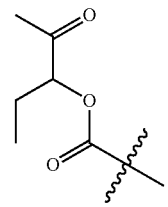 [SMILES: *C(=O)OC(CC)C(C)=O] (I-D)

(e) reacting a compound of formula (I-A) obtained in step (a) wherein $X^{1p}$ is

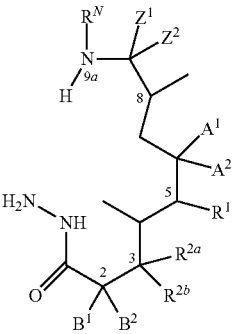

with hydrazine hydrate in a suitable solvent to give compound of formula (I-E), which is subset of formula (I) wherein $X^{1p}$ is —C(=O)—NH—NH$_2$ group, $X^{2p}$ is hydrogen, $Z^1$, $Z^2$, $A^1$, $A^2$, $R^1$, $R^{2a}$, $R^{2b}$, $B^1$, $B^2$ and $R^N$ are as defined for formula (I) above; or

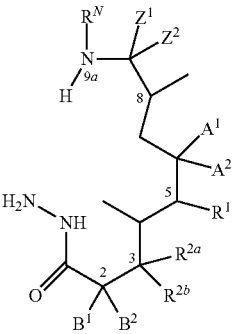 (I-E)

(f) reacting a compound of formula (I-A) obtained in step (a) wherein $X^{1p}$ is

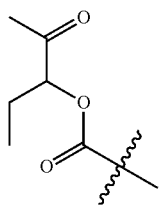 [SMILES: *C(=O)OC(CC)C(C)=O]

or a compound of formula (I-B) obtained in step (b) wherein $X^{1p}$ is —C(=O)OH with thiocarbonyldiimidazole followed by the amonolysis reaction conditions (provided when starting from compound of formula (I-A) then C/1- keto ester hydrolysis step (b) is usually performed prior amonolysis), or in alternative with thiocyanates or isothiocyanates to give compound of formula (I-FA), which is subset of formula (I) wherein $X^{1p}$ is —C(=O)OH group, $X^{2p}$ is —C(=S)NH$_2$ group, $Z^1$, $Z^2$, $A^1$, $A^2$, $R^1$, $R^{2a}$, $R^{2b}$, $B^1$, $B^2$ and $R^N$ are as defined for formula (I) above; or

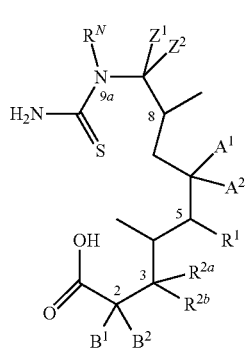

(I-FA)

(g) reacting a compound of formula (I-A) obtained in step (a) wherein $X^{1p}$ is

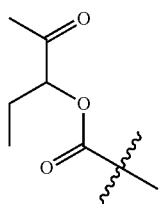

or a compound of formula (I-B) obtained in step (b) wherein $X^{1p}$ is —C(=O)OH with carbonyldiimidazole followed by the amonolysis reaction conditions (provided when starting from compound of formula (I-A) then C/1-keto ester hydrolysis step (b) is usually performed prior amonolysis), or in alternative with alkali metal cyanates or isocyanates to give compound of formula (1-FB), which is subset of formula (I) wherein $X^{1p}$ is —C(=O)OH group, $X^{2p}$ is —C(=O)NH$_2$ group, $Z^1$, $Z^2$, $A^1$, $A^2$, $R^1$, $R^{2a}$, $R^{2b}$, $B^1$, $B^2$ and $R^N$ are as defined for formula (I) above; or

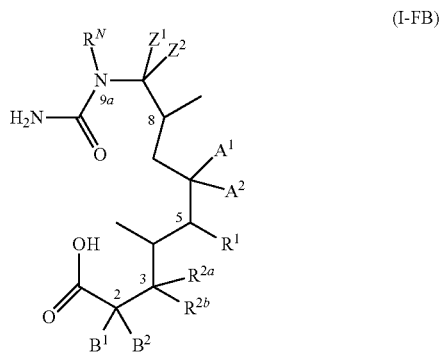

(I-FB)

(h) subjecting a compound of formula (I-A) obtained in step (a) wherein $X^{1p}$ is

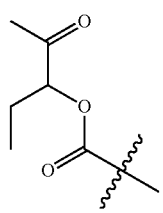 [SMILES: *C(=O)OC(CC)C(C)=O]

or a compound of formula (I-B) obtained in step (b) wherein $X^{1p}$ —C(=O)OH to the standard carboxylic acid reduction conditions to give compound of formula (I-KA-a), which is subset of formula (I) wherein $X^{1p}$ is —CH$_2$OH group, $X^{2p}$ is hydrogen, $Z^1$, $Z^2$, $A^1$, $A^2$, $R^1$, $R^{2a}$, $R^{2b}$, $B^1$, $B^2$ and $R^N$ are as defined for formula (I) above; or

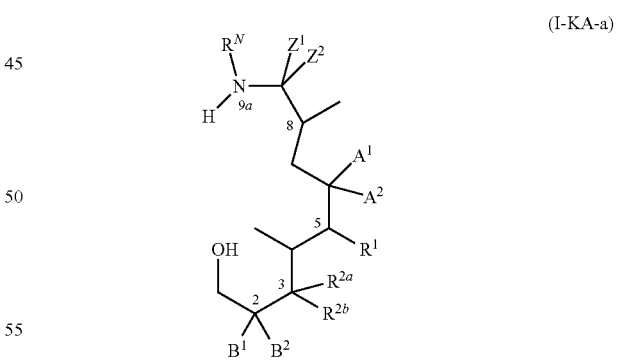

(I-KA-a)

(i) reacting a compound of formula (I-KA-a) obtained in step (h) wherein $X^{1p}$ is —CH$_2$OH group and $X^{2p}$ is hydrogen with the standard oxidizing reagents to give compound of formula (I-KA), which is subset of formula (I) wherein $X^{1p}$ is —C(=O)H group, $X^{2p}$ is hydrogen, $Z^1$, $Z^2$, $A^1$, $A^2$, $R^1$, $R^{2a}$, $R^{2b}$, $B^1$, $B^2$ and $R^N$ are as defined for formula (I) above; or

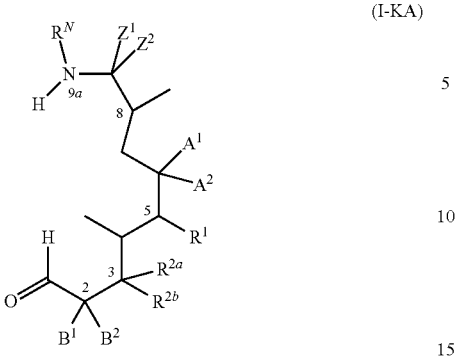

(j) subjecting compound of formula (I-C) obtained in step (c) where $X^{1p}$ is —C(=O)NH$_2$ group and $X^{2p}$ is hydrogen to dehydration reaction to give compound of formula (I-MN), which is subset of formula (I) wherein $X^{1p}$ is —CN, $X^{2p}$ is hydrogen, $Z^1$, $Z^2$, $A^1$, $A^2$, $R^1$, $R^{2a}$, $R^{2b}$, $B^1$, $B^2$ and $R^N$ are as defined for formula (I) above; or

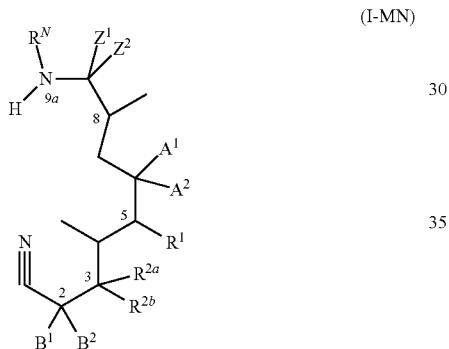

(k) reacting
   a. a compound of formula (I-C) obtained in step (c) where $X^{1p}$ —C(=O)NH$_2$, and $X^{2p}$ is hydrogen with Lawesson's or Bellau's reagents or with P$_4$S$_{10}$ alone or in combination with hexamethyldisiloxane, or in alternative
   b. a compound of formula (I-MN) obtained in step (j) where $X^{1p}$ —CN, and $X^{2p}$ is hydrogen using alkali metal hydrogen sulfide or ammonium sulfide under high pressure, phosphorus decasulfide, thioacids, thioacetic acid in combination with Lewis acid or benzylamine or calcium hydride, thioacetamide, DowexSH, O-dialkyldithiophosphates,12 diphenylphosphinodithioacids, sodium trimethylsilanethiolate, sodium hydrosulfide hydrate and diethyl amine hydrochloride, sodium hydrosulfide hydrate and magnesium chloride hexahydrate, and (P$_4$S$_{11}$) Na$_2$ to give compound of formula (I-M), which is subset of formula (I) wherein $X^1P$ is —C(=S)NH$_2$, $X^{2p}$ is hydrogen, $Z^1$, $Z^2$, $A^1$, $A^2$, $R^1$, $R^{2a}$, $R^{2b}$, $B^1$, $B^2$ and $R^N$ are as defined for formula (I) above; or (I) subjecting

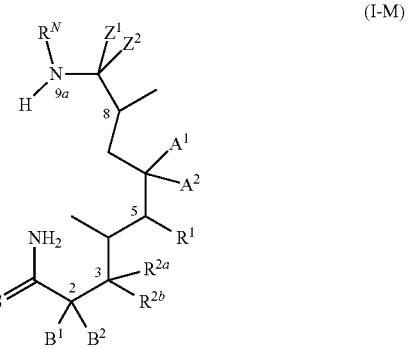

a. a compound of formula (I-B) obtained in step (b) where $X^{1p}$ —C(=O)OH, and $X^{2p}$ is hydrogen to the modified Curtius rearrangement followed by mild acidic hydrolysis or hydrogenation of the carbamate group; or
b. a compound of formula (I-A) obtained in step (a) where $X^{1p}$ is

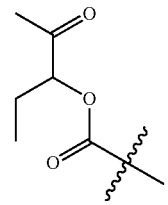 [SMILES: *C(=O)OC(CC)C(C)=O]

and $X^{2p}$ is hydrogen to the modified Lossen rearrangement followed by mild acidic hydrolysis or hydrogenation of the carbamate group,
   to give compound of formula (I-RE), which is subset of formula (I) wherein $X^{1p}$ is —NH$_2$, $X^{2p}$ is hydrogen, $Z^1$, $Z^2$, $A^1$, $A^2$, $R^1$, $R^{2a}$, $R^{2b}$, $B^1$, $B^2$ and $R^N$ are as defined for formula (I) above; and

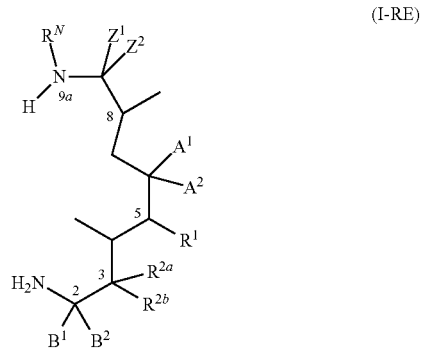

(m) if required after any of previous steps (a)-(l), subjecting the resulting compound to one or more of the following operations:
   (i) removal of the protecting group $R^p$,
   (ii) removal of S$^2$ sugar group and/or S$^1$ sugar group,
   (iii) conversion of the resulting compound of formula (I) into a salt or solvate thereof.

15. The process according to claim 13, wherein the compound of formula (I) is represented by formula (I-ii)

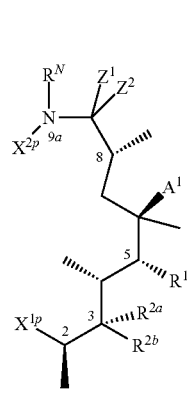

(I-ii)

wherein $X^{1p}$, $X^{2p}$, $R^N$, $Z^1$, $Z^2$, $A^1$, $R^1$, $R^{2a}$ and $R^{2b}$ are as defined above in claim 13.

16. The process according to claim 13, wherein
(a) $X^{2p}$ is hydrogen, $X^{1p}$ is

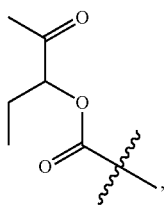

—C(=O)OH, —C(=O)NH$_2$, —C(=S)NH$_2$, —C(=O)NHNH$_2$, —CH$_2$NH$_2$, —CH$_2$OH, —C(=O)H, —CN or —NH$_2$;

(b) $X^{2p}$ is —C(=S)NH$_2$ or —C(=O)NH$_2$, $X^{1p}$ is —C(=O)OH; or (c) $X^{2p}$ is —CH(CH$_3$)C(=O)H and $X^{1p}$ is

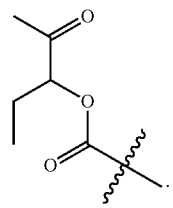

17. The process according to claim 13, wherein
(a) $X^{2p}$ is hydrogen, $X^{1p}$ is —C(=O)NH$_2$, —C(=S)NH$_2$, —C(=O)NHNH$_2$, —CH$_2$NH$_2$, —CH$_2$OH, —C(=O)H, —CN or —NH$_2$; or (b) $X^{2p}$ is —C(=S)NH$_2$ or —C(=O)NH$_2$, $X^{1p}$ is —C(=O)OH; or (c) $X^{2p}$ is —CH(CH$_3$)C(=O)H and $X^{1p}$ is

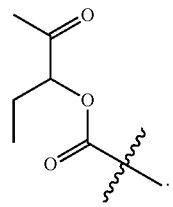

18. A pharmaceutical composition, comprising a pharmaceutically acceptable carrier and a pharmaceutically effective amount of a compound according to claim 1, optionally comprising a further therapeutic agent.

19. A method for the treatment of diseases or conditions selected from conditions involving inflammation or immune responses, and/or autoimmune diseases, comprising administering an amount of compound according to claim 1 to a subject in need thereof, or a pharmaceutical composition comprising the compound of claim 1, in an amount sufficient to effect said treatment, wherein the diseases or conditions are associated with IL-6 and/or TNF-alpha production.

20. The method according to claim 19, wherein the compound or the pharmaceutical composition is administered in combination with a further therapeutic agent.

* * * * *